US011214565B2

(12) United States Patent
Estrada et al.

(10) Patent No.: US 11,214,565 B2
(45) Date of Patent: Jan. 4, 2022

(54) COMPOUND, COMPOSITIONS, AND METHODS

(71) Applicant: Denali Therapeutics Inc., South San Francisco, CA (US)

(72) Inventors: Anthony A. Estrada, San Mateo, CA (US); Jianwen A. Feng, San Mateo, CA (US); Joseph P. Lyssikatos, South San Francisco, CA (US); Zachary K. Sweeney, Redwood City, CA (US); Javier de Vicente Fidalgo, Foster City, CA (US)

(73) Assignee: DENALI THERAPEUTICS INC., South San Francisco, CA (US)

( * ) Notice: Subject to any disclaimer, the term of this patent is extended or adjusted under 35 U.S.C. 154(b) by 0 days.

(21) Appl. No.: 15/777,205

(22) PCT Filed: Nov. 18, 2016

(86) PCT No.: PCT/US2016/062947
§ 371 (c)(1),
(2) Date: May 17, 2018

(87) PCT Pub. No.: WO2017/087905
PCT Pub. Date: May 26, 2017

(65) Prior Publication Data
US 2018/0327391 A1 Nov. 15, 2018

Related U.S. Application Data

(60) Provisional application No. 62/411,011, filed on Oct. 21, 2016, provisional application No. 62/411,064, filed on Oct. 21, 2016, provisional application No. 62/351,004, filed on Jun. 16, 2016, provisional application No. 62/350,927, filed on Jun. 16, 2016, provisional application No. 62/351,083, filed on Jun. 16, 2016, provisional application No. 62/350,988, filed on Jun. 16, 2016, provisional application No. 62/310,632, filed on Mar. 18, 2016, provisional application No. 62/307,285, filed on Mar. 11, 2016, provisional application No. 62/259,165, filed on Nov. 24, 2015, provisional application No. 62/258,244, filed on Nov. 20, 2015.

(51) Int. Cl.
*C07D 401/12* (2006.01)
*C07D 401/14* (2006.01)
*C07D 403/12* (2006.01)
*C07D 403/14* (2006.01)
*C07D 487/04* (2006.01)
*A61K 31/506* (2006.01)
*A61K 31/519* (2006.01)
*A61K 31/52* (2006.01)
*A61K 31/4439* (2006.01)
*C07D 413/14* (2006.01)
*C07D 417/14* (2006.01)
*C07D 471/04* (2006.01)

(52) U.S. Cl.
CPC ......... *C07D 403/12* (2013.01); *C07D 403/14* (2013.01); *C07D 413/14* (2013.01); *C07D 417/14* (2013.01); *C07D 471/04* (2013.01); *C07D 487/04* (2013.01)

(58) Field of Classification Search
CPC .. C07D 401/12; C07D 401/14; C07D 403/12; C07D 403/14; C07D 487/04; A61K 31/506; A61K 31/519; A61K 31/52; A61K 31/4439
See application file for complete search history.

(56) References Cited

U.S. PATENT DOCUMENTS

| | | | |
|---|---|---|---|
| 7,144,911 B2 | 12/2006 | Flynn et al. | |
| 8,815,882 B2 | 8/2014 | Baker-Glenn et al. | |
| 9,676,792 B2 | 6/2017 | Gray et al. | |
| 9,932,325 B2 * | 4/2018 | Estrada | C07B 59/002 |
| 2009/0105266 A1 | 4/2009 | Glatthar et al. | |
| 2013/0079324 A1 | 3/2013 | Cheng et al. | |
| 2013/0267513 A1 | 10/2013 | Chan et al. | |
| 2015/0051238 A1 | 2/2015 | Baker-Glenn et al. | |
| 2017/0362206 A1 | 12/2017 | Estrada et al. | |
| 2018/0208582 A1* | 7/2018 | Estrada | C07B 59/002 |
| 2019/0084975 A1 | 3/2019 | Estrada et al. | |
| 2020/0157081 A1 | 5/2020 | Estrada et al. | |

FOREIGN PATENT DOCUMENTS

| | | |
|---|---|---|
| CN | 105461694 | 4/2016 |
| WO | WO-2000/039108 | 7/2000 |
| WO | WO-2003/076658 | 9/2003 |

(Continued)

OTHER PUBLICATIONS

L. Tan et al., 58 Journal of Medicinal Chemistry, 6589-6606 (2015) (Year: 2015).*
Chan et al., "Discovery of a Highly Selective, Brain-Penetrant Aminopyrazole LRRK2 Inhibitor", ACS Medicinal Chemistry Letters, 2013, 4(1), 85-90.
Estrada et al., "Discovery of Highly Potent, Selective, and Brain-Penetrant Aminopyrazole Leucine-Rich Repeat Kinase 2 (LRRK2) Small Molecule Inhibitors", Journal of Medicinal Chemistry, 2014, 57(3), 921-936.
International Search Report and Written Opinion for PCT/US2016/062947 dated Mar. 6, 2017, 13 pages.
Jordan, V. C., Tamoxifen: A Most Unlikely Pioneering Medicine, Nature Reviews: Drug Discovery 2003, vol. 2, pp. 205-213.

(Continued)

*Primary Examiner* — Bruck Kifle
(74) *Attorney, Agent, or Firm* — Rothwell, Figg, Ernst & Manbeck, P.C.

(57) ABSTRACT

Compounds having activity as LRRK2 inhibitors are disclosed. The compounds are of formula (I) including stereoisomers, tautomers, pharmaceutically acceptable salts and prodrugs thereof. Methods associated with preparation and use of such compounds, as well as pharmaceutical compositions comprising such compounds are also disclosed.

15 Claims, No Drawings

(56) References Cited

FOREIGN PATENT DOCUMENTS

| | | |
|---|---|---|
| WO | WO-2004/060306 | 7/2004 |
| WO | WO-2005/086656 | 9/2005 |
| WO | WO-2006/014290 | 2/2006 |
| WO | WO-2007/009524 | 1/2007 |
| WO | WO-2007/117995 | 10/2007 |
| WO | WO-2007/149798 | 12/2007 |
| WO | WO-2008/118822 | 10/2008 |
| WO | WO-2008/128968 | 10/2008 |
| WO | WO-2008/137619 | 11/2008 |
| WO | WO-2008/147626 | 12/2008 |
| WO | WO-2009/032694 | 3/2009 |
| WO | WO-2009/127642 | 10/2009 |
| WO | WO-2010/101973 | 9/2010 |
| WO | WO-2010/111406 | 9/2010 |
| WO | WO-2011/060295 | 5/2011 |
| WO | WO-2011/151360 | 12/2011 |
| WO | WO-2011/156698 | 12/2011 |
| WO | WO-2012/058193 | 5/2012 |
| WO | WO 2012/062783 | 5/2012 |
| WO | WO-2012062783 A1 * 5/2012 ........... C07D 401/14 |
| WO | WO-2012/075046 | 6/2012 |
| WO | WO-2012/174338 | 12/2012 |
| WO | WO-2013/014162 | 1/2013 |
| WO | WO-2013/042006 | 3/2013 |
| WO | WO-2013/079493 | 6/2013 |
| WO | WO-2013/079494 | 6/2013 |
| WO | WO-2013/079495 | 6/2013 |
| WO | WO-2013/079496 | 6/2013 |
| WO | WO-2013/079505 | 6/2013 |
| WO | WO-2013/126283 | 8/2013 |
| WO | WO-2013/130976 | 9/2013 |
| WO | WO-2013130976 A1 * 9/2013 ........... A61K 31/506 |
| WO | WO 2013/164321 | 11/2013 |
| WO | WO 2013/164323 | 11/2013 |
| WO | WO-2014/116772 | 7/2014 |
| WO | WO-2014/130241 | 8/2014 |
| WO | WO-2014/135245 | 9/2014 |
| WO | WO-2014/150981 | 9/2014 |
| WO | WO-2014/170248 | 10/2014 |
| WO | WO-2014/181137 | 11/2014 |
| WO | WO-2014/181287 | 11/2014 |
| WO | WO 2015/113452 | 8/2015 |
| WO | WO-2015/131005 | 9/2015 |
| WO | WO-2015/148867 | 10/2015 |
| WO | WO-2015/148869 | 10/2015 |
| WO | WO-2016033100 | 3/2016 |
| WO | WO-2016/149311 | 9/2016 |
| WO | WO-2016/201370 | 12/2016 |
| WO | WO-2017/046675 | 3/2017 |
| WO | WO-2017/087282 | 5/2017 |
| WO | WO-2017/087905 | 5/2017 |
| WO | WO-2017/089390 | 6/2017 |
| WO | WO-2017/100703 | 6/2017 |
| WO | WO-2017/106771 | 6/2017 |
| WO | WO-2017/156493 | 9/2017 |
| WO | WO-2017218843 | 12/2017 |
| WO | WO-2018217946 | 11/2018 |

OTHER PUBLICATIONS

Wolff, Manfred E., Burger's Medicinal Chemistry and Drug Discovery—Fifth Edition, vol. 1: Principles and Practice, New York: John Wiley & Sons, 1994, pp. 975-977.

* cited by examiner

COMPOUND, COMPOSITIONS, AND METHODS

CROSS-REFERENCE TO RELATED APPLICATIONS

This application is a U.S. National Stage Application under 35 U.S.C. § 371 of International Application No. PCT/US2016/062947, filed Nov. 18, 2016, which claims the benefit under 35 U.S.C. § 119(e) to U.S. Provisional Application Ser. No. 62/258,244, filed Nov. 20, 2015, 62/259,165, filed Nov. 24, 2015, 62/307,285, filed Mar. 11, 2016, 62/310,632, filed Mar. 18, 2016, 62/350,927, filed Jun. 16, 2016, 62/350,988, filed Jun. 16, 2016, 62/351,004, filed Jun. 16, 2016, 62/351,083, filed Jun. 16, 2016, 62/411,011, filed Oct. 21, 2016, 62/411,064, filed Oct. 21, 2016, the contents of each is incorporated herein by reference in its entirety.

FIELD

The present disclosure relates generally to novel pyrazole-substituted pyrimidines and their use as therapeutic agents, for example, as inhibitors of LRRK2.

BACKGROUND

Neurodegenerative diseases such as Parkinson's disease, amyotrophic lateral sclerosis (ALS), Alzheimer's disease, Lewy body dementia, and Huntington's disease affects millions of people. Parkinson's disease is a chronic, progressive motor system disorder characterized by selective degeneration and cell death of dopaminergic neurons in the substantial nigra region of the brain. This leaves patients with impaired ability to direct and control their movements. The cause of the disease was generally considered to be sporatic and unknown, but significant advancements in understanding have been made in the last 15 years.

The genetic basis for the disease and associated pathogenic mechanisms have led exploration of the gene encoding leucine-rich repeat kinase 2 (LRRK2) protein and its association with hereditary Parkinson's disease (Paisan-Ruiz et al., Neuron, Vol. 44(4), 2004, 601-607). LRRK2 is a member of the ROCO protein family and shares 5 conserved domains with all other family members. Many mis-sense mutations to the LRRK2 gene have been linked with autosomal dominant Parkinson's disease in familial studies Trinh and Farrar, Nature Reviews in Neurology, Vol. 9, 2013, 445-454; Paisan-Ruiz et al., J. Parkinson's Disease, Vol. 3, 2013, 85-103). The most common pathogenic mutation, G2019S, occurs in the highly conserved kinase domain of LRRK2 (See Gilks et al., Lancet, Vol 365, 2005, 415-416). In vitro studies indicate Parkinson's disease-associated mutation leads to increased LRRK2 activity and a decreased rate of GTP hydrolysis (Guo et al., Experimental Cell Research, Vol. 313(16), 2007, 3658-3670). This evidence suggests the kinase and GTPase activities of LRRK2 are important for pathogenesis and the LRRK2 kinase domain may regulate overall LRRK2 function (See Cookson, Nat. Rev. Neurosci., Vol. 11, 2010, 791-797).

While progress has been made in this field, there remains a need for improved inhibitors of the LRRK2 receptor which are useful for treatment of various neurodegenerative diseases, such as Parkinson's disease, Alzheimer's disease and amyotrophic lateral sclerosis.

SUMMARY

Provided herein are compounds that are useful as inhibitors of LRRK2. The disclosure also provides compositions, including pharmaceutical compositions, kits that include the compounds, and methods of using (or administering) and making the compounds. The disclosure further provides compounds or compositions thereof for use in a method of treating a disease, disorder, or condition that is mediated, at least in part, by LRRK2. Moreover, the disclosure provides uses of the compounds or compositions thereof in the manufacture of a medicament for die treatment of a disease, disorder, or condition that is mediated, at least in part, by LRRK2.

In one embodiment, provided is a compound of formula (I):

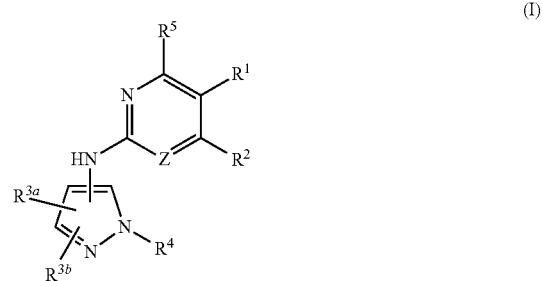

or a pharmaceutically acceptable salt, stereoisomer, or a mixture of stereoisomers, tautomer or prodrug thereof, wherein:

Z is N or CH;

$R^1$ is halo, cyano, $C_1$-$C_6$ alkyl, $C_1$-$C_6$ haloalkyl, $C_1$-$C_6$ alkoxy, $C_1$-$C_6$ haloalkoxy, cycloalkyl, cycloalkyloxy, cycloalkylalkyl, cycloalkylalkyloxy, $C_1$-$C_6$ alkylcarbonyl, $C_1$-$C_6$ alkyloxycarbonyl, aminocarbonyl, or heterocyclylcarbonyl, wherein each is optionally substituted; and $R^5$ is H; or $R^1$ and $R^5$ together with the atom to which they are attached form a 5-membered ring having the structure:

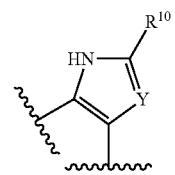

Y is N or $CR^6$;

$R^6$ is H, halo, cyano, $C_1$-$C_6$ alkyl, $C_{2-6}$alkenyl, $C_{2-6}$ alkynyl, $C_1$-$C_6$ alkoxy, $C_1$-$C_6$ heteroalkyl, $C_1$-$C_6$ haloalkyl, $C_1$-$C_6$ alkoxyalkyl, —S(O)$_w$($C_1$-$C_6$ alkyl), cycloalkyl, heterocyclyl, heteroaryl, aryl, acyl, or amido, wherein each is optionally substituted;

$R^{10}$ is H, halo, cyano, $C_1$-$C_6$ alkyl, $C_1$-$C_6$ haloalkyl, or cycloalkyl;

$R^2$ is $C_1$-$C_6$ alkyl, cycloalkyl, cycloalkylalkyl, $C_1$-$C_6$ alkoxy, cycloalkyloxy, cycloalkylalkyloxy, heterocyclyloxy, heterocyclylalkyloxy, amino, $C_1$-$C_6$ alkylamino, cycloalkylamino, cycloalkylalkylamino, heterocyclylamino, or heterocyclylalkylamino, wherein each is optionally substituted;

$R^{3a}$ and $R^{3b}$ are each independently H, halo, cyano, amino, $C_1$-$C_6$ alkyl, $C_2$-$C_6$ alkenyl, $C_2$-$C_6$ alkynyl, $C_1$-$C_6$ haloalkyl, $C_1$-$C_6$ hydroxylalkyl, $C_1$-$C_6$ alkoxyalkyl, $C_1$-$C_6$ heteroalkyl, $C_1$-$C_6$ cyanoalkyl, $C_1$-$C_6$ aminoalkyl, $C_1$-$C_6$ alkylsulfonyl, $C_1$-$C_6$ alkylsulfonylalkyl, cycloalkyl, cycloalkylalkyl, heterocyclyl, heterocyclylalkyl, aryl, heteroaryl, $C_1$-$C_6$ alkylcarbonyl, $C_1$-$C_6$ alkoxycarbonyl, aminocarbonyl, heterocyclylcarbonyl, or -$L^2$-$R^8$, wherein each is optionally substituted;

or $R^4$ and either $R^{3a}$ or $R^{3b}$ when attached to an adjacent carbon, together with the atoms bound thereto join to form a heterocyclyl or heteroaryl, wherein each heterocyclyl or heteroaryl is optionally substituted;

or $R^{3a}$ and $R^{3b}$ when attached to an adjacent carbon, together with the atoms bound thereto join to form a cycloalkyl, heterocyclyl, or heteroaryl, wherein each cycloalkyl, heterocyclyl, or heteroaryl is optionally substituted;

$R^4$ is H, $C_1$-$C_6$ alkyl, $C_2$-$C_6$alkenyl, $C_2$-$C_6$ alkynyl, $C_1$-$C_6$ haloalkyl, $C_1$-$C_6$ heteroalkyl, $C_1$-$C_6$ hydroxylalkyl, $C_1$-$C_6$ alkoxyalkyl, $C_1$-$C_6$ haloalkoxyalkyl, $C_1$-$C_6$ cyanoalkyl, $C_1$-$C_6$ aminoalkyl, $C_1$-$C_6$ alkylsulfonyl, $C_1$-$C_6$ alkylsulfonylalkyl, cycloalkyl, cycloalkylalkyl, heterocyclyl, heterocyclylalkyl, aryl, heteroaryl, heteroarylalkyl, $C_1$-$C_6$ alkylcarbonyl, $C_1$-$C_6$ alkoxycarbonyl, $C_1$-$C_6$ alkoxycarbonylalkyl, aminocarbonyl, heterocyclylcarbonyl, or -$L^1$-$R^7$, wherein each is optionally substituted;

$L^1$ is —S(O)$_p$—, —S(O)$_p$N($R^9$)—, —(CH$_2$)$_m$—, —C(O)—, —C(O)O—, or —C(O)N($R^9$)—;

each $L^2$ is independently —O—, —S(O)$_w$—, —(CH$_2$)$_m$—, —C(O)—, —C(O)O—, —OC(O)—, —C(O)N($R^9$)—, —N($R^9$)C(O)—, —N($R^9$)C(O)—, —OC(O)N($R^9$)—, —N($R^9$)C(O)N($R^9$)—, —S(O)$_p$N($R^9$)—, —N($R^9$)S(O)$_p$N($R^9$)—, or —N($R^9$)S(O)$_p$—;

$R^7$ is $C_1$-$C_6$ alkyl, $C_{2-6}$alkenyl, $C_{2-6}$alkynyl, $C_1$-$C_6$ alkoxy, $C_1$-$C_6$ heteroalkyl, cycloalkyl, cycloalkylalkyl, heterocyclyl, heterocyclylalkyl, aryl, arylalkyl, heteroaryl, or heteroarylalkyl, wherein each is optionally substituted;

each $R^8$ is independently $C_1$-$C_6$ alkyl, $C_2$-$C_6$ alkenyl, $C_2$-$C_6$ alkynyl, cycloalkyl, cycloalkylalkyl, heterocyclyl, heterocyclylalkyl, aryl, arylalkyl, heteroaryl, or heteroarylalkyl, wherein each is optionally substituted;

each $R^9$ is independently H, $C_1$-$C_6$ alkyl, $C_2$-$C_6$ alkenyl, $C_{2-6}$ alkynyl, cycloalkyl, cycloalkylalkyl, heterocyclyl, heterocyclylalkyl, aryl, arylalkyl, heteroaryl, or heteroarylalkyl;

each p is independently 1 or 2;

each w is independently 0, 1, or 2; and each m is independently 0, 1, 2, or 3;

provided that:

a) when $R^5$ is H, then Z is N, and $R^2$ is C-heterocyclyl, which is optionally substituted; and b) when $R^1$ and $R^5$ together with the atom to which they are attached form the 5-membered ring, then either:

i) $R^2$ is $C_1$-$C_6$ alkoxy, cycloalkyloxy, cycloalkylalkyloxy, heterocyclyloxy, heterocyclylalkyloxy, amino, $C_1$-$C_6$ alkylamino, cycloalkylamino, cycloalkylalkylamino, heterocyclylamino, or heterocyclylalkylamino; Z is N; $R^5$ is H; Y is N or C$R^6$; and $R^6$ is halo, $C_1$-$C_6$ haloalkyl or cycloalkyl; or ii) $R^2$ is $C_1$-$C_6$ alkyl, cycloalkyl or cycloalkylalkyl, wherein each is optionally substituted.

In one aspect, provided is a compound of formula (II):

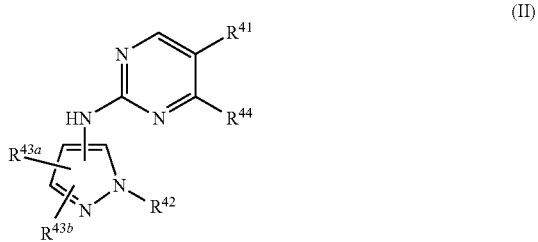

(II)

or a pharmaceutically acceptable salt, prodrug, stereoisomer, or a mixture of stereoisomers thereof, wherein:

$R^{41}$ is halo, cyano, $C_{1-6}$ alkyl, $C_{1-6}$ haloalkyl, $C_{1-6}$ alkoxy, $C_{1-6}$ haloalkoxy, cycloalkyl, cycloalkoxy, cycloalkylalkyl, cycloalkylalkoxy, or —C(O)$R^{45}$;

$R^{42}$ is:

a fused bicyclic ring system having a heterocyclyl or cycloalkyl fused to a heteroaryl, wherein the ring system is attached to the remainder of the molecule via the heterocyclyl or cycloalkyl and the ring system is independently optionally substituted with one or more halo, cyano, $C_{1-6}$ alkyl, $C_{1-6}$ haloalkyl, $C_{1-6}$ alkoxy, amino, $C_{1-6}$ hydroxyalkyl, $C_{1-6}$ alkoxyalkyl, $C_{1-6}$ cyanoalkyl, $C_{1-6}$ aminoalkyl, —S(O)$_2$($C_{1-6}$ alkyl), —$C_{1-6}$ alkylene-S(O)$_2$($C_{1-6}$ alkyl), —C(O)N$R^{46}R^{47}$, —N$R^{46}$C(O)$R^{47}$, —$C_{1-6}$ alkylene-C(O)N$R^{46}R^{47}$, —$C_{1-6}$ alkylene-N$R^{46}$C(O)$R^{47}$, —SO$_2$N$R^{46}R^{47}$, —N$R^{46}$SO$_2R^{47}$, —$C_{1-6}$ alkylene-SO$_2$N$R^{46}R^{47}$, —$C_{1-6}$ alkylene-N$R^{46}$SO$_2R^{47}$, —C(O)$R^{46}$, —OC(O)$R^{46}$, —C(O)$_2R^{46}$, —$C_{1-6}$ alkylene-C(O)$R^{46}$, —$C_{1-6}$ alkylene-OC(O)$R^{46}$, —$C_{1-6}$ alkylene-C(O)$_2R^{46}$, —O—C(O)N$R^{46}R^{47}$, —N$R^{46}$C(O)O$R^{47}$, —$C_{1-6}$ alkylene-O—C(O)N$R^{46}R^{47}$, —$C_{1-6}$ alkylene-N$R^{46}$C(O)O$R^{47}$, cycloalkyl, cycloalkylalkyl, heterocyclyl, heterocyclylalkyl, aryl, arylalkyl, heteroaryl, or heteroarylalkyl;

$C_{1-6}$ alkoxyalkyl substituted with one or more substituents independently selected from halo, amino, cyano, hydroxy, $C_{1-6}$ haloalkoxy, $C_{2-6}$alkenyl, $C_{2-6}$alkynyl, cyanoalkyl, —S(O)$_2$($C_{1-6}$ alkyl), —C(O)N$R^{46}R^{47}$, —N$R^{46}$C(O)$R^{47}$, —SO$_2$N$R^{46}R^{47}$, —N$R^{46}$SO$_2R^{47}$, —C(O)$R^{46}$, —OC(O)$R^{46}$, —C(O)$_2R^{46}$, —O—C(O)N$R^{46}R^{47}$, —N$R^{46}$C(O)O$R^{47}$, cycloalkyl, cycloalkylalkyl, heterocyclyl, heterocyclylalkyl, aryl, arylalkyl, heteroaryl, or heteroarylalkyl;

$C_{1-6}$ haloalkyl substituted with one or more substituents independently selected from amino, cyano, hydroxy, $C_{1-6}$ alkoxy-, $C_{1-6}$ haloalkoxy, $C_{2-6}$ alkenyl, $C_{2-6}$ alkynyl, cyanoalkyl, —S(O)$_2$($C_{1-6}$ alkyl), —C(O)N$R^{46}R^{47}$, —N$R^{46}$C(O)$R^{47}$, —SO$_2$N$R^{46}R^{47}$, —N$R^{46}$SO$_2R^{47}$, —C(O)$R^{46}$, —OC(O)$R^{46}$, —C(O)$_2R^{46}$, —O—C(O)N$R^{46}R^{47}$, —N$R^{46}$C(O)O$R^{47}$, cycloalkyl, cycloalkylalkyl, heterocyclyl, heterocyclylalkyl, aryl, arylalkyl, heteroaryl, or heteroarylalkyl;

$C_{1-6}$ cyanoalkyl optionally substituted with one or more substituents independently selected from halo, amino, hydroxy, $C_{1-6}$ haloalkoxy, $C_{2-6}$alkenyl, $C_{2-6}$ alkynyl, —S(O)$_2$($C_{1-6}$ alkyl), —C(O)N$R^{46}R^{47}$, —N$R^{46}$C(O)$R^{47}$, —SO$_2$N$R^{46}R^{47}$, —N$R^{46}$SO$_2R^{47}$, —C(O)$R^{46}$, —OC(O)$R^{46}$, —C(O)$R^{46}$, —O—C(O)N$R^{46}R^{47}$, —N$R^{46}$C(O)O$R^{4'}$, cycloalkyl, cycloalkylalkyl, heterocyclyl, heterocyclylalkyl, aryl, arylalkyl, heteroaryl, or heteroarylalkyl;

$C_{3-10}$ cycloalkyl substituted with one or more substituents independently selected from amino, $C_{2-6}$alkenyl, $C_{2-6}$alkynyl, cyanoalkyl, —S($C_{1-6}$ alkyl), —S(O)($C_{1-6}$ alkyl), —S(O)$_2$($C_{1-6}$ alkyl), —$C_{1-6}$ alkylene-S(O)$_2$ ($C_{1-6}$ alkyl), $C_{1-6}$ haloalkoxy, $C_{1-6}$ hydroxyalkyl, alkoxyalkyl substituted with one or more halo, cycloalkyl, cycloalkylalkyl, heterocyclyl, aryl, arylalkyl, heteroaryl, or heteroarylalkyl, wherein the heterocyclyl, heteroaryl, or heteroarylalkyl are optionally substituted with one or more substituents independently selected from $C_{1-6}$ alkyl, $C_{1-6}$ haloalkyl, or halo; or —X—C($R^{48}$)($R^{49}$)($R^{50}$), wherein:

X is $C_{1-6}$ alkylene optionally substituted with one or more halo;

R$^{48}$ and R$^{49}$, together with the carbon atom to which they are attached, form an optionally substituted C$_{3-10}$ cycloalkyl; and R$^{50}$ is cyanoalkyl, C$_{1-6}$ alkoxyalkyl, C$_{2-6}$alkenyl, C$_{2-6}$alkynyl, —S(O)$_2$(C$_{1-6}$ alkyl), C$_{1-6}$ haloalkoxy, C$_{1-6}$ hydroxyalkyl, C$_{1-6}$ alkoxyalkyl, cycloalkyl, cycloalkylalkyl, heterocyclyl, heterocyclylalkyl, aryl, arylalkyl, heteroaryl, or heteroarylalkyl;

R$^{43a}$ and R$^{43b}$ are each independently H, halo, cyano, C$_{1-6}$ alkyl, C$_{1-6}$ haloalkyl, C$_{1-6}$ hydroxyalkyl, C$_{1-6}$ alkoxyalkyl, C$_{1-6}$ cyanoalkyl, C$_{1-6}$, aminoalkyl, —S(O)$_2$(C$_{1-6}$ alkyl), —C$_{1-6}$ alkylene-S(O)$_2$(C$_{1-6}$ alkyl), cycloalkyl, cycloalkylalkyl, heterocyclyl, heterocyclylalkyl, aryl, arylalkyl, heteroaryl, heteroarylalkyl, amido, or —C(O)R$^{45}$;

R$^{44}$ is cycloalkyl, C-heterocyclyl, —N(R$^{51}$)$_2$, —OR$^{51}$, or —SR$^{51}$;

each R$^{45}$ is independently C$_{1-6}$ alkyl, C$_{1-6}$ alkoxy, —N(R$^{52}$)$_2$, or heterocyclyl, wherein each C$_{1-6}$ alkyl, C$_{1-6}$ alkoxy-, or heterocyclyl is optionally substituted;

each R$^{46}$ and R$^{47}$ is independently H, C$_{1-6}$ alkyl, C$_{2-6}$ alkenyl, C$_{2-6}$alkynyl, cycloalkyl, heterocyclyl, aryl, heteroalkyl, or heteroaryl, wherein each C$_{1-6}$ alkyl, C$_{2-6}$ alkenyl, C$_{2-6}$ alkynyl, cycloalkyl, heterocyclyl, aryl, heteroalkyl, or heteroaryl is optionally substituted;

each R$^{51}$ is independently H, C$_{1-6}$alkyl, C$_{2-6}$alkenyl, C$_{2-6}$alkynyl, C$_{1-6}$haloalkyl, C$_{1-6}$ alkoxyalkyl, C$_{1-6}$ hydroxyalkyl, C$_{1-6}$ aminoalkyl, —C$_{1-6}$ alkylene-S(O)$_2$(C$_{1-6}$ alkyl), C$_{1-6}$ cycloalkyl optionally substituted with one or more alkyl, C$_{3-6}$ cycloalkylalkyl optionally substituted with one or more C$_{1-6}$ alkyl, heterocyclyl optionally substituted with one or more R$^{53}$, or heterocyclylalkyl optionally substituted with one or more R$^{53}$; or two R$^{51}$, together with the nitrogen to which they are attached, form a three- to six-membered heterocyclyl optionally substituted with one or more R$^{53}$;

each R$^{52}$ is independently H or optionally substituted C$_{1-6}$ alkyl;

each R$^{53}$ is independently C$_{1-6}$ alkyl, C$_{1-6}$ haloalkyl, halo, oxo, alkoxy, amino, —S(O)$_2$(C$_{1-6}$ alkyl), C$_{1-6}$ alkoxyalkyl, cyano, heterocyclyl, heterocyclylalkyl, C$_{3-6}$cycloalkyl, C$_{3-6}$cycloalkylalkyl, C$_{3-6}$ cycloalkylsulfonyl, —C(O)R$^{54}$, or —C$_{1-6}$alkylene-C(O)R$^{54}$;

each R$^{54}$ is independently C$_{1-6}$ alkyl, C$_{1-6}$ alkoxy, amino optionally substituted with halo, C$_{1-6}$ haloalkyl, C$_{1-6}$hydroxyalkyl, hydroxy, C$_{1-6}$ alkoxyalkyl, cyanoalkyl, —C$_{1-6}$ alkylene-S(O)$_2$(C$_{1-6}$ alkyl), C$_{1-6}$ aminoalkyl, C$_{3-6}$ cycloalkyl, C$_{3-6}$ cycloalkylalkyl, heterocyclyl, or heterocyclylalkyl; and provided that when R$^{44}$ is cycloalkyl, —N(R$^{51}$)$_2$, or —OR$^{51}$, then R$^{42}$ is not an unsubstituted C$_{1-6}$ cyanoalkyl.

In another embodiment, a pharmaceutical composition is provided comprising a compound as described herein (e.g., a compound of Formula I, II, A-I, B-I, C-I, or D-I, or any subformula thereof), or a stereoisomer, mixture of stereoisomers, pharmaceutically acceptable salt, tautomer, or prodrug thereof, and a pharmaceutically acceptable carrier, diluent or excipient.

In another embodiment, a method for treating a disease or condition mediated, at least in part, by LRRK2, in a subject in need thereof is provided, the method comprising administering to the subject an effective amount of the pharmaceutical composition comprising a compound as described herein (e.g., a compound of Formula I, II, A-I, B-I, C-I, or D-I, or any subformula thereof), or a stereoisomer, mixture of stereoisomers, pharmaceutically acceptable salt, tautomer, or prodrug thereof, and a pharmaceutically acceptable carrier, diluent, or excipient.

In some embodiments, the method is for treatment of a neurodegenerative disease, a cancer, an inflammatory disease. In some embodiments, the method is for enhancing cognitive memory.

In another embodiment, a compound of Formula I, II, A-I, B-I, C-I, or D-I, or any subformula thereof, is provided for use in therapy. In some embodiments, the compound is provided for use in the treatment of a neurodegenerative disease, cancer, or an inflammatory disease.

In another embodiment, provided is a method for preparing a compound of formula (I), comprising coupling a compound of formula (b);

(b)

wherein X is halogen, with a compound of formula (c):

(c)

under conditions to provide the compound of formula (I), wherein R$^1$, R$^2$, R$^{3a}$, R$^{3b}$, R$^4$, R$^5$, and Z are as defined herein.

In another embodiment, provided is a method for preparing a compound of formula (II), comprising coupling a compound of formula (II-a):

(II-a)

wherein X is a leaving group (e.g., halo), with a compound of formula (II-b):

(II-b)

under conditions to provide the compound of formula (II), wherein R$^{41}$, R$^{42}$, R$^{43a}$, R$^{43b}$, and R$^{44}$ are as defined herein.

These and other aspects of the disclosure will be apparent upon reference to the following detailed description.

DETAILED DESCRIPTION

In the following description, certain specific details are set forth in order to provide a thorough understanding of various embodiments of the disclosure. However, one skilled in the art will understand that the invention may be practiced without these details.

1. Definitions

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this disclosure belongs.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through a line in a structure indicates a specified point of attachment of a group. Unless chemically or structurally required, no directionality or stereochemistry is indicated or implied by the order in which a chemical group is written or named.

The prefix "Cu-v" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "die compound" includes a plurality of such compounds and reference to "the assay" includes reference to one or more assays and equivalents thereof known to those skilled in the art.

"Amino" refers to a NH$_2$ group or the group —NR$^y$R$^z$ wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Alkyl" refers to a straight or branched hydrocarbon chain group consisting solely of carbon and hydrogen atoms, which is saturated or unsaturated (i.e., contains one or more double bonds (known as "alkenyl") and/or triple bonds (known as "alkynyl")), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, w-butenylene, propynylene, n-butynylene, and the like. The alkylene chain is attached to the rest of the molecule through a single or double bond and to the group through a single or double bond. The points of attachment of the alkylene chain to the rest of the molecule and to the group can be through one carbon or any two carbons within the chain. Unless stated otherwise specifically in the specification, an alkylene chain may be optionally substituted.

"Alkylcarbonyl" refers to a group of the formula —(C=O)R$_a$ where R$_a$ is an alkyl group as defined above containing one to twelve carbon atoms. Unless stated otherwise specifically in the specification, an alkylcarbonyl group is optionally substituted.

"Alkoxy" refers to a group of the formula —OR$^a$ where R$^a$ is an alkyl group as defined above containing one to twelve carbon atoms. A "haloalkoxy" is an alkoxy group as defined above, wherein at least one carbon-hydrogen bond is replaced with a carbon-halogen bond. Unless stated otherwise specifically in tire specification, an alkoxy or haloalkoxy group may be optionally substituted.

"Alkoxyalkyl" refers to a group of the formula —R$^b$OR$^a$ where R$^a$ is an alkyl group as defined above containing one to twelve carbon atoms and R$_b$ is an alkylene group as defined above. A "haloalkoxyalkyl" group is an alkoxyalkyl, wherein at least one carbon-hydrogen bond is replaced with a carbon-halogen bond. Unless stated otherwise specifically in the specification, an alkoxyalkyl or haloalkoxyalkyl group may be optionally substituted.

"Alkoxycarbonyl" refers to a group of the formula —(C=O)OR$^a$ where R$^a$ is an alkyl group as defined above containing one to twelve carbon atoms. Unless stated otherwise specifically in the specification, an alkoxycarbonyl group is optionally substituted.

"Alkoxycarbonylalkyl" refers to a group of the formula —R$^b$(C=O)OR$^a$ where R$^a$ is an alkyl group as defined above and R$^b$ is an alkylene as defined above. Unless otherwise specifically in the specification, an alkoxycarbonylalkyl group is optionally substituted.

"Alkylthio" refers to the group "alkyl-S—".

"Aminocarbonyl" refers to a group of the formula —(C=O)N(R$^a$)$_2$, where each R$^a$ is independently H or an alkyl group as defined above. Unless stated otherwise specifically in die specification, an aminocarbonyl group is optionally substituted.

"Aminoalkyl" refers to the group "-alkyl-NR$^y$R$^z$," wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Alkylsulfonyl" refers to a group of the formula —S(O)$_2$R$^a$ where R$^a$ is an alkyl group as defined above. Unless stated otherwise specifically in the specification, an alkylsulfonyl group may be optionally-substituted.

"Alkylsulfonylalkyl" refers to a group of the formula —$R^bS(O)_2R^a$ where $R^a$ is an alkyl group as defined above and $R_b$ is an alkylene group as defined above. Unless stated otherwise specifically in the specification, an alkylsulfonylalkyl group may be optionally substituted.

"Acyl" refers to a group —$C(O)R^y$, wherein $R^y$ is hydrogen, alkyl, alkenyl, alkynyl, cycloalkyl, heterocyclyl, aryl, heteroalkyl, or heteroaryl; each of which may be optionally substituted, as defined herein. Examples of acyl include formyl, acetyl, cyclohexylcarbonyl, cyclohexylmethyl-carbonyl and benzoyl.

"Amido" refers to both a "C-amido" group which refers to the group —$C(O)NR^yR^z$ and an "N-amido" group which refers to the group —$NR^yC(O)R^z$, wherein $R^y$ and $R^z$ are independently hydrogen, alkyl, alkenyl, alkynyl, cycloalkyl, heterocyclyl, aryl, heteroalkyl, or heteroaryl; each of which may be optionally substituted, as defined herein, or $R^y$ and $R^z$ are taken together to form a cycloalkyl or heterocyclyl; each of which may be optionally substituted, as defined herein.

"Amidino" refers to —$C(NR^y)(NR^z_2)$, wherein $R^y$ and $R^z$ are independently hydrogen, alkyl, alkenyl, alkynyl, cycloalkyl, heterocyclyl, aryl, heteroalkyl, or heteroaryl; each of which may be optionally substituted, as defined herein.

"Aryl" refers to a hydrocarbon ring system group comprising hydrogen, 6 to 18 carbon atoms and at least one aromatic ring. For purposes of this disclosure, the aryl group may be a monocyclic, bicyclic, tricyclic or tetracyclic ring system, which may include fused or bridged ring systems. Aryl groups include, but are not limited to, aryl groups derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl groups that are optionally substituted. "Arylalkyl" or "Aralkyl" refers to the group "aryl-alkyl-".

"Carboxyl ester" or "ester" refer to both —$OC(O)R^x$ and —$C(O)OR^x$ wherein $R^x$ is alkyl, alkenyl, alkynyl, cycloalkyl, heterocyclyl, aryl, heteroalkyl, or heteroaryl; each of which may be optionally-substituted, as defined herein.

"Cyanoalkyl" is an alkyl group as defined above, wherein at least one carbon-hydrogen bond is replaced with a carbon-cyano bond. Unless stated otherwise specifically in the specification, cyanoalkyl group may be optionally substituted.

"Cycloalkyl" or "carbocyclic ring" refers to a stable non-aromatic monocyclic or polycyclic hydrocarbon group consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic groups include, for example, cyclopropyl, cyclobutyl, cyclopentyl, cyclohexyl, cycloheptyl, and cyclooctyl. Polycyclic groups include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkyloxy" is a cycloalkyl group connected to the remainder of die molecule via an oxygen atom linker. Unless otherwise stated specifically in the specification, a cycloalkyloxy group may be optionally substituted.

"Cycloalkylalkyl" refers to a group of the formula —$R_bR_d$ where $R_b$ is an alkylene chain as defined above and $R_d$ is a cycloalkyl group as defined above. Unless stated otherwise specifically in the specification, a cycloalkylalkyl group may be optionally substituted.

"Cycloalkylalkyloxy" refers to a group of the formula —$OR_bR_d$ where $R_b$ is an alkylene chain as defined above and $R_d$ is a cycloalkyl group as defined above. Unless stated otherwise specifically in the specification, a cycloalkylalkyloxy group may be optionally substituted.

"Fused" refers to any ring structure described herein which is fused to an existing ring structure in the compounds of the disclosure. When the fused ring is a heterocyclyl ring or a heteroaryl ring, any carbon atom on the existing ring structure which becomes part of the fused heterocyclyl ring or die fused heteroaryl ring may be replaced with a nitrogen atom.

"Halo" or "halogen" refers to bromo, chloro, fluoro or iodo.

"Haloalkyl" refers to an alkyl group, as defined above, that is substituted by one or more halo groups, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heteroalkyl" refers to an alkyl group in which one or more of the carbon atoms (and any associated hydrogen atoms) are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2, or 3 carbon atoms may be independently replaced with the same or different heteroatomic group. Heteroatomic groups include, but are not limited to, —$NR^y$—, —O—, —S—, —$S(O)$—, —$S(O)_2$—, and die like, wherein $R^y$ is hydrogen, alkyl, alkenyl, alkynyl, cycloalkyl, heterocyclyl, aryl, heteroalkyl, or heteroaryl; each of which may be optionally substituted, as defined herein. Examples of heteroalkyl groups include ethers (e.g., —$CH_2OCH_3$, —$CH(CH_3)OCH_3$, —$CH_2CH_2OCH_3$, —$CH_2CH_2OCH_2CH_2OCH_3$, etc.), thioethers (e.g., —$CH_2SCH_3$, —$CH(CH_3)SCH_3$, —$CH_2CH_2SCH_3$, —$CH_2CH_2SCH_2CH_2SCH_3$, etc.), sulfones (e.g., —$CH_2S(O)_2CH_3$, —$CH(CH_3)S(O)_2CH_3$, —$CH_2CH_2S(O)_2CH_3$, —$CH_2CH_2S(O)_2CH_2CH_2OCH_3$, etc.), and amines (e.g., —$CH_2NR^yCH_3$, —$CH(CH_3)NR^yCH_3$, —$CH_2CH_2NR^yCH_3$, —$CH_2CH_2NR^yCH_2CH_2NR^yCH_3$, etc., where $R^y$ is hydrogen, alkyl, alkenyl, alkynyl, cycloalkyl, heterocyclyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Hydroxylalkyl" refers an alkyl group as defined above containing one to twelve carbon atoms which has been substituted by one or more hydroxyl groups. Unless stated otherwise specifically in the specification, hydroxylalkyl group may be optionally substituted.

"Heterocyclyl" or "heterocyclic ring" refers to a stable 3- to 18-membered non-aromatic ring group which consists of two to twelve carbon atoms and from one to six heteroatoms selected from the group consisting of nitrogen, oxygen and sulfur. Unless stated otherwise specifically in die specification, the heterocyclyl group may be a monocyclic, bicyclic, tricyclic or tetracyclic ring system, which may include fused or bridged ring systems; and the nitrogen, carbon or sulfur atoms in die heterocyclyl group may be optionally oxidized; the nitrogen atom may be optionally quaternized; and the heterocyclyl group may be partially or fully saturated. Examples of such heterocyclyl groups include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification. Unless stated otherwise specifically in the specification, a heterocyclyl group may be optionally substituted.

"C-heterocyclyl" refers to a heterocyclyl group as defined above where the point of attachment of the heterocyclyl group to the rest of the molecule is through a carbon atom in the heterocyclyl group. Unless stated otherwise specifically in the specification, a C-heterocyclyl group may be optionally-substituted.

"Heterocyclylcarbonyl" refers to a group of the formula —C(=O)$R_e$ where $R_e$ is a heterocyclyl group as defined above. Unless stated otherwise specifically in the specification, a heterocyclocarbonyl group may be optionally substituted.

"Heterocyclylalkyl" refers to a group of the formula —$R_b R_e$ where $R_b$ is an alkylene chain as defined above and $R_e$ is a heterocyclyl group as defined above. Unless stated otherwise specifically in the specification, a heterocyclylalkyl group may be optionally substituted.

"Heteroaryl" refers to a 5- to 14-membered ring system group comprising hydrogen atoms, one to thirteen carbon atoms, one to six heteroatoms selected from the group consisting of nitrogen, oxygen and sulfur, and at least one aromatic ring. For purposes of this disclosure, the heteroaryl group may be a monocyclic, bicyclic, tricyclic or tetracyclic ring system, which may include fused or bridged ring systems; and the nitrogen, carbon or sulfur atoms in the heteroaryl group may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"Heteroarylalkyl" refers to a group of die formula —$R_b R_e$ where $R_b$ is an alkylene chain as defined above and $R_e$ is a heteroaryl group as defined above. Unless stated otherwise specifically in the specification, a heteroarylalkyl group may be optionally substituted.

"Imino" refers=NH substituent or to a group —C(N$R^y$)$R^z$, wherein $R^y$ and $R^z$ are ach independently hydrogen, alkyl, alkenyl, alkynyl, cycloalkyl, heterocyclyl, aryl, heteroalkyl, or heteroaryl; each of which may be optionally substituted, as defined herein. "Imido" refers to a group —C(O)N$R^y$C(O)$R^z$, wherein $R^y$ and $R^z$ are each independently hydrogen, alkyl, alkenyl, alkynyl, cycloalkyl, heterocyclyl, aryl, heteroalkyl, or heteroaryl; each of which may be optionally substituted, as defined herein.

"Oxime" refers to the group —C$R^y$(=NOH) wherein $R^y$ is hydrogen, alkyl, alkenyl, alkynyl, cycloalkyl, heterocyclyl, aryl, heteroalkyl, or heteroaryl; each of which may be optionally substituted, as defined herein.

"Sulfonyl" refers to the group —S(O)$_2 R^y$, where $R^y$ is hydrogen, alkyl, alkenyl, alkynyl, cycloalkyl, heterocyclyl, aryl, heteroalkyl, or heteroaryl; each of which may be optionally substituted, as defined herein. Examples of sulfonyl are methylsulfonyl, ethylsulfonyl, phenylsulfonyl and toluenesulfonyl.

The term "substituted" used herein means any of the above groups (e.g., alkyl, alkylene, alkylcarbonyl, alkoxy, alkoxyalkyl, haloalkoxyalkyl, alkoxycarbonyl, alkoxycarbonylalkyl, aminylcarbonyl, aminylalkyl, alkylsulfonyl, alkylsulfonylalkyl, cyanoalkyl, hydroxylalkyl, aryl, aralkyl, cycloalkyl, cycloalkylalkyl, cycloalkyloxy, cycloalkylalkyloxy, haloalkyl, heterocyclyl, C-heterocyclyl, heterocyclylcarbonyl, heterocyclylalkyl, heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups.

"Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —N$R_g R_h$, —N$R_g$C(=O)$R_h$, —N$R_g$C(=O)N$R_g R_h$, —N$R_g$C(=O)O$R_h$, —N$R_g$SO$_2 R_h$, —OC(=O)N$R_g R_h$, —O$R_g$, —S$R_g$, —SO$R_g$, —SO$_2 R_g$, —OSO$_2 R_g$, —SO$_2$O$R_g$, =NSO$_2 R_g$, and —SO$_2$N$R_g R_h$. Substituted also means any of the above groups in which one or more hydrogen atoms are replaced with —C(=O)$R_g$, —C(=O)O$R_g$, —C(=O)N$R_g R_h$, —CH$_2$SO$_2 R_g$, —CH$_2$SO$_2$N$R_g R_h$. In the foregoing, $R_g$ and $R_h$ are the same or different and independently hydrogen, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, alkylaminyl, cyano, hydroxyl, imino, nitro, oxo, thioxo, halo, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of die group are themselves unsubstituted. For example, in some embodiments, the term "substituted alkyl" refers to an alkyl group having one or more substituents including hydroxy, halo, alkoxy, acyl, oxo, amino, cycloalkyl, heterocyclyl, aryl and heteroaryl. In other embodiments, the one or mote substituents may be further substituted with halo, alkyl, haloalkyl, hydroxy, alkoxy, cycloalkyl, heterocyclyl, aryl, or heteroaryl, each of which is substituted. In other embodiments, die substituents may be further substituted with halo, alkyl, haloalkyl, alkoxy, hydroxy, cycloalkyl, heterocyclyl, aryl, or heteroaryl, each of which is unsubstituted.

"Prodrug" is meant to indicate a compound that may be converted under physiological conditions or by solvolysis to a biologically active compound of die disclosure. Thus, the term "prodrug" refers to a metabolic precursor of a compound of the disclosure that is pharmaceutically acceptable. A prodrug may be inactive when administered to a subject in need thereof, but is converted in vivo to an active compound of die disclosure. Prodrugs are typically rapidly transformed in vivo to yield the parent compound of the disclosure, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the disclosure in vivo when such prodrug is administered to a mammalian subject. Prodrugs of a compound of the disclosure may be prepared by modifying functional groups present in the compound of the disclosure in such a way that the modifications are cleaved, either in routine manipulation or in vivo, to the parent compound of the disclosure. Prodrugs include compounds of the disclosure wherein a hydroxy, amino or mercapto group is bonded to any group that, when the prodrug of the compound of the disclosure is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the disclosure and the like.

This disclosure is also meant to encompass all pharmaceutically acceptable compounds of formula (I) being isotopically-labelled by having one or more atoms replaced by an atom having a different atomic mass or mass number. Examples of isotopes that can be incorporated into die disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^{3}H$, carbon-13, i.e. $^{13}C$ and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

This disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the disclosure includes compounds produced by a process comprising administering a compound of this disclosure to a mammal for a period of time sufficient to yield a metabolic product thereof. Such products are typically identified by administering a radiolabelled compound of the disclosure in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances may or may not occur, and that the description includes instances where said event or circumstance occurs and instances in which it does not. For example, "optionally substituted aryl" means that the aryl group may or may not be substituted and that the description includes both substituted aryl groups and aryl groups having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent suspending agent stabilizer, isotonic agent, solvent or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are die ammonium, sodium, potassium, calcium, and magnesium salts. Salts derived from organic bases include, but are not limited to, salts of primary, secondary, and tertiary amines, such as alkyl amines (i.e., NH$_2$(alkyl)), dialkyl amines (i.e., HN(alkyl)$_2$), trialkyl amines (i.e., N (alkyl)$_3$), substituted alkyl amines (i.e., NH$_2$(substituted alkyl)), disubstituted alkyl) amines (i.e., HN(substituted alkyl)$_2$), trisubstituted alkyl) amines (i.e., N(substituted alkyl)$_3$), alkenyl amines (i.e., NH$_2$(alkenyl)), dialkenyl amines (i.e., HN(alkenyl)$_2$), trialkenyl amines (i.e., N(alkenyl)$_3$), substituted alkenyl amines (i.e., NH$_2$(substituted alkenyl)), di(substituted alkenyl) amines (i.e., HN(substituted alkenyl)$_2$), trisubstituted alkenyl) amines (i.e., N(substituted alkenyl)$_3$, mono-, di- or tri-cycloalkyl amines (i.e., NH$_2$(cycloalkyl), HN(cycloalkyl)$_2$, N(cycloalkyl)$_3$), mono-, di- or tri-arylamines (i.e., NH$_2$(aryl), HN(aryl)$_2$, N(aryl)$_3$) or mixed amines, etc., substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the disclosure. As used herein, the term "solvate" refers to an aggregate that comprises one or more molecules of a compound of die disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compound of the disclosure may be true solvates, while in other cases, the compound of the disclosure may merely retain adventitious water or be a mixture of water plus some adventitious solvent.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

The compounds of this disclosure, or their pharmaceutically acceptable salts or tautomers may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule, for example, the conversion of a ketone to an enol via a proton shift. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers. The present disclosure includes tautomers of any said compounds.

2. Compounds

In one embodiment, provided is a compound of formula (I):

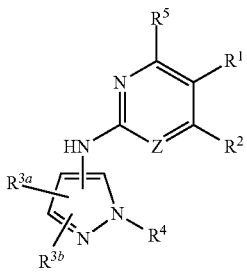
(I)

or a pharmaceutically acceptable salt, stereoisomer, or a mixture of stereoisomers, tautomer or prodrug thereof, wherein:

Z is N or CH;

$R^1$ is halo, cyano, $C_1$-$C_6$ alkyl, $C_1$-$C_6$ haloalkyl, $C_1$-$C_6$ alkoxy, $C_1$-$C_6$ haloalkoxy, cycloalkyl, cycloalkyloxy, cycloalkylalkyl, cycloalkylalkyloxy, $C_1$-$C_6$ alkylcarbonyl, $C_1$-$C_6$ alkyloxycarbonyl, aminocarbonyl, or heterocyclylcarbonyl, wherein each is optionally substituted; and $R^5$ is H; or $R^1$ and $R^5$ together with the atom to which they are attached form a 5-membered ring having the structure:

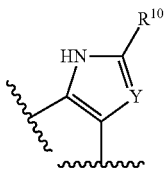

Y is N or $CR^6$;

$R^6$ is H, halo, cyano, $C_1$-$C_6$ alkyl, $C_{2-6}$ alkenyl, $C_{2-6}$ alkynyl, $C_1$-$C_6$ alkoxy, $C_1$-$C_6$ heteroalkyl, $C_1$-$C_6$ haloalkyl, $C_1$-$C_6$ alkoxyalkyl, —S(O)$_w$($C_1$-$C_6$ alkyl), cycloalkyl, heterocyclyl, heteroaryl, aryl, acyl, or amido, wherein each is optionally substituted;

$R^{10}$ is H, halo, cyano, $C_1$-$C_6$ alkyl, $C_1$-$C_6$ haloalkyl, or cycloalkyl;

$R^2$ is $C_1$-$C_6$ alkyl, cycloalkyl, cycloalkylalkyl, $C_1$-$C_6$ alkoxy, cycloalkyloxy, cycloalkylalkyloxy, heterocyclyloxy, heterocyclylalkyloxy, amino, $C_1$-$C_6$ alkylamino, cycloalkylamino, cycloalkylalkylamino, heterocyclylamino, or heterocyclylalkylamino, wherein each is optionally substituted;

$R^{3a}$ and $R^{3b}$ are each independently H, halo, cyano, amino, $C_1$-$C_6$ alkyl, $C_2$-$C_6$ alkenyl, $C_1$-$C_6$ alkynyl, $C_1$-$C_6$ haloalkyl, $C_1$-$C_6$ hydroxylalkyl, $C_1$-$C_6$ alkoxyalkyl, $C_1$-$C_6$ heteroalkyl, $C_1$-$C_6$ cyanoalkyl, $C_1$-$C_6$ aminoalkyl, $C_1$-$C_6$ alkylsulfonyl, $C_1$-$C_6$ alkylsulfonylalkyl, cycloalkyl, cycloalkylalkyl, heterocyclyl, heterocyclylalkyl, aryl, heteroaryl, $C_1$-$C_6$ alkylcarbonyl, $C_1$-$C_6$ alkoxycarbonyl, aminocarbonyl, heterocyclylcarbonyl, or -$L^2$-$R^8$, wherein each is optionally substituted;

or $R^4$ and either $R^{3a}$ or $R^{3b}$ when attached to an adjacent carbon, together with the atoms bound thereto join to form a heterocyclyl or heteroaryl, wherein each heterocyclyl or heteroaryl is optionally substituted;

or $R^{3a}$ and $R^{3b}$ when attached to an adjacent carbon, together with the atoms bound thereto join to form a cycloalkyl, heterocyclyl, or heteroaryl, wherein each cycloalkyl, heterocyclyl, or heteroaryl is optionally substituted;

$R^4$ is H, $C_1$-$C_6$ alkyl, $C_2$-$C_6$ alkenyl, $C_2$-$C_6$ alkynyl, $C_1$-$C_6$ haloalkyl, $C_1$-$C_6$ heteroalkyl, $C_1$-$C_6$ hydroxylalkyl, $C_1$-$C_6$ alkoxyalkyl, $C_1$-$C_6$ haloalkoxyalkyl, $C_1$-$C_6$ cyanoalkyl, $C_1$-$C_6$ aminoalkyl, $C_1$-$C_6$ alkylsulfonyl, $C_1$-$C_6$ alkylsulfonylalkyl, cycloalkyl, cycloalkylalkyl, heterocyclyl, heterocyclylalkyl, aryl, heteroaryl, heteroarylalkyl, $C_1$-$C_6$ alkylcarbonyl, $C_1$-$C_6$ alkoxycarbonyl, $C_1$-$C_6$ alkoxycarbonylalkyl, aminocarbonyl, heterocyclylcarbonyl, or -$L^1$-$R^7$, wherein each is optionally substituted;

$L^1$ is —S(O)$_p$—, —S(O)$_p$N($R^9$)—, —(CH$_2$)$_m$—, —C(O)—, —C(O)O—, or —C(O)N($R^9$)—;

each $L^2$ is independently —O—, —S(O)$_w$—, —(CH$_2$)$_m$—, —C(O)—, —C(O)O—, —OC(O)—, —C(O)N($R^9$)—, —N($R^9$)C(O)—, —N($R^9$)C(O)—, —OC(O)N($R^9$)—, —N($R^9$)C(O)N($R^9$)—, —S(O)$_p$N($R^9$)—, —N($R^9$)S(O)$_p$N($R^9$)—, or —N($R^9$)S(O)$_p$—;

$R^7$ is $C_1$-$C_6$ alkyl, $C_{2-6}$ alkenyl, $C_{2-6}$ alkynyl, $C_1$-$C_6$ alkoxy, $C_1$-$C_6$ heteroalkyl, cycloalkyl, cycloalkylalkyl, heterocyclyl, heterocyclylalkyl, aryl, arylalkyl, heteroaryl, or heteroarylalkyl, wherein each is optionally substituted;

each $R^8$ is independently $C_1$-$C_6$ alkyl, $C_2$-$C_6$ alkenyl, $C_2$-$C_6$ alkynyl, cycloalkyl, cycloalkylalkyl, heterocyclyl, heterocyclylalkyl, aryl, arylalkyl, heteroaryl, or heteroarylalkyl, wherein each is optionally substituted;

each $R^9$ is independently H, $C_1$-$C_6$ alkyl, $C_2$-$C_6$ alkenyl, $C_{2-6}$ alkynyl, cycloalkyl, cycloalkylalkyl, heterocyclyl, heterocyclylalkyl, aryl, arylalkyl, heteroaryl, or heteroarylalkyl;

each p is independently 1 or 2;
each w is independently 0, 1 or 2; and
each m is independently 0, 1, 2 or 3;
provided that:

a) when $R^5$ is H, then Z is N, and $R^2$ is C-heterocyclyl, which is optionally substituted; and b) when $R^1$ and $R^5$ together with die atom to which they are attached form the 5-membered ring, then either:

i) $R^2$ is $C_1$-$C_6$ alkoxy, cycloalkyloxy, cycloalkylalkyloxy, heterocyclyloxy, heterocyclylalkyloxy, amino, $C_1$-$C_6$ alkylamino, cycloalkylamino, cycloalkylalkylamino, heterocyclylamino, or heterocyclylalkylamino; Z is N; $R^5$ is H; Y is N or $CR^6$; and $R^6$ is halo, $C_1$-$C_6$ haloalkyl or cycloalkyl; or ii) $R^2$ is $C_1$-$C_6$ alkyl, cycloalkyl or cycloalkylalkyl, wherein each is optionally substituted.

In one embodiment, provided is a compound of formula (II):

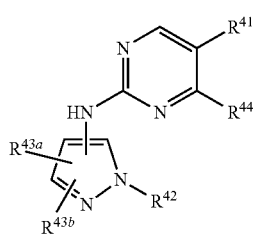
(II)

or a pharmaceutically acceptable salt, prodrug, stereoisomer, or a mixture of stereoisomers thereof, wherein:

$R^{41}$ is halo, cyano, $C_{1-6}$ alkyl, $C_{1-6}$ haloalkyl, $C_{1-6}$ alkoxy, $C_{1-6}$ haloalkoxy, cycloalkyl, cycloalkoxy, cycloalkylalkyl, cycloalkylalkoxy, or —C(O)$R^{45}$;

$R^{42}$ is:
a fused bicyclic ring system having a heterocyclyl or cycloalkyl fused to a heteroaryl, wherein the ring system is attached to die remainder of the molecule via the heterocyclyl or cycloalkyl and the ring system is independently optionally substituted with one or more halo, cyano, $C_{1-6}$ alkyl, $C_{1-6}$ haloalkyl, $C_{1-6}$ alkoxy, amino, $C_{1-6}$ hydroxyalkyl, $C_{1-6}$ alkoxyalkyl, $C_{1-6}$ cyanoalkyl, $C_{1-6}$ aminoalkyl, —S(O)$_2$($C_{1-6}$ alkyl), —$C_{1-6}$ alkylene-S(O)$_2$($C_{1-4}$ alkyl), —C(O)N$R^{46}R^{47}$, —N$R^{46}$C(O)$R^{47}$, —$C_{1-4}$ alkylene-C(O)N$R^{46}R^{47}$, —$C_{1-6}$ alkylene-N$R^{46}$C(O)$R^{47}$, —SO$_2$N$R^{46}R^{47}$, —N$R^{46}$SO$_2R^{47}$, —$C_{1-6}$ alkylene-SO$_2$N$R^{46}R^{47}$, —$C_{1-6}$ alkylene-N$R^{46}$SO$_2R^{47}$, —C(O)$R^{46}$, —OC(O)$R^{46}$, —C(O)$_2R^{46}$, —$C_{1-6}$ alkylene-C(O)$R^{46}$, —$C_{1-6}$ alkylene-OC(O)$R^{46}$, —$C_{1-6}$ alkylene-C(O)$_2R^{46}$, —O—C(O)N$R^{46}R^{47}$, —N$R^{46}$C(O)O$R^{47}$, —$C_{1-6}$ alkylene-O—C(O)N$R^{46}R^{47}$, —$C_{1-6}$ alkylene-N$R^{46}$C(O)O$R^{47}$, cycloalkyl, cycloalkylalkyl, heterocyclyl, heterocyclylalkyl, aryl, arylalkyl, heteroaryl, or heteroarylalkyl;

$C_{1-6}$ alkoxyalkyl substituted with one or more substituents independently selected from halo, amino, cyano, hydroxy, $C_{1-6}$ haloalkoxy, $C_{2-6}$alkenyl, $C_{2-6}$alkynyl, cyanoalkyl, —S(O)$_2$($C_{1-6}$ alkyl), —C(O)N$R^{46}R^{47}$, —N$R^{46}$C(O)$R^{47}$, —SO$_2$N$R^{46}R^{47}$, —N$R^{46}$SO$_2R^{47}$, —C(O)$R^{46}$, —OC(O)$R^{46}$, —C(O)$_2R^{46}$, —O—C(O)N$R^{46}R^{47}$, —N$R^{46}$C(O)$R^{47}$, cycloalkyl, cycloalkylalkyl, heterocyclyl, heterocyclylalkyl, aryl, arylalkyl, heteroaryl, or heteroarylalkyl;

$C_{1-6}$ haloalkyl substituted with one or more substituents independently selected from amino, cyano, hydroxy, $C_{1-6}$ alkoxy, $C_{1-6}$ haloalkoxy, $C_{2-6}$ alkenyl, $C_{2-6}$ alkynyl, cyanoalkyl, —S(O)$_2$($C_{1-6}$ alkyl), —C(O)N$R^{46}R^{47}$, —N$R^{46}$C(O)$R^{47}$, —SO$_2$N$R^{46}R^{47}$, —N$R^{46}$SO$_2R^{47}$, —C(O)$R^{46}$, —OC(O)$R^{46}$, —C(O)$_2R^{46}$, —O—C(O)N$R^{46}R^{47}$, —N$R^{46}$C(O)O$R^{47}$, cycloalkyl, cycloalkylalkyl, heterocyclyl, heterocyclylalkyl, aryl, arylalkyl, heteroaryl, or heteroarylalkyl;

$C_{1-6}$ cyanoalkyl optionally substituted with one or more substituents independently-selected from halo, amino, hydroxy, $C_{1-6}$ haloalkoxy, $C_{2-6}$ alkenyl, $C_{2-6}$ alkynyl, —S(O)$_2$($C_{1-6}$ alkyl), —C(O)N$R^{46}R^{47}$, —N$R^{46}$C(O)$R^{47}$, —SO$_2$N$R^{46}R^{47}$, —N$R^{46}$SO$_2R^{47}$, —C(O)$R^{46}$, —OC(O)$R^{46}$, —C(O)$_2R^{46}$, —O—C(O)N$R^{46}R^{47}$, —N$R^{46}$C(O)O$R^{47}$, cycloalkyl, cycloalkylalkyl, heterocyclyl, heterocyclylalkyl, aryl, arylalkyl, heteroaryl, or heteroarylalkyl;

$C_{3-10}$ cycloalkyl substituted with one or mote substituents independently selected from amino, $C_{2-6}$alkenyl, $C_{2-6}$alkynyl, cyanoalkyl, —S($C_{1-6}$ alkyl), —S(O)($C_{1-6}$ alkyl), —S(O)$_2$($C_{1-6}$ alkyl), —$C_{1-6}$ alkylene-S(O)$_2$($C_{1-6}$ alkyl), $C_{1-6}$ haloalkoxy, $C_{1-6}$ hydroxyalkyl, $C_{1-6}$ alkoxyalkyl substituted with one or more halo, cycloalkyl, cycloalkylalkyl, heterocyclyl, aryl, arylalkyl, heteroaryl, or heteroarylalkyl, wherein the heterocyclyl, heteroaryl, or heteroarylalkyl are optionally substituted with one or more substituents independently selected from $C_{1-6}$ alkyl, $C_{1-6}$ haloalkyl, or halo; or —X—C($R^{48}$)($R^{49}$)($R^{50}$), wherein:
X is $C_{1-6}$ alkylene optionally substituted with one or more halo;

$R^{48}$ and $R^{49}$, together with the carbon atom to which they are attached, form an optionally substituted $C_{3-10}$ cycloalkyl; and $R^{50}$ is cyanoalkyl, $C_{1-6}$ alkoxyalkyl, $C_{2-6}$alkenyl, $C_{2-6}$ alkynyl, —S(O)$_2$($C_{1-6}$ alkyl), $C_{1-6}$ haloalkoxy, $C_{1-6}$ hydroxyalkyl, $C_{1-6}$ alkoxyalkyl, cycloalkyl, cycloalkylalkyl, heterocyclyl, heterocyclylalkyl, aryl, arylalkyl, heteroaryl, or heteroarylalkyl;

$R^{43a}$ and $R^{43b}$ are each independently H, halo, cyano, $C_{1-6}$ alkyl, haloalkyl, $C_{1-6}$ hydroxy alkyl, $C_{1-6}$ alkoxyalkyl, $C_{1-6}$ cyanoalkyl, $C_{1-6}$ aminoalkyl, —S(O)$_2$($C_{1-6}$ alkyl), —$C_{1-6}$ alkylene-S(O)$_2$($C_{1-6}$ alkyl), cycloalkyl, cycloalkylalkyl, heterocyclyl, heterocyclylalkyl, and, arylalkyl, heteroaryl, heteroarylalkyl, amido, or —C(O)$R^{45}$;

$R^{44}$ is cycloalkyl, C-heterocyclyl, —N($R^{51}$)$_2$, —O$R^{51}$, or —S$R^{51}$;

each $R^{45}$ is independently $C_{1-6}$ alkyl, $C_{1-6}$ alkoxy, —N($R^{52}$)$_2$, or heterocyclyl, wherein each $C_{1-6}$ alkyl, $C_{1-6}$ alkoxy, or heterocyclyl is optionally substituted;

each $R^{46}$ and $R^{47}$ is independently H, $C_{1-6}$alkyl, $C_{2-6}$alkenyl, $C_{2-6}$alkynyl, cycloalkyl, heterocyclyl, aryl, heteroalkyl, or heteroaryl, wherein each $C_{1-6}$ alkyl, $C_{2-6}$ alkenyl, $C_{2-6}$ alkynyl, cycloalkyl, heterocyclyl, aryl, heteroalkyl, or heteroaryl is optionally substituted;

each $R^{51}$ is independently H, $C_{1-6}$alkyl, $C_{2-6}$alkenyl, $C_{2-6}$alkynyl, haloalkyl, $C_{1-6}$ alkoxyalkyl, $C_{1-6}$ hydroxyalkyl, $C_{1-6}$ aminoalkyl, —$C_{1-6}$ alkylene-S(O)$_2$($C_{1-6}$ alkyl), $C_{1-6}$ cycloalkyl optionally substituted with one or more alkyl, $C_{1-6}$ cycloalkylalkyl optionally substituted with one or more $C_{1-6}$ alkyl, heterocyclyl optionally substituted with one or more $R^{53}$, or heterocyclylalkyl optionally substituted with one or more $R^{53}$; or two $R^{51}$, together with die nitrogen to which they are attached, form a three- to six-membered heterocyclyl optionally substituted with one or more $R^{53}$;

each $R^{52}$ is independently H or optionally substituted $C_{1-6}$ alkyl;

each $R^{53}$ is independently $C_{1-6}$alkyl, $C_{1-6}$haloalkyl, halo, oxo, $C_{1-6}$ alkoxy, amino, —S(O)$_2$($C_{1-6}$ alkyl), $C_{1-6}$ alkoxyalkyl, cyano, heterocyclyl, heterocyclylalkyl, $C_{3-6}$ cycloalkyl, $C_{1-6}$ cycloalkylalkyl, $C_{3-6}$ cycloalkylsulfonyl. —C(O)$R^{54}$, or —$C_{1-6}$alkylene-C(O)$R^{54}$;

each $R^{54}$ is independently $C_{1-6}$ alkyl, $C_{1-6}$ alkoxy, amino optionally substituted with halo, $C_{1-6}$ haloalkyl, $C_{1-6}$hydroxyalkyl, hydroxy, $C_{1-6}$alkoxyalkyl, $C_{1-6}$ cyanoalkyl, —$C_{1-6}$ alkylene-S(O)$_2$($C_{1-6}$ alkyl), $C_{1-6}$ aminoalkyl, $C_{3-6}$ cycloalkyl, $C_{3-6}$ cycloalkylalkyl, heterocyclyl, or heterocyclylalkyl; and provided that when $R^{44}$ is cycloalkyl, —N($R^{51}$)$_2$, or —O$R^{51}$, then $R^{42}$ is not an unsubstituted $C_{1-6}$ cyanoalkyl.

In some embodiments, are provided compounds having activity as LRRK2 inhibitors, the compounds are of formula (A-I):

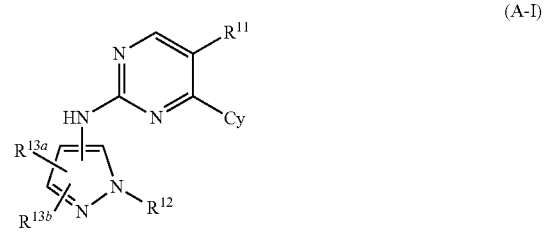

(A-I)

or a pharmaceutically acceptable salt, stereoisomer, mixture of stereoisomers, tautomer, or prodrug thereof, wherein:

Cy is optionally substituted cycloalkyl or optionally substituted C-heterocyclyl;

$R^{11}$ is halo, cyano, $C_1$-$C_6$ alkyl, $C_1$-$C_6$ haloalkyl, $C_1$-$C_6$ alkoxy, $C_1$-$C_6$ haloalkoxy, cycloalkyl, cycloalkyloxy, cycloalkylalkyl, cycloalkylalkyloxy, $C_1$-$C_6$ alkylcarbonyl, $C_1$-$C_6$ alkyloxycarbonyl, aminocarbonyl or heterocyclylcarbonyl;

$R^{12}$ is H, $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ haloalkoxyalkyl $C_1$-$C_6$ cyanoalkyl, $C_1$-$C_6$ aminoalkyl, $C_1$-$C_6$ alkylsulfonyl, cycloalkyl, cycloalkylalkyl, heterocyclyl, heterocyclylalkyl, aryl, heteroaryl, heteroarylylalkyl, $C_1$-$C_6$ alkylcarbonyl, $C_1$-$C_6$ alkoxycarbonyl, $C_1$-$C_6$ alkoxycarbonylalkyl, aminocarbonyl or heterocyclylcarbonyl, wherein each $C_1$-$C_6$ alkyl, cycloalkyl, cycloalkylalkyl, heterocyclyl, heterocyclylalkyl, aryl, heteroaryl, or heteroarylalkyl is optionally substituted; and $R^{13a}$ and $R^{13b}$ are each independently H, halo, cyano, $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ cyanoalkyl, $C_1$-$C_6$ aminoalkyl, $C_1$-$C_6$ alkylsulfonyl, $C_1$-$C_6$ alkylsulfonylalkyl, cycloalkyl, cycloalkylalkyl, heterocyclyl, heterocyclylalkyl, aryl, heteroaryl, $C_1$-$C_6$ alkylcarbonyl, $C_1$-$C_6$ alkoxycarbonyl, aminocarbonyl or heterocyclylcarbonyl, wherein each $C_1$-$C_6$ alkyl, cycloalkyl, cycloalkylalkyl, heterocyclyl, heterocyclylalkyl, aryl, heteroaryl, or heteroalkyl is optionally substituted or $R^{12}$ and either $R^{13a}$ or $R^{13b}$ when attached to an adjacent carbon, together with the atoms bound thereto join to form a heterocyclyl or heteroaryl which is optionally substituted.

In some embodiments, the compounds are of formula (A-I) or a pharmaceutically acceptable salt, stereoisomer, mixture of stereoisomers, tautomer, or prodrug thereof, wherein:

Cy is optionally substituted cycloalkyl or optionally substituted C-heterocyclyl;

$R^{11}$ is halo, cyano, $C_1$-$C_6$ alkyl, $C_1$-$C_6$ haloalkyl, $C_1$-$C_6$ alkoxy, $C_1$-$C_6$ haloalkoxy, cycloalkyl, cycloalkyloxy, cycloalkylalkyl, cycloalkylalkyloxy, $C_1$-$C_6$ alkylcarbonyl, $C_1$-$C_6$ alkyloxycarbonyl, aminocarbonyl or heterocyclylcarbonyl;

$R^{12}$ is H, $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ haloalkoxyalkyl $C_1$-$C_6$ cyanoalkyl, $C_1$-$C_6$ aminoalkyl, $C_1$-$C_6$ alkylsulfonyl, cycloalkyl, cycloalkylalkyl, heterocyclyl, heterocyclylalkyl, aryl, heteroaryl, heteroarylylalkyl, $C_1$-$C_6$ alkylcarbonyl, $C_1$-$C_6$ alkoxycarbonyl, $C_1$-$C_6$ alkoxycarbonylalkyl, aminocarbonyl or heterocyclylcarbonyl, wherein each $C_1$-$C_6$ alkyl, cycloalkyl, cycloalkylalkyl, heterocyclyl, heterocyclylalkyl, aryl, heteroaryl, or heteroarylalkyl is optionally substituted; and $R^{13a}$ and $R^{13b}$ are each independently H, halo, cyano, $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ cyanoalkyl, $C_1$-$C_6$ aminoalkyl, $C_1$-$C_6$ alkylsulfonyl, $C_1$-$C_6$ alkylsulfonylalkyl, cycloalkyl, cycloalkylalkyl, heterocyclyl, heterocyclylalkyl, aryl, heteroaryl, $C_1$-$C_6$ alkylcarbonyl, $C_1$-$C_6$ alkoxycarbonyl, aminocarbonyl or heterocyclylcarbonyl, wherein each $C_1$-$C_6$ alkyl, cycloalkyl, cycloalkylalkyl, heterocyclyl, heterocyclylalkyl, aryl, heteroaryl, or heteroalkyl is optionally-substituted.

In some embodiments, the compounds are of compounds having activity as LRRK2 inhibitors, the compounds of formula (A-I) or a pharmaceutically acceptable salt, stereoisomer, tautomer or prodrug thereof, wherein:

Cy is cycloalkyl or C-heterocyclyl;

$R^{11}$ is halo, cyano, $C_1$-$C_6$ alkyl, $C_1$-$C_6$ haloalkyl, $C_1$-$C_6$ alkoxy, $C_1$-$C_6$ haloalkoxy, cycloalkyl, cycloalkyloxy, cycloalkylalkyl, cycloalkylalkyloxy, $C_1$-$C_6$ alkylcarbonyl, $C_1$-$C_6$ alkyloxycarbonyl, aminylcarbonyl or heterocyclylcarbonyl;

$R^{12}$ is H, $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ haloalkoxyalkyl $C_1$-$C_6$ cyanoalkyl, $C_1$-$C_6$ aminylalkyl, $C_1$-$C_6$ alkylsulfonyl, cycloalkyl, cycloalkylalkyl, heterocyclyl, heterocyclylalkyl, aryl, heteroaryl, heteroarylylalkyl, $C_1$-$C_6$ alkylcarbonyl, $C_1$-$C_6$ alkoxycarbonyl, $C_1$-$C_6$ alkoxycarbonylalkyl, aminylcarbonyl or heterocyclylcarbonyl, and $R^{13a}$ and $R^{13b}$ are each independently H, halo, cyano, $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ cyanoalkyl, $C_1$-$C_6$ aminylalkyl, $C_1$-$C_6$ alkylsulfonyl, $C_1$-$C_6$ alkylsulfonylalkyl, cycloalkyl, cycloalkylalkyl, heterocyclyl, heterocyclylalkyl, aryl, heteroaryl, $C_1$-$C_6$ alkylcarbonyl, $C_1$-$C_6$ alkoxycarbonyl, aminylcarbonyl or heterocyclylcarbonyl.

In some embodiments, the compounds are of compounds having activity as LRRK2 inhibitors, the compounds of formula (A-I) or a pharmaceutically acceptable salt, stereoisomer, tautomer or prodrug thereof, wherein:

$R^{12}$ is:

a fused bicyclic ring system having a heterocyclyl or cycloalkyl fused to a heteroaryl, wherein the ring system is attached to the remainder of the molecule via the heterocyclyl or cycloalkyl and the ring system is independently optionally substituted with one or more halo, cyano, $C_{1-6}$ alkyl, $C_{1-6}$ haloalkyl, $C_{1-6}$ alkoxy, amino, hydroxyalkyl, $C_{1-6}$ alkoxyalkyl, $C_{1-6}$ cyanoalkyl, $C_{1-6}$ aminoalkyl, —S(O)$_2$($C_{1-6}$ alkyl), —$C_{1-6}$ alkylene-S(O)$_2$($C_{1-6}$ alkyl), —C(O)NR$^{16}$R$^{17}$, —NR$^{16}$C(O)R$^{17}$, —$C_{1-6}$ alkylene-C(O)NR$^{16}$R$^{17}$, —$C_{1-6}$ alkylene-NR$^{16}$C(O)R$^{17}$, —SO$_2$NR$^{16}$R$^{17}$, —NR$^{16}$SO$_2$R$^{17}$, —$C_{1-6}$ alkylene-SO$_2$NR$^{16}$R$^{17}$, —$C_{1-6}$ alkylene-NR$^{16}$SO$_2$R$^{17}$, —C(O)R$^{16}$, —OC(O)R$^{16}$, —C(O)$_2$R$^{16}$, —$C_{1-6}$ alkylene-C(O)R$^{16}$, —$C_{1-6}$ alkylene-OC(O)R$^{16}$, —$C_{1-6}$ alkylene-C(O)$_2$R$^{16}$, —O—C(O)NR$^{16}$R$^{17}$, —NR$^{16}$C(O)OR$^{17}$, —$C_{1-6}$ alkylene-O—C(O)NR$^{16}$R$^{17}$, —$C_{1-6}$ alkylene-NR$^{16}$C(O)OR$^{17}$, cycloalkyl, cycloalkylalkyl, heterocyclyl, heterocyclylalkyl, aryl, arylalkyl, heteroaryl, or heteroarylalkyl;

$C_{1-6}$ alkoxyalkyl substituted with one or more substituents independently selected from halo, amino, cyano, hydroxy, $C_{1-6}$ haloalkoxy, $C_{2-6}$alkenyl, $C_{2-6}$alkynyl, cyanoalkyl, —S(O)$_2$($C_{1-6}$ alkyl), —C(O)NR$^{16}$R$^{17}$, —NR$^{16}$C(O)R$^{17}$, —SO$_2$NR$^{16}$R$^{17}$, —NR$^{16}$SO$_2$R$^{17}$, —C(O)R$^{16}$, —OC(O)R$^{16}$, —C(O)$_2$R$^{16}$, —O—C(O)NR$^{16}$R$^{17}$, —NR$^{16}$C(O)OR$^{17}$, cycloalkyl, cycloalkylalkyl, heterocyclyl, heterocyclylalkyl, aryl, arylalkyl, heteroaryl, or heteroarylalkyl;

$C_{1-6}$ haloalkyl substituted with one or more substituents independently selected from amino, cyano, hydroxy, $C_{1-6}$ alkoxy, $C_{1-6}$ haloalkoxy, $C_{2-6}$ alkenyl, $C_{2-6}$ alkynyl, cyanoalkyl, —S(O)$_2$(C M alkyl), —C(O)NR$^{16}$R$^{17}$, —NR$^{16}$C(O)R$^{17}$, —SO$_2$NR$^{16}$R$^{17}$, —NR$^{16}$SO$_2$R$^{17}$, —C(O)R$^{16}$, —OC(O)R$^{16}$, —C(O)$_2$R$^{16}$, —O—C(O)NR$^{16}$R$^{17}$, —NR$^{16}$C(O)OR$^{17}$, cycloalkyl, cycloalkylalkyl, heterocyclyl, heterocyclylalkyl, aryl, arylalkyl, heteroaryl, or heteroarylalkyl;

$C_{1-6}$ cyanoalkyl optionally substituted with one or more substituents independently selected from halo, amino, hydroxy, $C_{1-6}$ haloalkoxy, $C_{2-6}$ alkenyl, $C_{1-6}$ alkynyl, —S(O)$_2$($C_{1-6}$ alkyl), —C(O)NR$^{16}$R$^{17}$, —NR$^{16}$C(O)R$^{17}$, —SO$_2$NR$^{16}$R$^{17}$, —NR$^{16}$SO$_2$R$^{17}$, —C(O)R$^{16}$, —OC(O)R$^{16}$, —C(O)$_2$R$^{16}$, —O—C(O)NR$^{16}$R$^{17}$, —NR$^{16}$C(O)OR$^{17}$, cycloalkyl, cycloalkylalkyl, heterocyclyl, heterocyclylalkyl, aryl, arylalkyl, heteroaryl, or heteroarylalkyl;

$C_{3-10}$ cycloalkyl substituted with one or more substituents independently selected from amino, $C_{1-6}$ alkenyl, $C_{2-6}$alkynyl, cyanoalkyl, —S($C_{1-6}$ alkyl), —S(O)($C_{1-6}$ alkyl), —S(O)$_2$($C_{1-6}$ alkyl), —$C_{1-6}$ alkylene-S(O)$_2$($C_{1-6}$ alkyl), $C_{1-6}$ haloalkoxy, $C_{1-6}$ hydroxyalkyl, $C_{1-6}$ alkoxyalkyl substituted with one or more halo, cycloalkyl, cycloalkylalkyl, heterocyclyl, aryl, arylalkyl, heteroaryl, or heteroarylalkyl, wherein the heterocyclyl, heteroaryl, or heteroarylalkyl are optionally substituted with one or more substituents independently selected from $C_{1-6}$ alkyl, $C_{1-6}$ haloalkyl, or halo; or —X$^2$—C(R$^{18}$)(R$^{19}$)(R$^{20}$), wherein:

X$^2$ is $C_{1-6}$ alkylene optionally substituted with one or more halo;

R$^{18}$ and R$^{19}$, together with the carbon atom to which they are attached, form an optionally substituted $C_{3-10}$ cycloalkyl; and R$^{20}$ is cyanoalkyl, $C_{1-6}$ alkoxyalkyl, $C_{2-6}$alkenyl, $C_{2-6}$alkynyl, —S(O)$_2$($C_{1-6}$ alkyl), $C_{1-6}$ haloalkoxy, $C_{1-6}$ hydroxyalkyl, $C_{1-6}$ alkoxyalkyl, cycloalkyl, cycloalkylalkyl, heterocyclyl, heterocyclylalkyl, aryl, arylalkyl, heteroaryl, or heteroarylalkyl;

provided that when Cy is cycloalkyl, then R$^{12}$ is not an unsubstituted $C_{1-6}$ cyanoalkyl.

In some embodiments, the compound is of formula (A-Ia):

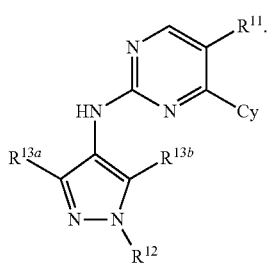

(A-Ia)

In some embodiments, the compound is of formula (A-Ib):

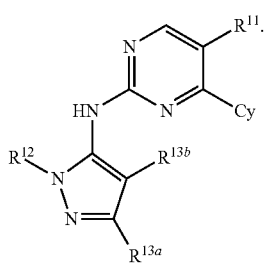

(A-Ib)

In some embodiments, Cy is optionally substituted with 1 to 3 substitutents. In some embodiments, the optional substituents independently are halo, $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ cyanoalkyl, $C_1$-$C_6$ aminoalkyl, $C_1$-$C_6$ alkylsulfonyl, $C_1$-$C_6$ alkylsulfonylalkyl, $C_1$-$C_6$ alkylsulfonylalkyl, cycloalkyl, cycloalkylalkyl, $C_1$-$C_6$ alkylcarbonyl, $C_1$-$C_6$ alkoxycarbonyl, aminocarbonyl or heterocyclylcarbonyl. In some embodiments, Cy is optionally substituted with halo. In some embodiments, Cy is optionally substituted with fluoro.

In some embodiments, Cy is optionally substituted cycloalkyl. In some embodiments, Cy is substituted with halo. In some embodiments, Cy is substituted with fluoro. In some embodiments, Cy is cycloalkyl.

In some embodiments, the compound is of formula (A-Ic):

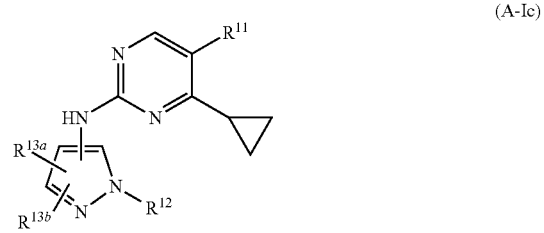

(A-Ic)

or a pharmaceutically acceptable salt, stereoisomer, mixture of stereoisomers, tautomer, or prodrug thereof, wherein:

R$^{11}$ is chloro or —CF$_3$;

R$^{12}$ is H, $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ haloalkoxyalkyl, $C_1$-$C_6$ alkoxycarbonylalkyl, $C_1$-$C_6$ aminoalkyl, $C_1$-$C_6$ alkylsulfonyl, cycloalkyl, cycloalkylalkyl, heterocyclyl, heterocyclylalkyl, aryl, heteroaryl, heteroarylalkyl, $C_1$-$C_6$ alkylcarbonyl, $C_1$-$C_6$ alkoxycarbonyl, $C_1$-$C_6$ alkoxycarbonylalkyl, aminocarbonyl or heterocyclylcarbonyl, wherein each $C_1$-$C_6$ alkyl, cycloalkyl, cycloalkylalkyl, heterocyclyl, heterocyclylalkyl, aryl, heteroaryl, or heteroarylalkyl is optionally substituted; and one of R$^{13a}$ and R$^{13b}$ is H, and the other of R$^{13a}$ and R$^{13b}$ is H, halo, or methyl.

In some embodiments, the compound is of formula (A-I'):

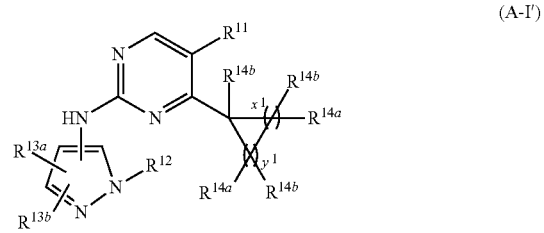

(A-I')

wherein:

x$^1$ and y$^1$ are each independently 1, 2 or 3;

R$^{14a}$ and R$^{14b}$ are, at each occurrence, independently either:

(a) H, halo, $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ cyanoalkyl, $C_1$-$C_6$ aminoalkyl, $C_1$-$C_6$ alkylsulfonyl, $C_1$-$C_6$ alkylsulfonylalkyl, $C_1$-$C_6$ alkylsulfonylalkyl, cycloalkyl, cycloalkylalkyl, $C_1$-$C_6$ alkylcarbonyl, $C_1$-$C_6$ alkoxycarbonyl, aminocarbonyl or heterocyclylcarbonyl, or (b) R$^{14a}$ is H, halo, cyano or $C_1$-$C_6$ alkyl, and R$^{14b}$ together with the carbon atom to which it is bound is taken together with an adjacent $R^{14b}$ and the carbon atom to which it is bound to form a carbon-carbon double bond.

In some embodiments, the compound is of formula (A-I'a):

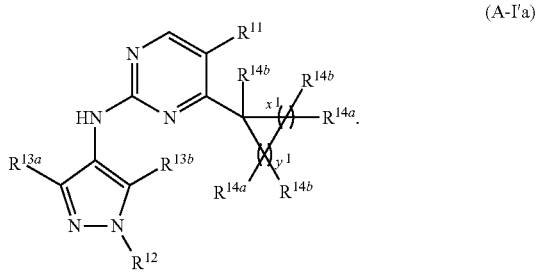

(A-I'a)

In some embodiments, the compound is of formula (A-I'b):

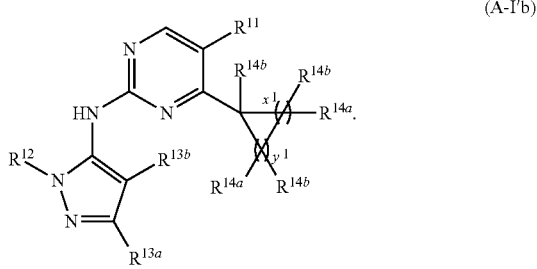

(A-I'b)

In some embodiments, Cy is saturated or unsaturated cyclopropyl, cyclobutyl or cyclopentyl. In some embodiments, cyclopropyl, cyclobutyl or cyclopentyl is optionally substituted. In some embodiments, Cy is cyclopropyl or cyclopent-1-en-1-yl.

In some embodiments, Cy is cyclopropyl, cyclopent-1-en-1-yl, cyclopentyl, cyclobutyl, trans-2-fluorocyclopropan-1-yl, or 1-fluorocyclopropan-1-yl.

In some embodiments, Cy is C-heterocyclyl. In one embodiment C-heterocyclyl is optionally-substituted. In some embodiments, Cy is 1-methyl-1H-pyrazol-4-yl.

In some embodiments, the compound is of formula (A-I"):

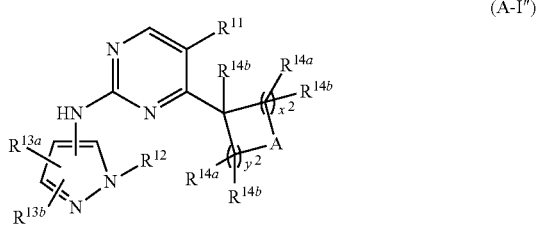

(A-I")

wherein:
A is O or $NR^{15}$; $x^2$ is 1, 2, 3, or 4; $y^2$ is 0, 1, 2, or 3;
$R^{14a}$ and $R^{14b}$ are, at each occurrence, independently either:
(a) H, halo, $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ cyanoalkyl, $C_1$-$C_6$ aminoalkyl, $C_1$-$C_6$ alkylsulfonyl, $C_1$-$C_6$ alkylsulfonylalkyl, $C_1$-$C_6$ alkylsulfonylalkyl, cycloalkyl, cycloalkylalkyl, $C_1$-$C_6$ alkylcarbonyl, $C_1$-$C_6$ alkyloxycarbonyl, aminocarbonyl or heterocyclylcarbonyl, or
(b) $R^{14a}$ is H, halo, cyano or $C_1$-$C_6$ alkyl, and $R^{14b}$ together with the carbon atom to which it is bound is taken together with an adjacent $R^{4b}$ and the carbon atom to which it is bound to form a carbon-carbon double bond; and
$R^{15}$ is H, $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ cyanoalkyl, $C_1$-$C_6$ alkylsulfonyl, $C_1$-$C_6$ alkylsulfonylalkyl, cycloalkyl, cycloalkylalkyl, $C_1$-$C_6$ alkylcarbonyl, $C_1$-$C_6$ alkoxycarbonyl, aminocarbonyl or heterocyclylcarbonyl.

In some embodiments, the compound is of formula (A-I"a):

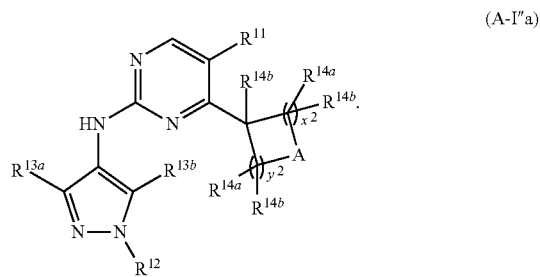

(A-I"a)

In some embodiments, the compound is of formula (A-I"b):

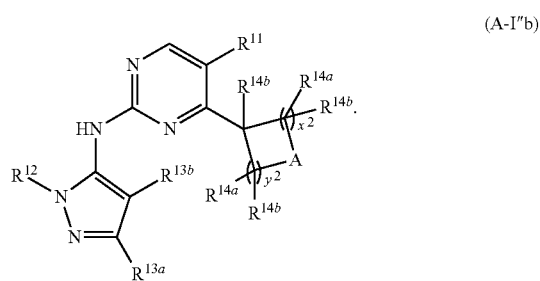

(A-I"b)

In some embodiments, $R^{11}$ is halo, cyano, $C_1$-$C_6$ alkyl or $C_1$-$C_6$ haloalkyl. In some embodiments, $R^{11}$ is $C_1$-$C_6$ haloalkyl. In some embodiments, $C_1$-$C_6$ haloalkyl is $C_1$-$C_6$ fluoroalkyl. In some embodiments, $C_1$-$C_6$ haloalkyl is trifluoromethyl.

In some embodiments, $R^{11}$ is cyano. In some, $R^{11}$ is halo. In some embodiments, halo is chloro.

In some embodiments, $R^{12}$ is $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ cyanoalkyl, $C_1$-$C_6$ aminoalkyl, $C_1$-$C_6$ alkylsulfonyl, cycloalkyl, heterocyclyl, heteroaryl wherein each cycloalkyl, heterocyclyl, or heteroaryl is optionally substituted. In some embodiments, $R^{12}$ is $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ cyanoalkyl or $C_1$-$C_6$ aminylalkyl. In some embodiments, $R^{12}$ is selected from methyl, ethyl, isopropyl, 2-methylprop-1-yl, 1-methylethyl, sulfonylmethyl, cyclopentyl, cyclopropyl, cyclobutyl, bicyclo[3.1.0]hexanyl, oxetanyl, tetrahydropyranyl, piperidinyl, 2-oxopyrrolidinyl, 2-oxopiperidinyl, 6,7-dihydro-5H-pyrrolo[1,2-a]imidazolyl, 6,7-dihydro-5H-pyrrolo[2,1-c][1,2,4]triazolyl, or 1H,4H,5H,6H-cyclopenta[c]pyrazolyl.

In some embodiments, $R^{12}$ is $C_1$-$C_6$ cyanoalkyl. In some embodiments. $R^{12}$ is 2-cyano-prop-2-yl.

In some embodiments, $R^{12}$ is heteroaryl or heteroarylalkyl. For example in some embodiments, $R^{12}$ is heteroarylalkyl, for example a 5-membered, nitrogen containing heteroarylalkyl. In some embodiments, $R^{12}$ is triazolylalkyl, for example 2-methyl-2-(1-methyl-1H-1,2,4-triazol-3-yl)propanyl.

In some embodiments, $R^{12}$ may be substituted with 1-3 groups independently selected from deuterium, halo, hydroxy, cyano, $C_1$-$C_6$ alkyl, cycloalkyl, aryl, heterocyclyl, heteroaryl, and acyl, aminoacyl. Each of the foregoing groups may also be further substituted halo, $C_1$-$C_6$ alkyl and $C_1$-$C_6$ haloalkyl. In some embodiments, $R^{12}$ may be substituted with 1-3 groups independently selected from fluoro, hydroxy, morpholinylmethyl, methyl, ethyl, deuterium, pyrazolyl, pyrrolyl, 1,2,4-triazolyl, 1,2,3-triazolyl, 1-ethyl-1,2,4-triazolyl, 1-methylpyrazolyl, 1-methylimidazolyl, 1-difluoromethyl-1,2,4-triazolyl, 2-difluoromethyl-1,2,4-triazolyl, 2-methyloxadiazolyl, 1-methyl-1,2,4-triazolyl, 2-methyl-1,2,4-triazolyl, acyl, or oxetanyl.

In some embodiments, $R^{12}$ is:

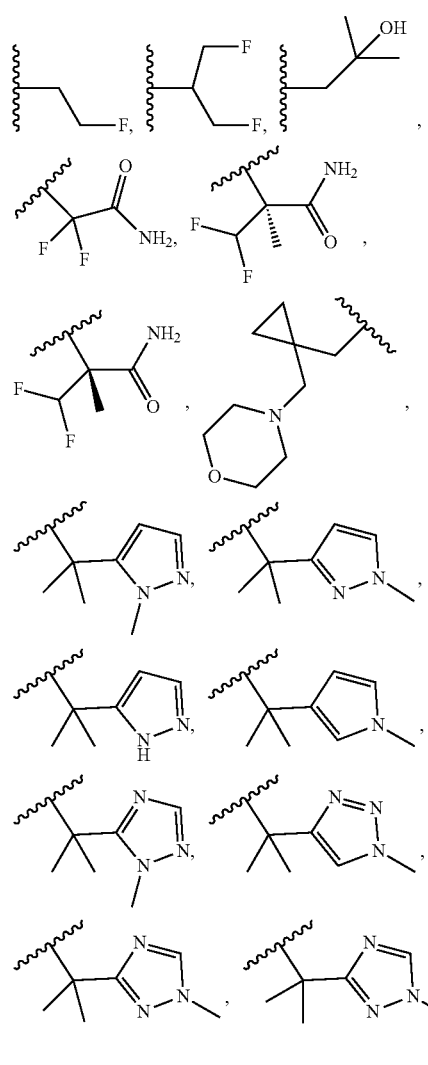

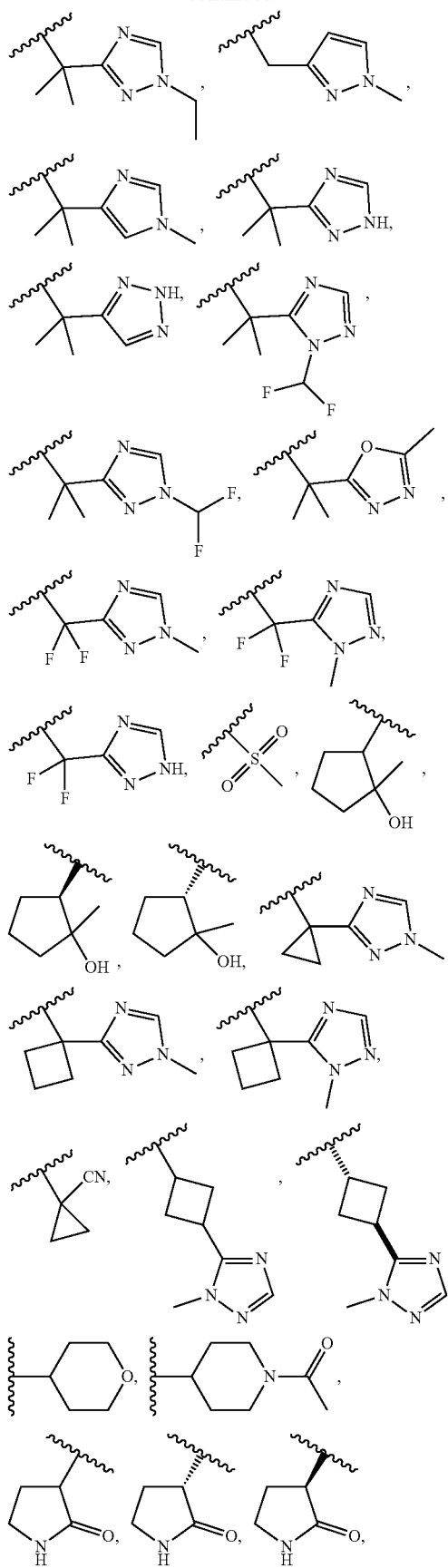

-continued

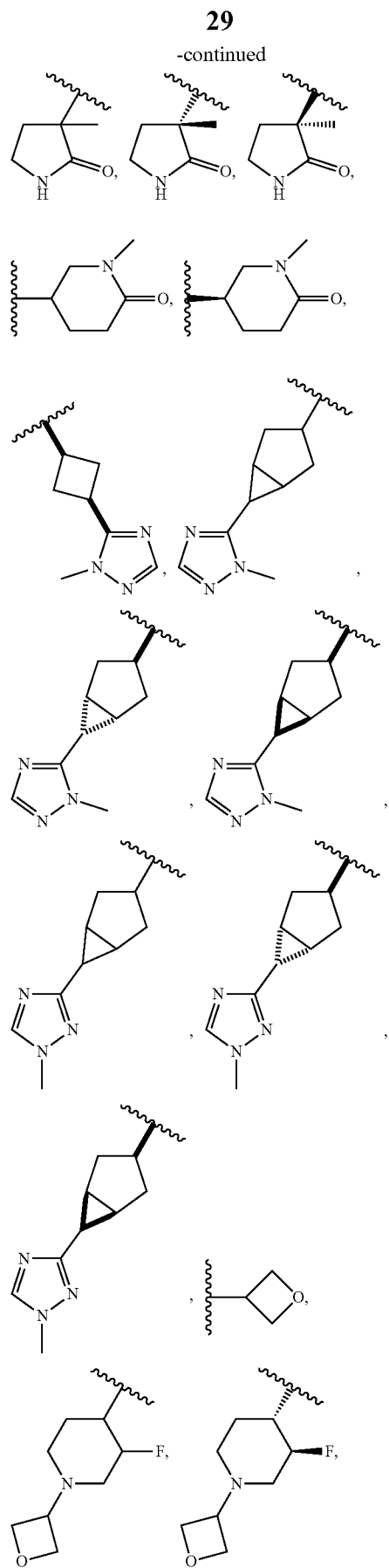

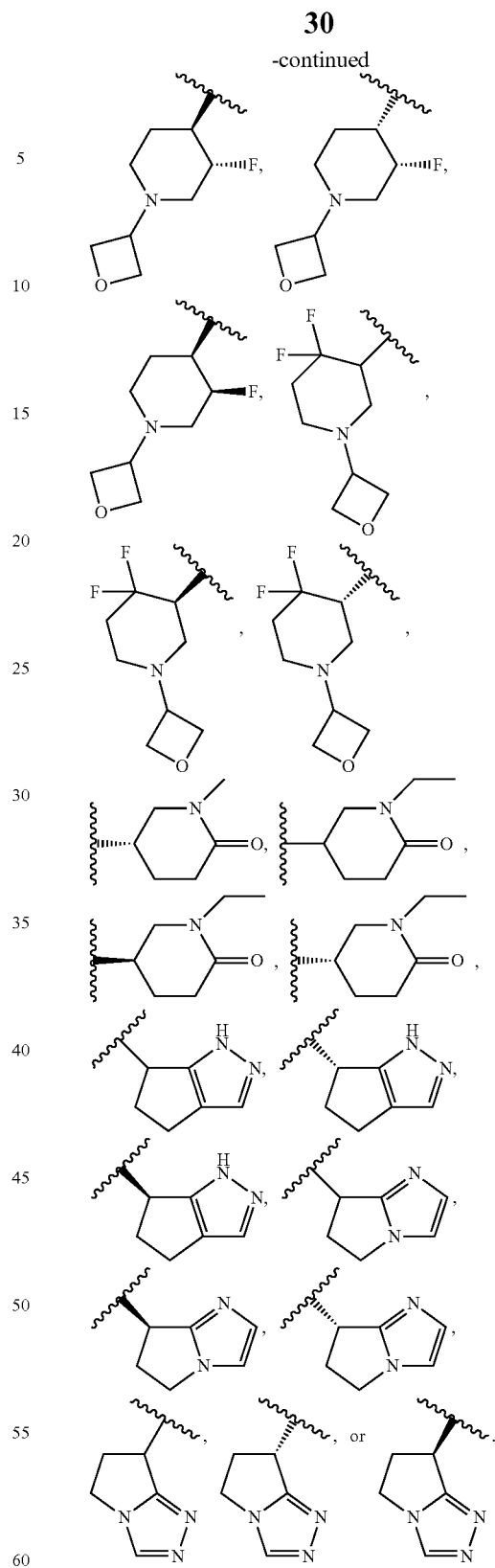

In some embodiments, one of $R^{13a}$ or $R^{13b}$ is H, and the other of $R^{13a}$ or $R^{13b}$ is halo, $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ cyanoalkyl, $C_1$-$C_6$ aminoalkyl, cycloalkyl, cycloalkylalkyl, $C_1$-$C_6$ alkylcarbonyl, $C_1$-$C_6$ alkyloxycarbonyl, aminocarbonyl or heterocyclylcarbonyl. In some embodiments, one of $R^{13a}$ or $R^{13b}$ is halo, $C_1$-$C_6$ alkyl or $C_1$-$C_6$ cyanoalkyl. In some embodiments $R^{13a}$ is H and $R^{13b}$ is halo, $C_1$-$C_6$ alkyl or $C_1$-$C_6$ cyanoalkyl. In some embodiments, $R^{13b}$ is H and $R^{13a}$ is halo, $C_1$-$C_6$ alkyl or $C_1$-$C_6$ cyanoalkyl. In some embodiments, $C_1$-$C_6$ alkyl is methyl. In some embodiments, $C_1$-$C_6$ cyanoalkyl is 2-cyano-prop-2-yl.

In some embodiments, die compound is selected from a compound in Table A-1. In various different embodiments, the compound has one of the structures set forth in Table A-1 below. The compounds in Table A-1 were each prepared and analyzed by mass spectrometry, liquid chromatography, and/or ¹H NMR. General methods by which the compounds may be prepared are provided below and in the Examples, Compounds in die examples were named by using either ChemBioDraw Ultra 13.0 or Chemaxon.

TABLE A-1

Exemplary Compounds

[Chemical structures A-1 through A-9 shown in table]

TABLE A-1-continued
Exemplary Compounds
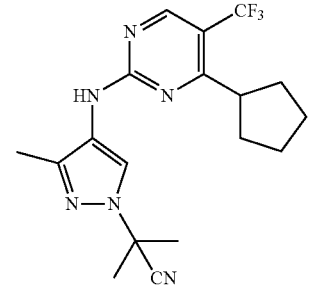 [SMILES: Cc1nn(C(C)(C)C#N)cc1Nc1ncc(C(F)(F)F)c(C2CCCC2)n1]
A-10
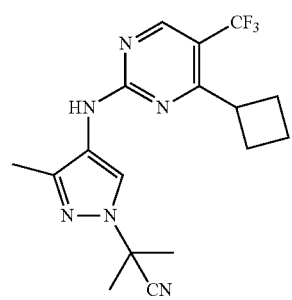 [SMILES: Cc1nn(C(C)(C)C#N)cc1Nc1ncc(C(F)(F)F)c(C2CCC2)n1]
A-11
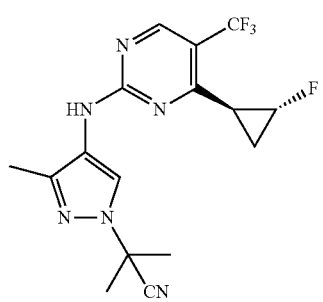
A-12
First eluting isomer
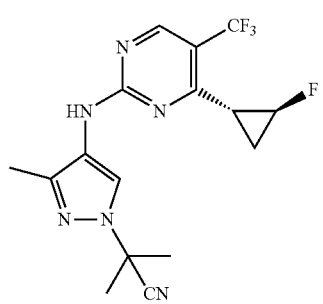
A-13
Second eluting isomer
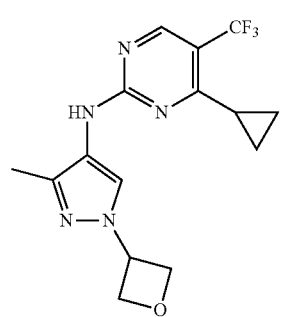 [SMILES: Cc1nn(C2COC2)cc1Nc1ncc(C(F)(F)F)c(C2CC2)n1]
A-14
TABLE A-1-continued
Exemplary Compounds
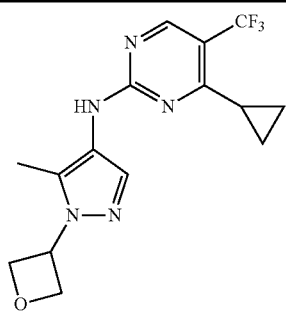
A-15
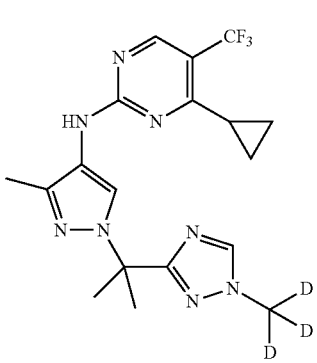 [SMILES: [2H]C([2H])([2H])n1cnc(C(C)(C)n2cc(Nc3ncc(C(F)(F)F)c(C4CC4)n3)c(C)n2)n1]
A-16
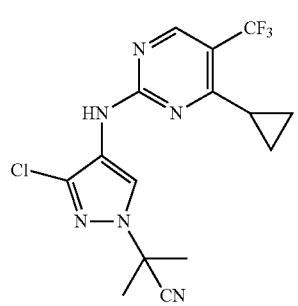 [SMILES: CC(C)(C#N)n1cc(Nc2ncc(C(F)(F)F)c(C3CC3)n2)c(Cl)n1]
A-17
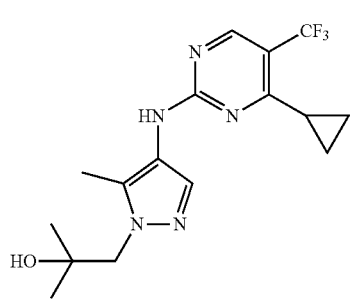 [SMILES: Cc1c(Nc2ncc(C(F)(F)F)c(C3CC3)n2)cnn1CC(C)(C)O]
A-18
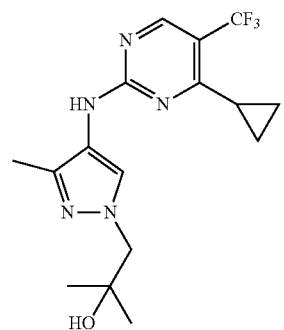 [SMILES: Cc1nn(CC(C)(C)O)cc1Nc1ncc(C(F)(F)F)c(C2CC2)n1]
A-19

TABLE A-1-continued
Exemplary Compounds
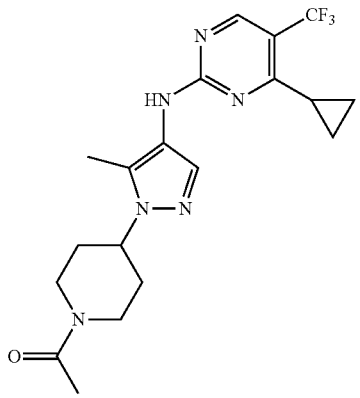 [SMILES: CC(=O)N1CCC(n2ncc(Nc3ncc(C(F)(F)F)c(C4CC4)n3)c2C)CC1] A-20
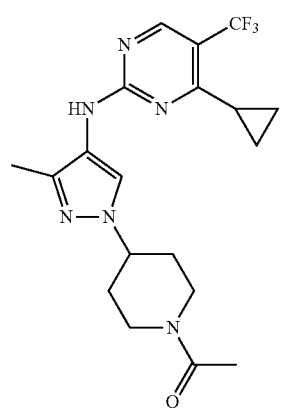 [SMILES: CC(=O)N1CCC(n2cc(Nc3ncc(C(F)(F)F)c(C4CC4)n3)c(C)n2)CC1] A-21
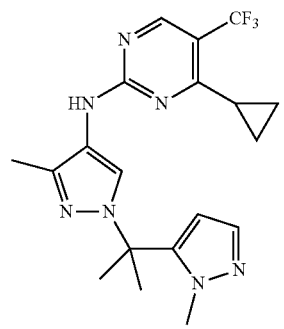 [SMILES: Cc1nn(C(C)(C)c2ccnn2C)cc1Nc1ncc(C(F)(F)F)c(C2CC2)n1] A-22
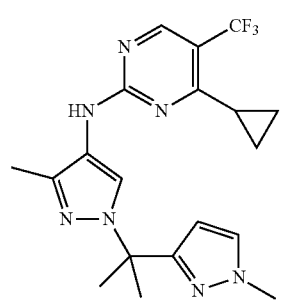 [SMILES: Cc1nn(C(C)(C)c2ccn(C)n2)cc1Nc1ncc(C(F)(F)F)c(C2CC2)n1] A-23
TABLE A-1-continued
Exemplary Compounds
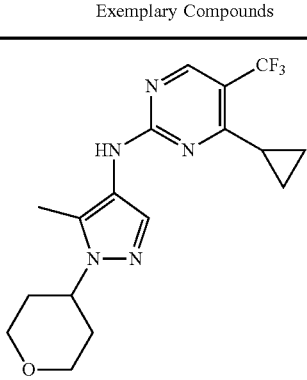 A-24
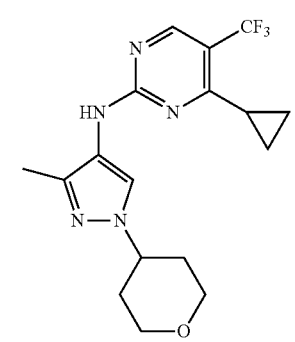 [SMILES: Cc1nn(C2CCOCC2)cc1Nc1ncc(C(F)(F)F)c(C2CC2)n1] A-25
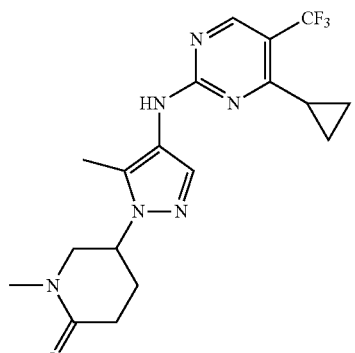 A-26
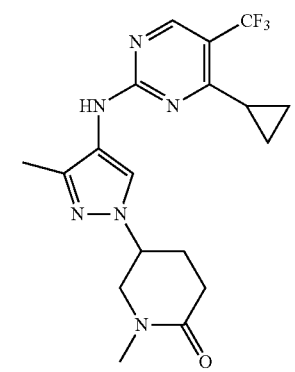 [SMILES: Cc1nn(C2CCC(=O)N(C)C2)cc1Nc1ncc(C(F)(F)F)c(C2CC2)n1] A-27

TABLE A-1-continued
Exemplary Compounds
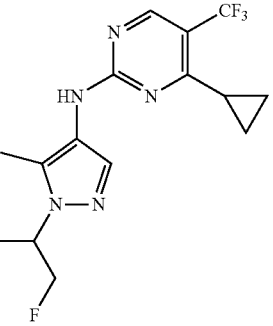 [SMILES: Cc1c(Nc2ncc(C(F)(F)F)c(C3CC3)n2)cnn1CCF]
A-28
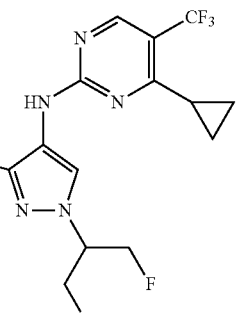
A-29
A-30
A-31
A-32
A-33
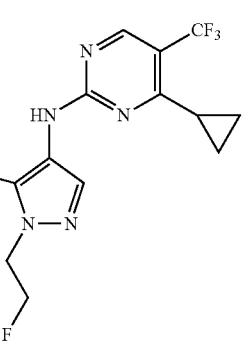
A-34
A-35
A-36
A-37

TABLE A-1-continued
Exemplary Compounds
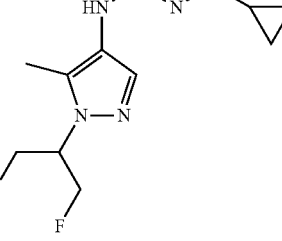
A-38
A-39
A-40
A-41
A-42
TABLE A-1-continued
Exemplary Compounds
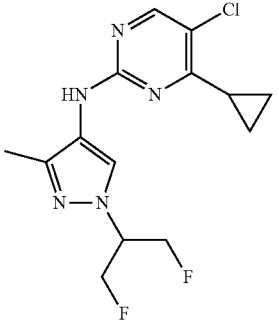 [SMILES: Cc1nn(C(CF)CF)cc1Nc1ncc(Cl)c(C2CC2)n1]
A-43
A-44
A-45
A-46

TABLE A-1-continued
Exemplary Compounds
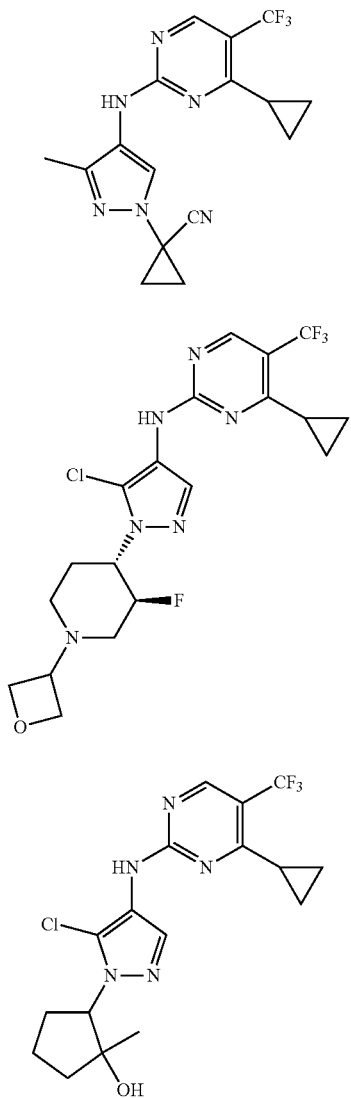
A-47
A-48
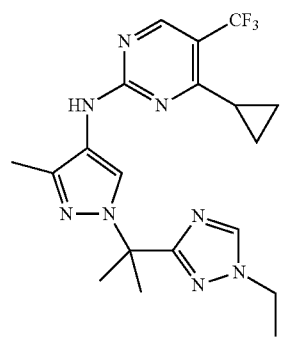 [SMILES: CCn1cnc(C(C)(C)n2cc(Nc3ncc(C(F)(F)F)c(C4CC4)n3)c(C)n2)n1]
A-49: First eluting isomer
A-50: Second eluting isomer
A-51
TABLE A-1-continued
Exemplary Compounds
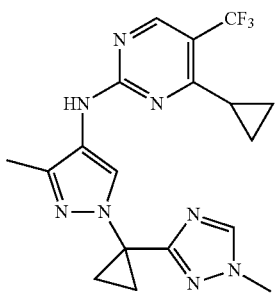 [SMILES: Cc1nn(C2(c3ncn(C)n3)CC2)cc1Nc1ncc(C(F)(F)F)c(C2CC2)n1]
A-52
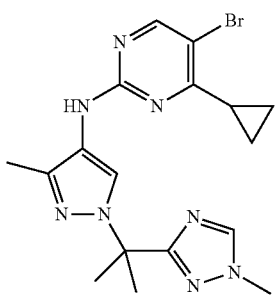 [SMILES: Cc1nn(C(C)(C)c2ncn(C)n2)cc1Nc1ncc(Br)c(C2CC2)n1]
A-53
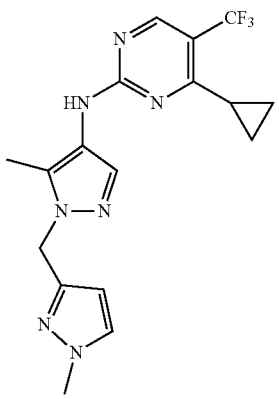 [SMILES: Cc1c(Nc2ncc(C(F)(F)F)c(C3CC3)n2)cnn1Cc1ccn(C)n1]
A-54
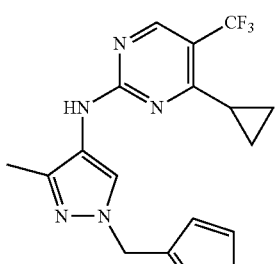
A-55
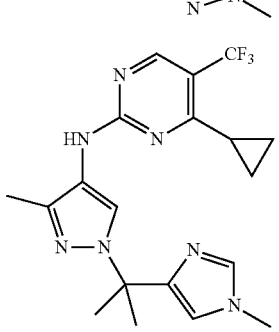
A-56

TABLE A-1-continued

Exemplary Compounds

A-57, A-58, A-59, A-60, A-61, A-62, A-63, A-64

TABLE A-1-continued
Exemplary Compounds
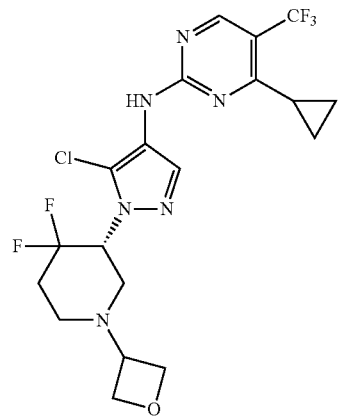 [SMILES: FC(F)(F)c1cnc(Nc2cnn([C@@H]3CN(C4COC4)CCC3(F)F)c2Cl)nc1C1CC1]
A-65
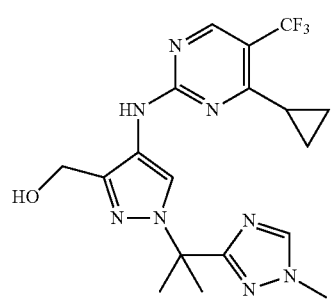 [SMILES: Cn1cnc(C(C)(C)n2cc(Nc3ncc(C(F)(F)F)c(C4CC4)n3)c(CO)n2)n1]
A-66
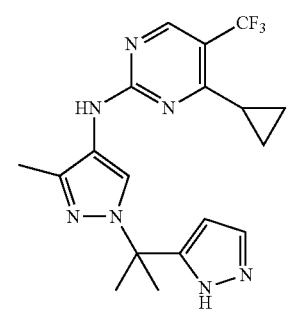 [SMILES: Cc1nn(C(C)(C)c2ccn[nH]2)cc1Nc1ncc(C(F)(F)F)c(C2CC2)n1]
A-67
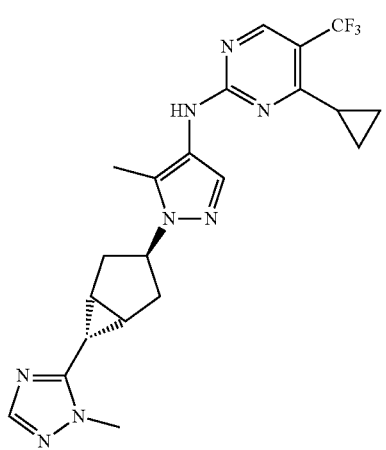
A-68
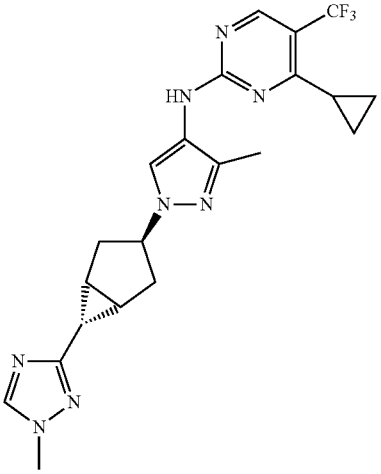
A-69
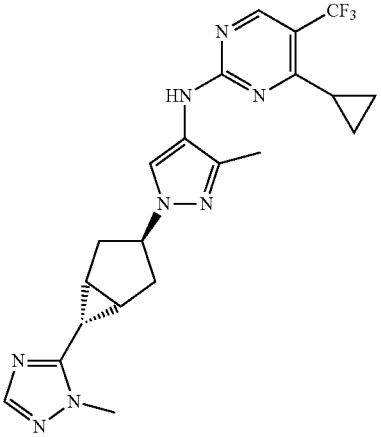
A-70
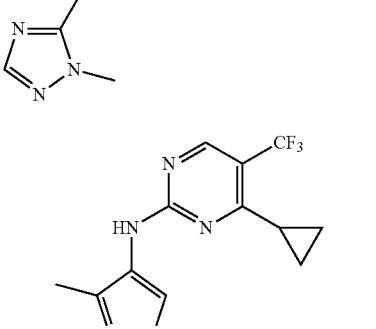
A-71
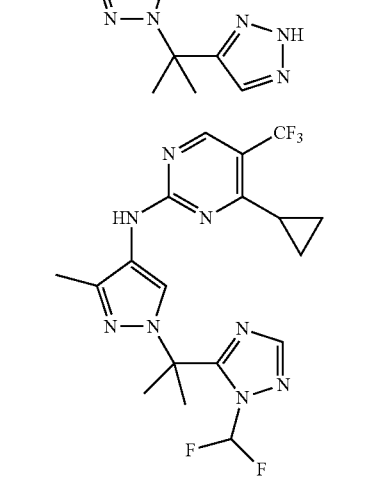
A-72

TABLE A-1-continued
Exemplary Compounds
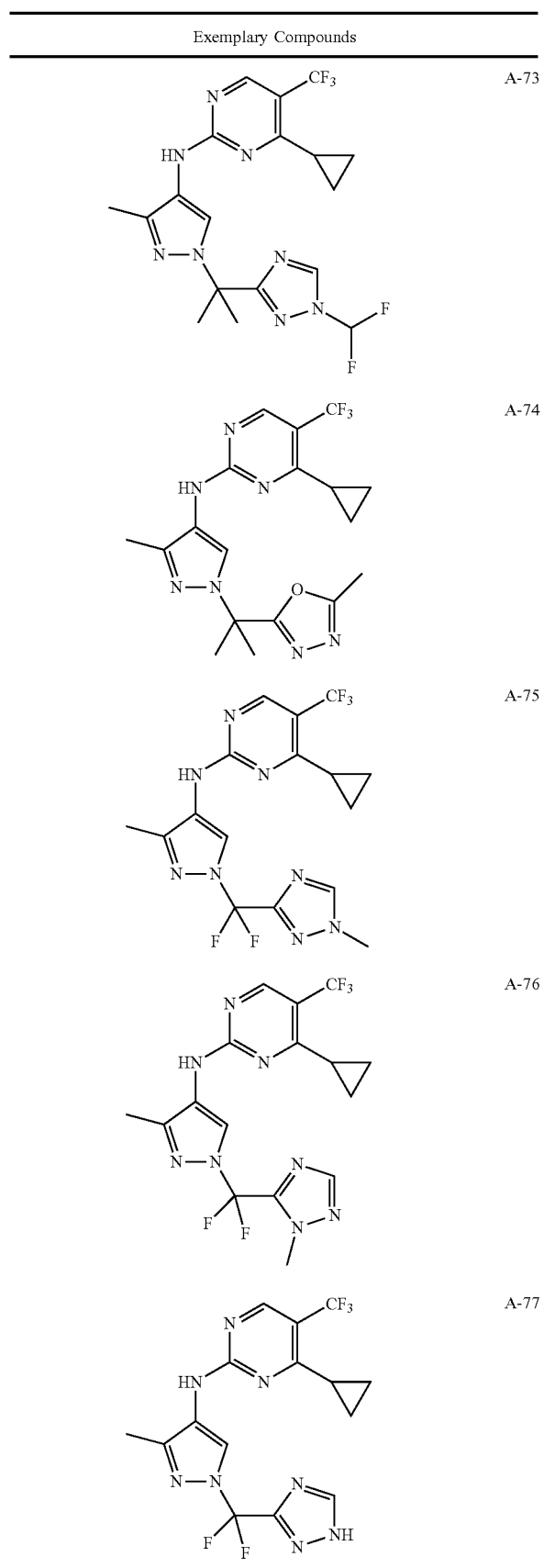
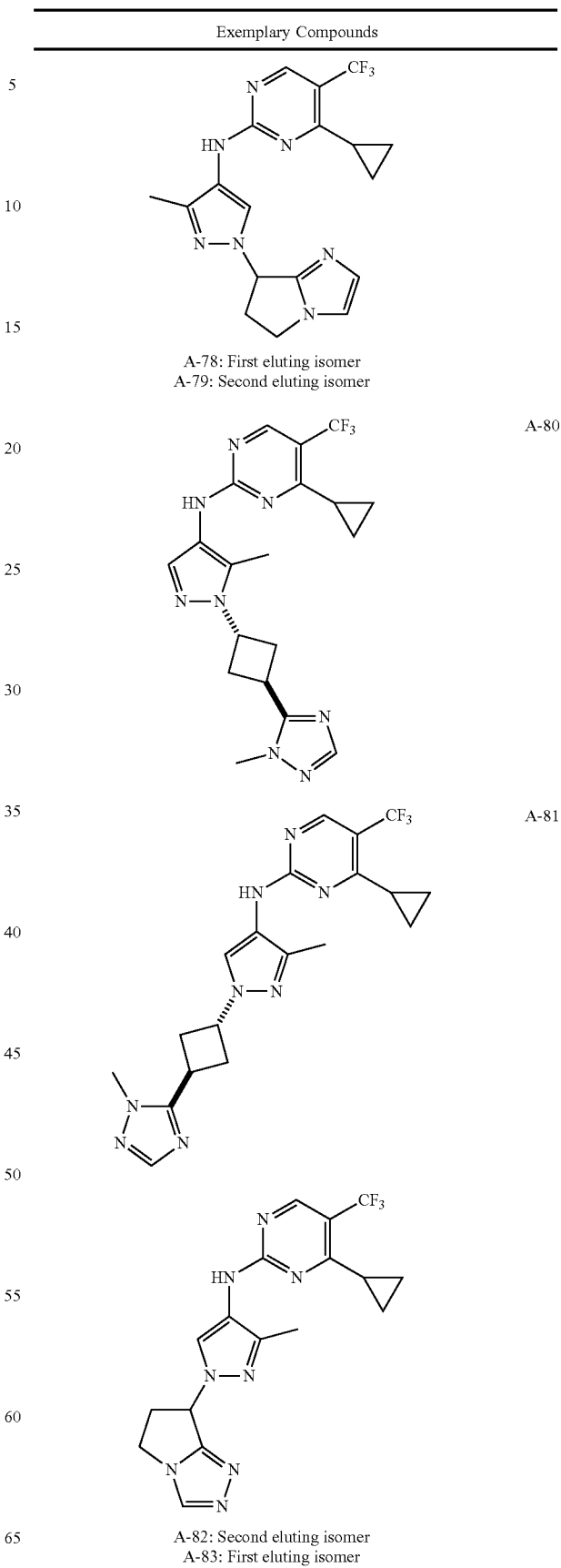
A-78: First eluting isomer
A-79: Second eluting isomer
A-82: Second eluting isomer
A-83: First eluting isomer TABLE A-1-continued
Exemplary Compounds
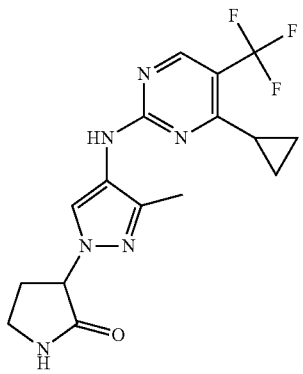
A-86: First eluting isomer
A-85: Third eluting isomer
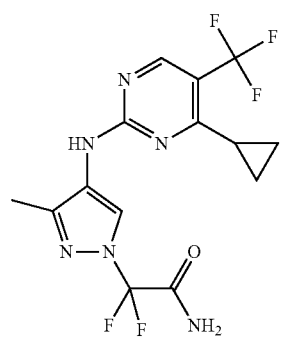 [SMILES: Cc1nn(C(F)(F)C(N)=O)cc1Nc1ncc(C(F)(F)F)c(C2CC2)n1]
A-87
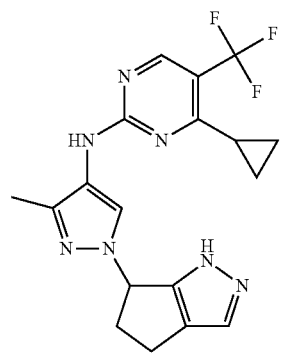
A-89: First eluting isomer
A-90: Second eluting isomer
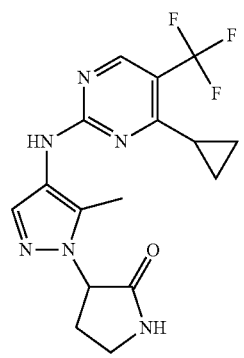
A-88: Second eluting isomer
A-91: Fourth eluting isomer
TABLE A-1-continued
Exemplary Compounds
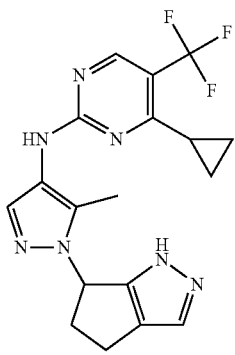
A-92: Third eluting isomer
A-84: Fourth eluting isomer
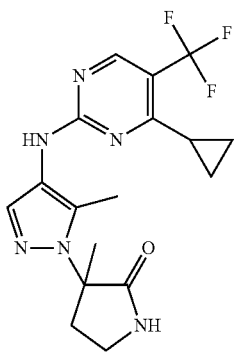 [SMILES: Cc1c(Nc2ncc(C(F)(F)F)c(C3CC3)n2)cnn1C1(C)CCNC1=O]
A-93
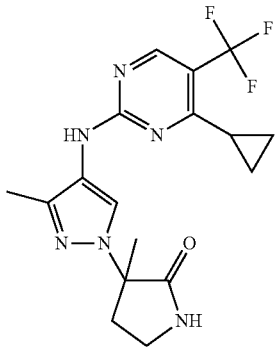
A-94: First eluting isomer
A-95: Second eluting isomer TABLE A-1-continued
Exemplary Compounds
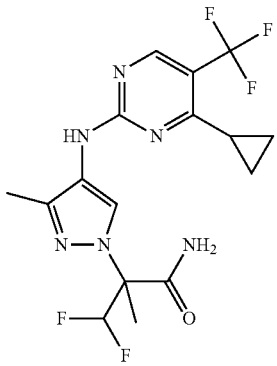
A-96: First eluting isomer
A-97: Second eluting isomer
Specific stereoisomers and regioisomers contemplated include the following in Table A-1A.
TABLE A-1A
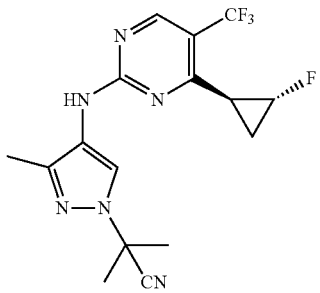 [SMILES: Cc1nn(C(C)(C)C#N)cc1Nc1ncc(C(F)(F)F)c([C@@H]2C[C@H]2F)n1]
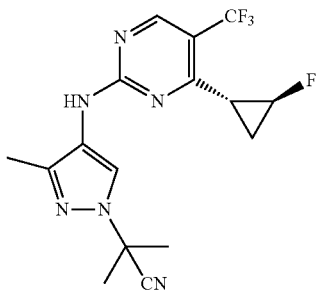 [SMILES: Cc1nn(C(C)(C)C#N)cc1Nc1ncc(C(F)(F)F)c([C@H]2C[C@@H]2F)n1]
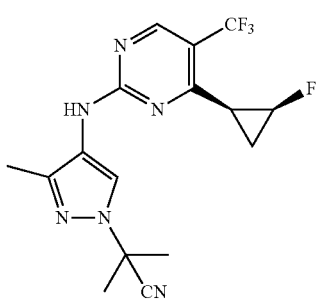 [SMILES: Cc1nn(C(C)(C)C#N)cc1Nc1ncc(C(F)(F)F)c([C@@H]2C[C@@H]2F)n1]
TABLE A-1A-continued
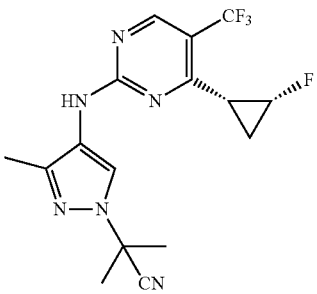 [SMILES: Cc1nn(C(C)(C)C#N)cc1Nc1ncc(C(F)(F)F)c([C@H]2C[C@H]2F)n1]
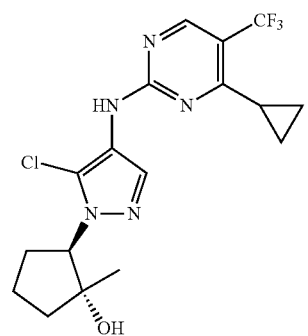 [SMILES: C[C@@]1(O)CCC[C@H]1n1ncc(Nc2ncc(C(F)(F)F)c(C3CC3)n2)c1Cl]
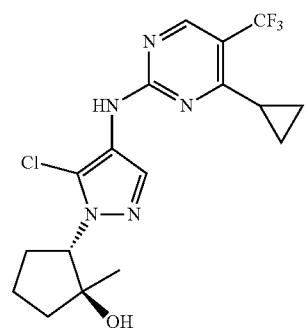 [SMILES: C[C@]1(O)CCC[C@@H]1n1ncc(Nc2ncc(C(F)(F)F)c(C3CC3)n2)c1Cl]
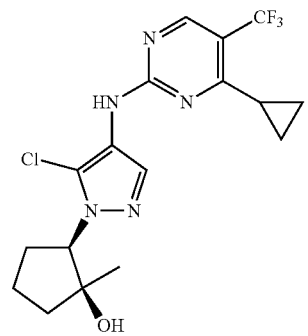 [SMILES: C[C@]1(O)CCC[C@H]1n1ncc(Nc2ncc(C(F)(F)F)c(C3CC3)n2)c1Cl]
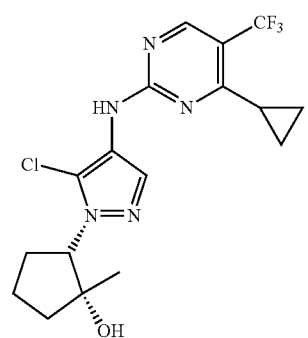

TABLE A-1A-continued
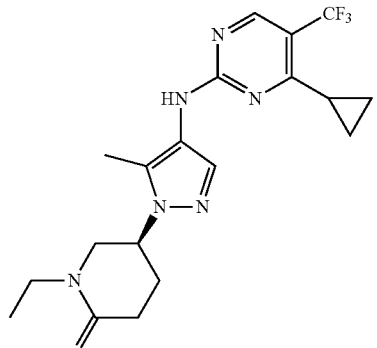
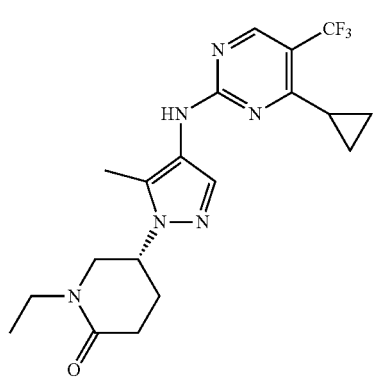 [SMILES: CCN1C[C@H](n2ncc(Nc3ncc(C(F)(F)F)c(C4CC4)n3)c2C)CCC1=O]
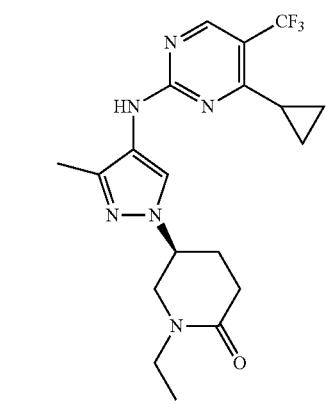 [SMILES: CCN1C[C@@H](n2cc(Nc3ncc(C(F)(F)F)c(C4CC4)n3)c(C)n2)CCC1=O]
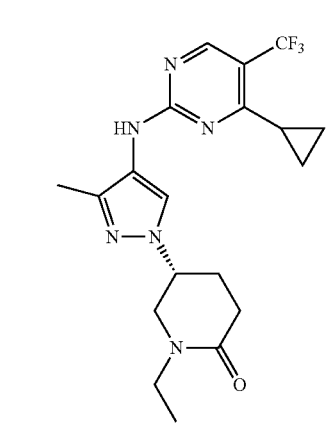
TABLE A-1A-continued
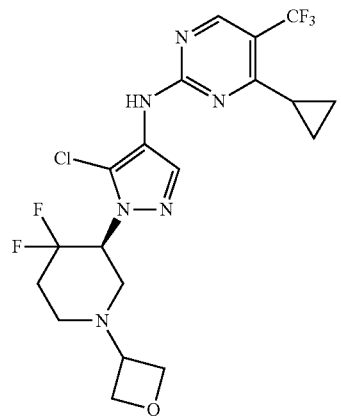 [SMILES: FC(F)(F)c1cnc(Nc2cnn([C@H]3CN(C4COC4)CCC3(F)F)c2Cl)nc1C1CC1]
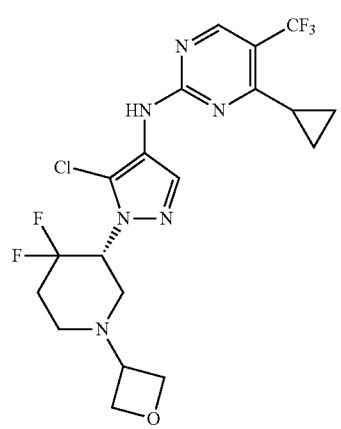 [SMILES: FC(F)(F)c1cnc(Nc2cnn([C@@H]3CN(C4COC4)CCC3(F)F)c2Cl)nc1C1CC1]
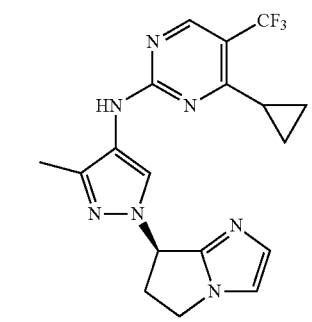 [SMILES: Cc1nn([C@@H]2CCn3ccnc32)cc1Nc1ncc(C(F)(F)F)c(C2CC2)n1]
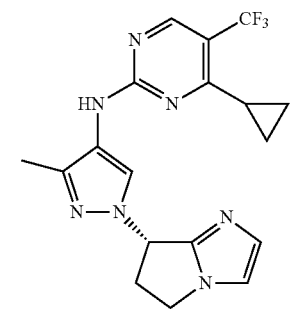 [SMILES: Cc1nn([C@H]2CCn3ccnc32)cc1Nc1ncc(C(F)(F)F)c(C2CC2)n1]

TABLE A-1A-continued
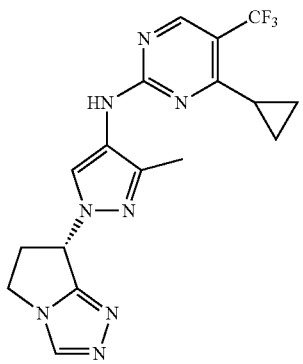 [SMILES: Cc1nn([C@H]2CCn3cnnc32)cc1Nc1ncc(C(F)(F)F)c(C2CC2)n1]
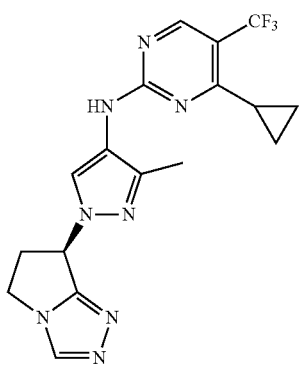 [SMILES: Cc1nn([C@@H]2CCn3cnnc32)cc1Nc1ncc(C(F)(F)F)c(C2CC2)n1]
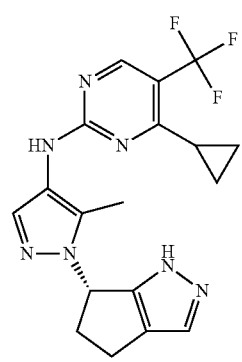 [SMILES: Cc1c(Nc2ncc(C(F)(F)F)c(C3CC3)n2)cnn1[C@H]1CCc2cn[nH]c21]
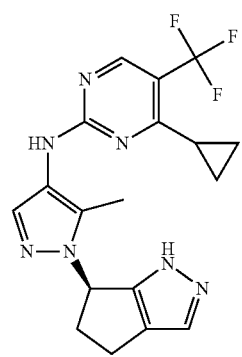 [SMILES: Cc1c(Nc2ncc(C(F)(F)F)c(C3CC3)n2)cnn1[C@@H]1CCc2cn[nH]c21]
TABLE A-1A-continued
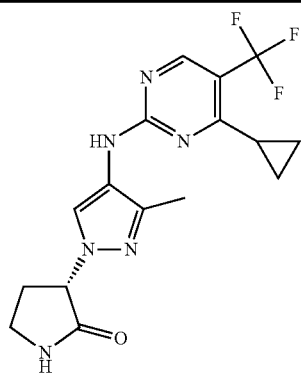
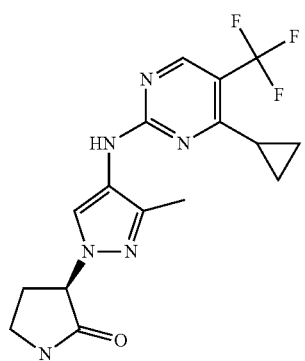
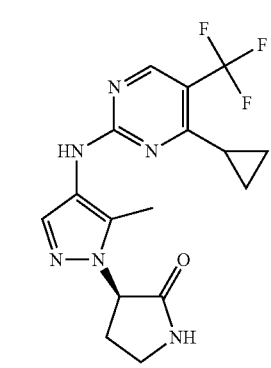 [SMILES: Cc1c(Nc2ncc(C(F)(F)F)c(C3CC3)n2)cnn1[C@@H]1CCNC1=O]
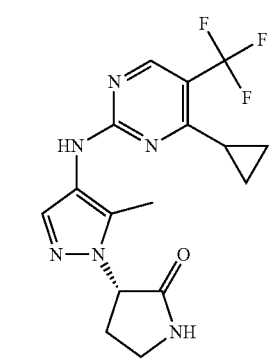 [SMILES: Cc1c(Nc2ncc(C(F)(F)F)c(C3CC3)n2)cnn1[C@H]1CCNC1=O]

TABLE A-1A-continued
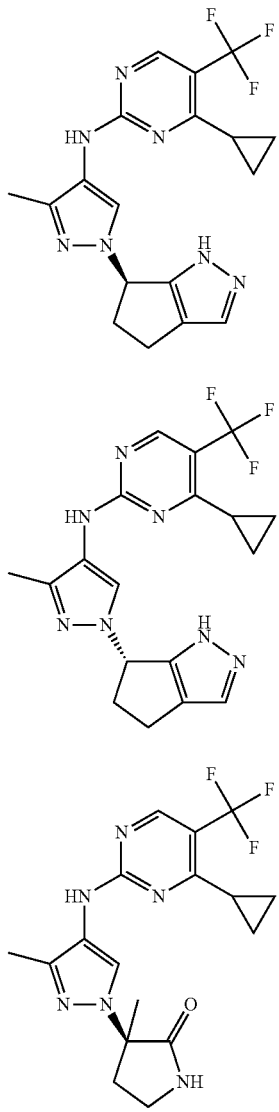
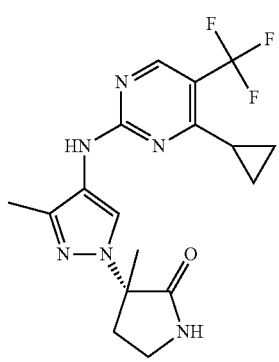 [SMILES: Cc1nn([C@@]2(C)CCNC2=O)cc1Nc1ncc(C(F)(F)F)c(C2CC2)n1]
TABLE A-1A-continued
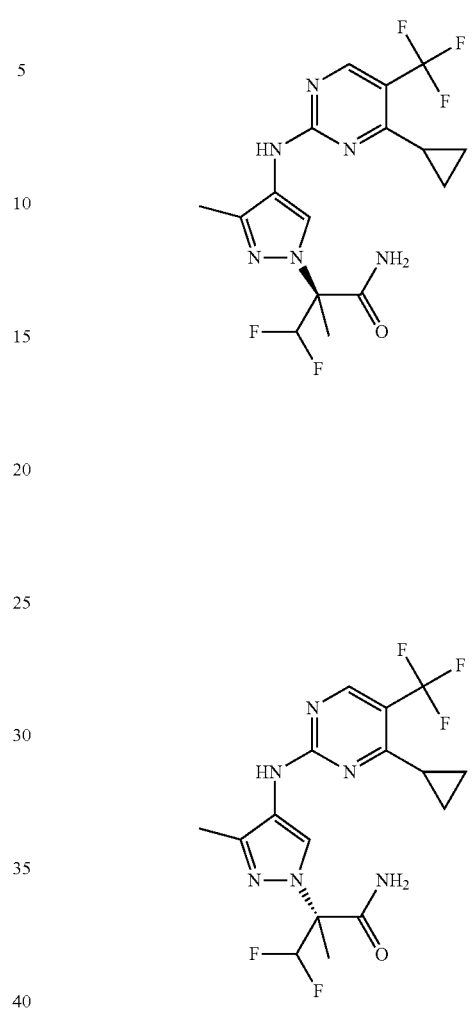
Also provided herein is a method of preparing a compound of formula (A-I), comprising coupling a compound of formula (A-a), comprising coupling a compound of formula (A-b):
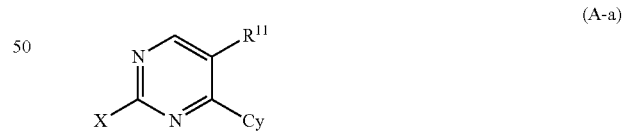
(A-a)
wherein X is halogen, with a compound of formula (A-b):
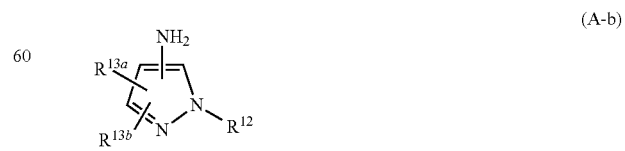
(A-b)
under conditions to provide the compound of formula (A-I).

As noted above, in one embodiment of the present disclosure, provided are LRRK2 inhibitors of formula (B-I):

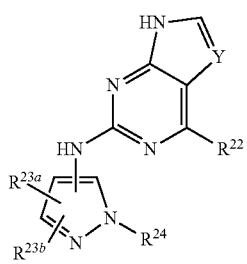

(B-I)

or a pharmaceutically acceptable salt, stereoisomer, mixture of stereoisomers, tautomer or prodrug thereof, wherein:

Y is N or $CR^{21}$;

$R^{21}$ is halo, $C_1$-$C_6$ haloalkyl or cycloalkyl;

$R^{22}$ is $C_1$-$C_6$ alkoxy; cycloalkyloxy, cycloalkylalkyloxy, heterocyclyloxy, heterocyclylalkyloxy, amino, $C_1$-$C_6$ alkylamino, cycloalkylamino, cycloalkylalkylamino, heterocyclylamino, or heterocyclylalkylamino;

$R^{23a}$ and $R^{23b}$ are each independently H, halo, cyano, $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ cyanoalkyl, $C_1$-$C_6$ aminoalkyl, $C_1$-$C_6$ alkylsulfonyl, $C_1$-$C_6$ alkylsulfonylalkyl, cycloalkyl, cycloalkylalkyl, heterocyclyl, heterocyclylalkyl, aryl, heteroaryl, $C_1$-$C_6$ alkylcarbonyl, $C_1$-$C_6$ alkyloxycarbonyl, aminocarbonyl or heterocyclylcarbonyl; and $R^{24}$ is H, $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ cyanoalkyl, $C_1$-$C_6$ aminoalkyl, $C_1$-$C_6$ alkylsulfonyl, $C_1$-$C_6$ alkylsulfonylalkyl, cycloalkyl, cycloalkylalkyl, heterocyclyl, heterocyclylalkyl, aryl, heteroaryl, heteroarylylalkyl, $C_1$-$C_6$ alkylcarbonyl, $C_1$-$C_6$ alkoxycarbonyl, $C_1$-$C_6$ alkoxycarbonylalkyl, aminocarbonyl or heterocyclylcarbonyl.

In one embodiment of the present disclosure, provided are LRRK2 inhibitors of formula (B-I), or a pharmaceutically acceptable salt, stereoisomer, tautomer or prodrug thereof, wherein:

Y is N or $CR^{21}$;

$R^{21}$ is halo;

$R^{22}$ is $C_1$-$C_6$ alkoxy; cycloalkyloxy, cycloalkylalkyloxy, heterocyclyloxy, heterocyclylalkyloxy, amino, $C_1$-$C_6$ alkylamino, cycloalkylamino, cycloalkylalkylamino, heterocyclylamino, or heterocyclylalkylamino;

$R^{23a}$ and $R^{23b}$ are each independently H, halo, cyano, $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ cyanoalkyl, $C_1$-$C_6$ aminoalkyl, $C_1$-$C_6$ alkylsulfonyl, $C_1$-$C_6$ alkylsulfonylalkyl, cycloalkyl, cycloalkylalkyl, heterocyclyl, heterocyclylalkyl, aryl, heteroaryl, $C_1$-$C_6$ alkylcarbonyl, $C_1$-$C_6$ alkyloxycarbonyl, aminocarbonyl or heterocyclylcarbonyl; and $R^{24}$ is H, $C_1$-$C_6$ alkyl, $C_1$-$C_6$ haloalkyl, $C_1$-$C_6$ hydroxylalkyl, $C_1$-$C_6$ alkoxyalkyl, $C_1$-$C_6$ cyanoalkyl, $C_1$-$C_6$ aminoalkyl, $C_1$-$C_6$ alkylsulfonyl, $C_1$-$C_6$ alkylsulfonylalkyl, cycloalkyl, cycloalkylalkyl, heterocyclyl, heterocyclylalkyl, aryl, heteroaryl, heteroarylylalkyl, $C_1$-$C_6$ alkylcarbonyl, $C_1$-$C_6$ alkoxycarbonyl, $C_1$-$C_6$ alkoxycarbonylalkyl, aminocarbonyl or heterocyclylcarbonyl.

In some embodiments, provided is a compound of formula (B-Ia):

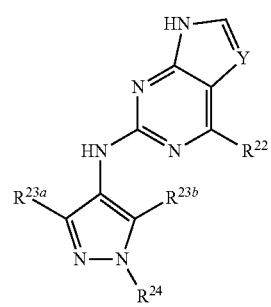

(B-Ia)

In some embodiments, provided is a compound of formula (B-Ib):

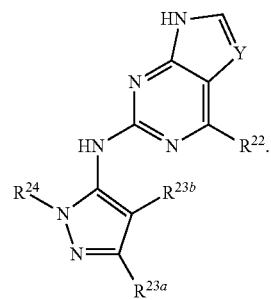

(B-Ib)

In some embodiments, Y is N. In other embodiments A is $CR^{21}$. In some embodiments, $R^{21}$ is chloro. In other embodiments. $R^{21}$ is fluoro.

In some embodiments, $R^{21}$ is $C_1$-$C_6$ haloalkyl. In other embodiments, $R^{21}$ is —$CF_3$. In other embodiments, $R^1$ is cycloalkyl. In other embodiments, $R^{21}$ is cyclopropyl.

In some embodiments, $R^{22}$ is $C_1$-$C_6$ alkoxy or $C_1$-$C_6$ alkylamino. In some embodiments, $R^{22}$ is $C_1$-$C_6$ alkoxy. In some embodiments, $R^2$ is methoxy or ethoxy. In some embodiments, $R^{22}$ is $C_1$-$C_6$ alkylamino. In some embodiments $R^{22}$ is methylamino or ethylamino.

In some embodiments, one of $R^{23a}$ or $R^{23b}$ is H, and the other of $R^{23a}$ or $R^{23b}$ is halo, $C_1$-$C_6$ alkyl, $C_1$-$C_6$ haloalkyl, $C_1$-$C_6$ alkoxyalkyl, $C_1$-$C_6$ hydroxylalkyl, $C_1$-$C_6$ cyanoalkyl, $C_1$-$C_6$ aminoalkyl, cycloalkyl, cycloalkylalkyl, $C_1$-$C_6$ alkylcarbonyl, $C_1$-$C_6$ alkyloxycarbonyl, aminocarbonyl or heterocyclylcarbonyl. In some embodiments, $R^{23a}$ or $R^{23b}$ is $C_1$-$C_6$ alkyl. In some embodiments, $R^{23a}$ is H and $R^{23b}$ is $C_1$-$C_6$ alkyl. In some embodiments, $R^{23b}$ is H and $R^{23a}$ is $C_1$-$C_6$ alkyl. In some embodiments, $C_1$-$C_6$ alkyl is methyl.

In some embodiments, $R^{24}$ is $C_1$-$C_6$ alkyl. In some embodiments, $C_1$-$C_6$ alkyl is methyl. In some embodiments, $R^{24}$ is $C_1$-$C_6$ cyanoalkyl. In some embodiments, $R^{24}$ is 2-cyano-prop-2-yl.

In various different embodiments, the compound has one of the structures set forth in Table B-1 below. The compounds in Table B-1 were each prepared and analyzed by mass spectrometry, liquid chromatography, and/or $^1$H NMR. General methods by which the compounds may be prepared are provided below and in the Examples.

TABLE B-1
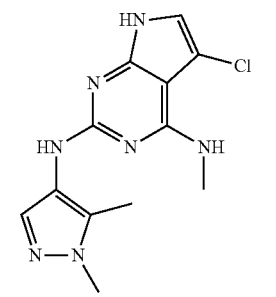 [SMILES: CNc1nc(Nc2cnn(C)c2C)nc2[nH]cc(Cl)c12] B-1
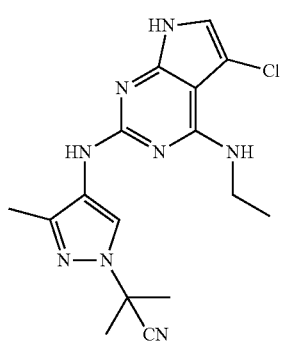 B-2
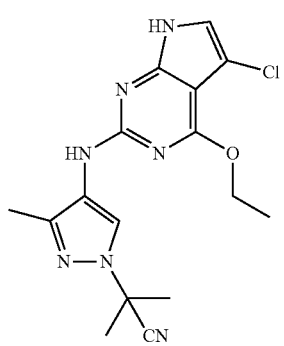 [SMILES: CCOc1nc(Nc2cn(C(C)(C)C#N)nc2C)nc2[nH]cc(Cl)c12] B-3
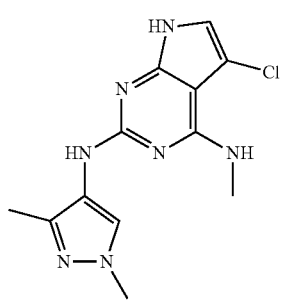 [SMILES: CNc1nc(Nc2cn(C)nc2C)nc2[nH]cc(Cl)c12] B-4
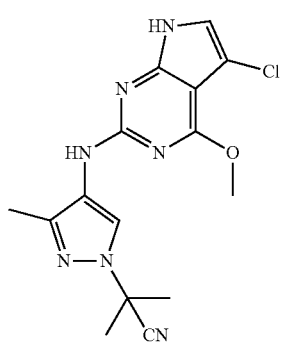 [SMILES: COc1nc(Nc2cn(C(C)(C)C#N)nc2C)nc2[nH]cc(Cl)c12] B-5
TABLE B-1-continued
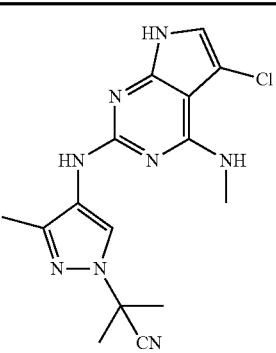 B-6
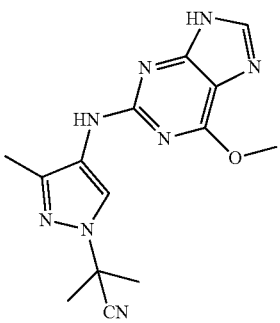 B-7
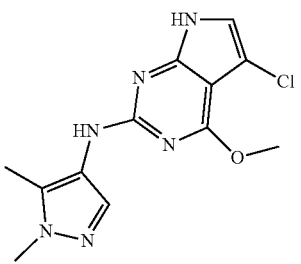 [SMILES: COc1nc(Nc2cnn(C)c2C)nc2[nH]cc(Cl)c12] B-8
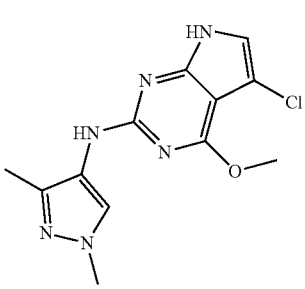 [SMILES: COc1nc(Nc2cn(C)nc2C)nc2[nH]cc(Cl)c12] B-9
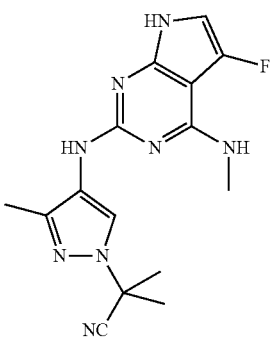 [SMILES: CNc1nc(Nc2cn(C(C)(C)C#N)nc2C)nc2[nH]cc(F)c12] B-10

TABLE B-1-continued

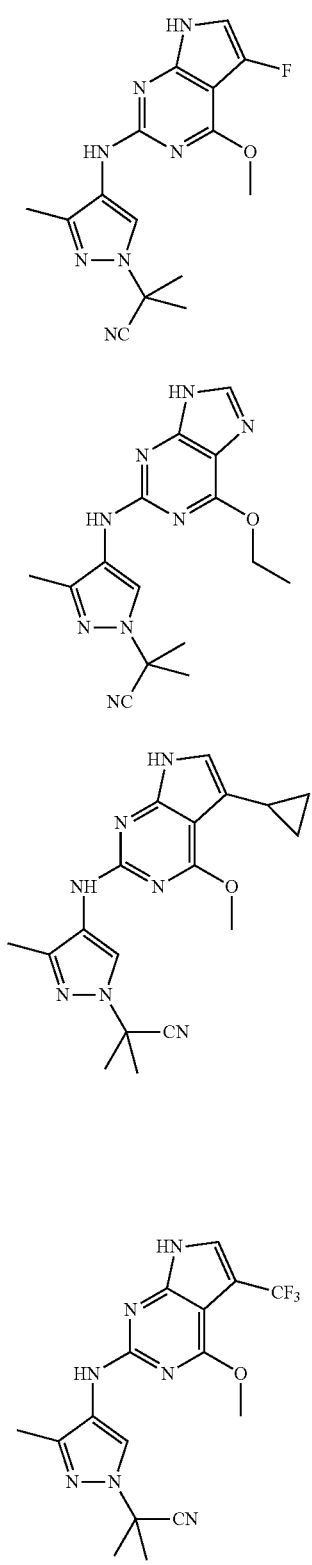

Also provided herein is a method of preparing a compound of formula (B-I), comprising coupling a compound of formula (B-a), wherein PG is an optional protecting group and X is halogen:

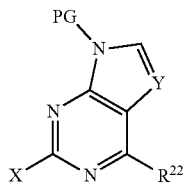

(B-a)

with a compound of formula (B-b):

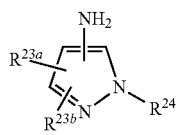

(B-b)

under conditions to provide the compound of formula (B-I).

In one embodiment, provided is a compound of Formula (C-I):

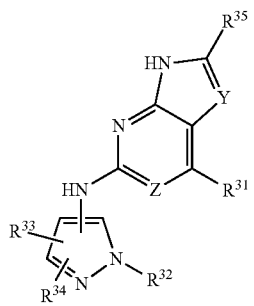

(C-I)

or a pharmaceutically acceptable salt, stereoisomer, or a mixture of stereoisomers, tautomer or prodrug thereof, wherein:

Y is N or $CR^{36}$;

Z is N or CH;

$R^{31}$ is $C_1$-$C_6$ alkyl, cycloalkyl or cycloalkylalkyl, each of which is optionally substituted;

$R^{32}$ is H, $C_1$-$C_6$ alkyl, $C_2$-$C_6$ alkenyl, $C_2$-$C_6$ alkynyl, $C_1$-$C_6$ heteroalkyl, cycloalkyl, heterocyclyl, aryl, heteroaryl, or -$L^3$-$R^{37}$, wherein each $C_1$-$C_6$ alkyl, $C_2$-$C_6$alkenyl, $C_2$-$C_6$alkynyl, cycloalkyl, heterocyclyl, aryl, or heteroaryl is optionally substituted;

$R^{33}$ and $R^{34}$ are each independently H, halo, cyano, amino, $C_1$-$C_6$ alkyl, $C_2$-$C_6$ alkenyl, $C_2$-$C_6$ alkynyl, $C_1$-$C_6$ heteroalkyl, cycloalkyl, heterocyclyl, aryl, heteroaryl, or -$L^4$-$R^{38}$, wherein each $C_1$-$C_6$ alkyl, $C_2$-$C_6$ alkenyl, $C_2$-$C_6$ alkynyl, cycloalkyl, heterocyclyl, aryl, or heteroaryl is optionally substituted; or or $R^{33}$ and $R^{34}$ together with the atom to which they are attached form a cycloalkyl, heterocyclyl or heteroaryl, wherein each cycloalkyl, heterocyclyl, and heteroaryl is optionally substituted;

or $R^{32}$ and $R^{33}$ together with the atom to which they are attached form a heterocyclyl or heteroaryl, wherein each heterocyclyl and heteroaryl is optionally substituted;

$R^{35}$ is H, halo, cyano, $C_1$-$C_6$ alkyl, $C_1$-$C_6$ haloalkyl, or cycloalkyl;

$R^{36}$ is H, halo, cyano, $C_1$-$C_6$ alkyl, $C_{2-6}$ alkenyl, $C_{2-6}$ alkynyl, $C_1$-$C_6$ alkoxy, $C_1$-$C_6$ heteroalkyl, $C_1$-$C_6$ haloalkyl, $C_1$-$C_6$ alkoxyalkyl, —S(O)$_w$($C_1$-$C_6$ alkyl), cycloalkyl, heterocyclyl, heteroaryl, aryl, acyl, or amido, wherein each alkyl, alkoxyl, haloalkyl, alkoxyalkyl, cycloalkyl, heterocyclyl, heteroaryl, aryl, acyl, or amido are independently optionally substituted;

$L^3$ is —S(O)$_p$—, —S(O)$_p$N(R$^9$)—, —(CH$_2$)$_m$—, —C(O)—, —C(O)O—, or —C(O)N(R$^{39}$)—;

each $L^4$ is independently —O—, —S(O)$_w$—, —(CH$_2$)$_m$—, —C(O)—, —C(O)O—, —OC(O)—, —C(O)N(R$^{39}$)—, —N(R$^{39}$)C(O)—, —N(R$^9$)C(O)—, —OC(O)N(R$^{39}$)—, —N(R$^{39}$)C(O)N(R$^{39}$)—, —S(O)$_p$N(R$^{39}$)—, —N(R$^{39}$)S(O)$_p$N(R$^9$)—, or —N(R$^{39}$)S(O)$_p$—;

$R^{37}$ is $C_1$-$C_6$ alkyl, $C_{2-6}$ alkenyl, $C_{2-6}$ alkynyl, $C_1$-$C_6$ alkoxy, $C_1$-$C_6$ heteroalkyl, cycloalkyl, cycloalkylalkyl, heterocyclyl, heterocyclylalkyl, aryl, arylalkyl, heteroaryl, or heteroarylalkyl, wherein each $C_1$-$C_6$ alkyl, $C_2$-$C_6$ alkenyl, $C_2$-$C_6$ alkynyl, cycloalkyl, cycloalkylalkyl, heterocyclyl, heterocyclylalkyl, aryl, arylalkyl, heteroaryl, or heteroarylalkyl is optionally substituted;

each $R^{38}$ is independently $C_1$-$C_6$ alkyl, $C_2$-$C_6$ alkenyl, $C_2$-$C_6$ alkynyl, cycloalkyl, cycloalkylalkyl, heterocyclyl, heterocyclylalkyl, aryl, arylalkyl, heteroaryl, or heteroarylalkyl, wherein each $C_1$-$C_6$ alkyl, $C_{2-6}$ alkenyl, $C_{2-6}$ alkynyl, cycloalkyl, cycloalkylalkyl, heterocyclyl, heterocyclylalkyl, aryl, arylalkyl, heteroaryl, or heteroarylalkyl is optionally substituted;

each $R^{39}$ is independently H, $C_1$-$C_6$ alkyl, $C_2$-$C_6$ alkenyl, $C_{2-6}$alkynyl, cycloalkyl, cycloalkylalkyl, heterocyclyl, heterocyclylalkyl, aryl, arylalkyl, heteroaryl, or heteroarylalkyl;

each p is independently 1 or 2;

each w is independently 0, 1, or 2; and each m is independently 0, 1, 2, or 3.

In certain embodiments, provided is a compound of Formula (C-I), or a pharmaceutically acceptable salt, stereoisomer, or a mixture of stereoisomers, tautomer or prodrug thereof, wherein:

Y is N or CR$^{36}$;

Z is N or CH;

$R^{31}$ is $C_1$-$C_6$ alkyl, cycloalkyl, or cycloalkylalkyl;

$R^{32}$ is H, $C_1$-$C_6$ alkyl, $C_2$-$C_6$ alkenyl, $C_2$-$C_6$ alkynyl, cycloalkyl, heterocyclyl, aryl, heteroaryl, or -L$^3$-R$^{37}$, wherein each $C_1$-$C_6$ alkyl, $C_2$-$C_6$alkenyl, $C_2$-$C_6$alkynyl, cycloalkyl, heterocyclyl, aryl, or heteroaryl is optionally substituted;

$R^{33}$ and $R^{34}$ are each independently H, halo, cyano, amino, $C_1$-$C_6$ alkyl, $C_2$-$C_6$ alkenyl, $C_2$-$C_6$ alkynyl, cycloalkyl, heterocyclyl, aryl, heteroaryl, or -L$^4$-R$^{38}$, wherein each $C_1$-$C_6$ alkyl, $C_2$-$C_6$ alkenyl, $C_2$-$C_6$ alkynyl, cycloalkyl, heterocyclyl, aryl, or heteroaryl is optionally substituted; or or $R^{33}$ and $R^{34}$ together with the atom to which they are attached form a cycloalkyl, heterocyclyl or heteroaryl, wherein each cycloalkyl, heterocyclyl, and heteroaryl is optionally substituted;

or $R^{32}$ and $R^{33}$ together with the atom to which they are attached form a heterocyclyl, or heteroaryl, wherein each heterocyclyl, and heteroaryl is optionally substituted;

$R^{35}$ is H, halo, cyano, $C_1$-$C_6$ alkyl, $C_1$-$C_6$ haloalkyl, or cycloalkyl;

$R^{36}$ is H, halo, cyano, $C_1$-$C_6$ alkyl, $C_1$-$C_6$ haloalkyl, $C_1$-$C_6$ alkoxyalkyl, —S(O)$_2$($C_1$-$C_6$ alkyl), cycloalkyl, heterocyclyl, heteroaryl, aryl, acyl, or amido;

$L^3$ is —S(O)$_2$—, —C(O)—, —C(O)O—, or —C(O)N(R$^{39}$)—;

each $L^4$ is independently —O—, —S—, —S(O)$_2$—, —C(O)—, —C(O)O—, —OC(O)—, —C(O)N(R$^{39}$)—, or —N(R$^{39}$)C(O)—;

$R^{37}$ is $C_1$-$C_6$ alkyl, $C_{2-6}$ alkenyl, $C_{2-6}$ alkanyl, cycloalkyl, cycloalkylalkyl, heterocyclyl, heterocyclylalkyl, and, arylalkyl, heteroaryl, or heteroarylalkyl, wherein each $C_1$-$C_6$ alkyl, $C_2$-$C_6$ alkenyl, $C_2$-$C_6$ alkynyl, cycloalkyl, cycloalkylalkyl, heterocyclyl, heterocyclylalkyl, aryl, arylalkyl, heteroaryl, or heteroarylalkyl is optionally substituted;

each $R^{38}$ is independently $C_1$-$C_6$ alkyl, $C_2$-$C_6$ alkenyl, $C_2$-$C_6$ alkynyl, cycloalkyl, cycloalkylalkyl, heterocyclyl, heterocyclylalkyl, aryl, arylalkyl, heteroaryl, or heteroarylalkyl, wherein each $C_1$-$C_6$ alkyl, $C_{2-6}$ alkenyl, $C_{2-6}$ alkynyl, cycloalkyl, cycloalkylalkyl, heterocyclyl, heterocyclylalkyl, aryl, arylalkyl, heteroaryl, or heteroarylalkyl is optionally substituted; and each $R^{39}$ is independently H, $C_1$-$C_6$ alkyl, $C_2$-$C_6$ alkenyl, $C_{2-6}$alkynyl, cycloalkyl, cycloalkylalkyl, heterocyclyl, heterocyclylalkyl, aryl, arylalkyl, heteroaryl, or heteroarylalkyl.

Also provided is a compound having the formula (C-Ia):

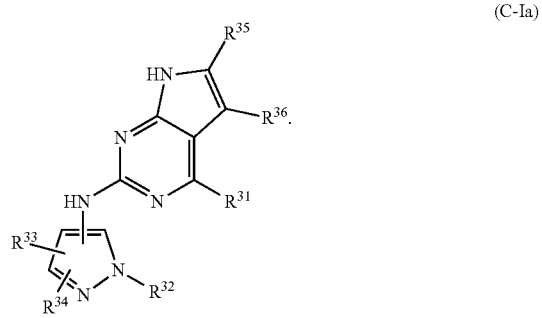

(C-Ia)

Also provided is a compound having the formula (C-Ib):

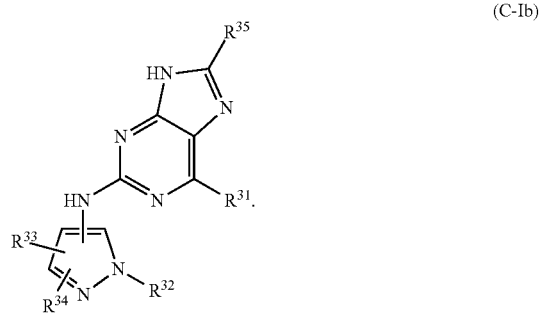

(C-Ib)

Also provided is a compound having the formula (C-Ic):

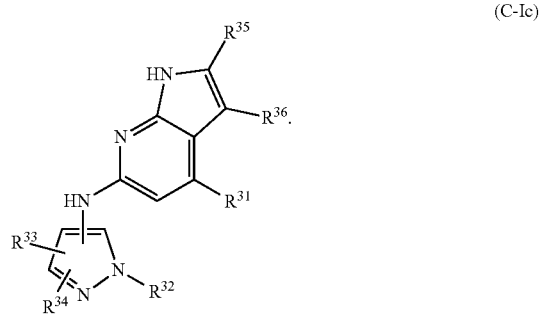

(C-Ic)

Also provided is a compound having the formula (C-Id):

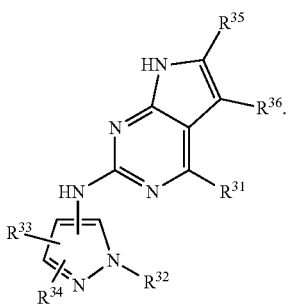

(C-Id)

Also provided is a compound having the formula (C-Ie):

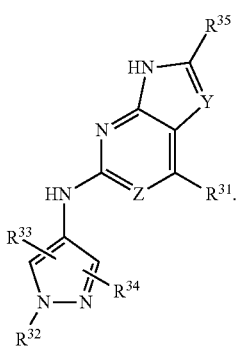

(C-Ie)

Also provided is a compound having the formula (C-If):

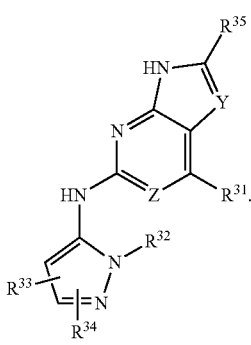

(C-If)

In one embodiment, $R^{31}$ is cycloalkyl. In certain embodiments, $R^{31}$ is cyclopropyl.

In one embodiment, $R^{32}$ is $C_1$-$C_6$ alkyl optionally substituted with one or more halo, cyano, cycloalkyl, haloalkoxy, or optionally substituted heteroaryl, or cycloalkyl, optionally substituted with one or more $C_1$-$C_6$ alkyl. In one embodiment, $R^{32}$ is $C_1$-$C_6$ alkyl, $C_1$-$C_6$ haloalkyl, cycloalkylalkyl, or $C_1$-$C_6$ cyanoalkyl. In one embodiment, $R^{32}$ is optionally substituted $C_1$-$C_6$ alkyl. In one embodiment, $R^{32}$ is $C_1$-$C_6$ alkyl. In one embodiment, $R^{32}$ is methyl. In one embodiment, $R^{32}$ is optionally substituted cycloalkyl. In one embodiment, $R^{32}$ is cycloalkyl. In one embodiment, $R^{32}$ is cyclopropyl.

In one embodiment, $R^{32}$ and $R^{33}$ are $C_1$-$C_6$ alkyl. In one embodiment, at least one of $R^{32}$ and $R^{33}$ are methyl.

In one embodiment, $R^{32}$ and $R^{33}$ together with the atom to which they are attached form a heterocyclyl or heteroaryl, wherein each heterocyclyl and heteroaryl is optionally substituted. In certain embodiments, $R^{32}$ and $R^{33}$ together with the atom to which they are attached form a heterocyclyl, which is optionally substituted with cycloalkyl.

In one embodiment, $R^{34}$ is H.

In one embodiment, $R^{33}$ and $R^{34}$ together with the atom to which they are attached form a cycloalkyl, heterocyclyl or heteroaryl, wherein each cycloalkyl, heterocyclyl and heteroaryl is optionally substituted.

In one embodiment, $R^{35}$ is H or optionally substituted $C_1$-$C_6$ alkyl. In one embodiment, $R^{35}$ is optionally substituted $C_1$-$C_6$ alkyl. In one embodiment, $R^{35}$ is H or $C_1$-$C_6$ alkyl. In one embodiment, $R^{35}$ is $C_1$-$C_6$ alkyl. In one embodiment, $R^{35}$ is methyl. In one embodiment, $R^{35}$ is H. In one embodiment, $R^{35}$ is H or methyl. In one embodiment $R^{35}$ is cycloalkyl. In one embodiment, $R^{35}$ is cyclopropyl. In one embodiment, $R^{35}$ is cycloalkyl and $R^{32}$ is cycloalkyl or cycloalkylalkyl.

In one embodiment $R^{35}$ is H; one of $R^{33}$ and $R^{34}$ is H and the other is halo, cyano, amino, $C_1$-$C_6$ alkyl, $C_2$-$C_6$ alkenyl, $C_2$-$C_6$ alkynyl, $C_1$-$C_6$ heteroalkyl, cycloalkyl, heterocyclyl, aryl, heteroaryl, or -$L^4$-$R^{38}$, wherein each $C_1$-$C_6$ alkyl, $C_2$-$C_6$ alkenyl, $C_2$-$C_6$ alkynyl, cycloalkyl, heterocyclyl, aryl, or heteroaryl is optionally substituted.

In one embodiment, Y is N. In one embodiment Y is $CR^{36}$. In one embodiment $R^{36}$ is optionally substituted $C_1$-$C_6$ alkyl, cycloalkyl, halo or cyano. In one embodiment $R^{36}$ is $C_1$-$C_6$ haloalkyl, cycloalkyl, halo or cyano. In one embodiment, $R^{36}$ is H, halo or cyano. In one embodiment, $R^{36}$ is H. In one embodiment $R^{36}$ is halo. In one embodiment, $R^{36}$ is cyano.

In one embodiment Z is N. In one embodiment Z is CH.

In some embodiments, when $R^{32}$ is $C_1$-$C_6$ alkyl, $C_2$-$C_6$ alkenyl, $C_1$-$C_6$ alkynyl, cycloalkyl, heterocyclyl, aryl, or heteroaryl, $R^{32}$ is optionally substituted with one or more substituents independently selected from alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadine, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —Si$(R^{102})_3$, wherein each $R^{102}$ is independently hydrogen, alkyl, alkenyl, alkynyl, heteroalkyl, cycloalkyl, aryl, heteroaryl or heterocyclyl.

In some embodiments, when $R^{32}$ or $R^{33}$ together with the carbon atom to which they are attached, form a heterocyclyl or heteroaryl optionally substituted with one or more substituents independently selected from alkyl, alkenyl, alkynyl, alkoxy, alkylthio, acyl, amido, amino, amidino, and, aralkyl, azido, carbamoyl, carboxyl, carboxyl ester, cyano, cycloalkyl, cycloalkylalkyl, guanadine, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —Si$(R^{102})_3$, wherein each $R^{102}$ is independently hydrogen, alkyl, alkenyl, alkynyl, heteroalkyl, cycloalkyl, aryl, heteroaryl or heterocyclyl.

In one embodiment, $R^{32}$ or $R^{33}$ together with the carbon atom to which they are attached form an optionally substituted heterocyclyl. In one embodiment, $R^{32}$ or $R^{33}$ together with the carbon atom to which they are attached form an optionally substituted heterocyclyl, wherein the heterocylyl is pyrrolidinyl. In one embodiment, heterocyclyl is optionally substituted with cycloalkyl.

In some embodiments, when $R^{33}$ or $R^{34}$ are each independently $C_1$-$C_6$ alkyl, $C_2$-$C_6$ alkenyl, $C_2$-$C_6$ alkynyl, cycloalkyl, heterocyclyl, aryl, or heteroaryl, $R^{33}$ or $R^{34}$ are each independently optionally substituted with one or more substituents independently selected from alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadine, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —Si($R^{102}$)$_3$, wherein each $R^{102}$ is independently hydrogen, alkyl, alkenyl, alkynyl, heteroalkyl, cycloalkyl, aryl, heteroaryl or heterocyclyl.

In some embodiments, $R^{33}$ and $R^{34}$, together with the carbon atom to which they are attached, form a cycloalkyl, heterocyclyl or heteroaryl optionally substituted with one or more substituents independently selected from alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadine, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —Si($R^{102}$)$_3$, wherein each $R^{102}$ is independently hydrogen, alkyl, alkenyl, alkynyl, heteroalkyl, cycloalkyl, aryl, heteroaryl or heterocyclyl.

In some embodiments, when $R^{37}$ is $C_1$-$C_6$ alkyl, $C_{2-6}$ alkenyl, $C_{2-6}$ alkynyl, cycloalkyl, cycloalkylalkyl, heterocyclyl, heterocyclylalkyl, aryl, arylalkyl, heteroaryl, or heteroarylalkyl, $R^{37}$ is optionally substituted with one or more substituents independently selected from alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadine, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —Si($R^{102}$)$_3$, wherein each $R^{102}$ is independently hydrogen, alkyl, alkenyl, alkynyl, heteroalkyl, cycloalkyl, aryl, heteroaryl or heterocyclyl.

In some embodiments, when $R^{38}$ is $C_1$-$C_6$ alkyl, $C_{2-6}$ alkenyl, $C_{2-6}$ alkynyl, cycloalkyl, cycloalkylalkyl, heterocyclyl, heterocyclylalkyl, aryl, arylalkyl, heteroaryl, or heteroarylalkyl, $R^{38}$ is optionally substituted with one or more substituents independently selected from alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadine, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —Si($R^{102}$)$_3$, wherein each $R^{102}$ is independently hydrogen, alkyl, alkenyl, alkynyl, heteroalkyl, cycloalkyl, aryl, heteroaryl or heterocyclyl.

In one embodiment, a compound may be selected from those compounds in Table C-1. Also included within the disclosure are pharmaceutically acceptable salt, stereoisomer, or a mixture of stereoisomers, tautomer or prodrug thereof. In certain embodiments, provided are compounds of Table C-1 for use in the methods described herein.

TABLE C-1

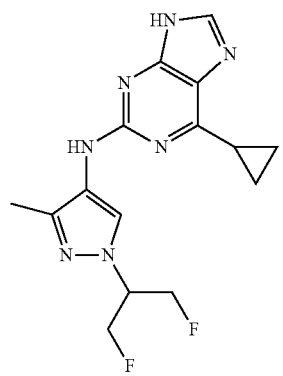 [SMILES: Cc1nn(C(CF)CF)cc1Nc1nc(C2CC2)c2nc[nH]c2n1]

C-1

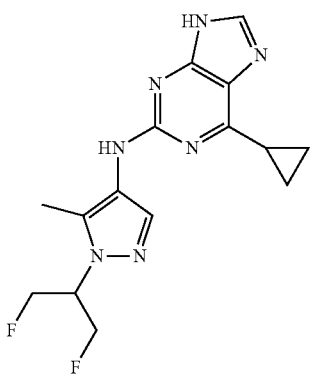 [SMILES: Cc1c(Nc2nc(C3CC3)c3nc[nH]c3n2)cnn1C(CF)CF]

C-2

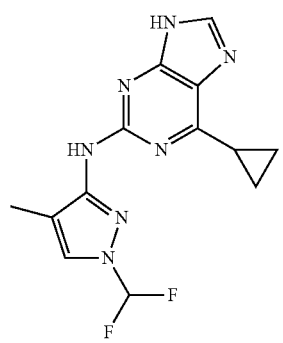 [SMILES: Cc1cn(C(F)F)nc1Nc1nc(C2CC2)c2nc[nH]c2n1]

C-3

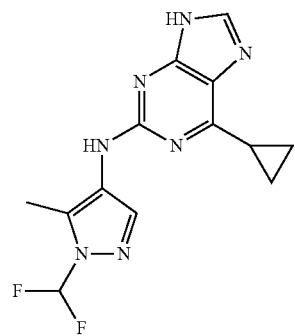 [SMILES: Cc1c(Nc2nc(C3CC3)c3nc[nH]c3n2)cnn1C(F)F]

C-4

TABLE C-1-continued
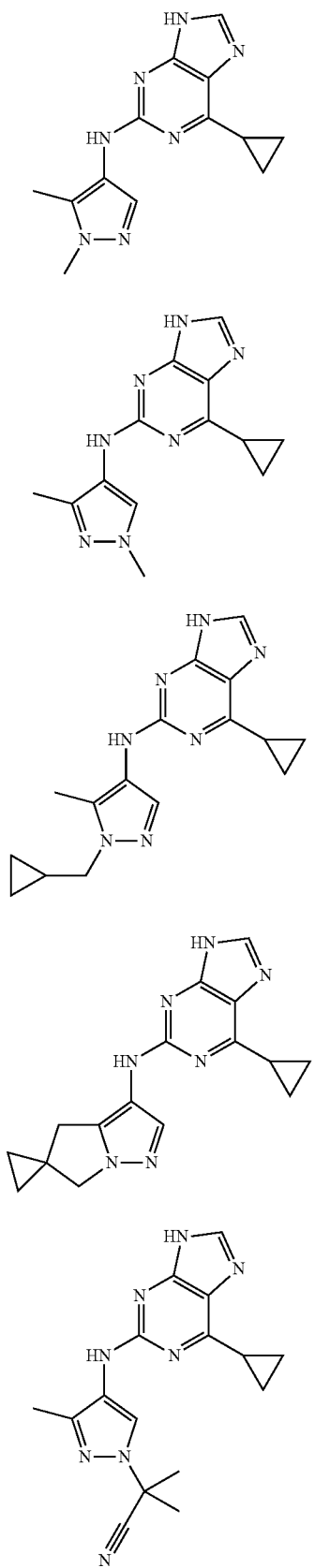
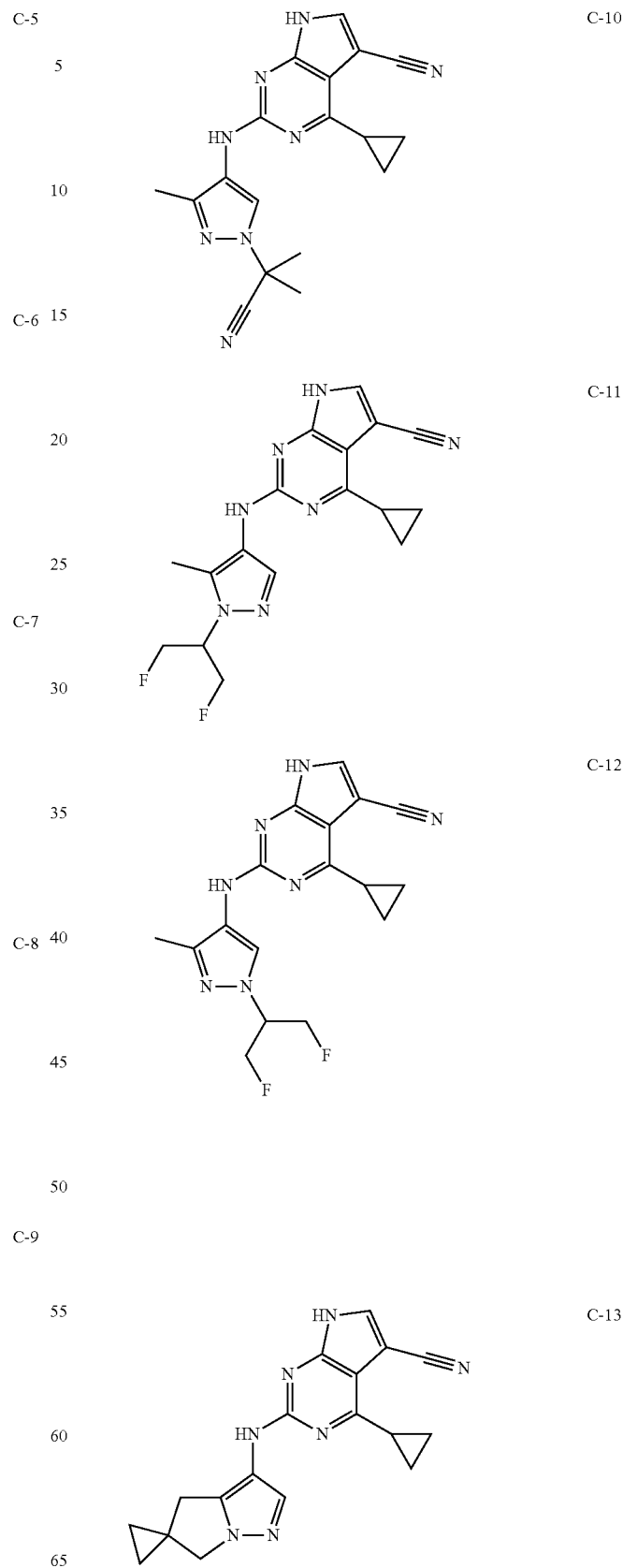

TABLE C-1-continued
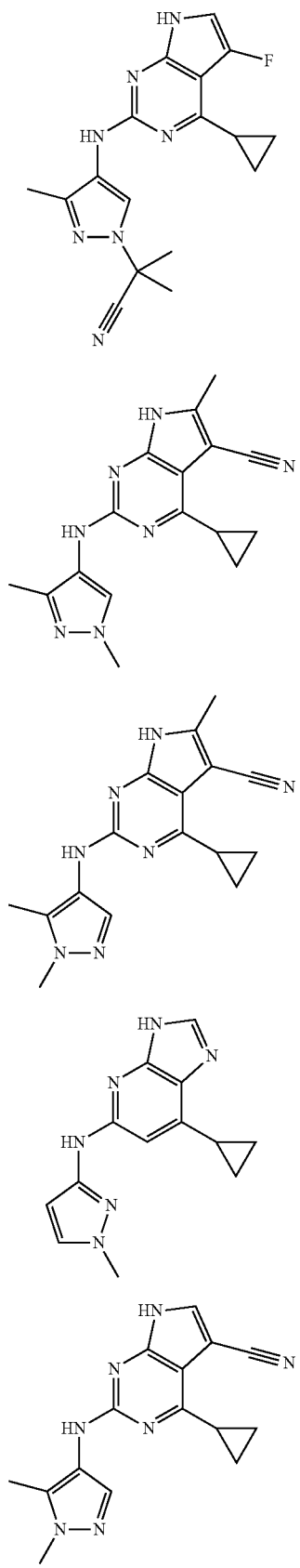
C-14
C-15
C-16
C-17
C-18
TABLE C-1-continued
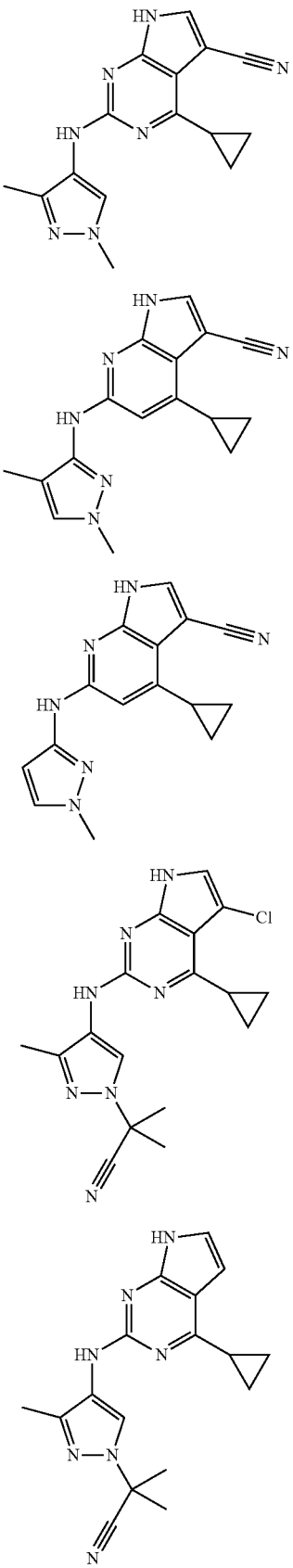
C-19
C-20
C-21
C-22
C-23

TABLE C-1-continued
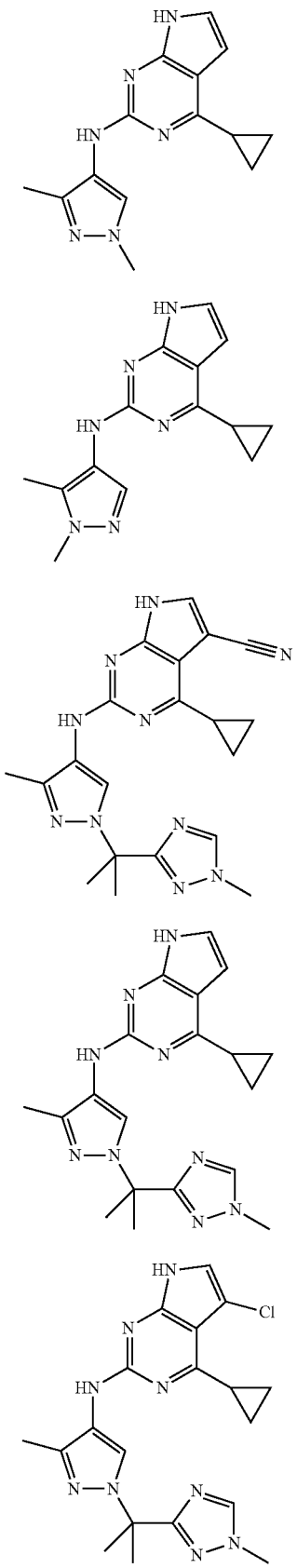
C-24
C-25
C-26
C-27
C-28
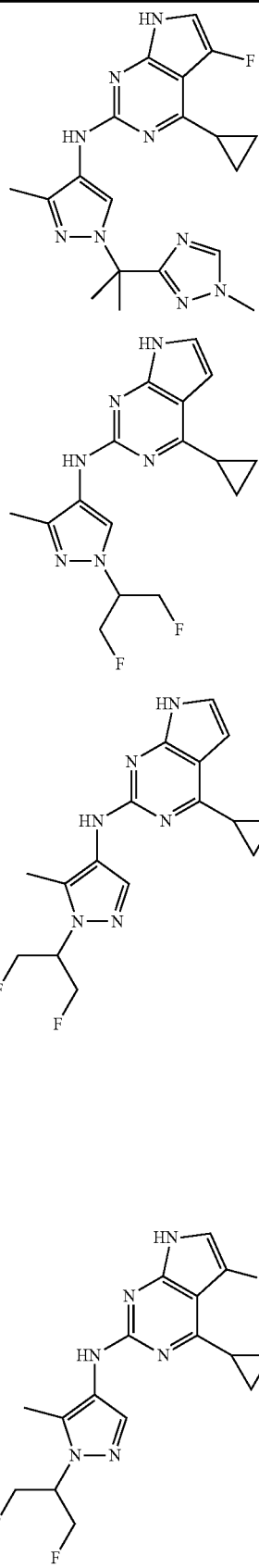
C-29
C-30
C-31
C-32

TABLE C-1-continued
| | |
|---|---|
| 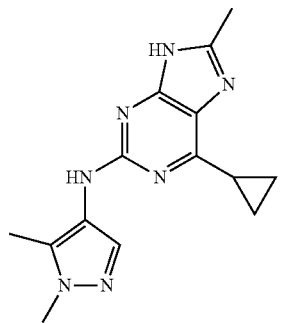 [SMILES: Cc1nc2c(C3CC3)nc(Nc3cnn(C)c3C)nc2[nH]1] C-33 | 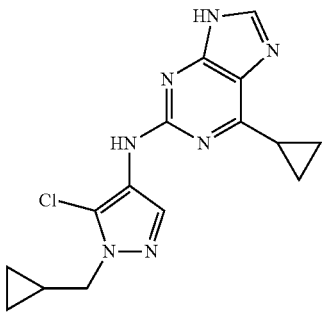 C-38 |
| 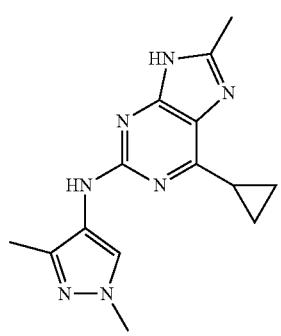 [SMILES: Cc1nc2c(C3CC3)nc(Nc3cn(C)nc3C)nc2[nH]1] C-34 | 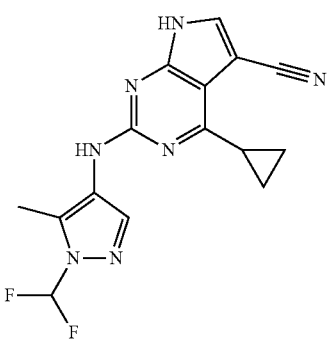 C-39 |
| 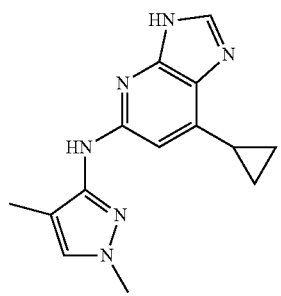 [SMILES: Cc1cn(C)nc1Nc1cc(C2CC2)c2nc[nH]c2n1] C-35 | 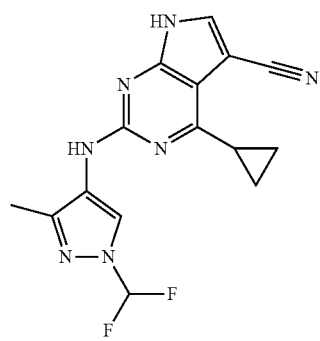 C-40 |
| 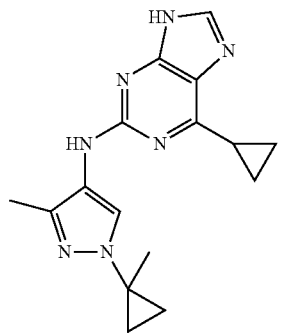 [SMILES: Cc1nn(C2(C)CC2)cc1Nc1nc(C2CC2)c2nc[nH]c2n1] C-36 | 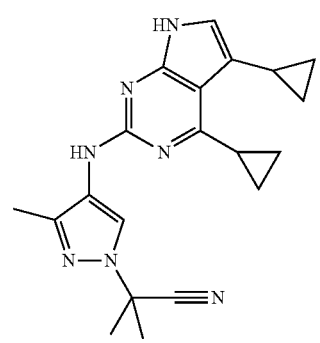 C-41 |
| 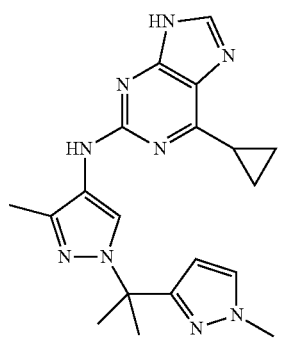 [SMILES: Cc1nn(C(C)(C)c2ccn(C)n2)cc1Nc1nc(C2CC2)c2nc[nH]c2n1] C-37 | 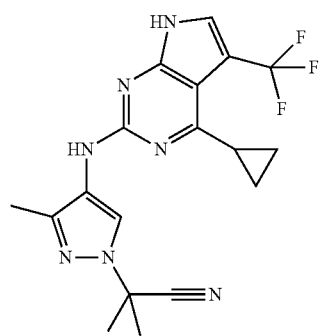 [SMILES: Cc1nn(C(C)(C)C#N)cc1Nc1nc(C2CC2)c2c(C(F)(F)F)c[nH]c2n1] C-42 |

TABLE C-1-continued
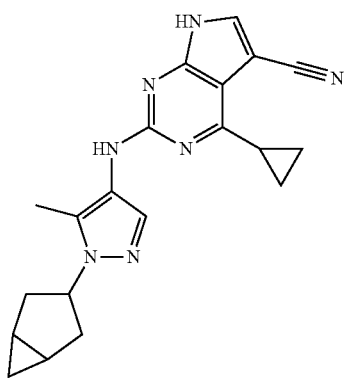 [SMILES: Cc1c(Nc2nc(C3CC3)c3c(C#N)c[nH]c3n2)cnn1C1CC2CC2C1]
C-43
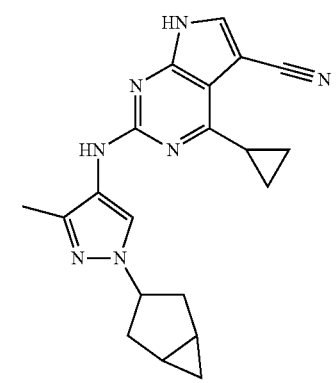 [SMILES: Cc1nn(C2CC3CC3C2)cc1Nc1nc(C2CC2)c2c(C#N)c[nH]c2n1]
C-44
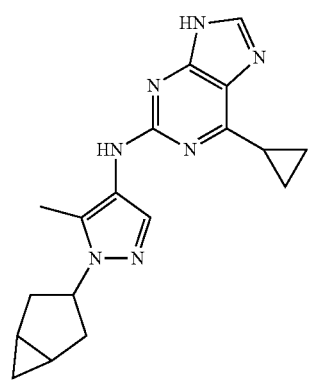 [SMILES: Cc1c(Nc2nc(C3CC3)c3nc[nH]c3n2)cnn1C1CC2CC2C1]
C-45
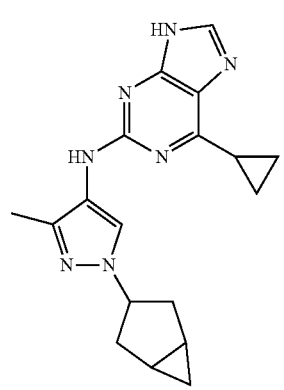 [SMILES: Cc1nn(C2CC3CC3C2)cc1Nc1nc(C2CC2)c2nc[nH]c2n1]
C-46
TABLE C-1-continued
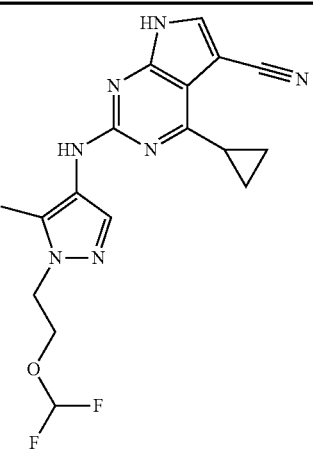
C-47

TABLE C-1-continued

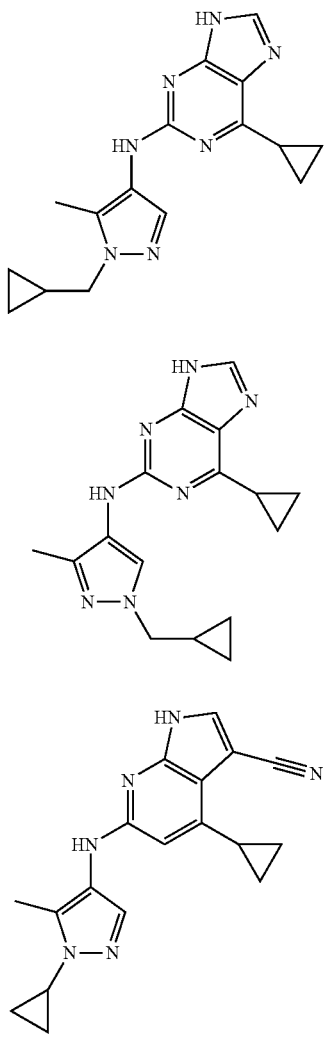

C-51

C-52

C-53

TABLE C-1-continued

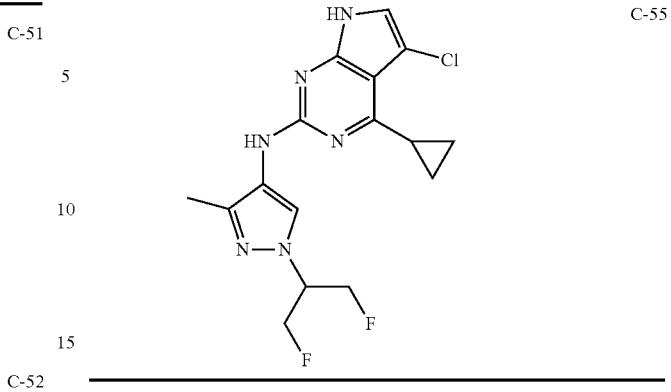

C-55

In another embodiment provided is a method for preparing a compound of formula (C-I), comprising coupling a compound of formula (C-a):

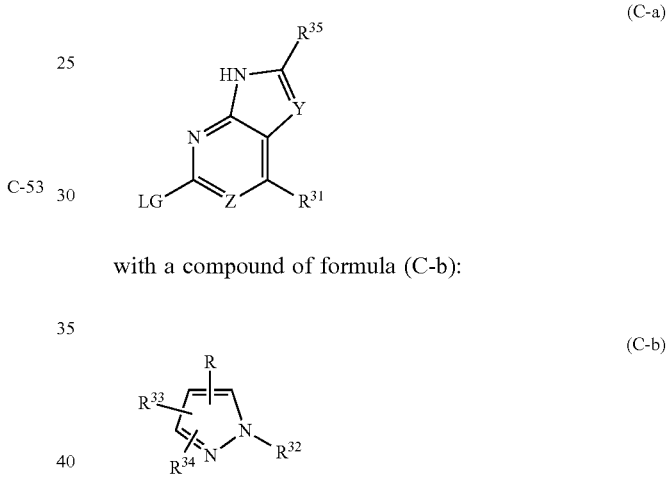

(C-a)

with a compound of formula (C-b):

(C-b)

under conditions to provide the compound of formula (C-I), wherein R is nitro or an optionally protected amino, and LG is a leaving group.

In one embodiment, provided is a compound of Formula (D-I):

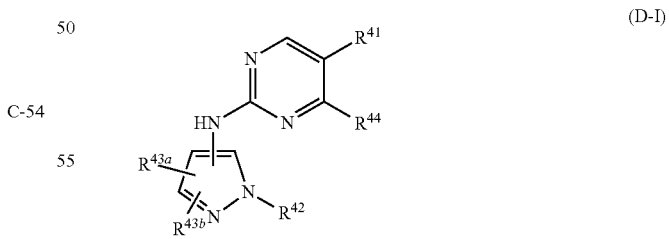

(D-I)

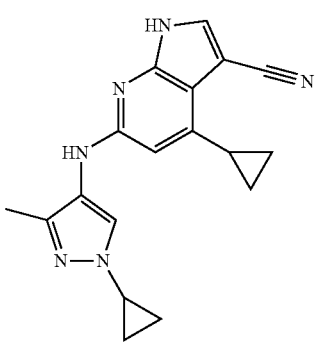 [SMILES: Cc1nn(C2CC2)cc1Nc1cc(C2CC2)c2c(C#N)c[nH]c2n1]

C-54 or a pharmaceutically acceptable salt, prodrug, stereoisomer, or a mixture of stereoisomers thereof, wherein:

$R^{41}$ is halo, cyano, $C_{1-6}$ alkyl, $C_{1-6}$ haloalkyl, $C_{1-6}$ alkoxy, $C_{1-6}$ haloalkoxy, cycloalkyl, cycloalkoxy, cycloalkylalkyl, cycloalkylalkoxy, or —C(O)$R^{45}$;

$R^{42}$ is:

a fused bicyclic ring system having a heterocyclyl or cycloalkyl fused to a heteroaryl, wherein the ring system is attached to the remainder of the molecule via the heterocyclyl or cycloalkyl and the ring system is independently optionally substituted with one or more halo, cyano, $C_{1-6}$ alkyl, $C_{1-6}$ haloalkyl, $C_{1-6}$ alkoxy, amino, $C_{1-6}$ hydroxyalkyl, $C_{1-6}$ alkoxyalkyl, $C_{1-6}$ cyanoalkyl, $C_{1-6}$ aminoalkyl, —S(O)$_2$(C$_{1-6}$ alkyl), —C$_{1-6}$ alkylene-S(O)$_2$(C$_{1-6}$ alkyl), —C(O)NR$^{46}$R$^{47}$, —NR$^{46}$C(O)R$^{47}$, —C$_{1-6}$ alkylene-C(O)NR$^{46}$R$^{47}$, —C$_{1-6}$ alkylene-NR$^{46}$C(O)R$^{47}$, —SO$_2$NR$^{46}$R$^{47}$, —NR$^{46}$SO$_2$R$^{47}$, —C$_{1-6}$ alkylene-SO$_2$NR$^{46}$R$^{47}$, —C$_{1-6}$ alkylene-NR$^{46}$SO$_2$R$^{47}$, —C(O)R$^{46}$, —OC(O)R$^{46}$, —C(O)$_2$R$^{46}$, —C$_{1-6}$ alkylene-C(O)R$^{46}$, —C$_{1-6}$ alkylene-OC(O)R$^{46}$, —C$_{1-6}$ alkylene-C(O)$_2$R$^{46}$, —O—C(O)NR$^{46}$R$^{47}$, —NR$^{46}$C(O)OR$^{47}$, —C$_{1-6}$ alkylene-O—C(O)NR$^{46}$R$^{47}$, —C$_{1-6}$ alkylene-NR$^{46}$C(O)OR$^{47}$, cycloalkyl, cycloalkylalkyl, heterocyclyl, heterocyclylalkyl, aryl, arylalkyl, heteroaryl, or heteroarylalkyl;

$C_{1-6}$ alkoxyalkyl substituted with one or more substituents independently selected from halo, amino, cyano, hydroxy, $C_{1-6}$ haloalkoxy, $C_{2-6}$alkenyl, $C_{2-6}$alkynyl, cyanoalkyl, —S(O)$_2$(C$_{1-6}$ alkyl), —C(O)NR$^{46}$R$^{47}$, —NR$^{46}$C(O)R$^{47}$, —SO$_2$NR$^{46}$R$^{47}$, —NR$^{46}$SO$_2$R$^{47}$, —C(O)R$^{46}$, —OC(O)R$^{46}$, —C(O)$_2$R$^{46}$, —O—C(O)NR$^{46}$R$^{47}$, —NR$^{46}$C(O)OR$^{47}$, cycloalkyl, cycloalkylalkyl, heterocyclyl, heterocyclylalkyl, aryl, arylalkyl, heteroaryl, or heteroarylalkyl;

$C_{1-6}$ haloalkyl substituted with one or more substituents independently selected from amino, cyano, hydroxy, $C_{1-6}$ alkoxy, $C_{1-6}$ haloalkoxy, $C_{2-6}$alkenyl, $C_{2-6}$alkynyl, cyanoalkyl, —S(O)$_2$(CH alkyl), —C(O)NR$^{46}$R$^{47}$, —NR$^{46}$C(O)R$^{47}$, —SO$_2$NR$^{46}$R$^{47}$, —NR$^{46}$SO$_2$R$^{47}$, —C(O)R$^{46}$, —OC(O)R$^{46}$, —C(O)$_2$R$^{46}$, —O—C(O)NR$^{46}$R$^{47}$, —NR$^{46}$C(O)OR$^{47}$, cycloalkyl, cycloalkylalkyl, heterocyclyl, heterocyclylalkyl, aryl, arylalkyl, heteroaryl, or heteroarylalkyl;

$C_{1-6}$ cyanoalkyl optionally substituted with one or more substituents independently selected from halo, amino, hydroxy, $C_{1-6}$ haloalkoxy, $C_{2-6}$ alkenyl, $C_{2-6}$ alkynyl, —S(O)$_2$(C$_{1-6}$ alkyl), —C(O)NR$^{46}$R$^{47}$, —NR$^{46}$C(O)R$^{47}$, —SO$_2$NR$^{46}$R$^{47}$, —NR$^{46}$SO$_2$R$^{47}$, —C(O)R$^{46}$, —OC(O)R$^{46}$, —C(O)$_2$R$^{46}$, —O—C(O)NR$^{46}$R$^{47}$, —NR$^{46}$C(O)OR$^{47}$, cycloalkyl, cycloalkylalkyl, heterocyclyl, heterocyclylalkyl, aryl, arylalkyl, heteroaryl, or heteroarylalkyl;

$C_{3-10}$ cycloalkyl substituted with one or more substituents independently selected from amino, $C_{2-6}$ alkenyl, $C_{2-6}$ alkynyl, cyanoalkyl, —S(C$_{1-6}$ alkyl), —S(O)(C$_{1-6}$ alkyl), —S(O)$_2$(C$_{1-6}$ alkyl), —C$_{1-6}$ alkylene-S(O)$_2$(C$_{1-6}$ alkyl), $C_{1-6}$ haloalkoxy, $C_{1-6}$ hydroxyalkyl, $C_{1-6}$ alkoxyalkyl substituted with one or more halo, cycloalkyl, cycloalkylalkyl, heterocyclyl, aryl, arylalkyl, heteroaryl, or heteroarylalkyl, wherein the heterocyclyl, heteroaryl or heteroarylalkyl are optionally substituted with one or more substituents independently selected from $C_{1-6}$ alkyl, $C_{1-6}$ haloalkyl, or halo; or —X—C(R$^{48}$)(R$^{49}$)(R$^{50}$), wherein:
X is $C_{1-6}$ alkylene optionally substituted with one or more halo;
R$^{48}$ and R$^{49}$, together with the carbon atom to which they are attached, form an optionally substituted $C_{3-10}$ cycloalkyl; and
R$^{50}$ is cyanoalkyl, $C_{1-6}$ alkoxyalkyl, $C_{2-6}$ alkenyl, $C_{2-6}$ alkynyl, —S(O)$_2$(C$_{1-6}$ alkyl), $C_{1-6}$ haloalkoxy, $C_{1-6}$ hydroxyalkyl, $C_{1-6}$ alkoxyalkyl, cycloalkyl, cycloalkylalkyl, heterocyclyl, heterocyclylalkyl, aryl, arylalkyl, heteroaryl, or heteroarylalkyl;

R$^{43a}$ and R$^{43b}$ are each independently H, halo, cyano, $C_{1-6}$ alkyl, $C_{1-6}$ haloalkyl, $C_{1-6}$ hydroxyalkyl, $C_{1-6}$ alkoxyalkyl, $C_{1-6}$ cyanoalkyl, $C_{1-6}$ aminoalkyl, —S(O)$_2$(C$_{1-6}$ alkyl), —C$_{1-6}$ alkylene-S(O)$_2$(C$_{1-6}$ alkyl), cycloalkyl, cycloalkylalkyl, heterocyclyl, heterocyclylalkyl, aryl, arylalkyl, heteroaryl, heteroarylalkyl, amido, or —C(O)R$^5$;

R$^{44}$ is —N(R$^{51}$)$_2$, —OR$^{51}$, or —SR$^{51}$;

each R$^{45}$ is independently $C_{1-6}$ alkyl, $C_{1-6}$ alkoxy, —N(R$^{52}$)$_2$, or heterocyclyl, wherein each $C_{1-6}$ alkyl, $C_{1-6}$ alkoxy, or heterocyclyl is optionally substituted;

each R$^{46}$ and R$^{47}$ is independently H, $C_{1-6}$ alkyl, $C_{2-6}$ alkenyl, $C_{2-6}$ alkynyl, cycloalkyl, heterocyclyl, aryl, heteroalkyl, or heteroaryl, wherein each $C_{1-6}$ alkyl, $C_{2-6}$ alkenyl, $C_{2-6}$ alkynyl, cycloalkyl, heterocyclyl, aryl, heteroalkyl, or heteroaryl is optionally substituted;

each R$^{51}$ is independently H, alkyl, $C_{2-6}$ alkenyl, $C_{2-6}$ alkynyl, $C_{1-6}$ haloalkyl, $C_{1-6}$ alkoxyalkyl, $C_{1-6}$ hydroxyalkyl, $C_{1-6}$ aminoalkyl, —C$_{1-6}$ alkylene-S(O)$_2$(C$_{1-6}$ alkyl), cycloalkyl optionally substituted with one or more $C_{1-6}$ alkyl, $C_{3-6}$ cycloalkylalkyl optionally substituted with one or more $C_{1-6}$ alkyl, heterocyclyl optionally substituted with one or more R$^{13}$, or heterocyclylalkyl optionally substituted with one or more R$^{53}$; or two R$^{51}$, together with die nitrogen to which they are attached, form a three- to six-membered heterocyclyl optionally substituted with one or more R$^{53}$;

each R$^{52}$ is independently H or optionally substituted $C_{1-6}$ alkyl;

each R$^{53}$ is independently $C_{1-6}$ alkyl, $C_{1-6}$ haloalkyl, halo, oxo, $C_{1-6}$ alkoxy, amino, —S(O)$_2$(C$_{1-6}$ alkyl), $C_{1-6}$ alkoxyalkyl, cyano, heterocyclyl, heterocyclylalkyl, $C_{3-6}$ cycloalkyl, $C_{3-6}$ cycloalkylalkyl, $C_{1-6}$ cycloalkylsulfonyl, —C(O)R$^{54}$, or —C$_{1-6}$alkylene-C(O)R$^{54}$;

each R$^{54}$ is independently $C_{1-6}$ alkyl, $C_{1-6}$ alkoxy, amino optionally substituted with halo, $C_{1-6}$ haloalkyl, $C_{1-6}$ hydroxyalkyl, hydroxy, $C_{1-6}$ alkoxyalkyl, $C_{1-6}$ cyanoalkyl, —C$_{1-6}$ alkylene-S(O)$_2$(C$_{1-6}$ alkyl), $C_{1-6}$ aminoalkyl, $C_{3-6}$ cycloalkyl, $C_{3-6}$ cycloalkylalkyl, heterocyclyl, or heterocyclylalkyl; and provided that when R$^{44}$ is —N(R$^{51}$)$_2$ or —OR$^{51}$, R$^{42}$ is not an unsubstituted $C_{1-6}$ cyanoalkyl.

In one embodiment, provided is a compound of Formula (D-I), or a pharmaceutically acceptable salt, prodrug, stereoisomer, or a mixture of stereoisomers thereof, wherein:

R$^{41}$ is halo, cyano, $C_{1-6}$ alkyl, $C_{1-6}$ haloalkyl, $C_{1-6}$ alkoxy, $C_{1-6}$ haloalkoxy, cycloalkyl, cycloalkoxy, cycloalkylalkyl, cycloalkylalkoxy, or —C(O)R$^{45}$:

R$^{42}$ is:
a fused bicyclic ring system having a heterocyclyl or cycloalkyl fused to a heteroaryl, wherein the ring system is attached to die remainder of die molecule via the heterocyclyl or cycloalkyl and the ring system is independently optionally substituted with one or more halo, cyano, $C_{1-6}$ alkyl, $C_{1-6}$ haloalkyl, $C_{1-6}$ alkoxy, amino, $C_{1-6}$ hydroxyalkyl, $C_{1-6}$ alkoxyalkyl, $C_{1-6}$ cyanoalkyl, $C_{1-6}$ aminoalkyl, —S(O)$_2$(C$_{1-6}$ alkyl), —C$_{1-6}$ alkylene-S(O)$_2$(C$_{1-6}$ alkyl), —C(O)NR$^{46}$R$^{47}$, —NR$^{46}$C(O)R$^{47}$, —C$_{1-6}$ alkylene-C(O)NR$^{46}$R$^{47}$, —C$_{1-6}$ alkylene-NR$^{46}$C(O)R$^{47}$, —SO$_2$NR$^{46}$R$^{47}$, —NR$^{46}$SO$_2$R$^{47}$, —C$_{1-6}$ alkylene-SO$_2$NR$^{46}$R$^{47}$, —C$_{1-6}$ alkylene-NR$^{46}$SO$_2$R$^{47}$, —C(O)R$^{46}$, —OC(O)R$^{46}$, —C(O)$_2$R$^{46}$, —C$_{1-6}$ alkylene-C(O)R$^{46}$, —C$_{1-6}$ alkylene-OC(O)R$^{46}$, —C$_{1-6}$ alkylene-C(O)$_2$R$^{46}$, —O—C(O)NR$^{46}$R$^{47}$, —NR$^{46}$C(O)OR$^{47}$, —C$_{1-6}$ alkylene-O—C(O)NR$^{46}$R$^{47}$, —C$_{1-6}$ alkylene-NR$^{46}$C (O)OR$^{47}$, cycloalkyl, cycloalkylalkyl, heterocyclyl, heterocyclylalkyl, aryl, arylalkyl, heteroaryl, or heteroarylalkyl;

C$_{1-6}$ alkoxyalkyl substituted with one or more halo, amino, cyano, hydroxy, C$_{1-6}$ haloalkoxy, C$_{2-6}$ alkenyl, C$_{1-6}$ alkynyl, cyanoalkyl, —S(O)$_2$(C$_{1-6}$ alkyl), —C(O)NR$^{46}$R$^{47}$, —NR$^{46}$C(O)R$^{47}$, —SO$_2$NR$^{46}$R$^{47}$, —NR$^{44}$SO$_2$R$^{47}$, —C(O)R$^{46}$, —C(O)R$^{46}$, —C(O)$_2$R$^{46}$, —O—C(O)NR$^{46}$R$^{47}$, —NR$^{46}$C(O)OR$^{4'}$, cycloalkyl, cycloalkylalkyl, heterocyclyl, heterocyclylalkyl, aryl, arylalkyl, heteroaryl, or heteroarylalkyl;

C$_{1-6}$ haloalkyl substituted with amino, cyano, hydroxy, C$_{1-6}$ alkoxy, C$_{1-6}$ haloalkoxy, C$_{2-6}$ alkenyl, C$_{1-6}$ alkynyl, cyanoalkyl, —S(O)$_2$(C$_{1-6}$ alkyl), —C(O)NR$^{46}$R$^{47}$, —NR$^{46}$C(O)R$^{47}$, —SO$_2$NR$^{46}$R$^{47}$, —NR$^{46}$SO$_2$R$^{47}$, —C(O)R$^{46}$, —OC(O)R$^{46}$, —C(O)$_2$R$^{46}$, —O—C(O)NR$^{46}$R$^{47}$, —NR$^{46}$C(O)OR$^{47}$, cycloalkyl, cycloalkylalkyl, heterocyclyl, heterocyclylalkyl, aryl, arylalkyl, heteroaryl, or heteroarylalkyl;

C$_{1-6}$ cyanoalkyl optionally substituted with one or more halo, amino, hydroxy, C$_{1-6}$ haloalkoxy, C$_{1-6}$ alkenyl, C$_{1-6}$ alkynyl, —S(O)$_2$(C$_{1-6}$ alkyl), —C(O)NR$^{46}$R$^{47}$, —NR$^{46}$C(O)R$^{47}$, —SO$_2$NR$^{46}$R$^{47}$, —NR$^{46}$SO$_2$R$^{47}$, —C(O)R$^{46}$, —C(O)R$^{46}$, —C(O)$_2$R$^{46}$, —O—C(O)NR$^{46}$R$^{47}$, —NR$^{46}$C(O)OR$^{47}$, cycloalkyl, cycloalkylalkyl, heterocyclyl, heterocyclylalkyl, aryl, arylalkyl, heteroaryl, or heteroarylalkyl;

C$_{3-10}$ cycloalkyl substituted with one or more amino, C$_{2-6}$ alkenyl, C$_{2-6}$ alkynyl, cyanoalkyl, —S(C$_{1-6}$ alkyl), —S(O)(C$_{1-6}$ alkyl), —S(O)$_2$(C$_{1-6}$ alkyl), —C$_{1-6}$ alkylene-S(O)$_2$(C$_{1-6}$ alkyl), C$_{1-6}$ haloalkoxy, C$_{1-6}$ hydroxyalkyl, C$_{1-6}$ alkoxyalkyl substituted with one or more halo, cycloalkyl, cycloalkylalkyl, heterocyclyl, aryl, arylalkyl, heteroaryl, or heteroarylalkyl; or —X—C(R$^{48}$)(R$^{49}$)(R$^{50}$), wherein:
X is C$_{1-6}$ alkylene optionally substituted with one or more halo;
R$^{48}$ and R$^{49}$, together with the carbon atom to which they are attached, form an optionally substituted C$_{3\text{-}m}$ cycloalkyl; and
R$^{50}$ is cyanoalkyl, C$_{1-6}$ alkoxyalkyl, C$_{2-6}$alkenyl, C$_{2-6}$alkynyl, —S(O)$_2$(C$_{1-6}$ alkyl), C$_{1-6}$ haloalkoxy, C$_{1-6}$ hydroxyalkyl, C$_{1-6}$ alkoxyalkyl, cycloalkyl, cycloalkylalkyl, heterocyclyl, heterocyclylalkyl, aryl, arylalkyl, heteroaryl, or heteroarylalkyl;

R$^{43a}$ and R$^{43b}$ are each independently H, halo, cyano, C$_{1-6}$ alkyl, C$_{1-6}$ haloalkyl, C$_{1-6}$ hydroxyalkyl, C$_{1-6}$ alkoxyalkyl, C$_{1-6}$ cyanoalkyl, C$_{1-6}$ aminoalkyl, —S(O)$_2$(C$_{1-6}$ alkyl), —C$_{1-6}$ alkylene-S(O)$_2$(C$_{1-6}$ alkyl), cycloalkyl, cycloalkylalkyl, heterocyclyl, heterocyclylalkyl, aryl, arylalkyl, heteroaryl, heteroarylalkyl, amido, or —C(O)R$^{45}$;

R$^{44}$ is —N(R$^{51}$)$_2$, —OR$^{51}$, and —SR$^{51}$;

each R$^{45}$ is independently C$_{1-6}$ alkyl, C$_{1-6}$ alkoxy, —N(R$^{52}$)$_2$, or heterocyclyl, wherein each C$_{1-6}$ alkyl, C$_{1-6}$ alkoxy, or heterocyclyl is optionally substituted;

each R$^{46}$ and R$^{47}$ is independently H, C$_{1-6}$ alkyl, C$_{2-6}$alkenyl, C$_{2-6}$alkynyl, cycloalkyl, heterocyclyl, aryl, heteroalkyl, or heteroaryl, wherein each C$_{1-6}$ alkyl, C$_{2-6}$ alkenyl, C$_{2-6}$ alkynyl, cycloalkyl, heterocyclyl, aryl, heteroalkyl, or heteroaryl is optionally substituted;

each R$^{51}$ is independently H, alkyl, C$_{2-6}$alkenyl, C$_{2-6}$alkynyl, haloalkyl, C$_{1-6}$ alkoxyalkyl, C$_{1-6}$ hydroxyalkyl, C$_{1-6}$ aminoalkyl, —C$_{1-6}$ alkylene-S(O)$_2$(C$_{1-6}$ alkyl), C$_{3-6}$ cycloalkyl optionally substituted with one or more C$_{1-6}$ alkyl, C$_{3-6}$ cycloalkylalkyl optionally substituted with one or more C$_{1-6}$ alkyl, heterocyclyl optionally substituted with one or more R$^{53}$, or heterocyclylalkyl optionally substituted with one or more R$^{53}$; or two R$^{51}$, together with die nitrogen to which they are attached, form a three- to six-membered heterocyclyl optionally substituted with one or more R$^{53}$;

each R$^{52}$ is independently H or optionally substituted C$_{1-6}$ alkyl;

each R$^{53}$ is independently C$_{1-6}$ alkyl, C$_{1-6}$ haloalkyl, halo, oxo, C$_{1-6}$ alkoxy, amino, —S(O)$_2$(C$_{1-6}$ alkyl), C$_{1-6}$ alkoxyalkyl, cyano, heterocyclyl, heterocyclylalkyl, C$_{3-6}$ cycloalkyl, C$_{3-6}$ cycloalkylalkyl, C$_{1-6}$ cycloalkylsulfonyl, —C(O)R$^{54}$, or —C$_{1-6}$alkylene-C(O)R$^{54}$;

each R$^{54}$ is independently C$_{1-6}$ alkyl, C$_{1-6}$ alkoxy, amino optionally substituted with halo, C$_{1-6}$ haloalkyl, C$_{1-6}$ hydroxyalkyl, hydroxy, C$_{1-6}$ alkoxyalkyl, C$_{1-6}$ cyanoalkyl, —C$_{1-6}$ alkylene-S(O)$_2$(C$_{1-6}$ alkyl), C$_{1-6}$ aminoalkyl, C$_{3-6}$ cycloalkyl, C$_{3-6}$ cycloalkylalkyl, heterocyclyl, or heterocyclylalkyl; and provided that when R$^{44}$ is —N(R$^{51}$)$_2$ or —OR$^{51}$, R$^{42}$ is not C$_{1-6}$ cyanoalkyl.

Also provided is a compound having the formula (D-Ia):

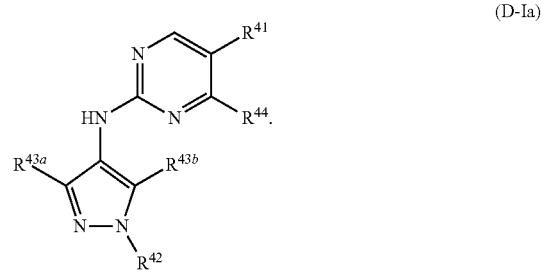

(D-Ia)

Also provided is a compound having the formula (D-Ib):

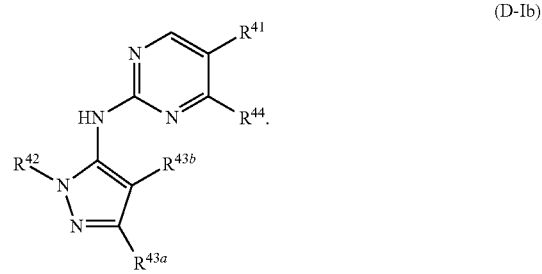

(D-Ib)

In certain embodiments, R$^{44}$ is —N(R$^{51}$)$_2$, and each R$^{51}$ is independently H or C$_{1-6}$ alkyl. In certain embodiments, R$^{44}$ is —N(R$^{51}$)$_2$, and one R$^{51}$ is H and the other R$^{51}$ is C$_{1-3}$ alkyl.

In certain embodiments, R$^{41}$ is halo, cyano, C$_{1-6}$ alkyl, or C$_{1-6}$ haloalkyl. In certain embodiments, R$^{41}$ is C$_{1-6}$ haloalkyl. In certain embodiments, R$^{41}$ is C$_{1-6}$ fluoroalkyl. In certain embodiments, R$^{41}$ is trifluoromethyl. In certain embodiments, R$^{41}$ is cyano. In certain embodiments, R$^{41}$ is halo. In certain embodiments, R$^{41}$ is chloro.

In certain embodiments, one of R$^{43a}$ or R$^{43b}$ is H, and the other of R$^{43a}$ or R$^{43b}$ is halo, cyano, C$_{1-6}$ alkyl, C$_{1-6}$ haloalkyl, C$_{1-6}$ hydroxyalkyl, C$_{1-6}$ alkoxyalkyl, C$_{1-6}$ cyanoalkyl, C$_{1-6}$ aminoalkyl, —S(O)$_2$(C$_{1-6}$ alkyl), —C$_{1-6}$ alkylene-S(O)$_2$ (C$_{1-6}$ alkyl), cycloalkyl, cycloalkylalkyl, heterocyclyl, heterocyclylalkyl, aryl, arylalkyl, heteroaryl, heteroarylalkyl, amido, or —C(O)R$^{45}$.

In certain embodiments, one of $R^{43a}$ or $R^{43b}$ is halo, $C_{1-6}$ alkyl, or $C_{1-6}$ cyanoalkyl. In certain embodiments, $R^{43a}$ is H, and $R^{43b}$ is halo, $C_{1-6}$ alkyl, or $C_{1-6}$ cyanoalkyl. In certain embodiments, alkyl is methyl. In certain embodiments, $C_{1-6}$ cyanoalkyl is 2-cyano-prop-2-yl.

In certain embodiments, $R^{43b}$ is hydrogen.

In certain embodiments, $R^{42}$ is:

$C_{1-6}$ alkoxyalkyl substituted with one or more halo, amino, cyano, hydroxy, $C_{1-6}$ haloalkoxy, $C_{2-6}$ alkenyl, $C_{2-6}$ alkynyl, cyanoalkyl, —S(O)$_2$(C$_{1-6}$ alkyl), —C(O)NR$^{46}$R$^{47}$, —NR$^{46}$C(O)R$^{47}$, —SO$_2$NR$^{46}$R$^{47}$, —NR$^{46}$SO$_2$R$^{47}$, —C(O)R$^{46}$, —OC(O)R$^{46}$, —C(O)$_2$R$^{46}$, —O—C(O)NR$^{46}$R$^{47}$, —NR$^{46}$C(O)OR$^{47}$, cycloalkyl, cycloalkylalkyl, heterocyclyl, heterocyclylalkyl, aryl, arylalkyl, heteroaryl, or heteroarylalkyl;

$C_{1-6}$ haloalkyl substituted with amino, cyano, hydroxy, $C_{1-6}$ alkoxy, $C_{1-6}$ haloalkoxy, $C_{2-6}$ alkenyl, $C_{2-6}$ alkynyl, cyanoalkyl, —S(O)$_2$(C$_{1-6}$ alkyl), —C(O)NR$^{46}$R$^{47}$, —NR$^{46}$C(O)R$^{47}$, —SO$_2$NR$^{46}$R$^{47}$, —NR$^{46}$SO$_2$R$^{47}$, —C(O)R$^{46}$, —OC(O)R$^{46}$, —C(O)$_2$R$^{46}$, —O—C(O)NR$^{46}$R$^{47}$, —NR$^{46}$C(O)OR$^{47}$, cycloalkyl, cycloalkylalkyl, heterocyclyl, heterocyclylalkyl, aryl, arylalkyl, heteroaryl, or heteroarylalkyl;

$C_{1-6}$ cyanoalkyl optionally substituted with one or more halo, amino, hydroxy, $C_{1-6}$ haloalkoxy, $C_{2-6}$ alkenyl, $C_{2-6}$ alkynyl, —S(O)$_2$(C$_{1-6}$ alkyl), —C(O)NR$^{46}$R$^{47}$, —NR$^{46}$C(O)R$^{47}$, —SO$_2$NR$^{46}$R$^{47}$, —NR$^{46}$SO$_2$R$^{47}$, —C(O)R$^{46}$, —OC(O)R$^{46}$, —C(O)$_2$R$^{46}$, —O—C(O)NR$^{46}$R$^{47}$, —NR$^{46}$C(O)OR$^{47}$, cycloalkyl, cycloalkylalkyl, heterocyclyl, heterocyclylalkyl, aryl, arylalkyl, heteroaryl, or heteroarylalkyl;

$C_{3-10}$ cycloalkyl substituted with one or more amino, $C_{2-6}$ alkenyl, $C_{2-6}$ alkynyl, cyanoalkyl, —S(C$_{1-6}$ alkyl), —S(O)(C$_{1-6}$ alkyl), —S(O)$_2$(C$_{1-6}$ alkyl), —CH, alkylene-S(O)$_2$(C$_{1-6}$ alkyl), $C_{1-6}$ haloalkoxy, $C_{1-6}$ hydroxyalkyl, $C_{1-6}$ alkoxyalkyl substituted with one or more halo, cycloalkyl, cycloalkylalkyl, heterocyclyl, aryl, arylalkyl, heteroaryl, or heteroarylalkyl; or

—X—C(R$^{48}$)(R$^{49}$)(R$^{50}$).

In certain embodiments, $R^{42}$ is:

$C_{1-6}$ alkoxyalkyl substituted with one or more substituents independently selected from halo, amino, cyano, hydroxy, haloalkoxy, $C_{2-6}$ alkenyl, $C_{2-6}$ alkynyl, cyanoalkyl, —S(O)$_2$ (C$_{1-6}$ alkyl), —C(O)NR$^{46}$R$^{47}$, —NR$^{46}$C(O)R$^{47}$, —SO$_2$NR$^{46}$R$^{47}$, —NR$^{46}$SO$_2$R$^{47}$, —C(O)R$^{46}$, —OC(O)R$^{46}$, —C(O)$_2$R$^{46}$, —O—C(O)NR$^{46}$R$^{47}$, —NR$^{44}$C(O)OR$^{47}$, cycloalkyl, cycloalkylalkyl, heterocyclyl, heterocyclylalkyl, aryl, arylalkyl, heteroaryl, or heteroarylalkyl;

$C_{1-6}$ haloalkyl substituted with one or more substituents independently selected from amino, cyano, hydroxy, $C_{1-6}$ alkoxy, $C_{1-6}$ haloalkoxy, $C_{2-6}$ alkenyl, $C_{2-6}$ alkynyl, cyanoalkyl. —S(O)$_2$(C$_{1-6}$ alkyl), —C(O)NR$^{46}$R$^{47}$, —NR$^{46}$C(O)R$^{47}$, —SO$_2$NR$^{46}$R$^{47}$, —NR$^{46}$SO$_2$R$^{47}$, —C(O)R$^{46}$, —OC(O)R$^{46}$, —C(O)$_2$R$^{41'}$, —O—C(O)NR$^{46}$R$^{47}$, —NR$^{46}$C(O)OR$^{47}$, cycloalkyl, cycloalkylalkyl, heterocyclyl, heterocyclylalkyl, aryl, arylalkyl, heteroaryl, or heteroarylalkyl;

$C_{1-6}$ cyanoalkyl optionally substituted with one or more substituents independently selected from halo, amino, hydroxy, $C_{1-6}$ haloalkoxy, $C_{2-6}$ alkenyl, $C_{2-6}$ alkynyl, —S(O)$_2$ (C$_{1-6}$ alkyl), —C(O)NR$^{46}$R$^{47}$, —NR$^{46}$C(O)R$^{47}$, —SO$_2$NR$^{46}$R$^{47}$, —NR$^{46}$SO$_2$R$^{47}$, —C(O)R$^{46}$, —OC(O)R$^{46}$, —C(O)$_2$R$^{46}$, —O—C(O)NR$^{46}$R$^{47}$, —NR$^{46}$C(O)OR$^{47}$, cycloalkyl, cycloalkylalkyl, heterocyclyl, heterocyclylalkyl, aryl, arylalkyl, heteroaryl, or heteroarylalkyl;

$C_{3-10}$ cycloalkyl substituted with one or more substituents independently selected from amino, $C_{2-6}$ alkenyl, $C_{2-6}$ alkynyl, cyanoalkyl, —S(C$_{1-6}$ alkyl), —S(O)(C$_{1-6}$ alkyl), —S(O)$_2$ (C$_{1-6}$ alkyl), —CH, alkylene-S(O)$_2$(C$_{1-6}$ alkyl), $C_{1-6}$ haloalkoxy, $C_{1-6}$ hydroxyalkyl, $C_{1-6}$ alkoxyalkyl substituted with one or more halo, cycloalkyl, cycloalkylalkyl, heterocyclyl, aryl, arylalkyl, heteroaryl, or heteroarylalkyl, wherein the heterocyclyl, heteroaryl or heteroarylalkyl are optionally substituted with one or more substituents independently selected from alkyl, $C_{1-6}$ haloalkyl, or halo; or

—X—C(R$^{48}$)(R$^{49}$)(R$^{50}$).

In certain embodiments, $R^{47}$ is:

$C_{1-6}$ alkoxyalkyl substituted with one to three substituents independently selected from halo, amino, cyano, hydroxy, $C_{1-6}$ haloalkoxy, $C_{2-6}$ alkenyl, $C_{2-6}$ alkynyl, cyanoalkyl, —S(O)$_2$(C$_{1-6}$ alkyl), —C(O)NR$^{46}$R$^{47}$, —NR$^{46}$C(O)R$^{47}$, —SO$_2$NR$^{46}$R$^{47}$, —NR$^{46}$SO$_2$R$^{47}$, —C(O)R$^{46}$, —OC(O)R$^{46}$, —C(O)$_2$R$^{46}$, —O—C(O)NR$^{46}$R$^{47}$, —NR$^{46}$C(O)OR$^{47}$, cycloalkyl, cycloalkylalkyl, heterocyclyl, heterocyclylalkyl, aryl, arylalkyl, heteroaryl, or heteroarylalkyl;

$C_{1-6}$ haloalkyl substituted with one to three substituents independently selected from amino, cyano, hydroxy, $C_{1-6}$ alkoxy, $C_{1-6}$ haloalkoxy, $C_{2-6}$ alkenyl, $C_{2-6}$ alkynyl, cyanoalkyl, —S(O)$_2$(C$_{1-6}$ alkyl), —C(O)NR$^{46}$R$^{47}$, —NR$^{46}$C(O)R$^{47}$, —SO$_2$NR$^{46}$R$^{47}$, —NR$^{46}$SO$_2$R$^{47}$, —C(O)R$^{46}$, —OC(O)R$^{46}$, —C(O)$_2$R$^{46}$, —O—C(O)NR$^{46}$R$^{47}$, —NR$^{46}$C(O)OR$^{47}$, cycloalkyl, cycloalkylalkyl, heterocyclyl, heterocyclylalkyl, aryl, arylalkyl, heteroaryl, or heteroarylalkyl;

$C_{1-6}$ cyanoalkyl optionally substituted with one to three substituents independently selected from halo, amino, hydroxy, $C_{1-6}$ haloalkoxy, $C_{2-6}$ alkenyl, $C_{2-6}$ alkynyl, —S(O)$_2$ (C$_{1-6}$ alkyl), —C(O)NR$^{46}$R$^{47}$, —NR$^{46}$C(O)R$^{47}$, —SO$_2$NR$^{46}$R$^{47}$, —NR$^{46}$SO$_2$R$^{47}$, —C(O)R$^{46}$, —OC(O)R$^{46}$, —C(O)$_2$R$^{46}$, —O—C(O)NR$^{46}$R$^{47}$, —NR$^{46}$C(O)OR$^{47}$, cycloalkyl, cycloalkylalkyl, heterocyclyl, heterocyclylalkyl, aryl, arylalkyl, heteroaryl, or heteroarylalkyl;

$C_{3-10}$ cycloalkyl substituted with one to three substituents independently selected from amino, $C_{2-6}$ alkenyl, $C_{2-6}$ alkynyl, cyanoalkyl, —S(C$_{1-6}$ alkyl), —S(O)(C$_{1-6}$ alkyl), —S(O)$_2$ (C$_{1-6}$ alkyl), —C$_{1-6}$ alkylene-S(O)$_2$(C$_{1-6}$ alkyl), $C_{1-6}$ haloalkoxy, $C_{1-6}$ hydroxyalkyl, $C_{1-6}$ alkoxyalkyl substituted with one or three halo, cycloalkyl, cycloalkylalkyl, heterocyclyl, aryl, arylalkyl, heteroaryl, or heteroarylalkyl, wherein die heterocyclyl, heteroaryl or heteroarylalkyl are optionally substituted with one to three substituents independently selected from $C_{1-6}$ alkyl, $C_{1-6}$ haloalkyl, or halo; or —X—C(R$^{48}$)(R$^{49}$)(R$^{50}$), wherein:

X is $C_{1-6}$ alkylene optionally substituted with one to three halo;

$R^{48}$ and $R^{49}$, together with the carbon atom to which they are attached, form an optionally substituted $C_{3-10}$ cycloalkyl; and $R^{50}$ is cyanoalkyl, $C_{1-6}$ alkoxyalkyl, $C_{2-6}$ alkenyl, $C_{2-6}$ alkynyl, —S(O)$_2$(C$_{1-6}$ alkyl), $C_{1-6}$ haloalkoxy, $C_{1-6}$ hydroxyalkyl, $C_{1-6}$ alkoxyalkyl, cycloalkyl, cycloalkylalkyl, heterocyclyl, heterocyclylalkyl, aryl, arylalkyl, heteroaryl, or heteroarylalkyl.

In certain embodiments, $R^{42}$ is $C_{1-6}$ alkoxyalkyl substituted with one or more substituents independently selected from halo, amino, cyano, hydroxy, $C_{1-6}$ haloalkoxy, $C_{2-6}$ alkenyl, $C_{2-6}$ alkynyl, cyanoalkyl. —S(O)$_2$(C$_{1-6}$ alkyl), —C(O)NR$^{46}$R$^{47}$, —NR$^{4<}$ C(O)R$^{47}$, —SO$_2$NR$^{46}$R$^{47}$, —NR$^{46}$SO$_2$R$^{47}$, —C(O)R$^{46}$, —OC(O)R$^{46}$, —C(O)$_2$R$^{46}$, —O—C(O)NR$^{46}$R$^{47}$, —NR$^{46}$C(O)OR$^{47}$, cycloalkyl, cycloalkylalkyl, heterocyclyl, heterocyclylalkyl, aryl, arylalkyl, heteroaryl, or heteroarylalkyl.

In certain embodiments, $R^{42}$ is $C_{1-6}$ alkoxyalkyl substituted with one to three substituents independently selected from halo, amino, cyano, hydroxy, $C_{1-6}$ haloalkoxy, $C_{2-6}$ alkenyl, $C_{2-4}$ alkynyl, cyanoalkyl, —$S(O)_2(C_{1-6}$ alkyl), —$C(O)NR^{46}R^{47}$, —$NR^{46}C(O)R^{47}$, —$SO_2NR^{46}R^{47}$, —$NR^{46}SO_2R^{47}$, —$C(O)R^{46}$, —$OC(O)R^{46}$, —$C(O)_2R^{46}$, —$O$—$C(O)NR^{46}R^{47}$, —$NR^{46}C(O)OR^{47}$, cycloalkyl, cycloalkylalkyl, heterocyclyl, heterocyclylalkyl, aryl, arylalkyl, heteroaryl, or heteroarylalkyl.

In certain embodiments, $R^{42}$ is $C_{1-6}$ alkoxyalkyl substituted with one or more halo. In certain embodiments, $R^{42}$ is $C_{1-6}$ alkoxyalkyl substituted with one to three fluoro. In certain embodiments, $R^{42}$ is $C_{1-6}$ haloalkyl substituted with one or more substituents independently selected from amino, cyano, hydroxy, $C_{1-6}$ alkoxy, $C_{1-6}$ haloalkoxy, $C_{2-6}$alkenyl, $C_{2-6}$alkynyl, cyanoalkyl, —$S(O)_2(C_{1-6}$ alkyl), —$C(O)NR^{46}R^{47}$, —$NR^{46}C(O)R^{47}$, —$SO_2NR^{46}R^{47}$, —$NR^{46}SO_2R^{47}$, —$C(O)R^{46}$, —$OC(O)R^{46}$, —$C(O)_2R^{46}$, —$O$—$C(O)NR^{46}R^{47}$, —$NR^{46}C(O)OR^{47}$, cycloalkyl, cycloalkylalkyl, heterocyclyl, heterocyclylalkyl, aryl, arylalkyl, heteroaryl, or heteroarylalkyl.

In certain embodiments, $R^{42}$ is $C_{1-6}$ haloalkyl substituted with one to three substituents independently selected from amino, cyano, hydroxy, $C_{1-6}$ alkoxy, $C_{1-6}$ haloalkoxy, $C_{2-6}$alkenyl, $C_{2-6}$ alkynyl, cyanoalkyl. —$S(O)_2(C_{1-6}$ alkyl), —$C(O)NR^{46}R^{47}$, —$NR^{4<}$, $C(O)R^{47}$, —$SO_2NR^{46}R^{47}$, —$NR^{46}SO_2R^{47}$, —$C(O)R^{46}$, —$OC(O)R^{46}$, —$C(O)_2R^{46}$, —$O$—$C(O)NR^{46}R^{47}$, —$NR^{46}C(O)OR^{47}$, cycloalkyl, cycloalkylalkyl, heterocyclyl, heterocyclylalkyl, aryl, arylalkyl, heteroaryl, or heteroarylalkyl.

In certain embodiments, $R^{42}$ is $C_{1-6}$ haloalkyl substituted with —$C(O)NR^{46}R^{47}$ or cyano. In certain embodiments, $R^{42}$ is $C_{1-3}$ haloalkyl substituted with —$C(O)NR^{46}R^{47}$. In certain embodiments, $R^{42}$ is $C_{1-3}$ haloalkyl substituted with cyano.

In certain embodiments, $R^{42}$ is $C_{3-6}$ cycloalkyl substituted with one or more cyanoalkyl, —$S(C_{1-6}$ alkyl), —$S(O)(C_{1-6}$ alkyl), —$S(O)_2(C_{1-6}$ alkyl), $C_{1-6}$ haloalkoxy, $C_{1-3}$ alkoxyalkyl substituted with one or more halo, or heteroaryl.

In certain embodiments, $R^{42}$ is $C_{3-6}$ cycloalkyl substituted with one or more substituents independently selected from cyanoalkyl, —$S(C_{1-6}$ alkyl), —$S(O)(C_{1-6}$ alkyl), —$S(O)_2$ ($C_{1-6}$ alkyl), $C_{1-6}$ haloalkoxy, $C_{1-3}$ alkoxyalkyl substituted with one or more halo, heterocyclyl, or heteroaryl, wherein the heterocyclyl or heteroaryl is optionally substituted with one or more substituents independently selected from $C_{1-6}$ alkyl, $C_{1-6}$ haloalkyl, or halo.

In certain embodiments, $R^{42}$ is $C_{3-6}$ cycloalkyl substituted with one to three substituents independently selected from cyanoalkyl, —$S(C_{1-4}$ alkyl), —$S(O)(C_{1-6}$ alkyl), —$S(O)_2$ ($C_{1-6}$ alkyl), $C_{1-6}$ haloalkoxy, $C_{1-3}$ alkoxyalkyl substituted with one to three halo, heterocyclyl, or heteroaryl, wherein the heterocyclyl or heteroaryl is optionally substituted with one to three substituents independently selected from $C_{1-6}$ alkyl, $C_{1-6}$ haloalkyl, or halo.

In certain embodiments, $R^{42}$ is a fused bicyclic ring system having a heterocyclyl fused to a heteroaryl, wherein the ring system is attached to the remainder of the molecule via the heterocyclyl. In certain embodiments, $R^{42}$ is a fused bicyclic ring system having a cycloalkyl fused to a heteroaryl, wherein the ring system is attached to the remainder of the molecule via the cycloalkyl.

In certain embodiments, $R^{42}$ is a fused bicyclic ring system having a heterocyclyl fused to a heteroaryl selected from the group consisting of:

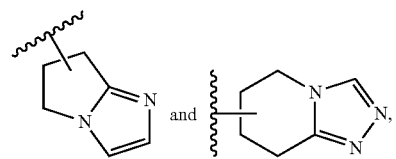

each of which is optionally substituted with $C_{1-3}$ alkyl, and wherein the wavy line indicates die point of attachment to die remainder of die molecule. In certain embodiments, $C_{1-3}$ alkyl is methyl.

In certain embodiments, $R^{42}$ is a fused bicyclic ring system having a heterocyclyl fused to a heteroaryl selected from the group consisting of:

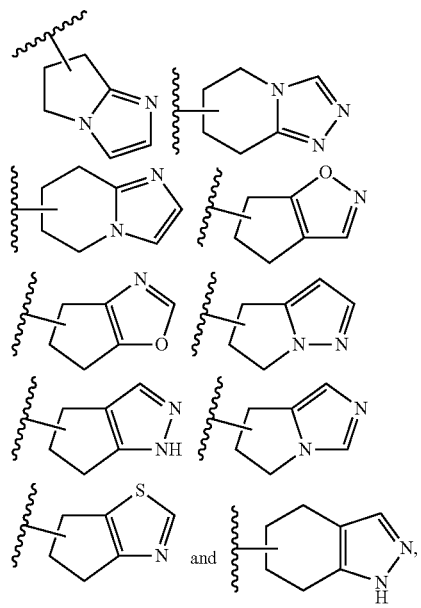

each of which is optionally substituted with one to three substituents independently selected from $C_{1-3}$ alkyl or halo, and wherein the wavy line indicates the point of attachment to the remainder of die molecule. In certain embodiments, $C_{1-3}$ alkyl is methyl.

In certain embodiments, $R^{42}$ is a fused bicyclic ring system having a heterocyclyl fused to a heteroaryl selected from the group consisting of:

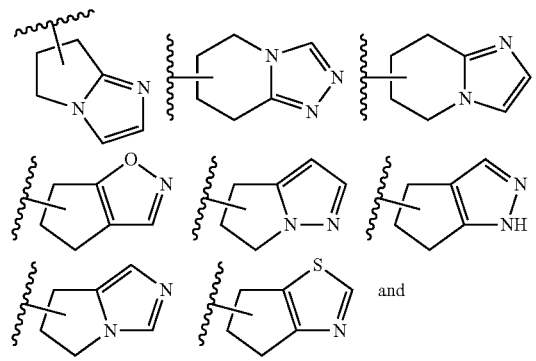

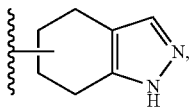

each of which is optionally substituted with one to three substituents independently selected from $C_{1-3}$ alkyl or halo, and wherein the wavy line indicates the point of attachment to the remainder of die molecule. In certain embodiments, $C_{1-3}$ alkyl is methyl.

In certain embodiments, $R^{42}$ is a fused bicyclic ring system having a heterocyclyl fused to a heteroaryl selected from the group consisting of:

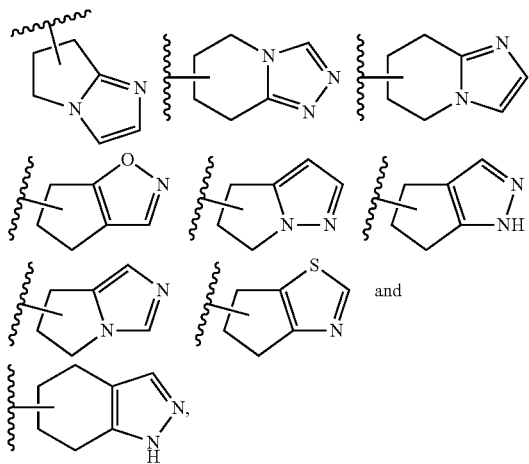

and each of which is optionally substituted with one to three $C_{1-3}$ alkyl, and wherein the wavy line indicates the point of attachment to the remainder of the molecule. In certain embodiments, $C_{1-3}$ alkyl is methyl.

Also provided is a compound having the formula (D-II):

(D-II)

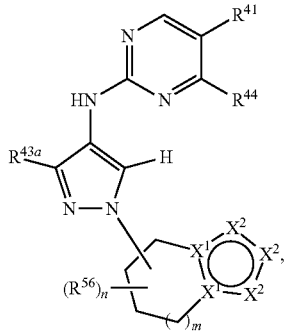

wherein each $X^1$ is independently C or N;
each $X^2$ is independently $CR^{55}$, N, $NR^{55}$, O, or S,
each $R^{55}$ and $R^{56}$ is independently H, halo, cyano, $C_{1-6}$ alkyl, $C_{1-6}$ haloalkyl, $C_{1-6}$ alkoxy, amino, $C_{1-6}$ hydroxyalkyl, $C_{1-6}$ alkoxyalkyl, $C_{1-6}$ cyanoalkyl, $C_{1-6}$ aminoalkyl, $-S(O)_2$ ($C_{1-6}$ alkyl), $-C_{1-6}$ alkylene-$S(O)_2(C_{1-6}$ alkyl), $-C(O)NR^{46}R^{47}$, $-NR^{46}C(O)R^{47}$, $-C_{1-6}$ alkylene-$C(O)NR^{46}R^{47}$, $-C_{1-6}$ alkylene-$NR^{46}C(O)R^{47}$, $-SO_2NR^{46}R^{47}$, $-NR^{46}SO_2R^{47}$, $-C_{1-6}$ alkylene-$SO_2NR^{46}R^{47}$, $-C_{1-6}$ alkylene-$NR^{46}SO_2R^{47}$, $-C(O)R^{46}$, $-OC(O)R^{46}$, $-C(O)_2R^{46}$, $-C_{1-6}$ alkylene-$C(O)R^{46}$, $-C_{1-6}$ alkylene-$OC(O)R^{46}$, $-C_{1-6}$ alkylene-$C(O)_2R^{46}$, $-O-C(O)NR^{46}R^{47}$, $-NR^{46}C(O)OR^{47}$, $-C_{1-6}$ alkylene-O—$C(O)NR^{46}R^{47}$, $-C_{1-6}$ alkylene-$NR^{46}C(O)OR^{47}$, cycloalkyl, cycloalkylalkyl, heterocyclyl, heterocyclylalkyl, aryl, arylalkyl, heteroaryl, or heteroarylalkyl;

m is 0 or 1; and n is 0, 1, 2 or 3.

The remaining variables of formula (D-II) are as defined herein. Also provided is a compound having the formula (D-II) or a pharmaceutically acceptable salt, prodrug, stereoisomer, or a mixture of stereoisomers thereof.

In some embodiments, at least one $X^1$ or $X^2$ is a heteroatom.

Also provided is a compound having the formula (D-IIa):

(D-IIa)

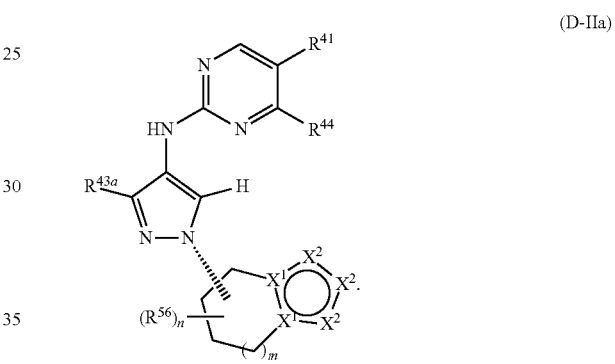

Also provided is a compound having the formula (D-IIb):

(D-IIb)

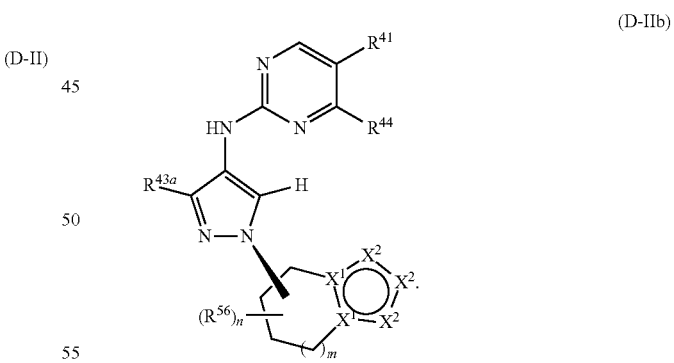

In certain embodiments

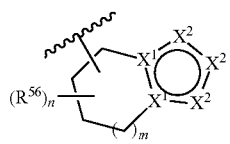

is:
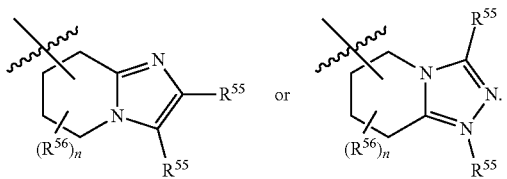
In certain embodiments
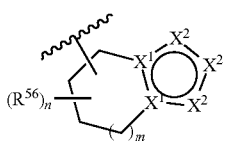
is:
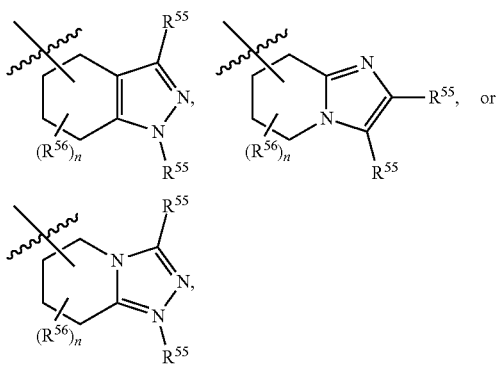
In certain embodiments,
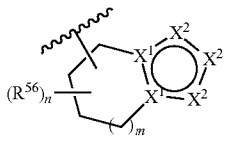
is selected from:
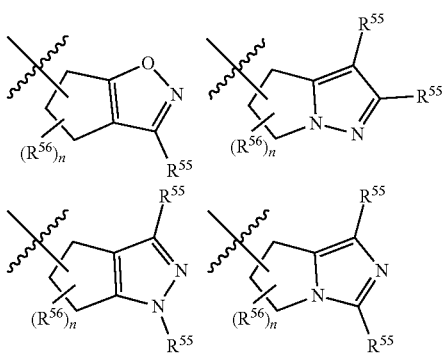
-continued
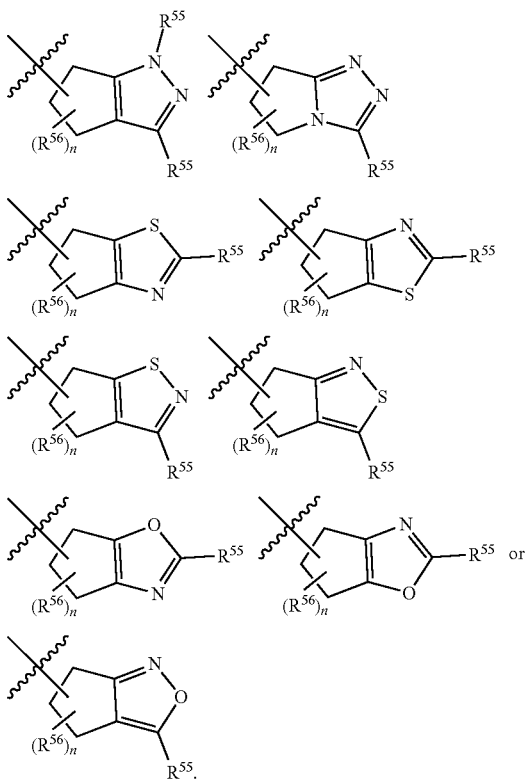
In certain embodiments,
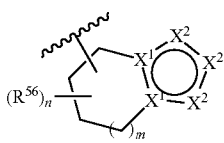
is:
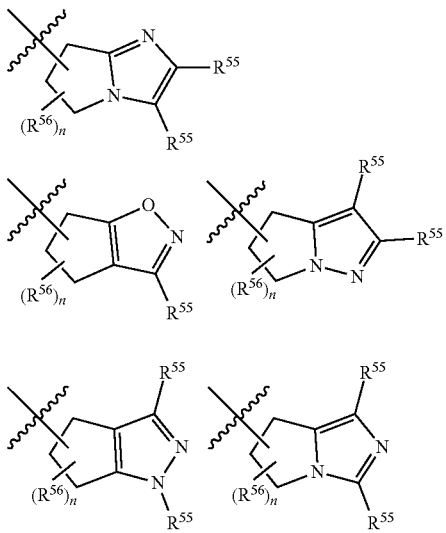

-continued

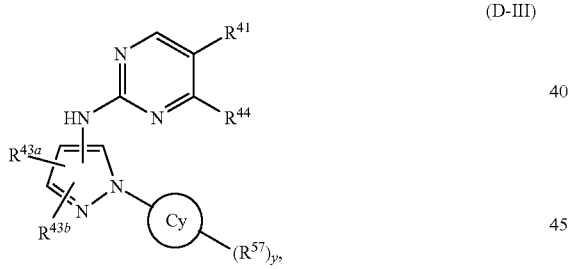

In some embodiments, $R^{42}$ is not quinuclidinyl, quinolinyl, isoquinolinyl, benzimidazolyl, benzothiazolidinyl, benzoxazolyl, dihydroquinolinyl, dihydroisoquinolinyl, tetrahydroquinolinyl, or tetrahydroisoquinolinyl.

Also provided is a compound having the formula (D-III):

(D-III)

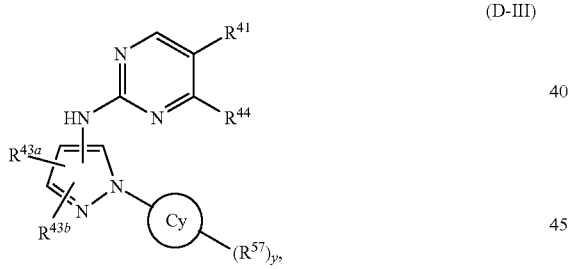

or a pharmaceutically acceptable salt, prodrug, stereoisomer, or a mixture of stereoisomers thereof, wherein:
Cy is $C_{3-10}$ cycloalkyl;
y is 1, 2, or 3;
each $R^5$, is independently selected from amino, $C_{2-6}$ alkenyl, $C_{2-6}$ alkynyl, cyanoalkyl, —S($C_{1-6}$ alkyl), —S(O)($C_{1-6}$ alkyl), —S(O)$_2$($C_{1-6}$ alkyl), —$C_{1-6}$ alkylene-S(O)$_2$($C_{1-6}$ alkyl), $C_{1-6}$ haloalkoxy, $C_{1-6}$ hydroxyalkyl, $C_{1-6}$ alkoxyalkyl substituted with one or more halo, cycloalkyl, cycloalkylalkyl, heterocyclyl, aryl, arylalkyl, heteroaryl, or heteroarylalkyl, wherein the heterocyclyl, heteroaryl or heteroarylalkyl are optionally substituted with one or more substituents independently selected from $C_{1-6}$ alkyl, $C_{1-6}$ haloalkyl, or halo; and
the remaining variables are as defined herein.

In some embodiments, each $R^{57}$ is independently selected from amino, $C_{2-6}$ alkenyl, $C_{2-6}$ alkynyl, cyanoalkyl, —S($C_{1-6}$ alkyl), —S(O)($C_{1-6}$ alkyl), —S(O)$_2$($C_{1-6}$ alkyl), —$C_{1-6}$ alkylene-S(O)$_2$($C_{1-6}$ alkyl), $C_{1-6}$ haloalkoxy, $C_{1-6}$ hydroxyalkyl, $C_{1-6}$ alkoxyalkyl substituted with one to three halo, cycloalkyl, cycloalkylalkyl, heterocyclyl, aryl, arylalkyl, heteroaryl, or heteroarylalkyl, wherein the heterocyclyl, heteroaryl or heteroarylalkyl are optionally substituted with one to three substituents independently selected from $C_{1-6}$ alkyl, $C_{1-6}$ haloalkyl, or halo.

Also provided is a compound having the formula (D-IIIa):

(D-IIIa)

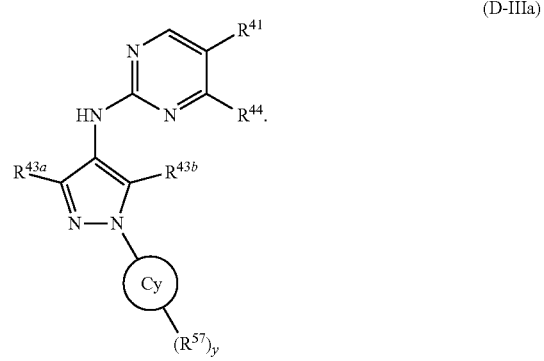

Also provided is a compound having the formula (D-IIIb):

(D-IIIb)

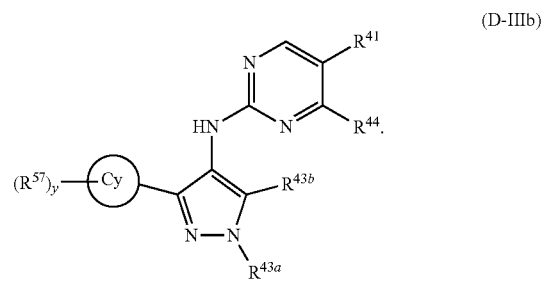

Also provided is a compound having the formula (D-IIIc):

(D-IIIc)

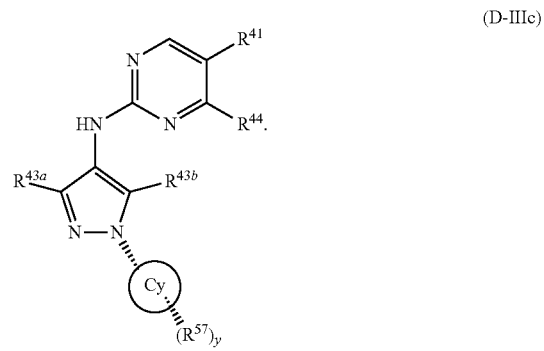

Also provided is a compound having the formula (D-IIId):

(D-IIId)

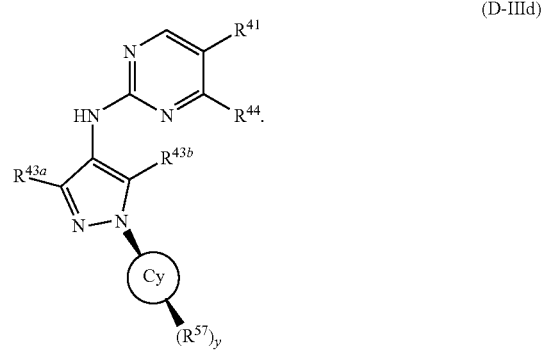

Also provided is a compound having the formula (D-IIIe):

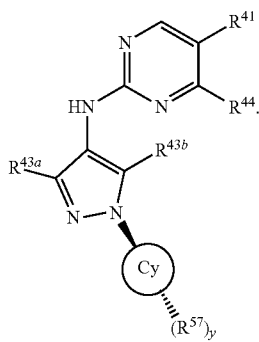

(D-IIIe)

Also provided is a compound having the formula (D-IIIf):

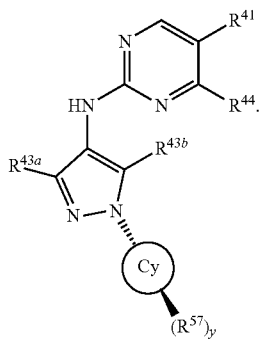

(D-IIIf)

In some embodiments, $R^{57}$ is a heteroaryl optionally substituted with one to three substituents independently selected from $C_{1-6}$ alkyl, $C_{1-6}$ haloalkyl, or halo.

In some embodiments, y is 1, and $R^{57}$ is a heteroaryl optionally substituted with one to three substituents independently selected from $C_{1-6}$ alkyl, $C_{1-6}$ haloalkyl, or halo. In some embodiments, y is 1, and $R^{57}$ is a heteroaryl selected from die group consisting of pyrazolyl, triazolyl, oxazolyl, or thiadiazolyl, each of which is optionally substituted with one to three substituents independently selected from $C_{1-6}$ alkyl, $C_{1-6}$ haloalkyl, or halo. In some embodiments, v is 1, and $R^{57}$ is a heterocyclyl optionally substituted with one to three substituents independently selected from $C_{1-6}$ alkyl, haloalkyl, or halo. In some embodiments, $R^{57}$ is a heterocyclyl selected from the group consisting piperazinyl or pyrrolidinyl, each of which is optionally substituted with one to three substituents independently selected from $C_{1-6}$ alkyl, haloalkyl, or halo.

In some embodiments, Cy is $C_{3-6}$ cycloalkyl. In some embodiments, Cy is cyclobutyl. In some embodiments, Cy is cyclopentyl.

In some embodiments, each $R^{51}$ is independently H, $C_{1-6}$ alkyl, $C_{2-6}$ alkenyl, $C_{2-6}$ alkynyl, $C_{1-6}$ haloalkyl, $C_{1-6}$ alkoxyalkyl, $C_{1-6}$ hydroxyalkyl, $C_{1-6}$ aminoalkyl, —$C_{1-6}$ alkylene-$S(O)_2(C_{1-6}$ alkyl), $C_{3-6}$ cycloalkyl optionally substituted with one to three $C_{1-6}$ alkyl, $C_{3-6}$ cycloalkylalkyl optionally substituted with one or three $C_{1-6}$ alkyl, heterocyclyl optionally substituted with one to three $R^{53}$, or heterocyclylalkyl optionally substituted with one to three $R^{53}$; or two $R^{51}$, together with the nitrogen to which they are attached, form a three- to six-membered heterocyclyl optionally substituted with one to three $R^{53}$.

In some embodiments, when $R^{45}$ is $C_{1-6}$ alkyl, $C_{1-6}$ alkoxy, or heterocyclyl or when $R^{52}$ is $C_{1-6}$ alkyl, $R^{45}$ or $R^{52}$ is optionally substituted with one or more substituents independently selected from alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadine, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —$Si(R^y)_3$, wherein each $R^y$ is independently hydrogen, alkyl, alkenyl, alkynyl, heteroalkyl, cycloalkyl, aryl, heteroaryl or heterocyclyl.

In some embodiments, when $R^{45}$ is $C_{1-6}$ alkyl, $C_{1-6}$ alkoxy, or heterocyclyl or when $R^{52}$ is $C_{1-6}$ alkyl, $R^{45}$ or $R^{52}$ is optionally substituted with one to three substituents independently selected from alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadine, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —$Si(R^y)_3$, wherein each $R^y$ is independently hydrogen, alkyl, alkenyl, alkynyl, heteroalkyl, cycloalkyl, aryl, heteroaryl or heterocyclyl.

In some embodiments, $R^{48}$ and $R^{49}$, together with the carbon atom to which they are attached, form a $C_{3-10}$ cycloalkyl optionally substituted with one or more substituents independently selected from alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadine, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —$Si(R^y)_3$, wherein each $R^y$ is independently hydrogen, alkyl, alkenyl, alkynyl, heteroalkyl, cycloalkyl, aryl, heteroaryl or heterocyclyl.

In some embodiments, $R^{48}$ and $R^{49}$, together with the carbon atom to which they are attached, form a $C_{3-10}$ cycloalkyl optionally substituted with one to three substituents independently selected from alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadino, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —$Si(R^y)_3$, wherein each $R^y$ is independently hydrogen, alkyl, alkenyl, alkynyl, heteroalkyl, cycloalkyl, aryl, heteroaryl or heterocyclyl.

In some embodiments, when $R^{46}$ and $R^{47}$ are $C_{1-6}$ alkyl, $C_{2-6}$ alkenyl, $C_{2-6}$ alkynyl, cycloalkyl, heterocyclyl, aryl, heteroalkyl, or heteroaryl, $R^{46}$ or $R^{47}$ is optionally substituted with one or more substituents independently selected from alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadino, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or $-Si(R^y)_3$, wherein each $R^y$ is independently hydrogen, alkyl, alkenyl, alkynyl, heteroalkyl, cycloalkyl, aryl, heteroaryl or heterocyclyl.

In some embodiments, when $R^{46}$ and $R^{47}$ are $C_{1-6}$ alkyl, $C_{2-6}$ alkenyl, $C_{2-6}$ alkynyl, cycloalkyl, heterocyclyl, aryl, heteroalkyl, or heteroaryl, $R^{46}$ or $R^{47}$ is optionally substituted with one to three substituents independently selected from alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadino, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or $-Si(R^y)_3$, wherein each $R^y$ is independently hydrogen, alkyl, alkenyl, alkynyl, heteroalkyl, cycloalkyl, aryl, heteroaryl or heterocyclyl.

In one embodiment, a compound may be selected from those compounds in Table D-1. Also included within die disclosure are pharmaceutically acceptable salts, prodrugs, stereoisomers or a mixture of stereoisomers thereof. In certain embodiments, provided are compounds of Table D-1 for use in the methods described herein.

TABLE D-1

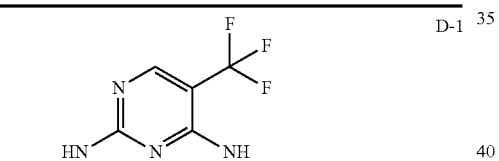

D-1

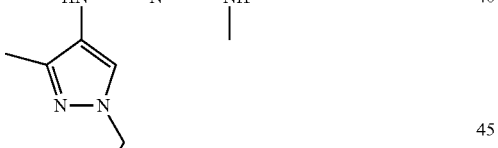

D-2

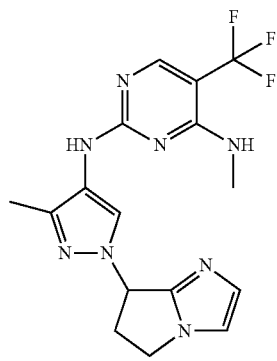

D-3: First eluting stereoisomer
D-4: Second eluting stereoisomer

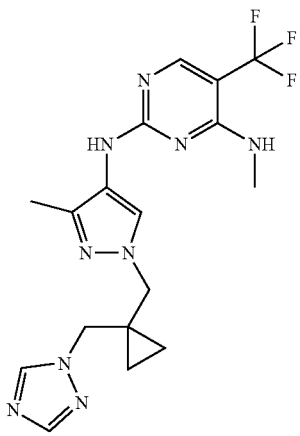 [SMILES: CNc1nc(Nc2cn(CC3(Cn4cncn4)CC3)nc2C)ncc1C(F)(F)F]

D-5

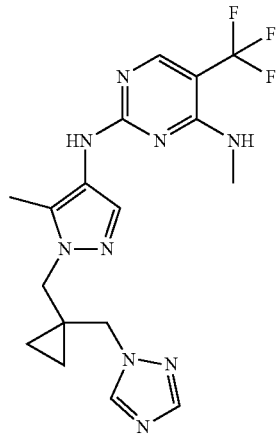 [SMILES: CNc1nc(Nc2cnn(CC3(Cn4cncn4)CC3)c2C)ncc1C(F)(F)F]

D-6

TABLE D-1-continued
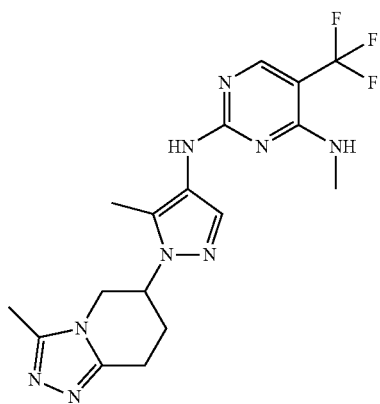 [SMILES: CNc1nc(Nc2cnn(C3CCc4nnc(C)n4C3)c2C)ncc1C(F)(F)F]
D-7
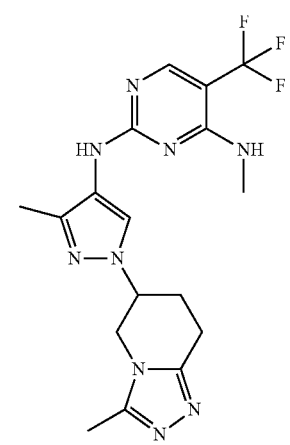 [SMILES: CNc1nc(Nc2cn(C3CCc4nnc(C)n4C3)nc2C)ncc1C(F)(F)F]
D-8
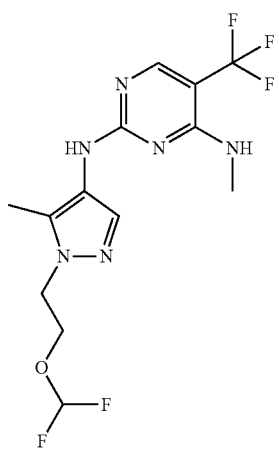 [SMILES: CNc1nc(Nc2cnn(CCOC(F)F)c2C)ncc1C(F)(F)F]
D-9
TABLE D-1-continued
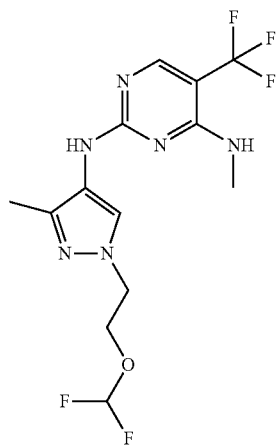 [SMILES: CNc1nc(Nc2cn(CCOC(F)F)nc2C)ncc1C(F)(F)F]
D-10
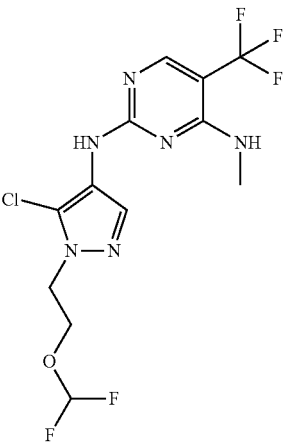 [SMILES: CNc1nc(Nc2cnn(CCOC(F)F)c2Cl)ncc1C(F)(F)F]
D-11
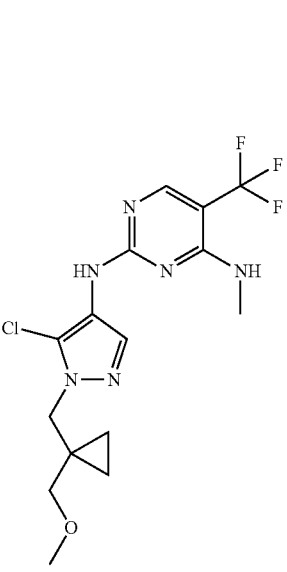 [SMILES: CNc1nc(Nc2cnn(CC3(COC)CC3)c2Cl)ncc1C(F)(F)F]
D-12

TABLE D-1-continued
D-13
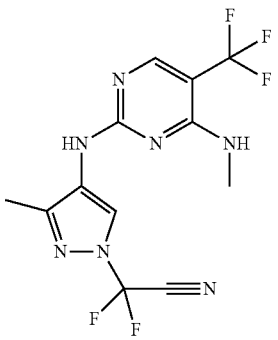 [SMILES: CNc1nc(Nc2cn(C(F)(F)C#N)nc2C)ncc1C(F)(F)F]
D-14
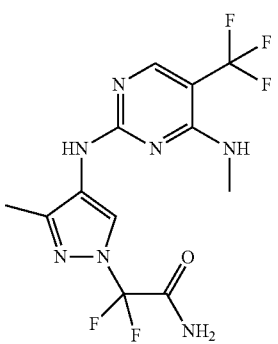 [SMILES: CNc1nc(Nc2cn(C(F)(F)C(N)=O)nc2C)ncc1C(F)(F)F]
D-15
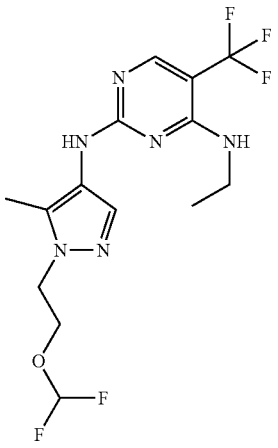 [SMILES: CCNc1nc(Nc2cnn(CCOC(F)F)c2C)ncc1C(F)(F)F]
D-16
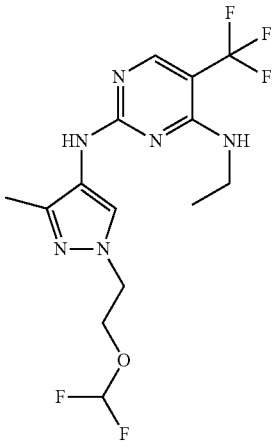 [SMILES: CCNc1nc(Nc2cn(CCOC(F)F)nc2C)ncc1C(F)(F)F]
TABLE D-1-continued
D-17
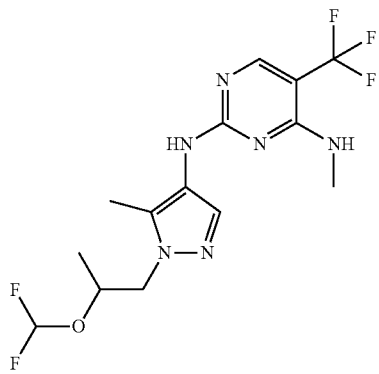 [SMILES: CNc1nc(Nc2cnn(CC(C)OC(F)F)c2C)ncc1C(F)(F)F]
D-18
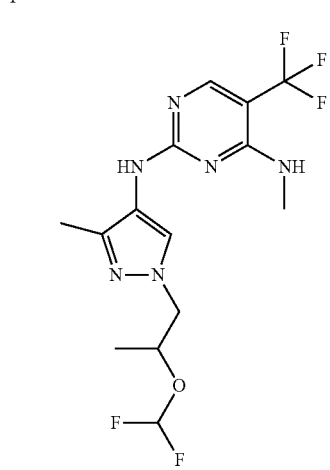
D-19
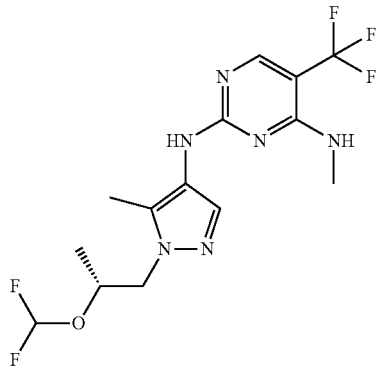 [SMILES: CNc1nc(Nc2cnn(C[C@@H](C)OC(F)F)c2C)ncc1C(F)(F)F]
D-20
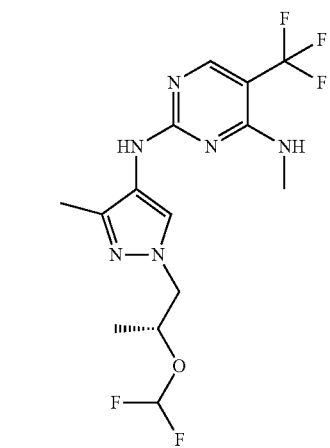 [SMILES: CNc1nc(Nc2cn(C[C@@H](C)OC(F)F)nc2C)ncc1C(F)(F)F]

TABLE D-1-continued
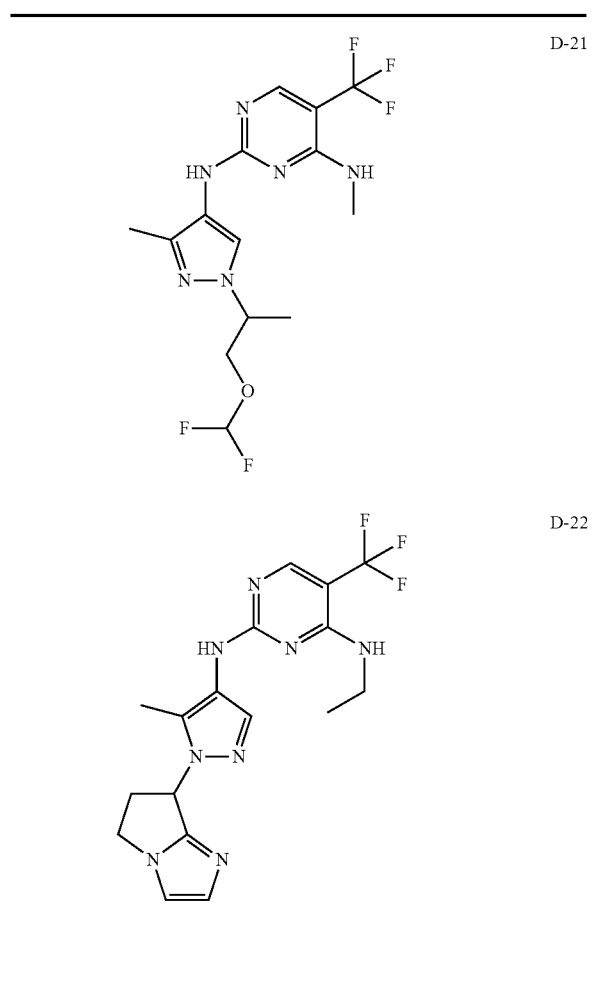
D-21
D-22
D-23: First eluting stereoisomer
D-24: Second eluting stereoisomer
TABLE D-1-continued
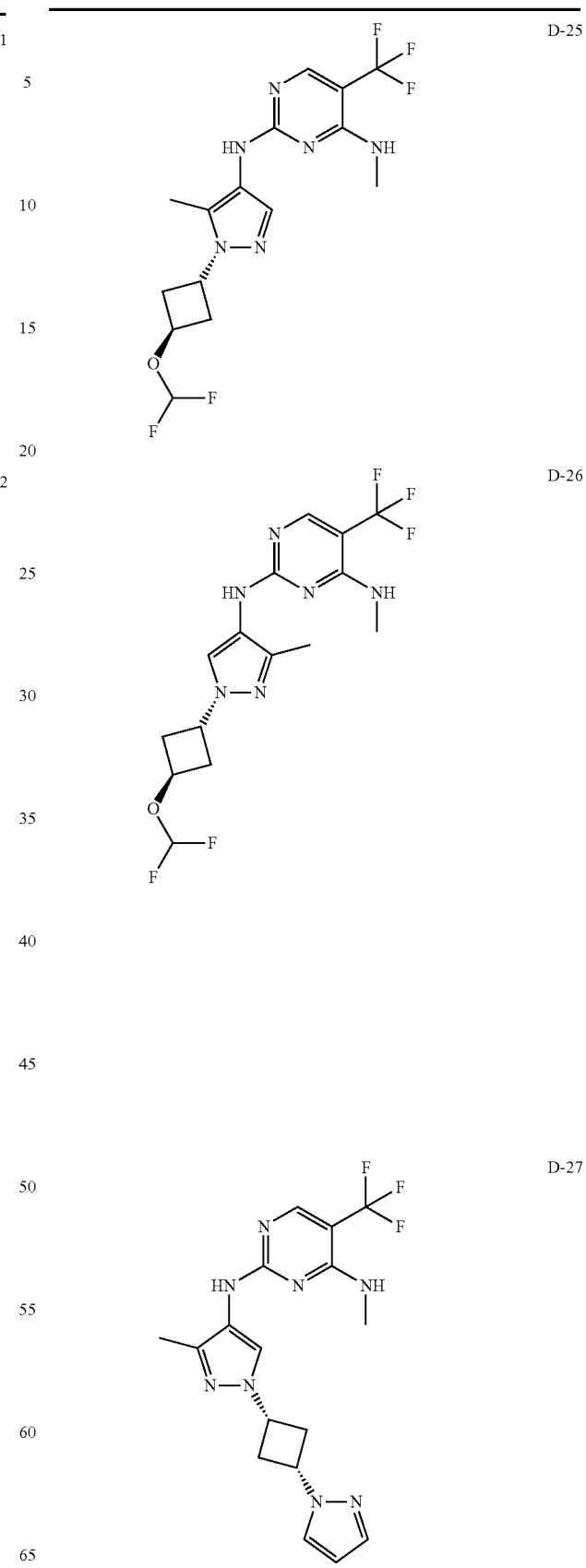
D-25
D-26
D-27

TABLE D-1-continued
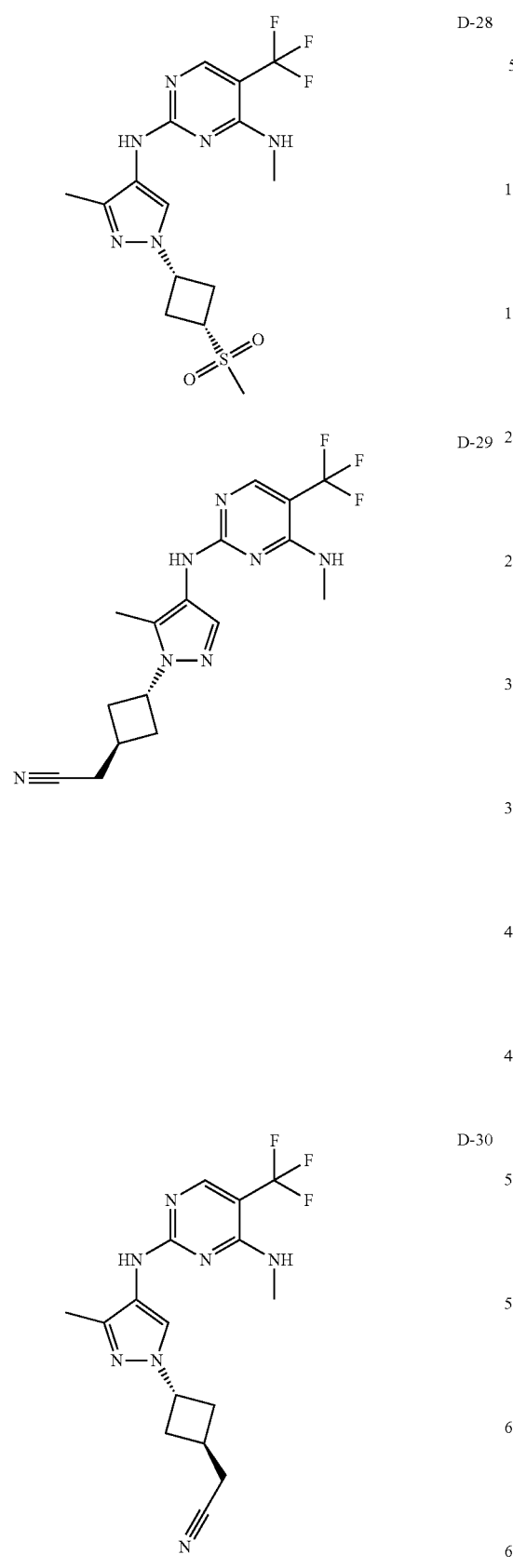
D-28
D-29
D-30
TABLE D-1-continued
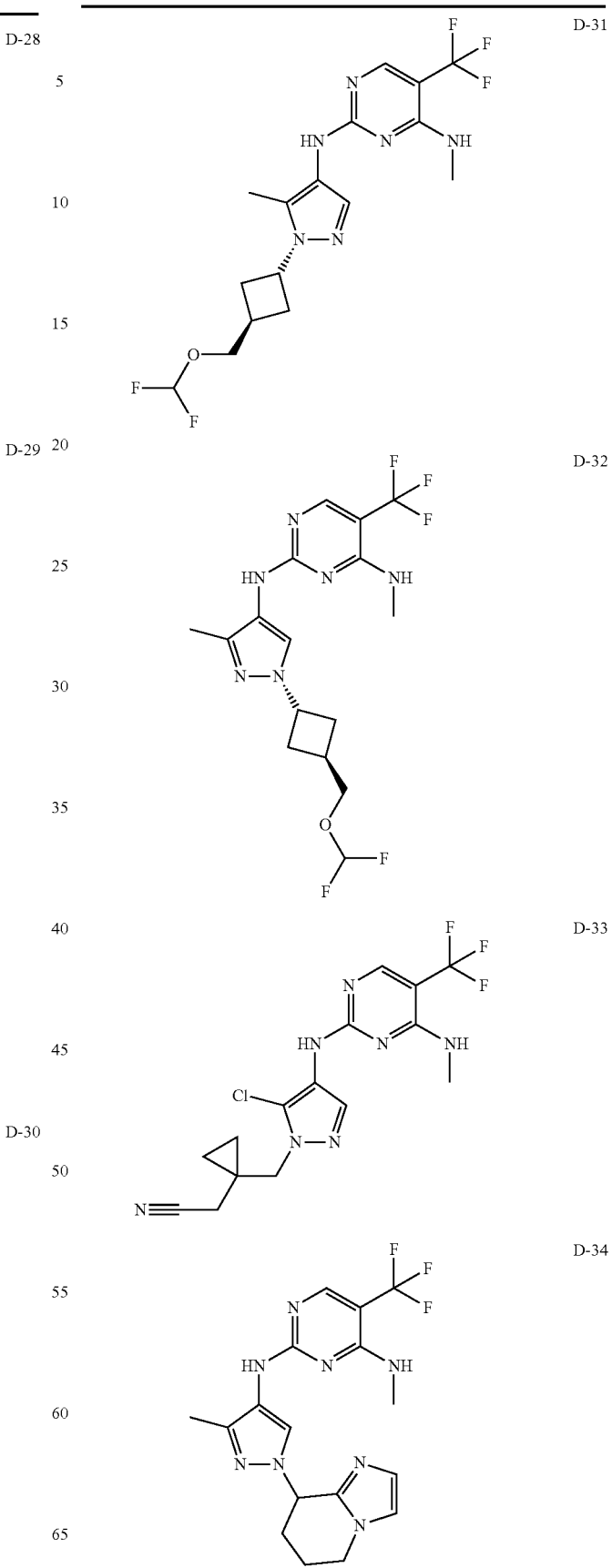
D-31
D-32
D-33
D-34

TABLE D-1-continued
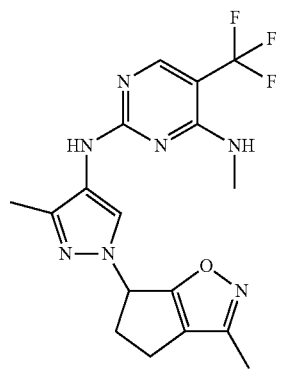 [SMILES: CNc1nc(Nc2cn(C3CCc4c(C)noc43)nc2C)ncc1C(F)(F)F]
D-35
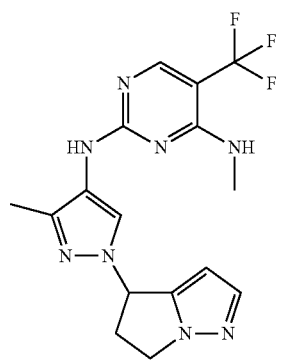 [SMILES: CNc1nc(Nc2cn(C3CCn4nccc43)nc2C)ncc1C(F)(F)F]
D-36
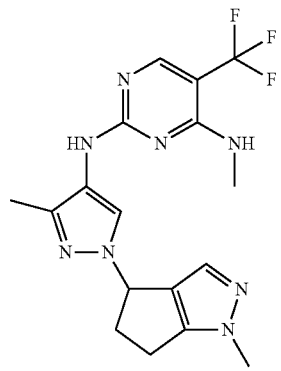 [SMILES: CNc1nc(Nc2cn(C3CCc4c3cnn4C)nc2C)ncc1C(F)(F)F]
D-37
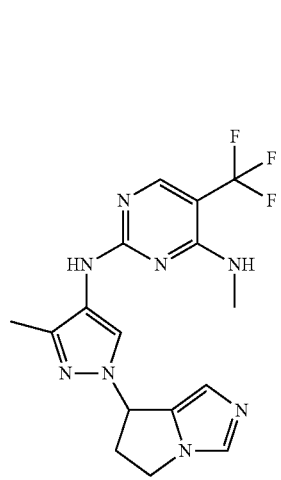 [SMILES: CNc1nc(Nc2cn(C3CCn4cncc43)nc2C)ncc1C(F)(F)F]
D-38
TABLE D-1-continued
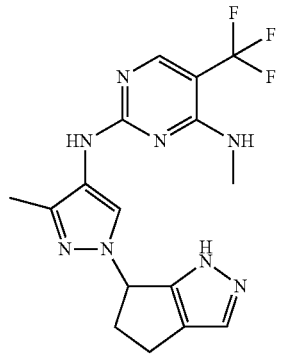 [SMILES: CNc1nc(Nc2cn(C3CCc4cn[nH]c43)nc2C)ncc1C(F)(F)F]
D-39
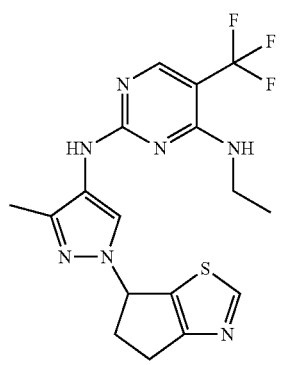 [SMILES: CCNc1nc(Nc2cn(C3CCc4ncsc43)nc2C)ncc1C(F)(F)F]
D-40
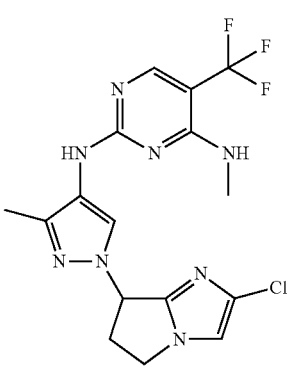 [SMILES: CNc1nc(Nc2cn(C3CCn4cc(Cl)nc43)nc2C)ncc1C(F)(F)F]
D-41
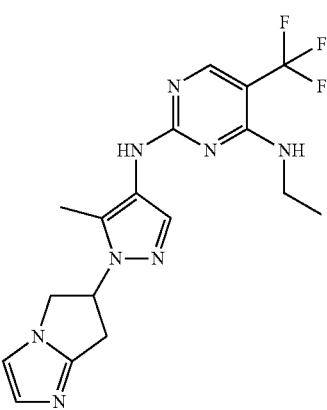 [SMILES: CCNc1nc(Nc2cnn(C3Cc4nccn4C3)c2C)ncc1C(F)(F)F]
D-42

TABLE D-1-continued
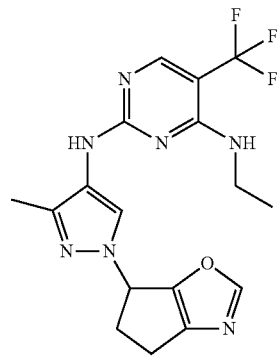 [SMILES: CCNc1nc(Nc2cn(C3CCc4ncoc43)nc2C)ncc1C(F)(F)F]
D-43
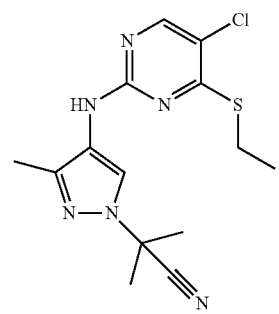 [SMILES: CCSc1nc(Nc2cn(C(C)(C)C#N)nc2C)ncc1Cl]
D-44
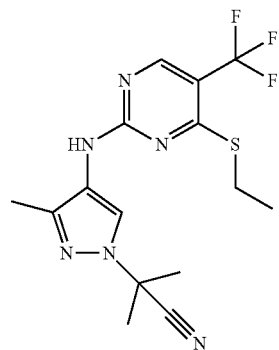 [SMILES: CCSc1nc(Nc2cn(C(C)(C)C#N)nc2C)ncc1C(F)(F)F]
D-45
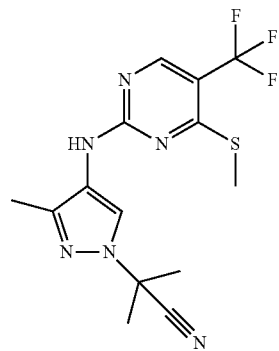 [SMILES: CSc1nc(Nc2cn(C(C)(C)C#N)nc2C)ncc1C(F)(F)F]
D-46
TABLE D-1-continued
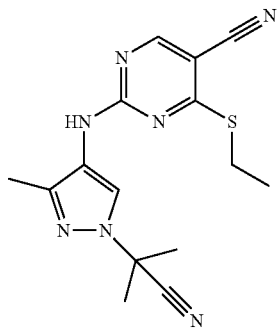 [SMILES: CCSc1nc(Nc2cn(C(C)(C)C#N)nc2C)ncc1C#N]
D-47
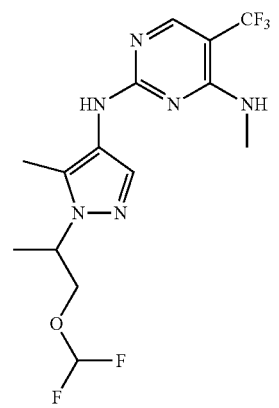 [SMILES: CNc1nc(Nc2cnn(C(C)COC(F)F)c2C)ncc1C(F)(F)F]
D-48
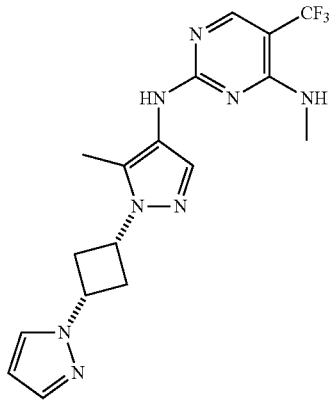
D-49
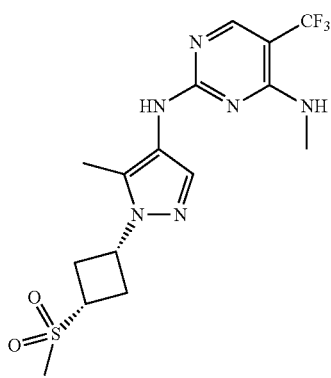 [SMILES: CNc1nc(Nc2cnn([C@H]3C[C@@H](S(C)(=O)=O)C3)c2C)ncc1C(F)(F)F]
D-50

TABLE D-1-continued
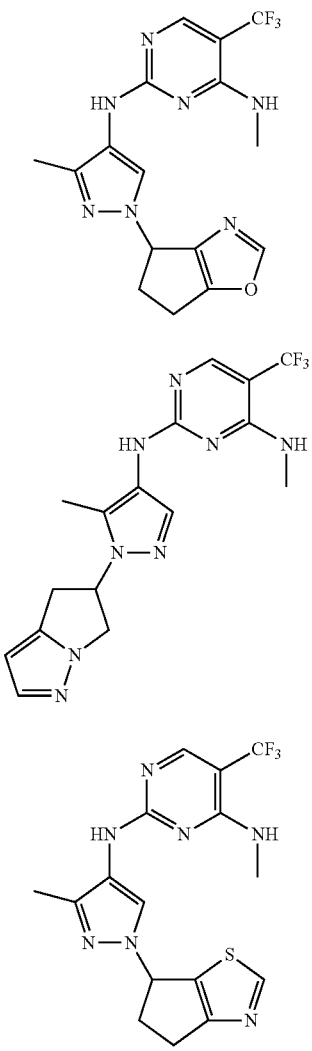
D-51
D-52
D-53
D-54
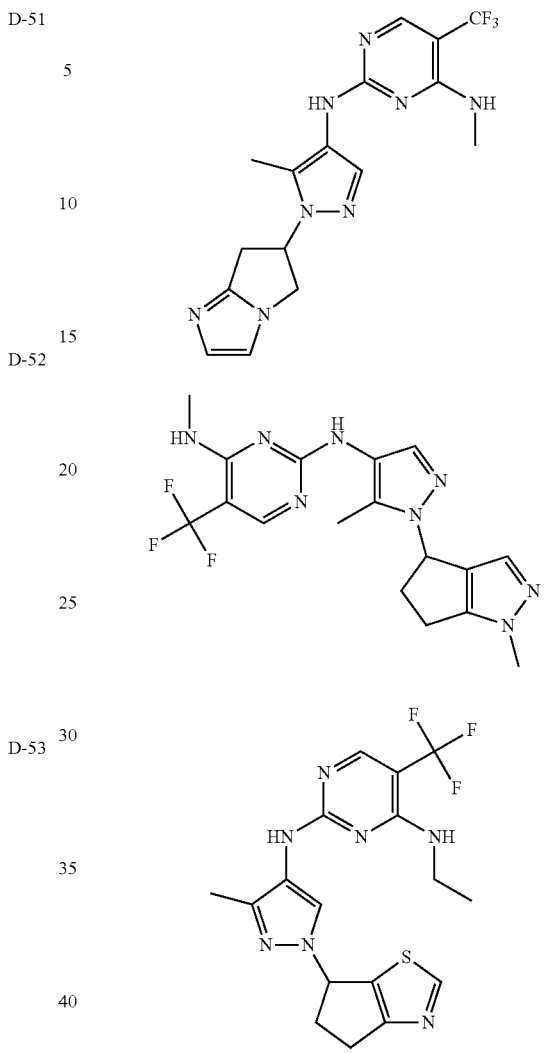
D-55
D-56
D-57: First eluting stereoisomer
D-86: Second eluting stereoisomer
D-58
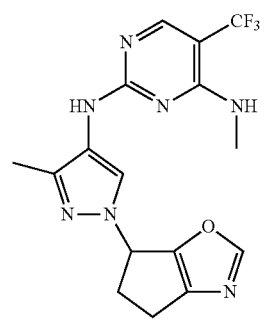 [SMILES: CNc1nc(Nc2cn(C3CCc4ncoc43)nc2C)ncc1C(F)(F)F]

TABLE D-1-continued
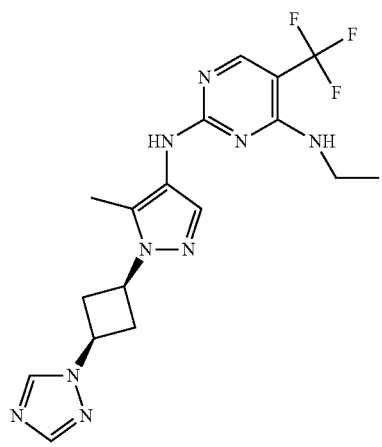 [SMILES: CCNc1nc(Nc2cnn([C@H]3C[C@@H](n4cncn4)C3)c2C)ncc1C(F)(F)F]
D-59
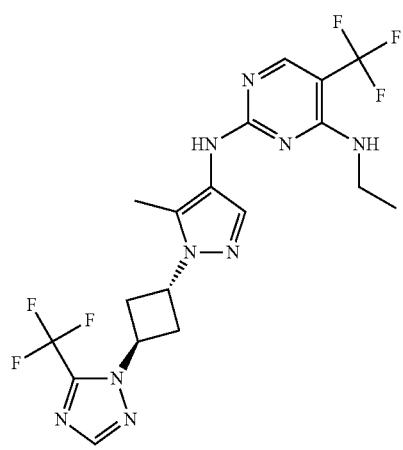 [SMILES: CCNc1nc(Nc2cnn([C@H]3C[C@H](n4ncnc4C(F)(F)F)C3)c2C)ncc1C(F)(F)F]
D-60: First eluting stereoisomer
D-163: Second eluting stereoisomer
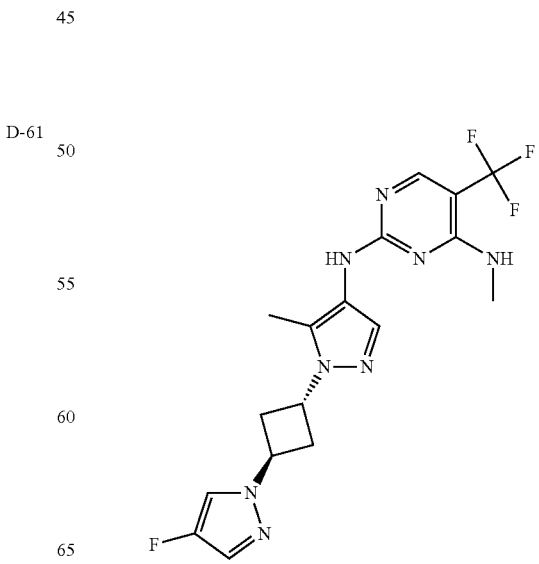
D-61
TABLE D-1-continued
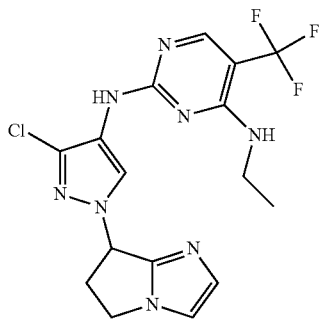
D-62: First eluting stereoisomer
D-105: Second eluting stereoisomer
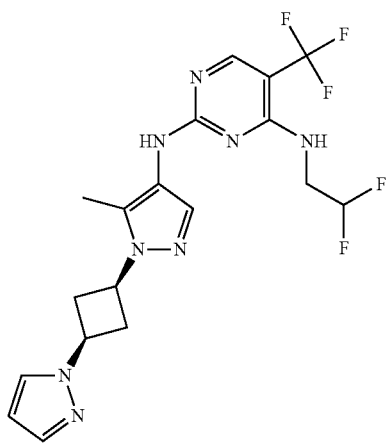 [SMILES: Cc1c(Nc2ncc(C(F)(F)F)c(NCC(F)F)n2)cnn1[C@H]1C[C@@H](n2cccn2)C1]
D-63
D-64

TABLE D-1-continued
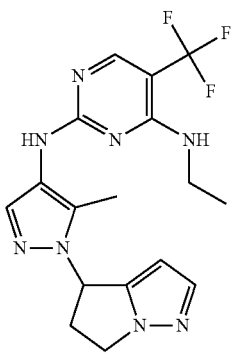
D-65: Second eluting stereoisomer
D-122: First eluting stereoisomer
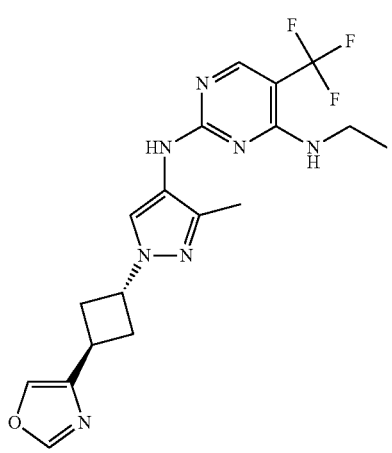 [SMILES: CCNc1nc(Nc2cn([C@H]3C[C@H](c4cocn4)C3)nc2C)ncc1C(F)(F)F]
D-66
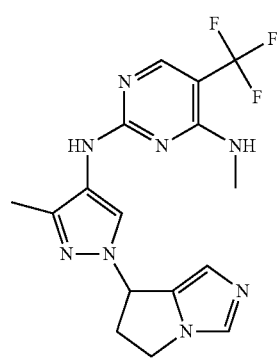
D-67: First eluting stereoisomer
D-130: Second eluting stereoisomer
TABLE D-1-continued
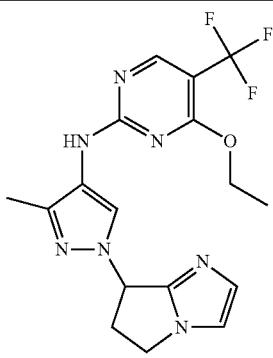
D-68: Second eluting stereoisomer
D-132: First eluting stereoisomer
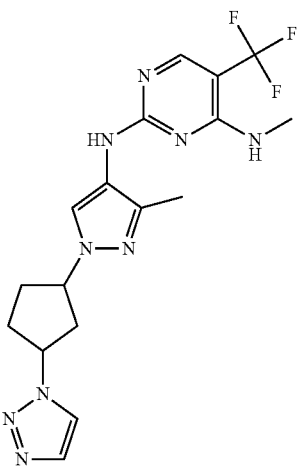
D-69: Third eluting stereoisomer
D-143: Fourth eluting stereoisomer
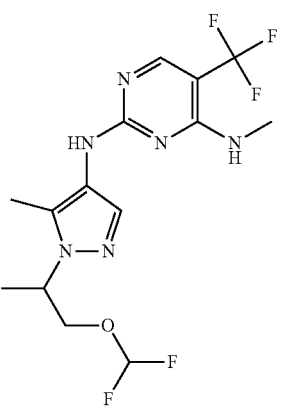
D-70: First eluting stereoisomer
D-96: Second eluting stereoisomer TABLE D-1-continued
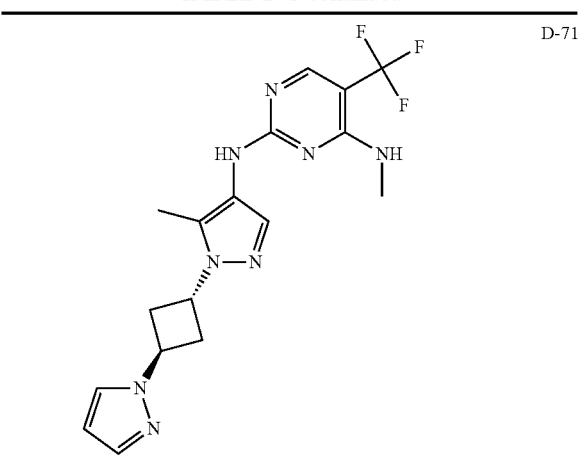
D-71
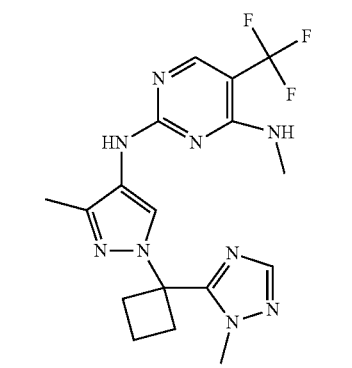 [SMILES: CNc1nc(Nc2cn(C3(c4ncnn4C)CCC3)nc2C)ncc1C(F)(F)F]
D-72
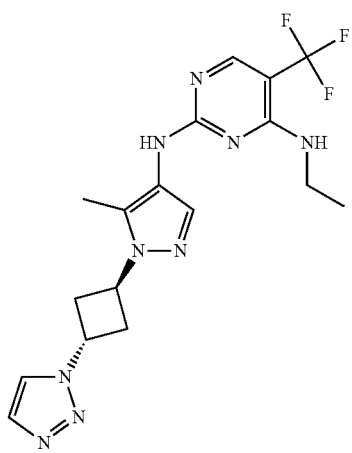 [SMILES: CCNc1nc(Nc2cnn([C@H]3C[C@H](n4ccnn4)C3)c2C)ncc1C(F)(F)F]
D-73
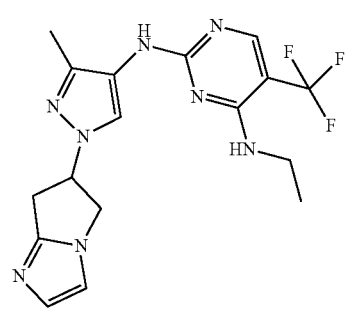
D-74: Second eluting stereoisomer
D-102: First eluting stereoisomer
TABLE D-1-continued
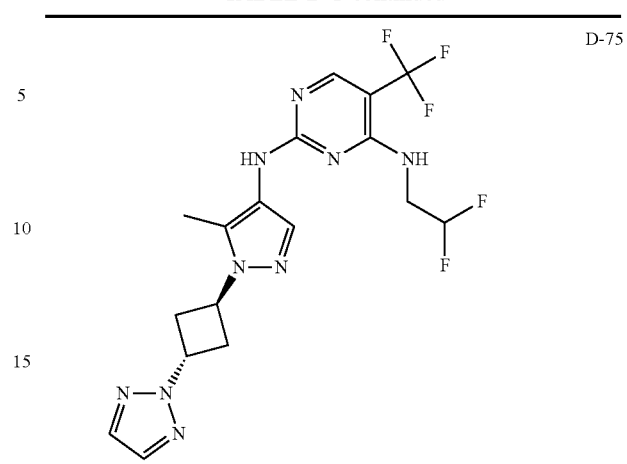
D-75
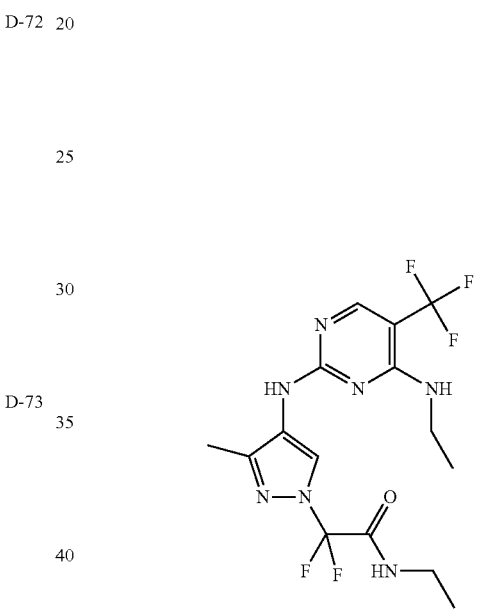
D-76
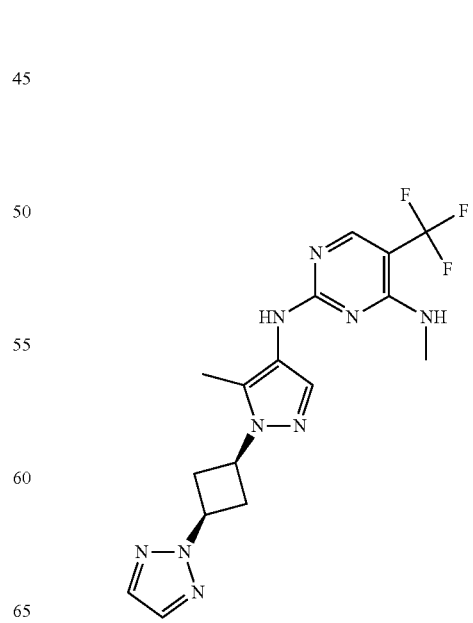
D-77

TABLE D-1-continued
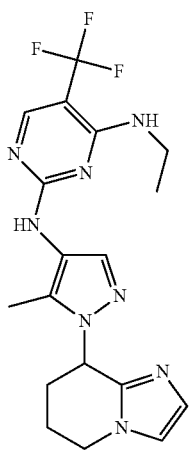
D-78: First eluting stereoisomer
D-151: Second eluting stereoisomer
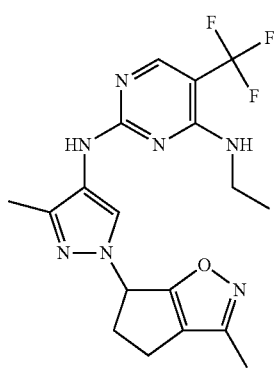
D-79: Second eluting stereoisomer
D-171: First eluting stereoisomer
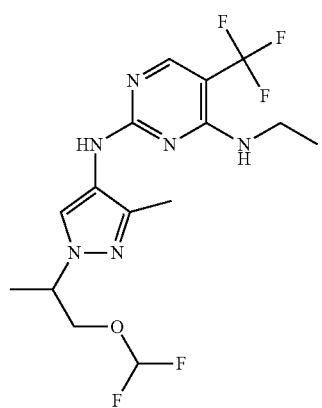 [SMILES: CCNc1nc(Nc2cn(C(C)COC(F)F)nc2C)ncc1C(F)(F)F]
D-80
TABLE D-1-continued
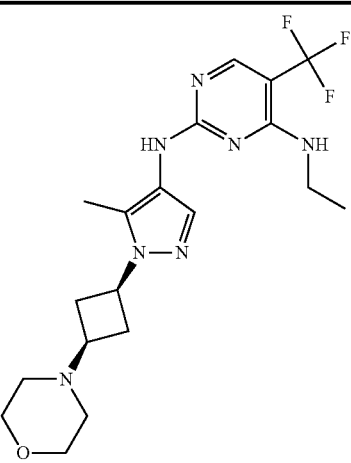
D-81
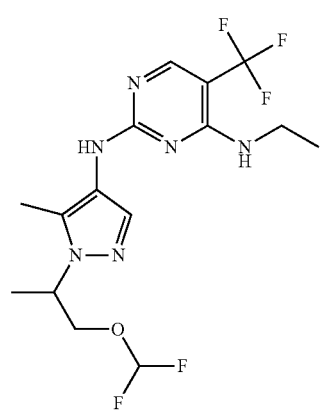
D-82: Second eluting stereoisomer
D-174: First eluting stereoisomer
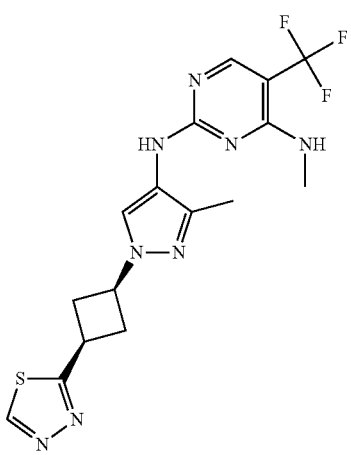 [SMILES: CNc1nc(Nc2cn([C@H]3C[C@@H](c4nncs4)C3)nc2C)ncc1C(F)(F)F]
D-83

TABLE D-1-continued
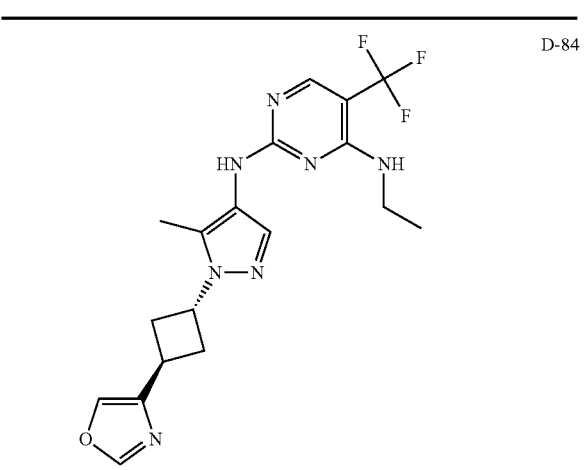
D-84
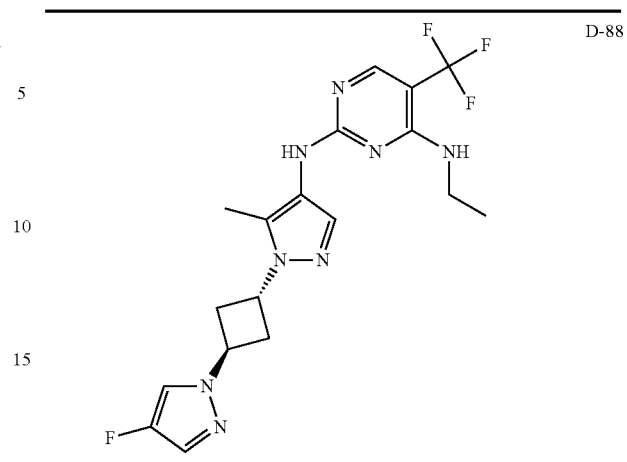
D-88
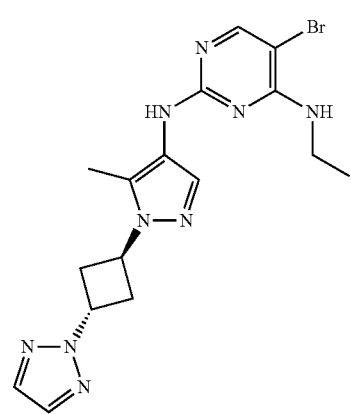
D-85
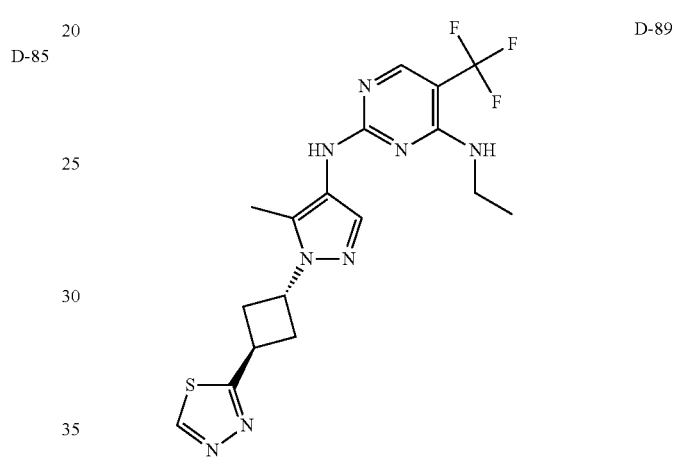
D-89
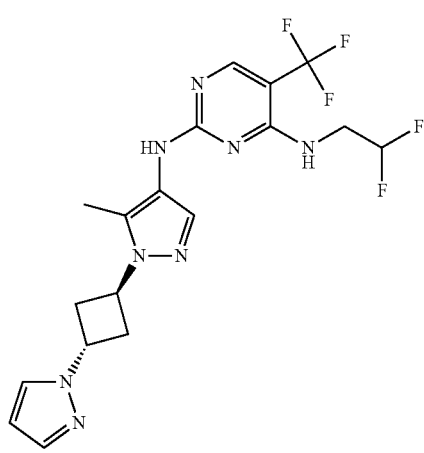 [SMILES: Cc1c(Nc2ncc(C(F)(F)F)c(NCC(F)F)n2)cnn1[C@H]1C[C@H](n2cccn2)C1]
D-87
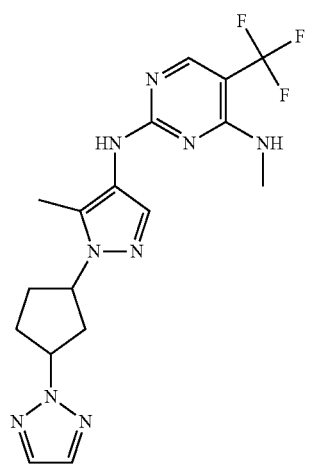
D-90: First eluting stereoisomer
D-107: Second eluting stereoisomer TABLE D-1-continued
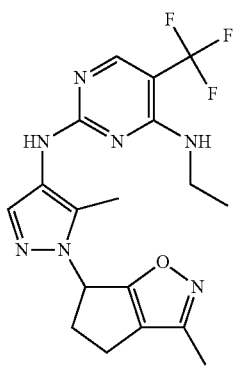 [SMILES: CCNc1nc(Nc2cnn(C3CCc4c(C)noc43)c2C)ncc1C(F)(F)F]
D-91
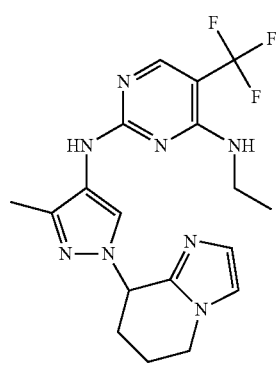
D-92: First eluting stereoisomer
D-170: Second eluting stereoisomer
D-93
TABLE D-1-continued
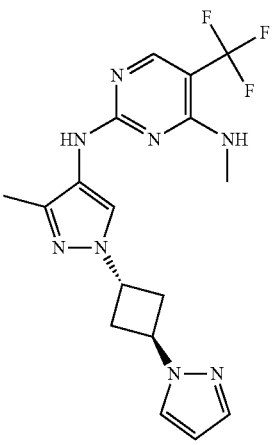 [SMILES: CNc1nc(Nc2cn([C@H]3C[C@H](n4cccn4)C3)nc2C)ncc1C(F)(F)F]
D-94
D-95
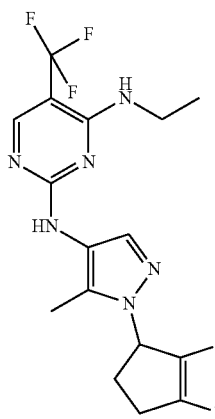
D-97
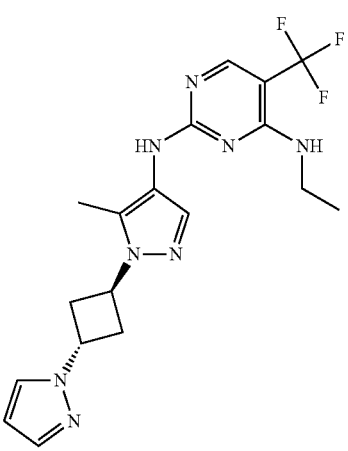 [SMILES: CCNc1nc(Nc2cnn([C@H]3C[C@H](n4cccn4)C3)c2C)ncc1C(F)(F)F]
D-98

TABLE D-1-continued
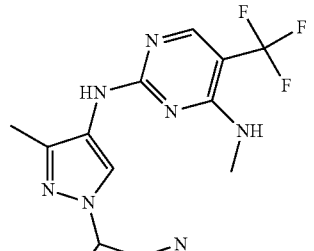
D-99
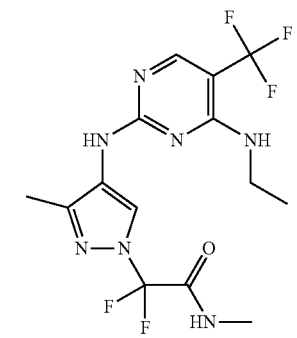 [SMILES: CCNc1nc(Nc2cn(C(F)(F)C(=O)NC)nc2C)ncc1C(F)(F)F]
D-100
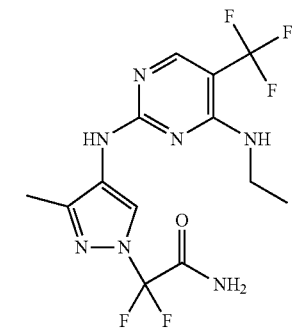 [SMILES: CCNc1nc(Nc2cn(C(F)(F)C(N)=O)nc2C)ncc1C(F)(F)F]
D-101
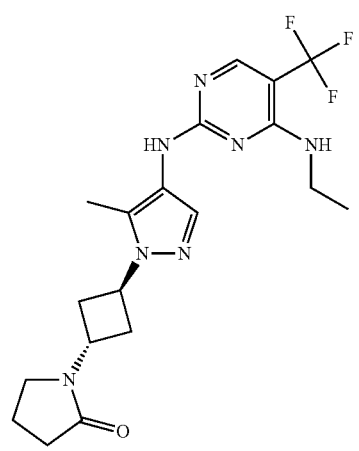 [SMILES: CCNc1nc(Nc2cnn([C@H]3C[C@H](N4CCCC4=O)C3)c2C)ncc1C(F)(F)F]
D-103
TABLE D-1-continued
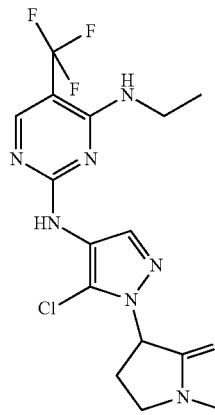
D-104
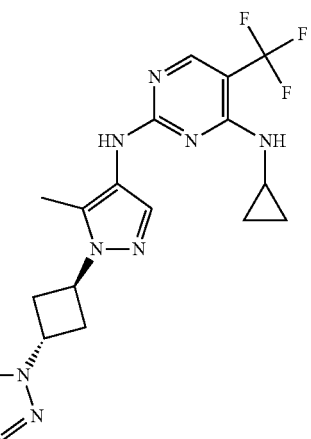
D-106
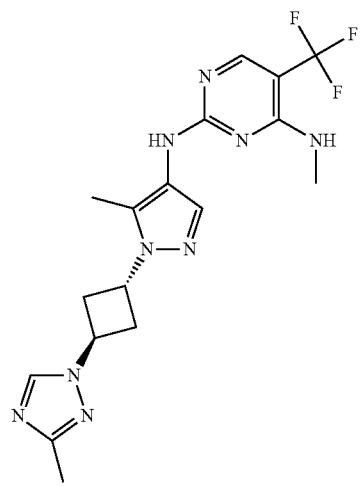 [SMILES: CNc1nc(Nc2cnn([C@H]3C[C@H](n4cnc(C)n4)C3)c2C)ncc1C(F)(F)F]
D-108

TABLE D-1-continued
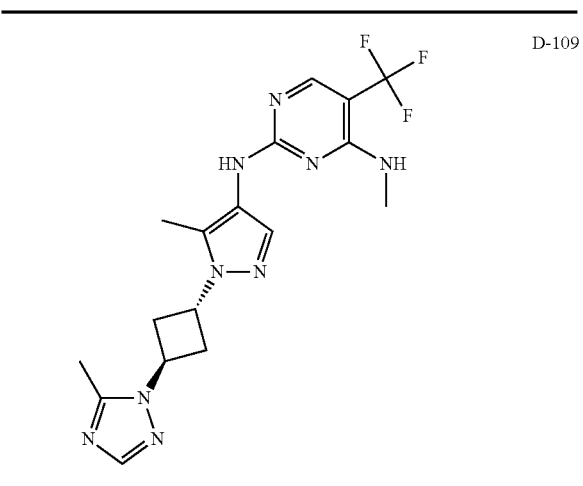
D-109
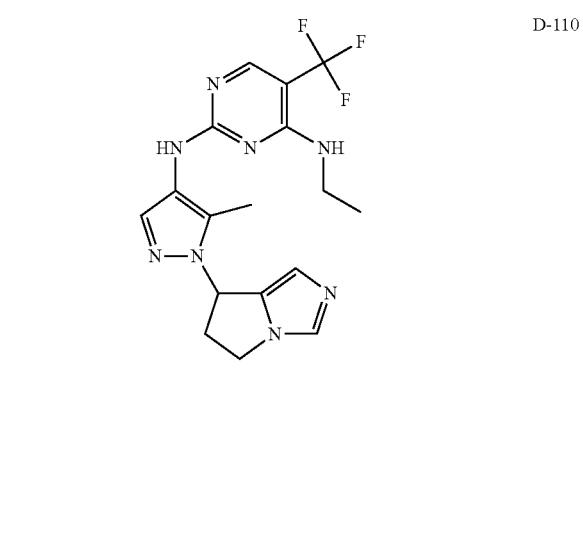
D-110
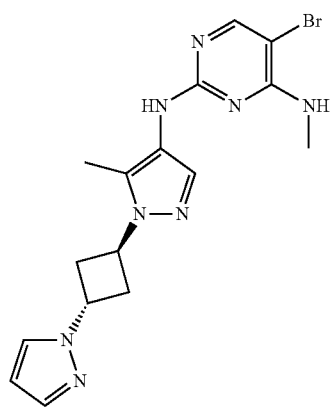 [SMILES: CNc1nc(Nc2cnn([C@H]3C[C@H](n4cccn4)C3)c2C)ncc1Br]
D-111
TABLE D-1-continued
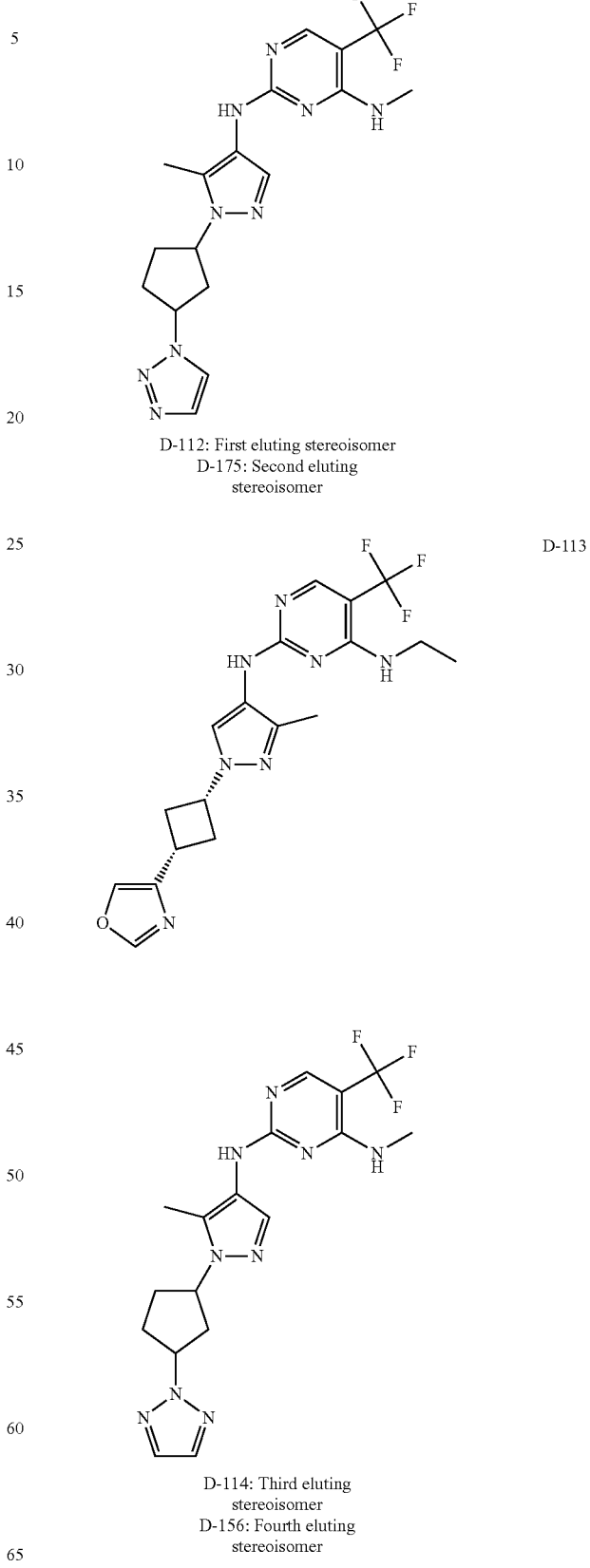
D-112: First eluting stereoisomer
D-175: Second eluting stereoisomer
D-113
D-114: Third eluting stereoisomer
D-156: Fourth eluting stereoisomer TABLE D-1-continued
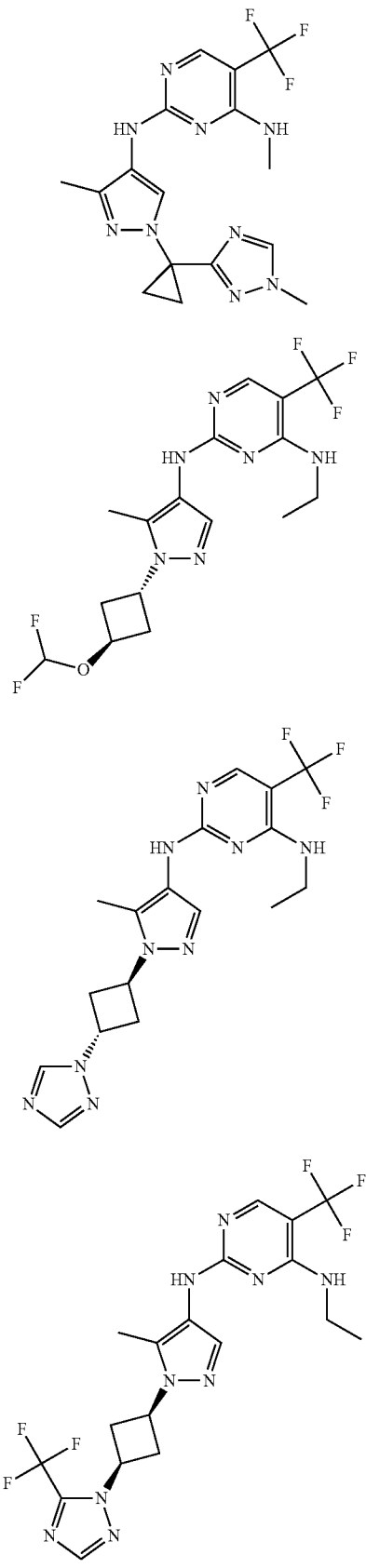
D-115
D-116
D-117
D-118
TABLE D-1-continued
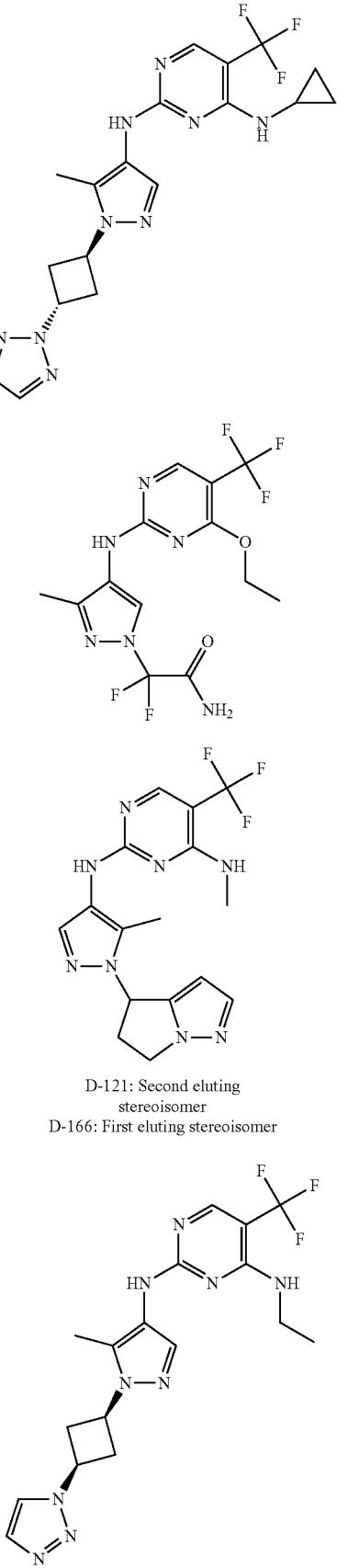
D-119
D-120
D-121: Second eluting stereoisomer
D-166: First eluting stereoisomer
D-123

TABLE D-1-continued
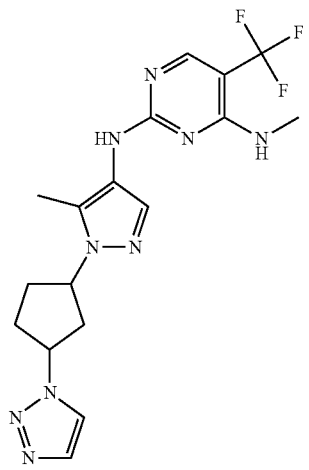 [SMILES: CNc1nc(Nc2cnn(C3CCC(n4ccnn4)C3)c2C)ncc1C(F)(F)F]
D-124
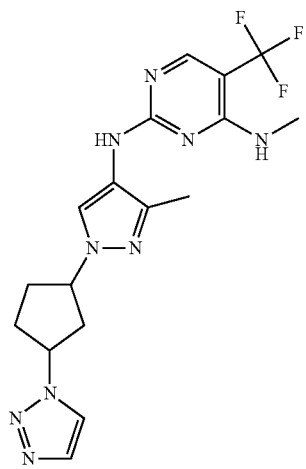 [SMILES: CNc1nc(Nc2cn(C3CCC(n4ccnn4)C3)nc2C)ncc1C(F)(F)F]
D-125
D-126
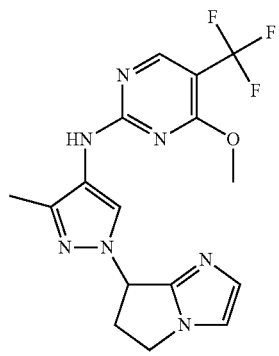
D-127: First eluting stereoisomer
D-142: Second eluting stereoisomer
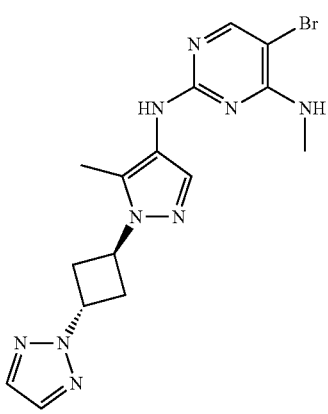 [SMILES: CNc1nc(Nc2cnn([C@H]3C[C@H](n4nccn4)C3)c2C)ncc1Br]
D-128
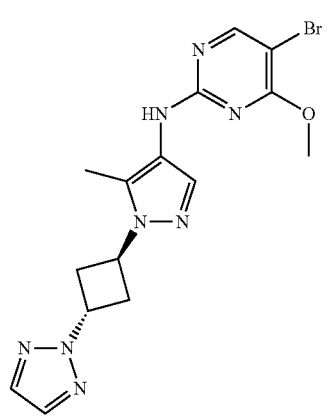 [SMILES: COc1nc(Nc2cnn([C@H]3C[C@H](n4nccn4)C3)c2C)ncc1Br]
D-129
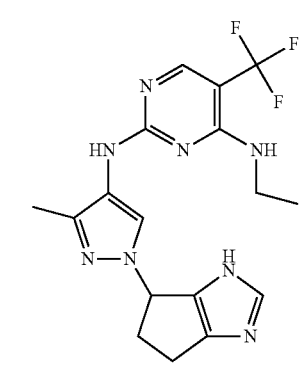 [SMILES: CCNc1nc(Nc2cn(C3CCc4nc[nH]c43)nc2C)ncc1C(F)(F)F]
D-131

TABLE D-1-continued
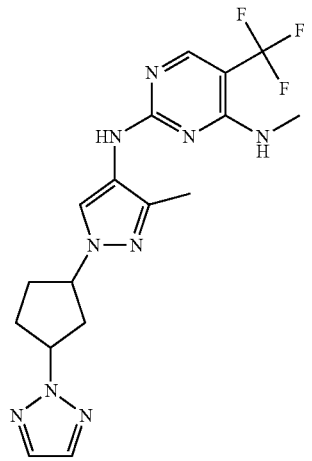
D-133: First eluting stereoisomer
D-134: Second eluting stereoisomer
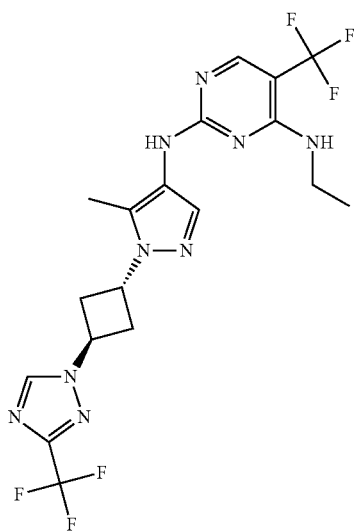 [SMILES: CCNc1nc(Nc2cnn([C@H]3C[C@H](n4cnc(C(F)(F)F)n4)C3)c2C)ncc1C(F)(F)F]
D-135
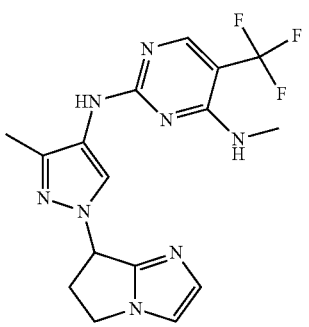 [SMILES: CNc1nc(Nc2cn(C3CCn4ccnc43)nc2C)ncc1C(F)(F)F]
D-137
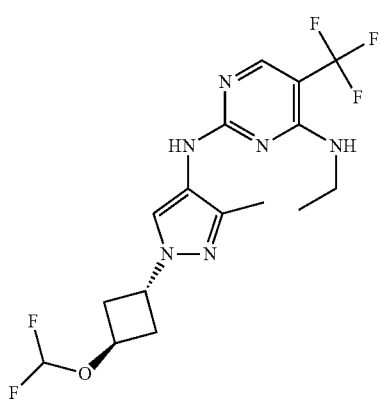 [SMILES: CCNc1nc(Nc2cn([C@H]3C[C@H](OC(F)F)C3)nc2C)ncc1C(F)(F)F]
D-138
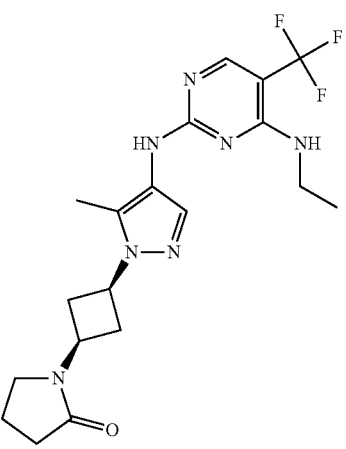 [SMILES: CCNc1nc(Nc2cnn([C@H]3C[C@@H](N4CCCC4=O)C3)c2C)ncc1C(F)(F)F]
D-139
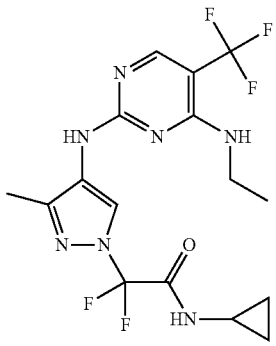 [SMILES: CCNc1nc(Nc2cn(C(F)(F)C(=O)NC3CC3)nc2C)ncc1C(F)(F)F]
D-140

TABLE D-1-continued
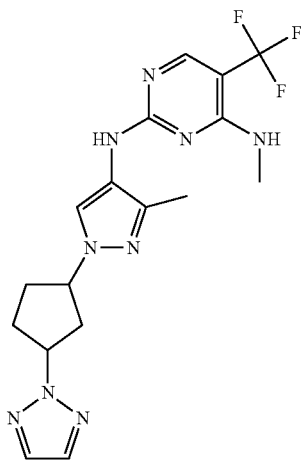
D-141: First eluting stereoisomer
D-149: Second eluting stereoisomer
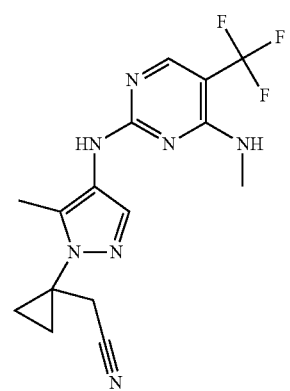 [SMILES: CNc1nc(Nc2cnn(C3(CC#N)CC3)c2C)ncc1C(F)(F)F]
D-144
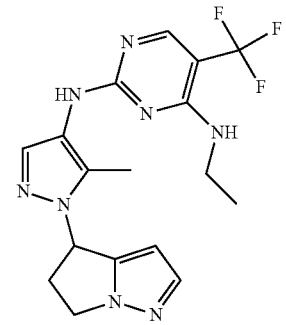 [SMILES: CCNc1nc(Nc2cnn(C3CCn4nccc43)c2C)ncc1C(F)(F)F]
D-145
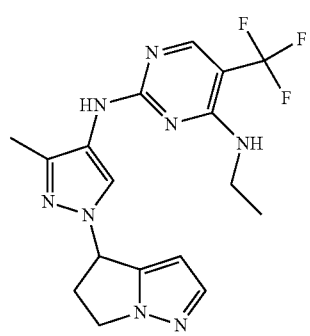 [SMILES: CCNc1nc(Nc2cn(C3CCn4nccc43)nc2C)ncc1C(F)(F)F]
D-146
TABLE D-1-continued
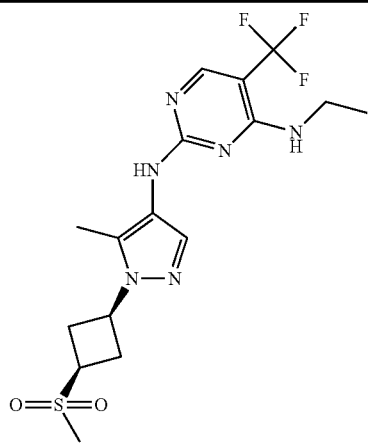
D-147
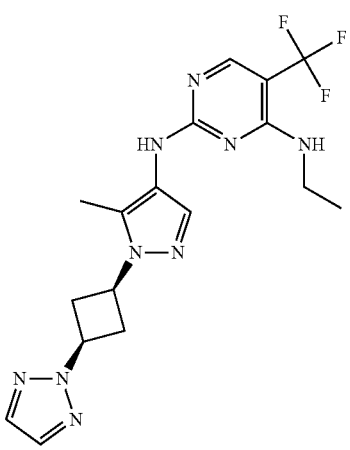 [SMILES: CCNc1nc(Nc2cnn([C@H]3C[C@@H](n4nccn4)C3)c2C)ncc1C(F)(F)F]
D-148
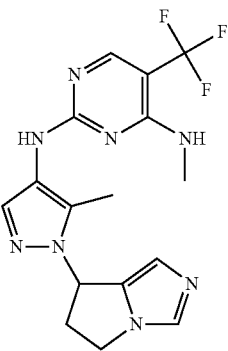 [SMILES: CNc1nc(Nc2cnn(C3CCn4cncc43)c2C)ncc1C(F)(F)F]
D-150

TABLE D-1-continued
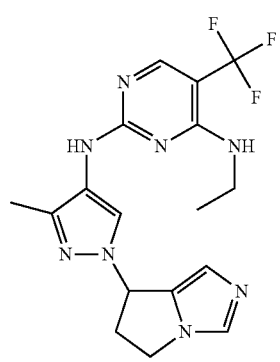
D-152: Second eluting stereoisomer
D-172: First eluting stereoisomer
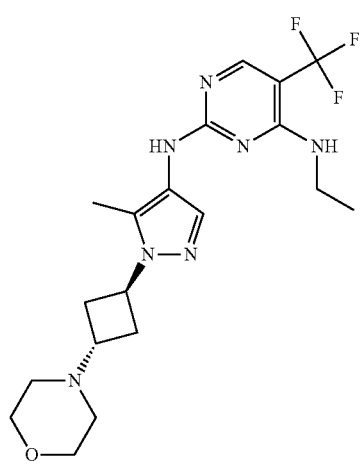 [SMILES: CCNc1nc(Nc2cnn([C@H]3C[C@H](N4CCOCC4)C3)c2C)ncc1C(F)(F)F]
D-153
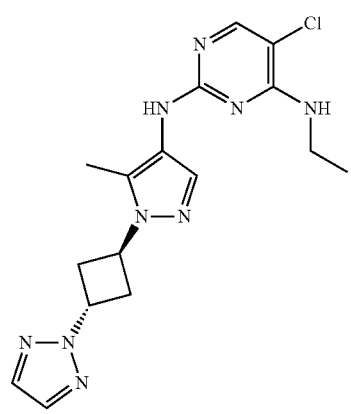 [SMILES: CCNc1nc(Nc2cnn([C@H]3C[C@H](n4nccn4)C3)c2C)ncc1Cl]
D-154
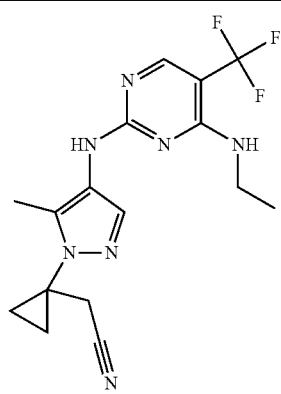
D-155
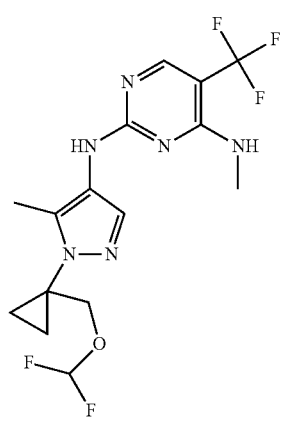 [SMILES: CNc1nc(Nc2cnn(C3(COC(F)F)CC3)c2C)ncc1C(F)(F)F]
D-157
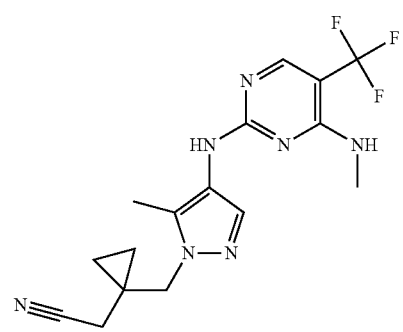 [SMILES: CNc1nc(Nc2cnn(CC3(CC#N)CC3)c2C)ncc1C(F)(F)F]
D-157a
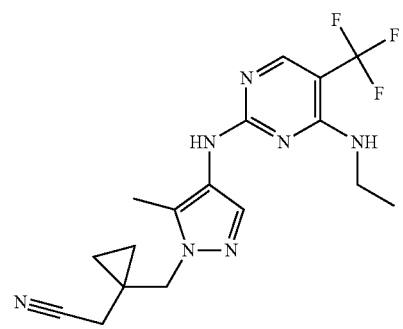 [SMILES: CCNc1nc(Nc2cnn(CC3(CC#N)CC3)c2C)ncc1C(F)(F)F]
D-158

TABLE D-1-continued
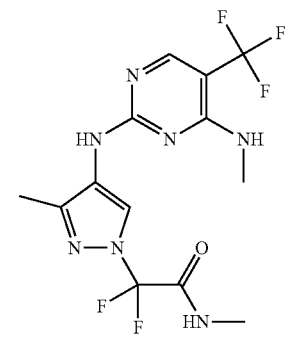 [SMILES: CNC(=O)C(F)(F)n1cc(Nc2ncc(C(F)(F)F)c(NC)n2)c(C)n1]
D-159
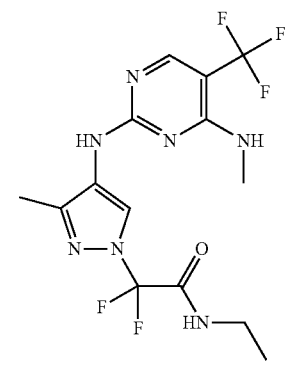 [SMILES: CCNC(=O)C(F)(F)n1cc(Nc2ncc(C(F)(F)F)c(NC)n2)c(C)n1]
D-160
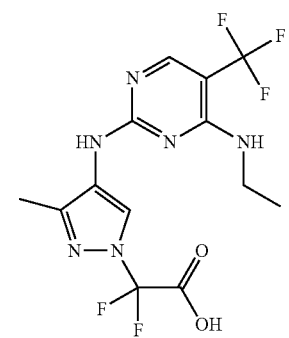 [SMILES: CCNc1nc(Nc2cn(C(F)(F)C(=O)O)nc2C)ncc1C(F)(F)F]
D-161
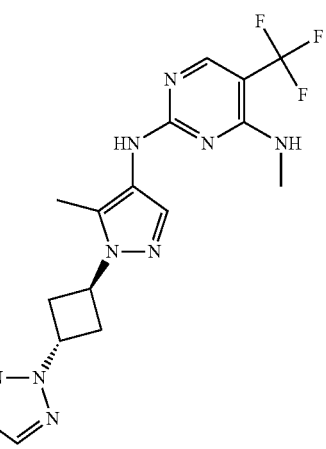
D-162
TABLE D-1-continued
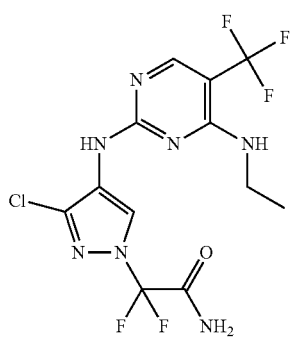 [SMILES: CCNc1nc(Nc2cn(C(F)(F)C(N)=O)nc2Cl)ncc1C(F)(F)F]
D-164
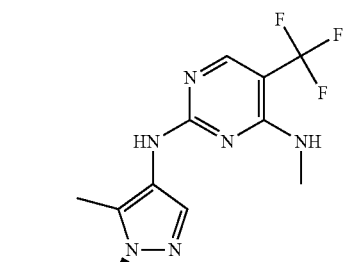
D-165
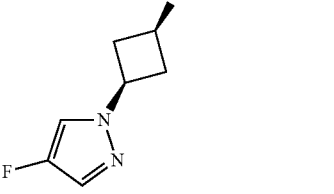
D-167

TABLE D-1-continued
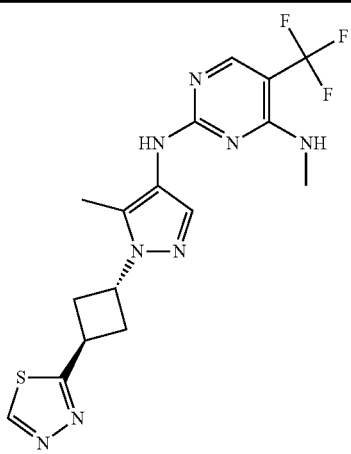
D-168
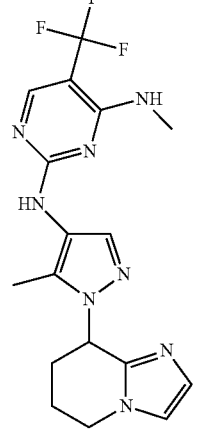
D-169
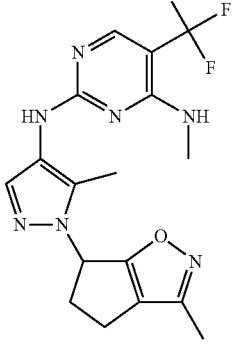
D-173: Second eluting stereoisomer
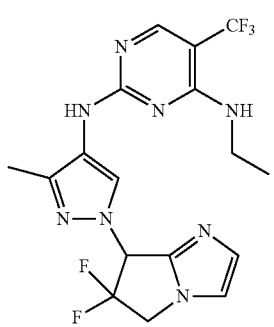 [SMILES: CCNc1nc(Nc2cn(C3c4nccn4CC3(F)F)nc2C)ncc1C(F)(F)F]
D-176
TABLE D-1-continued
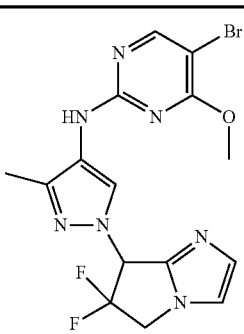
D-177
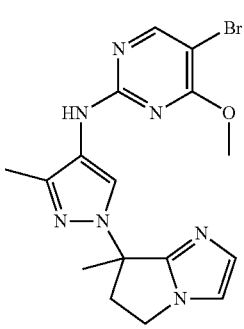 [SMILES: COc1nc(Nc2cn(C3(C)CCn4ccnc43)nc2C)ncc1Br]
D-178
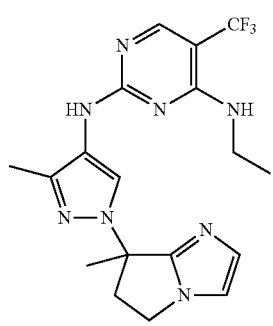 [SMILES: CCNc1nc(Nc2cn(C3(C)CCn4ccnc43)nc2C)ncc1C(F)(F)F]
D-179
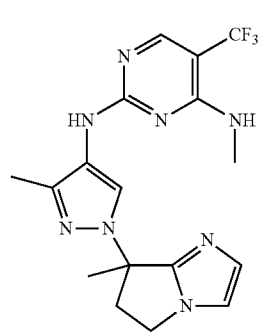 [SMILES: CNc1nc(Nc2cn(C3(C)CCn4ccnc43)nc2C)ncc1C(F)(F)F]
D-180
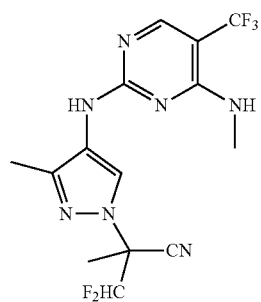
D-181

TABLE D-1-continued
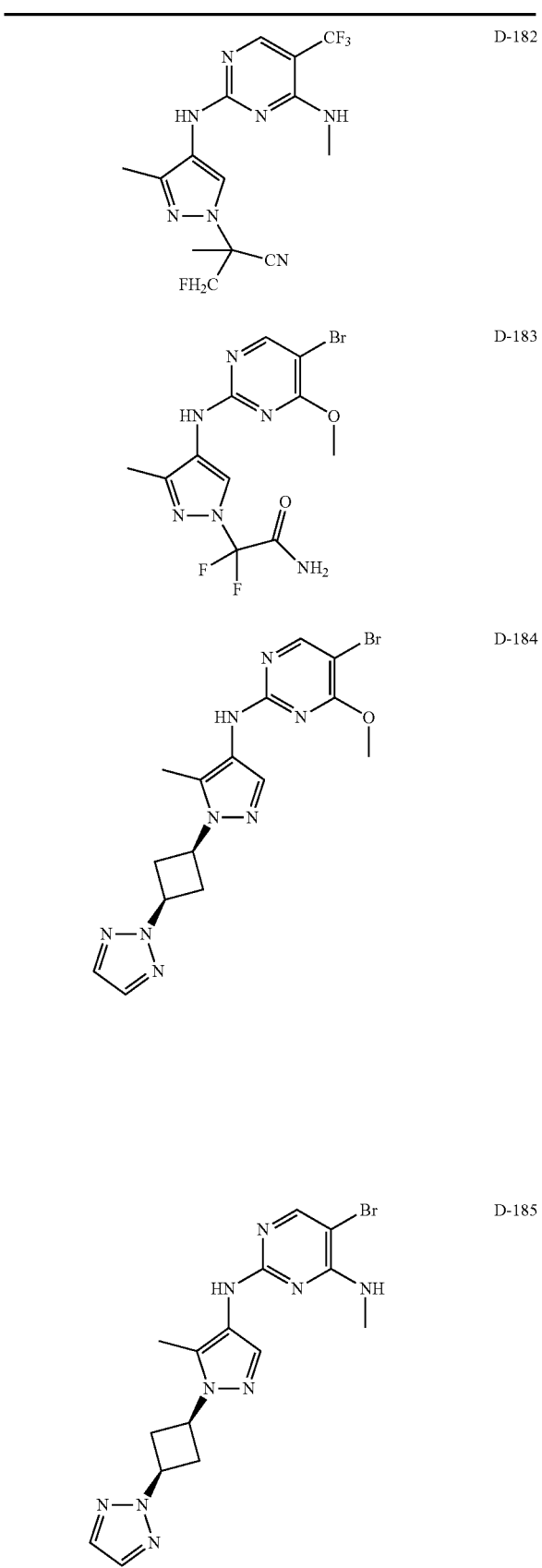
D-182
D-183
D-184
D-185
TABLE D-1-continued
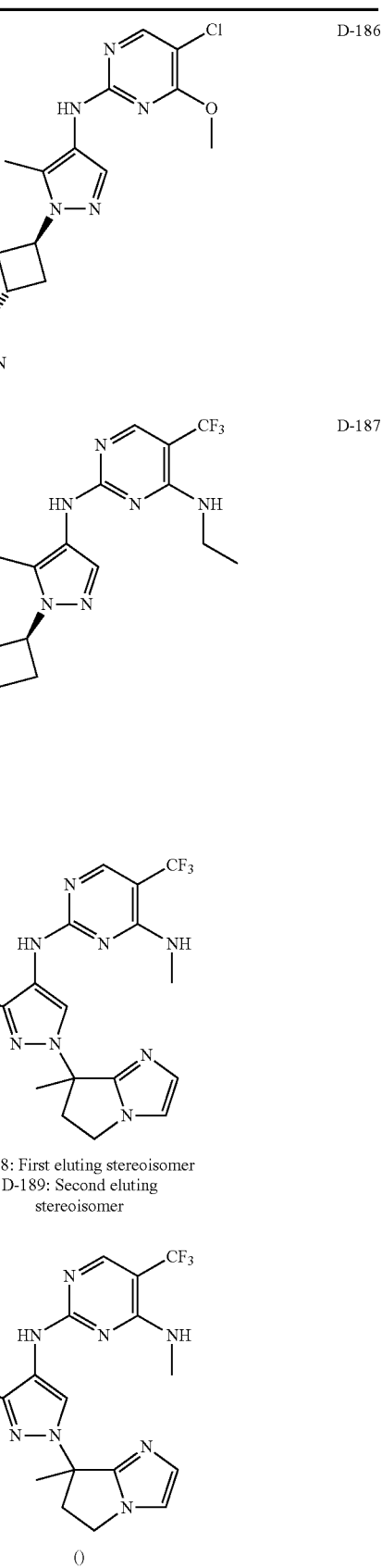
D-186
D-187
D-188: First eluting stereoisomer
D-189: Second eluting stereoisomer TABLE D-1-continued
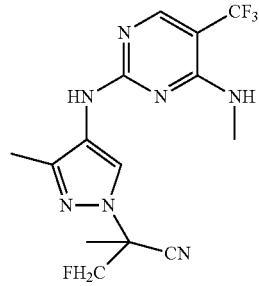
D-190: First eluting stereoisomer
D-191: Second eluting stereoisomer
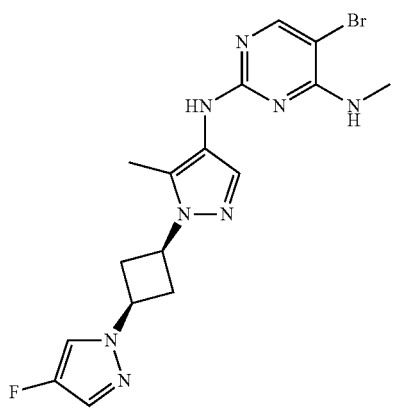 [SMILES: CNc1nc(Nc2cnn([C@H]3C[C@@H](n4cc(F)cn4)C3)c2C)ncc1Br]
D-192
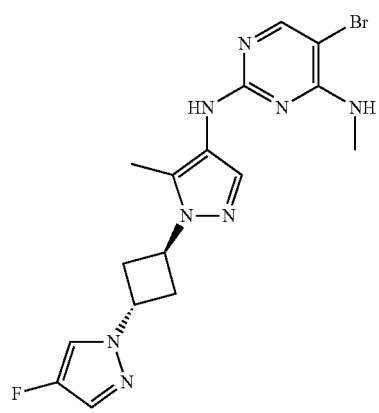 [SMILES: CNc1nc(Nc2cnn([C@H]3C[C@H](n4cc(F)cn4)C3)c2C)ncc1Br]
D-193
TABLE D-1-continued
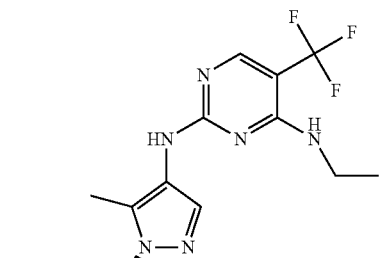
D-194
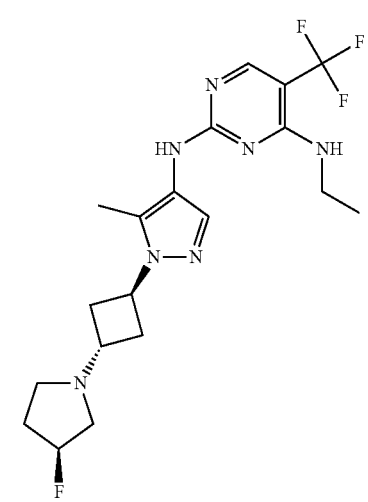 [SMILES: CCNc1nc(Nc2cnn([C@H]3C[C@H](N4CC[C@H](F)C4)C3)c2C)ncc1C(F)(F)F]
D-195
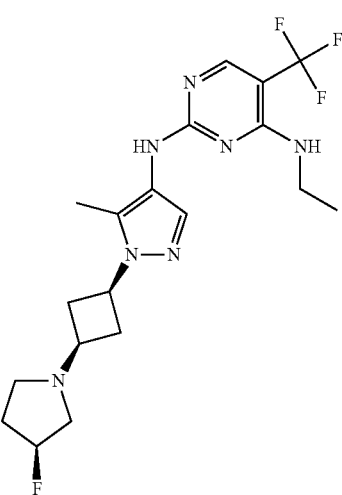 [SMILES: CCNc1nc(Nc2cnn([C@H]3C[C@@H](N4CC[C@H](F)C4)C3)c2C)ncc1C(F)(F)F]
D-196

TABLE D-1-continued

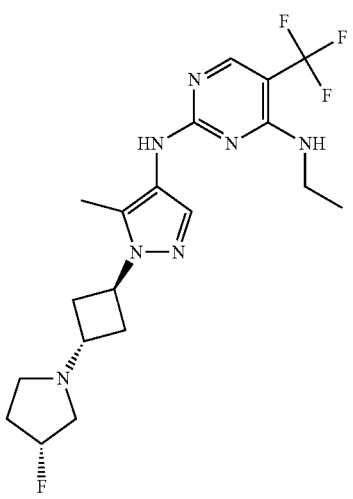 [SMILES: CCNc1nc(Nc2cnn([C@H]3C[C@H](N4CC[C@@H](F)C4)C3)c2C)ncc1C(F)(F)F]

D-197

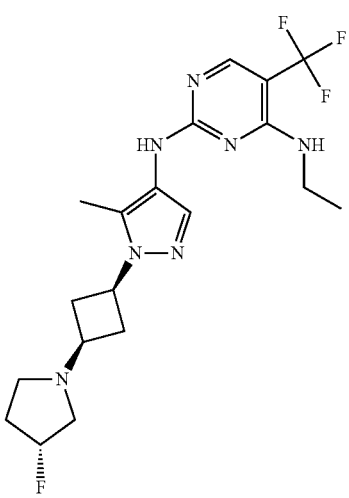 [SMILES: CCNc1nc(Nc2cnn([C@H]3C[C@@H](N4CC[C@@H](F)C4)C3)c2C)ncc1C(F)(F)F]

D-198

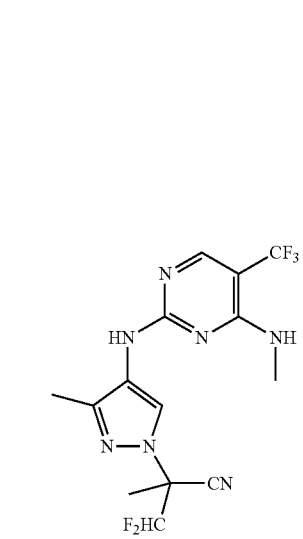

D-199: First eluting stereoisomer
D-200: Second eluting stereoisomer

TABLE D-1-continued

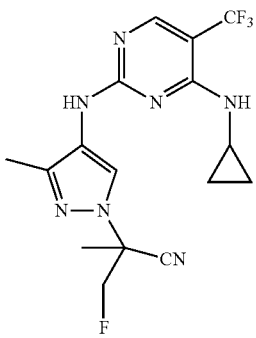

D-201: First eluting stereoisomer
D-202: Second eluting stereoisomer

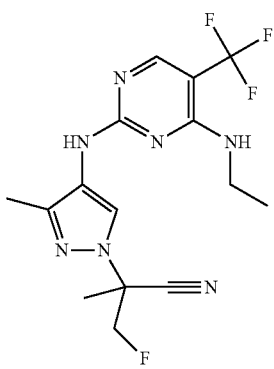 [SMILES: CCNc1nc(Nc2cn(C(C)(C#N)CF)nc2C)ncc1C(F)(F)F]

D-203

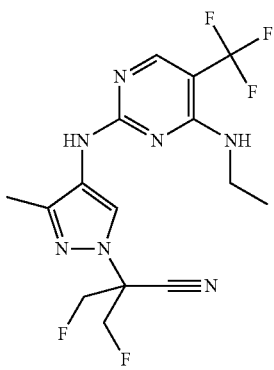 [SMILES: CCNc1nc(Nc2cn(C(C#N)(CF)CF)nc2C)ncc1C(F)(F)F]

D-204

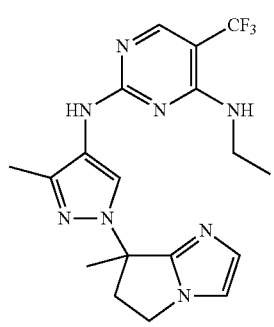

D-205: First eluting stereoisomer
D-206: Second eluting stereoisomer

Representative stereoisomers of various compounds of Table D-1 are shown in Table D-2 below. In one embodiment, a compound may be selected from those compounds in Table D-1 or Table D-2. Also included within the disclosure are pharmaceutically acceptable salts, prodrugs, stereoisomers or a mixture of stereoisomers thereof. In certain embodiments, provided are compounds of Table D-1 or Table D-2 for use in the methods described herein.
TABLE D-2
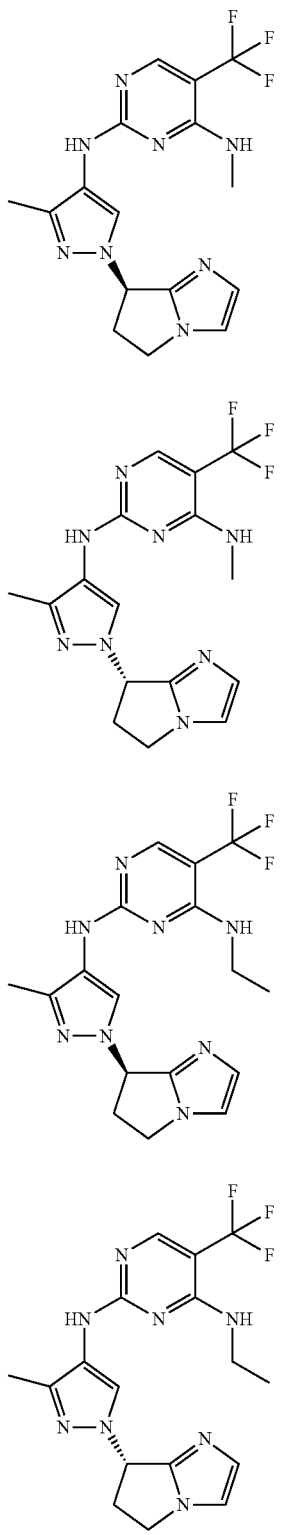
TABLE D-2-continued
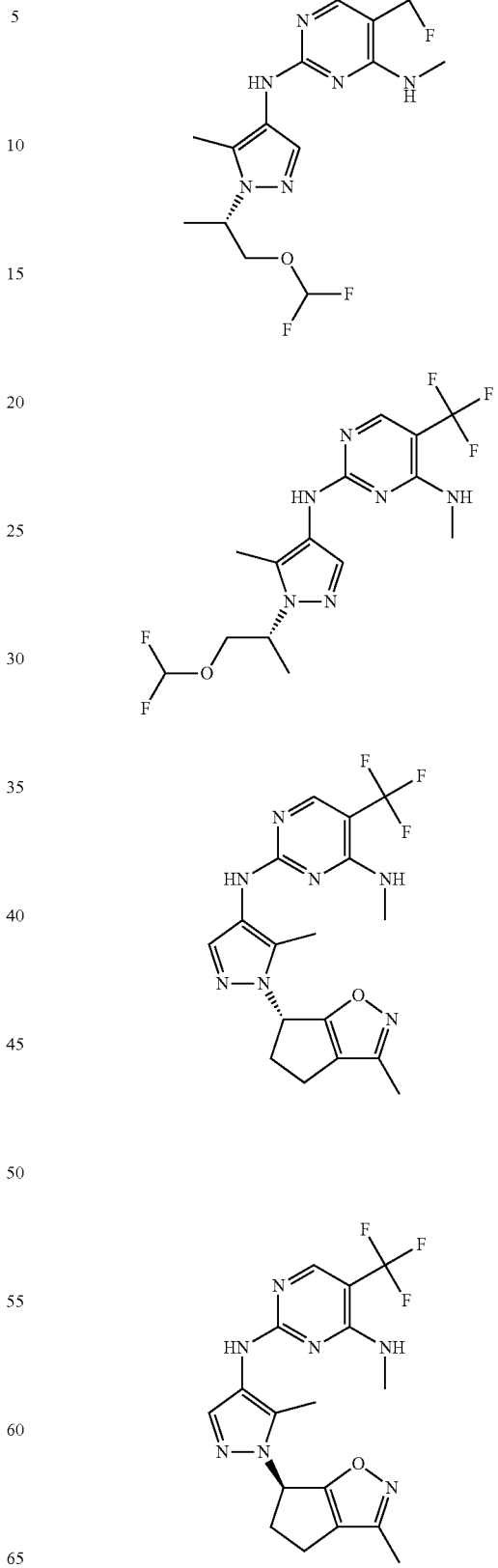

TABLE D-2-continued
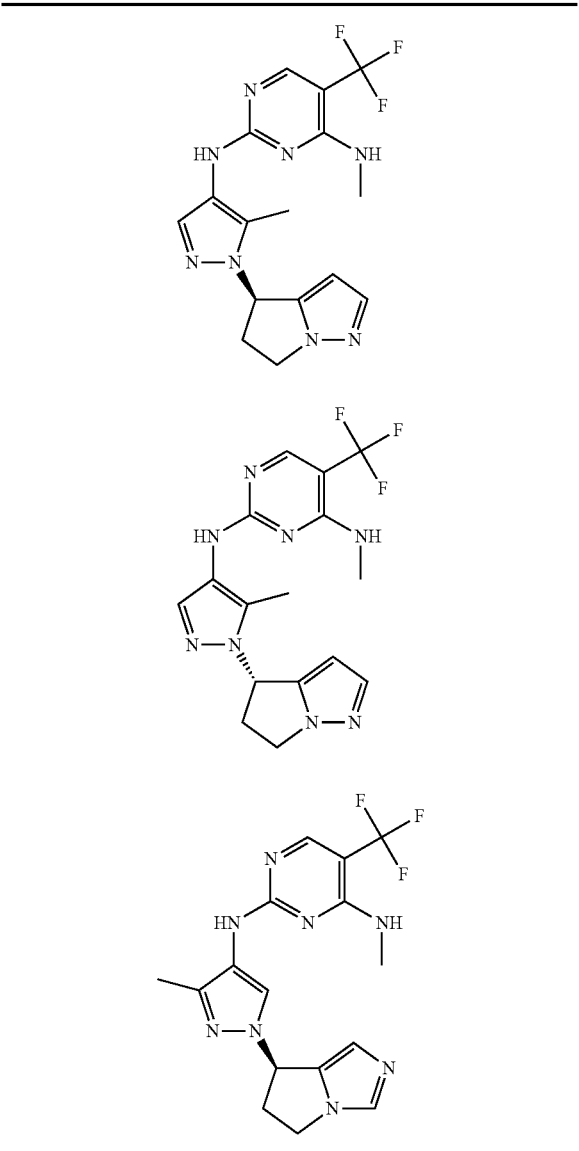
TABLE D-2-continued
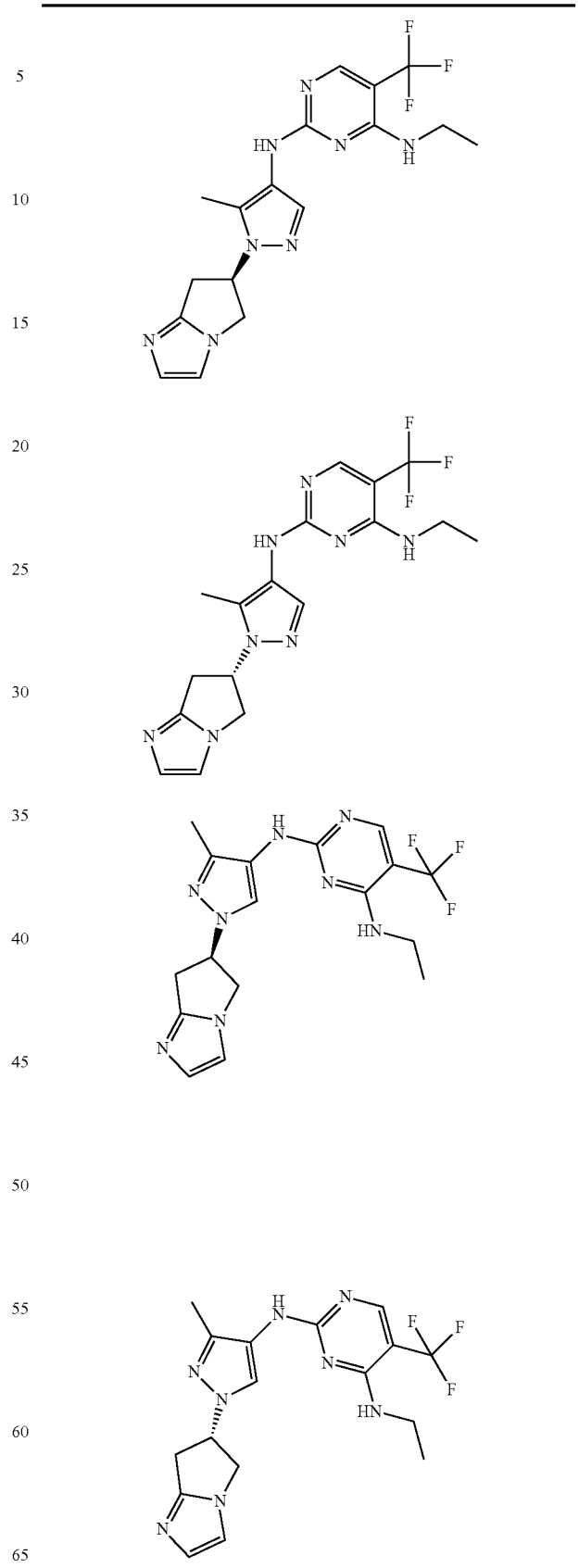

TABLE D-2-continued
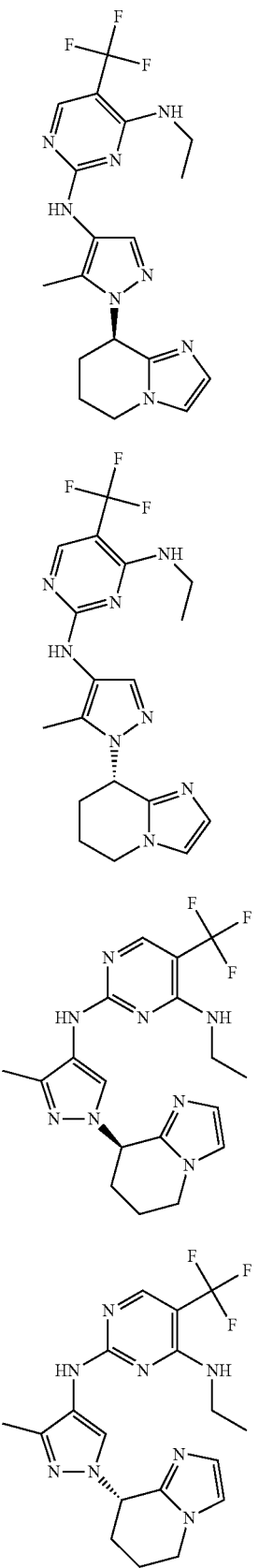
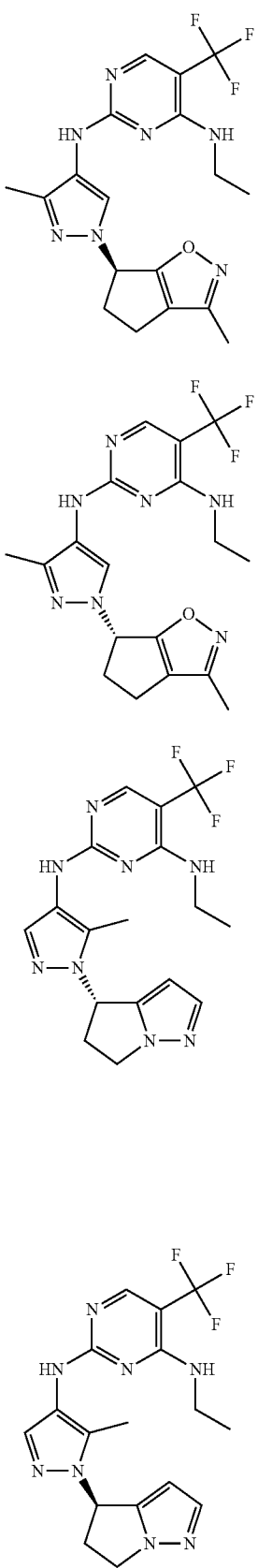

TABLE D-2-continued
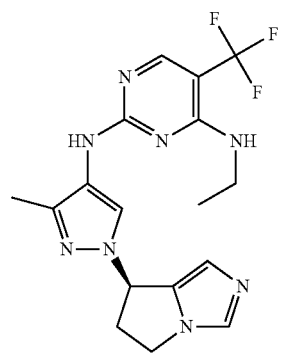 [SMILES: CCNc1nc(Nc2cn([C@@H]3CCn4cncc43)nc2C)ncc1C(F)(F)F]
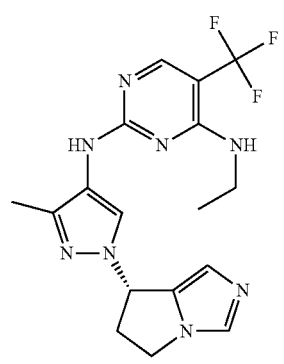 [SMILES: CCNc1nc(Nc2cn([C@H]3CCn4cncc43)nc2C)ncc1C(F)(F)F]
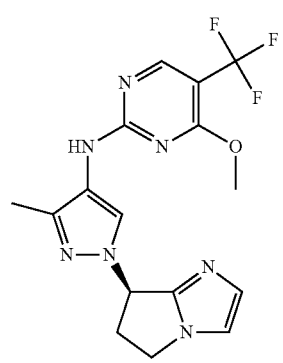 [SMILES: COc1nc(Nc2cn([C@@H]3CCn4ccnc43)nc2C)ncc1C(F)(F)F]
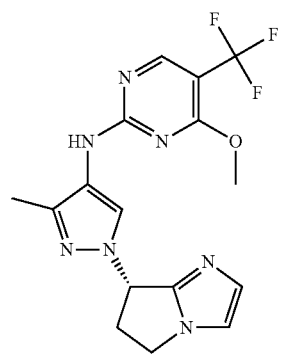 [SMILES: COc1nc(Nc2cn([C@H]3CCn4ccnc43)nc2C)ncc1C(F)(F)F]
TABLE D-2-continued
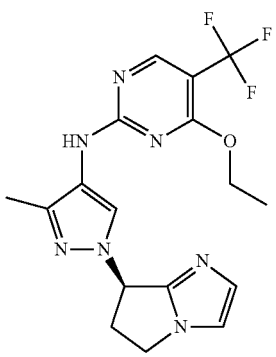 [SMILES: CCOc1nc(Nc2cn([C@@H]3CCn4ccnc43)nc2C)ncc1C(F)(F)F]
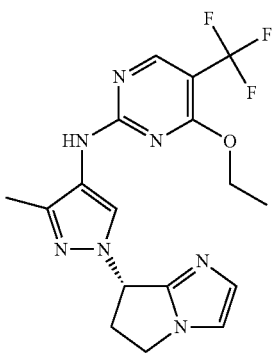 [SMILES: CCOc1nc(Nc2cn([C@H]3CCn4ccnc43)nc2C)ncc1C(F)(F)F]
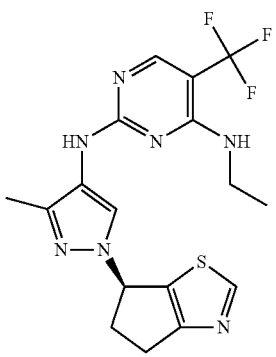 [SMILES: CCNc1nc(Nc2cn([C@@H]3CCc4ncsc43)nc2C)ncc1C(F)(F)F]
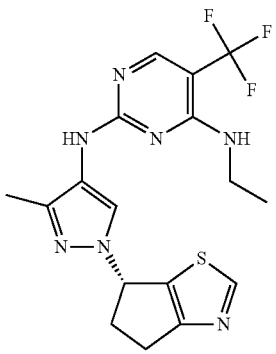 [SMILES: CCNc1nc(Nc2cn([C@H]3CCc4ncsc43)nc2C)ncc1C(F)(F)F]

TABLE D-2-continued
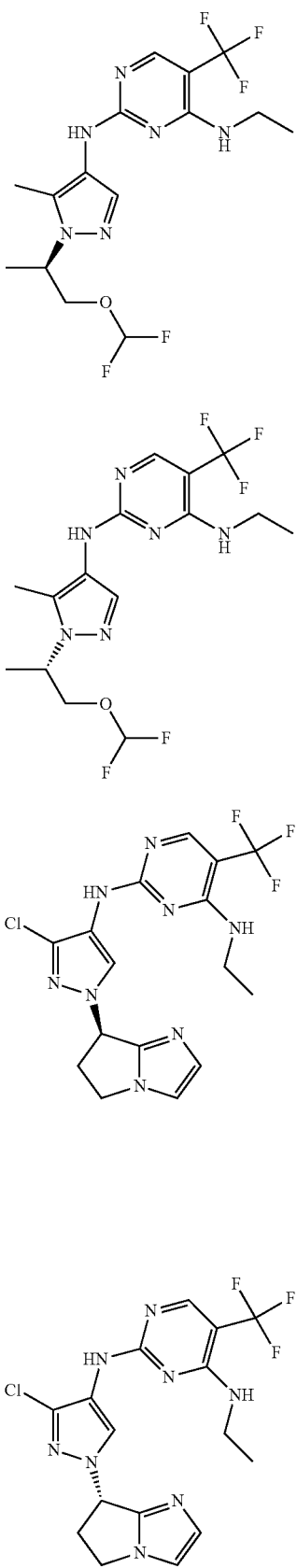
TABLE D-2-continued
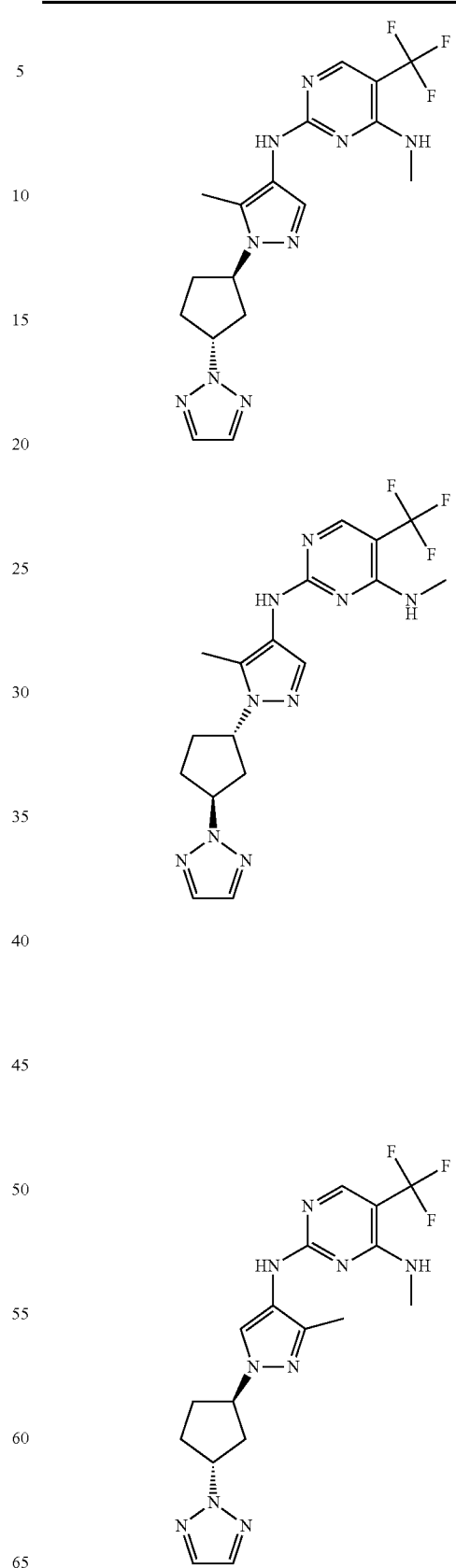

TABLE D-2-continued
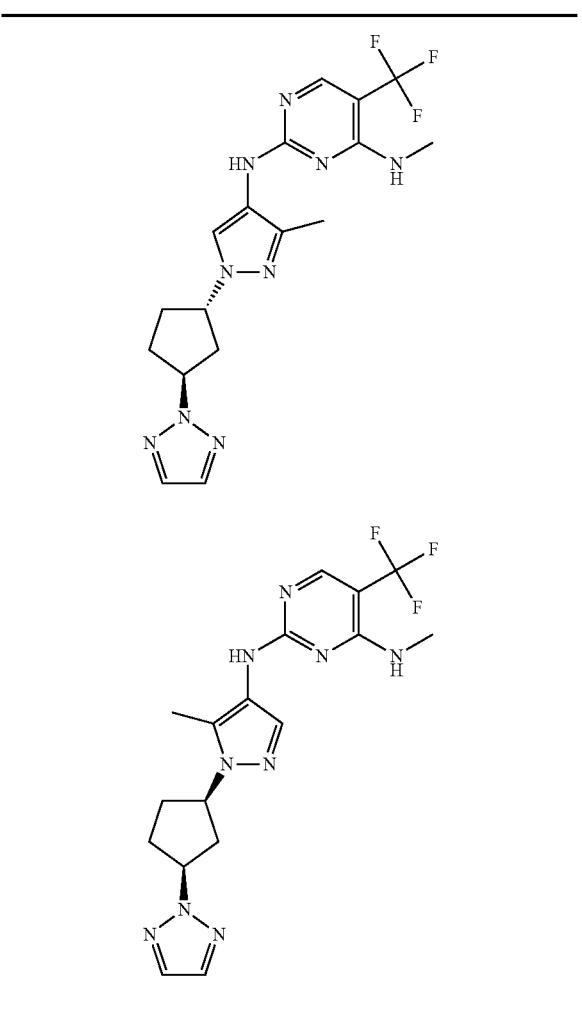
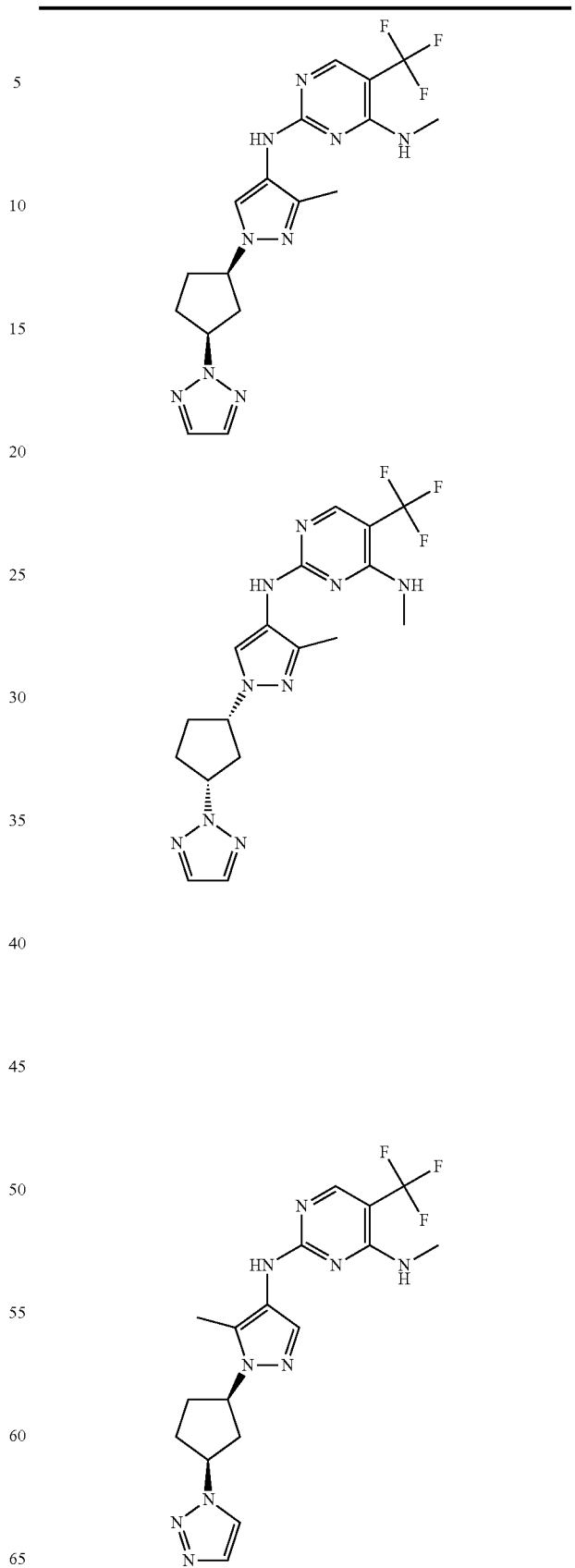

TABLE D-2-continued
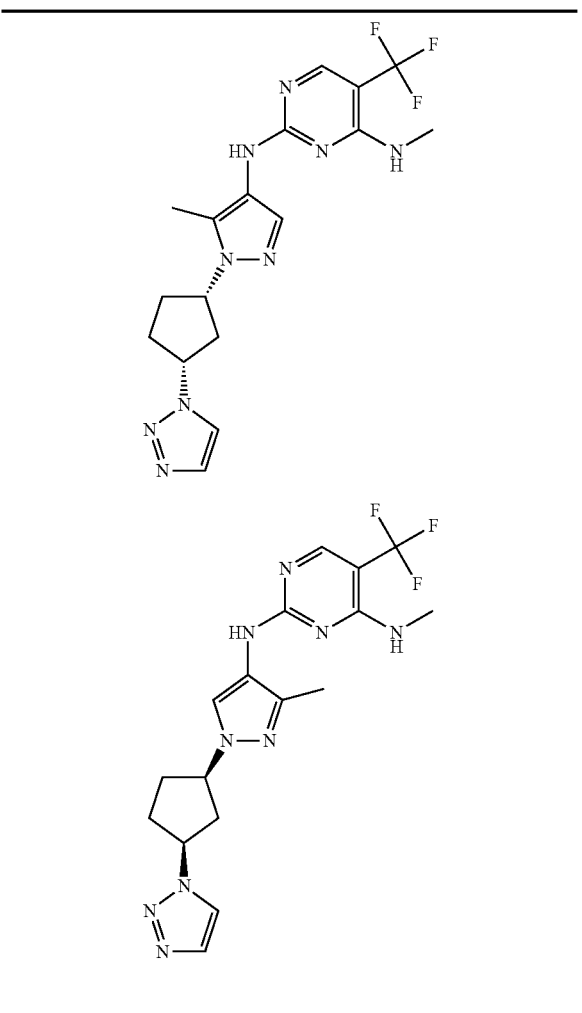
TABLE D-2-continued
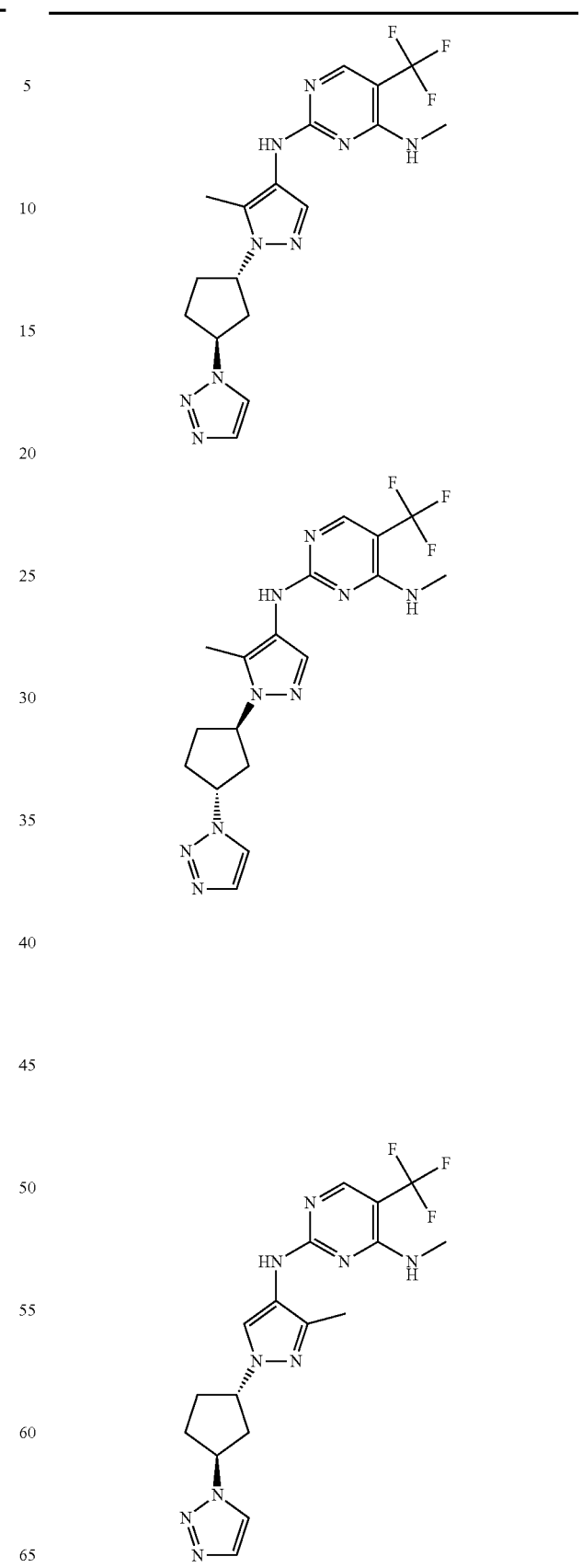

TABLE D-2-continued
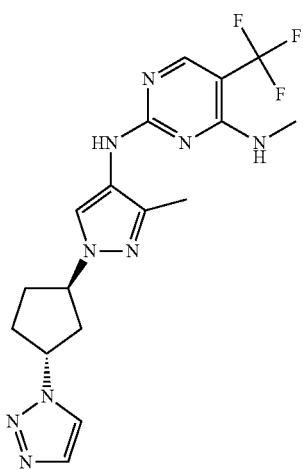 [SMILES: CNc1nc(Nc2cn([C@@H]3CC[C@@H](n4ccnn4)C3)nc2C)ncc1C(F)(F)F]
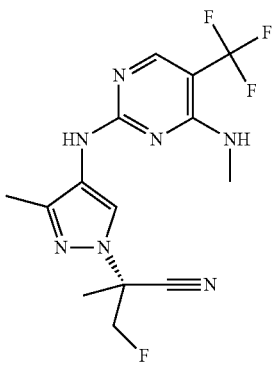 [SMILES: CNc1nc(Nc2cn([C@](C)(C#N)CF)nc2C)ncc1C(F)(F)F]
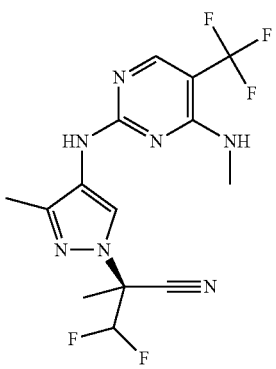 [SMILES: CNc1nc(Nc2cn([C@@](C)(C#N)C(F)F)nc2C)ncc1C(F)(F)F]
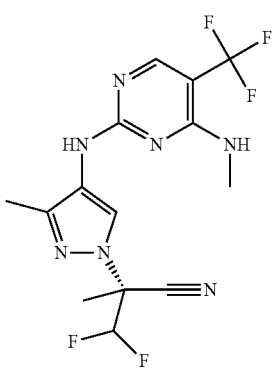 [SMILES: CNc1nc(Nc2cn([C@](C)(C#N)C(F)F)nc2C)ncc1C(F)(F)F]
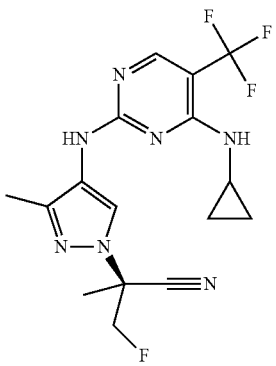 [SMILES: Cc1nn([C@@](C)(C#N)CF)cc1Nc1ncc(C(F)(F)F)c(NC2CC2)n1]

TABLE D-2-continued

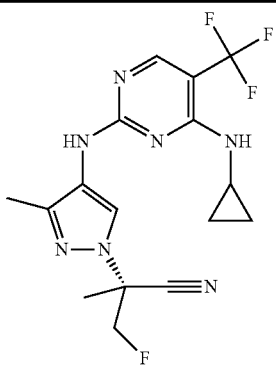

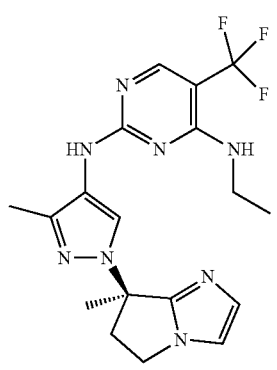 [SMILES: CCNc1nc(Nc2cn([C@]3(C)CCn4ccnc43)nc2C)ncc1C(F)(F)F]

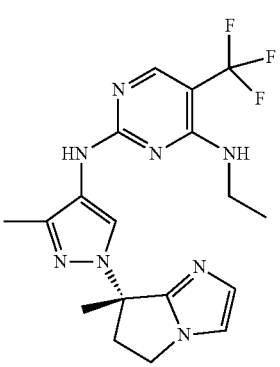 [SMILES: CCNc1nc(Nc2cn([C@@]3(C)CCn4ccnc43)nc2C)ncc1C(F)(F)F]

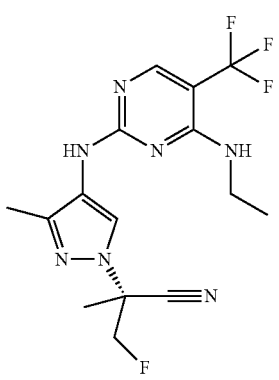 [SMILES: CCNc1nc(Nc2cn([C@](C)(C#N)CF)nc2C)ncc1C(F)(F)F]

TABLE D-2-continued

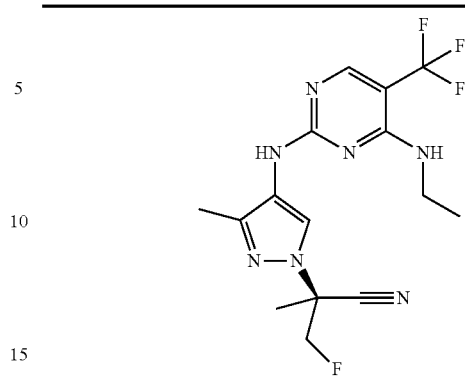

Also provided herein is a method of preparing a compound of formula (D-I), comprising coupling a compound of formula (D-a):

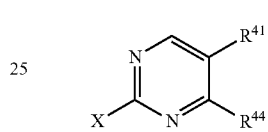

(D-a)

wherein X is a leaving group (e.g., halo), with a compound of formula (D-b):

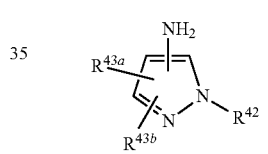

(D-b)

under conditions to provide the compound of formula (D-I), wherein each of the variables is as defined herein.

It is understood that any embodiment of the compounds of a formula described herein, including substructures thereof, and any of the specific substituents set forth herein in the compounds of any of the formulas as set forth above, may be independently combined with other embodiments and/or substituents of compounds of any of the formulas to form embodiments of the inventions not specifically set forth above. In addition, in the event that a list of substituents is listed for any particular R group in a particular embodiment and/or claim, it is understood that each individual substituent may be deleted from the particular embodiment and/or claim and that the remaining list of substituents will be considered to be within the scope of the invention. It is understood that in the present description, combinations of substituents and/or variables of the depicted formulae are permissible only if such contributions result in stable compounds.

3. Pharmaceutical Compositions and Modes of Administration

For the purposes of administration, the compounds of the present disclosure may be administered as a raw chemical or may be formulated as pharmaceutical compositions. Pharmaceutical compositions of the present disclosure comprise a compound of any formula described herein and a pharmaceutically acceptable carrier, diluent or excipient. Accordingly, different embodiments are directed to pharmaceutical compositions comprising any one or more of the foregoing compounds or a pharmaceutically acceptable salt, prodrug or tautomer thereof, and a pharmaceutically acceptable carrier, diluent or excipient, are also provided in various embodiments.

The pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with die tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Examples of such formulations include, but are not limited to DMSO, 10 mM DMSO, 8% hydroxypropyl-beta-cyclodextrin in PBS, propylene glycol, etc. For example, in a certain embodiment the compounds of the disclosure can be used as 4 mM solution in 8% hydroxypropyl-beta-cyclodextrin in PBS for parenteral administration.

As set out herein, certain embodiments of the present compounds may contain a basic functional group, such as amino or methylamino ($NCH_3$), and are, thus, capable of forming pharmaceutically-acceptable salts with pharmaceutically-acceptable acids. The term "pharmaceutically-acceptable salts" in this respect refers to the relatively non-toxic, inorganic and organic acid addition salts of compounds of the present disclosure. These salts can be prepared in situ in the administration vehicle ortho dosage form manufacturing process, or by separately reacting a purified compound of the disclosure in its free base form with a suitable organic or inorganic acid, and isolating the salt thus formed during subsequent purification. Representative salts include die hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19.)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present disclosure may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present disclosure. These salts can likewise be prepared in situ in the administration vehicle or the dosage form manufacturing process, or by separately reacting the purified compound in its free acid form with a suitable base, such as die hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and die like; and metal chelating agents, such as citric acid, ethylenediamine tetraacetic acid (EDTA), sorbitol, tartaric acid, phosphoric acid, and the like.

Formulations of the present disclosure include those suitable for oral, nasal, topical (including buccal and sublingual), rectal, vaginal and/or parenteral administration. The formulations may conveniently be presented in unit dosage form and may be prepared by any methods well know n in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In certain embodiments, a formulation of the present disclosure comprises an excipient selected from the group consisting of cyclodextrins, liposomes, micelle forming agents, e.g., bile acids, and polymeric carriers, e.g., polyesters and polyanhydrides; and a compound of the present disclosure. In certain embodiments, an aforementioned formulation renders orally bioavailable a compound of the present disclosure.

Methods of preparing these formulations or compositions include the step of bringing into association a compound of the present disclosure with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. A compound of the present disclosure may also be administered as a bolus, electuary or paste.

In solid dosage forms of the disclosure for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and nonionic surfactants; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present disclosure, such as dragees, capsules, pills and granules, may optionally be scored or prepared with coatings and shells, such as enteric coatings and other coatings well known in die pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in die form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the disclosure include pharmaceutically acceptable emulsions, microemulsions, solutions, suspensions, syrups and elixirs. In addition to die active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the disclosure for rectal or vaginal administration may be presented as a suppository, which may be prepared by mixing one or mote compounds of the disclosure with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present disclosure which are suitable for vaginal administration also include pessaries, tampons, creams, gels, pastes, foams or spray formulations containing such carriers as are known in the art to be appropriate.

Dosage forms for the topical or transdermal administration of a compound of this disclosure include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux. Such transdermal patches may be used to provide continuous or discontinuous infusion of the compounds described herein in controlled amounts. Such patches may be constructed for continuous, pulsatile, or on demand delivery of pharmaceutical agents.

Ophthalmic formulations, eye ointments, powders, solutions and the like, are also contemplated as being within the scope of this disclosure.

Pharmaceutical compositions of this disclosure suitable for parenteral administration comprise one or more compounds of die disclosure in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenyl sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on die ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

The compositions that include at least one compound described herein or a pharmaceutically acceptable salt, tautomer, stereoisomer, mixture of stereoisomers, prodrug, or deuterated analog thereof can be formulated so as to provide quick, sustained or delayed release of die active ingredient after administration to the subject by employing procedures known in die art. Controlled release drug delivery systems for oral administration include osmotic pump systems and dissolutional systems containing polymer-coated reservoirs or drug-polymer matrix formulations.

4. Treatment Methods and Uses

"Treatment" or "treating" is an approach for obtaining beneficial or desired results including clinical results. Beneficial or desired clinical results may include one or more of the following: a) inhibiting die disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of die disease or condition); and/or c) relieving the disease, that is, causing die regression of clinical symptoms (e.g., ameliorating the disease state, providing partial or total remission of the disease or condition, enhancing effect of another medication, delaying the progression of the disease, increasing die quality of life and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of as described herein. The therapeutically effective amount may vary-depending on the subject, and disease or condition being treated, the weight and age of the subject, the severity of the disease or condition, and the manner of administering, which can readily be determined by one of ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety- or tolerance dosage in human or non-human subjects. Such properties may be examined using commonly known methods to those skilled in the art.

LRRK2 has been associated with the transition from mild cognitive impairment to Alzheimer's disease; L-Dopa induced dyskinesia (Hurley et al., Eur. J. Neurosci., Vol. 26, 2007, 171-177); CNS disorders associated with neuroprogenitor cell proliferation and migration, and regulation of LRRK2 may have utility in improving neurological outcomes following ischemic injury, and stimulating restoration of CNS function following neuronal injury such as ischemic stroke, traumatic brain injury, or spinal cord injury (Milosevic et al., Neurodegen., Vol. 4, 2009, 25; See Zhang et al., J. Neurosci. Res. Vol. 88, 2010, 3275-3281); Parkinson's disease. Alzheimer's disease, multiple sclerosis, and HIV-induced dementia (See Milosevic et al., Mol. Neurodegen., Vol. 4, 2009, 25); kidney, breast, prostate (e.g. solid tumor), blood and lung cancer, and acute myeologenouse leukemia (AML); lymphomas and leukemias (See Ray-et al., J. Immunolo., Vol. 230, 2011, 109); multiple myeoloma (Chapman et al., Nature, Vol. 471, 2011, 467-472); papillary renal and thyroid carcinomas; multiple myeloma (Chapman et al., Nature, Vol. 471, 2011, 467-472); diseases of the immune system, including rheumatoid arthritis, systemic lupus erythematosus autoimmune hemolytic anemia, pure red cell aplasia, idiopathic thrombocytopenic pupura (ITP), Evans syndrome, vasculitis, bullous skin disorders, type 1 diabetes mellitus, Sjogren's syndrome, Delvic's disease, and inflammatory myopathies (Nakamura et al., DNA Res. Vol. 13(4), 2006, 169-183; See Engel et al., Pharmacol. Rev. Vol. 63, 2011, 127-156; Homam et al., J. Clin. Neuromuscular Disease, Vol. 12, 2010, 91-102); ankylosing spondylitis and leprosy infection (DAnoy et al., PLoS Genetics, Vol. 6(12), 2010, e1001195, 1-5; see Zhang et al., N. Eng. J. Med. Vol. 361, 2009, 2609-2618); alpha-synucleinopathies, taupathies (See Li et al., 2010 Neurodegen. Dis. Vol. 7, 2010, 265-271); Gaucher disease (See Westbroek et al., Trends. Mol. Med. Vol. 17, 2011, 485-493); tauopathy diseases characterized by hyperphosphorylation of Tau such as argyrophilic grain disease, Pick's disease, corticobasal degeneration, progressive supranuclear palsy, and inherited frontotemporal dementia and parkinsonism linked to chromosome 17 (See Goedert, M and Jakes, R, Biochemica et Biophysica Acta, Vol. 1739, 2005, 240-250); diseases characterized by diminished dopamine levels such as withdrawal symptoms/relapse associated with drug addiction (See Rothman et al., og. Brain Res., Vol. 172, 2008, 385); microglial proinflammatory responses (See Moehle et al., J. Neuroscience Vol. 32, 2012, 1602-1611); Crohn's disease pathogenesis (see Barrett et al., Nature Genetics, Vol. 40, 2008, 955-962); and amyotrophic lateral sclerosis (ALS).

It is suggested that increased LRRK2 activity may be characteristic of ALS. Significantly elevated levels of LRRK2 mRNA have been observed in fibroblasts of Niemann-Pick Type C (NPC) disease patients, indicating abnormal LRRK2 function may play a role in lysosomal disorders.

In another aspect, the present disclosure relates to a method of treating a disease or condition mediated, at least in part, by LRRK2. In particular, the disclosure provides methods for preventing or treating a disorder associated with LRRK2 in a mammal, comprising the step of administering to said mammal a therapeutically effective amount of a compound of structure (I) or therapeutic preparation of the present disclosure. In some embodiments the LRRK-mediated disease or condition is a neurodegenerative disease, for examples a central nervous system (CNS) disorder, such as Parkinson's disease (PD), Alzheimer's disease (AD), dementia (including Lewy body dementia and cascular dementia), amyotrophic lateral sclerosis (ALS), age related memory dysfunction, mild cognitive impairment (i.e. including die transition from mild cognitive impairment to Alzheimer's disease), argyrophilic grain disease, lysosomal disorders (for example, Niemann-PickType C disease, Gaucher disease) corticobasal degeneration, progressive supranuclear palsy, inherited frontotemporal dementia and parkinsonism linked to chromosome 17 (FTDP-17), withdrawal symptoms/relapse associated with drug addiction, L-Dopa induced dyskinesia, Huntington's disease (HD), and HIV-associated dementia (HAD). In other embodiments the disorder is an ischemic disease of organs including but not limited to brain, heart, kidney, and liver.

In some other embodiments, the disease or condition mediated, at least in part, by LRRK2, is cancer. In certain embodiments, the cancer is thyroid, renal (including papillary renal), breast, lung, blood, and prostate cancers (e.g. solid tumor), leukemias (including acute myelogenous leukemia (AML)), lymphomas, or leukemias. In some embodiments, the cancer is kidney cancer, breast cancer, prostate cancer, blood cancer, papillary cancer, lung cancer, acute myelogenous leukemia or multiple myeloma.

In other embodiments, the presently disclosed compounds are used in methods for treatment of inflammatory disorders. In some embodiments, the disorder is an inflammatory disease of the intestines such as Crohn's disease or ulcerative colitis (both generally known together as inflammatory bowel disease). In other embodiments, the inflammatory disease is leprosy, amyotrophic lateral sclerosis, rheumatoid arthritis, or ankylosing spondylitis. In some embodiments, the inflammatory disease is leprosy, Crohn's disease, inflammatory bowel disease, ulcerative colitis, amyotrophic lateral sclerosis, rheumatoid arthritis or ankylosing spondylitis.

In other embodiments, the presently disclosed compounds are used in methods for treatment of multiple sclerosis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies.

Other embodiments include methods for enhancing cognitive memory of a subject, the method comprising administering an effective amount of a composition comprising the compound of a formula described herein to a subject in need thereof.

The term "trauma" as used herein refers to any physical damage to the body caused by violence, accident, fracture etc. The term "ischemia" refers to a cardiovascular disorder characterized by a low-oxygen state usually due to the obstruction of the arterial blood supply or inadequate blood flow leading to hypoxia in the tissue. The term "stroke" refers to cardiovascular disorders caused by a blood clot or bleeding in the brain, most commonly caused by an interruption in the flow of blood in the brain as from clot blocking a blood vessel, and in certain embodiments of the disclosure the term stroke refers to ischemic stroke or hemorrhagic stroke. The term "myocardial infarction" refers to a cardiovascular disorder characterized by localized necrosis resulting from obstruction of the blood supply.

In certain embodiments, a compound or pharmaceutical composition is administered orally. In other embodiments, the compound or pharmaceutical composition is administered intravenously. Alternative routes of administration include sublingual, intramuscular, and transdermal administrations.

In certain embodiments, die present disclosure relates to compounds for inhibiting cell death, wherein the compounds are represented by the structure of any formula described herein. In certain embodiments, the compounds of the present disclosure are inhibitors of cell death. In any event, the compounds of the present disclosure preferably exert their effect on inhibiting cell death at a concentration less than about 50 micromolar, more preferably at a concentration less than about 10 micromolar, and most preferably at a concentration less than 1 micromolar.

The compounds of the disclosure can be tested in standard animal models of stroke and standard protocols such as described by Hara, H., et al. Proc Natl Acad Sci USA, 1997. 94(5): 2007-12.

When the compounds of the present disclosure are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The preparations of the present disclosure may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present disclosure, which may be used in a suitable hydrated form, and/or the pharmaceutical compositions of the present disclosure, are formulated into pharmaceutically-acceptable dosage forms by conventional methods known to those of skill in the art.

Actual dosage levels of the active ingredients in the pharmaceutical compositions of this disclosure may be varied so as to obtain an amount of the active ingredient that is effective to achieve the desired therapeutic response for a particular patient, composition, and mode of administration, without being toxic to die patient.

The selected dosage level will depend upon a variety of factors including the activity of the particular compound of the present disclosure employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors w ell known in the medical arts. A daily, weekly, or monthly dosage (or other time interval) can be used.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required to achieve the desired therapeutic effect and then gradually increasing the dosage until the desired effect is achieved.

In general, a suitable daily dose of a compound of the disclosure will be that amount of the compound that is the lowest dose effective to produce a therapeutic effect (e.g., inhibit necrosis). Such an effective dose will generally depend upon the factors described above. Generally doses of the compounds of this disclosure for a patient, when used for die indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight.

If desired, the effective daily dose of die active compound may be administered as two, three, four, five, six or more sub-doses administered separately at appropriate intervals throughout the day, optionally, in unit dosage forms.

In another aspect of the disclosure the compounds can be administered in combination with other agents, including (but not limited to) compounds that are apoptosis inhibitors; PARP poly(ADP-ribose) polymerase inhibitors; Src inhibitors; agents fertile treatment of cardiovascular disorders; anti-inflammatory agents, anti-thrombotic agents; fibrinolytic agents; anti-platelet agents, lipid reducing agents, direct thrombin inhibitors; glycoprotein IIb/IIIa receptor inhibitors; calcium channel blockers; beta-adrenergic receptor blocking agents; cyclooxygenase (e.g., COX-1 and COX-2) inhibitors; angiotensin system inhibitor (e.g., angiotensin-converting enzyme (ACE) inhibitors); renin inhibitors; and/or agents that bind to cellular adhesion molecules and inhibit the ability of white blood cells to attach to such molecules (e.g., polypeptides, polyclonal and monoclonal antibodies).

The disclosure also provides combinations of two or more compounds that inhibit cellular necrosis (e.g., a compound as disclosed herein and an additional agent for inhibiting necrosis). The disclosure also provides combinations of one or more compounds that inhibit cellular necrosis combined with one or more additional agents or compounds (e.g., other therapeutic compounds for treating a disease, condition, or infection).

5. Kits

The disclosure also provides kits including one or more compounds or combinations of the disclosure, or a pharmaceutically acceptable salt, tautomer, stereoisomer, mixture of stereoisomers, prodrug, or deuterated analog thereof, and suitable packaging. A kit can also include one or more additional agents or compounds described herein. The different components of the kit can be provided in different containers. The kit can be compartmentalized to receive the containers in close confinement. The kit can also contain instructions for using the compounds according to the disclosure.

As used herein, a kit such as a compartmentalized kit includes any kit in which compounds or agents are contained in separate containers. Illustrative examples of such containers include, but are not limited to, small glass containers, plastic containers or strips of plastic or paper. Particularly preferred types of containers allow the skilled worker to efficiently transfer reagents from one compartment to another compartment such that the samples and reagents are not cross-contaminated and the agents or solutions of each container can be added in a quantitative fashion from one compartment to another. Such containers include, but are not limited to, a container that will accept a compound or combination of compounds and/or other agents of the disclosure. One or more compounds or agents can be provided as a powder (e.g. lyophilized powder) or precipitate. Such compound(s) can be resuspended prior to administration in a solution that may be provided as part of the kit or separately available. A kit can contain compounds or agents in other forms such as liquids, gels, solids, as described herein. Different compounds and/or agents may be provided in different forms in a single kit.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, preloaded syringe, or intravenous bag.

EXAMPLES

The examples and preparations provided below further illustrate and exemplify the compounds of the present disclosure and methods for testing such compounds. It is to be understood that the scope of the present disclosure is not limited in any way by the scope of the following examples. In the following examples, and throughout the specification and claims, molecules with a single chiral center (such as compound (I)), unless otherwise noted, exist as a racemic mixture. Single enantiomers may be obtained by methods known to those skilled in die art.

The following examples are provided for purposes of illustration, not limitation. It should be appreciated by those of skill in the art that the techniques disclosed in the examples which follow represent techniques to function well in the practice of the disclosure, and thus can be considered to constitute specific modes for its practice. However, those of skill in the art should, in light of die present disclosure, appreciate that many changes can be made in the embodiments which are disclosed and still obtain a like or similar result without departing from the spirit and scope of the disclosure.

6. General Experimental Methods

The compounds of die present invention can be prepared according to any number of methods known in the art, including those methods specifically described in the Examples below. The following General Reaction Scheme I illustrates a method of making compounds of this disclosure, i.e., compounds of formula (I), wherein $R^1$, $R^2$, $R^{3a}$, $R^{3b}$, $R^4$, $R^5$ and Z are as defined above, and X and X' are independently halogens.

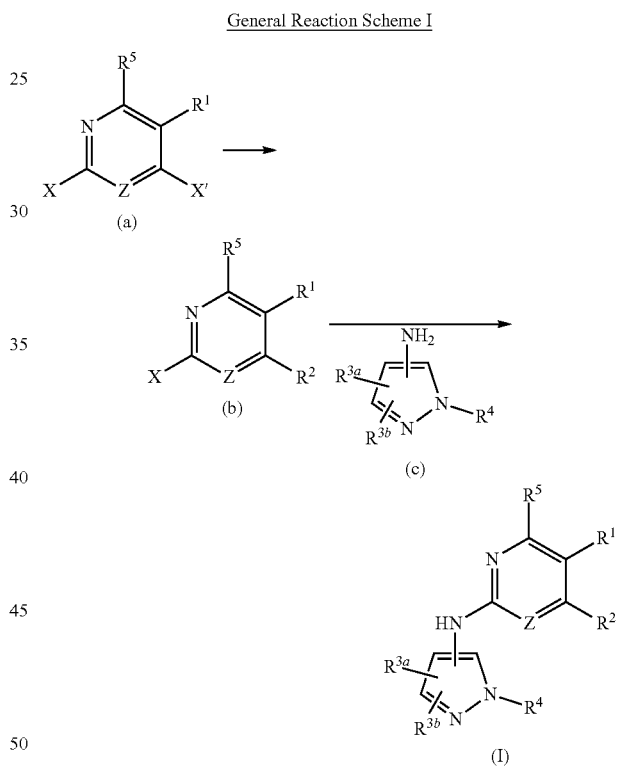

Referring to General Reaction Scheme I, compound (a) is purchased from commercial sources or prepared according to methods known in the art. Coupling (for example, Buchwald-Hartwig or Suzuki coupling) of (a) with H—$R^2$ or an appropriately functionalized derivative thereof (e.g., boronic acid derivative) yields compound (b). Amination of compound (b) with pyrazole (c) yields desired compound of formula I. Modifications to the above General Scheme are also possible, for example the coupling and amination steps can be reversed.

It is understood that one skilled in the art may be able to make these compounds by similar methods or by combining other methods known to one skilled in the art. It is also understood that one skilled in die art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc, or synthesized according to sources known to those skilled in the art (see, for example, Advanced Organic Chemistry: Reactions, Mechanisms, and Structure, 5th edition (Wiley, December 2000)) or prepared as described in this disclosure.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diaryalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and die like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W, and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in die art, although such protected derivatives of compounds of this disclosure may not possess pharmacological activity as such, they may be administered to a mammal and thereafter metabolized in die body to form compounds of the disclosure which are pharmacologically active. Such derivatives may therefore be described as "prodrugs". All prodrugs of compounds of this disclosure are included within the scope of the disclosure.

Furthermore, all compounds of the disclosure which exist in free base or acid form can be converted to their pharmaceutically acceptable salts by treatment with the appropriate inorganic or organic base or acid by methods known to one skilled in die art. Salts of the compounds of die disclosure can be converted to their free base or acid form by standard techniques.

Where die preparation of starting materials is not described, these are commercially available, known in the literature or readily obtainable by those skilled in the art using standard procedures. Where it is stated that compounds were prepared analogously to earlier examples or intermediates, it will be appreciated by die skilled person that die reaction time, number of equivalents of reagents and temperature can be modified for each specific reaction and that it may be necessary or desirable to employ different work-up or purification techniques.

A: Compound Preparation

In the following examples, all non-aqueous reactions were carried out in oven-dried or flame-dried glassware under nitrogen atmosphere. All chemicals were purchased from commercial vendors and used as is, unless otherwise specified. Reactions were magnetically stirred and monitored by thin layer chromatography (TLC) with 250 μm pre-coated silica gel plates, visualized either with UV, or in an iodine chamber. Flash column chromatography was performed using silica gel (100-200 mesh). Chemical shifts are reported relative to chloroform ($\delta$7.26), methanol ($\delta$3.31), or DMSO ($\delta$2.50) for $^1$H NMR. HPLC analysis was performed on Shimadzu 20AB HPLC system with a photodiode array detector and Luna-C18(2) 2.0×50 mm, 5 um column at a flow rate of 1.2 mL/min with a gradient solvent Mobile phase A (MPA, $H_2O$+0.037% (v/v) TFA): Mobile phase B (MPB, ACN+0.018% (v/v) TFA) (0.01 min, 10% MPB; 4 min, 80% MPB; 4.9 min. 80% MPB; 4.92 min, 10% MPB; 5.5 min, 10% MPB). LCMS was detected under 220 and 254 nm or used evaporative light scattering (ELSD) detection as well as positive electrospray ionization (MS). Semi-preparative HPLC was performed by either acidic or neutral condition. Acidic: Luna C18 100×30 mm, 5 μm; MPA: HCl/$H_2O$=0.04%, or formic acid/$H_2O$=0.2% (v/v); MPB: ACN. Neutral: Waters Xbridge 150-25, 5 μm; MPA: 10 mM $NH_4HCO_3$ in $H_2O$; MPB: ACN. Gradient for both conditions: 10% of MPB to 80% of MPB within 12 min at a flow rate of 20 mL/min. then 100% MPB over 2 min, 10% MPB over 2 min, UV detector.

Example A-1

Synthesis of 2-(4-Amino-3-methyl-pyrazol-1-yl)-2-methyl-propanenitrile (A-1)

Methyl 2-methyl-2-(3-methyl-4-nitro-pyrazol-1-yl) propanoate

To a solution of 3-methyl-4-nitro-1H-pyrazole (40 g, 314.71 mmol) in DMF (700 mL) was added NaH (18.88 g, 472.06 mmol, 60% purity) at 0° C. over a period of 30 min under $N_2$. The reaction was then stirred at 25° C. for 2 h followed by the addition of methyl 2-bromo-2-methylpropanoate (85.46 g, 472.06 mmol, 61.04 mL) dropwise at 0° C. The reaction mixture was warmed to 25° C. and stirred at 25° C. for another 16 h. TLC (petroleum ether/ethyl acetate=5:1) showed the starting material was consumed completely. The reaction was quenched by ice water slowly and then extracted with EtOAc (3×700 mL). The combined organic phase was washed with brine (3×200 mL), dried over anhydrous $Na_2SO_4$, filtered and concentrated in vacuo. The residue was purified by column chromatography on silica gel (petroleum ether/ethyl acetate=30:1-15:1), to yield the desired product as a light yellow solid. $^1$H NMR (400 MHz, $CDCl_3$): $\delta$ 8.29 (s, 1H), 3.72 (s, 1H), 2.51 (s, 1H), 1.84 (s, 6H).

2-Methyl-2-(3-methyl-4-nitro-pyrazol-1-yl) propanoic acid

To a mixture of methyl 2-methyl-2-(3-methyl-4-nitropyrazol-1-yl)propanoate (69.7 g, 306.75 mmol) in THF (1 L) and $H_2O$ (250 mL) was added $LiOH \cdot H_2O$ (15.45 g, 368.10 mmol) at 25° C. under $N_2$. The mixture was then stirred at 25° C. for 16 h. TLC (petroleum ether/ethyl acetate=5:1) showed the reaction was completed. The reaction mixture was concentrated in vacuo. The residual aqueous solution was washed with ethyl acetate (50 mL). The aqueous phase was then cooled to 0° C., adjusted to approximately pH 1-2, and filtered to yield the desired product as a white solid. $^1$H NMR (400 MHz, $CDCl_3$): $\delta$ 8.65 (s, 1H), 2.48 (s, 1H), 1.83 (s, 6H).

2-Methyl-2-(3-methyl-4-nitro-pyrazol-1-ylpropanamide

To a solution of 2-methyl-2-(3-methyl-4-nitro-pyrazol-1-yl) propanoic acid (25 g, 117.27 mmol) in DCM (500 mL)

was added 8 drops of DMF, followed by oxalyl dichloride (29.77 g, 234.54 mmol) at 0° C. under $N_2$. Then the mixture was stirred at 25° C. for a further 2 h. TLC (petroleum ether/ethyl acetate=3:1) showed reaction was completed. The reaction solution was concentrated in vacuo. The residue solid was dissolved in THF (300 mL) and added dropwise into a stirred solution of $NH_4OH$ (413.61 g, 11.80 mol, 454.52 mL) at 0° C. The reaction was stirred at 25° C. for 1 h. TLC (ethyl acetate) showed reaction was completed. The solution was then concentrated in vacuo and partitioned between EtOAc (100 mL) and water (100 mL), and the aqueous phase was extracted with ethyl acetate (3×80 mL). The combined organic phase was washed with brine (3×40 mL), dried over anhydrous $Na_2SO_4$, filtered and concentrated in vacuo, to yield the desired compound as a yellow solid. $^1$H NMR (400 MHz, MeOD): δ 8.81 (s, 1H), 7.16-7.26 (m, 2H), 2.42 (s, 3H), 1.71 (s, 3H).

2-Methyl-2-(3-methyl-4-nitro-1H-pyrazol-1-ylpropanenitrile

A solution of 2-methyl-2-(3-methyl-4-nitro-pyrazol-1-yl-propanamide (22 g, 103.67 mmol) in $POCl_3$ (132 g, 860.89 mmol, 80 mL) was stirred at 90° C. for 1 h. TLC showed the reaction was completed. The mixture was cooled to 20° C. and concentrated in vacuo at 50° C. The residue was poured into ice-water (w/w=1/1) (200 mL) and stirred for 10 min. The aqueous phase was adjusted to pH=7 with $NaHCO_3$ solution, extracted with ethyl acetate (4×80 mL). The combined organic phase was washed with brine (40 mL), dried with anhydrous $Na_2SO_4$, filtered and concentrated in vacuo. The desired product was afforded as a yellow solid.

2-(4-Amino-3-methyl-pyrazol-1-yl)-2-methyl-propanenitrile

To a mixture of 2-methyl-2-(3-methyl-4-nitro-1H-pyrazol-1-yl)propanenitrile (10 g, 51.5 mmol) in EtOH (240 mL) and $H_2O$ (60 mL) was added $NH_4Cl$ (13.77 g, 257.5 mmol) in one portion at 25° C., followed by Fe (14.38 g, 257.5 mmol). The mixture was heated to 80° C. and stirred for 1 h. TLC showed the reaction was completed. The solution was cooled to 20° C. The mixture was extracted with ethyl acetate (3×100 mL), the combined organic layers were washed with $NaHCO_3$ solution (50 mL) and brine (50 mL). The organic layers were dried over $Na_2SO_4$, filtered and concentrated. The desired product was afforded as a dark brown solid. $^1$H NMR (400 MHz, $CDCl_3$): δ 7.17 (s, 1H), 2.18 (s, 3H), 1.91 (s, 6H).

2-[4-[(5-trifluoromethyl-4-chloro-pyrimidin-2-yl)amino]-3-methyl-pyrazol-1-yl]-2-methyl-propanenitrile A mixture of 2,4-dichloro-5-(trifluoromethyl) pyrimidine (2.00 g, 9.22 mmol), 2-(4-amino-3-methyl-1H-pyrazol-1-yl)-2-methylpropanenitrile (1.51 g, 9.22 mmol), $NaHCO_3$ (2.32 g, 27.66 mmol, 1.08 mL) in acetonitrile (20 mL) was stirred at 25° C. for 3 h under $N_2$ atmosphere. LC-MS showed complete reaction of starting material. Two new peaks were show n in LC-MS and 85% of desired compound was detected. The reaction mixture was filtered and the filtrate was concentrated in vacuo to afford the crude desired product as a brown oil. The crude product was often used in the next synthetic step without further purification. A portion of the crude product was purified by prep-HPLC the pure desired product was afforded as a white solid. $^1$H NMR ($CDCl_3$ 400 MHz): δ 8.48-8.68 (m, 1H), 8.15 (s, 1H), 6.97 (bs, 1H), 2.29 (s, 3H), 2.01 (s, 6H).

2-[4-[(5-trifluoromethyl-4-cyclopropyl-pyrimidin-2-yl)amino]-3-methyl-pyrazol-1-yl]-2-methyl-propanenitrile (A-1)

A mixture of 2-[4-[(5-trifluoromethyl-4-chloro-pyrimidin-2-yl)amino]-3-methyl-pyrazol-1-yl]-2-methyl-propanenitrile (100.00 mg, 290.09 μmol, 1.00 eq), cyclopropylboronic acid (124.59 mg, 1.45 mmol), $Pd(OAc)_2$ (6.51 mg, 29.01 μmol, 0.10 eq), $PCy_3$ (16.27 mg, 58.02 μmol, 18.70 μL) and CsF (132.19 mg, 870.27 μmol, 32.09 μL) in dioxane (5.00 mL) was de-gassed under $N_2$ and then heated to 90° C. for 12 hours under $N_2$. LC-MS was used to monitor reaction progress. The reaction mixture was diluted with $H_2O$ (20 mL) and extracted with ethyl acetate (3×20 mL). The combined organic layers were washed with brine (5 mL), dried over $Na_2SO_4$, filtered and concentrated in vacuo to give a residue. The residue was purified by column chromatography ($SiO_2$, petroleum ether/ethyl acetate=10:1-3:1) followed by prep-HPLC (neutral condition) to provide the title compound. $^1$H NMR ($CDCl_3$ 400 MHz): δ 8.45 (s, 1H), 8.12 (s, 1H) 6.73 (bs, 1H), 2.20-2.34 (m, 4H), 2.00 (s, 6H), 1.26-1.35 (m, 2H), 1.11-1.23 (m, 2H). HPLC: RT 3.1 min. MS: m/z: 351.2 $[M+H]^+$.

Example A-2

Synthesis of 2-[4-[(5-chloro-4-cyclopropyl-pyrimidin-2-yl)amino]-3-methyl-pyrazol-1-yl]-2-methyl-propanenitrile (A-2)

2,5-dichloro-4-cyclopropyl-pyrimidine

A mixture of 2,4,5-trichloropyrimidine (750 mg, 4.09 mmol), cyclopropylboronic acid (1.76 g, 20.45 mmol), CsF (1.86 g, 12.27 mmol), $Pd(OAc)_2$ (91 mg, 409 uμmol) and $PCy_3$ (114 mg, 409 μmol) in 1,4-dioxane (20 mL) was degassed and purged with $N_2$ for 3 times, and then the mixture was stirred at 90° C. for 16 h under $N_2$ atmosphere. The solution was concentrated in vacuo. To the residue was added water (20 mL), extracted with ethyl acetate (3×15 mL). The organic layers were combined, washed with brine (10 mL), dried over $Na_2SO_4$, filtered and concentrated to give a crude product. The crude product was purified by silica gel column chromatography (petroleum ether/ethyl acetate=100% petroleum ether-10:1) to afford the crude desired compound. $^1$H NMR (400 MHz, $CDCl_3$):δ8.38 (s, 1H), 3.72 (s, 1H), 2.44~2.49 (m, 1H), 1.23~1.32 (m, 4H). LC/MS: RT 0.833 min. m/z=188.9, 190.9 $[M+H]^+$.

2-[4-[(5-chloro-4-cyclopropyl-pyrimidin-2-yl)amino]-3-methyl-pyrazol-yl]-2-methyl-propanenitrile (A-2)

To a solution of 2,5-dichloro-4-cyclopropyl-pyrimidine (230 mg, 547.50 μmol) and 2-(4-amino-3-methyl-1H-pyrazol-1-yl)-2-methylpropanenitrile (prepared as described in the examples above; 404 mg, 2.46 mmol) in 1,4-dioxane (10 mL) was added p-TsOH (9 mg, 54.75 μmol). The mixture was stirred at 100° C. for 16 h. The mixture was concentrated in vacuo. To the residue was added water (10 mL), adjusted to pH=7 with $NaHCO_3$ solution, extracted with ethyl acetate (3×10 mL). The organic layers were combined, washed with brine (10 mL), dried over $Na_2SO_4$, filtered and concentrated in vacuo. The residue was purified by prep- HPLC (neutral condition) and lyophilized to provide the title compound. $^1$H NMR (400 MHz, CDCl3):δ8.19 (s, 1H), 8.10 (s, 1H), 6.44 (br, 1H), 2.41~2.47 (m, 1H), 2.27 (s, 3H), 2.00 (s, 6H), 1.20~1.21 (m, 2H), 1.14~1.16 (m, 2H). HPLC: RT 3.34 min. MS: (M+H+) m/z: 317.1.

Example A-3

Synthesis of 2-[[1-(1-cyano-1-methyl-ethyl)-3-methyl-pyrazol-4-yl]amino]-4-cyclopropyl-pyrimidine-5-carbonitrile (A-3)

4-chloro-2-[[1-(1-cyano-1-methyl-ethyl)-3-methyl-pyrazol-4-yl]amino]pyrimidine-5-carbonitrile To a solution of 2,4-dichloropyrimidine-5-carbonitrile (530 mg, 3.05 mmol) in CH$_3$CN (10 mL) was added NaHCO$_3$ (768 mg, 9.15 mmol) and 2-(4-amino-3-methyl-1H-pyrazol-1-yl)-2-methylpropanenitrile (500 mg, 3.05 mmol) at 25° C. The mixture was stirred at 25° C. for 16 h. The solution was concentrated in vacuo to give a residue. To the residue was added water (20 mL), extracted with ethyl acetate (3×15 mL). The organic layers were combined, washed with brine (10 mL), dried over Na$_2$SO$_4$, and filtered. The filtrate was concentrated in vacuo to give a crude product. The crude product was purified by prep-HPLC (neutral condition). The eluent was extracted with ethyl acetate (3×20 mL), washed with brine (10 mL), dried over Na$_2$SO$_4$, filtered and concentrated in vacuo to afford the desired crude product as a brown solid. $^1$H NMR (400 MHz, CDCl$_3$): δ8.51~8.61 (m, 1H), 8.13 (s, 1H), 7.08~7.15 (m, 1H), 2.28~2.30 (m, 3H), 2.01 (s, 6H). LC/MS: RT 0.750 min, m/z=302.0 [M+H]$^+$.

2-[[1-(1-cyano-1-methyl-ethyl)-3-methyl-pyrazol-4-yl]amino]-4-cyclopropyl-pyrimidine-5-carbonitrile (A-3)

A mixture of 4-chloro-2-[[1-(1-cyano-1-methyl-ethyl)-3-methyl-pyrazol-4-yl]amino]pyrimidine-5-carbonitrile (140 mg, 463.99 µmol), cyclopropylboronic acid (199 mg, 2.32 mmol), K$_3$PO$_4$ (295 mg, 1.39 mmol), Pd(dppf)Cl$_2$ (34 mg, 46.40 µmol) and Ag$_2$O (11 mg, 46.40 µmol) in 1,4-dioxane (1 mL) was degassed and purged with N$_2$ for 3 times, and then the mixture was stirred at 80° C. for 16 h under N$_2$. The solution was concentrated in vacuo to give a residue. To the residue was added water (10 mL), extracted with ethyl acetate (3×10 mL). The organic layers were combined, washed with brine (10 mL), dried over Na$_2$SO$_4$, filtered and concentrated in vacuo. The crude product was purified by prep-HPLC (neutral condition) and lyophilized to afford the title compound. $^1$H NMR (400 MHz, CDCl$_3$): δ 8.43~8.50 (m, 1H), 8.10 (s, 1H), 6.73~6.94 (m, 1H), 2.37 (m, 1H), 2.28 (s, 3H), 1.99 (s, 6H), 1.30 (m, 4H). HPLC: RT 80 min. MS: m/z: 308.2 [M+H]$^+$.

Example A-4

Synthesis of 2-[4-[[4-(cyclopenten-1-yl)-5-(trifluoromethyl)pyrimidin-2-yl]amino]-3-methyl-pyrazol-1-yl]-2-methyl-propanenitrile (A-4); and 2-[4-[[4-cyclopentyl-5-(trifluoromethyl)pyrimidin-2-yl] amino]-3-methyl-pyrazol-1-yl]-2-methyl-propanenitrile (A-10) 2-[4-[[4-(cyclopenten-1-yl)-5-(trifluoromethyl)pyrimidin-2-yl]amino]-3-methyl-pyrazol-1-yl]-2-methyl-propanenitrile (A-4)

2-(4-((4-chloro-5-(trifluoromethyl)pyrimidin-2-yl)amino)-3-methyl-1H-pyrazol-1-yl)-2-methylpropanenitrile was prepared according to the procedures described above. A mixture of 2-(4-((4-chloro-5-(trifluoromethyl)pyrimidin-2-yl)amino)-3-methyl-1H-pyrazol-1-yl)-2-methylpropanenitrile (300 mg, 870.27 µmol), cyclopenten-1-ylboronic acid (584 mg, 5.22 mmol), Cs$_2$CO$_3$ (850 mg, 2.61 mmol) and Pd(dppf)Cl$_2$ (63 mg, 87.03 µmol) in 1,4-dioxane (3 mL), acetonitrile (3 mL) and H$_2$O (1 mL) was degassed and purged with N$_2$ for 3 times, and then the mixture was stirred at 90° C. for 16 h under N$_2$. The reaction mixture was concentrated in vacuo to remove solvent. The residue was purified by prep-TLC (SiO$_2$, petroleum ether/ethyl acetate=4:1) to afford title compound. $^1$H NMR (400 MHz, CDCl$_3$): δ8.61 (s, 1H), 8.24 (s, 1H), 6.88 (s, 1H), 2.86 (s, 2H), 2.62 (s, 2H), 2.29 (s, 1H), 2.02~2.07 (m, 2H), 2.00 (s, 6H). HPLC: RT 3.69 min. MS: m/z: 399.1 [M+Na]$^+$ 2-[4-[[4-cyclopentyl-5-(trifluoromethyl)pyrimidin-2-yl]amino]-3-methyl-pyrazol-1-yl]-2-methyl-propanenitrile (A-10)

To a solution of 2-[4-[[4-(cyclopenten-1-yl)-5-(trifluoromethyl)pyrimidin-2-yl]amino]-3-methyl-pyrazol-1-yl]-2-methyl-propanenitrile (200 mg, 0.53 mmol) in EtOAc (20 mL) was added Pd/C (10%, 0.1 g) under N$_2$. The suspension was degassed and purged with H$_2$ for 3 times. The mixture was stirred under H$_2$ (15 psi) at 25° C. for 3 h. The reaction solution was filtered through a pad of celite. The filtrate was concentrated in vacuo to give a crude product. The crude product was purified by prep-HPLC (neutral condition) and lyophilized to afford tide compound. $^1$H NMR (400 MHz, CDCl$_3$): δ 8.51 (s, 1H), 8.25 (s, 1H), 6.80 (s, 1H), 3.40 (m, 1H), 2.31 (s, 3H), 2.00~2.04 (m, 8H), 1.91 (m, 4H), 1.73 (m, 2H). HPLC: RT 3.06 min. MS: m/z: 379.2 [M+H]$^+$ Example A-5

Synthesis of 2-(5-((4-cyclopropyl-5-(trifluoromethyl)pyrimidin-2-yl)amino)-1-methyl-1H-pyrazol-3-yl)-2-methylpropanenitrile (A-5)

2,2-dimethyl-3-oxopentanedinitrile

A stirred suspension of NaH (1.3 g, 31.88 mmol, 60% purity) in THF (25 mL) was heated to 75° C. To this was added a mixture of 2,2-dimethyl-2-cyanoacetic acid ethyl ester (3 g, 21.25 mmol) and CH$_3$CN (1.7 mL, 31.88 mmol) in THF (20 mL) dropwise over a period of 45 min. The resulting pale yellow suspension was heated at 70° C. for a further 15 h. The reaction mixture was poured into water (150 mL) and the resulting solution was extracted with EtOAc (2×100 mL). The aqueous layer was separated, acidified to pH 2 with aqueous 1 M HCl, and extracted with EtOAc (2×100 mL). The combined organic layers were dried over Na$_2$SO$_4$ and then concentrated under reduced pressure to afford 2,2-dimethyl-3-oxopentanedinitrile as yellow oil. LCMS: RT 0.213 min, m/z=137.1 [M+H]$^+$.

2-(5-amino-1-methyl-1H-pyrazol-3-yl)-2-methylpropanenitrile

A mixture of 2,2-dimethyl-3-oxopentanedinitrile (5-2) (500 mg, 3.67 mmol) and methylhydrazine (0.2 mL, 3.67 mmol) in EtOH (20 mL) was treated with conc HCl (0.4 mL, 11 mmol) in at 25° C. The mixture was stirred at 90° C. for 12 h. The mixture was poured into ice-water (20 mL) and extracted with EtOAc (20 mL×3). The combined organic phase was concentrated under reduced pressure to give a residue. The residue was purified on a short silica gel plug eluting with DCM to DCM:MeOH (10:1) to give 2-(5-amino-1-methyl-1H-pyrazol-3-yl)-2-methylpropanenitrile as a yellow oil. LCMS: RT 0.456 min, m/z=165.2 [M+H]$^+$.

2-chloro-4-cyclopropyl-5-(trifluoromethyl)pyrimidine

To a solution of 2,4-dichloro-5-(trifluoromethyl)pyrimidine (300 mg, 1.38 mmol) in CH$_3$CN (9 mL) and H$_2$O (9 mL) was added cyclopropane carboxylic acid (357 mg, 4.14 mmol), (NH$_4$)$_2$S$_2$O$_8$ (1.57 g, 6.90 mmol) and AgNO$_3$ (940 mg, 5.52 mmol) at 25° C. The reaction mixture was warmed to 60° C. and stirred for 6 h under N$_2$. The reaction was quenched by ice water and then extracted with EtOAc (20 mL×3). The combined organic phase was washed with brine (20 mL×3), dried over anhydrous Na$_2$SO$_4$, filtered and concentrated under reduced pressure. The residue was purified by prep-TLC (PE:EtOAc=20:1), to give 2-chloro-4-cyclopropyl-5-(trifluoromethyl)pyrimidine as a colorless oil. $^1$H NMR (400 MHz, CDCl$_3$): δ 8.57 (s, 1H), 2.17-2.26 (m, 1H), 1.31-1.40 (m, 2H), 1.16-1.25 (m, 3H).

2-(5-((4-cyclopropyl-5-(trifluoromethyl)pyrimidin-2-yl)amino)-1-methyl-1H-pyrazol-3-yl)-2-methylpropanenitrile (A-5)

To a solution of 2-(5-amino-1-methyl-1H-pyrazol-3-yl)-2-methylpropanenitrile (100 mg, 0.6 mmol) in n-BuOH (1 mL) was added 2-chloro-4-cyclopropyl-5-(trifluoromethyl)pyrimidine (136 mg, 0.6 mmol) and a drop of trifluoroacetic acid (5.00 µL) at 25° C. The solution was stirred at 100° C. for 1.5 h under microwave irradiation. The mixture was concentrated under reduced pressure to give a residue. The residue was purified by prep-HPLC (column: Luna C8 100*30 5u; liquid phase: [A-10 mM NH$_4$HCO$_3$ in H$_2$O; B-ACN] B %: 35%-60%, 12 min]) to give 2-(5-((4-cyclopropyl-5-(trifluoromethyl)pyrimidin-2-yl)amino)-1-methyl-1H-pyrazol-3-yl)-2-methylpropanenitrile. $^1$H NMR. (400 MHz, DMSO): δ 8.57 (s, 1H), 7.26 (br. s., 1H), 6.26 (s, 1H), 3.62 (s, 3H), 2.06-2.16 (m, 1H), 1.60 (s, 6H), 1.12 (d, J=6.4 Hz, 4H). HPLC: RT 3.34 min. MS: m/z: 351.1 [M+H]$^+$.

Example A-6

Synthesis of 2-((1-(2-cyanopropan-2-yl)-3-methyl-1H-pyrazol-4-yl)amino)-4-cyclopentylpyrimidine-5-carbonitrile (A-6)

This compound can be synthesized using a method analogous to Example A-4 or Example A-10.

Example A-7

Synthesis of 4-cyclopropyl-N-(3-methyl-1-methylsulfonyl-pyrazol-4-yl)-5-(trifluoromethyl)pyrimidin-2-amine (A-7)

3-methyl-1-methylsulfonyl-4-nitro-pyrazole

To a mixture of 3-methyl-4-nitro-1H-pyrazole (1 g, 7.87 mmol) and triethylamine (1.59 g, 15.74 mmol) in DCM (50 mL) was added MsCl (1.35 g, 11.81 mmol) dropwise at 0° C. Then the mixture was stirred at 25° C. for 12 h. The mixture was poured into aq. sat. NH$_4$Cl (10 mL). The aqueous phase was extracted with ethyl acetate (4×20 mL). The combined organic phase was washed with brine (4×20 mL), dried with anhydrous Na$_2$SO$_4$, filtered and concentrated in vacuo. The residue was purified by silica gel column chromatography (petroleum ether/ethyl acetate=3:1) to afford the desired compound as a white solid. $^1$H NMR (400 MHz, CDCl$_3$): δ8.760 (s, 1H), 3.468 (s, 3H) 2.651 (s, 3H). LC/MS: RT 0.569 min, m/z=206 [M+H]$^+$.

3-methyl-1-methylsulfonyl-pyrazol-4-amine

To a solution of 3-methyl-1-methylsulfonyl-4-nitro-pyrazole (600 mg, 2.92 mmol) in ethanol (10 mL) and water (5 mL) was added Fe (817 mg, 14.62 mmol) and NH$_4$Cl (782 mg, 14.62 mmol). The reaction was stirred at 80° C. for 2 h. The reaction mixture was filtered and the filtrate was concentrated. The mixture was added with water (10 mL) and extracted with ethyl acetate (3×20 mL). The combined organic phase was washed with brine (10 mL), dried with anhydrous Na$_2$SO$_4$, filtered and concentrated in vacuo to afford the desired product. LC/MS: RT 0.094 min, m/z=176 [M+H]$^+$.

4-chloro-N-(3-methyl-1-methylsulfonyl-pyrazol-4-yl)-5-(trifluoromethyl) pyrimidin-2-amine To a mixture of 3-methyl-1-methylsulfonyl-pyrazol-4-amine (346 mg, 1.97 mmol) and 2,4-dichloro-5-(trifluoromethyl)pyrimidine (427 mg, 1.97 mmol) in acetonitrile (10 mL) was added NaHCO$_3$ (418 mg, 3.94 mmol) in one portion at 25° C. The mixture was stirred at 25° C. for 12 h. The reaction mixture was filtered and the filtrate was concentrated in vacuo. The residue was purified by prep-HPLC (TFA acidic) to afford the desired product as a white solid. $^1$H NMR (400 MHz, CDCl$_3$):δ8.672 (s, 1H), 8.577 (s, 1H) 7.112 (s, 1H) 3.331 (s, 1H) 2.398 (s, 1H). LC/MS: RT 0.830 min, m/z=356 [M+H]$^+$.

4-cyclopropyl-N-(3-methyl-1-methylsulfonyl-pyrazol-4-yl)-5-(trifluoromethyl)pyrimidin-2-amine (A-7)

To a mixture of 4-chloro-N-(3-methyl-1-methylsulfonyl-pyrazol-4-yl)-5-(trifluoromethyl) pyrimidin-2-amine (250 mg, 702.80 µmol) and cyclopropylboronic acid (362 mg, 4.22 mmol) in 1,4-dioxane (5 mL) was added CsF (320 mg, 2.11 mmol), Pd(OAc)$_2$ (15.8 mg, 70.28 µmol) and PCy$_3$ (19.7 mg, 70.28 µmol) in one portion at 25° C. under N$_2$. The mixture was stirred at 90° C. for 12 h. The mixture was cooled to 25° C. and concentrated in vacuo at 35° C. The residue was poured into water (10 mL). The aqueous phase was extracted with ethyl acetate (3×20 mL). The combined organic phase was washed with brine (3×20 mL), dried with anhydrous Na$_2$SO$_4$, filtered and concentrated in vacuo. The residue was purified by prep-HPLC to afford title compound. $^1$H NMR (400 MHz, CDCl$_3$): δ8.524 (s, 2 H), 6.757 (s, 1H), 3.300 (s, 3H) 2.400 (s, 3H) 2.290 (s, 1H) 1.333 (s, 2H) 1.229 (s, 2H). HPLC. RT 3.36 min. MS: m/z: 362.1[M+H]$^+$ Example A-8

Synthesis of 4-cyclopropyl-N-(3-methyl-1-(2-(1-methyl-1H-1,2,4-triazol-3-yl)propan-2-yl)-1H-pyrazol-4-yl)-5-(trifluoromethyl)pyrimidin-2-amine (A-8)

(E)-N-((dimethylamino)methylene)-2-methyl-2-(3-methyl-4-nitro-1H-pyrazol-1-yl)propanamide 2-methyl-2-(3-methyl-4-nitro-1H-pyrazol-1-ylpropanamide used as starting material for this reaction was prepared according to the procedure described in the above examples. A mixture of 2-methyl-2-(3-methyl-4-nitro-1H-pyrazol-1-yl)propanamide (5 g, 23.56 mmol) and DMF-DMA (28.07 g, 235.60 mmol) was stirred at 95° C. for 2 h. The mixture was concentrated in vacuo to give afford the crude desired product as a brown oil. The crude product was used in the next synthetic step without further purification. LC/MS: RT 0.655 min, m/z=268 [M+H]$^+$.

3-(2-(3-methyl-4-nitro-1H-pyrazol-1-yl)propan-2-yl)-1H-1,2,4-triazole

To a solution of (E)-N-((dimethylamino)methylene)-2-methyl-2-(3-methyl-4-nitro-1H-pyrazol-1-ylpropanamide (6.6 g, 24.69 mmol) in acetic acid (50 mL) was added $NH_2H_2O$ (18.92 g, 370.35 mmol, 18.37 mL, 98% purity). The mixture was stirred at 95° C. for 1.5 h. The reaction mixture was adjusted by addition of sat. $NaHCO_3$ (200 mL) at 0° C. to pH=9, and then extracted with ethyl acetate (3×100 mL). The combined organic layers were washed with brine (50 mL), dried over $Na_2SO_4$, filtered and concentrated in vacuo to afford the crude desired product as a brown solid. The crude product was used in die next synthetic step without further purification. LC/MS: RT 0.581 min, m/z=237 [M+H]$^+$.

1-methyl-3-(2-(3-methyl-4-nitro-1H-pyrazol-1-yl) propan-2-yl)-1H-1,2,4-triazole

To a solution of 3-(2-(3-methyl-4-nitro-1H-pyrazol-1-yl)propan-2-yl)-1H-1,2,4-triazole (6 g, 25.40 mmol) in acetonitrile (30 mL) was added methyl iodide (4.33 g, 30.48 mmol) and then $Cs_2CO_3$ (8.28 g, 25.40 mmol). The mixture was stirred at 50° C. for 12 h. The reaction mixture was filtered and the filtrate was concentrated in vacuo. The residue was purified by column chromatography on silica gel (petroleum ether/ethyl acetate=5:1-100% ethyl acetate) to afford the desired product as a yellow oil. $^1$H NMR (400 MHz, CDCl3): δ ppm 8.18-8.21 (m, 1H) 7.98-8.01 (m, 1H) 3.92 (s, 3H) 2.53 (s, 3H) 2.03 (s, 6H). LC/MS: RT 0.638 min. m/z=251 [M+H]$^+$.

3-methyl-1-(2-(1-methyl-1H-1,2,4-triazol-3-yl)propan-2-yl)-1H-pyrazol-4-amine

To a solution of 1-methyl-3-(2-(3-methyl-4-nitro-1H-pyrazol-1-yl)propan-2-yl)-1H-1,2,4-triazole (2.8 g, 11.19 mmol) in ethanol (50 mL) was added Pd—C (10%, 0.95 g) under $N_2$. The suspension was degassed in vacuo and purged with $H_2$ several times. The mixture was stirred under $H_2$ (15 psi) at 50° C. for 2 h. The reaction mixture was filtered and the filtrate was concentrated in vacuo to afford the crude desired product as a brown solid. The crude product was used in the next synthetic step without further purification. $^1$H NMR (400 MHz, CDCl3): δ 7.90-7.94 (m, 1H) 7.13 (s, 1H) 3.88 (s, 3H) 2.17 (s, 3H) 1.97 (s, 6H).

4-chloro-N-(3-methyl-1-(2-(1-methyl-1H-1,2,4-triazol-3-yl)propan-2-yl)-1H-pyrazol-4-yl)-5-(trifluoromethyl)pyrimidin-2-amine A mixture of 3-methyl-1-(2-(1-methyl-1H-1,2,4-triazol-3-yl)propan-2-yl)-1H-pyrazol-4-amine (400 mg, 1.82 mmol), 2,4-dichloro-5-(trifluoromethyl)pyrimidine (394.9 mg, 1.82 mmol) and $NaHCO_3$ (458.69 mg, 5.46 mmol) in $CH_3CN$ (4 mL) was stirred at 25° C. for 3 h under $N_2$. The reaction mixture was filtered and the filtrate was concentrated in vacuo. The residue was purified by prep-HPLC (neutral condition) to afford the desired compound as an off-white solid. $^1$H NMR (400 MHz, CDCl$_3$): δ ppm 8.39-8.62 (m, 1H) 7.89-8.10 (m, 2H) 6.87-7.09 (m, 1H) 3.90 (s, 3H) 2.23 (s, 3H) 2.05 (s, 6H). LC/MS: RT 0.785 min, m/z=401 [M+H]$^+$.

4-cyclopropyl-N-(3-methyl-1-(2-(1-methyl-1H-1,2,4-triazol-3-yl)propan-2-yl)-1H-pyrazol-4-yl)-5-(trifluoromethyl)pyrimidin-2-amine (A-8)

A mixture of 4-chloro-N-(3-methyl-1-(2-(1-methyl-1H-1,2,4-triazol-3-yl)propan-2-yl)-1H-pyrazol-4-yl)-5-(trifluoromethyl)pyrimidin-2-amine (100 mg, 249.51 μmol), cyclopropylboronic acid (107.16 mg, 1.25 mmol), Pd(OAc)$_2$ (5.6 mg, 24.95 μmol), PCy$_3$ (13.99 mg, 49.90 μmol) and CsF (113.7 mg, 748.53 μmol) in dioxane (2 mL) was stirred at 90° C. for 12 h under $N_2$. The mixture was filtered and concentrated in vacuo. The residue was purified by column chromatography on silica gel (petroleum ether/ethyl acetate=10:1-100% ethyl acetate), and further purified by prep-HPLC (neutral condition) to provide title compound. $^1$H NMR (400 MHz, CDCl3): δ 8.32-8.44 (m, 1H) 7.81-8.02 (m, 2H) 6.59-6.86 (m, 1H) 3.91 (s, 3H) 2.24 (m, 4H) 2.04 (s, 6H) 1.17-1.29 (m, 2H) 1.03-1.14 (m, 2H). LC/MS: RT 2.707 min. MS: m/z: 407.2 [M+H]$^+$ Example A-9

Synthesis of 2-methyl-2-(3-methyl-4-((4-(1-methyl-1H-pyrazol-4-yl)-5-(trifluoromethyl)pyrimidin-2-yl) amino)-1H-pyrazol-1-yl)propanenitrile (A-9)

2-methyl-2-(3-methyl-4-((4-(1-methyl-1H-pyrazol-4-yl)-5-(trifluoromethyl)pyrimidin-2-yl)amino)-1H-pyrazol-1-yl)propanenitrile (A-9)

2-(4-((4-chloro-5-(trifluoromethyl)pyrimidin-2-yl) amino)-3-methyl-1H-pyrazol-1-yl)-2-methylpropanenitrile was prepared according to the procedure described in the above examples. To a solution of 2-(4-((4-chloro-5-(trifluoromethyl)pyrimidin-2-yl)amino)-3-methyl-1H-pyrazol-1-yl)-2-methylpropanenitrile (150 mg, 0.4 mmol) in dioxane (8 mL) and water (2 mL) was added 1-methyl-4-(4,4,5,5-tetramethyl-1,3,2-dioxaborolan-2-yl)-1H-pyrazole (109 mg, 0.5 mmol) and $K_2CO_3$ (180 mg, 1.3 mmol) at 25° C. The solution was degassed with nitrogen for 5 min followed by addition of Pd(dppf)Cl$_2$ (32 mg, 0.04 mmol) under $N_2$. The mixture was stirred at 90° C. for 12 h. The mixture was concentrated in vacuo to give a residue. The residue was purified by prep-HPLC (neutral condition) to provide the title compound. $^1$H NMR (400 MHz, DMSO): δ 9.36-9.71 (m, 1H), 8.66 (s, 1H), 8.21 (s, 1H), 7.91 (br. s., 1H), 3.91 (s, 3H), 2.18 (br. s., 3H), 1.94 (s, 6H). HPLC: RT 2.92 min. MS: m/z: 391.1 [M+H]$^+$.

Example A-10

Synthesis of 2-[4-[[4-cyclobutyl-5-(trifluoromethyl) pyrimidin-2-yl]amino]-3-methyl-pyrazol-1-yl]-2-methyl-propanenitrile (A-11)

2-[4-[[4-cyclobutyl-5-(trifluoromethyl)pyrimidin-2-yl]amino]-3-methyl-pyrazol-1-yl]-2-methyl-propanenitrile (A-11)

To a solution of 2,5-dichloro-4-cyclobutylpyrimidine (200 mg, 845.24 μmol) and 2-(4-amino-3-methyl-1H-pyrazol-1-yl)-2-methylpropanenitrile (139 mg, 845.24 μmol) in 1,4-dioxane (5 mL) was added p-TsOH (87 mg, 507.14 μmol). The mixture was stirred at 100° C. for 12 h. To the solution was added aq. sat. NaHCO$_3$ solution (15 mL), stirred for 10 min, the aqueous phase was extracted with EtOAc (3×10 mL). The organic layers were combined, washed with brine (10 mL), dried over Na$_2$SO$_4$, filtered and concentrated under reduced pressure. The residue was purified by prep-HPLC (neutral condition) to give 2-(4-((5-chloro-4-cyclobutylpyrimidin-2-yl)amino)-3-methyl-1H-pyrazol-1-yl)-2-methylpropanenitrile. $^1$H NMR (400 MHz, CDCl$_3$): δ 8.06-8.59 (m, 2H), 6.90 (br. s., 1H), 3.88 (s., 1H), 2.46-2.58 (m, 2H), 2.24-2.40 (m, 5H), 1.91-2.18 (m, 8H). HPLC: RT 3.76 min. MS: (M+H$^+$) m/z: 365.1.

Example A-11

Synthesis of 2-(4-((4-2-fluorocyclopropyl)-5-(trifluoromethyl)pyrimidin-2-yl)amino)-3-methyl-1H-pyrazol-1-yl)-2-methylpropanenitrile (A-12 and A-13)

4-(2-fluorocyclopropyl)-2-(methylsulfonyl)-5-(trifluoromethyl)pyrimidine

To a solution of 2-(methylsulfonyl)-5-(trifluoromethyl) pyrimidine (500 mg, 2.21 mmol) in CH$_3$CN (15 mL) and H$_2$O (15 mL) was added 2-fluorocyclopropanecarboxylic acid (207 mg, 2.0 mmol), (NH$_4$)$_2$S$_2$O$_8$ (2.5 g, 11 mmol) and AgNO$_3$ (1.5 g, 8.8 mmol). Then the mixture was stirred at 25° C. for 12 h. The resulting mixture was extracted with EtOAc (3×15 mL). The combined organic extracts were concentrated under reduced pressure to give residue. The residue was purified by prep-TLC (PE:EtOAc=1:1) to give 4-(2-fluorocyclopropyl)-2-(methylsulfonyl)-5-(trifluoromethyl)pyrimidine as a white solid. LCMS: RT 0.787 min, m/z=285.1 [M+H]$^+$.

2-(4-((4-(2-fluorocyclopropyl)-5-(trifluoromethyl) pyrimidin-2-yl)amino)-3-methyl-1H-pyrazol-1-yl)-2-methylpropanenitrile (A-12 and A-13)

To a solution of 4-(2-fluorocyclopropyl)-2-(methylsulfonyl)-5-(trifluoromethyl)pyrimidine (50 mg, 0.176 mmol) in dioxane (1 mL) was added 2-(4-amino-3-methyl-1H-pyrazol-1-yl)-2-methylpropanenitrile (35 mg, 0.221 mmol) and p-TsOH (9.1 mg, 0.05 mmol) under N$_2$. Then die mixture was stirred at 100° C. for 1 h. The mixture was concentrated under reduced pressure to give a residue. The residue was purified by prep-HPLC (neutral condition) to give the crude material, which was further purified by chiral SFC to give two peaks of 2-(4-((4-(2-fluorocyclopropyl)-5-(trifluoromethyl)pyrimidin-2-yl)amino)-3-methyl-1H-pyrazol-1-yl)-2-methylpropanenitrile, peak 1 and peak 2.

Peak 1: $^1$H NMR (400 MHz, CHLOROFORM-d): δ 8.49 (br. s., 1H), 8.06 (br. s., 1H), 4.88-5.08 (m, 1H), 2.68 (br. s., 1H) 2.28 (s, 3H), 1.99 (s, 6H), 1.58-1.60 (m, 2H). HPLC: RT 2.958 min. MS: (M+H$^+$) m/z: 369.2.

Peak 2: $^1$H NMR (400 MHz, CHLOROFORM-d): δ 8.49 (br. s., 1H), 8.06 (br. s., 1H), 4.87-5.07 (m, 1H), 2.70 (br. s., 1H), 2.27 (s, 3H), 1.99 (s, 6H) 1.62 (d, 6.2 Hz, 2H). HPLC: RT 2.956 min. MS: (M+H$^+$) m/z: 369.2.

Example A-12

Synthesis of 4-cyclopropyl-N-[3-methyl-1-(oxetan-3-yl) pyrazol-4-yl]-5-(trifluoromethyl)pyrimidin-2-amine and 4-cyclopropyl-N-[5-methyl-1-(oxetan-3-yl)pyrazol-4-yl]-5-(trifluoromethyl)pyrimidin-2-amine (A-14 and A-15)

3-methyl-4-nitro-1-(oxetan-3-yl)pyrazole and 5-methyl-4-nitro-1-(oxetan-3-yl)pyrazole To a solution of PPh$_3$ (20.64 g, 78.68 mmol) in THF (30 mL) was added DIAB (15.91 g, 78.68 mmol, 15.30 mL), 3-methyl-4-nitro-1H-pyrazole (5 g, 39.34 mmol) and oxetan-3-ol (2.91 g, 39.34 mmol) at 0° C. Then the mixture was stirred at 25° C. for 12 h. The mixture was concentrated under reduced pressure. The residue was purified by silica gel column chromatography (SiO$_2$, PE:EtOAc=50:1 to 5:1). The mixture of 3-methyl-4-nitro-1-(oxetan-3-yl)pyrazole and 5-methyl-4-nitro-1-(oxetan-3-yl)pyrazole was obtained as a yellow solid.

3-methyl-1-(oxetan-3-yl)pyrazol-4-amine and 5-methyl-1-(oxetan-3-yl)-pyrazol-4-amine To a solution of Pd/C (3 g, 10% purity) in MeOH (10 mL) was added 3-methyl-4-nitro-1-(oxetan-3-yl)pyrazole and 5-methyl-4-nitro-1-(oxetan-3-yl)pyrazole (5 g, 37.3 mmol), then the mixture was stirred at 25° C. under H$_2$ (15 psi) for 2 h. The reaction was filtered and the filtrate was concentrated under reduced pressure to give 3-methyl-1-(oxetan-3-yl)pyrazol-4-amine and 5-methyl-1-(oxetan-3-yl)-pyrazol-4-amine as a dark brown oil.

4-cyclopropyl-N-[3-methyl-1-(oxetan-3-yl) pyrazol-4-yl]-5-(trifluoromethyl)pyrimidin-2-amine and 4-cyclopropyl-N-[5-methyl-1-(oxetan-3-yl)pyrazol-4-yl]-5-(trifluoromethyl)pyrimidin-2-amine (A-14 and A-15)

2-chloro-4-cyclopropyl-5-(trifluoromethyl)pyrimidine (300 mg, 1.35 mmol), 3-methyl-1-(oxetan-3-yl)pyrazol-4-amine, 5-methyl-1-(oxetan-3-yl)-pyrazol-4-amino (271 mg, 1.77 mmol) and TEA (273 mg, 2.7 mmol, 374.26 μL) were taken up into a microwave tube in n-BuOH (8 mL). The sealed tube was heated at 120° C. for 90 min under microwave. After cooling to 25° C., the mixture was concentrated under reduced pressure. The residue was purified by prep-TLC (SiO$_2$, PE:EtOAc=3:1 to 1:1) to provide 4-cyclopropyl-N-[3-methyl-1-(oxetan-3-yl) pyrazol-4-yl]-5-(trifluoromethyl)pyrimidin-2-amine and 4-cyclopropyl-N-[5-methyl-1-(oxetan-3-yl)pyrazol-4-yl]-5-(trifluoromethyl) pyrimidin-2-amine (A-14 and A-15).

4-cyclopropyl-N-[3-methyl-1-(oxetan-3-yl) pyrazol-4-yl]-5-(trifluoromethyl)pyrimidin-2-amine (A-14)

$^1$H NMR (400 MHz, CDCl$_3$): δ8.45 (s, 1H), 8.01 (br. s., 1H), 6.68 (br. s., 1H), 5.38 (quin, J=6.93 Hz, 1H), 5.06 (d, J=65 Hz, 4H), 2.29 (s, 3H), 2.25 (br. s., 1H), 1.60 (s, 2H), 1.24-1.33 (m, 2H), 1.15 (br. s., 2H). HPLC. RT 2.97 min MS: (M+H$^+$) m/z=340.1.

4-cyclopropyl-N-[5-methyl-1-(oxetan-3-yl)pyrazol-4-yl]-5-(trifluoromethyl)pyrimidin-2-amine (A-15)

$^1$H NMR (400 MHz, CDCl$_3$): δ 8.39 (s, 1H), 7.75 (br. s., 1H), 6.50 (br s, 1H), 5.41 (quin, J=7.06 Hz, 1H), 5.24 (t, J=6.40 Hz, 2H), 4.94-5.05 (m, 2H), 2.13-2.24 (m, 4H), 1.24 (br. s., 2H), 1.10 (dd, J=7.50, 3.09 Hz, 2H). HPLC. RT 2.93 min. MS: (M+H$^+$) m/z=340.1.

Example A-13

Synthesis of 4-cyclopropyl-N-[3-methyl-1-[1-methyl-1-[1-(trideuteriomethyl)-1,2,4-triazol-3-yl]ethyl]pyrazol-4-yl]-5-(trifluoromethyl)pyrimidin-2-amine (A-16)

3-[1-methyl-1-(3-methyl-4-nitro-pyrazol-1-yl)ethyl]-1-(trideuteriomethyl)-1,2,4-triazole To a solution of 3-(2-(3-methyl-4-nitro-1H-pyrazol-1-yl)propan-2-yl)-1H-1,2,4-triazole (1 g, 4.23 mmol) in CH$_3$CN (15 mL) was added Cs$_2$CO$_3$ (1.38 g, 4.23 mmol) and trideuterio(iodo)methane (720 mg, 5.08 mmol, 309 µL). The mixture was stirred at 50° C. for 12 h. The reaction mixture was filtered and concentrated under reduced pressure. The residue was purified by silica gel column chromatography (PE:EtOAc=5:1 to 0:1) to give 3-[1-methyl-1-(3-methyl-4-nitro-pyrazol-1-yl)ethyl]-1-(trideuteriomethyl)-1,2,4-triazole as an off-white solid. LCMS: RT 0.633 min, m/z=254 [M+H]$^+$.

3-methyl-1-[1-methyl-1-[1-(trideuteriomethyl)-1,2,4-triazol-3-yl]ethyl]pyrazol-4-amine To a solution of 3-[1-methyl-1-(3-methyl-4-nitro-pyrazol-1-yl)ethyl]-1-(trideuteriomethyl)-1,2,4-triazole (300 mg, 1.18 mmol) in EtOH (10 mL) was added Pd—C (10%, 0.125 g) under N$_2$. The suspension was degassed under vacuum and purged with H$_2$ several times. The mixture was stirred under H$_2$ (15 psi) at 50° C. for 2 h. The reaction mixture was filtered and the filtrate was concentrated to give 3-methyl-1-[1-methyl-1-[1-(trideuteriomethyl)-1,2,4-triazol-3-yl]ethyl]pyrazol-4-amine as a brown solid. The crude product was used into the next step without further purification. LCMS: RT 0.225 min, m/z=224 [M+H]$^+$.

4-cyclopropyl-N-[3-methyl-1-[1-methyl-1-[1-(trideuteriomethyl)-1,2,4-triazol-3-yl]ethyl]pyrazol-4-yl]-5-(trifluoromethyl)pyrimidin-2-amine (A-16)

To a solution of 4-cyclopropyl-2-(methylsulfonyl)-5-(trifluoromethyl pyrimidine (346 mg, 1.30 mmol) and 3-methyl-1-[1-methyl-1-[1-(trideuteriomethyl)-1,2,4-triazol-3-yl]ethyl]pyrazol-4-amine (290 mg, 1.30 mmol) in 1,4-dioxane (10 mL) was added p-TsOH (67 mg, 390.00 µmol). The mixture was stirred at 100° C. for 2 h. The reaction mixture was diluted with H$_2$O (50 mL) and extracted with EtOAc (3×20 mL). The combined organic layers were washed with brine (5 mL), dried over Na$_2$SO$_4$, filtered and concentrated under reduced pressure. The residue was purified by prep-HPLC (neutral condition) to give title compound 4-cyclopropyl-N-[3-methyl-1-[1-methyl-1-[1-(trideuteriomethyl)-1,2,4-triazol-3-yl]ethyl]pyrazol-4-yl]-5-(trifluoromethyl)pyrimidin-2-amino (A-16). $^1$H NMR (400 MHz, CHLOROFORM-d): δ 8.30-8.56 (m, 1H), 7.79-8.14 (m, 2H), 6.52-6.93 (m, 1H), 2.14-2.30 (m, 4H), 2.04 (s, 6H), 1.18-1.26 (m, 2H), 1.04-1.14 (m, 2H). HPLC: RT 2.429 min. MS: (M+H$^+$) m/z: 410.2.

Example A-14

Synthesis of 2-(3-chloro-4-((4-cyclopropyl-5-(trifluoromethyl)pyrimidin-2-yl)amino)-1H-pyrazol-1-yl)-2-methylpropanenitrile (A-17)

3-chloro-1H-pyrazol-4-amine hydrochloride

Into a 2 L three-necked round-bottom flask affixed with an overhead stirrer, a temperature probe, an addition funnel and a nitrogen inlet were added ethanol (500 mL) and 4-nitro-1H-pyrazole (40 g, 354 mmol). To this solution was added, in one portion, conc. HCl (290 mL) (note: rapid exotherm observed from 15° C. to 39° C.) and the resulting mixture was purged with nitrogen for 5 minutes. Palladium on alumina (5% w/w) (2.1 g) was added to the mixture and stirred at room temperature while triethylsilane (208 g, 1789 mmol) was added dropwise over 2 h. The reaction, which started to slowly exotherm from 35° C. to 45° C. over 1 h, was stirred for a total of 16 h and vacuum filtered through a plug of celite to give a biphasic mixture. The mixture was transferred to a separatory funnel. The bottom aqueous layer was collected and rotary evaporated to dryness with the aid of acetonitrile (3×100 mL). The resulting yellow solid was suspended in acetonitrile (100 mL) and allowed to stand for 0.5 h at room temperature followed by 1 h at 0° C. The solids were filtered and washed with acetonitrile (50 mL) to afford 3-chloro-1H-pyrazol-4-amine hydrochloride as a white solid, which was used to next step without purification. LCMS: RT 0.1 min, m/z=118 [M+H]$^+$. $^1$H NMR (400 MHz, DMSO-d6): δ 10.49 (br. s, 2H), 8.02 (s, 0.59H), 7.74 (s, 0.31H), 5.12 (br. s, 1H).

tert-butyl (3-chloro-1H-pyrazo4-yl) carbamate

Into a 2 L round bottom flask was added 3-chloro-1H-pyrazo4-amino hydrochloride (30 g, 195 mmol) and THF (150 mL). To this mixture were added di-tert-butyldicarbonate (46.8 g, 214 mmol) followed by sodium bicarbonate (36 g, 428.7 mmol) and water (15 mL). The mixture was stirred for 16 h, diluted with water (150 mL) and ethyl acetate (150 mL) and transferred to a separatory funnel. This gave three layers; bottom—a white gelatinous precipitate, middle-light yellow aqueous, top-auburn organic. The phases were separated collecting the white gelatinous precipitate and the aqueous layer together. The aqueous was extracted with ethyl acetate (2×100 mL) and the ethyl acetate extracts were combined, washed with brine (80 mL), dried over anhydrous sodium sulfate, filtered and rotary evaporated to give crude product. The crude product was purified by column chromatography (PE:EtOAc=6:1 to 3:1) to get tert-butyl (3-chloro-1H-pyrazo4-yl) carbamate as a white solid. LCMS: RT 0.66 min, m/z=218 [M+H]$^+$. $^1$H NMR (400 MHz, CDCl$_3$): δ 11.04 (br. s, 1H), 7.91 (br. s, 1H), 6.28 (br. s, 1H), 1.52 (s, 9H).

Methyl 2-(4-((tert-butoxycarbonyl)amino)-3-chloro-1H-pyrazol-1-yl)-2-methylpropanoate To a solution of tert-butyl N-(3-chloro-1H-pyrazol-4-yl) carbamate (2 g, 9.19 mmol) in DMF (20 mL) was added NaH (404 mg, 10.11 mmol, 60% purity) at 0° C. The mixture was stirred at 25° C. for 1 h. Methyl 2-bromo-2-methylpropanoate (1.83 g, 10.11 mmol) was added to the mixture at 0°

C. and stirred at 25° C. for 1 h. The reaction mixture was quenched by addition of ice water (150 mL) and extracted with EtOAc (3×50 mL). The combined organic layers were washed with saturated brine (3×50 mL), dried over $Na_2SO_4$, filtered and concentrated under reduced pressure to give methyl 2-(4-((tert-butoxycarbonyl)amino)-3-chloro-1H-pyrazol-1-yl)-2-methylpropanoate as a yellow oil. LCMS: RT 0.849 min, m/z=318.2 [M+H]$^+$. $^1$H NMR (400 MHz, $CDCl_3$): δ 7.92 (s, 1H), 6.25 (s, 1H), 3.70 (s, 3H), 1.81 (s, 6H), 1.52 (s, 9H).

tert-butyl (1-(1-amino-2-methyl-1-oxopropan-2-yl)-3-chloro-1H-pyrazol-4-yl)carbamate A solution of methyl 2-[4-(tert-butoxycarbonylamino)-3-chloro-pyrazol-1-yl]-2-methyl-propanoate (3 g, 9.44 mmol) in methanol (50 mL) saturated with $NH_3$ was stirred at 80° C. for 16 h in a 100 mL of sealed tube. The reaction mixture was concentrated under reduced pressure to give tert-butyl (1-(1-amino-2-methyl-1-oxopropan-2-yl)-3-chloro-1H-pyrazol-4-yl)carbamate as a yellow gum. LCMS: RT 0.736 min, m/z=303.1 [M+H]$^+$. $^1$H NMR (400 MHz, $CDCl_3$): δ 7.99 (s, 1H), 6.30 (br. s., 1H), 5.92 (br. s., 1H), 5.58 (br. s., 1H), 1.82 (s, 6H), 1.51 (s, 9H).

tert-butyl (3-chloro-1-(2-cyanopropan-2-yl)-1H-pyrazol-4-yl)carbamate

To a solution of tert-butyl (1-(1-amino-2-methyl-1-oxopropan-2-yl)-3-chloro-1H-pyrazol-4-yl)carbamate (200 mg, 660.59 μmol) in pyridine (3 mL) was added $POCl_3$ (152 mg, 990.89 μmol) at 0° C. The mixture was stirred at 0° C. for 1 h. The reaction mixture was quenched by addition of water (30 mL) at 0° C., and then extracted with EtOAc (3×10 mL). The combined organic layers were washed with brine (10 mL), dried over $Na_2SO_4$, filtered and concentrated under reduced pressure to give tert-butyl (3-chloro-1-(2-cyanopropan-2-yl)-1H-pyrazol-4-yl)carbamate as a red solid. LCMS: RT 0.837 min, m/z=285.2 [M+H]$^+$.

2-(3-chloro-4-((4-cyclopropyl-5-(trifluoromethyl)pyrimidin-2-yl)amino)-1H-pyrazol-1-yl)-2-methyl-propanenitrile (A-17)

A mixture of tert-butyl (3-chloro-1-(2-cyanopropan-2-yl)-1H-pyrazol-4-yl)carbamate (150 mg, 526.80 μmol), 4-cyclopropyl-2-methylsulfonyl-5-(trifluoromethyl)pyrimidine (175 mg, 526.80 μmol) and PTSA (226.79 mg, 1.32 mmol) in 1,4-dioxane (3 mL) was stirred at 100° C. for 2 h. The reaction mixture was concentrated under reduced pressure to give a residue. The residue was diluted with $H_2O$ (20 mL), adjusted to pH=8 by aq. $NaHCO_3$ and then extracted with EtOAc (3×10 mL). The combined organic layers were washed with brine (10 mL), dried over $Na_2SO_4$, filtered and concentrated under reduced pressure to give a residue, which was purified by prep-HPLC (neutral condition) to give title compound 2-(3-chloro-4-((4-cyclopropyl-5-(trifluoromethyl)pyrimidin-2-yl)amino)-1H-pyrazol-1-yl)-2-methyl-propanenitrile (A-17). $^1$H NMR (400 MHz, $CDCl_3$): δ 8.50 (br. s., 1H), 8.31 (br. s., 1H), 6.95 (br. s., 1H), 2.28 (br. s., 1H), 2.02 (s, 6H), 1.11-1.37 (m, 4H). HPLC: RT: 3.70 min. MS: m/z: 371.1 [M+H]$^+$.

Example A-15

Synthesis of 1-[4-[[4-cyclopropyl-5-(trifluoromethyl)pyrimidin-2-yl]amino]-3-methyl-pyrazol-1-yl]-2-methyl-propan-2-ol and 1-[4-[[4-cyclopropyl-5-(trifluoromethyl)pyrimidin-2-yl]amino]-5-methyl-pyrazol-1-yl]-2-methyl-propan-2-ol (A-18 and A-19)

2-methyl-1-(3-methyl-4-nitro-pyrazol-1-yl)propan-2-ol and 2-methyl-1-(S-methyl-4-nitro-1H-pyrazol-1-yl)propan-2-ol To a mixture of 3-methyl-4-nitro-1H-pyrazole (1.50 g, 11.80 mmol) and 2,2-dimethyloxirane (2.43 g, 33.75 mmol, 3 mL) in DMF (19 mL) was added $Cs_2CO_3$ (7.69 g, 23.60 mmol) at 25° C. then heated to 100° C. and stirred for 3 h. The mixture was cooled to 25° C. and poured into water (100 mL) then extracted with EtOAc (5×40 mL), washed with brine (3×20 mL), dried over anhydrous $Na_2SO_4$, filtered and concentrated under reduced pressure to give a mixture of compound 2-methyl-1-(3-methyl-4-nitro-pyrazol-1-yl)propan-2-ol and 2-methyl-1-(5-methyl-4-nitro-1H-pyrazol-1-yl)propan-2-ol as a red brown oil. LCMS: RT 0.485 min, m/z=200.2 [M+H]$^+$.

1-(4-amino-3-methyl-pyrazol-1-yl)-2-methyl-propan-2-ol and 1-(4-amino-5-methyl-1H-pyrazol-1-yl)-2-methylpropan-2-ol A solution of the mixture 2-methyl-1-(3-methyl-4-nitro-pyrazol-1-yl)propan-2-ol and 2-methyl-1-(5-methyl-4-nitro-1H-pyrazol-1-yl)propan-2-ol (1.00 g, 5.02 mmol) in EtOH (20 mL) was treated with Pd/C (10%, 0.3 g). The suspension was degassed and purged with $H_2$ for 3 times. The mixture was stirred under $H_2$ (15 PSI) at 25° C. for 16 h. The reaction mixture was filtered and concentrated under reduced pressure to give the mixture compound 1-(4-amino-3-methyl-pyrazol-1-yl)-2-methyl-propan-2-ol and 1-(4-amino-5-methyl-1H-pyrazol-1-yl)-2-methylpropan-2-ol as a brown oil. LCMS: RT 0.111 min, m/z=170.2 [M+H]$^+$.

1-[4-[[4-cyclopropyl-5-(trifluoromethyl)pyrimidin-2-yl]amino]-3-methyl-pyrazol-1-yl]-2-methyl-propan-2-ol and 1-[4-[[4-cyclopropyl-5-(trifluoromethyl)pyrimidin-2-yl]amino]-5-methyl-pyrazol-1-yl]-2-methyl-propan-2-ol A mixture of 1-(4-amino-3-methyl-pyrazol-1-yl)-2-methyl-propan-2-ol and 1-(4-amino-5-methyl-pyrazol-1-yl)-2-methyl-propan-2-ol) (300 mg, 1.77 mmol), 2-chloro-4-cyclopropyl-5-(trifluoromethyl)pyrimidine (591 mg, 1.59 mmol) and $Et_3N$ (537 mg, 5.31 mmol, 736.05 μL) were taken up into a microwave tube in n-BuOH (3 mL). The sealed tube was heated at 120° C. for 60 min under microwave. The reaction mixture was cooled to 25° C. and filtered. The residue was purified by prep-HPLC (neutral) and further separated by SFC to provide 1-[4-[[4-cyclopropyl-5-(trifluoromethyl)pyrimidin-2-yl]amino]-3-methyl-pyrazol-1-yl]-2-methyl-propan-2-ol as a white solid and 1-[4-[[4-cyclopropyl-5-(trifluoromethyl)pyrimidin-2-yl]amino]-5-methyl-pyrazol-1-yl]-2-methyl-propan-2-ol as a white solid.

1-[4-[[4-cyclopropyl-5-(trifluoromethyl)pyrimidin-2-yl]amino]-3-methyl-pyrazol-1-yl]-2-methyl-propan-2-ol (A-19)

$^1$H NMR (400 MHz, $CDCl_3$): δ ppm 8.39 (s, 1H), 7.65 (s, 1H), 6.50 (br. s., 1H), 4.40 (s, 1H), 3.98 (s, 2H), 2.26 (s, 1H), 2.19 (s, 3H), 1.24-1.28 (m, 1H), 1.19 (s, 8H), 1.04-1.12 (m, 2H). HPLC: RT 2.91 min. MS: [M+H]$^+$ m/z: 356.2.

1-[4-[[4-cyclopropyl-5-(trifluoromethyl)pyrimidin-2-yl]amino]-5-methyl-pyrazol-1-yl]-2-methyl-propan-2-ol (A-18)

$^1$H NMR (400 MHz, CDCl$_3$): δ ppm 8.42 (br s, 1H), 7.78 (br. s., 1H), 6.73 (br. s., 1H), 3.88-4.06 (m, 3H), 2.25 (s, 4H), 1.23-1.28 (m, 2H), 1.19 (s, 6H), 1.09-1.15 (m, 2H). HPLC: RT 2.91 min. MS: [M+H]$^+$ m/z: 356.2.

Example A-16

Synthesis of 1-[4-[4-[[4-cyclopropyl-5-(trifluoromethyl)pyrimidin-2-yl]amino]-5-methyl-pyrazol-1-yl]-1-piperidyl]ethanone and 1-[4-[4-[[4-cyclopropyl-5-(trifluoromethyl)pyrimidin-2-yl]amino]-3-methyl-pyrazol-1-yl]-1-piperidyl]ethanone (A-20 and A-21)

1-[4-(5-methyl-4-nitro-pyrazol-1-yl)-1-piperidyl]ethanone and 1-[4-(3-methyl-4-nitro-pyrazol-1-yl)-1-piperidyl]ethanone To a mixture of 1-(4-hydroxy-1-piperidyl)ethanone (500 mg, 3.49 mmol), 3-methyl-4-nitro-1H-pyrazole (487 mg, 3.84 mmol) and PPh$_3$ (1.37 g, 5.24 mmol) in THF (30 mL) was added DIAB (1.06 g, 5.24 mmol) at 0° C. under N$_2$. The mixture was then stirred at 25° C. for 16 h. The mixture was poured into ice-water (100 mL) and extracted with EtOAc (3×50 mL). The combined organic phase was washed with brine, dried with anhydrous Na$_2$SO$_4$, filtered and concentrated. The residue was purified by silica gel column chromatography (PE:EtOAc=1:1) to afford a mixture of 1-[4-(5-methyl-4-nitro-pyrazol-1-yl)-1-piperidyl]ethanone and 1-[4-(3-methyl-4-nitro-pyrazol-1-yl)-1-piperidyl]ethanone as a white solid. LCMS: RT 0.603 min, m/z=253.2 [M+H]$^+$.

1-[4-(4-amino-5-methyl-pyrazol-1-yl)-1-piperidyl]ethanone and 1-[4-(4-amino-3-methyl-pyrazol-1-yl)-1-piperidyl]ethanone To a mixture of 1-[4-(5-methyl-4-nitro-pyrazol-1-yl)-1-piperidyl]ethanone and 1-[4-(3-methyl-4-nitro-pyrazol-1-yl)-1-piperidyl]ethanone (400 mg, 1.59 mmol) was in MeOH (20 mL) added Pd—C (0.2 g) under N$_2$. The suspension was degassed under vacuum and purged with H$_2$ three times. The mixture was stirred under H$_2$ (15 psi) at 25° C. for 1 h. The reaction mixture was filtered and the filtrate was concentrated to give a mixture 1-[4-(4-amino-5-methyl-pyrazol-1-yl)-1-piperidyl]ethanone and 1-[4-(4-amino-3-methyl-pyrazol-1-yl)-1-piperidyl]ethanone as a dark-brown solid. LCMS: RT 0.731 min, m/z=223.1 [M+H]$^+$.

1-[4-[4-[[4-cyclopropyl-5-(trifluoromethyl)pyrimidin-2-yl]amino]-5-methyl-pyrazol-1-yl]-1-piperidyl]ethanone and 1-[4-[4-[[4-cyclopropyl-5-(trifluoromethyl)pyrimidin-2-yl]amino]-3-methyl-pyrazol-1-yl]-1-piperidyl]ethanone (A-20 and A-21)

To a mixture of 1-[4-(4-amino-5-methyl-pyrazol-1-yl)-1-piperidyl]ethanone and 1-[4-(4-amino-3-methyl-pyrazol-1-yl)-1-piperidyl]ethanone (250 mg, 1.13 mmol) in 1,4-dioxane (2 mL) was added 4-cyclopropyl-2-(methylsulfonyl)-5-(trifluoromethyl)pyrimidine (150 mg, 563 μmol) and p-TsOH (29 mg, 169 μmol) at 25° C. under N$_2$. The mixture was then heated to 100° C. and stirred for 2 h. The mixture was cooled to 25° C. and poured into ice-water (30 mL). The aqueous phase was extracted with EtOAc (20 mL×3). The combined organic phase was washed with brine, dried with anhydrous Na$_2$SO$_4$, filtered and concentrated. The residue was purified by prep-HPLC (neutral), which was further separated by SFC to give 1-[4-[4-[[4-cyclopropyl-5-(trifluoromethyl)pyrimidin-2-yl]amino]-5-methyl-pyrazol-1-yl]-1-piperidyl]ethanone (A-20) and 1-[4-[4-[[4-cyclopropyl-5-(trifluoromethyl)pyrimidin-2-yl]amino]-3-methyl-pyrazol-1-yl]-1-piperidyl]ethanone (A-21).

1-[4-[4-[[4-cyclopropyl-5-(trifluoromethyl)pyrimidin-2-yl]amino]-5-methyl-pyrazol-1-yl]-1-piperidyl]ethanone (A-20)

$^1$H NMR (400 MHz, CDCl$_3$): δ 8.37 (s, 1H), 7.63 (br. s., 1H), 6.60 (br. s., 1H), 4.76 (d, J=13.43 Hz, 1H), 4.20 (tt, J=4.20, 11.11 Hz, 1H), 4.01 (d, J=13.93 Hz, 1H), 3.18-3.28 (m, 1H), 2.69-2.79 (m, 1H), 2.17-2.31 (m, 5H), 2.12-2.16 (m, 3H), 1.90-2.11 (m, 3H), 1.16-1.25 (m, 2H), 1.03-1.10 (m, 2H). HPLC: RT 2.413 min. MS: [M+H]$^+$ m/z: 409.2.

1-[4-[4-[[4-cyclopropyl-5-(trifluoromethyl)pyrimidin-2-yl]amino]-3-methyl-pyrazol-1-yl]-1-piperidyl]ethanone (A-21)

$^1$H NMR (400 MHz, CDCl$_3$): δ 8.43 (br s., 1H), 7.81 (br. s., 1H), 6.67 (br. s., 1H), 4.76 (d, J=14.05 Hz, 1H), 4.25 (tt, J=4.00, 11.37 Hz, 1H), 3.96 (d, J=13.80 Hz, 1H), 3.24 (t, J=12.05 Hz, 1H), 2.69-2.84 (m, 1H), 2.16-2.28 (m, 6H), 2.15 (s, 3H), 1.84-2.02 (m, 2H), 1.24-1.28 (m, 2H), 1.14 (br. s., 2H). HPLC: RT 2.406 min. MS: [M+H]$^+$ m/z: 409.2.

Example A-17

Synthesis of 4-cyclopropyl-N-(3-methyl-1-(2-(1-methyl-1H-pyrazol-5-yl)propan-2-yl)-1H-pyrazol-4-yl)-5-(trifluoromethyl)pyrimidin-2-amine and 4-cyclopropyl-N-(3-methyl-1-(2-(1-methyl-1H-pyrazol-3-yl)propan-2-yl)-1H-pyrazol-4-yl)-5-(trifluoromethyl)pyrimidin-2-amine (A-22 and A-23)

3-methyl-3-(3-methyl-4-nitro-1H-pyrazol-1-yl)butan-2-one

To a solution of 3-methyl-4-nitro-1H-pyrazole (10 g, 78.68 mmol) in DMF (50 mL) was added portionwise NaH (4.72 g, 118.02 mmol, 60% purity) at 0° C. over 30 min. After addition, the mixture was stirred at 20° C. for 30 min, and then 3-bromo-3-methylbutan-2-one (15.58 g, 94.42 mmol) was added dropwise at 0° C. The resulting mixture was stirred at 20° C. for 11 h. The reaction mixture was quenched by addition of H$_2$O (250 mL) at 0° C., and extracted with EtOAc (3×100 mL). The combined organic layers were washed with brine (50 mL), dried over Na$_2$SO$_4$, filtered and concentrated under reduced pressure to give a residue. The residue was purified by column chromatography on silica gel (PE/EtOAc=20/1 to 3/1). 3-methyl-3-(3-methyl-4-nitro-1H-pyrazol-1-yl)butan-2-one was obtained as a yellow solid. LCMS: RT 0.674 min, m/z=212 [M+H]+. $^1$H NMR (400 MHz, CDCl$_3$): δ ppm 8.30 (s, 1H) 2.56 (s, 3H) 1.98 (s, 3H) 1.75 (s, 6H).

(E)-1-(dimethylamino)-4-methyl-4-(3-methyl-4-nitro-1H-pyrazol-1-yl)pent-1-en-3-one A mixture of 3-methyl-3-(3-methyl-4-nitro-1H-pyrazol-1-yl)butan-2-one (7.5 g, 35.51 mmol) and DMF-DMA (42.31 g, 355.08 mmol, 47.01 mL) was stirred at 110° C. for 12 hrs under $N_2$ atmosphere. The mixture was concentrated under reduced pressure to give (E)-1-(dimethylamino)-4-methyl-4-(3-methyl-4-nitro-1H-pyrazol-1-yl)pent-1-en-3-one as a yellow solid. The crude product was used in the next step without further purification. LCMS: RT 0.675 min, m/z=267 [M+H]$^+$.

3-methyl-1-(2-(1-methyl-1H-pyrazol-5-yl)propan-2-yl)-4-nitro-1H-pyrazole and 3-methyl-1-(2-(1-methyl-1H-pyrazol-3-yl)propan-2-yl)-4-nitro-1H-pyrazole To a solution of (E)-1-(dimethylamino)-4-methyl-4-(3-methyl-4-nitro-1H-pyrazol-1-yl)pent-1-en-3-one (10.8 g, 40.56 mmol) in AcOH (100 mL) was added dropwise methylhydrazine (70.07 g, 608.40 mmol, 79.62 mL) at 0° C. over 30 min. The resulting mixture was stirred at 100° C. for 1.5 h. The reaction mixture was quenched by addition $H_2O$ (100 mL) at 0° C., and then added with sat. $NaHCO_3$ (200 mL) to pH=8 and extracted with EtOAc (3×100 mL). The combined organic layers were washed with brine (50 mL), dried over $Na_2SO_4$, filtered and concentrated under reduced pressure. The residue was purified by column chromatography on silica gel (PE/EtOAc=20/1 to 3/1). 3-methyl-1-(2-(1-methyl-1H-pyrazol-3-yl)propan-2-yl)-4-nitro-1H-pyrazole was obtained as an off-white solid, confirmed by HNMR and NOE. 3-methyl-1-(2-(1-methyl-1H-pyrazol-5-yl)propan-2-yl)-4-nitro-1H-pyrazole was obtained as an off-white solid, confirmed by HNMR and NOE.

3-methyl-1-(2-(1-methyl-1H-pyrazol-3-yl)propan-2-yl)-4-nitro-1H-pyrazole $^1$H NMR (400 MHz, $CDCl_3$): δ ppm 7.99 (s, 1H) 7.34 (d, J=2.0 Hz, 1H) 6.16 (d, J=2.0 Hz, 1H) 3.91 (s, 3H) 2.54 (s, 3H) 1.96 (s, 6H). LCMS: RT 0.701 min, m/z=250 [M+H]$^+$.

3-methyl-1-(2-(1-methyl-1H-pyrazol-5-yl)propan-2-yl)-4-nitro-1H-pyrazole $^1$H NMR (400 MHz, $CDCl_3$): δ ppm 8.00 (s, 1H) 7.46 (d, J=2.0 Hz, 1H) 6.35 (d, J=2.4 Hz, 1H) 3.47 (s, 3H) 2.56 (s, 3H) 1.98 (s, 6H). LCMS: RT 0.673 min, m/z=250 [M+H]$^+$.

3-methyl-1-(2-(1-methyl-1H-pyrazol-5-yl)propan-2-yl)-1H-pyrazol-4-amine

To a solution of 3-methyl-1-(2-(1-methyl-1H-pyrazol-5-yl)propan-2-yl)-4-nitro-1H-pyrazole (3 g, 12.04 mmol) in MeOH (60 mL) was added Pd—C (10%, 1.28 g) under $N_2$. The suspension was degassed under vacuum and purged with $H_2$ several times. The mixture was stirred under $H_2$ (15 psi) at 20° C. for 2 hrs. The reaction mixture was filtered and die filtrate was concentrated under reduced pressure to give 3-methyl-1-(2-(1-methyl-1H-pyrazol-5-yl)propan-2-yl)-1H-pyrazol-4-amine as a brown solid. The crude product was used in the next step without further purification. $^1$H NMR (400 MHz, CDCl3): δ ppm 7.39 (d, J=2.0 Hz, 1H) 6.78 (s, 1H) 6.26 (d, J=2.0 Hz, 1H) 3.37 (s, 3H) 2.19 (s, 3H) 1.86 (s, 6H).

3-methyl-1-(2-(1-methyl-1H-pyrazol-3-yl)propan-2-yl)-1H-pyrazol-4-amine

To a solution of 3-methyl-1-(2-(1-methyl-1H-pyrazol-3-yl)propan-2-yl)-4-nitro-1H-pyrazole (2 g, 8.02 mmol) in MeOH (40 mL) was added Pd—C (10%, 0.85 g) under $N_2$. The suspension was degassed under vacuum and purged with $H_2$ several times. The mixture was stirred under $H_2$ (15 psi) at 20° C. for 2 hrs. The reaction mixture was filtered and the filtrate was concentrated under reduced pressure to give 3-methyl-1-(2-(1-methyl-1H-pyrazol-3-yl)propan-2-yl)-1H-pyrazol-4-amino as a brown solid. The crude product was used in the next step without further purification. $^1$H NMR (400 MHz, $CDCl_3$): δ ppm 7.23 (d, J=2.0 Hz, 1H) 6.98 (s, 1H) 5.96 (d, J=2.4 Hz, 1H) 3.87 (s, 3H) 2.60-2.73 (bs, 2H) 2.20 (s, 3H) 1.90 (s, 6H).

4-cyclopropyl-N-(3-methyl-1-(2-(1-methyl-1H-pyrazol-5-yl)propan-2-yl)-1H-pyrazol-4-yl)-5-(trifluoromethyl)pyrimidin-2-amine (A-22)

To a mixture of 3-methyl-1-(2-(1-methyl-1H-pyrazol-5-yl)propan-2-yl)-1H-pyrazol-4-amine (100 mg, 456.02 μmol) and 2-chloro-4-cyclopropyl-5-(trifluoromethyl)pyrimidine (67.67 mg, 304.01 μmol) in 1,4-dioxane (3 mL) was added p-TsOH (15.71 mg, 91.20 μmol) in one portion at 25° C. under $N_2$. The mixture was heated to 100° C. and stirred for 2 h. The mixture was added with water (5 mL) and then adjusted to pH=7 by adding $NaHCO_3$ (3 mL). The reaction mixture was then extracted with EtOAc (3×4 mL). The combined organic phase was washed with brine (5 mL), dried with anhydrous $Na_2SO_4$, filtered and concentrated under reduced pressure. The residue was purified by prep-HPLC (neutral condition) to give 4-cyclopropyl-N-(3-methyl-1-(2-(1-methyl-1H-pyrazol-5-yl)propan-2-yl)-1H-pyrazol-4-yl)-5-(trifluoromethyl)pyrimidin-2-amine.
$^1$HNMR (400 MHz, $CDCl_3$): δ ppm 8.35-8.43 (m, 1H) 7.57-7.72 (m, 1H) 7.41-7.48 (m, 1H) 6.63-6.79 (m, 1H) 6.28-6.38 (m, 1H) 3.42 (s, 3H) 2.27 (s, 3H) 2.12-2.23 (m, 1H) 1.95 (s, 6H) 0.90-1.15 (m, 4H). HPLC: RT 2.821 min. MS: (M+H$^+$) m/z: 406.

4-cyclopropyl-N-(3-methyl-1-(2-(1-methyl-1H-pyrazol-3-yl)propan-2-yl)-1H-pyrazol-4-yl)-5-(trifluoromethyl)pyrimidin-2-amine (A-23)

To a mixture of 3-methyl-1-(2-(1-methyl-1H-pyrazol-3-yl)propan-2-yl)-1H-pyrazol-4-amine (100 mg, 456.02 μmol) and 2-chloro-4-cyclopropyl-5-(trifluoromethyl)pyrimidine (67.67 mg, 304.01 μmol) in 1,4-dioxane (3 mL) was added p-TsOH (15.71 mg, 91.20 μmol) in one portion at 25° C. under $N_2$. The mixture was then heated to 100° C. and stirred for 2 h. The crude product was added with water (5 mL) and then adjusted to pH=7 by adding $NaHCO_3$ (3 mL). The reaction mixture was then extracted with EtOAc (3×4 mL). The combined organic phase was washed with brine (5 mL), dried with anhydrous $Na_2SO_4$, filtered and concentrated under reduced pressure. The residue was purified by prep-HPLC (neutral condition) to give 4-cyclopropyl-N-(3-methyl-1-(2-(1-methyl-1H-pyrazol-3-yl)propan-2-yl)-1H-pyrazol-4-yl)-5-(trifluoromethyl)pyrimidin-2-amine. $^1$H NMR (400 MHz, $CDCl_3$): δ ppm 8.30-8.43 (m, 1H) 7.64-7.79 (m, 1H) 7.28-7.32 (m, 1H) 6.57-6.84 (m, 1H) 5.94-6.15 (m, 1H) 3.91 (s, 3H) 2.26 (s, 3H) 2.14-2.22 (m, 1H) 1.97 (s, 6H) 1.10-1.20 (m, 2H) 1.02-1.10 (m, 2H). HPLC: RT 2.817 min. MS: [M+H]$^+$ m/z: 406.

Example A-18

Synthesis of 4-cyclopropyl-N-(5-methyl-1-tetrahydropyran-4-yl-pyrazol-4-yl)-5-(trifluoromethyl)pyrimidin-2-amine and 4-cyclopropyl-N-(3-methyl-1-tetrahydropyran-4-yl-pyrazol-4-yl)-5-(trifluoromethyl)pyrimidin-2-amine (A-24 and A-25)

5-methyl-4-nitro-1-tetrahydropyran-4-yl-pyrazole and 3-methyl-4-nitro-1-tetrahydro-2H-pyran-4-yl-pyrazole To a mixture of 3-methyl-4-nitro-1H-pyrazole (5 g, 39.34 mmol) and tetrahydropyran-4-ol (4.82 g, 47.21 mmol, 4.73 mL) in THF (70 mL) was added PPh$_3$ (15.48 g, 59.01 mmol) and DIAB (11.93 g, 59.01 mmol, 11.47 mL) in one portion at 0° C. under N$_2$. The mixture was stirred at 0° C. for 60 min, then warmed to 25° C. and stirred for 16 h. The mixture was pouted into the mixture of PE and EtOAc (PE:EtOAc=1:1) (100 mL), filtered and concentrated under reduced pressure. The residue was purified by silica gel column chromatography (PE:EtOAc=5:1) to afford 5-methyl-4-nitro-1-tetrahydropyran-4-yl-pyrazole and 3-methyl-4-nitro-1-tetrahydro-2H-pyran-4-yl-pyrazole as yellow solids. LCMS: RT 0.610 min, m/z=212.2 [M+H]$^+$.

5-methyl-1-tetrahydropyran-4-yl-pyrazol-4-amine and 3-methyl-1-tetrahydro-2H-pyran-4-yl-pyrazol-4-amine To a mixture of 5-methyl-4-nitro-1-(tetrahydropyran-4-yl)-1H-pyrazole and 3-methyl-4-nitro-1-tetrahydro-2H-pyran-4-yl-pyrazole (3 g, 14.20 mmol) in MeOH (60 mL) was added Pd/C (1 g, 10%) under N$_2$. The suspension was degassed under reduced pressure and purged with H$_2$ several times. The mixture was stirred under H$_2$ (15 psi) at 25° C. for 2 h. The reaction mixture was filtered and the filtrate was concentrated under reduced pressure. The crude product 5-methyl-1-tetrahydropyran-4-yl-pyrazol-4-amine and 3-methyl-1-tetrahydro-2H-pyran-4-yl-pyrazol-4-amine was used into the next step without further purification. LCMS: RT 0.482 min, m/z=182.1 [M+H]$^+$.

4-cyclopropyl-N-(5-methyl-1-tetrahydropyran-4-yl-pyrazol-4-yl)-5-(trifluoromethyl)pyrimidin-2-amine and 4-cyclopropyl-N-(3-methyl-1-tetrahydropyran-4-yl-pyrazol-4-yl)-5-(trifluoromethyl)pyrimidin-2-amine (A-24 and A-25)

5-methyl-1-tetrahydropyran-4-yl-pyrazol-4-amine, 3-methyl-1-tetrahydro-pyran-4-yl-pyrazol-4-amine (200 mg, 1.31 mmol), 2-chloro-4-cyclopropyl-5-(trifluoromethyl)pyrimidine (251 mg, 1.13 mmol) and TEA (398 mg, 3.93 mmol, 544.77 µL) were taken up into a microwave tube in n-BuOH (2 mL). The sealed tube was heated at 120° C. for 90 min under microwave. The mixture was cooled to 25° C. and concentrated under reduced pressure. The residue was poured into ice-water (5 mL). The aqueous phase was extracted with EtOAc (3×2 mL). The combined organic phase was washed with brine (5 mL), dried over anhydrous Na$_2$SO$_4$, filtered and concentrated under reduced pressure. The residue was purified by prep-TLC (SiO$_2$, PE:EtOAc=1:1) to provide 4-cyclopropyl-N-(5-methyl-1-tetrahydropyran-4-yl-pyrazol-4-yl)-5-(trifluoromethyl)pyrimidin-2-amine and 4-cyclopropyl-N-(3-methyl-1-tetrahydropyran-4-yl-pyrazol-4-yl)-5-(trifluoromethyl)pyrimidin-2-amino was obtained.

4-cyclopropyl-N-(5-methyl-1-tetrahydropyran-4-yl-pyrazol-4-yl)-5-(trifluoromethyl)pyrimidin-2-amine (A-24)

$^1$H NMR (400 MHz, CDCl$_3$): δ8.39 (s, 1H), 7.66 (br. s., 1H), 6.28-6.92 (m, 1H), 4.12-4.26 (m, 3H), 3.49-3.62 (m, 2H), 2.33 (qd, 7=12.40, 4.58 Hz, 2H), 2.23 (s, 3H), 1.87 (dd, J=12.80, 2.13 Hz, 2H), 1.23 (br. s, 2H), 1.04-1.12 (m, 2H). HPLC: RT 3.06 min. MS: [M+H]$^+$ m/z=368.2.

4-cyclopropyl-N-(3-methyl-1-tetrahydropyran-4-yl-pyrazol-4-yl)-5-(trifluoromethyl)pyrimidin-2-amine (A-25)

$^1$H NMR (400 MHz, CDCl$_3$): δ 8.42 (br. s., 1H), 7.83 (br. s., 1H), 4.23-4.33 (m, 1H), 4.12 (d, J=11.04 Hz, 2H), 3.56 (t, 7=11.73 Hz, 2H), 2.26 (s, 3H), 1.98-2.17 (m, 4H), 1.25-1.31 (m, 2H), 1.16 (br. s., 2H). HPLC: RT 3.15 min. MS. [M+H]$^+$ m/z=368.2.

Example A-19

Synthesis of 5-(4-((4-cyclopropyl-5-(trifluoromethyl)pyrimidin-2-yl)amino)-5-methyl-1H-pyrazol-1-yl)-1-methylpiperidin-2-one and 5-(4-((4-cyclopropyl-5-(trifluoromethyl)pyrimidin-2-yl)amino)-3-methyl-1H-pyrazol-1-yl)-1-methylpiperidin-2-one (A-26 and A-27)

5-((tert-butyldiphenylsilyl)oxy)piperidin-2-one

To a solution of 5-hydroxypiperidin-2-one (4.5 g, 39.09 mmol) in DMF (60 mL) was added imidazole (7.98 g, 117.27 mmol), followed by TBDPSCl (16.11 g, 58.64 mmol) at 0° C. The mixture was stirred at 25° C. for 12 h. The solution was added with water (120 mL), extracted with EtOAc (3×30 mL). The organic layers were combined, washed with brine (3×20 mL), dried over Na$_2$SO$_4$, filtered and concentrated under reduced pressure to get a residue, which was purified by silica gel chromatography (PE:EtOAc=10:1 to 1:1) to give 5-((tert-butyldiphenylsilyl)oxy)piperidin-2-one as an off-white solid. LCMS: RT 0.943 min, m/z=354.3 [M+H]$^+$. $^1$H NMR (400 MHz, CDCl$_3$): δ 7.62-7.69 (m, 4H), 7.42-7.48 (m, 2H), 7.36-7.42 (m, 4H), 6.19 (br. s., 1H), 4.06-4.12 (m, 1H), 3.15-3.27 (m, 2H), 2.66 (ddd, J=17.42, 9.48, 6.17 Hz, 1H), 2.27 (dt, J=17.86, 5.84 Hz, 1H), 1.74-1.95 (m, 2H), 1.02-1.12 (m, 9H).

5-((tert-butyldiphenylsilyl)oxy)-1-methylpiperidin-2-one

To a solution of 5-[tert-butyl(diphenyl)silyl]oxypiperidin-2-one (1 g, 2.83 mmol) in DMF (15 mL) at 0° C. was added NaH (158.4 mg, 3.96 mmol), the mixture was stirred at 25° C. for 1 h and then CH$_3$I (802.99 mg, 5.66 mmol) was added. The mixture was stirred at 25° C. for 11 h. The reaction mixture was quenched by addition of H$_2$O (50 mL), extracted with EtOAc (3×50 mL). The combined organic layers were washed with brine (2×50 mL), dried over Na$_2$SO$_4$, filtered and concentrated under reduced pressure to give a residue, which was purified by silica gel chromatography (PE:EtOAc=1:1 to 1:3) to give 5-((tert-butyldiphenyl-

5-hydroxy-1-methylpiperidin-2-one

To a solution of 5-[tert-butyl(diphenyl)silyl]oxy-1-methyl-piperidin-2-one (400 mg, 1.09 mmol) in MeOH (15 mL) was added KF (633.29 mg, 10.90 mmol). The mixture was stirred at 85° C. for 12 h. The reaction mixture was concentrated under reduced pressure to get a residue, which was slurried with DCM/MeOH (V/V, 10/1, 40 mL), the suspension was filtered and the filtrate was concentrated to get a residue, which was dissolved in $H_2O$ (20 mL). The solution was extracted with MTBE (2×25 mL), the aqueous phase was concentrated under reduced pressure to give 5-hydroxy-1-methyl-piperidin-2-one as a white solid.

1-methyl-5-(5-methyl-4-nitro-1H-pyrazol-1-yl)piperidin-2-one and 1-methyl-5-(3-methyl-4-nitro-1H-pyrazol-1-yl)piperidin-2-one To a solution of 5-hydroxy-1-methyl-piperidin-2-one (175 mg, 1.35 mmol), 3-methyl-4-nitro-1H-pyrazole (5) (205.9 mg, 1.62 mmol) and $PPh_3$ (531.14 mg, 2.03 mmol) in THF (15 mL) was added DIAB (409.48 mg, 2.03 mmol) at 0° C. The mixture was stirred at 25° C. for 12 h. The reaction mixture was concentrated under reduced pressure to get a residue, which was purified by prep-TLC ($SiO_2$, DCM: MeOH=20:1) to give a mixture of 1-methyl-5-(5-methyl-4-nitro-1H-pyrazol-1-yl)piperidin-2-one and 1-methyl-5-(3-methyl-4-nitro-1H-pyrazol-1-yl)piperidin-2-one as yellow solid. LCMS: RT 0.577 min, m/z=239.1 [M+H]$^+$.

5-(4-amino-5-methyl-1H-pyrazol-1-yl)-1-methylpiperidin-2-one and 5-(4-amino-3-methyl-1H-pyrazol-1-yl)-1-methylpiperidin-2-one To a mixture of 1-methyl-5-(5-methyl-4-nitro-1H-pyrazol-1-yl)piperidin-2-one and 1-methyl-5-(3-methyl-4-nitro-1H-pyrazol-1-yl)piperidin-2-one (180 mg, 755.54 μmol) in MeOH (10 mL) was added Pd/C (10%, 60 mg) under $N_2$. The suspension was degassed and purged with $H_2$ for 3 times. The mixture was stirred under $H_2$ (15 Psi) at 25° C. for 4 h. It was filtered over celite, the filter cake was washed with MeOH (20 mL×2), the filtrate was combined and concentrated under reduced pressure to give a mixture of 5-(4-amino-5-methyl-1H-pyrazol-1-yl)-1-methylpiperidin-2-one and 5-(4-amino-3-methyl-1H-pyrazol-1-yl)-1-methylpiperidin-2-one (as yellow oil. LCMS: RT 0.194 min, m/z=209.1 [M+H]$^+$.

5-(4-((4-cyclopropyl-5-(trifluoromethyl)pyrimidin-2-yl)amino)-5-methyl-1H-pyrazol-1-yl)-1-methylpiperidin-2-one and 5-(4-((4-cyclopropyl-5-(trifluoromethyl)pyrimidin-2-yl)amino)-3-methyl-1H-pyrazol-1-yl)-1-methylpiperidin-2-one (A-26 and A-27)

A mixture of 5-(4-amino-5-methyl-1H-pyrazol-1-yl)-1-methylpiperidin-2-one and 5-(4-amino-3-methyl-1H-pyrazol-1-yl)-1-methylpiperidin-2-one (107 mg, 513.78 μmol), 4-cyclopropyl-2-methylsulfonyl-5-(trifluoromethyl)pyrimidine (137 mg, 513.78 μmol) and $TsOH.H_2O$ (49 mg, 256.89 μmol) in 1,4-dioxane (15 mL) was degassed and purged with $N_2$ for 3 times, and then the mixture was stirred at 100° C. for 2 h under $N_2$. It was poured into $H_2O$ (15 mL), adjusted to pH=8 with aq. $NaHCO_3$, extracted with EtOAc (2×30 mL). The combined organic phase was dried over $Na_2SO_4$, filtered and concentrated under reduced pressure to get a residue, which was purified by prep-HPLC (neutral) first and then it was re-purified by SFC to give 5-(4-((4-cyclopropyl-5-(trifluoromethyl)pyrimidin-2-yl)amino)-5-methyl-1H-pyrazol-1-yl)-1-methylpiperidin-2-one (14 mg) and 5-(4-((4-cyclopropyl-5-(trifluoromethyl)pyrimidin-2-yl)amino)-3-methyl-1H-pyrazol-1-yl)-1-methylpiperidin-2-one.

5-(4-((4-cyclopropyl-5-(trifluoromethyl)pyrimidin-2-yl)amino)-5-methyl-1H-pyrazol-1-yl)-1-methylpiperidin-2-one (A-26)

$^1$H NMR (400 MHz, $CDCl_3$): δ 8.39 (s, 1H), 7.67 (br. s, 1H), 6.51 (br. s., 1H), 4.42-4.60 (m, 1H), 3.91 (dd, J=11.69, 9.92 Hz, 1H), 3.46 (ddd, J=12.13, 5.51, 1.76 Hz, 1H), 3.00 (s, 3H), 2.65 (d, J=3.97 Hz, 1H), 2.42-2.59 (m, 2H), 2.25 (s, 3H), 2.17 (d, J=1.76 Hz, 2H), 1.22 (br. s., 2H), 1.09 (dd, J=7.72, 3.31 Hz, 2H). HPLC: Retention Time: 2.87 min. MS: (M+H$^+$) m/z: 395.2.

5-(4-((4-cyclopropyl-5-(trifluoromethyl)pyrimidin-2-yl)amino)-3-methyl-1H-pyrazol-1-yl)-1-methylpiperidin-2-one (A-27)

$^1$HNMR (400 MHz, $CDCl_3$). A 8.43 (s, 1H), 7.86 (br. s., 1H), 6.49-6.87 (m, 1H), 4.56 (d, J=6.62 Hz, 1H), 3.71 (d, J=7.06 Hz, 2H), 3.00 (s, 3H), 2.48-2.64 (m, 2H), 2.34-2.45 (m, 1H), 2.17-2.34 (m, 4H), 1.22-1.30 (m, 2H), 1.15 (br. s., 2H). HPLC: Retention Time: 2.86 min. MS: (M+H$^+$) m/z: 395.2.

Example A-20

Synthesis of 4-cyclopropyl-N-[1-[2-fluoro-1-(fluoromethyl)ethyl]-5-methyl-pyrazol-4-yl]-5-(trifluoromethyl)pyrimidin-2-amine and 4-cyclopropyl-N-[1-[2-fluoro-1-(fluoromethyl)ethyl]-3-methyl-pyrazol-4-yl]-5-(trifluoromethyl)pyrimidin-2-amine (A-28 and A-29)

1-[2-fluoro-1-(fluoromethyl)ethyl]-5-methyl-4-nitro-pyrazole and 1-[2-fluoro-1-(fluoromethyl)ethyl]-3-methyl-4-nitro-pyrazole To a mixture of 5-methyl-4-nitro-1H-pyrazole (727 mg, 5.72 mmol) and 1,3-difluoropropan-2-ol (500 mg, 5.20 mmol) in THF (50 mL) was added $PPh_3$ (2.05 g, 7.80 mmol) and DIAB (1.58 g, 7.80 mmol) at 0° C. under $N_2$. Then the mixture was stirred at 25° C. for 16 h. The mixture was poured into ice-water (100 mL) and extracted with EtOAc (3×50 mL). The combined organic phase was washed with brine, dried with anhydrous $Na_2SO_4$, filtered and concentrated. The residue was purified by silica gel column chromatography (PE:EtOAc=10:1) to afford a mixture of 1-[2-fluoro-1-(fluoromethyl)ethyl]-5-methyl-4-nitro-pyrazole and 1-[2-fluoro-1-(fluoromethyl)ethyl]-3-methyl-4-nitro-pyrazole as a colorless oil. LCMS: RT 0.620 min, m/z=206.1 [M+H]$^+$.

1-[2-fluoro-1-(fluoromethylboryl]-5-methyl-pyrazol-4-amine and 1-[2-fluoro-1-(fluoromethyl)ethyl]-3-methyl-pyrazol-4-amine To a mixture of 1-[2-fluoro-1-(fluoromethyl)ethyl]-5-methyl-4-nitro-pyrazole and 1-[2-fluoro-1-(fluoromethyl)ethyl]-3-methyl-4-nitro-pyrazole (1 g, 4.87 mmol) in EtOH (36 mL) and $H_2O$ (9 mL) was added $NH_4Cl$ (783 mg, 14.64 mmol) and Fe (817 mg, 14.64 mmol) at 25° C. under $N_2$. The mixture was then heated to 80° C. and stirred for 2 h. The mixture was cooled to 25° C., filtered and the filtrate was concentrated to afford a mixture of 1-[2-fluoro-1-(fluoromethyl)ethyl]-5-methyl-pyrazol-4-amine and 1-[2-fluoro-1-(fluoromethyl)ethyl]-3-methyl-pyrazol-4-amino as a black-brown solid. LCMS: RT 0.228 min, m/z=176.1 $[M+H]^+$.

4-cyclopropyl-N-[1-[2-fluoro-1-(fluoromethyl) ethyl]-5-methyl-pyrazol-4-yl]-5-(trifluoromethyl) pyrimidin-2-amine and 4-cyclopropyl-N-[1-[2-fluoro-1-(fluoromethyl)ethyl]-3-methyl-pyrazol-4-yl]-5-(trifluoromethyl)pyrimidin-2-amine (A-28 and A-29)

To a mixture of 1-[2-fluoro-1-(fluoromethyl)ethyl]-5-methyl-pyrazol-4-amine and 1-[2-fluoro-1-(fluoromethyl) ethyl]-3-methyl-pyrazol-4-amine (157 mg, 901 nmol) in 1,4-dioxane (3 mL) was added 4-cyclopropyl-2-(methylsulfonyl)-5-(trifluoromethyl)pyrimidine (120 mg, 450 µmol) and p-TsOH (23 mg, 135 µmol) at 25° C. under $N_2$. The mixture was then heated to 100° C. and stirred for 2 h. The mixture was cooled to 25° C. and poured into ice-water (30 mL). The aqueous phase was extracted with EtOAc (3×20 mL). The combined organic phase was washed with brine, dried with anhydrous $Na_2SO_4$, filtered and concentrated. The residue was separated by prep-TLC (PE:EtOAc=3:1) to give desired products, which were further purified by prep-HPLC (neutral) to give 4-cyclopropyl-N-[1-[2-fluoro-1-(fluoromethyl)ethyl]-5-methyl-pyrazol-4-yl]-5-(trifluoromethyl)pyrimidin-2-amino and 4-cyclopropyl-N-[1-[2-fluoro-1-(fluoromethyl)ethyl]-3-methyl-pyrazol-4-yl]-5-(trifluoromethyl)pyrimidin-2-amine.

4-cyclopropyl-N-[1-[2-fluoro-1-(fluoromethyl) ethyl]-5-methyl-pyrazol-4-yl]-5-(trifluoromethyl) pyrimidin-2-amine (A-28)

$^1$H NMR (400 MHz, $CDCl_3$): δ 8.39 (s, 1H), 7.72 (s, 1H), 6.56 (br. s., 1H), 4.77-4.91 (m, 4H), 4.67-4.76 (m, 1H), 2.24 (s, 3H), 2.19 (dd, J=1.57, 4.71 Hz, 1H), 1.22 (br. s., 2H), 1.04-1.13 (m, 2H). HPLC: RT 2.870 min. MS: $[M+H]^+$ m/z: 362.1.

4-cyclopropyl-N-[1-[2-fluoro-1-(fluoromethyl) ethyl]-3-methyl-pyrazol-4-yl]-5-(trifluoromethyl) pyrimidin-2-amine (A-29)

$^1$H NMR (400 MHz, $CDCl_3$): δ 8.43 (br. s., 1H), 7.96 (s, 1H), 6.71 (br. s., 1H), 4.75-4.94 (m, 4H), 4.62-4.72 (m, 1H), 2.26 (s, 4H), 1.26-1.30 (m, 2H), 1.14-1.15 (m, 2H). HPLC: Retention Time: 2.871 min. MS: $[M+H]^+$ m/z: 362.1.

Example A-21

Synthesis of 4-cyclopropyl-N-(1-(2-fluoroethyl)-5-methyl-1H-pyrazol-4-yl)-5-(trifluoromethyl)pyrimidin-2-amine and 4-cyclopropyl-N-(1-(2-fluoroethyl)-3-methyl-1H-pyrazol-4-yl)-5-(trifluoromethyl)pyrimidin-2-amine (A-30 and A-31)

1-(2-fluoroethyl)-5-methyl-4-nitro-1H-pyrazole and 1-(2-fluoroethyl)-3-methyl-4-nitro-1H-pyrazole To a solution of 5-methyl-4-nitro-1H-pyrazole (2 g, 15.74 mmol) in DMF (10 mL) was added $Cs_2CO_3$ (9.74 g, 29.90 mmol) and 1-bromo-2-fluoroethane (5.99 g, 47.21 mmol). The mixture was stirred at 100° C. for 3 h. The reaction mixture was diluted with $H_2O$ (70 mL) and extracted with EtOAc (3×30 mL). The combined organic layers were washed with brine (30 mL), dried over $Na_2SO_4$, filtered and concentrated under reduced pressure to give 1-(2-fluoroethyl)-5-methyl-4-nitro-1H-pyrazole and 1-(2-fluoroethyl)-3-methyl-4-nitro-1H-pyrazole as a pale-yellow oil. The crude product was used into the next step without further purification. LCMS: RT 0.377, 0.464 min, m/z=174 $[M+H]^+$.

1-(2-fluoroethyl)-5-methyl-1H-pyrazol-4-amine and 1-(2-fluoroethyl)-3-methyl-1H-pyrazol-4-amine To a solution of 1-(2-fluoroethyl)-5-methyl-4-nitro-1H-pyrazole and 1-(2-fluoroethyl)-3-methyl-4-nitro-1H-pyrazole (2 g, 11.55 mmol) in EtOH (48 mL) was added $H_2O$ (12 mL) and $NH_4Cl$ (3.09 g, 57.75 mmol), then Fe (3.23 g, 57.75 mmol). Then the mixture was heated to 80° C. and stirred at 80° C. for 1 h. The mixture was cooled to 25° C., filtered and concentrated. The aqueous phase was extracted with EtOAc (3×5 mL). The combined organic phase was washed with brine (10 mL), dried with anhydrous $Na_2SO_4$ and concentrated under reduced pressure, to give the crude product 1-(2-fluoroethyl)-5-methyl-1H-pyrazol-4-amine and 1-(2-fluoroethyl)-3-methyl-1H-pyrazol-4-amino, which was used into the next step without further purification. LCMS: RT 0.114 min, m/z=144.2 $[M+H]^+$.

4-cyclopropyl-N-(1-(2-fluoroethyl)-5-methyl-1H-pyrazol-4-yl)-5-(trifluoromethyl)pyrimidin-2-amine and 4-cyclopropyl-N-(1-(2-fluoroethyl)-3-methyl-1H-pyrazol-4-yl)-5-(trifluoromethyl)pyrimidin-2-amine (A-30 and A-31)

To a solution of 1-(2-fluoroethyl)-5-methyl-1H-pyrazol-4-amine and 1-(2-fluoroethyl)-3-methyl-1H-pyrazol-4-amine (161 mg, 1.13 mmol) and 4-cyclopropyl-2-(methylsulfonyl)-5-(trifluoromethyl)pyrimidine (150 mg, 563.40 µmol) in 1,4-dioxane (3 mL) was added p-TsOH (29 mg, 169.02 µmol) under $N_2$. The mixture was stirred at 100° C. for 2 h. The reaction mixture was quenched by addition of $H_2O$ (15 mL) at 0° C., and then added with sat. $NaHCO_3$ (10 mL) to pH=8 and extracted with EtOAc (3×10 mL). The combined organic layers were washed with brine (5 mL), dried over $Na_2SO_4$, filtered and concentrated under reduced pressure. The residue was purified by prep-HPLC (neutral condition). 4-cyclopropyl-N-(1-(2-fluoroethyl)-5-methyl-1H-pyrazol-4-yl)-5-(trifluoromethyl)pyrimidin-2-amino and 4-cyclopropyl-N-(1-(2-fluoroethyl)-3-methyl-1H-pyrazol-4-yl)-5-(trifluoromethyl)pyrimidin-2-amine were obtained.

4-cyclopropyl-N-(1-(2-fluoroethyl)-5-methyl-1H-pyrazol-4-yl)-5-(trifluoromethyl)pyrimidin-2-amine (A-30)

$^1$H NMR: (400 MHz, CHLOROFORM-d) δ 8.39 (s, 1H), 7.66 (s, 1H), 6.51 (br. s, 1H), 4.68-4.89 (m, 2H), 4.27-4.43 (m, 2H), 2.12-2.30 (m, 4H), 1.18-1.29 (m, 2H), 1.02-1.12 (m, 2H). HPLC: RT 3.07 min. MS. $[M+H]^+$ m/z: 330.2.

4-cyclopropyl-N-(1-(2-fluoroethyl)-3-methyl-1H-pyrazol-4-yl)-5-(trifluoromethyl)pyrimidin-2-amine (A-31)

$^1$H NMR: (400 MHz, CHLOROFORM-d) δ 8.43 (s, 1H), 7.86 (s, 1H), 6.66 (br, 1H), 4.65-4.86 (m, 2H), 4.27-4.43 (m,

2H), 2.15-2.30 (m, 4H), 1.23-1.33 (m, 3H), 1.08-1.18 (m, 2H). HPLC: RT 3.13 min. MS: [M+H]+ m/z: 330.2.

Example A-22

Synthesis of 2-(4-((5-chloro-4-cyclobutylpyrimidin-2-yl)amino)-3-methyl-1H-pyrazol-1-yl)-2-methyl-propanenitrile (A-32)

2-(4-((5-chloro-4-cyclobutylpyrimidin-2-yl)amino)-3-methyl-1H-pyrazol-1-yl)-2-methylpropanenitrile (A-32)

To a mixture of 2-(4-amino-3-methyl-1H-pyrazol-1-yl)-2-methylpropanenitrile (150 mg, 0.94 mmol) in 1,4-dioxane (2 mL) was added 2,5-dichloro-4-cyclobutylpyrimidine (186 mg, 0.91 mmol) and p-TsOH (315 mg, 1.83 mmol) at 25° C. under $N_2$. The mixture was stirred at 100° C. for 12 h. The reaction mixture was concentrated under reduced pressure. The residue was purified by prep-HPLC (neutral) to give 2-(4-((5-chloro-4-cyclobutylpyrimidin-2-yl)amino)-3-methyl-1H-pyrazol-1-yl)-2-methylpropanenitrile. $^1$H NMR (400 MHz, CDCl$_3$): δ 8.31 (s, 1H), 8.19 (s, 1H), 6.61 (s, 1H), 3.87~3.91 (m, 1H), 2.33~2.47 (m, 4H), 2.30 (s, 3H), 2.09~2.11 (m, 1H), 1.94~1.99 (m, 7H). HPLC: RT 3.63 min. MS: [M+H]+ m/z: 331.1.

Example A-23

Synthesis of 5-chloro-4-cyclopropyl-N-(3-methyl-1-(2-(1-methyl-1H-pyrazol-5-yl)propan-2-yl)-1H-pyrazol-4-yl)pyrimidin-2-amine (33) and 5-chloro-4-cyclopropyl-N-(3-methyl-1-(2-(1-methyl-1H-pyrazol-3-yl)propan-2-yl)-1H-pyrazol-4-yl)pyrimidin-2-amine (A-34)

5-chloro-4-cyclopropyl-N-(3-methyl-1-(2-(1-methyl-1H-pyrazol-3-yl)propan-2-yl)-1H-pyrazol-4-yl)pyrimidin-2-amine (A-34)

To a mixture of 3-methyl-1-[1-methyl-1-(1-methylpyrazol-3-yl)ethyl]pyrazol-4-amine (100 mg, 456.02 μmol) and 2,5-dichloro-4-cyclopropyl-pyrimidine (57 mg, 304.01 μmol) in 1,4-dioxane (3 mL) was added p-TsOH (15 mg, 91.20 μmol) at 25° C. Then the mixture was heated to 100° C. and stirred for 2 h. The mixture was added to water (5 mL) and adjusted to pH=7 by adding aq. NaHCO$_3$ (2 mL). Then it was extracted with EtOAc (3 mL×3), washed with brine (5 mL), dried over anhydrous Na$_2$SO$_4$, filtered and concentrated under reduced pressure. The residue was purified by prep-HPLC (neutral) to give compound 5-chloro-4-cyclopropyl-N-[3-methyl-1-[1-methyl-1-(1-methylpyrazol-3-yl)ethyl]pyrazol-4-yl]pyrimidin-2-amino. $^1$H NMR (400 MHz, CDCl$_3$): δ ppm 8.12 (s, 1H), 7.71 (s, 1H), 7.28 (d, J=1.51 Hz, 1H), 6.42 (br. s., 1H), 6.04 (s, 1H), 3.91 (s, 3H), 2.35-2.42 (m, 1H), 2.25 (s, 3H), 1.96 (s, 6H), 1.02-1.10 (m, 4H). HPLC: RT 2.641 min. MS: [M+H]+ m/z: 372.2.

Compound A-33 was prepared in analogous manner.

Example A-24

Synthesis of 5-chloro-4-cyclopropyl-N-(3-methyl-1-(2-(1-methyl-1H-1,2,4-triazol-3-yl)propan-2-yl)-1H-pyrazol-4-yl)pyrimidin-2-amine (A-35)

5-chloro-4-cyclopropyl-N-(3-methyl-1-(2-(1-methyl-1H-1,2,4-triazol-3-yl)propan-2-yl)-1H-pyrazol-4-yl)pyrimidin-2-amine (A-35)

To a solution of 2,5-dichloro-4-cyclopropylpyrimidine (200 mg, 1.06 mmol) and 3-methyl-1-(2-(1-methyl-1H-1,2,4-triazol-3-yl)propan-2-yl)-1H-pyrazol-4-amine (280 mg, 1.27 mmol) in 1,4-dioxane (2 mL) was added TFA (36 mg, 318.00 nmol) under $N_2$. The mixture was stirred at 100° C. for 2 h. The reaction mixture was quenched by addition sat. NaHCO$_3$ (10 mL) at 0° C. and then diluted with H$_2$O (10 mL) and extracted with EtOAc (3×10 mL). The combined organic layers were washed with brine (5 mL), dried over Na$_2$SO$_4$, filtered and concentrated under reduced pressure. The residue was purified by prep-HPLC (neutral condition) to give 5-chloro-4-cyclopropyl-N-(3-methyl-1-(2-(1-methyl-1H-1,2,4-triazol-3-yl)propan-2-yl)-1H-pyrazol-4-yl)pyrimidin-2-amine. $^1$H NMR (400 MHz, CHLOROFORM-d): δ 8.13 (s, 1H), 7.97 (s, 1H), 7.88 (s, 1H), 6.42 (br, 1H), 3.91 (s, 3H), 2.33-2.45 (m, 1H), 2.23 (s, 3H), 2.04 (s, 6H), 1.11-1.16 (m, 2H), 1.04-1.10 (m, 2H). HPLC: RT 2.68 min. MS: [M+H]+ m/z: 373.1.

Example A-25

Synthesis of N-(3-chloro-1-(2-(1-methyl-1H-1,2,4-triazol-3-yl)propan-2-yl)-1H-pyrazol-4-yl)-4-cyclopropyl-5-(trifluoromethyl)pyrimidin-2-amine and N-(3-chloro-1-(2-(1-methyl-1H-1,2,4-triazol-5-yl)propan-2-yl)-1H-pyrazol-4-yl)-4-cyclopropyl-5-(trifluoromethyl)pyrimidin-2-amine (A-36 and A-37)

(E)-tert-butyl (3-chloro-1-(1-(((dimethylamino)methylene)amino)-2-methyl-1-oxopropan-2-yl)-1H-pyrazol-4-yl)carbamate A solution of tert-butyl N-[1-(2-amino-1,1-dimethyl-2-oxo-ethyl)-3-chloro-pyrazol-4-yl]carbamate (2 g, 6.61 mmol) in DMF-DMA (20 mL) was degassed and purged with $N_2$ for 3 times, and then the mixture was stirred at 110° C. for 2 h under $N_2$. The reaction mixture was concentrated under reduced pressure to give (E)-tert-butyl (3-chloro-1-(1-(((dimethylamino)methylene)amino)-2-methyl-1-oxopropan-2-yl)-1H-pyrazol-4-yl)carbamate as a yellow-gum. LCMS: RT 0.738 min, m/z=358.2 [M+H]+.

tert-butyl (3-chloro-1-(2-(1-methyl-1H-1,2,4-triazol-3-yl)propan-2-yl)-1H-pyrazol-4-yl)carbamate and tert-butyl (3-chloro-1-(2-(1-methyl-1H-1,2,4-triazol-5-yl)propan-2-yl)-1H-pyrazol-4-yl)carbamate To a solution of (E)-tert-butyl (3-chloro-1-(1-(((dimethylamino)methylene)amino)-2-methyl-1-oxopropan-2-yl)-1H-pyrazol-4-yl)carbamate (2 g, 5.59 mmol) in AcOH (20 mL) was added methylhydrazine (3.86 g, 33.54 mmol, 4.39 mL, 40% purity). The mixture was stirred at 95° C. for 1 h. The reaction mixture was concentrated under reduced pressure. The residue was diluted with water (20 mL), adjusted to pH=8 by aq. NaHCO$_3$ and extracted with EtOAc (3×20 mL). The combined organic layers were washed with saturated brine (20 mL), dried over Na$_2$SO$_4$, filtered and concentrated under reduced pressure to give a residue. The residue was purified by silica gel column chromatography (PE:EtOAc=1:1 to 1:2) to give tert-butyl (3-chloro-1-(2-(1-methyl-1H-1,2,4-triazol-3-yl)propan-2-yl)-1H-pyrazol-4-yl)carbamate and tert-butyl (3-chloro-1-(2-(1-methyl-1H-1,2,4-triazol-5-yl)propan-2-yl)-1H-pyrazol-4-yl)carbamate as a yellow oil. LCMS: RT 0.728 min, m/z=341.2 [M+H]+.

N-(3-chloro-1-(2-(1-methyl-1H-1,2,4-triazol-3-yl)propan-2-yl)-1H-pyrazol-4-yl)-4-cyclopropyl-5-(trifluoromethyl)pyrimidin-2-amine (A-36)

A mixture of 4-cyclopropyl-2-methylsulfonyl-5-(trifluoromethyl)pyrimidine (219 mg, 821.57 μmol), tert-butyl (3-chloro-1-(2-(1-methyl-1H-1,2,4-triazol-3-yl)propan-2-yl)-1H-pyrazol-4-yl)carbamate (700 mg, 40% purity, 328.6 µmol) and PTSA (354 mg, 2.05 mmol) in 1,4-dioxane (8 mL) was degassed and purged with $N_2$ for 3 times, and then the mixture was stirred at 100° C. for 2 h under $N_2$. The reaction mixture was concentrated under reduced pressure. The residue was diluted with $H_2O$ (60 mL), adjusted to pH=8 by aq. $NaHCO_3$ and then extracted with EtOAc (3×20 mL). The combined organic layers were washed with brine (30 mL), dried over $Na_2SO_4$, filtered and concentrated under reduced pressure to give a residue, which was purified by prep-HPLC (neutral condition) to give N-(3-chloro-1-(2-(1-methyl-1H-1,2,4-triazol-3-yl)propan-2-yl)-1H-pyrazol-4-yl)-4-cyclopropyl-5-(trifluoromethyl)pyrimidin-2-amine. $^1$H NMR (400 MHz, $CDCl_3$): δ 8.42 (br. s., 1H), 7.99 (br. s., 1H), 7.91 (br. s., 1H), 7.01 (br. s., 1H), 3.92 (s, 3H), 2.23 (br. s., 1H), 2.04 (s, 6H), 1.21 (br. s., 2H), 1.12 (d, 7.03 Hz, 2H). HPLC: RT: 3.22 min. MS: m/z: 427.2 [M+H]$^+$.

N-(3-chloro-1-(2-(1-methyl-1H-1,2,4-triazol-5-yl)propan-2-yl)-1H-pyrazol-4-yl)-4-cyclopropyl-5-(trifluoromethyl)pyrimidin-2-amine (A-37)

A mixture of 4-cyclopropyl-2-methylsulfonyl-5-(trifluoromethyl)pyrimidine (117 mg, 440.13 µmol), tert-butyl (3-chloro-1-(2-(1-methyl-1H-1,2,4-triazol-5-yl)propan-2-yl)-1H-pyrazol-4-yl)carbamate (150 mg, 440.13 µmol) and PTSA (189.48 mg, 1.1 mmol) in dioxane (3 mL) was degassed and purged with $N_2$ for 3 times, and then the mixture was stirred at 100° C. for 3 h under $N_2$. The reaction mixture was concentrated under reduced pressure. The residue was diluted with $H_2O$ (60 mL), adjusted to pH=8 by aq. $NaHCO_3$ and then extracted with EtOAc (3×20 mL). The combined organic layers were washed with brine (30 mL), dried over $Na_2SO_4$, filtered and concentrated under reduced pressure to give a residue, which was purified by prep-HPLC (neutral condition) to give N-(3-chloro-1-(2-(1-methyl-1H-1,2,4-triazol-5-yl)propan-2-yl)-1H-pyrazol-4-yl)-4-cyclopropyl-5-(trifluoromethyl)pyrimidin-2-amino. $^1$H NMR (400 MHz, $CDCl_3$): δ 0.95-1.27 (m, 4H), 2.05 (s, 6H), 2.22 (br. s., 1H), 3.43 (br. s., 3H), 7.07 (br. s., 1H), 7.84 (s, 1H), 8.44 (br. s., 1H). HPLC. RT: 3.24 min. MS: m/z: 427.2 [M+H]$^+$.

Example A-26

Synthesis of 2-(4-((4-(1-fluorocyclopropyl)-5-(trifluoromethyl)pyrimidin-2-yl)amino)-3-methyl-1H-pyrazol-1-yl)-2-methylpropanenitrile (A-38)

4-(1-fluorocyclopropyl)-2-(methylsulfonyl)-5-(trifluoromethyl)pyrimidine

To a solution of 2-(methylsulfonyl)-5-(trifluoromethyl)pyrimidine (300 mg, 1.33 mmol) in $CH_3CN$ (9.00 mL) and $H_2O$ (9.00 mL) was added 1-fluorocyclopropanecarboxylic acid (125 mg, 1.2 mmol), $(NH_4)_2S_2O_8$ (1.5 g, 6.65 mmol) and $AgNO_3$ (904 mg, 5.32 mmol). Then the mixture was stirred at 20° C. for 12 h. The resulting mixture was extracted with EtOAc (3×5 mL). The combined organic extracts were concentrated under reduced pressure. The residue was purified by prep-TLC ($SiO_2$. PE:EtOAc=1:1) to give 4-(1-fluorocyclopropyl)-2-(methylsulfonyl)-5-(trifluoromethyl)pyrimidine as a white solid. LCMS: RT 1.28 min, m/z=285.0 [M+H]$^+$.

2-(4-((4-(1-fluorocyclopropyl)-5-(trifluoromethyl)pyrimidin-2-yl)amino)-3-methyl-1H-pyrazol-1-yl)-2-methylpropanenitrile (A-38)

To a solution of 4-(1-fluorocyclopropyl)-2-(methylsulfonyl)-5-(trifluoromethyl)pyrimidine (45 mg, 0.158 mmol) in 1,4-dioxane (1 mL) was added 2-(4-amino-3-methyl-1H-pyrazol-1-yl)-2-methylpropanenitrile (26 mg, 0.158 mmol) and p-TsOH (8.2 mg, 0.05 mmol) under $N_2$. Then the mixture was stirred at 100° C. for 1 h. The mixture was concentrated under reduced pressure. The residue was purified by prep-HPLC (neutral) to give 2-(4-((4-(1-fluorocyclopropyl)-5-(trifluoromethyl)pyrimidin-2-yl)amino)-3-methyl-1H-pyrazol-1-yl)-2-methylpropanenitrile. $^1$H NMR (400 MHz, CHLOROFORM-d): δ 8.67 (br. s., 1H), 7.89-8.21 (m, 1H), 6.60-6.96 (m, 1H), 2.27 (s, 3H), 1.99 (s, 6H), 1.56 (br. s., 2H), 1.55-1.59 (m, 2H), 1.53 (s, 2H), 1.50-1.55 (m, 1H). HPLC. RT 3.49 min. MS: (M+H$^+$) m/z: 369.2.

Example A-27

Synthesis of 4-cyclopropyl-N-(3-methyl-1-(2-(1-methyl-1H-1,2,3-triazol-4-yl)propan-2-yl)-1H-pyrazol-4-yl)-5-(trifluoromethyl)pyrimidin-2-amine (A-39)

2-methyl-2-(3-methyl-4-nitro-1H-pyrazol-1-yl)propan-1-ol

To a solution of ethyl 2-methyl-2-(3-methyl-4-nitro-1H-pyrazol-1-yl)propanoate (20 g, 82.9 mmol) in MeOH (200 mL) was added $NaBH_4$ (6.3 g, 165.8 mmol) at 0° C. The reaction mixture was stirred at 0° C. for 2 h. The mixture was cooled to 20° C. and poured into sat. $NH_4Cl$ (400 mL). The aqueous phase was extracted with EtOAc (3×200 mL). The combined organic phase was washed with brine (200 mL), dried over anhydrous $Na_2SO_4$, filtered and concentrated under reduced pressure to give a residue, which was purified by silica gel column chromatography (PE:EtOAc=20:1 to 1:1) to give 2-methyl-2-(3-methyl-4-nitro-1H-pyrazol-1-yl)propan-1-ol as a yellow solid. $^1$H NMR (400 MHz, CHLOROFORM-d): δ 8.20-8.24 (m, 1H), 3.73-3.81 (m, 2H), 3.11 (br. s., 1H), 2.42-2.54 (m, 3H), 1.54 (s, 6H).

2-methyl-2-(3-methyl-4-nitro-1H-pyrazol-1-yl)propanal

To a solution of 2-methyl-2-(3-methyl-4-nitro-1H-pyrazol-1-yl)propan-1-ol (5 g, 25 mmol) in DCM (350 mL) was added DMP (11.7 g, 27.6 mmol, in DCM (40 mL) portionwise at 0° C. The reaction mixture was stirred at 20° C. for 12 h under $N_2$. Sat. $NaHCO_3$ and $Na_2S_2O_3$ were added into the reaction mixture. The resulting mixture was stirred for 0.5 h. The organic phase was separated, washed with $NaHCO_3$, brine (20 mL), dried over anhydrous $Na_2SO_4$, filtered and concentrated under reduced pressure to give a residue, which was purified by silica gel column chromatography (PE:EtOAc=5:1) to give 2-methyl-2-(3-methyl-4-nitro-1H-pyrazol-1-yl)propanal as a yellow solid. $^1$H NMR (400 MHz, CHLOROFORM-d):δ9.56-9.63 (m, 1H), 8.28 (s, 1H), 2.55 (s, 3H), 1.70 (s, 6H).

3-methyl-1-(2-methylbut-3-yn-2-yl)-4-nitro-1H-pyrazole

To a solution of 2-methyl-2-(3-methyl-4-nitro-1H-pyrazol-1-yl)propanal (1.6 g, 8.1 mmol) in MeOH (50 mL) was added dimethyl (1-diazo-2-oxopropyl)phosphonate (3.2 g, 16.2 mmol) and $K_2CO_3$ (2.3 mg, 16.2 mmol) in one portion at 25° C. The reaction mixture was stirred at 25° C. for 16 h under $N_2$. The mixture was cooled to 20° C. and poured into ice-water (40 mL). The aqueous phase was extracted with EtOAc (3×40 mL). The combined organic phase was washed with brine (20 mL), dried over anhydrous $Na_2SO_4$, filtered and concentrated under reduced pressure to give a residue, which was purified by silica gel column chromatography (PE:EtOAc=10:1) to give 3-methyl-1-(2-methylbut-3-yn-2-yl)-4-nitro-1H-pyrazole as a yellow oil. $^1$H NMR (400 MHz, CHLOROFORM-d): δ 8.55 (s, 1H), 2.73 (s, 1H), 2.54 (s, 3H), 1.84 (s, 6H).

1-methyl-4-(2-(3-methyl-4-nitro-1H-pyrazol-1-yl) propan-2-yl)-1H-1,2,3-triazole

To a solution of 3-methyl-1-(2-methylbut-3-yn-2-yl)-4-nitro-1H-pyrazole (200 mg, 1.0 mmol) in t-BuOH (0.5 mL) and water (2 mL) was added CuI (40 mg, 0.2 mmol), $CH_3I$ (177 mg, 0.08 mL, 1.3 mmol) and $NaN_3$ (75 mg, 1.1 mmol). The reaction mixture was stirred at 70° C. for 2 h. The reaction mixture was diluted with EtOAc and 35% ammonia (5 mL). The mixture was stirred for 30 min and the two phase separated. The organic layer was dried over $Na_2SO_4$, filtered and evaporated to give a residue, which was purified by prep-TLC ($SiO_2$, EtOAc) to give 1-methyl-4-(2-(3-methyl-4-nitro-1H-pyrazol-1-yl)propan-2-yl)-1H-1,2,3-triazole as a light yellow solid. LCMS: RT 0.645 min, m/z=251.1 $[M+H]^+$.

3-methyl-1-(2-(1-methyl-1H-1,2,3-triazol-4-yl)propan-2-yl)-1H-pyrazol-4-amine

To a solution of 1-methyl-4-(2-(3-methyl-4-nitro-1H-pyrazol-1-yl)propan-2-yl)-1H-1,2,3-triazole (150 mg, 0.6 mmol) in EtOH (8 mL) and water (2 mL) was added Fe (100 mg, 1.8 mmol) and $NH_4Cl$ (96 mg, 1.8 mmol), then the mixture was stirred at 100° C. for 2 h. The reaction was concentrated under reduced pressure to give residue, which was diluted with EtOAc (2×10 mL) and filtered. The filtrate was concentrated under reduced pressure to give the title 3-methyl-1-(2-(1-methyl-1H-1,2,3-triazol-4-yl)propan-2-yl)-1H-pyrazol-4-amine as a yellow oil. LCMS: RT 0.098 min, m/z=221.2 $[M+H]^+$.

4-cyclopropyl-N-(3-methyl-1-(2-(1-methyl-1H-1,2,3-triazol-4-yl)propan-2-yl)-1H-pyrazol-4-yl)-5-(trifluoromethyl)pyrimidin-2-amine (A-39)

To a solution of 3-methyl-1-(2-(1-methyl-1H-1,2,3-triazol-4-yl)propan-2-yl)-1H-pyrazol-4-amine (79 mg, 0.36 mmol) in 1,4-dioxane (2 mL) was added 4-cyclopropyl-2-(methylsulfonyl)-5-(trifluoromethyl)pyrimidine (105 mg, 0.39 mmol) and TFA (82 mg, 0.05 mL, 0.72 mmol). Then the mixture was stirred at 100° C. for 2 h. The mixture was concentrated under reduced pressure to give a residue, which was purified by prep-HPLC (neutral) to give 4-cyclopropyl-N-(3-methyl-1-(2-(1-methyl-1H-1,2,3-triazol-4-yl)propan-2-yl)-1H-pyrazol-4-yl)-5-(trifluoromethyl)pyrimidin-2-amino. $^1$H NMR (400 MHz, CHLOROFORM-d):δ8.39 (br. s., 1H), 7.92 (br. s., 1H), 7.20 (s, 1H), 6.71 (br. s., 1H), 4.03 (s, 3H), 2.25 (s, 3H), 2.20 (d, J=5.6 Hz, 1H), 2.03 (s, 6H), 1.19 (br. s., 2H), 1.07-1.13 (m, 2H). HPLC: RT 2.88 min. MS: $[M+H]^+$ m/z: 407.1.

Example A-28

Synthesis of 4-cyclopropyl-N-(3-methyl-1-(2-(2-methyl-2H-1,2,3-triazol-4-yl)propan-2-yl)-1H-pyrazol-4-yl)-5-(trifluoromethyl)pyrimidin-2-amine (A-40)

4-(2-(3-methyl-4-nitro-1H-pyrazol-1-yl)propan-2-yl)-2H-1,2,3-triazole

To a solution of $TMSN_3$ (984 mg, 8.5 mmol, 1.2 mL) in MeOH (2.5 mL) and DMF (20 mL) was added 3-methyl-1-(2-methylbut-3-yn-2-yl)-4-nitro-1H-pyrazole (1.1 g, 5.7 mmol) and CuI (109 mg, 0.7 mmol). The reaction mixture was stirred at 110° C. for 12 h under $N_2$. The mixture was cooled to 20° C. and poured into ice-water (100 mL). The aqueous phase was extracted with EtOAc (3×50 mL). The combined organic phase was washed with brine (50 mL), dried over anhydrous $Na_2SO_4$, filtered and concentrated under reduced pressure to give a residue, which was purified by silica gel column chromatography (PE:EtOAc=1:1) to give 4-(2-(3-methyl-4-nitro-1H-pyrazol-1-yl)propan-2-yl)-2H-1,2,3-triazole as a yellow oil. LCMS: RT 0.691 min, m/z=237.2 $[M+H]^+$.

2-methyl-4-(2-(3-methyl-4-nitro-1H-pyrazol-1-yl) propan-2-yl)-2H-1,2,3-triazole

To a solution of 4-(2-(3-methyl-4-nitro-1H-pyrazol-1-yl)propan-2-yl)-2H-1,2,3-triazole (1 g, 4.23 mmol) in MeOH (20 mL) was $CH_3I$ (902 mg, 0.4 mL, 6.35 mmol) and $Cs_2CO_3$ (4.2 g, 12.7 mmol) under $N_2$, then the mixture was stirred at 50° C. for 12 h. The mixture was filtered and filtrate was concentrated under reduced pressure to give residue, which was purified by prep-TLC ($SiO_2$, PE:EtOAc=5:1) to give 2-methyl-4-(2-(3-methyl-4-nitro-1H-pyrazol-1-yl)propan-2-yl)-2H-1,2,3-triazole as a yellow solid. LCMS: RT 0.775 min, m/z=251.2 $[M+H]^+$.

3-methyl-1-(2-(2-methyl-2H-1,2,3-triazol-4-yl)propan-2-yl)-1H-pyrazol-4-amine

To a solution of Pd/C (20 mg) in THF (10 mL) was added 2-methyl-4-(2-(3-methyl-4-nitro-1H-pyrazol-1-yl)propan-2-yl)-2H-1,2,3-triazole (100 mg, 0.4 mmol) under $H_2$, then the mixture was stirred at 30° C. for 12 h. The reaction was concentrated under reduced pressure to give a residue, which was diluted with EtOAc (2×15 mL) and filtered. The filtrate was concentrated under reduced pressure to give 3-methyl-1-(2-(2-methyl-2H-1,2,3-triazol-4-yl)propan-2-yl)-1H-pyrazol-4-amine as a brown solid. LCMS: RT 0.112 min, m/z=221.2 $[M+H]^+$.

4-cyclopropyl-N-(3-methyl-1-(2-(2-methyl-2H-1,2,3-triazol-4-yl)propan-2-yl)-1H-pyrazol-4-yl)-5-(trifluoromethyl)pyrimidin-2-amine (A-40)

To a solution of 3-methyl-1-(2-(2-methyl-2H-1,2,3-triazol-4-yl)propan-2-yl)-1H-pyrazol-4-amine (90 mg, 0.41 mmol) in 1,4-dioxane (1 mL) was added 4-cyclopropyl-2-(methylsulfonyl)-5-(trifluoromethyl)pyrimidine (30 mg, 0.11 mmol) and TFA (23 mg, 0.02 mL, 0.20 mmol). Then the mixture was stirred at 100° C. for 2 h. The mixture was concentrated under reduced pressure to give a residue, which was purified by prep-HPLC (neutral) to give 4-cyclopropyl-N-(3-methyl-1-(2-(2-methyl-2H-1,2,3-triazol-4-yl)propan-2-yl)-1H-pyrazol-4-yl)-5-(trifluoromethyl)pyrimidin-2- amine. ¹H NMR (400 MHz, CHLOROFORM-d): δ 8.39 (br. s., 1H), 7.81 (br. s., 1H), 7.34 (br. s., 1H), 6.69 (br. s., 1H), 4.17 (s, 3H), 2.25 (s, 3H), 2.16-2.23 (m, 1H), 1.98 (s, 6H), 1.16 (br. s., 2H), 1.10 (d, 8.0 Hz, 2H). HPLC: RT 2.25 min. MS: [M+H]⁺ m/z: 407.2.

Example A-29

Synthesis of 4-cyclopropyl-N-[3-methyl-1-[1-(1-methyl-1,2,4-triazol-3-yl)cyclobutyl]pyrazol-4-yl]-5-(trifluoromethyl)pyrimidin-2-amine and 4-cyclopropyl-N-[3-methyl-1-[1-(2-methyl-1,2,4-triazol-3-yl)cyclobutyl]pyrazol-4-yl]-5-(trifluoromethyl)pyrimidin-2-amine (A-41 and A-42)

Ethyl 1-(3-methyl-4-nitro-1H-pyrazol-1-yl)cyclobutanecarboxylate

To a mixture of 3-methyl-4-nitro-1H-pyrazole (2.33 g, 18.35 mmol) in DMF (10 mL) was added NaH (927 mg, 23.18 mmol, 60%) in one portion at 0° C. under N₂. After that ethyl 1-bromocyclobutanecarboxylate (4 g, 19.32 mmol) was added and the mixture was stirred at 100° C. for 12 h. The mixture was poured into ice-water (70 mL) and stirred for 5 min. The aqueous phase was extracted with EtOAc (3×30 mL). The combined organic phase was washed with brine (2×20 mL), dried with anhydrous Na₂SO₄, filtered and concentrated under reduced pressure. The residue was purified by silica gel column chromatography (PE:EtOAc=10:1 to 2:1) to give ethyl 1-(3-methyl-4-nitro-1H-pyrazol-1-yl)cyclobutanecarboxylate as a white solid. ¹H NMR (400 MHz, CDCl3): δ ppm 8.08-8.20 (m, 1H) 4.00-4.22 (m, 2H) 2.54-2.93 (m, 3H) 2.48 (s, 3H) 2.09-2.36 (m, 1H) 1.92-2.05 (m, 1H) 1.14-1.25 (m, 3H).

1-(3-methyl-4-nitro-1H-pyrazol-1-yl)cyclobutanecarboxylic acid

To a mixture of ethyl 1-(3-methyl-4-nitro-pyrazol-1-yl)cyclobutanecarboxylate (600 mg, 2.37 mmol) in THF (10 mL) and water (10 mL) was added LiOH.H₂O (298.34 mg, 7.11 mmol) in one portion at 25° C. under N₂. The mixture was stirred at 25° C. for 12 h. The mixture was extracted with EtOAc (2×10 mL). And the aqueous phase was adjusted to pH=3 with 1 N HCl, then extracted with EtOAc (3×10 mL). The combined organic phase was dried over anhydrous Na₂SO₄, filtered and concentrated under reduced pressure, to give 1-(3-methyl-4-nitro-1H-pyrazol-1-yl)cyclobutanecarboxylic acid as a white solid. ¹H NMR (400 MHz, CDCl₃): δ ppm 9.94 (br. s., 1H) 8.14-8.29 (m, 1H) 2.89-3.01 (m, 2H) 2.73-2.84 (m, 2H) 2.59-2.69 (m, 1H) 2.55 (s, 2H) 2.22-2.48 (m, 1H) 2.03-2.17 (m, 1H).

1-(3-methyl-4-nitro-1H-pyrazol-1-yl)cyclobutanecarboxamide

To a solution of 1-(3-methyl-4-nitro-pyrazol-1-yl)cyclobutanecarboxylic acid (2.4 g, 10.66 mmol) and DMF (30 µL) in DCM (30 mL) was added oxalyl chloride (2.71 g, 21.32 mmol) at 0° C. under N₂. The reaction was stirred at 25° C. for 2 h. Then the mixture was concentrated. The residue was taken up in THF (50 mL) and added into NH₃.H₂O (50 mL) at 0° C., and then the reaction mixture was stirred at 25° C. for another 12 h. The mixture was extracted with MTBE (3×50 mL). The combined organic phase was washed with brine (2×50 mL), dried over anhydrous Na₂SO₄, filtered and concentrated under reduced pressure. The residue was purified by silica gel column chromatography (PE. EtOAc=10:1 to 1:1) to give 1-(3-methyl-4-nitro-1H-pyrazol-1-yl)cyclobutanecarboxamide as a white solid.

(E)-N-((dimethylamino)methylene)-1-(3-methyl-4-nitro-1H-pyrazol-1-yl)cyclobutanecarboxamide A mixture of 1-(3-methyl-4-nitro-1H-pyrazol-1-yl)cyclobutanecarboxamide (1 g, 4.46 mmol) in DMF-DMA (15 mL) was stirred at 95° C. for 2 h. The mixture was concentrated under reduced pressure. And the crude product was used directly in next step as is. LCMS: RT 0.667 min, m/z=280 [M+H]⁺.

1-methyl-3-[1-(4-nitropyrazol-1-yl)cyclobutyl]-1,2,4-triazole and 1-methyl-5-[1-(3-methyl-4-nitro-pyrazol-1-yl)cyclobutyl]-1,2,4-triazole To a mixture of (E)-N-((dimethylamino)methylene)-1-(3-methyl-4-nitro-1H-pyrazol-1-yl)cyclobutanecarboxamide (1.25 g, 4.46 mmol) in AcOH (10 mL) was added methyl hydrazine (1.23 g, 26.76 mmol, 1.40 mL) in one portion at 25° C. under N₂. The mixture was stirred at 95° C. for 2 h. The mixture was concentrated and added with water (20 mL). The aqueous phase was extracted with EtOAc (2 mL). The combined organic phase was washed with aq. NaHCO₃ (20 mL), dried over anhydrous Na₂SO₄, filtered and concentrated under reduced pressure. The residue was purified by silica gel column chromatography (PE: EtOAc=50:1 to 1:1) to give 1-methyl-3-[1-(4-nitropyrazol-1-yl)cyclobutyl]-1,2,4-triazole and 1-methyl-5-[1-(3-methyl-4-nitro-pyrazol-1-yl)cyclobutyl]-1,2,4-triazole as a white solid. LCMS: RT=0.667 min, m/z=263 [M+H]⁺.

3-methyl-1-[1-(1-methyl-1,2,4-triazol-3-yl)cyclobutyl]pyrazol-4-amine

To a solution of 1-methyl-3-[1-(3-methyl-4-nitro-pyrazol-1-yl)cyclobutyl]-1,2,4-triazole (500 mg, 1.91 mmol) in MeOH (20 mL) was added Pd/C (50 mg, 10% purity) under N₂. The suspension was degassed under vacuum and purged with H₂ three times. The mixture was stirred under H₂ (15 psi) at 25° C. for 2 h. The reaction mixture was filtered and the filtrate was concentrated under reduced pressure to give 3-methyl-1-[1-(1-methyl-1,2,4-triazol-3-yl)cyclobutyl] pyrazol-4-amine as a yellow oil. LCMS: RT 0.945 min, m/z=263 [M+H]⁺. ¹H NMR (400 MHz, CDCl3): δ ppm 7.93 (s, 1H) 7.08 (s, 1H) 3.86 (s, 4H) 2.86 (dt, J=6.37, 3.15 Hz, 2H) 2.17-2.22 (m, 3H) 2.16 (s, 3H) 1.98-2.02 (m, 2H).

4-cyclopropyl-N-[3-methyl-1-[1-(1-methyl-1,2,4-triazol-3-yl)cyclobutyl]pyrazol-4-yl]-5-(trifluoromethyl)pyrimidin-2-amine (A-41)

To a mixture of 3-methyl-1-[1-(1-methyl-1,2,4-triazol-3-yl)cyclobutyl]pyrazol-4-amine (50 mg, 215.26 µmol) and 4-cyclopropyl-2-methylsulfonyl-5-(trifluoromethyl)pyrimidine (57.31 mg, 215.26 µmol) in 1,4-dioxane (3 mL) was added p-TsOH (11.12 mg, 64.58 µmol) in one portion at 25° C. under N₂. The mixture was stirred at 110° C. for 5 h. The residue was poured into ice-water (5 mL) and stirred for 5 min. The aqueous phase was extracted with EtOAc (2×10 mL). The combined organic phase was washed with brine (10 mL), dried over anhydrous Na₂SO₄, filtered and concentrated under reduced pressure. The product was purification by prep-HPLC (NH₄HCO₃) to give 4-cyclopropyl- N-[3-methyl-1-[1-(1-methyl-1,2,4-triazol-3-yl)cyclobutyl]pyrazol-4-yl]-5-(trifluoromethyl)pyrimidin-2-amine. $^1$H NMR (400 MHz, CDCl$_3$): δ ppm 8.32 (br. s., 1H) 7.84-7.94 (m, 1H) 7.75 (br. s., 1H) 6.44-6.68 (m, 1H) 3.78-3.89 (m, 3H) 2.85-3.05 (m, 5H) 2.19 (s, 3H) 2.13 (br. s., 1H) 1.91-2.03 (m, 2H) 1.51 (s, 2H) 1.15 (br. s., 2H) 0.96-1.05 (m, 2H). HPLC: Retention Time: 2.563 min. MS: [M+H]$^+$ m/z: 419.

3-methyl-1-[1-(2-methyl-1,2,4-triazol-3-yl)cyclobutyl]pyrazol-4-amine

To a solution of 1-methyl-5-[1-(3-methyl-4-nitro-pyrazol-1-yl)cyclobutyl]-1,2,4-triazole (200 mg, 762.57 μmol) in MeOH (10 mL) was added Pd/C (50 mg, 10% purity) under N$_2$. The suspension was degassed under vacuum and purged with H$_2$ three times. The mixture was stirred under H$_2$ (15 psi) at 25° C. for 2 h. The reaction mixture was filtered and the filtrate was concentrated under reduced pressure to give 3-methyl-1-[1-(2-methyl-1,2,4-triazol-3-yl)cyclobutyl]pyrazol-4-amine as a yellow oil.

4-cyclopropyl-N-[3-methyl-1-[1-(2-methyl-1,2,4-triazol-3-yl)cyclobutyl]pyrazol-4-yl]-5-(trifluoromethyl)pyrimidin-2-amine (A-42)

To a mixture of 3-methyl-1-[1-(2-methyl-1,2,4-triazol-3-yl)cyclobutyl]pyrazol-4-amine (50 mg, 215.26 μmol) and 4-cyclopropyl-2-methylsulfonyl-5-(trifluoromethyl)pyrimidine (57.31 mg, 215.26 μmol) in 1,4-dioxane (5 mL) was added p-TsOH (37.07 mg, 215.26 μmol) in one portion at 25° C. under N$_2$. The mixture was stirred at 110° C. for 5 h. The residue was poured into ice-water (10 mL) and stirred for 5 min. The aqueous phases were extracted with EtOAc (2×10 mL). The combined organic phase was washed with brine (10 mL), dried with anhydrous Na$_2$SO$_4$, filtered and concentrated under reduced pressure. The product was purification by HPLC (NH$_4$HCO$_3$) to give 4-cyclopropyl-N-[3-methyl-1-[1-(2-methyl-1,2,4-triazol-3-yl)cyclobutyl]pyrazol-4-yl]-5-(trifluoromethyl)pyrimidin-2-amine. 1H NMR (400 MHz, CDCl3): δ ppm 8.39 (s, 1H) 7.89 (s, 1H) 7.49-7.67 (m, 1H) 6.65 (br. s., 1H) 3.58 (s, 3H) 3.08-3.18 (m, 2H) 2.97-3.06 (m, 2H) 2.29 (s, 3H) 1.96-2.22 (m, 3H) 1.10 (dd, J=7.72, 2.87 Hz, 4H). HPLC: RT 3.19 min. MS. [M+H]$^+$ m/z: 419.

Example A-30

Synthesis of 5-chloro-4-cyclopropyl-N-[1-[2-fluoro-1-(fluoromethyl)ethyl]-5-methyl-pyrazol-4-yl]pyrimidin-2-amine and 5-chloro-4-cyclopropyl-N-[1-[2-fluoro-1-(fluoromethyl)ethyl]-3-methyl-pyrazol-4-yl]pyrimidin-2-amine (A-43 and A-44)

5-chloro-4-cyclopropyl-N-[1-[2-fluoro-1-(fluoromethyl)ethyl]-5-methyl-pyrazol-4-yl]pyrimidin-2-amine and 5-chloro-4-cyclopropyl-N-[1-[2-fluoro-1-(fluoromethyl)ethyl]-3-methyl-pyrazol-4-yl]pyrimidin-2-amine (A-43 and A-44)

To a solution of 2,5-dichloro-4-cyclopropylpyrimidine (120 mg, 634.79 μmol) and a mixture 1-(1,3-difluoropropan-2-yl)-5-methyl-1H-pyrazol-4-amine and 1-(1,3-difluoropropan-2-yl)-3-methyl-1H-pyrazol-4-amine (56 mg, 317.4 μmol) in 1,4-dioxane (5 mL) was added p-TsOH (164 mg, 952.19 μmol). The mixture was stirred at 100° C. for 4 h. The reaction mixture was concentrated under reduced pressure. The residue was basified to pH=7 with aq. Na$_2$HCO$_3$ solution, extracted with EtOAc (3×10 mL). The organic layers were combined, washed with brine (10 mL), dried over Na$_2$SO$_4$, filtered and concentrated under reduced pressure to give a crude product, which was purified by prep-TLC (PE:EtOAc=1:1), to give two separated crude product, which was further purified by prep-HPLC (neutral) to give 5-chloro-4-cyclopropyl-N-[1-[2-fluoro-1-(fluoromethyl)ethyl]-5-methyl-pyrazol-4-yl]pyrimidin-2-amine and 5-chloro-4-cyclopropyl-N-[1-[2-fluoro-1-(fluoromethyl)ethyl]-3-methyl-pyrazol-4-yl]pyrimidin-2-amine.

5-chloro-4-cyclopropyl-N-[1-[2-fluoro-1-(fluoromethyl)ethyl]-5-methyl-pyrazol-4-yl]pyrimidin-2-amine (A-43)

$^1$H NMR (400 MHz, CDCl$_3$): δ 8.13 (s, 1H), 7.72 (s, 1H), 6.21 (br. s., 1H), 4.90 (d, J=6.02 Hz, 2H), 4.67-4.81 (m, 3H), 2.34-2.42 (m, 1H), 2.23 (s, 3H), 1.11-1.17 (m, 2H), 1.03-1.10 (m, 2H). HPLC: RT 3.09 min. MS: [M+H]$^+$ m/z: 328.2.

5-chloro-4-cyclopropyl-N-[1-[2-fluoro-1-(fluoromethyl)ethyl]-3-methyl-pyrazol-4-yl]pyrimidin-2-amine (A-44)

$^1$H NMR (400 MHz, CDCl$_3$): δ 8.17 (s, 1H), 7.94 (s, 1H), 6.41 (br. s., 1H), 4.76-4.93 (m, 4H), 4.60-4.75 (m, 1H), 2.37-2.47 (m, 1H), 2.25 (s, 3H), 1.17-1.23 (m, 2H), 1.09-1.16 (m, 2H). HPLC. RT 3.14 min. MS: [M+H]$^+$ m/z: 328.2.

Example A-31

Synthesis of N-[5-chloro-1-[2-fluoro-1-(fluoromethyl)ethyl]pyrazol-4-yl]-4-cyclopropyl-5-(trifluoromethyl)pyrimidin-2-amine and N-[3-chloro-1-[2-fluoro-1-(fluoromethyl)ethyl]pyrazol-4-yl]-4-cyclopropyl-5-(trifluoromethyl)pyrimidin-2-amine (A-45 and A-46)

N-[5-chloro-1-[2-fluoro-1-(fluoromethyl)ethyl]pyrazol-4-yl]-4-cyclopropyl-5-(trifluoromethyl)pyrimidin-2-amine and N-[3-chloro-1-[2-fluoro-1-(fluoromethyl)ethyl]pyrazol-4-yl]-4-cyclopropyl-5-(trifluoromethyl)pyrimidin-2-amine (A-45 and A-46)

To a mixture of 5-chloro-1-[2-fluoro-1-(fluoromethyl)ethyl]pyrazol-4-amine and 3-chloro-1-(1,3-difluoropropan-2-yl)-1H-pyrazol-4-amine (110 mg, 562.37 μmol) and 4-cyclopropyl-2-methylsulfonyl-5-(trifluoromethyl)pyrimidine (100 mg, 374.91 μmol) in 1,4-dioxane (3 mL) was added p-TsOH (19 mg, 112.47 μmol) at 25° C. under N$_2$. The mixture was heated to 100° C. and stirred for 2 h. The mixture was cooled to 25° C. and adjusted to pH=7-8 with a solution of NaHCO$_3$ then extracted with EtOAc (3×5 mL). The combined organics were washed with brine (5 mL), dried over anhydrous Na$_2$SO$_4$, filtered and concentrated under reduced pressure. The residue was purified by prep-HPLC (neutral) to give N-[5-chloro-1-[2-fluoro-1-(fluoromethyl)ethyl]pyrazol-4-yl]-4-cyclopropyl-5-(trifluoromethyl)pyrimidin-2-amine and N-[3-chloro-1-[2-fluoro-1-(fluoromethyl)ethyl]pyrazol-4-yl]-4-cyclopropyl-5-(trifluoromethyl)pyrimidin-2-amine.

N-[5-chloro-1-[2-fluoro-1-(fluoromethyl)ethyl]pyrazol-4-yl]-4-cyclopropyl-5-(trifluoromethyl)pyrimidin-2-amine (A-45)

$^1$H NMR (400 MHz, CDCl$_3$): δ ppm 8.45 (s, 1H) 8.11 (s, 1H) 6.72 (br. s., 1H) 4.75-5.02 (m, 5H) 2.24 (br. s., 1H)

1.27-1.32 (m, 2H) 1.15 (dd, J=7.72, 3.31 Hz, 2H). HPLC: RT 3.113 min. MS: [M+H]$^+$ m/z: 382.1.

N-[3-chloro-1-[2-fluoro-1-(fluoromethyl)ethyl]pyrazol-4-yl]-4-cyclopropyl-5-(trifluoromethyl)pyrimidin-2-amine (A-46)

$^1$H NMR (400 MHz, CDCl$_3$): δ ppm 8.48 (br. s., 1H) 8.10 (br. s., 1H) 6.91 (br. s., 1H) 4.64-4.95 (m, 5H) 2.26 (br. s., 1H) 1.27-1.33 (m, 2H) 1.18 (br. s., 2H). HPLC: RT 3.159 min. MS: [M+H]$^+$ m/z: 382.2.

Example A-32

Synthesis of 1-[4-[[4-cyclopropyl-5-(trifluoromethyl)pyrimidin-2-yl]amino]-3-methyl-pyrazol-1-yl] cyclopropanecarbonitrile (A-47)

1-(4-amino-3-methyl-pyrazol-1-yl)cyclopropanecarbonitrile

To a mixture of 1-(3-methyl-4-nitro-pyrazol-1-yl)cyclopropanecarbonitrile (100 mg, 520.37 μmol) in EtOH (2 mL) and H$_2$O (500 μL) was added NH$_4$Cl (139 mg, 2.60 mmol) and Fe (145 mg, 2.60 mmol) at 20° C. The mixture was then heated to 80° C. and stirred for 1 h. The mixture was cooled to 20° C., filtered and concentrated. The residue was added with water (10 mL) and then extracted with EtOAc (3×3 mL), washed with brine (5 mL), dried over anhydrous Na$_2$SO$_4$, filtered and concentrated under reduced pressure, to give 1-(4-amino-3-methyl-pyrazol-1-yl)cyclopropanecarbonitrile as a brown oil. LCMS: RT 0.107 min, m/z=163.2 [M+H]$^+$.

1-[4-[[4-cyclopropyl-5-(trifluoromethyl)pyrimidin-2-yl]amino]-3-methyl-pyrazol-1-yl]cyclopropanecarbonitrile (A-47)

To a mixture of 1-(4-amino-3-methyl-pyrazol-1-yl)cyclopropanecarbonitrile (111 mg, 684.38 μmol) and 4-cyclopropyl-2-methylsulfonyl-5-(trifluoromethyl)pyrimidine (121 mg, 456.25 μmol) in 1,4-dioxane (3 mL) was added p-TsOH (23 mg, 136.88 μmol) at 25° C. under N$_2$. The mixture was heated to 100° C. and stirred for 2 h. The mixture was cooled to 25° C. and adjusted pH=7-8 by adding aq.NaHCO$_3$. Then the mixture was extracted with EtOAc (3×5 mL), washed with brine (5 mL), dried over anhydrous Na$_2$SO$_4$, filtered and concentrated under reduced pressure. The residue was purified by prep-HPLC (neutral) to give compound 1-[4-[[4-cyclopropyl-5-(trifluoromethyl)pyrimidin-2-yl]amino]-3-methyl-pyrazol-1-yl]cyclopropanecarbonitrile. LCMS: RT 0.898 min, m/z=349.2 [M+H]$^+$. $^1$H NMR (400 MHz, CDCl$_3$): δ ppm 8.46 (br. s., 1H), 8.02 (br. s., 1H), 6.68 (br. s., 1H), 2.26 (s, 4H), 1.80 (d, J=5.73 Hz, 4H), 1.29 (br. s., 2H), 1.17 (br. s., 2H). HPLC: RT 2.826 min. MS: [M+H]$^+$ m/z: 349.2.

Example A-33

Synthesis of N-(5-chloro-1-((3S,4S)-3-fluoro-1-(oxetan-3-yl)piperidin-4-yl)-1H-pyrazol-4-yl)-4-cyclopropyl-5-(trifluoromethyl)pyrimidin-2-amine (A-48)

5-chloro-1-((3S,4S)-3-fluoro-1-(oxetan-3-yl)piperidin-4-yl)-1H-pyrazol-4-amine

To a solution of (3S,4S)-4-(5-chloro-4-nitro-pyrazol-1-yl)-3-fluoro-1-(oxetan-3-yl)piperidine (150 mg, 492.27 μmol) in EtOH (2 mL) and water (500 μL) was added Fe (82.48 mg, 1.48 mmol) and NH4Cl (79 mg, 1.48 mmol). The reaction was stirred at 90° C. for 2 h. The reaction solution was concentrated under reduced pressure to give residue, which was washed with EtOAc (2×5 mL) and filtered. The filtrate was concentrated under reduced pressure to give 5-chloro-1-[(3S,4S)-3-fluoro-1-(oxetan-3-yl)-4-piperidyl]pyrazol-4-amine as a brown solid, which was used without further purification.

N-(5-chloro-1-((3S,4S)-3-fluoro-1-(oxetan-3-yl) piperidin-4-yl)-1H-pyrazol-4-yl)-4-cyclopropyl-5-(trifluoromethyl)pyrimidin-2-amine (A-48)

To a solution of 4-cyclopropyl-2-(methylsulfonyl)-5-(trifluoromethyl pyrimidine (130 mg, 0.5 mmol) in 1,4-dioxane (2 mL) was added 5-chloro-1-((3S,4S)-3-fluoro-1-(oxetan-3-yl)piperidin-4-yl)-1H-pyrazol-4-amine (134 mg, 0.5 mmol) and p-TsOH (25 mg, 0.15 mmol) at 25° C. The solution was heated at 100° C. for 1 h. The mixture was concentrated under reduced pressure. The residue was purified by prep-HPLC (neutral condition) to give N-(5-chloro-1-((3S,4S)-3-fluoro-1-(oxetan-3-yl)piperidin-4-yl)-1H-pyrazol-4-yl)-4-cyclopropyl-5-(trifluoromethyl)pyrimidin-2-amine. $^1$H NMR: (400 MHz, CHLOROFORM-d): δ 8.43 (s, 1H), 8.07 (s, 1H), 6.70 (br. s., 1H), 4.93-5.14 (m, 1H), 4.56-4.74 (m, 4H), 4.24-4.36 (m, 1H), 3.66 (quin, J=6.39 Hz, 1H), 3.16-3.26 (m, 1H), 2.85 (d, J=9.70 Hz, 1H), 2.28-2.43 (m, 1H), 2.22 (br. s., 1H), 1.97-2.17 (m, 4H), 1.23-1.34 (m, 3H), 1.09-1.17 (m, 2H). HPLC. RT 2.851 min. MS: [M+H]$^+$ m/z: 461.1.

Example A-34

Synthesis of 2-(5-chloro-4-((4-cyclopropyl-5-(trifluoromethyl)pyrimidin-2-yl)amino)-1H-pyrazol-1-yl)-1-methylcyclopentanol (A-49 and A-50)

2-(4-amino-5-chloro-1H-pyrazol-1-yl)-1-methylcyclopentanol (A-34-2)

To a solution of 2-(5-chloro-4-nitro-1H-pyrazol-1-yl)-1-methylcyclopentanol (150 mg, 0.61 mmol) in EtOH (2 mL) and H$_2$O (500 μL) was added Fe (102 mg, 1.83 mmol) and NH$_4$Cl (98 mg, 1.83 mmol). The reaction mixture was stirred at 90° C. for 1 h. The reaction mixture was concentrated under reduced pressure to give a residue, which was diluted with EtOAc (2×3 mL) and filtered. The filtrate was concentrated to give 2-(4-amino-5-chloro-1H-pyrazol-1-yl)-1-methylcyclopentanol as brown solid. LCMS: RT 0.113 min, m/z=216.1 [M+H]$^+$.

2-(5-chloro-4-((4-cyclopropyl-5-(trifluoromethyl) pyrimidin-2-yl)amino)-1H-pyrazol-1-yl)-1-methylcyclopentanol (A-49, A-50)

To a solution of 4-cyclopropyl-2-(methylsulfonyl)-5-(trifluoromethyl)pyrimidine (150 mg, 0.56 mmol) in dioxane (2 mL) was added 2-(4-amino-5-chloro-1H-pyrazol-1-yl)-1-methylcyclopentanol (122 mg, 0.56 mmol) and p-TsOH (29 mg, 0.17 mmol) at 25° C. Then die mixture was stirred at 100° C. for 1 h. The mixture was concentrated under reduced pressure to give a residue, which was purified by prep-HPLC (NH$_4$HCO$_3$) to give 48 mg of crude product, which was further purified by chiral SFC to give two peaks of target isomers, peak 1 and peak 2.

¹H NMR (400 MHz, CHLOROFORM-d): δ 8.42 (s, 1H), 7.99 (s, 1H), 6.81 (br. s., 1H), 4.63 (L J=7.2 Hz, 1H), 2.35-2.48 (m, 2H), 2.22 (br. s., 1H), 1.90-2.07 (m, 3H), 1.71-1.81 (m, 1H), 1.25-1.30 (m, 2H), 1.12 (dd, J=8.0, 3.09 Hz, 2H), 0.97 (s, 3H). HPLC: RT 3.043 min. MS. [M+H]⁺ m/z: 402.1.

¹H NMR (400 MHz, CHLOROFORM): δ 8.42 (s, 1H), 8.00 (s, 1H), 6.77 (br. s., 1H), 4.63 (t, J=12 Hz, 1H), 2.35-2.48 (m, 2H), 2.22 (br. s, 1H), 1.87-2.08 (m, 3H), 1.72-1.81 (m, 1H), 1.24-1.30 (m, 2H), 1.12 (dd, J=7.2, 3.31 Hz, 2H), 0.97 (s, 3H). HPLC: Retention Time: 3.045 min. MS. [M+H]⁺ m/z: 402.1.

Example A-35

Synthesis of 4-cyclopropyl-N-(1-(2-(1-ethyl-1H-1,2,4-triazol-3-yl)propan-2-yl)-3-methyl-1H-pyrazol-4-yl)-5-(trifluoromethyl)pyrimidin-2-amine (A-51)

1-ethyl-3-(2-(3-methyl-4-nitro-1H-pyrazol-1-yl)propan-2-yl)-1H-1,2,4-triazole

To a solution of 3-(2-(3-methyl-4-nitro-1H-pyrazol-1-yl)propan-2-yl)-1H-1,2,4-triazole (2 g, 8.47 mmol) in CH₃CN (30 mL) was added EtI (1.59 g, 10.16 mmol, 813 μL) and Cs₂CO₃ (2.76 g, 8.47 mmol). The mixture was stirred at 50° C. for 12 h. The reaction mixture was filtered and concentrated under reduced pressure. The residue was purified by silica gel column chromatography (PE:EtOAc=5:1 to 0:1) to give 1-ethyl-3-(2-(3-methyl-4-nitro-1H-pyrazol-1-yl)propan-2-yl)-1H-1,2,4-triazole as a yellow solid. LCMS: RT 0.684 min, m/z=265 [M+H]+.

1-(2-(1-ethyl-1H-1,2,4-triazol-3-yl)propan-2-yl)-3-methyl-1H-pyrazol-4-amine

To a solution of 1-ethyl-3-(2-(3-methyl-4-nitro-1H-pyrazol-1-yl)propan-2-yl)-1H-1,2,4-triazole (1.67 g, 6.32 mmol) in EtOH (35 mL) was added Pd—C (10%, 0.67 g) under N₂. The suspension was degassed under vacuum and purged with H₂ several times. The mixture w as stirred under H₂ (15 psi) at 50° C. for 2 h. The reaction mixture was filtered and the filtrate was concentrated to give 1-(2-(1-ethyl-1H-1,2,4-triazol-3-yl)propan-2-yl)-3-methyl-1H-pyrazol-4-amine as a brown solid. The crude product was used into the next step without further purification.

4-cyclopropyl-N-(1-(2-(1-ethyl-1H-1,2,4-triazol-3-yl)propan-2-yl)-3-methyl-1H-pyrazol-4-yl)-5-(trifluoromethyl)pyrimidin-2-amine (A-51)

To a solution of 4-cyclopropyl-2-(methylsulfonyl)-5-(trifluoromethyl)pyrimidine (70 mg, 262.92 μmol) and 1-(2-(1-ethyl-1H-1,2,4-triazol-3-yl)propan-2-yl)-3-methyl-1H-pyrazol-4-amine (62 mg, 262.92 μmol) in 1,4-dioxane (3 mL) was added p-TsOH (14 mg, 78.88 μmol). The mixture was stirred at 100° C. for 2 h. The reaction mixture was diluted with H₂O (15 mL) and adjusted with sat. NaHCO₃ to pH=9 and extracted with EtOAc (3×10 mL). The combined organic layers were washed with brine (5 mL), dried over Na₂SO₄, filtered and concentrated under reduced pressure. The residue was purified by prep-HPLC (neutral condition) to give 4-cyclopropyl-N-(1-(2-(1-ethyl-1H-1,2,4-triazol-3-yl)propan-2-yl)-3-methyl-1H-pyrazol-4-yl)-5-(trifluoromethyl)pyrimidin-2-amine. ¹H NMR: (400 MHz, CHLOROFORM-d) δ 8.38 (s, 1H), 7.99 (s, 1H), 7.86 (s, 1H), 6.78 (br, s, 1H), 4.20 (q, J=14.4, 7.2 Hz, 2H), 2.14-2.28 (m, 4H), 2.04 (s, 6H), 1.53 (t, J=7.2 Hz, 3H), 1.17-1.25 (m, 2H), 1.02-1.12 (m, 2H). HPLC: RT 2.626 min. MS. [M+H]⁺ m/z: 421.2.

Example A-36

Synthesis of 4-cyclopropyl-N-[3-methyl-1-[1-(1-methyl-1,2,4-triazol-3-yl)cyclopropyl]pyrazol-4-yl]-5-(trifluoromethyl)pyrimidin-2-amine (A-52)

3-methyl-1-[1-(1-methyl-1,2,4-triazol-3-yl)cyclopropyl]pyrazol-4-amine

To a solution of 1-methyl-3-(1-(3-methyl-4-nitro-1H-pyrazol-1-yl)cyclopropyl)-1H-1,2,4-triazole (150 mg, 604.25 μmol) in EtOH (20 mL) was added Pd—C (10% 20 mg) under N₂. The suspension was degassed under reduced pressure and purged with H₂ several times. The mixture was stirred under H₂ (15 psi) at 45° C. for 6 h. The reaction mixture was filtered and the filtrate was concentrated, to give the crude 3-methyl-1-[1-(1-methyl-1,2,4-triazol-3-yl)cyclopropyl]pyrazol-4-amine which was used into die next step without further purification. LCMS: RT 0.822 min, m/z=219.3 [M+H]⁺.

4-cyclopropyl-N-[3-methyl-1-[1-(1-methyl-1,2,4-triazol-3-yl)cyclopropyl]pyrazol-4-yl]-5-(trifluoromethyl)pyrimidin-2-amine (A-52)

To a mixture of 1-methyl-3-(1-(3-methyl-4-nitro-1H-pyrazol-1-yl)cyclopropyl)-1H-1,2,4-triazole (87 mg, 326.77 μmol) and 4-cyclopropyl-2-(methylsulfonyl)-5-(trifluoromethyl)pyrimidine (71 mg, 326.77 μmol) in 1,4-dioxane (4 mL) was added TFA (112 mg, 980.31 μmol, 73 μL) at 20° C. under N₂. The mixture was heated to 80° C. and stirred for 5 h. The mixture was cooled to 20° C. and was adjusted to pH=8 by adding aq.NaHCO₃ and extracted with EtOAc (3×5 mL). The combined organic phase was washed with brine (10 mL), dried over anhydrous Na₂SO₄, filtered and concentrated under reduced pressure. The residue was purified by prep-HPLC (neutral) to give 4-cyclopropyl-N-[3-methyl-1-[1-(1-methyl-1,2,4-triazol-3-yl)cyclopropyl]pyrazol-4-yl]-5-(trifluoromethyl)pyrimidin-2-amine. ¹H NMR (400 MHz, CDCl₃): δ 8.41 (br. s., 1H), 8.00 (br. s., 1H), 7.88 (s, 1H), 6.71 (br. s., 1H), 3.82 (s, 3H), 2.28 (s, 3H), 2.17-2.25 (m, 1H), 1.74 (d, J=4.64 Hz, 4H), 1.26 (br. s., 2H), 1.08-1.14 (m, 2H). HPLC: Retention Time: 2.362 min. MS: (M+H⁺) m/z=405.2.

Example A-37

Synthesis of 5-bromo-4-cyclopropyl-N-(3-methyl-1-(2-(1-methyl-1H-1,2,4-triazol-3-yl)propan-2-yl)-1H-pyrazol-4-yl)pyrimidin-2-amine (A-53)

5-bromo-2-chloro-4-cyclopropylpyrimidine

To a solution of 5-bromo-2-chloropyrimidine (5 g, 25.9 mmol) in H₂O (150 mL) and CH₃CN (150 mL) was added cyclopropanecarboxylic acid (2.2 g, 25.9 mmol), (NH₄)₂S₂O₈ (14.8 g, 164.6 mmol) and AgNO₃ (8.8 g, 8.8 mmol). The reaction mixture was stirred at 20° C. for 72 h. The reaction was quenched by ice water slowly and then extracted with EtOAc (3×150 mL). The combined organic phase was washed with brine (150 mL), dried over anhydrous Na₂SO₄, filtered and concentrated under reduced pressure to give a residue, which was purified by prep-TLC (SiO$_2$, PE:EtOAc=10:1) to give 5-bromo-2-chloro-4-cyclopropylpyrimidine as a pale yellow oil. MS: m/z=234.9 [M+H]$^+$.

5-bromo-4-cyclopropyl-N-(3-methyl-1-(2-(1-methyl-1H-1,2,4-triazol-3-yl)propan-2-yl)-1H-pyrazol-4-yl)pyrimidin-2-amine (A-23)

To a solution of 5-bromo-2-chloro-4-cyclopropylpyrimidine (120 mg, 0.51 mmol) in 1,4-dioxane (1 mL) was added 3-methyl-1-(2-(1-methyl-1H-1,2,4-triazol-3-yl)propan-2-yl)-1H-pyrazol-4-amine (113 mg, 0.51 mmol) and p-TsOH (27 mg, 0.15 mmol). The reaction mixture was stirred at 100° C. for 2 h. The mixture was concentrated under reduced pressure to give a residue, which was purified by prep-TLC (SiO$_2$. PE:EtOAc=1:1) to give 5-bromo-4-cyclopropyl-N-(3-methyl-1-(2-(1-methyl-1H-1,2,4-triazol-3-yl)propan-2-yl)-1H-pyrazol-4-yl)pyrimidin-2-amine. $^1$H NMR (400 MHz, CHLOROFORM-d): δ 8.22 (s, 1H), 7.95 (s, 1H), 7.87 (s, 1H), 6.39 (br. s., 1H), 3.90 (s, 3H), 2.34-2.43 (m, 1H), 2.22 (s, 3H), 2.03 (s, 6H), 1.10-1.14 (m, 2H), 1.03-1.08 (m, 2H). HPLC: RT 2.70 min. MS: [M+H]$^+$ m/z: 417.1.

Example A-38

Synthesis of 4-cyclopropyl-N-[5-methyl-1-[(1-methylpyrazol-3-yl)methyl]pyrazol-4-yl]-5-(trifluoromethyl)pyrimidin-2-amine (A-54)

5-methyl-1-[(1-methylpyrazol-3-yl)methyl]pyrazol-4-amine

To a solution of 5-methyl-1-[(1-methylpyrazol-3-yl)methyl]-4-nitro-pyrazole (540 mg, 2.44 mmol) in MeOH (30 mL) was added Pd—C (10%, 250 mg) under N$_2$ at 20° C. The suspension was degassed under vacuum and purged with H$_2$ several times. The mixture was stirred under H$_2$ (15 psi) at 40° C. for 5 h. The mixture was cooled to 20° C. and concentrated to give 5-methyl-1-[(1-methylpyrazol-3-yl)methyl]pyrazol-4-amine as a white solid. LCMS: RT 0.882 min, m/z=192.3 [M+H]$^+$.

4-cyclopropyl-N-[5-methyl-1-[(1-methylpyrazol-3-yl)methyl]pyrazol-4-yl]-5-(trifluoromethyl)pyrimidin-2-amine (A-54)

To a mixture of 5-methyl-1-[(1-methylpyrazol-3-yl)methyl]pyrazol-4-amine (80 mg, 418.34 μmol) and 4-cyclopropyl-2-(methylsulfonyl)-5-(trifluoromethyl)pyrimidine (123 mg, 460.17 μmol) in 1,4-dioxane (1.00 mL) was added TFA (95 mg, 836.68 μmol, 61 μL) at 20° C. The mixture was then heated to 100° C. and stirred for 3 h. The mixture was cooled to 20° C. and concentrated. The residue was adjusted pH=7-8 by adding aq. NaHCO$_3$, then was extracted with EtOAc (3×3 mL), washed with brine (3 mL), dried over anhydrous Na$_2$SO$_4$, filtered and concentrated under reduced pressure. The residue was purified by prep-HPLC (neutral) to give 4-cyclopropyl-N-[5-methyl-1-[(1-methylpyrazol-3-yl)methyl]pyrazol-4-yl]-5-(trifluoromethyl)pyrimidin-2-amine. LCMS: RT 0.882 min, m/z=192.3 [M+H]$^+$. $^1$H NMR (400 MHz, CDCl$_3$): δ ppm 8.37 (s, 1H), 7.64 (br. s., 1H), 7.28-7.29 (m, 1H), 6.51 (br. s., 1H), 6.08 (br. s., 1H), 5.27 (s, 2H), 3.87 (s, 3H), 2.13-2.25 (m, 4H), 1.20 (br. s., 1H), 1.02-1.09 (m, 2H). HPLC: RT 2.489 min. MS: [M+H]$^+$ m/z: 378.1.

Example A-39

Synthesis of 4-cyclopropyl-N-(3-methyl-1-((1-methyl-1H-pyrazol-3-yl)methyl)-1H-pyrazol-4-yl)-5-(trifluoromethyl)pyrimidin-2-amine (A-55)

3-methyl-1-((1-methyl-1H-pyrazol-3-yl)methyl)-1H-pyrazol-4-amine

To a solution of 5-methyl-1-[(1-methylpyrazol-3-yl)methyl]-4-nitro-pyrazole (120 mg, 542.45 μmol) in MeOH (4 mL) was added Pd—C (10% 0.05 g) under N$_2$. The suspension was degassed under vacuum and purged with H$_2$ several times. The mixture was stirred under H$_2$ (15 psi) at 40° C. for 2 h. The reaction mixture was filtered and tire filtrate was concentrated to get 3-methyl-1-((1-methyl-1H-pyrazol-3-yl)methyl)-1H-pyrazol-4-amine as a black brown oil. LCMS: RT 0.765 min, m/z=214.2 [M+Na]$^+$. $^1$H NMR (400 MHz, CDCl$_3$): δ 7.00 (s, 1H), 6.14 (d, J=2.21 Hz, 1H), 5.12 (s, 2H), 3.87 (s, 3H), 2.71 (d, J=7.06 Hz, 2H), 2.18 (s, 3H).

4-cyclopropyl-N-(3-methyl-1-((1-methyl-1H-pyrazol-3-yl)methyl)-1H-pyrazol-4-yl)-5-(trifluoromethyl)pyrimidin-2-amine (A-55)

To a mixture of 3-methyl-1-((1-methyl-1H-pyrazol-3-yl)methyl)-1H-pyrazol-4-amine (100 mg, 522.93 μmol) and 4-cyclopropyl-2-(methylsulfonyl)-5-(trifluoromethyl)pyrimidine (139 mg, 522.93 μmol) in 1,4-dioxane (2 mL) was added TFA (119 mg, 1.05 mmol) and then the mixture was stirred at 100° C. for 2 h under N$_2$. The reaction mixture was concentrated under reduced pressure to give a residue, which was purified by prep-HPLC (neutral condition) to give 4-cyclopropyl-N-(3-methyl-1-((1-methyl-1H-pyrazol-3-yl)methyl)-1H-pyrazol-4-yl)-5-(trifluoromethyl)pyrimidin-2-amine. $^1$H NMR (400 MHz, CDCl$_3$): δ 8.38 (br. s., 1H), 7.74 (br. s., 1H), 7.30 (br. s., 1H), 6.76 (br. s., 1H), 6.19 (s, 1H), 5.23 (s, 2H), 3.90 (s, 3H), 2.24 (s, 3H), 2.18 (d, J=8.16 Hz, 1H), 1.19 (br. s., 2H), 1.07 (dd, J=7.53, 3.26 Hz, 2H). HPLC: RT 2.93 min. MS: [M+H]$^+$ m/z=378.1.

Example A-40

Synthesis of 4-cyclopropyl-N-(3-methyl-1-(2-(1-methyl-1H-imidazol-4-yl)propan-2-yl)-1H-pyrazol-4-yl)-5-(trifluoromethyl)pyrimidin-2-amine (A-56)

3-methyl-3-(3-methyl-4-nitro-1H-pyrazol-1-yl)butan-2-one

To a solution of 3-methyl-4-nitro-1H-pyrazole (10 g, 78.68 mmol) in DMF (50 mL) was added portionwise NaH (4.72 g, 118.02 mmol, 60% purity) at 0° C. over a period of 30 min under N$_2$. The reaction mixture was warmed to 20° C. and stirred at 20° C. for 1 h. Then 3-bromo-3-methyl-butan-2-on56c (15.58 g, 94.41 mmol) was added dropwise at 0° C. over a period of 30 min. The reaction mixture was warmed to 20° C. and stirred at 20° C. for another 5 h. The reaction mixture was quenched by pouring into ice water (350 mL) slowly and then extracted with EtOAc (3×100 mL). The combined organic layers were washed with brine (2<50 mL), dried over anhydrous Na$_2$SO$_4$, filtered and concentrated under reduced pressure. The residue was purified by silica gel column chromatography (PE:EtOAc=10:1 to 3:1) to give 3-methyl-3-(3-methyl-4-nitro-1H-pyrazol-1-yl)butan-2-one as a light yellow solid. LCMS: RT 0.670 min, m/z=212.2 [M+H]$^+$.

1-bromo-3-methyl-3-(3-methyl-4-nitro-1H-pyrazol-1-yl)butan-2-one

A mixture of 3-methyl-3-(3-methyl-4-nitro-pyrazol-1-yl)butan-2-one (6.7 g, 31.72 mmol), CuBr$_2$ (12.04 g, 53.92 mmol) in EtOAc (80 mL) and CHCl$_3$ (80 mL) was degassed and purged with N$_2$ for 3 times, and then the mixture was stirred at 80° C. for 24 h under N$_2$. The reaction mixture was filtered and concentrated under reduced pressure. The residue was purified by silica gel column chromatography (PE:EtOAc=10:1 to 3:1) to give 1-bromo-3-methyl-3-(3-methyl-4-nitro-1H-pyrazol-1-yl)butan-2-one as a yellow solid. LCMS: RT 1.035 min, m/z=290.0 [M+H]$^+$.

3-methyl-1-(2-(2-(methylthio)-1H-imidazol-4-yl)propan-2-yl)-4-nitro-1H-pyrazole

To a mixture of 1-bromo-3-methyl-3-(3-methyl-4-nitro-pyrazol-1-yl)butan-2-one (10 g; 34.47 mmol) and 2-Methyl-2-thiopseudourea sulfate (2:1) (11.51 g, 41.36 mmol) in EtOH (200 mL) was added AcONa (8.48 g, 103.41 mmol) at 20° C. Then the mixture was heated to 90° C. and stirred for 12 h. The mixture was cooled to 20° C., quenched by pouring into ice-water (50 mL), concentrated under reduced pressure, and extracted with EtOAc (3×20 mL). The combined organic phase was washed with brine (20 mL), dried over anhydrous Na$_2$SO$_4$, filtered and concentrated under reduced pressure. The residue was purified by silica gel column chromatography (PE:EtOAc=10:1 to 3:1) to give 3-methyl-1-(2-(2-(methylthio)-1H-imidazol-4-yl)propan-2-yl)-4-nitro-1H-pyrazole as a yellow solid. LCMS: RT 0.664 min, m/z=282.1 [M+H]$^+$.

1-(2-(1H-imidazol-4-yl)propan-2-yl)-3-methyl-4-nitro-1H-pyrazole

To a solution of 3-methyl-1-[1-methyl-1-(2-methylsulfanyl-1H-imidazol-4-yl)ethyl]-4-nitro-pyrazole (1 g, 3.55 mmol) in THF (20 mL) was added Et$_3$SiH (1.24 g, 10.66 mmol) and Pd/C (756 mg, 710.91 µmol, 10% purity) at 0° C. The mixture was stirred at 20° C. for 60 h. The reaction mixture was filtered and concentrated under reduced pressure. The residue was purified by flash silica gel chromatography (ISCOS®; 20 g SepaFlash® Silica Flash Column, Eluent of 0100% EtOAc/PE gradient at 100 mL/min) to give 1-(2-(1H-imidazol-4-yl)propan-2-yl)-3-methyl-4-nitro-1H-pyrazole as a yellow solid. LCMS: RT 0.186 min, m/z=236.2 [M+H]$^+$.

3-methyl-1-(2-(1-methyl-1H-imidazol-4-yl)propan-2-yl)-4-nitro-1H-pyrazole

To a solution of 1-[1-(1H-imidazol-4-yl)-1-methyl-ethyl]-3-methyl-4-nitro-pyrazole (120 mg, 510.12 µmol) in CH$_3$CN (2 mL) was added MeI (87 mg, 612.14 µmol) and Cs$_2$CO$_3$ (166 mg, 510.12 µmol). The mixture was stirred at 20° C. for 12 h. The reaction mixture was filtered and concentrated under reduced pressure. The residue was purified by prep-TLC (SiO$_2$, EtOAc) to give 3-methyl-1-(2-(1-methyl-1H-imidazol-4-yl)propan-2-yl)-4-nitro-1H-pyrazole as a yellow solid. LCMS: RT 0.236 min, m/z=250.1 [M+H]$^+$. $^1$H NMR (400 MHz, CDCl$_3$): δ ppm 8.05-8.11 (m, 1H), 7.41-7.48 (m, 1H), 6.82-6.89 (m, 1H), 3.70 (s, 3H), 2.54 (s, 3H), 1.94 (s, 6H).

3-methyl-1-(2-(1-methyl-1H-imidazol-4-yl)propan-2-yl)-1H-pyrazol-4-amine

To a solution of 3-methyl-1-[1-methyl-1-(1-methylimidazol-4-yl)ethyl]-4-nitro-pyrazole (150 mg, 601.76 µmol) in MeOH (10 mL) was added Pd—C (10%, 128 mg) under N$_2$. The suspension was degassed under vacuum and purged with H$_2$ several times. The mixture was stirred under H$_2$ (15 psi) at 30° C. for 2 h. The reaction mixture was filtered and the filtrate was concentrated to give 3-methyl-1-(2-(1-methyl-1H-imidazol-4-yl)propan-2-yl)-1H-pyrazol-4-amine as a brown oil. LCMS: RT 0.387 min, m/z=220.3 [M+H]$^+$.

4-cyclopropyl-N-(3-methyl-1-(2-(1-methyl-1H-imidazol-4-yl)propan-2-yl)-1H-pyrazol-4-yl)-5-(trifluoromethyl)pyrimidin-2-amine (A-56)

To a solution of 3-methyl-1-[1-methyl-1-(1-methylimidazol-4-yl)ethyl]pyrazol-4-amine (120 mg, 547.22 µmol) and 4-cyclopropyl-2-(methylsulfonyl)-5-(trifluoromethyl)pyrimidine (146 mg, 547.22 µmol) in 1,4-dioxane (5 mL) was added TFA (31 mg, 273.61 µmol). The mixture was stirred at 100° C. for 1 h. The reaction mixture was diluted with H$_2$O (20 mL) and aq. NaHCO$_3$ (20 mL), extracted with EtOAc (3×10 mL). The combined organic layers were washed with brine (10 mL), dried over Na$_2$SO$_4$, filtered and concentrated under reduced pressure. The residue was purified by prep-HPLC (neutral condition) to give 4-cyclopropyl-N-(3-methyl-1-(2-(1-methyl-1H-imidazol-4-yl)propan-2-yl)-1H-pyrazol-4-yl)-5-(trifluoromethyl)pyrimidin-2-amine. $^1$H NMR (400 MHz, CDCl$_3$): δ ppm 8.30-8.47 (m, 1H), 7.74-7.94 (m, 1H), 7.36-7.45 (m, 1H), 6.53-6.78 (m, 2H), 3.65 (s, 3H), 2.26 (s, 3H), 2.14-2.23 (m, 1H), 1.96 (s, 6H), 1.15-1.28 (m, 2H), 1.03-1.12 (m, 2H). HPLC: RT 2.467 min. MS: m/z: 406.2 [M+H]$^+$.

Example A-41

Synthesis of 1-[5-chloro-4-[(4-cyclopropyl-5-(trifluoromethyl)pyrimidin-2-yl]amino]pyrazol-1-yl)-2-methyl-propan-2-ol (A-57)

To a mixture of 1-(4-amino-5-chloro-1H-pyrazol-1-yl)-2-methylpropan-2-ol (70 mg, 369.12 µmol) and 4-cyclopropyl-2-(methylsulfonyl)-5-(trifluoromethyl)pyrimidine (98 mg, 369.12 µmol) in 1,4-dioxane (5 mL) was added TFA (84 mg, 738.24 µmol, 55 µL) at 20° C. under N$_2$. The mixture was heated to 90° C. and stirred for 5 h. The mixture was cooled to 20° C. and adjusted to pH=8 by adding aq. NaHCO$_3$. The aqueous phase was extracted with EtOAc (3×10 mL). The combined organic phase was washed with brine (10 mL), dried over anhydrous Na$_2$SO$_4$, filtered and concentrated under reduced pressure. The residue was purified by prep-HPLC (neutral) to give 1-[5-chloro-4-[[4-cyclopropyl-5-(trifluoromethyl)pyrimidin-2-yl]amino]pyrazol-1-yl]-2-methyl-propan-2-ol. $^1$H NMR (400 MHz, CDCl$_3$): δ 8.11 (d, J=9.66 Hz, 2H), 7.87 (s, 1H), 6.68 (br. s., 1H), 5.13-5.25 (m, 1H), 3.81 (s, 3H), 3.05 (d, J=4.14 Hz, 3H), 2.28 (s, 3H), 1.73 (s, 4H). HPLC: RT 2.723 min. MS: [M+H]$^+$ m/z=376.1.

Example A-42

Synthesis of N-(1-(2-(1H-1,2,4-triazol-3-yl)propan-2-yl)-3-methyl-1H-pyrazol-4-yl)-4-cyclopropyl-5-(trifluoromethyl)pyrimidin-2-amine (A-58)

1-(2-(1H-1,2,4-triazol-3-yl)propan-2-yl)-3-methyl-1H-pyrazol-4-amine

To a solution of 3-(2-(3-methyl-4-nitro-1H-pyrazol-1-yl)propan-2-yl)-1H-1,2,4-triazole (2 g, 8.47 mmol) in EtOH (40 mL) was added Pd—C (10% 0.9 g) under $N_2$. The suspension was degassed under vacuum and purged with $H_2$ several times. The mixture was stirred under $H_2$ (15 psi) at 50° C. for 2 h. The reaction mixture was filtered and the filtrate was concentrated to give 1-(2-(1H-1,2,4-triazol-3-yl)propan-2-yl)-3-methyl-1H-pyrazol-4-amine as a brown solid. The crude product was used into the next step without further purification.

N-(1-(2-(1H-1,2,4-triazol-3-yl)propan-2-yl)-3-methyl-1H-pyrazol-4-yl)-4-cyclopropyl-5-(trifluoromethyl)pyrimidin-2-amine (A-58)

To a solution of 4-cyclopropyl-2-(methylsulfonyl)-5-(trifluoromethyl)pyrimidine (129 mg, 484.85 μmol) and 1-(2-(1H-1,2,4-triazol-3-yl)propan-2-yl)-3-methyl-1H-pyrazol-4-amine (100 mg, 484.85 μmol) in 1,4-dioxane (5 mL) was added TFA (110 mg, 969.70 μmol). The mixture was stirred at 100° C. for 2 h. The reaction mixture was diluted with $H_2O$ (20 mL), adjusted with sat. $NaHCO_3$ (10 mL) to pH=8-9 and extracted with EtOAc (3×10 mL). The combined organic layers were washed with brine (5 mL), dried over $Na_2SO_4$, filtered and concentrated under reduced pressure to give a residue, which was purified by prep-HPLC (FA condition) to give an FA salt of the product (36 mg). The salt was purified by prep-HPLC (neutral) to give N-(1-(2-(1H-1,2,4-triazol-3-yl)propan-2-yl)-3-methyl-1H-pyrazol-4-yl)-4-cyclopropyl-5-(trifluoromethyl)pyrimidin-2-amine $^1$H NMR: (400 MHz, CDCl3): (400 MHz, CHLOROFORM-d) δ 11.39 (bs, 1H), 8.41 (s, 1H), 8.03 (s, 1H), 7.96 (s, 1H), 7.03 (bs, 1H), 2.27 (s, 3H), 2.18-2.25 (m, 1H), 2.05 (s, 6H), 1.20-1.30 (m, 2H), 1.07-1.18 (m, 2H). HPLC: RT 2.301 min. MS. [M+H]$^+$ m/z: 393.2.

Example A-43

Synthesis of (S)-5-(4-((4-cyclopropyl-5-(trifluoromethyl)pyrimidin-2-yl)amino)-5-methyl-1H-pyrazol-1-yl)-1-ethylpiperidin-2-one, (R)-5-(4-((4-cyclopropyl-5-(trifluoromethyl)pyrimidin-2-yl)amino)-5-methyl-1H-pyrazol-1-yl)-1-ethylpiperidin-2-one, (S)-5-(4-((4-cyclopropyl-5-(trifluoromethyl)pyrimidin-2-yl)amino)-3-methyl-1H-pyrazol-1-yl)-1-ethylpiperidin-2-one, and (R)-5-(4-((4-cyclopropyl-5-(trifluoromethyl)pyrimidin-2-yl)amino)-3-methyl-1H-pyrazol-1-yl)-1-ethylpiperidin-2-one (A-59, A-60, A-61, and A-62)

5-((tert-butyldiphenylsilyl)oxy)-1-ethylpiperidin-2-one

To a solution of 5-[tert-butyl(diphenyl)silyl]oxypiperidin-2-one (2 g, 5.66 mmol) in DMF (10 mL) was added portionwise NaH (340 mg, 8.49 mmol, 60% purity) at 0° C. over 20 min. After addition, the mixture was stirred at 20° C. for 40 min, and then EtI (1.32 g, 8.49 mmol) was added dropwise at 0° C. The resulting mixture was stirred at 20° C. for 11 h. The reaction mixture was poured into ice-water (80 mL) and extracted with EtOAc (3×30 mL). The combined organic layers were washed with brine (3×10 mL), dried over $Na_2SO_4$, filtered and concentrated under reduced pressure. The residue was purified by silica gel column chromatography (PE:EtOAc=5:1 to 0:1) to give 5-((tert-butyldiphenylsilyl)oxy)-1-ethylpiperidin-2-one as a yellow oil. LCMS. RT 1.008 min, m/z=382.2 [M+H]$^+$.

1-ethyl-5-hydroxypiperidin-2-one

To a solution of 5-[tert-butyl(diphenyl)silyl]oxy-1-ethyl-piperidin-2-one (1.5 g, 3.93 mmol) in MeOH (30 mL) was added RF (4.57 g, 78.60 mmol) at 25° C. under $N_2$. The mixture was then heated to 70° C. and stirred for 48 h. The mixture was cooled to 25° C. and concentrated under reduced pressure. The residue was poured into DCM:MeOH=10:1 (50 mL) and stirred for 30 min, followed by filtration. The filtrate was concentrated under reduced pressure. The residue was dissolved in water (50 mL) and extracted with MTBE (2×20 mL). The aqueous phase was concentrated under reduced pressure to give 1-ethyl-5-hydroxypiperidin-2-one as a colorless oil. LCMS: RT 0.206 min, m/z=144.2 [M+H]$^+$.

1-ethyl-5-(5-methyl-4-nitro-1H-pyrazol-1-yl)piperidin-2-one & 1-ethyl-5-(3-methyl-4-nitro-1H-pyrazol-1-yl)piperidin-2-one To a solution of 1-ethyl-5-hydroxy-piperidin-2-one (530 mg, 3.70 mmol), 3-methyl-4-nitro-1H-pyrazole (706 mg, 5.55 mmol) and $PPh_3$ (1.46 g, 5.55 mmol) in THF (20 mL) was added dropwise DIAB (1.12 g, 5.55 mmol) at 0° C. over 20 min. After addition, the mixture was stirred at this temperature for 40 min, and then the resulting mixture was stirred at 20° C. for 11 h. The reaction mixture was concentrated under reduced pressure. The residue was purified by silica gel column chromatography (PE:EtOAc=5:1 to 0:1) to give a mixture of 1-ethyl-5-(5-methyl-4-nitro-1H-pyrazol-1-yl)piperidin-2-one and 1-ethyl-5-(3-methyl-4-nitro-1H-pyrazol-1-yl)piperidin-2-one as a yellow solid. LCMS: RT 0.881 min, m/z=253.1 [M+H]$^+$.

5-(4-amino-5-methyl-1H-pyrazol-1-yl)-1-ethylpiperidin-2-one and 5-(4-amino-3-methyl-1H-pyrazol-1-yl)-1-ethylpiperidin-2-one To a solution of 1-ethyl-5-(5-methyl-4-nitro-pyrazol-1-yl)piperidin-2-one and 1-ethyl-5-(3-methyl-4-nitro-pyrazol-1-yl)piperidin-2-one (420 mg, 1.66 mmol) in MeOH (40 mL) was added Pd/C (10%, 176 mg) under $N_2$. The suspension was degassed under vacuum and purged with $H_2$ several times. The mixture was stirred under $H_2$ (15 psi) at 20° C. for 2 h. The reaction mixture was filtered and the filtrate was concentrated to give a mixture of 5-(4-amino-5-methyl-1H-pyrazol-1-yl)-1-ethylpiperidin-2-one and 5-(4-amino-3-methyl-1H-pyrazol-1-yl)-1-ethylpiperidin-2-one as a brown oil. LCMS: RT 0.566 min, m/z=223.3 [M+H]$^+$.

(S)-5-(4-((4-cyclopropyl-5-(trifluoromethyl)pyrimidin-2-yl)amino)-5-methyl-1H-pyrazol-1-yl)-1-ethylpiperidin-2-one, (R)-5-(4-((4-cyclopropyl-5-(trifluoromethyl)pyrimidin-2-yl)amino)-5-methyl-1H-pyrazol-1-yl)-1-ethylpiperidin-2-one, (S)-5-(4-((4-cyclopropyl-5-(trifluoromethyl)pyrimidin-2-yl)amino)-3-methyl-1H-pyrazol-1-yl)-1-ethylpiperidin-2-one, and (R)-5-(4-((4-cyclopropyl-5-(trifluoromethyl)pyrimidin-2-yl)amino)-3-methyl-1H-pyrazol-1-yl)-1-ethylpiperidin-2-one (A-59, A-60, A-61, and A-62)

To a solution of 5-(4-amino-5-methyl-pyrazol-1-yl)-1-ethyl-piperidin-2-one and 5-(4-amino-3-methyl-pyrazol-1-yl)-1-ethyl-piperidin-2-one (310 mg, 1.39 mmol), and 4-cyclopropyl-2-(methylsulfonyl)-5-(trifluoromethyl)pyrimidine (370 mg, 1.39 mmol) in 1,4-dioxane (10 mL) was added TFA (317 mg, 2.78 mmol). The mixture was stirred at 100° C. for 2 h. The reaction mixture was diluted with H$_2$O (30 mL), adjusted with aq. NaHCO$_3$ (30 mL) to pH=8 and extracted with EtOAc (3×30 mL). The combined organic layers were washed with brine (30 mL), dried over Na$_2$SO$_4$, filtered and concentrated under reduced pressure to give crude product. The crude product was triturated with DMF (5 mL). The undissolved solid was filtered to give crude product as a solid. This crude product was separated by SFC to give 5-(4-((4-cyclopropyl-5-(trifluoromethyl)pyrimidin-2-yl)amino)-3-methyl-1H-pyrazol-1-yl)-1-ethylpiperidin-2-one as a single enantiomer (Peak 1 in SFC) and 5-(4-((4-cyclopropyl-5-(trifluoromethyl)pyrimidin-2-yl)amino)-3-methyl-1H-pyrazol-1-yl)-1-ethylpiperidin-2-one as a single enantiomer (Peak 2 in SFC). The DMF filtrate was concentrated to give crude product. This crude product was purified by prep-HPLC (TFA) and then twice of SFC to give 5-(4-((4-cyclopropyl-5-(trifluoromethyl)pyrimidin-2-yl)amino)-5-methyl-1H-pyrazol-1-yl)-1-ethylpiperidin-2-one as a single enantiomer (Peak 1 in SFC) and 5-(4-((4-cyclopropyl-5-(trifluoromethyl)pyrimidin-2-yl)amino)-5-methyl-1H-pyrazol-1-yl)-1-ethylpiperidin-2-one as a single enantiomer (Peak 2 in SFC).

First Eluting Isomer (Peak 1): (S)-5-(4-((4-cyclopropyl-5-(trifluoromethyl)pyrimidin-2-yl)amino)-5-methyl-1H-pyrazol-1-yl)-1-ethylpiperidin-2-one (A-59)

$^1$H NMR (400 MHz, MD$_3$OD): δ ppm 8.25-8.45 (m, 1H), 7.48-7.67 (m, 1H), 4.64-4.79 (m, 1H), 3.72-3.84 (m, 1H), 3.56-3.63 (m, 1H), 3.44-3.54 (m, 1H), 3.35-3.43 (m, 1H), 2.50-2.61 (m, 2H), 2.32-2.44 (m, 1H), 2.25 (s, 3H), 2.09-2.21 (m, 2H), 0.98-1.34 (m, 7H). HPLC: RT 2.480 min. MS: m/z: 409.2 [M+H]$^+$. SFC. RT 5.72 min, ee=100%.

Second Eluting Isomer (Peak 2): 5-(4-((4-cyclopropyl-5-(trifluoromethyl)pyrimidin-2-yl)amino)-5-methyl-1H-pyrazol-1-yl)-1-ethylpiperidin-2-one (A-60)

$^1$H NMR (400 MHz, CD$_3$OD): δ ppm 8.21-8.48 (m, 1H), 7.43-7.71 (m, 1H), 4.67-4.80 (m, 1H), 3.72-3.83 (m, 1H), 3.56-3.62 (m, 1H), 3.44-3.54 (m, 1H), 3.34-3.43 (m, 1H), 2.49-2.60 (m, 2H), 2.33-2.44 (m, 1H), 2.25 (s, 3H), 2.08-2.21 (m, 2H), 0.97-1.34 (m, 7H). HPLC: RT 2.487 min. MS: m/z: 409.1 [M+H]$^+$. SFC: RT 6.33 min, ee=100%.

First Eluting Isomer (Peak 1): 5-(4-((4-cyclopropyl-5-(trifluoromethyl)pyrimidin-2-yl)amino)-3-methyl-1H-pyrazol-1-yl)-1-ethylpiperidin-2-one (A-61)

$^1$H NMR (400 MHz, CD$_3$OD): δ ppm 8.34-8.43 (m, 1H), 7.84-7.94 (m, 1H), 4.54-4.69 (m, 1H), 3.69-3.79 (m, 2H), 3.38-3.52 (m, 2H), 2.46-2.57 (m, 2H), 2.32-2.43 (m, 1H), 2.22-2.30 (m, 1H), 2.19 (s, 4H), 1.18-1.31 (m, 2H), 1.07-1.17 (m, 5H). HPLC: RT 2.468 min. MS: m/z: 409.1 [M+H]$^+$. SFC: RT 4.87 min, ee=100%.

Second Eluting Isomer (Peak 2):5-(4-((4-cyclopropyl-5-(trifluoromethyl)pyrimidin-2-yl)amino)-3-methyl-1H-pyrazol-1-yl)-1-ethylpiperidin-2-one (A-62)

$^1$H NMR (400 MHz, CD$_3$OD): δ ppm 8.34-8.42 (m, 1H), 7.83-7.95 (m, 1H), 4.56-4.71 (m, 1H), 3.68-3.80 (m, 2H), 3.37-3.53 (m, 2H), 2.45-2.58 (m, 2H), 2.32-2.43 (m, 1H), 2.23-2.30 (m, 1H), 2.19 (s, 4H), 1.19-1.30 (m, 2H), 1.06-1.18 (m, 5H). HPLC: RT 2.464 min. MS: m/z: 409.1 [M+H]$^+$. SFC: RT 5.67 min, ee=98.02%.

Example A-44

Synthesis of N-[5-chloro-1-[[1-(morpholinomethyl)cyclopropyl]methyl]pyrazol-4-yl]-4-cyclopropyl-5-(trifluoromethyl)pyrimidin-2-amine (A-63)

N-[5-chloro-1-[[1-(morpholinomethyl)cyclopropyl]methyl]pyrazol-4-yl]-4-cyclopropyl-5-(trifluoromethyl)pyrimidin-2-amine (A-63)

To a mixture of 5-chloro-1-((1-(morpholinomethyl)cyclopropyl)methyl)-1H-pyrazol-4-amine (70 mg, 258.53 μmol) and 4-cyclopropyl-2-(methylsulfonyl)-5-(trifluoromethyl)pyrimidine (75.71 mg, 284.38 μmol) in 1,4-dioxane (3 mL) was added TFA (58.96 mg, 517.06 μmol) in one portion at 20° C. under N$_2$. The mixture was stirred at 90° C. for 6 h. The mixture was concentrated under reduced pressure. The residue was poured into aq. NaHCO$_3$ (10 mL) and stirred for 5 min. The aqueous phase was extracted with EtOAc (3×5 mL). The combined organic phase was washed with brine (10 mL), dried with anhydrous Na$_2$SO$_4$, filtered and concentrated under reduced pressure. The residue was purified by prep-HPLC (NH$_4$HCO$_3$) to give N-(5-chloro-1-((1-(morpholinomethyl)cyclopropyl)methyl)-1H-pyrazol-4-yl)-4-cyclopropyl-5-(trifluoromethyl)pyrimidin-2-amine. $^1$H NMR (400 MHz, CDCl$_3$): δ ppm 8.43 (s, 1H) 7.98 (s, 1H) 6.70 (br. s., 1H) 4.19 (s, 2H) 3.67 (t, J=4.52 Hz, 4H) 2.43 (br. s., 4H) 2.15-2.28 (m, 3H) 1.26-1.36 (m, 2H) 1.08-1.20 (m, 2H) 0.68-0.79 (m, 2H) 0.38-0.48 (m, 2H). HPLC: RT 2.44 min. MS: [M+H]$^+$ m/z: 457.

Example A-45

Synthesis of N-(5-chloro-1-(4,4-difluoro-1-(oxetan-3-yl)piperidin-3-yl)-1H-pyrazol-4-yl)-4-cyclopropyl-5-(trifluoromethyl)pyrimidin-2-amine (64) and N-(5-chloro-1-(4,4-difluoro-1-(oxetan-3-yl)piperidin-3-yl)-1H-pyrazol-4-yl)-4-cyclopropyl-5-(trifluoromethyl)pyrimidin-2-amine (A-65)

5-chloro-1-(4,4-difluoro-1-(oxetan-3-yl)piperidin-3-yl)-1H-pyrazol-4-amine

To a mixture of 3-(5-chloro-4-nitro-1H-pyrazol-1-yl)-4,4-difluoro-1-(oxetan-3-yl)piperidine (1.1 g, 3.41 mmol) in EtOH (48 mL) and H$_2$O (12 mL) was added NH$_4$Cl (911 mg, 17.05 mmol) and Fe (951 mg, 17.05 mmol) at 20° C. Then the mixture was heated to 80° C. and stirred for 2 h. The mixture was cooled to 20° C., filtered and concentrated under reduced pressure. The residue was added with water (10 mL) then extracted with EtOAc (3×5 mL). The combined organic phase was washed with brine (5 mL), dried over anhydrous Na$_2$SO$_4$, filtered and concentrated under reduced pressure, to give 5-chloro-1-(4,4-difluoro-1-(oxetan-3-yl)piperidin-3-yl)-1H-pyrazol-4-amine as a red brown solid. LCMS: RT 0.103 min, m/z=293.1 [M+H]$^+$.

N-(5-chloro-1-(4,4-difluoro-1-(oxetan-3-yl)piperidin-3-yl)-1H-pyrazol-4-yl)-4-cyclopropyl-5-(trifluoromethyl)pyrimidin-2-amine and N-(5-chloro-1-(4,4-difluoro-1-(oxetan-3-yl)piperidin-3-yl)-1H-pyrazol-4-yl)-4-cyclopropyl-5-(trifluoromethyl)pyrimidin-2-amine (A-64 and A-65)

A mixture of 5-chloro-1-(4,4-difluoro-1-(oxetan-3-yl)piperidin-3-yl)-1H-pyrazol-4-amine (200 mg, 683.27 µmol), 2-chloro-4-cyclopropyl-5-(trifluoromethyl)pyrimidine (167 mg, 751.60 µmol), Pd$_2$(dba)$_3$ (63 mg, 68.33 µmol), XPhos (65 mg, 136.65 µmol) and Cs$_2$CO$_3$ (534 mg, 1.64 mmol) in 1,4-dioxane (10 mL) was degassed and purged with N$_2$ for 3 times, and then the mixture was stirred at 100° C. for 12 h under N$_2$. The residue was purified by prep-TLC (SiO$_2$, PE/Ethyl acetate=1/1) to give crude product. The crude was further separated by SFC to provide N-(5-chloro-1-(4,4-difluoro-1-(oxetan-3-yl)piperidin-3-yl)-1H-pyrazol-4-yl)-4-cyclopropyl-5-(trifluoromethyl)pyrimidin-2-amine as a single enantiomer (peak 1) and N-(5-chloro-1-(4,4-difluoro-1-(oxetan-3-yl)piperidin-3-yl)-1H-pyrazol-4-yl)-4-cyclopropyl-5-(trifluoromethyl)pyrimidin-2-amine as a single enantiomer (peak 2).

First Eluting Isomer (Peak 1): N-(5-chloro-1-(4,4-difluoro-1-(oxetan-3-yl)piperidin-3-yl)-1H-pyrazol-4-yl)-4-cyclopropyl-5-(trifluoromethyl)pyrimidin-2-amine (A-64)

$^1$H NMR: (400 MHz, CHLOROFORM-d) δ ppm 8.44 (s, 1H), 8.12 (s, 1H), 6.74 (bs, 1H), 4.66-4.81 (m, 3H), 4.56-4.64 (m, 2H), 3.64-3.76 (m, 1H), 3.04-3.14 (m, 1H), 2.93-3.02 (m, 1H), 2.79-2.89 (m, 1H), 2.10-2.41 (m, 4H), 1.24-1.35 (m, 2H), 1.07-1.18 (m, 2H). HPLC. RT 2.914. MS: [M+H]$^+$ m/z: 479.2. SFC: ee: 99.66%.

Second Eluting Isomer (Peak 2): N-(5-chloro-1-(4,4-difluoro-1-(oxetan-3-yl)piperidin-3-yl)-1H-pyrazol-4-yl)-4-cyclopropyl-5-(trifluoromethyl)pyrimidin-2-amine (A-65)

1H NMR: (400 MHz, CHLOROFORM-d) δ ppm 8.44 (s, 1H), 8.12 (s, 1H), 6.73 (bs, 1H), 4.66-4.82 (m, 3H), 4.54-4.65 (m, 2H), 3.63-3.79 (m, 1H), 3.05-3.16 (m, 1H), 2.92-3.03 (m, 1H), 2.78-2.89 (m, 1H), 2.09-2.42 (m, 4H), 1.23-1.37 (m, 2H), 1.04-1.20 (m, 2H). HPLC: RT 2.911. MS: [M+H]$^+$ m/z: 479.1. SFC: ee: 98.9%.

Example A-46

Synthesis of 4-cyclopropyl-N-[3-methyl-1-[1-methyl-1-(1H-pyrazol-5-yl)ethyl]pyrazol-4-yl]-5-(trifluoromethyl)pyrimidin-2-amine (A-67)

3-methyl-3-(3-methyl-4-nitro-pyrazol-1-yl)butan-2-one

To a solution of 3-methyl-4-nitro-1H-pyrazole (6.42 g, 50.51 mmol) in DMF (100 mL) was added NaH (2.42 g, 60.61 mmol) at 0° C. under N$_2$. The mixture was allowed to warmed to 25° C. and stirred for 2 h. Then the mixture was cooled to 0° C. and added with 3-bromo-3-methyl-butan-2-one (10 g, 60.61 mmol). The mixture was then stirred at 25° C. for 16 h. The mixture was poured into ice-water (600 mL). The aqueous phase was extracted with EtOAc (3×200 mL). The combined organic phase was washed with brine (2×200 mL), dried with anhydrous Na$_2$SO$_4$, filtered and concentrated. The residue was purified by silica gel column chromatography (PE:EtOAc=10:1) to afford 3-methyl-3-(3-methyl-4-nitro-pyrazol-1-yl)butan-2-one as light yellow solid. LCMS: RT 0.704 min, m/z=212.1 [M+H]$^+$. $^1$H NMR (400 MHz, CHLOROFORM-d): δ 8.30 (s, 1H), 2.56 (s, 3H), 1.98 (s, 3H), 1.74 (s, 6H).

(E)-1-(dimethylamino)-4-methyl-4-(3-methyl-4-nitro-pyrazol-1-yl)pent-1-en-3-one

A mixture of 3-methyl-3-(3-methyl-4-nitro-pyrazol-1-yl)butan-2-one (6.2 g, 29.35 mmol) and DMF-DMA (34.98 g, 293 mmol, 38.86 mL) was heated to 110° C. and stirred for 6 h. The mixture was cooled to 0° C. and yellow solid was precipitated out. The mixture was filtered to give (E)-1-(dimethylamino)-4-methyl-4-(3-methyl-4-nitro-pyrazol-1-yl)pent-1-en-3-one as a yellow solid. LCMS: RT 0.691 min, m/z=267.1 [M+H]$^+$. $^1$H NMR (400 MHz, CHLOROFORM-d) δ 8.28 (s, 1H), 7.65 (d, 7=12.17 Hz, 1H), 4.55 (d, J=12.30 Hz, 1H), 3.09 (br. s., 3H), 2.72 (br. s., 3H), 2.55 (s, 3H), 1.76 (s, 6H).

3-methyl-1-[1-methyl-1-(1H-pyrazol-5-yl)ethyl]-4-nitro-pyrazole

To a mixture of (E)-1-(dimethylamino)-4-methyl-4-(3-methyl-4-nitro-pyrazol-1-yl)pent-1-en-3-one (2 g, 7.51 mmol) in AcOH (10 mL) was added hydrazine hydrate (1.88 g, 37.55 mmol, 1.83 mL). The mixture was then heated to 100° C. and stirred for 2 h. The mixture was cooled to 25° C. and concentrated under reduced pressure. The residue was poured into saturated aqueous NaHCO$_3$ (100 mL). The aqueous phase was extracted with EtOAc (3×50 mL). The combined organic phase was washed with brine (100 mL), dried with anhydrous Na$_2$SO$_4$, filtered and concentrated to give 3-methyl-1-[1-methyl-1-(1H-pyrazol-5-yl)ethyl]-4-nitro-pyrazole as a yellow solid, which was used for next step directly. LCMS: RT 0.692 min, m/z=236.1 [M+H]$^+$.

3-methyl-1-[1-methyl-1-(1H-pyrazol-5-yl)ethyl] pyrazol-4-amine

To a solution of 3-methyl-1-[1-methyl-1-(1H-pyrazol-5-yl)ethyl]-4-nitro-pyrazole (1.87 g, 7.95 mmol) in MeOH (30 mL) was added Pd—C (10%, 0.6 g) under N$_2$. The suspension was degassed under vacuum and purged with H$_2$ three times. The mixture was stirred under H$_2$ (15 psi) at 25° C. for 2 h. The reaction mixture was filtered and the filtrate was concentrated to give 3-methyl-1-[1-methyl-1-(1H-pyrazol-5-yl)ethyl]pyrazol-4-amine as black-brown oil. LCMS: RT 0.109 min, m/z=206.1 [M+H]$^+$.

4-cyclopropyl-N-[3-methyl-1-[1-methyl-1-(1H-pyrazol-5-yl)ethyl]pyrazol-4-yl]-5-(trifluoromethyl)pyrimidin-2-amine (A-67)

To a mixture of 4-cyclopropyl-2-methylsulfonyl-5-(trifluoromethyl)pyrimidine (100 mg, 375 µmol) and 3-methyl-1-[1-methyl-1-(1H-pyrazol-5-yl)ethyl]pyrazol-4-amine (77 mg, 375.60 µmol) in 1,4-dioxane (2 mL) was added TFA (85 mg, 751 µmol) at 25° C. under N$_2$. The mixture was then heated to 90° C. and stirred for 3 h. The mixture was cooled to 25° C. and poured into saturated aqueous NaHCO$_3$ (30 mL). The aqueous phase was extracted with EtOAc (3 mL). The combined organic phase was washed with brine (10 mL), dried with anhydrous Na$_2$SO$_4$, filtered and concentrated to give a residue. The residue was purified by prep-HPLC (neutral) to afford 4-cyclopropyl-N-[3-methyl-1-[1-methyl-1-(1H-pyrazol-5-yl)ethyl]pyrazol-4-yl]-5-(trifluoromethyl)pyrimidin-2-amine. $^1$H NMR (400 MHz, CDCl$_3$): 8.39 (br. s., 1H), 7.83 (br. s., 1H), 7.51 (br. s., 1H), 6.80 (br. s., 1H), 6.19 (br. s., 1H), 2.28 (s, 3H), 2.20 (br. s., 1H), 2.00 (s, 6H), 1.19 (d, J=9.70 Hz, 2H), 1.05-1.13 (m, 2H). HPLC. RT 2.589 min. MS: [M+H]$^+$ m/z: 392.2.

Example A-47

Synthesis of 4-cyclopropyl-N-(3-methyl-1-((1R,3r,5S,6r)-6-(1-methyl-1H-1,2,4-triazol-3-yl)bicyclo[3.1.0]hexan-3-yl)-1H-pyrazol-4-yl)-5-(trifluoromethyl)pyrimidin-2-amine (A-69) and 4-cyclopropyl-N-(3-methyl-1-((1R,3s,5S,6r)-6-(1-methyl-1H-1,2,4-triazol-5-yl)bicyclo[3.1.0]hexan-3-yl)-1H-pyrazol-4-yl)-5-(trifluoromethyl)pyrimidin-2-amine (A-70) and 4-cyclopropyl-N-(5-methyl-1-((1R,3s,5S,6r)-6-(1-methyl-1H-1,2,4-triazol-5-yl)bicyclo[3.1.0]hexan-3-yl)-1H-pyrazol-4-yl)-5-(trifluoromethyl)pyrimidin-2-amine (A-68)

1-(cyclopent-3-en-1-yl)-5-methyl-4-nitro-1H-pyrazole and 1-(cyclopent-3-en-1-yl)-3-methyl-4-nitro-1H-pyrazole To a solution of 3-methyl-4-nitro-1H-pyrazole (20 g, 157.36 mmol), cyclopent-3-en-1-ol (15.88 g, 188.83 mmol) and PPh$_3$ (61.91 g, 236.04 mmol) in THF (300 mL) was added DIAD (47.73 g, 236.04 mmol) at 0° C. The mixture was stirred at 25° C. for 12 h. The reaction mixture was concentrated under reduced pressure to give a residue, which was purified by silica gel chromatography (PE:EtOAc=50:1 to 20:1) to give a mixture of 1-(cyclopent-3-en-1-yl)-5-methyl-4-nitro-1H-pyrazole and 1-(cyclopent-3-en-1-yl)-3-methyl-4-nitro-1H-pyrazole as a yellow oil. LCMS: RT 1.301 min, m/z=194.1 [M+H]$^+$.

Ethyl 3-(5-methyl-4-nitro-1H-pyrazol-1-yl)bicyclo[3.1.0]hexane-6-carboxylate and ethyl 3-(3-methyl-4-nitro-1H-pyrazol-1-yl)bicyclo[3.1.0]hexane-6-carboxylate To a mixture of 1-cyclopent-3-en-1-yl-5-methyl-4-nitro-pyrazole and 1-cyclopent-3-en-1-yl-3-methyl-4-nitro-pyrazole (10 g, 51.76 mmol), bis [(Z)-1-methyl-3-oxo-but-1-enoxy]copper (948 mg, 3.62 mmol) in DCE (300 mL) was added a solution of ethyl 2-diazoacetate (23.6 g, 207.04 mmol) in DCE (600 mL) over a period of 12 h at 90° C. The mixture was stirred at 90° C. for 4 h. The reaction mixture was concentrated under reduced pressure to give a residue, which was purified by silica gel column chromatography (PE:EtOAc=20:1 to 5:1) to give a mixture of ethyl 3-(5-methyl-4-nitro-1H-pyrazol-1-yl)bicyclo[3.1.0]hexane-6-carboxylate and ethyl 3-(3-methyl-4-nitro-1H-pyrazol-1-yl)bicyclo[3.1.0]hexane-6-carboxylate as a yellow solid. LCMS: RT 0.831 min, m/z=280.1 [M+H]$^+$.

3-(5-methyl-4-nitro-1H-pyrazol-1-yl)bicyclo[3.1.0]hexane-6-carboxylic acid and 3-(3-methyl-4-nitro-1H-pyrazol-1-yl)bicyclo[3.1.0]hexane-6-carboxylic acid To a mixture of ethyl 3-(5-methyl-4-nitro-pyrazol-1-yl)bicyclo[3.1.0]hexane-6-carboxylate (4) and ethyl 3-(3-methyl-4-nitro-1H-pyrazol-1-yl)bicyclo[3.1.0]hexane-6-carboxylate (4A) (2.6 g, 9.31 mmol) in THF (40 mL) and H$_2$O (10 mL) was added LiOH.H$_2$O (781 mg, 18.62 mmol). The mixture was stirred at 25° C. for 12 h. The reaction mixture was poured into H$_2$O (30 mL) and extracted with MTBE (20 mL×2), the aqueous layer was separated and adjusted to pH=3 by 1N HCl, then it was extracted with EtOAc (2×30 mL), dried over Na$_2$SO$_4$, concentrated under reduced pressure to give a mixture of 3-(5-methyl-4-nitro-1H-pyrazol-1-yl)bicyclo[3.1.0]hexane-6-carboxylic acid and 3-(3-methyl-4-nitro-1H-pyrazol-1-yl)bicyclo[3.1.0]hexane-6-carboxylic acid as a white solid. LCMS: RT 1.072 min, m/z=252.1 [M+H]$^+$.

3-(5-methyl-4-nitro-1H-pyrazol-1-yl)bicyclo[3.1.0]hexane-6-carboxamide and 3-(3-methyl-4-nitro-1H-pyrazol-1-yl)bicyclo[3.1.0]hexane-6-carboxamide To a mixture of 3-(5-methyl-4-nitro-pyrazol-1-yl)bicyclo[3.1.0]hexane-6-carboxylic acid and 3-(5-methyl-4-nitro-pyrazol-1-yl)bicyclo[3.1.0]hexane-6-carboxylic acid (800 mg, 3.18 mmol) in DCM (20 mL) was added DMF (200 µL) and (COCl)$_2$ (807 mg, 6.36 mmol) drop-wise at 0° C. over a period of 10 min under N$_2$. The reaction mixture was then stirred at 25° C. for 1 h, concentrated under reduced pressure to give a residue. Then the residue was dissolved in THF (20 mL) and added dropwise to NH$_3$.H$_2$O (7.8 g, 222.6 mmol) at 25° C. The resulting mixture was stirred at 25° C. for 3 h. The reaction mixture was concentrated under reduced pressure and extracted with EtOAc (50 mL×2). The combined organic phase was washed with brine (50 mL), dried over Na$_2$SO$_4$, filtered and concentrated under reduced pressure to give a mixture of 3-(5-methyl-4-nitro-1H-pyrazol-1-yl)bicyclo[3.1.0]hexane-6-carboxamide and 3-(3-methyl-4-nitro-1H-pyrazol-1-yl)bicyclo[3.1.0]hexane-6-carboxamide. LCMS: RT 1.158 min, m/z=251.1 [M+H]$^+$.

(E)-N-((dimethylamino)methylene)-3-(5-methyl-4-nitro-1H-pyrazol-1-yl)bicyclo[3.1.0]hexane-6-carboxamide and (E)-N-((dimethylamino)methylene)-3-(3-methyl-4-nitro-1H-pyrazol-1-yl)bicyclo[3.1.0]hexane-6-carboxamide A mixture of 3-(5-methyl-4-nitro-pyrazol-1-yl)bicyclo[3.1.0]hexane-6-carboxamide and 3-(3-methyl-4-nitro-pyrazol-1-yl)bicyclo[3.1.0]hexane-6-carboxamide (800 mg, 3.2 mmol) in DMF-DMA (3.81 g, 32 mmol) was heated to 95° C. and stirred for 2 h. The mixture was cooled to 25° C., concentrated under reduced pressure to give a residue, which was slurried with MTBE (10 mL), filtered to give pure (E)-N-((dimethylamino)methylene)-3-(3-methyl-4-nitro-1H-pyrazol-1-yl)bicyclo[3.1.0]hexane-6-carboxamide (0.6 g) as a white solid. The filtrate was concentrated under reduced pressure to give a mixture of (E)-N-((dimethylamino)methylene)-3-(5-methyl-4-nitro-1H-pyrazol-1-yl)bicyclo[3.1.0]hexane-6-carboxamide and (E)-N-((dimethylamino)methylene)-3-(3-methyl-4-nitro-1H-pyrazol-1-yl)bicyclo[3.1.0]hexane-6-carboxamide. LCMS: RT 1.16 min, m/z=306.1 [M+H]$^+$.

3-(3-(3-methyl-4-nitro-1H-pyrazol-1-yl)bicyclo[3.1.0]hexan-6-yl)-1H-1,2,4-triazole To a solution of (E)-N-((dimethylamino)methylene)-3-(3-methyl-4-nitro-1H-pyrazol-1-yl)bicyclo[3.1.0]hexane-6-carboxamide (800 mg, 2.62 mmol) in AcOH (8 mL) was added NH$_2$NH$_2$.H$_2$O (1.97 g, 39.3 mmol). The mixture was stirred at 95° C. for 2 h. The reaction mixture was concentrated under reduced pressure and poured into ice-water (20 mL), adjusted to pH=9 with aq. NaHCO$_3$, and extracted with EtOAc (50 mL×2). The combined organic layers were washed with brine (50 mL), dried over Na$_2$SO$_4$, filtered and concentrated under reduced pressure, to give 3-(3-(3-methyl-4-nitro-1H-pyrazol-1-yl)bicyclo[3.1.0]hexan-6-yl)-1H-1,2,4-triazole. LCMS: RT 0.633 min, m/z=275.1 [M+H]$^+$.

1-methyl-3-(3-(3-methyl-4-nitro-1H-pyrazol-1-yl)bicyclo[3.1.0]hexan-6-yl)-1H-1,2,4-triazole and 1-methyl-5-(3-(3-methyl-4-nitro-1H-pyrazol-1-yl)bicyclo[3.1.0]hexan-6-yl)-1H-1,2,4-triazole To a solution of 3-[3-(3-methyl-4-nitro-pyrazol-1-yl)-6-bicyclo[3.1.0]hexanyl]-1H-1,2,4-triazole (8) (400 mg, 1.46 mmol) in MeCN (20 mL) was added MeI (248 mg, 1.75 mmol) and Cs$_2$CO$_3$ (476 mg, 1.46 mmol). The mixture was stirred at 50° C. for 12 h. The reaction mixture was filtered and concentrated under reduced pressure to give a residue, which was purified by prep-TLC (SiO$_2$, DCM:MeOH=10:1) to give a mixture of 1-methyl-3-(3-(3-methyl-4-nitro-1H-pyrazol-1-yl)bicyclo[3.1.0]hexan-6-yl)-1H-1,2,4-triazole and 1-methyl-5-(3-(3-methyl-4-nitro-1H-pyrazol-1-yl)bicyclo[3.1.0]hexan-6-yl)-1H-1,2,4-triazole. LCMS: RT 0.677 min, m/z=289.1 [M+H]$^+$.

3-methyl-1-(6-(1-methyl-1H-1,2,4-triazol-3-yl)bicyclo[3.1.0]hexan-3-yl)-1H-pyrazol-4-amine and 3-methyl-1-(6-(1-methyl-1H-1,2,4-triazol-5-yl)bicyclo[3.1.0]hexan-3-yl)-1H-pyrazol-4-amine A mixture of 1-methyl-3-(3-(3-methyl-4-nitro-1H-pyrazol-1-yl)bicyclo[3.1.0]hexan-6-yl)-1H-1,2,4-triazole and 1-methyl-5-(3-(3-methyl-4-nitro-1H-pyrazol-1-yl)bicyclo[3.1.0]hexan-6-yl)-1H-1,2,4-triazole (300 mg, 1.04 mmol), NH$_4$Cl (278 mg, 5.2 mmol) and Fe (290 mg, 5.2 mmol) in EtOH (25 mL) and H$_2$O (5 mL) was stirred at 90° C. for 2 h. It was filtered and die filtrate was concentrated under reduced pressure to give a residue, which was slurried with DCM:MeOH (V:V, 10:1.15 mL), filtered and the filtrate was concentrated under reduced pressure to give a mixture of 3-methyl-1-(6-(1-methyl-1H-1,2,4-triazol-3-yl)bicyclo[3.1.0]hexan-3-yl)-1H-pyrazol-4-amine and 3-methyl-1-(6-(1-methyl-1H-1,2,4-triazol-5-yl)bicyclo[3.1.0]hexan-3-yl)-1H-pyrazol-4-amine. LCMS: RT 0.369 min, m/z=259.2 [M+H]$^+$.

4-cyclopropyl-N-(3-methyl-1-((1R,3r,5S,6r)-6-(1-methyl-1H-1,2,4-triazol-3-yl)bicyclo[3.1.0]hexan-3-yl)-1H-pyrazol-4-yl)-5-(trifluoromethyl)pyrimidin-2-amine (A-69) and 4-cyclopropyl-N-(3-methyl-1-((1R,3s,5S,6r)-6-(1-methyl-1H-1,2,4-triazol-5-yl)bicyclo[3.1.0]hexan-3-yl)-1H-pyrazol-4-yl)-5-(trifluoromethyl)pyrimidin-2-amine (A-70)

A mixture of 3-methyl-1-(6-(1-methyl-1H-1,2,4-triazol-3-yl)bicyclo[3.1.0]hexan-3-yl)-1H-pyrazol-4-amine and 3-methyl-1-(6-(1-methyl-1H-1,2,4-triazol-5-yl)bicyclo[3.1.0]hexan-3-yl)-1H-pyrazol-4-amino (200 mg, 774.23 μmol), 4-cyclopropyl-2-methylsulfonyl-5-(trifluoromethyl)pyrimidine (247 mg, 929 μmol) and TFA (177 mg, 1.55 mmol) in 1,4-dioxane (30 mL) was degassed and purged with N$_2$ for 3 times, and then the mixture was stirred at 95° C. for 4 h under N$_2$. It was poured into H$_2$O (15 mL), adjusted to pH=8 with aq.NaHCO$_3$, extracted with EtOAc (30 mL×2). The combined organic phase was dried over Na$_2$SO$_4$, filtered and concentrated under reduced pressure to get a residue, which was purified by prep-HPLC (neutral) to give 4-cyclopropyl-N-(3-methyl-1-((1R,3r,5S,6r)-6-(1-methyl-1H-1,2,4-triazol-3-yl)bicyclo[3.1.0]hexan-3-yl)-1H-pyrazol-4-yl)-5-(trifluoromethyl)pyrimidin-2-amine (69) and 4-cyclopropyl-N-(3-methyl-1-((1R,3s,5S,6r)-6-(1-methyl-1H-1,2,4-triazol-5-yl)bicyclo[3.1.0]hexan-3-yl)-1H-pyrazol-4-yl)-5-(trifluoromethyl)pyrimidin-2-amino (70).

4-cyclopropyl-N-(3-methyl-1-((1R,3r,5S,6r)-6-(1-methyl-1H-1,2,4-triazol-3-yl)bicyclo[3.1.0]hexan-3-yl)-1H-pyrazol-4-yl)-5-(trifluoromethyl)pyrimidin-2-amine (A-69)

$^1$H NMR (400 MHz, CDCl$_3$): δ 8.41 (d, J=18.96 Hz, 1H), 7.76-7.91 (m, 2H), 6.55-6.71 (m, 1H), 4.30-4.45 (m, 1H), 3.85 (s, 3H), 2.33-2.59 (m, 4H), 2.15-2.29 (m, 4H), 1.96-2.04 (m, 3H), 1.22-1.30 (m, 2H), 1.05-1.17 (m, 2H). HPLC: RT 2.96 min. MS. [M+H]$^+$ m/z: 445.2.

4-cyclopropyl-N-(3-methyl-1-((1R,3s,5S,6r)-6-(1-methyl-1H-1,2,4-triazol-5-yl)bicyclo[3.1.0]hexan-3-yl)-1H-pyrazol-4-yl)-5-(trifluoromethyl)pyrimidin-2-amine (A-70)

$^1$H NMR (400 MHz, CDCl$_3$): δ 8.43 (br. s., 1H), 7.74-7.93 (m, 1H), 7.71 (s, 1H), 6.58-6.81 (m, 1H), 4.41 (t, J=8.16 Hz, 1H), 3.90 (s, 3H), 2.36-2.60 (m, 4H), 2.25 (s, 3H), 2.05-2.21 (m, 3H), 1.77 (br. s., 1H), 1.27 (br. s., 2H), 1.04-1.19 (m, 2H). HPLC: RT 2.60 min. MS: [M+H]$^+$ 445.2.

1-methyl-5-(3-(5-methyl-4-nitro-1H-pyrazol-1-yl)bicyclo[3.1.0]hexan-6-yl)-1H-1,2,4-triazole and 1-methyl-5-(3-(3-methyl-4-nitro-1H-pyrazol-1-yl)bicyclo[3.1.0]hexan-6-yl)-1H-1,2,4-triazole To a mixture of (E)-N-((dimethylamino)methylene)-3-(5-methyl-4-nitro-1H-pyrazol-1-yl)bicyclo[3.1.0]hexane-6-carboxamide and (E)-N-((dimethylamino)methylene)-3-(3-methyl-4-nitro-1H-pyrazol-1-yl)bicyclo[3.1.0]hexane-6-carboxamide (200 mg, crude) in AcOH (8 mL) was added methylhydrazine (1.32 g, 11.50 mmol). The mixture was stirred at 95° C. for 2 h. The reaction mixture was concentrated under reduced pressure and poured into ice-water (20 mL), adjusted to pH=9 with aq. NaHCO$_3$, and extracted with EtOAc (50 mL×2). The combined organic layers were washed with brine (50 mL), dried over Na$_2$SO$_4$, filtered and concentrated under reduced pressure to give a mixture of 1-methyl-5-(3-(5-methyl-4-nitro-1H-pyrazol-1-yl)bicyclo[3.1.0]hexan-6-yl)-1H-1,2,4-triazole and 1-methyl-5-(3-(3-methyl-4-nitro-1H-pyrazol-1-yl)bicyclo[3.1.0]hexan-6-yl)-1H-1,2,4-triazole as yellow oil. LCMS: RT 0.950 min, m/z=289.1 [M+H]$^+$.

5-methyl-1-(6-(1-methyl-1H-1,2,4-triazol-5-yl)bicyclo[3.1.0]hexan-3-yl)-1H-pyrazol-4-amine and 3-methyl-1-(6-(1-methyl-1H-1,2,4-triazol-5-yl)bicyclo[3.1.0]hexan-3-yl)-1H-pyrazol-4-amine A mixture of 1-methyl-5-(3-(5-methyl-4-nitro-1H-pyrazol-1-yl)bicyclo[3.1.0]hexan-6-yl)-1H-1,2,4-triazole and 1-methyl-5-(3-(3-methyl-4-nitro-1H-pyrazol-1-yl)bicyclo [3.1.0]hexan-6-yl)-1H-1,2,4-triazole (0.2 g, crude), NH$_4$Cl (195 mg, 3.64 mmol) and Fe (203 mg, 3.64 mmol) in EtOH (25 mL) and H$_2$O (5 mL) was stirred at 90° C. for 2 h. It was filtered and the filtrate was concentrated under reduced pressure to give a residue, which was slurry with DCM:MeOH (V:V, 10:1, 15 mL), filtered and the filtrate was concentrated under reduced pressure to give a mixture of 5-methyl-1-(6-(1-methyl-1H-1,2,4-triazol-5-yl)bicyclo[3.1.0]hexan-3-yl)-1H-pyrazol-4-amine and 3-methyl-1-(6-(1-methyl-1H-1,2,4-triazol-5-yl)bicyclo[3.1.0]hexan-3-yl)-1H-pyrazol-4-amine as a yellow oil. LCMS: RT 0.320 min, m/z=259.2 [M+H]$^+$.

4-cyclopropyl-N-(5-methyl-1-((1R,3s,5S,6r)-6-(1-methyl-1H-1,2,4-triazol-5-yl)bicyclo[3.1.0]hexan-3-yl)-1H-pyrazol-4-yl)-5-(trifluoromethyl)pyrimidin-2-amine (A-68)

A mixture of 5-methyl-1-(6-(1-methyl-1H-1,2,4-triazol-5-yl)bicyclo[3.1.0]hexan-3-yl)-1H-pyrazol-4-amine and 3-methyl-1-(6-(1-methyl-1H-1,2,4-triazol-5-yl)bicyclo[3.1.0]hexan-3-yl)-1H-pyrazol-4-amine (188 mg, crude), 4-cyclopropyl-2-methylsulfonyl-5-(trifluoromethyl)pyrimidine (235 mg, 883 μmol) and TFA (168 mg, 1.47 mmol) in 1,4-dioxane (30 mL) was degassed and purged with N$_2$ for 3 times, and then the mixture was stirred at 95° C. for 4 h under N$_2$. It was poured into H$_2$O (15 mL), adjusted to pH=8 with aq.NaHCO$_3$, extracted with EtOAc (30 mL×2). The combined organic phase was dried over Na$_2$SO$_4$, filtered and concentrated under reduced pressure to get a residue, which was purified by prep-HPLC (neutral) and then it was separated by SFC to give 4-cyclopropyl-N-(5-methyl-1-((1R,3s,5S,6r)-6-(1-methyl-1H-1,2,4-triazol-5-yl)bicyclo[3.1.0]hexan-3-yl)-1H-pyrazol-4-yl)-5-(trifluoromethyl)pyrimidin-2-amine (68). $^1$H NMR (400 MHz, CDCl$_3$): δ 8.38 (s, 1H), 7.55-7.74 (m, 2H), 6.44-6.70 (m, 1H), 4.37 (br. s., 1H), 3.92 (s, 3H), 2.66 (br. s., 2H), 2.40 (dd, J=13.16, 7.89 Hz, 2H), 2.21 (s, 3H), 2.16 (br. s., 2H), 1.73 (br. s., 1H), 1.19-1.25 (m, 2H), 1.08 (d, J=4.38 Hz, 2H). HPLC: RT 2.86 min. MS: [M+H]$^+$ m/z: 445.2.

Example A-48

Synthesis of N-(1-(2-(2H-1,2,3-triazol-4-yl)propan-2-yl)-3-methyl-1H-pyrazol-4-yl)-4-cyclopropyl-5-(trifluoromethyl)pyrimidin-2-amine (A-71)

1-(2-(2H-1,2,3-triazol-4-yl)propan-2-yl)-3-methyl-1H-pyrazol-4-amine

To a solution of 4-(2-(3-methyl-4-nitro-1H-pyrazol-1-yl)propan-2-yl)-2H-1,2,3-triazole (100 mg, 0.42 mmol) in EtOH (2 mL) and water (0.5 mL) was added NH$_4$Cl (68 mg, 1.27 mmol) and Fe (71 mg, 1.27 mmol), then the mixture was stirred at 100° C. for 1 h. The reaction mixture was concentrated under reduced pressure, then diluted with EtOAc (5 mL×2) and filtered. The filtrate was concentrated under reduced pressure to give 1-(2-(2H-1,2,3-triazol-4-yl)propan-2-yl)-3-methyl-1H-pyrazol-4-amine as a brown solid. LCMS: RT 0.11 min, m/z=207.2 [M+H]$^+$.

N-(1-(2-(2H-1,2,3-triazol-4-yl)propan-2-yl)-3-methyl-1H-pyrazol-4-yl)-4-cyclopropyl-5-(trifluoromethyl)pyrimidin-2-amine (A-71)

To a solution of 1-(2-(2H-1,2,3-triazol-4-yl)propan-2-yl)-3-methyl-1H-pyrazol-4-amine (40 mg, 0.19 mmol) in 1,4-dioxane (2 mL) was added 4-cyclopropyl-2-(methylsulfonyl)-5-(trifluoromethyl)pyrimidine (57 mg, 0.21 mmol) and TFA (44 mg, 0.029 mL, 0.39 mmol). Then the mixture was stirred at 100° C. for 1 h. The mixture was concentrated under reduced pressure to give a residue, which was purified by prep-HPLC (neutral) to give N-(1-(2-(2H-1,2,3-triazol-4-yl)propan-2-yl)-3-methyl-1H-pyrazol-4-yl)-4-cyclopropyl-5-(trifluoromethyl)pyrimidin-2-amine. $^1$H NMR 400 MHz, CHLOROFORM-d): δ 8.40 (br. s., 1H), 7.90 (br. s., 1H), 7.47 (br. s., 1H), 6.88 (br. s., 1H), 2.27 (s, 3H), 2.21 (br. s., 1H), 2.03 (s, 6H), 1.19 (br. s., 2H), 1.11 (d, J=7.6 Hz, 2H). HPLC: Retention Time: 2.81 min. MS: [M+H]$^+$ m/z: 393.1.

Example A-49

Synthesis of 4-cyclopropyl-N-(1-(2-(1-(difluoromethyl)-1H-1,2,4-triazol-3-yl)propan-2-yl)-3-methyl-1H-pyrazol-4-yl)-5-(trifluoromethyl)pyrimidin-2-amine (A-72) and 4-cyclopropyl-N-(1-(2-(1-(difluoromethyl)-1H-1,2,4-triazol-5-yl)propan-2-yl)-3-methyl-1H-pyrazol-4-yl)-5-(trifluoromethyl)pyrimidin-2-amine (A-73)

1-(difluoromethyl)-3-[1-methyl-1-(3-methyl-4-nitropyrazol-1-yl)ethyl]-1,2,4-triazole and 1-(difluoromethyl)-5-[1-methyl-1-(3-methyl-4-nitro-pyrazol-1-yl)ethyl]-1,2,4-triazole To a mixture of 3-[1-methyl-1-(3-methyl-4-nitro-pyrazol-1-yl)ethyl]-1H-1,2,4-triazole (5 g, 21.17 mmol) in DMF (50 mL) was added K$_2$CO$_3$ (8.78 g, 63.51 mmol) at 20° C. The mixture was heated to 90° C. then chloro(difluoro)methane was bubbled into the mixture at 90° C. for 1 h. The mixture was cooled to 20° C. and poured into ice-water (300 mL). The aqueous phase was extracted with EtOAc (3×100 mL). The combined organics were washed with brine (50 mL), dried over anhydrous Na$_2$SO$_4$, filtered and concentrated under reduced pressure. The residue was purified by silica gel column chromatography (PE:EtOAc=10:1 to 0:1) to give 1-(difluoromethyl)-3-[1-methyl-1-(3-methyl-4-nitro-pyrazol-1-yl)ethyl]-1,2,4-triazole as a yellow oil and 1-(difluoromethyl)-5-[1-methyl-1-(3-methyl-4-nitro-pyrazol-1-yl)ethyl]-1,2,4-triazole as a yellow oil. LCMS: RT 0.735 min, m/z=287.2 [M+H]$^+$.

1-(2-(1-(difluoromethyl)-1H-1,2,4-triazol-3-yl)propan-2-yl)-3-methyl-1H-pyrazol-4-amine To a mixture of 1-(difluoromethyl)-3-[1-methyl-1-(3-methyl-4-nitro-pyrazol-1-yl)ethyl]-1,2,4-triazole (2.37 g, 8.28 mmol) in EtOH (96 mL) and H$_2$O (24 mL) was added NH$_4$Cl (2.21 g, 41.40 mmol) and Fe (2.31 g, 41.40 mmol) at 20° C. The mixture was heated to 80° C. and stirred for 1 h. The mixture was cooled to 20° C. and concentrated under reduced pressure. The residue was added with water (30 mL). The aqueous phase was extracted with EtOAc (3×10 mL), washed with brine (10 mL), dried over anhydrous Na$_2$SO$_4$, filtered and concentrated under reduced pressure to give 1-(2-(1-(difluoromethyl)-1H-1,2,4-triazol-3-yl)propan-2-yl)-3-methyl-1H-pyrazol-4-amine as a brown oil. LCMS: RT 1.012 min, m/z=257.2 [M+H]$^+$.

4-cyclopropyl-N-(1-(2-(1-(difluoromethyl)-1H-1,2,4-triazol-3-yl)propan-2-yl)-3-methyl-1H-pyrazol-4-yl)-5-(trifluoromethyl)pyrimidin-2-amine To a mixture of 1-(2-(1-(difluoromethyl)-1H-1,2,4-triazol-3-yl)propan-2-yl)-3-methyl-1H-pyrazol-4-amine (100 mg, 390.24 µmol) and 4-cyclopropyl-2-methylsulfonyl-5-(trifluoromethyl)pyrimidine (86 mg, 325.20 µmol) in 1,4-dioxane (1 mL) was added TFA (74 mg, 650.40 µmol, 48.16 µL) at 20° C. The mixture was heated to 90° C. and stirred for 2 h. The mixture was cooled to 20° C. and adjusted pH=7-8 by adding aq. NaHCO$_3$. The aqueous phase was extracted with EtOAc (3×5 mL), washed with brine (5 mL), dried over anhydrous Na$_2$SO$_4$, filtered and concentrated under reduced pressure. The residue was purified by prep-HPLC (neutral) to give 4-cyclopropyl-N-(1-(2-(1-(difluoromethyl)-1H-1,2,4-triazol-3-yl)propan-2-yl)-3-methyl-1H-pyrazol-4-yl)-5-(trifluoromethyl)pyrimidin-2-amine as a brown solid. LCMS: RT 0.855 min, m/z=443.2 [M+H]+. $^1$H NMR (400 MHz, CDCl$_3$) δ ppm 8.45 (br. s., 1H), 8.40 (br. s., 1H), 7.97 (br. s., 1H), 7.04-7.42 (m, 2H), 6.73 (br. s., 1H), 2.25 (s, 4H), 2.06 (s, 6H), 1.18-1.29 (m, 2H), 1.03-1.16 (m, 2H). HPLC: RT 2.871 min. MS: [M+H]$^+$ m/z: 443.1.

1-(2-(1-(difluoromethyl)-1H-1,2,4-triazol-5-yl)propan-2-yl)-3-methyl-1H-pyrazol-4-amine To a mixture of 1-(difluoromethyl)-5-[1-methyl-1-(3-methyl-4-nitro-pyrazol-1-yl)ethyl]-1,2,4-triazole (1.97 g, 6.88 mmol) in EtOH (48 mL) and H$_2$O (12 mL) was added NH$_4$Cl (1.84 g, 34.41 mmol) and Fe (1.92 g, 34.41 mmol) at 20° C. The mixture was heated to 80° C. and stirred for 1 h. The mixture was cooled to 20° C. and concentrated under reduced pressure. The residue was added into water (20 mL) and extracted with EtOAc (3×8 mL). The combined organic phase was washed with brine (10 mL), dried over anhydrous Na$_2$SO$_4$, filtered and concentrated under reduced pressure to give 1-(2-(1-(difluoromethyl)-1H-1,2,4-triazol-5-yl)propan-2-yl)-3-methyl-1H-pyrazol-4-amine as a brown solid. LCMS: RT 0.924 min, m/z=257.2 [M+H]$^+$.

4-cyclopropyl-N-(1-(2-(1-(difluoromethyl)-1H-1,2,4-triazol-5-yl)propan-2-yl)-3-methyl-1H-pyrazol-4-yl)-5-(trifluoromethyl)pyrimidin-2-amine (A-73)

To a mixture of 1-(2-(1-(difluoromethyl)-1H-1,2,4-triazol-5-yl)propan-2-yl)-3-methyl-1H-pyrazol-4-amine (100 mg, 390.24 µmol) and 4-cyclopropyl-2-methylsulfonyl-5-(trifluoromethyl)pyrimidine (86 mg, 325.20 µmol) in 1,4-dioxane (1 mL) was added TFA (74 mg, 650.40 µmol, 48.16 µL) at 20° C. The mixture was heated to 90° C. and stirred for 2 h. The mixture was cooled to 20° C. and adjusted pH=7-8 by adding sat, aq. NaHCO$_3$ then was extracted with EtOAc (3×5 mL), washed with brine (5 mL), dried over anhydrous Na$_2$SO$_4$, filtered and concentrated under reduced pressure. The residue was purified by prep-HPLC (neutral) to give 4-cyclopropyl-N-(1-(2-(1-(difluoromethyl)-1H-1,2,4-triazol-5-yl)propan-2-yl)-3-methyl-1H-pyrazol-4-yl)-5-(trifluoromethyl)pyrimidin-2-amine. LCMS: RT 0.829 min, m/z=443.2 [M+H]$^+$. $^1$H NMR (400 MHz, CDCl3) δ ppm 8.45 (s, 1H), 8.43 (br. s., 1H), 8.01 (br. s., 1H), 6.76 (br. s., 1H), 6.19-6.54 (m, 1H), 2.20-2.30 (m, 4H), 2.05-2.15 (m, 6H), 1.14 (d, J=7.53 Hz, 4H). HPLC: RT 2.671 min. MS: [M+H]$^+$ m/z: 443.2.

Example A-50

Synthesis of 4-cyclopropyl-N-(3-methyl-1-(2-(5-methyl-1,3,4-oxadiazol-2-yl)propan-2-yl)-1H-pyrazol-4-yl)-5-(trifluoromethyl)pyrimidin-2-amine (A-74)

N'-acetyl-2-methyl-2-(3-methyl-4-nitro-1H-pyrazol-1-yl)propanehydrazide

To a solution of 2-methyl-2-(3-methyl-4-nitro-1H-pyrazol-1-yl)propanoic acid (2 g, 9.38 mmol) in DCM (80 mL) was added acetohydrazide (834 mg, 11.3 mmol), HATU (7.13 g, 18.8 mmol) and DIPEA (2.4 g, 3.3 mL, 18.8 mmol). The reaction mixture was stirred at 20° C. for 1 h. The mixture was concentrated under reduced pressure to give a residue, which was purified by silica gel column chromatography (PE:EtOAc=10:1 to EtOAc) to give N'-acetyl-2-methyl-2-(3-methyl-4-nitro-1H-pyrazol-1-ylpropanohydrazide as a yellow oil. LCMS: RT 0.627 min, m/z=270.2 [M+H]$^+$.

2-(4-((4-cyclopropyl-5-(trifluoromethyl)-7-((2-(trimethylsilyl)ethoxy)methyl)-7H-pyrrolo 2-methyl-5-(2-(3-methyl-4-nitro-1H-pyrazol-1-yl)propan-2-yl)-1,3,4-oxadiazole A solution of N$^1$-acetyl-2-methyl-2-(3-methyl-4-nitro-1H-pyrazol-1-ylpropanohydrazide (200 mg, 0.74 mmol) in POCl$_3$ (1 mL) was stirred at 100° C. for 2 h. The reaction mixture was poured into ice-water (2 mL), and extracted with EtOAc (3×2 mL). The combined organic layer was dried over Na$_2$SO$_4$ and concentrated under reduced pressure to give a residue, which was purified by prep-TLC (SiO$_2$, PE:EtOAc=1:1) to give 2-(4-((4-cyclopropyl-5-(trifluoromethyl)-7-((2-(trimethylsilyl)ethoxy)methyl)-7H-pyrrolo 2-methyl-5-(2-(3-methyl-4-nitro-1H-pyrazol-1-yl)propan-2-yl)-1,3,4-oxadiazole as a white solid. LCMS: RT 0.662 min, m/z=252.2 [M+H]$^+$.

3-methyl-1-(2-(5-methyl-1,3,4-oxadiazol-2-yl)propan-2-yl)-1H-pyrazol-4-amine

To a solution of Pd/C (80 mg) in MeOH (20 mL) was added 2-methyl-5-(2-(3-methyl-4-nitro-1H-pyrazol-1-yl)propan-2-yl)-1,3,4-oxadiazole (170 mg, 0.68 mmol), then the mixture was stirred at 20° C. for 2 h under H$_2$ (15 psi). The reaction mixture was concentrated under reduced pressure to give residue, which was diluted with EtOAc (3×20 mL). The filtrate was concentrated under reduced pressure to give 3-methyl-1-(2-(5-methyl-1,3,4-oxadiazol-2-yl)propan-2-yl)-1H-pyrazol-4-amino as a yellow solid. LCMS: RT 0.102 min, m/z=222.2 [M+H]$^+$.

4-cyclopropyl-N-(3-methyl-1-(2-(5-methyl-1,3,4-oxadiazol-2-yl)propan-2-yl)-1H-pyrazol-4-yl)-5-(trifluoromethyl)pyrimidin-2-amine (A-74)

To a solution of 3-methyl-1-(2-(5-methyl-1,3,4-oxadiazol-2-yl)propan-2-yl)-1H-pyrazol-4-amino (130 mg, 0.59 mmol) in 1,4-dioxane (3 mL) was added 4-cyclopropyl-2-(methylsulfonyl)-5-(trifluoromethyl)pyrimidine (157 mg, 0.59 mmol) and TFA (67 mg, 0.04 mL, 0.59 mmol). Then the mixture was stirred at 80° C. for 2 h. The mixture was concentrated under reduced pressure to give a residue, which was purified by prep-HPLC (neutral) to give 4-cyclopropyl-N-(3-methyl-1-(2-(5-methyl-1,3,4-oxadiazol-2-yl)propan-2-yl)-1H-pyrazol-4-yl)-5-(trifluoromethyl)pyrimidin-2-amino. $^1$H NMR (400 MHz, CHLOROFORM-d):δ8.42 (br. s., 1H), 7.96 (br. s., 1H), 6.67 (br. s., 1H), 2.51 (s, 3H), 2.24 (s, 3H), 2.20-2.24 (m, 1H), 2.07 (s, 6H), 1.23 (br. s., 2H), 1.14 (br. s., 2H). HPLC: RT 3.10 min. MS: [M+H]$^+$ m/z: 408.2.

Example A-51

Synthesis of (R)-4-cyclopropyl-N-(1-(6,7-dihydro-5H-pyrrolo[1,2-a]imidazol-7-yl)-3-methyl-1H-pyrazol-4-yl)-5-(trifluoromethyl)pyrimidin-2-amine and (S)-4-cyclopropyl-N-(1-(6,7-dihydro-5H-pyrrolo[1,2-a]imidazol-7-yl)-3-methyl-1H-pyrazol-4-yl)-5-(trifluoromethyl)pyrimidin-2-amine (A-78 and A-79)

(R)-4-cyclopropyl-N-(1-(6,7-dihydro-5H-pyrrolo[1,2-a]imidazol-7-yl)-3-methyl-1H-pyrazol-4-yl)-5-(trifluoromethyl)pyrimidin-2-amine and (S)-4-cyclopropyl-N-(1-(6,7-dihydro-5H-pyrrolo[1,2-a]imidazol-7-yl)-3-methyl-1H-pyrazol-4-yl)-5-(trifluoromethyl)pyrimidin-2-amine (A-78 and A-79)

To a solution of 1-(6,7-dihydro-5H-pyrrolo[1,2-a]imidazol-7-yl)-5-methyl-pyrazol-4-amino (200 mg, 984.06 μmol) and 1-(6,7-dihydro-5H-pyrrolo[1,2-a]imidazol-7-yl)-3-methyl-pyrazol-4-amine and 4-cyclopropyl-2-methylsulfonyl-5-(trifluoromethyl)pyrimidine (262 mg, 984.06 μmol) in 1,4-dioxane (5 mL) was added TFA (56 mg, 492.03 μmol). The mixture was stirred at 100° C. for 1 h. The reaction mixture was diluted with H$_2$O (20 mL), and adjusted with aq. NaHCO$_3$ (10 mL) to pH=8 and extracted with EtOAc (3×10 mL). The combined organic layers were washed with brine (10 mL), dried over Na$_2$SO$_4$, filtered and concentrated under reduced pressure to give a residue. The residue was purified by prep-HPLC (neutral) to give 70 mg mixture of product, which was purified by SFC to give (R)-4-cyclopropyl-N-(1-(6,7-dihydro-5H-pyrrolo[1,2-a]imidazol-7-yl)-3-methyl-1H-pyrazol-4-yl)-5-(trifluoromethyl)pyrimidin-2-amine (peak 1 in SFC, stereochemistry randomly assigned), and (S)-4-cyclopropyl-N-(1-(6,7-dihydro-5H-pyrrolo[1,2-a]imidazol-7-yl)-3-methyl-1H-pyrazol-4-yl)-5-(trifluoromethyl)pyrimidin-2-amine (peak 2 in SFC, stereochemistry randomly assigned).

First Eluting Isomer (Peak 1): 4-cyclopropyl-N-(1-(6,7-dihydro-5H-pyrrolo[1,2-a]imidazol-7-yl)-3-methyl-1H-pyrazol-4-yl)-5-(trifluoromethyl)pyrimidin-2-amine (A-78)

$^1$H NMR (400 MHz, CD$_3$OD): δ ppm 8.40 (s, 1H), 7.60-8.05 (m, 1H), 7.23-7.34 (m, 1H), 7.10-7.22 (m, 1H), 5.73-5.85 (m, 1H), 4.27-4.44 (m, 1H), 4.11-4.25 (m, 1H), 3.18-3.31 (m, 1H), 2.76-2.93 (m, 1H), 2.20 (br. s., 4H), 1.01-1.39 (m, 4H). HPLC: RT 2.373 min. MS: m/z: 390.2 [M+H]$^+$. SFC: RT 2.52 min.

Second Eluting Isomer (Peak 2): 4-cyclopropyl-N-(1-(6,7-dihydro-5H-pyrrolo[1,2-a]imidazol-7-yl)-3-methyl-1H-pyrazol-4-yl)-5-(trifluoromethyl)pyrimidin-2-amino (A-79)

$^1$H NMR (400 MHz, CD$_3$OD): δ ppm 8.41 (s, 1H), 7.69-8.07 (m, 1H), 7.29-7.41 (m, 1H), 7.18-7.27 (m, 1H), 5.77-5.93 (m, 1H), 4.31-4.49 (m, 1H), 4.14-4.28 (m, 1H), 3.21-3.30 (m, 1H), 2.77-2.93 (m, 1H), 2.20 (br. s., 4H), 1.03-1.38 (m, 4H). HPLC: RT 2.369 min. MS: m/z: 390.1 [M+H]$^+$. SFC: RT 2.58 min.

Example A-52

Synthesis of 4-cyclopropyl-N-(1-(difluoro(1-methyl-1H-1,2,4-triazol-3-yl)methyl)-3-methyl-1H-pyrazol-4-yl)-5-(trifluoromethyl)pyrimidin-2-amine (A-77), 4-cyclopropyl-N-[1-[difluoro(1H-1,2,4-triazol-3-yl)methyl]-3-methyl-pyrazol-4-yl]-5-(trifluoromethyl)pyrimidin-2-amine (A-75) and 4-cyclopropyl-N-[1-[difluoro-(2-methyl-1,2,4-triazol-3-yl)methyl]-3-methyl-pyrazol-4-yl]-5-(trifluoromethyl)pyrimidin-2-amine (A-76)

N'-acetyl-2-methyl-2-(3-methyl-4-nitro-1H-pyrazol-1-yl)propanehydrazide

To a solution of tert-butyl N-[1-(2-amino-1,1-difluoro-2-oxo-ethyl)-3-methyl-pyrazol-4-yl]carbamate (653 mg, 2.25 mmol) and 4-cyclopropyl-2-methylsulfonyl-5-(trifluoromethyl)pyrimidine (599 mg, 2.25 mmol) in 1,4-dioxane (10 mL) was added p-TsOH (387 mg, 2.25 mmol). The mixture was stirred at 100° C. for 10 h. The reaction solution was concentrated under reduced pressure. The residue was added with water (20 mL), adjusted to pH=7 with aq.NaHCO$_3$. The aqueous phase was extracted with EtOAc (3×10 mL). The organic layers were combined, washed with brine (5 mL), dried over Na$_2$SO$_4$, filtered and concentrated under reduced pressure to give 2-[4-[[4-cyclopropyl-5-(trifluoromethyl)pyrimidin-2-yl]amino]-3-methyl-pyrazol-1-yl]-2,2-difluoro-acetamide as a yellow solid. LCMS: RT 0.822 min, m/z=377.1 [M+H]$^+$.

2-[4-[[4-cyclopropyl-5-(trifluoromethyl)pyrimidin-2-yl]amino]-3-methyl-pyrazol-1-yl]-N-(dimethylaminomethylene)-2,2-difluoro-acetamide A mixture of 2-[4-[[4-cyclopropyl-5-(trifluoromethyl)pyrimidin-2-yl]amino]-3-methyl-pyrazol-1-yl]-2,2-difluoro-acetamide (720 mg, 1.91 mmol), DMF-DMA (3.25 g, 27.27 mmol, 3.61 mL) was degassed and purged with N$_2$ for 3 times, and then the mixture was stirred at 10-30° C. for 12 h under N$_2$. The reaction mixture was concentrated under reduced pressure to give 2-[4-[[4-cyclopropyl-5-(trifluoromethyl)pyrimidin-2-yl]amino]-3-methyl-pyrazol-1-yl]-N-(dimethylaminomethylene)-2,2-difluoro-acetamide as a yellow oil. LCMS: RT 0.807 min, m/z=432.1 [M+H]$^+$.

4-cyclopropyl-N-(1-(difluoro(1H-1,2,4-triazol-3-yl)methyl)-3-methyl-1H-pyrazol-4-yl)-5-(trifluoromethyl)pyrimidin-2-amine (A-77)

To a solution of (NE)-2-[4-[[4-cyclopropyl-5-(trifluoromethyl)pyrimidin-2-yl]amino]-3-methyl-pyrazol-1-yl]-N-(dimethylaminomethylene)-2,2-difluoro-acetamide (200 mg, 463.65 μmol) in AcOH (2 mL) was added NH$_2$NH$_2$.H$_2$O (23 mg, 463.65 μmol, 22.53 μL). The mixture was stirred at 15° C. for 2 h. The reaction solution was poured into ice-water (5 mL), adjusted to pH=7 with aq. NaHCO$_3$, extracted with EtOAc (3×5 mL). The organic layers were combined, washed with brine (5 mL), dried over Na$_2$SO$_4$, filtered and concentrated under reduced pressure. The residue was purified by prep-HPLC(FA) to give 4-cyclopropyl-N-[1-[difluoro(1H-1,2,4-triazol-3-yl)methyl]-3-methyl-pyrazol-4-yl]-5-(trifluoromethyl)pyrimidin-2-amine. $^1$H NMR 400 MHz. CHLOROFORM-d): δ 8.40 (s., 1H), 8.28 (s., 2H), 6.51-6.97 (br, 1H), 2.21 (s, 4H), 1.17-1.26 (m, 2H), 1.09 (m, 2H). HPLC: RT 2.76 min MS: (M+H$^+$) m z 401.1

4-cyclopropyl-N-[1-[difluoro(1-methyl-1H-1,2,4-triazol-3-yl)methyl]-3-methyl-pyrazol-4-yl]-5-(trifluoromethyl)pyrimidin-2-amino and 4-cyclopropyl-N-[1-[difluoro-(2-methyl-1,2,4-triazol-3-yl)methyl]-3-methyl-pyrazol-4-yl]-5-(trifluoromethyl)pyrimidin-2-amine (A-75 and A-76)

To a solution of 4-cyclopropyl-N-[1-[difluoro(1H-1,2,4-triazol-3-yl)methyl]-3-methyl-pyrazol-4-yl]-5-(trifluoromethyl)pyrimidin-2-amine (500 mg, 1.25 mmol, crude) in MeCN (10 mL) was added MeI (532 mg, 3.75 mmol, 233.27 µL) and $K_2CO_3$ (518 mg, 3.75 mmol). The mixture was stirred at 15° C. for 10 h. The mixture was filtered and the filtrate was concentrated under reduced pressure. The residue was purified by prep-HPLC (FA) to give 4-cyclopropyl-N-[1-[difluorodi-methyl-1,2,4-triazol-3-yl)methyl]-3-methyl-pyrazol-4-yl]-5-(trifluoromethyl)pyrimidin-2-amine and 4-cyclopropyl-N-[1-[difluoro-(2-methyl-1,2,4-triazol-3-yl)methyl]-3-methyl-pyrazol-4-yl]-5-(trifluoromethyl)pyrimidin-2-amine.

4-cyclopropyl-N-[1-[difluoro(1-methyl-1H-1,2,4-triazol-3-yl)methyl]-3-methyl-pyrazol-4-yl]-5-(trifluoromethyl)pyrimidin-2-amine (A-75)

$^1$H NMR (400 MHz, CHLOROFORM-d):δ8.46 (s., 1H), 8.29 (s., 1H), 8.17 (s, 1H), 6.89 (br. s., 1H), 4.04 (s, 3H), 2.16-2.33 (m, 4H), 1.24-1.32 (m, 2H), 1.15 (m, 2H). HPLC: RT 3.23 min. MS: [M+H]$^+$ m/z: 415.1.

4-cyclopropyl-N-[1-[difluoro-(2-methyl-1,2,4-triazol-3-yl)methyl]-3-methyl-pyrazol-4-yl]-5-(trifluoromethyl)pyrimidin-2-amine (A-76)

$^1$H NMR (400 MHz, CHLOROFORM-d) δ8.49 (s, 1H), 8.25-8.43 (m, 1H), 7.99 (s, 1H), 6.79 (br. s, 1H), 4.02 (s, 3H), 2.17-2.33 (m, 4H), 1.29 (m, 2H), 1.19 (m, 2H). HPLC: RT 3.47 min. MS: [M+H]$^+$ m/z: 415.1.

Example A-53

Synthesis of 4-cyclopropyl-N-(5-methyl-1-((1R,3S)-3-(1-methyl-1H-1,4-triazol-5-yl)cyclobutyl)-1H-pyrazol-4-yl)-5-(trifluoromethyl)pyrimidin-2-amine and 4-cyclopropyl-N-(3-methyl-1-((1R,3S)-3-(1-methyl-1H-1,2,4-triazol-5-yl)cyclobutyl)-1H-pyrazol-4-yl)-5-(trifluoromethyl)pyrimidin-2-amine (A-80 and A-81)

3-(5-methyl-4-nitro-1H-pyrazol-1-yl)cyclobutanecarboxamide and 3-(3-methyl-4-nitro-1H-pyrazol-1-yl)cyclobutanecarboxamide To a mixture of 3-(5-methyl-4-nitro-pyrazol-1-yl)cyclobutanecarboxylic acid and 3-(3-methyl-4-nitro-pyrazol-1-yl)cyclobutanecarboxylic acid (1 g, 4.44 mmol) in DCM (15 mL) was added a solution of oxalyl chloride (1.13 g, 8.88 mmol, 777.34 µL) and DMF (162.26 mg, 2.22 mmol) dropwise at 0° C. and stirred at 15° C. for 1 h. The reaction mixture was concentrated to get a residue. A mixture of the residue in THF (10 mL) was added to $NH_3·H_2O$ (20 mL) and stirred at 15° C. for 1 h. The mixture was concentrated to get 3-(5-methyl-4-nitro-1H-pyrazol-1-yl)cyclobutanecarboxamide and 3-(3-methyl-4-nitro-1H-pyrazol-1-yl)cyclobutanecarboxamide (1.2 g, crude). LCMS: RT 0.53 min, m/z=225.2 [M+H]$^+$.

N-((dimethylamino)methylene)-3-(5-methyl-4-nitro-1H-pyrazol-1-yl)cyclobutanecarboxamide and N-((dimethylamino)methylene)-3-(3-methyl-4-nitro-1H-pyrazol-1-yl)cyclobutanecarboxamide A solution of 3-(5-methyl-4-nitro-1H-pyrazol-1-yl)cyclobutanecarboxamide and 3-(3-methyl-4-nitro-1H-pyrazol-1-yl)cyclobutanecarboxamide (500 mg, 2.23 mmol) in DMF-DMA (5 mL) was stirred at 80° C. for 2 h. The reaction mixture was concentrated under reduced pressure to get N-((dimethylamino)methylene)-3-(5-methyl-4-nitro-1H-pyrazol-1-yl)cyclobutanecarboxamide and N-((dimethylamino)methylene)-3-(3-methyl-4-nitro-1H-pyrazol-1-yl)cyclobutanecarboxamide as a yellow gum. LCMS: RT 0.548 mm, m/z=280.2 [M+H]$^+$.

1-methyl-5-((1r,3r)-3-(3-methyl-4-nitro-1H-pyrazol-1-yl)cyclobutyl)-1H-1,2,4-triazole and 1-methyl-5-((1r,3r)-3-(5-methyl-4-nitro-1H-pyrazol-1-yl)cyclobutyl)-1H-1,2,4-triazole To a solution of N-((dimethylamino)methylene)-3-(5-methyl-4-nitro-1H-pyrazol-1-yl)cyclobutanecarboxamide and N-((dimethylamino)methylene)-3-(3-methyl-4-nitro-1H-pyrazol-1-yl)cyclobutanecarboxamide (620 mg, 2.23 mmol) in $CH_3COOH$ (6 mL) was added methylhydrazine (2.57 g, 22.30 mmol, 2.92 mL, 40% purity). The mixture was stirred at 90° C. for 2 h. The reaction mixture was concentrated under reduced pressure. The residue was diluted with water (60 mL), adjust to pH=8 by aq. $NaHCO_3$, and extracted with EtOAc (3×30 mL). The combined organic layers were washed with brine (20 mL), dried over $Na_2SO_4$, filtered and concentrated under reduced pressure to give a residue. The residue was purified by prep-TLC ($SiO_2$, DCM:MeOH=20:1), to give 1-methyl-5-((1r,3r)-3-(3-methyl-4-nitro-1H-pyrazol-1-yl)cyclobutyl)-1H-1,2,4-triazole and 1-methyl-5-((1 r,3r)-3-(5-methyl-4-nitro-1H-pyrazol-1-yl)cyclobutyl)-1H-1,2,4-triazole. LCMS. RT 0.881 mm, m/z=263.1 [M+H]$^+$.

5-methyl-1-((1r,3r)-3-(1-methyl-1H-1,2,4-triazol-5-yl)cyclobutyl)-1H-pyrazol-4-amine To a solution of 1-methyl-5-((1r,3r)-3-(5-methyl-4-nitro-1H-pyrazol-1-yl)cyclobutyl)-1H-1,2,4-triazole (40 mg, 152.51 µmol) in MeOH (4 mL) was added Pd—C (10%, 0.02 g) under $N_2$. The suspension was degassed under vacuum and purged with $H_2$ several times. The mixture was stirred under $H_2$ (15 psi) at 15° C. for 2 h. The reaction mixture was filtered and the filtrate was concentrated to give 5-methyl-1-((1r,3r)-3-(1-methyl-1H-1,2,4-triazol-5-yl)cyclobutyl)-1H-pyrazol-4-amine as a yellow solid. LCMS: RT 0.173 mm, m/z=233.1[M+H]$^+$.

3-methyl-1-((1 r,3r)-3-(1-methyl-1H-1,2,4-triazol-5-yl)cyclobutyl)-1H-pyrazol-4-amine To a solution of 1-methyl-5-((1r,3r)-3-(3-methyl-4-nitro-1H-pyrazol-1-yl)cyclobutyl)-1H-1,2,4-triazole (60 mg, 228.78 µmol) in EtOH (2 mL) and $H_2O$ (0.5 mL) was added Fe (64 mg, 1.14 mmol) and $NH_4Cl$ (61 mg, 1.14 mmol). The mixture was stirred at 80° C. for 2 h. The reaction mixture was filtered and the filtrate was concentrated. The residue was added with EtOAc and filtered. The filtrate was concentrated to give 3-methyl-1-((1r,3r)-3-(1-methyl-1H-1,2,4-triazol-5-yl)cyclobutyl)-1H-pyrazol-4-amine as a yellow gum.

4-cyclopropyl-N-(5-methyl-1-((1r,3r)-3-(1-methyl-1H-1,2,4-triazol-5-yl)cyclobutyl)-1H-pyrazol-4-yl)-5-(trifluoromethyl)pyrimidin-2-amine (A-80)

A mixture of 5-methyl-1-((1r,3r)-3-(1-methyl-1H-1,2,4-triazol-5-yl)cyclobutyl)-1H-pyrazol-4-amine (35 mg, 150.68 µmol), 4-cyclopropyl-2-methylsulfonyl-5-(trifluoromethyl)pyrimidine (32 mg, 120.54 µmol) and TsOH.H$_2$O (29 mg, 150.68 µmol) in 1,4-dioxane (3 mL) was degassed and purged with N$_2$ for 3 times, and then the mixture was stirred at 90° C. for 6 h under N$_2$. The residue was diluted with H$_2$O (20 mL), adjusted to pH=8 by aq. NaHCO$_3$ and then extracted with EtOAc (3×10 mL). The combined organic layers were washed with brine (10 mL), dried over Na$_2$SO$_4$, filtered and concentrated under reduced pressure to give a residue, which was purified by prep-HPLC (FA) to give 4-cyclopropyl-N-(5-methyl-1-((1r,3r)-3-(1-methyl-1H-1,2,4-triazol-5-yl)cyclobutyl)-1H-pyrazol-4-yl)-5-(trifluoromethyl)pyrimidin-2-amine. $^1$H NMR (400 MHz, CDCl$_3$): δ 8.38 (s, 1H), 7.87 (s, 1H), 7.74 (br. s., 1H), 5.11 (t, J=7.59 Hz, 1H), 3.81 (s, 3H), 3.76 (dt, J=9.47, 4.67 Hz, 1H), 3.22 (q, J=9.62 Hz, 2H), 2.85 (t, J=8.47 Hz, 2H), 2.19 (s, 4H) 1.25 (d, J=2.51 Hz, 2H), 1.09 (dd, J=7.59, 3.20 Hz, 2H). HPLC: RT: 3.06 min. MS: m/z: 419.2 [M+H]$^+$

4-cyclopropyl-N-(3-methyl-1-((1r,3r)-3-(1-methyl-1H-1,2,4-triazol-5-yl)cyclobutyl)-1H-pyrazol-4-yl)-5-(trifluoromethyl)pyrimidin-2-amine (A-81)

A mixture of 3-methyl-1-((1r,3r)-3-(1-methyl-1H-1,2,4-triazol-5-yl)cyclobutyl)-1H-pyrazol-4-amine (50 mg, 215.25 µmol), 4-cyclopropyl-2-methylsulfonyl-5-(trifluoromethyl)pyrimidine (46 mg, 172.20 µmol), TsOH.H$_2$O (61 mg, 322.88 µmol) in ethylene glycol monomethyl ether (2 mL) was degassed and purged with N$_2$ for 3 times, and then the mixture was stirred at 110° C. for 5 h under N$_2$. The reaction mixture was concentrated under reduced pressure. The residue was diluted with H$_2$O (20 mL), adjusted to pH=8 by aq. NaHCO$_3$ and then extracted with EtOAc (3×10 mL). The combined organic layers were washed with brine (10 mL), dried over Na$_2$SO$_4$, filtered and concentrated under reduced pressure to give a residue, which was purified by prep-HPLC (FA) to give 4-cyclopropyl-N-(3-methyl-1-((1r,3r)-3-(1-methyl-1H-1,2,4-triazol-5-yl)cyclobutyl)-1H-pyrazol-4-yl)-5-(trifluoromethyl)pyrimidin-2-amine. $^1$HNMR (400 MHz, CDCl$_3$): δ 8.42 (br. s., 1H), 7.86 (s, 1H), 7.80 (br. s., 1H), 5.07 (t, J=7.72 Hz, 1H), 3.81 (s, 3H), 3.73 (dt, J=9.22, 4.80 Hz, 1H), 3.11-3.20 (m, 2H), 2.87 (br. s., 2H), 2.30 (s, 3H), 2.23 (br. s., 1H), 1.23-1.30 (m, 2H), 1.06-1.19 (m, 2H). HPLC: RT: 2.90 min. MS: m/z: 419.1 [M+H]$^+$.

Example A-54

Synthesis of 4-cyclopropyl-N-[1-[(7R)-6,7-dihydro-5H-pyrrolo[2,1-c][1,2,4]triazol-7-yl]-3-methyl-pyrazol-4-yl]-5-(trifluoromethyl)pyrimidin-2-amine and 4-cyclopropyl-N-[1-[(7S)-6,7-dihydro-5H-pyrrolo[2,1-c][1,2,4]triazol-7-yl]-3-methyl-pyrazol-4-yl]-5-(trifluoromethyl)pyrimidin-2-amine (A-82 and A-83)

3-(3-methyl-4-nitro-pyrazol-1-yl)pyrrolidin-2-one

To a solution of 3-methyl-4-nitro-1H-pyrazole (4.15 g, 32.64 mmol), 3-hydroxypyrrolidin-2-one (3 g, 29.67 mmol) and PPh3 (11.67 g, 44.51 mmol) in THF (100 mL) was added DIAB (9 g, 44.51 mmol) at 0° C. under N2. The mixture was stirred at 25° C. for 6 h. The mixture was filtered and filtrate was concentrated to give a residue. The residue was purified by silica gel column chromatography (PE:EtOAc=1:1) to give a crude product, which was triturated with MTBE (20 mL), to give 3-(3-methyl-4-nitropyrazol-1-ylpyrrolidin-2-one as a white solid. LCMS: RT 0.226 min, m/z=211.2 [M+H]+. 1H NMR (400 MHz, DMSO-d6): δ 8.89 (s, 1H), 8.25 (br. s., 1H), 5.09 (t, J=9.10 Hz, 1H), 3.27-3.42 (m, 3H), 2.53-2.60 (m, 2H), 2.43 (s, 3H).

3-(3-methyl-4-nitro-pyrazol-1-yl)pyrrolidine-2-thione

To a mixture of 3-(3-methyl-4-nitro-pyrazol-1-yl)pyrrolidin-2-one (1.1 g, 5.23 mmol) in toluene (20 mL) was added Lawesson's reagent (1.06 g, 2.62 mmol). The mixture was then heated to 110° C. and stirred for 2 h. The mixture was concentrated under reduced pressure to give a residue. The residue was added with EtOAc (10 mL) and filtered. The filtrate was concentrated to afford 3-(3-methyl-4-nitro-pyrazol-1-yl)pyrrolidine-2-thione as a white solid. LCMS. RT 0.458 min, m/z=227.1 [M+H]+. 1H NMR (400 MHz, DMSO-d6): δ 10.75 (br. s., 1H), 8.92 (s, 1H), 5.33 (t, J=8.60 Hz, 1H), 3.59-3.72 (m, 2H), 2.59-2.69 (m, 3H), 2.43 (s, 3H).

3-methyl-1-(5-methylsulfanyl-3,4-dihydro-2H-pyrrol-4-yl)-4-nitro-pyrazole

To a mixture of 3-(3-methyl-4-nitro-pyrazol-1-yl)pyrrolidine-2-thione (1.07 g, 4.73 mmol) and K2CO3 (3.27 g, 23.65 mmol) in THF (20 mL) was added CH3I (3.36 g, 23.65 mmol, 1.47 mL). The mixture was then stirred at 25° C. for 16 h. The reaction mixture was filtered and the filtrate was concentrated to give 3-methyl-1-(5-methylsulfanyl-3,4-dihydro-2H-pyrrol-4-yl)-4-nitro-pyrazole) as a white solid. LCMS: RT 0.839 min, m/z=241.1 [M+H]+.

7-(3-methyl-4-nitro-pyrazol-1-yl)-6,7-dihydro-5H-pyrrolo[2,1-c][1,2,4]triazole To a solution of 3-methyl-1-(5-methylsulfanyl-3,4-dihydro-2H-pyrrol-4-yl)-4-nitro-pyrazole (800 mg, 3.33 mmol) in HCOOH (2 mL) and triethoxymethane (2 mL) was added formohydrazide (199 mg, 3.33 mmol) at 25° C. under N2. The mixture was then heated to 150° C. and stirred for 2 h. The mixture was cooled to 25° C. and concentrated under reduced pressure. The residue was poured into ice-water (100 mL). The aqueous phase was extracted with EtOAc (3×50 mL). The combined organic phase was washed with brine (50 mL), dried with anhydrous Na2SO4, filtered and concentrated. The residue was purified by prep-TLC (SiO$_2$, CH2Cl2:MeOH=10:1) to afford 7-(3-methyl-4-nitro-pyrazol-1-yl)-6,7-dihydro-5H-pyrrolo[2,1-c][1,2,4]triazole as a yellow solid. LCMS: RT 0.218 min, m/z=235.1 [M+H]+. 1H NMR (400 MHz. DMSO-d6): δ 9.03 (s, 1H), 8.56 (s, 1H), 6.03 (dd, J=3.97, 8.38 Hz, 1H), 4.27 (ddd, J=6.40, 7.94, 10.81 Hz, 1H), 4.15 (ddd, J=4.41, 8.38, 11.03 Hz, 1H), 3.24-3.30 (m, 1H), 2.86-2.95 (m, 1H), 2.39 (s, 3H).

1-(6,7-dihydro-5H-pyrrolo[2,1-c][1,2,4]triazol-7-yl)-3-methyl-pyrazol-4-amine To a solution of 7-(3-methyl-4-nitro-pyrazol-1-yl)-6,7-dihydro-5H-pyrrolo[2,1-c][1,2,4]triazole (123 mg, 525.17 µmol) in MeOH (10 mL) was added Pd—C (10% 20 mg) under N2. The suspension was degassed under vacuum and purged with H2 three times. The mixture was stirred under H2 (15 psi) at 25° C. for 2 h. The reaction mixture was filtered and the filtrate was concentrated to afford 1-(6,7-dihydro-5H-pyrrolo[2,1-c][1,2,4]triazol-7-yl)-3-methyl-pyrazol-4-amine as a yellow gum. LCMS: RT 0.085 min, m/z=205.1 [M+H]+.

4-cyclopropyl-N-[1-[(7R)-6,7-dihydro-5H-pyrrolo[2,1-c][1,2,4]triazol-7-yl]-3-methyl-pyrazol-4-yl]-5-(trifluoromethyl)pyrimidin-2-amine and 4-cyclopropyl-N-[1-[(7S)-6,7-dihydro-5H-pyrrolo[2,1-c][1,2,4]triazol-7-yl]-3-methyl-pyrazol-4-yl]-5-(trifluoromethyl)pyrimidin-2-amine (A-82 and A-83)

To a mixture of 1-(6,7-dihydro-5H-pyrrolo[2,1-c][1,2,4]triazol-7-yl)-3-methyl-pyrazol-4-amine (81 mg, 396.61 µmol) and 4-cyclopropyl-2-methylsulfonyl-5-(trifluoromethyl)pyrimidine (105 mg, 396.61 µmol) in ethylene glycol monomethyl ether (2 mL) was added TFA (4 mg, 39.66 µmol). The mixture was then heated to 100° C. and stirred for 2 h. The mixture was cooled to 25° C. and poured into saturated aqueous NaHCO3 (30 mL). The aqueous phase was extracted with EtOAc (3×10 mL). The combined organic phase was washed with brine (10 mL), dried with anhydrous Na2SO4, filtered and concentrated to give a residue. The residue was purified by prep-HPLC (neutral) and further separated by SFC to afford 4-cyclopropyl-N-[1-[(7R)-6,7-dihydro-5H-pyrrolo[2,1-c][1,2,4]triazol-7-yl]-3-methyl-pyrazol-4-yl]-5-(trifluoromethyl)pyrimidin-2-amine and 4-cyclopropyl-N-[1-[(7S)-6,7-dihydro-5H-pyrrolo[2,1-c][1,2,4]triazol-7-yl]-3-methyl-pyrazol-4-yl]-5-(trifluoromethyl)pyrimidin-2-amine.

First eluting isomer (A-83): 1H NMR (400 MHz, CDCl3): δ 8.40 (br. s., 1H), 8.22 (s, 1H), 7.91 (br. s., 1H), 6.59-6.94 (m, 1H), 5.64-5.75 (m, 1H), 4.34-4.46 (m, 1H), 4.12-4.23 (m, 1H), 3.18-3.38 (m, 2H), 2.19 (s, 4H), 1.23 (br. s., 2H), 1.13 (d, J=6.17 Hz, 2H). HPLC. RT 2.45 min. MS: [M+H]+ m/z: 391.1. SFC: RT 2.46 min.

Second eluting isomer (A-82): 1H NMR (400 MHz, CDCl3): δ 8.38 (d, J=5.73 Hz, 1H), 8.20 (d, J=6.62 Hz, 1H), 7.87 (br. s., 1H), 6.74-7.12 (m, 1H), 5.66 (br. s., 1H), 4.37 (br. s., 1H), 4.15 (br. s., 1H), 3.11-3.40 (m, 2H), 1.97-2.34 (m, 4H), 1.19 (br. s, 2H), 1.09 (br. s., 2H). HPLC: RT 2.46 min. MS: [M+H]+ m/z: 391.1. SFC: RT 3.78 min.

Example A-55

The following compounds were made according to similar procedures described above. The LCMS conditions used to isolate the compounds are as provided above in the general method.

| No. | MS [M + H]+ |
|---|---|
| A-84 | 390.2 |
| A-85 | 367.1 |
| A-86 | 367.1 |
| A-87 | 377.1 |
| A-88 | 367.1 |
| A-89 | 390.2 |
| A-90 | 390.2 |
| A-91 | 367.1 |
| A-92 | 390.2 |
| A-93 | 381.2 |
| A-94 | 381.1 |
| A-95 | 381.2 |
| A-96 | 405.2 |
| A-97 | 405.2 |

B: Compound Preparation

In die following Examples, all non-aqueous reactions were carried out in oven-dried or flame-dried glassware under nitrogen atmosphere. All chemicals were purchased from commercial vendors and used as is, unless otherwise specified. Reactions were magnetically stirred and monitored by thin layer chromatography (TLC) with 250 µm pre-coated silica gel plates, visualized either with UV, or in an iodine chamber. Flash column chromatography was performed using silica gel (100-200 mesh). Chemical shifts are reported relative to chloroform (δ 7.26), methanol (δ 3.31), or DMSO (δ 2.50) for $^1$H NMR. HPLC analysis was performed on Shimadzu 20AB HPLC system with a photodiode array detector and Luna-C18(2) 2.0×50 mm, 5 µm column at a flow rate of 1.2 mL/min with a gradient solvent Mobile phase A (MPA, H$_2$O+0.037% (v/v) TFA): Mobile phase B (MPB, ACN+0.018% (v/v) TFA) (0.01 min, 10% MPB; 4 min, 80% MPB; 4.9 min, 80% MPB; 4.92 min, 10% MPB; 5.5 min, 10% MPB). LCMS was detected under 220 and 254 nm or used evaporative light scattering (ELSD) detection as well as positive electrospray ionization (MS). Semi-preparative HPLC was performed by either acidic or neutral condition. Acidic: Luna C18 100×30 mm, 5 µm; MPA: HCl/H$_2$O=0.04%, or formic acid/H$_2$O=0.2% (v/v); MPB: ACN. Neutral: Waters Xbridge 150×25, 5 µm; MPA: 10 mM NH$_4$HCO$_3$ in H$_2$O; MPB: ACN. Gradient for both conditions: 10% of MPB to 80% of MPB within 12 min at a flow rate of 20 mL/min, then 100% MPB over 2 min, 10% MPB over 2 min, UV detector. SFC analysis was performed on Thar analytical SFC system with a UV/Vis detector and series of chiral columns including AD-3, AS-H, OJ-3, OD-3, AY-3 and IC-3, 4.6×100 mm, 3 um column at a flow rate of 4 mL/min with a gradient solvent Mobile phase A (MPA, CO$_2$): Mobile phase B (MPB, MeOH+0.05% (v/v) IPAm) (0.01 min. 10% MPB; 3 min, 40% MPB; 3.5 min, 40% MPB; 3.56-5 min, 10% MPB). SFC preparative was performed on Thar 80 preparative SFC system with a UV/Vis detector and series of chiral preparative columns including AD-H, AS-H, OJ-H, OD-H, AY-H and IC-H, 30×250 mm, 5 um column at a flow rate of 65 mL/min with a gradient solvent Mobile phase A (MPA, CO$_2$): Mobile phase B (MPB, MeOH+0.1% (v/v) NH$_3$H$_2$O) (0.01 min, 10% MPB; 5 min, 40% MPB; 6 min, 40% MPB; 6.1-10 min, 10% MPB).

Example B-1

Synthesis of 2-(4-Amino-3-methyl-pyrazol-1-yl)-2-methyl-propanenitrile

Methyl 2-methyl-2-(3-methyl-4-nitro-pyrazol-1-yl)propanoate

To a solution of 3-methyl-4-nitro-1H-pyrazole (40 g, 314.71 mmol) in DMF (700 mL) was added NaH (18.88 g, 472.06 mmol, 60% purity) at 0° C. over a period of 30 min under N$_2$. The reaction was then stirred at 25° C. for 2 h followed by the addition of methyl 2-bromo-2-methylpropanoate (85.46 g, 472.06 mmol, 61.04 mL) dropwise at 0° C. The reaction mixture was warmed to 25° C. and stirred at 25° C. for another 16 h. TLC (petroleum ether/ethyl acetate=5:1) showed the starting material was consumed completely. The reaction was quenched by ice water slowly and then extracted with EtOAc (3×700 mL). The combined organic phase was washed with brine (3×200 mL), dried over anhydrous $Na_2SO_4$, filtered and concentrated in vacuo. The residue was purified by column chromatography on silica gel (petroleum ether/ethyl acetate=30:1-15:1), to yield the desired product as a light yellow solid (69.70 g, 97.47%). $^1$H NMR (400 MHz, $CDCl_3$): δ 8.29 (s, 1H), 3.72 (s, 1H), 2.51 (s, 1H), 1.84 (s, 6H).

2-Methyl-2-(3-methyl-4-nitro-pyrazol-1-yl) propanoic acid

To a mixture of methyl 2-methyl-2-(3-methyl-4-nitro-pyrazol-1-yl)propanoate (69.7 g, 306.75 mmol) in THF (1 L) and $H_2O$ (250 mL) was added $LiOH.H_2O$ (15.45 g, 368.10 mmol) at 25° C. under $N_2$. The mixture was then stirred at 25° C. for 16 h. TLC (petroleum ether/ethyl acetate=5:1) showed the reaction was completed. The reaction mixture was concentrated in vacuo. The residual aqueous solution was washed with ethyl acetate (50 mL). The aqueous phase was then cooled to 0° C., adjusted to approximately pH 1-2, and filtered to yield the desired product as a white solid (53 g, 81.04%). $^1$H NMR (400 MHz, $CDCl_3$): δ 8.65 (s, 1H), 2.48 (s, 1H), 1.83 (s, 6H).

2-Methyl-2-(3-methyl-4-nitro-pyrazol-1-yl)propanamide

To a solution of 2-methyl-2-(3-methyl-4-nitro-pyrazol-1-yl) propanoic acid (25 g, 117.27 mmol) in DCM (500 mL) was added 8 drops of DMF, followed by oxalyl dichloride (29.77 g, 234.54 mmol) at 0° C. under $N_2$. Then die mixture was stirred at 25° C. for a further 2 h. TLC (petroleum ether/ethyl acetate=3:1) showed reaction was completed. The reaction solution was concentrated in vacuo. The residue solid was dissolved in THF (300 mL) and added dropwise into a stirred solution of $NH_4OH$ (413.61 g, 11.80 mol, 454.52 mL) at 0° C. The reaction was stirred at 25° C. for 1 h. TLC (ethyl acetate) showed reaction was completed. The solution was then concentrated in vacuo and partitioned between EtOAc (100 mL) and water (100 mL), and die aqueous phase was extracted with ethyl acetate (3×80 mL). The combined organic phase was washed with brine (3×40 mL), dried over anhydrous $Na_2SO_4$, filtered and concentrated in vacuo, to yield tire desired compound as a yellow solid (22 g, 103.67 mmol, 88.4%). $^1$H NMR (400 MHz, MeOD): δ 8.81 (s, 1H), 7.16-7.26 (m, 2H), 2.42 (s, 3H), 1.71 (s, 3H).

2-Methyl-2-(3-methyl-4-nitro-1H-pyrazol-1-yl)propanenitrile

A solution of 2-methyl-2-(3-methyl-4-nitro-pyrazol-1-yl-propanamide (22 g, 103.67 mmol) in $POCl_3$ (132 g, 860.89 mmol, 80 mL) was stirred at 90° C. for 1 h. TLC showed the reaction was completed. The mixture was cooled to 20° C. and concentrated in vacuo at 50° C. The residue was poured into ice-water (w/w=1/1) (200 mL) and stirred for 10 min. The aqueous phase was adjusted to pH=7 with $NaHCO_3$ solution, extracted with ethyl acetate (4×80 mL). The combined organic phase was washed with brine (40 mL), dried with anhydrous $Na_2SO_4$, filtered and concentrated in vacuo. The desired product was afforded as a yellow solid (20 g, 99.35%).

2-(4-Amino-3-methyl-pyrazol-1-yl)-2-methyl-propanenitrile

To a mixture of 2-methyl-2-(3-methyl-4-nitro-1H-pyrazol-1-ylpropanenitrile (10 g, 51.5 mmol) in EtOH (240 mL) and $H_2O$ (60 mL) was added $NH_4Cl$ (13.77 g, 257.5 mmol) in one portion at 25° C., followed by Fe (14.38 g, 257.5 mmol). The mixture was heated to 80° C. and stirred for 1 h. TLC showed the reaction was completed. The solution was cooled to 20° C. The mixture was extracted with ethyl acetate (3×100 mL), the combined organic layers were washed with $NaHCO_3$ solution (50 mL) and brine (50 mL). The organic layers were dried over $Na_2SO_4$, filtered and concentrated to afford the desired product. $^1$H NMR (400 MHz, $CDCl_3$): δ 7.17 (s, 1H), 2.18 (s, 3H), 1.91 (s, 6H).

Example B-2

Synthesis of 2-[4-[[5-Chloro-4-(methylamino)-7H-pyrrolo[2,3-d]pyrimidin-2-yl]amino]-3-methyl-pyrazol-1-yl]-2-methyl-propanenitrile (B-6)

2,4,5-trichloro-7H-pyrrolo[2,3-d]pyrimidine

To a mixture of 2,4-dicholo-7H-pyrrolo[2,3-d]pyrimidine (1 g, 5.32 mmol) in THF (3 mL) and DCM (12 mL) was added NCS (852 mg, 6.38 mmol) in one portion at 25° C. The mixture was stirred under microwave at 90° C. for 2.5 h. LC/MS showed the reaction was completed. Two new peaks were shown on LC/MS and 74% of desired (M+H$^+$=221.9) was detected. The mixture was added to brine and extracted with DCM. The organics were dried over anhydrous $Na_2SO_4$ and concentrated in vacuo. The crude product was purified by column chromatography on silica gel (petroleum ether/ethyl acetate=50:1-5:1), to yield the desired product as a yellow solid (750 mg, 63.37%). $^1$H NMR (400 MHz, $CDCl_3$): δ 10.70 (s., 1H) 8.16 (s, 1H) 4.14 (s, 3H).

2,5-Dichloro-N-methyl-7H-pyrrolo[2,3-d]pyrimidin-4-amine

To a mixture of 2,4,5-trichloro-7H-pyrrolo[2,3-d]pyrimidine (600 mg, 2.7 mmol) and triethylamine (272.92 mg, 2.7 mmol, 373.86 uL) in methanol (2 mL) was added $MeNH_2$ (EtOH solution, 1 mL) in one portion. The solution was stirred at 25° C. for 12 h. LC/MS showed the reaction was completed. The mixture was concentrated in vacuo, washed by MTBE and filtered to yield the desired product (493 mg, 84.12%). MS: m/z: 215.1 [M+H]$^+$ 2-[4-[[5-Chloro-4-(methylamino)-7H-pyrrolo[2,3-d]pyrimidin-2-yl]amino]-3-methyl-pyrazol-1-yl]-2-methyl-propanenitrile To a solution of 2,5-dichloro-N-methyl-7H-pyrrolo[2,3-d]pyrimidin-4-amine (150 mg, 691.05 umol) in t-BuOH (5 mL) was added TFA (78.79 mg, 691.05 umol, 51.16 uL) and 2-(4-Amino-3-methyl-pyrazol-1-yl)-2-methyl-propanenitrile (113 mg, 691.05 umol). The mixture was stirred at 80° C. for 16 h. LC/MS showed starting material was consumed and a main peak of desired MS observed. The mixture was concentrated in vacuo. The residue was purified by prep-HPLC (HCl condition), to yield the desired product. $^1$H NMR (400 MHz, MeOD): δ 8.21 (s, 1H), 6.96 (s, 1H), 3.19 (s, 1H), 2.27 (s, 1H). HPLC: RT 1.91 min. MS: m/z: 345.1 [M+H]$^+$.

Example B-3

Synthesis of 2-[4-[(5-chloro-4-methoxy-7H-pyrrolo [2,3-d]pyrimidin-2-yl)amino]-3-methyl-pyrazol-1-yl]-2-methyl-propanenitrile (B-5)

2,5-dichloro-4-methoxy-7H-pyrrolo[2,3-d]pyrimidine

To a solution of 2,4,5-trichloro-7H-pyrrolo[2,3-J]pyrimidine (300 mg, 1.35 mmol) in MeOH (5 mL) was added NaOMe (145.85 mg, 2.7 mmol) in one portion at 25° C. The mixture was stirred at 60° C. for 12 h. LC/MS showed the reaction was completed. The residue was poured into water (10 mL) and stirred for 5 min. The aqueous phase was extracted with ethyl acetate (3×10 mL), dried with anhydrous $Na_2SO_4$, filtered and concentrated in vacuo to give the crude 2,5-dichloro-4-methoxy-7H-pyrrolo[2,3-d]pyrimidine (280 mg crude) which was used in the next step without further purification.

2-[4-[(5-chloro-4-methoxy-7H-pyrrolo[2,3-d]pyrimidin-2-yl)amino]-3-methyl-pyrazol-1-yl]-2-methyl-propanenitrile To a mixture of 2,5-dichloro-4-methoxy-7H-pyrrolo[2,3-d]pyrimidine (150 mg, 687.95 μmol) and 2-(4-amino-3-methyl-1H-pyrazol-1-yl)-2-methylpropanenitrile (135.56 mg, 825.54 μmol) in t-BuOH (5 mL) was added TFA (156.88 mg, 1.38 mmol, 101.87 μL) in one portion at 25° C. under $N_2$. The mixture was stirred at 100° C. for 12 h. The mixture was concentrated when HPLC indicated the reaction had reached completion. The crude product was purified by prep-HPLC (neutral) to yield the desired product. $^1$H NMR (400 MHz, MeOD): δ 8.249 (s, 1H), 6.827 (s, 1H), 4.072 (s, 3H), 2.274 (s, 3H), 2.274 (s, 6H). HPLC. RT 2.58 min. MS: m/z: 345.1 [M+H]$^+$.

Example B-4

Synthesis of 5-chloro-N-(1,5-dimethylpyrazol-4-yl)-4-methoxy-7H-pyrrolo[2,3-d]pyrimidin-2-amine (B-8) and 5-chloro-N-(1,3-dimethylpyrazol-4-yl)-4-methoxy-7H-pyrrolo[2,3-d]pyrimidin-2-amine (B-9)

Trimethyl-[2-[(2,4,5-trichloropyrrolo[2,3-d]pyrimidin-7-yl)methoxy]ethyl]silane To a solution of 2,4,5-trichloro-7H-pyrrolo[2,3-d]pyrimidine (800 mg, 3.60 mmol) in DMF (8 mL) was added NaH (158 mg, 3.96 mmol, 60% purity) at 0° C. under $N_2$. The solution was stirred at 0° C. for 30 min. Then SEM-Cl (719 mg, 4.32 mmol) was added to the solution at 0° C. The solution was stirred at 25° C. for 2.5 h. To the mixture was poured into $NH_4Cl$ solution. The solution was extracted with ethyl acetate (3×15 mL). The organic layers were combined, washed with brine (10 mL), dried over $Na_2SO_4$, filtered and concentrated to afford the desired product as a brown oil (1.20 g, 94.5%). The product was used in the next reaction without further purification. LC/MS: RT 1.897 min, m/z=352.1, 354.1 [M+H]$^+$.

2-[(2,5-dichloro-4-methoxy-pyrrolo[2,3-d]pyrimidin-7-yl)methoxy]ethyl-trimethyl-silane To a solution of trimethyl-[2-[(2,4,5-trichloropyrrolo[2,3-d]pyrimidin-7-yl)methoxy]ethyl]silane (850 mg, 2.41 mmol) in methanol (5 mL) was added NaOMe (260 mg, 4.82 mmol) in one portion at 25° C. under $N_2$. The mixture was stirred at 25° C. for 2 h. The mixture was poured into water (10 mL), extracted with ethyl acetate (3×3 mL). The combined organic phase was washed with brine (10 mL), dried with anhydrous $Na_2SO_4$, filtered and concentrated in vacuo. The residue was purified by prep-TLC ($SiO_2$, petroleum ether/ethyl acetate=5:1) to afford the desired product as a white solid (500 mg, 59.57%).

5-chloro-N-(1,5-dimethyl-1H-pyrazol-4-yl)-4-methoxy-7H-pyrrolo[2,3-d]pyrimidin-2-amine To a mixture of 2-[(2,5-dichloro-4-methoxy-pyrrolo[2,3-d]pyrimidin-7-yl)methoxy]ethyl-trimethyl-silane (250 mg, 718 umol) and 1,5-dimethyl-1H-pyrazol-4-amine and 1,3-dimethyl-1H-pyrazol-4-amine (88 mg, 790 umol) in 1,4-dioxane (5 mL) was added $Pd_2(dba)_3$ (66 mg, 71.8 umol), BINAP (45 mg, 71.8 umol) and $Cs_2CO_3$ (702 mg, 2.15 mmol) in one portion at 25° C. under $N_2$. The mixture was stirred at 90° C. for 12 h. The mixture was concentrated in vacuo at 35° C. The residue was poured into water, extracted with EtOAc (3×20 mL). The combined organic phase was washed with brine (2×10 mL), dried with anhydrous $Na_2SO_4$, filtered and concentrated in vacuo. The residue was purified by prep-TLC ($SiO_2$, petroleum ether/ethyl acetate=3:1) to afford the desired compounds as a white solid (250 mg, 82.34%).

5-chloro-N-(1,5-dimethylpyrazol-4-yl)-4-methoxy-7H-pyrrolo[2,3-d]pyrimidin-2-amine & 5-chloro-N-(1,3-dimethylpyrazol-4-yl)-4-methoxy-7H-pyrrolo[2,3-d]pyrimidin-2-amine To a solution of 5-chloro-N-(1,5-dimethyl-1H-pyrazol-4-yl)-4-methoxy-7H-pyrrolo[2,3-d]pyrimidin-2-amino (250 mg, 591.04 μmol) in DCM (10 mL) was added TFA (2 mL) in one portion at 25° C. The mixture was stirred at 40° C. for 3 hours. The mixture was concentrated in vacuo at 35° C. The crude product was dissolved in THF (10 mL) and sat. $NaHCO_3$ solution (10 mL) was added. The mixture was stirred at 25° C. for 12 h. The aqueous phase was extracted with ethyl acetate (3×20 mL). The combined organic phase was washed with brine (2×10 mL), dried with anhydrous $Na_2SO_4$, filtered and concentrated in vacuo. The residue was purified by prep-HPLC (HCl acidic condition) to give 5-chloro-N-(1,5-dimethylpyrazol-4-yl)-4-methoxy-7H-pyrrolo[2,3-d]pyrimidin-2-amine and 5-chloro-N-(1,3-dimethylpyrazol-4-yl)-4-methoxy-7H-pyrrolo[2,3-d]pyrimidin-2-amine.

5-chloro-N-(1,5-dimethylpyrazol-4-yl)-4-methoxy-7H-pyrrolo[2,3-d]pyrimidin-2-amino $^1$H NMR (400 MHz, MeOD):δ7.816 (s, 1H), 7.023 (s, 1H), 4.208 (s, 3H), 3.929 (s, 3H) 2.337 (s, 3H). HPLC: RT 2.29 min. MS: m/z: 293.1 [M+H]$^+$.

5-chloro-N-(1,3-dimethylpyrazol-4-yl)-4-methoxy-7H-pyrrolo[2,3-d]pyrimidin-2-amine $^1$H NMR (400 MHz, MeOD):δ8 014 (s, 1H), 7.019 (s, 1H), 4.207 (s, 3H), 3.961 (s, 3H) 2.276 (s, 3H). HPLC RT 2.18 min. MS: m/z: 293.1 [M+H]$^+$.

Example B-5

Synthesis of 5-chloro-N²-(1,5-dimethylpyrazol-4-yl)-N4-methyl-7H-pyrrolo[2,3-d]pyrimidine-2,4-diamine (B-1) and 5-chloro-N²-(1,3-dimethylpyrazol-4-yl)-N⁴-methyl-7H-pyrrolo[2,3-d]pyrimidine-2,4-diamine & 5-chloro-N²-(1,3-dimethyl-1H-pyrazol-4-yl)-N⁴-methyl-7H-pyrrolo[2,3-d]pyrimidine-2,4-diamine (B-4)

2,5-dichloro-N-methyl-7-(2-trimethylsilylethoxymethyl)pyrrolo[2,3-d]pyrimidin-4-amine To a solution of trimethyl-[2-[(2,4,5-trichloropyrrolo[2,3-d]pyrimidin-7-yl)methoxy]ethyl]silane (1.20 g, 3.40 mmol) in ethanol (20 mL) was added MeNH₂ (640 mg, 6.80 mmol, 33% purity in EtOH). The mixture was stirred at 25° C. for 24 h. TLC (petroleum ethenediyl acetate=5:1) showed the reaction was completed. The mixture was concentrated in vacuo. The residue was purified by column chromatography (SiO₂, petroleum ether/ethyl acetate=100:1-ethyl acetate) to afford the desired product as a colorless gum (600 mg, 50.81%). ¹H NMR (400 MHz, CDCl₃): δ6.93 (S, 1H), 5.95 (br, 1H), 5.47 (s, 2H), 3.50~3.54 (t, 2H), 3.17~3.18 (d, 3H), 0.90~0.94 (t, 2H), 0.02 (s, 9H). LC/MS: RT 0.954 min, m/z=347.1, 349.1 [M+H]⁺.

5-chloro-N2-(1,5-dimethylpyrazol-4-yl)-N4-methyl-7-(2-trimethylsilylethoxymethyl)pyrrolo[2,3-d]pyrimidine-2,4-diamine A mixture of 2,5-dichloro-N-methyl-7-(2-trimethylsilylethoxymethyl)pyrrolo[2,3-d]pyrimidin-4-amine (400 mg, 1.15 mmol), 1,5-dimethylpyrazol-4-amine (89 mg, 805 umol), Cs₂CO₃ (1.12 g, 3.45 mmol), XPhos (55 mg, 115 umol) and Pd₂(dba)₃ (105 mg, 115 umol) in 1,4-dioxane (20 mL) was degassed and purged with N₂ for 3 times, and then the mixture was stirred at 110° C. for 16 h under N₂. TLC (petroleum ether/ethyl acetate=10:1) showed the reaction was completed. The solution was concentrated in vacuo to give a residue. To the residue was added water (10 mL), extracted with ethyl acetate (3×15 mL). Organic layers were combined, washed with brine (10 mL), dried over Na₂SO₄, filtered and concentrated to give a crude product. The crude was purified by column chromatography (SiO₂, petroleum ether/ethyl acetate=30:1-10:1) to afford a mixture that contained die two desired products as a colorless gum (260 mg, ratio-1:1, 53.6%). The mixture was used in the next step without further purification. LC/MS: RT 1.449 min, m/z=422.3 [M+H]⁺.

5-chloro-N2-(1,5-dimethylpyrazol-4-yl)-N4-methyl-7H-pyrrolo[2,3-d]pyrimidine-2,4-diamine and 5-chloro-N2-(1,3-dimethylpyrazol-4-yl)-N4-methyl-7H-pyrrolo[2,3-d]pyrimidine-2,4-diamine & 5-chloro-N2-(1,3-dimethyl-1H-pyrazol-4-yl)-N4-methyl-7H-pyrrolo[2,3-d]pyrimidine-2,4-diamine To a solution of a mixture of 5-chloro-N2-(1,5-dimethylpyrazol-4-yl)-N4-methyl-7-(2-trimethylsilylethoxymethyl)pyrrolo[2,3-d]pyrimidine-2,4-diamine (260 mg, 616 μmol, also containing 5-chloro-N2-(1,3-dimethyl-1H-pyrazol-4-yl)-N4-methyl-7-((2-(trimethylsilylethoxy)methyl)-7H-pyrrolo[2,3-d]pyrimidine-2,4-diamine) in DCM (20 mL) was added TFA (6.16 g, 54.03 mmol). The mixture was stirred at 50° C. for 3 h. TLC (petroleum ether/ethyl acetate=1:1) showed the reaction was completed. The solution was concentrated in vacuo. The residue was dissolved in THF (20 mL) and 20 mL of sat. NaHCO₃ solution was added to the solution. Then the solution was stirred at 25° C. for 6 h. The solution was extracted with ethyl acetate (3×20 mL), organic layers were combined, washed with brine (15 mL), dried over Na₂SO₄, filtered and concentrated to give a crude product. The crude product was purified by prep-HPLC (neutral condition) and lyophilized to afford the desired products.

5-chloro-N2-(1,5-dimethylpyrazol-4-yl)-N4-methyl-7H-pyrrolo[2,3-d]pyrimidine-2,4-diamine ¹H NMR (400 MHz, CDCl3):δ9.19 (br, 1H), 7.59 (s, 1H), 6.34 (s, 1H), 6.03 (br, 1H), 5.69 (br, 1H), 3.73 (s, 3H), 3.10-3.13 (d, 3H), 2.17 (s, 3H). HPLC: RT 1.691 min. MS: m/z: 292.1 [M+H]⁺

5-chloro-N2-(1,3-dimethyl-1H-pyrazol-4-yl)-N4-methyl-7H-pyrrolo[2,3-d]pyrimidine-2,4-diamine ¹H NMR (400 MHz, CDCl3):δ9.13 (br, 1H), 7.73 (s, 1H), 6.42 (s, 1H), 6.18 (br, 1H), 5.73 (br, 1H), 3.80 (s, 3H), 3.10-3.13 (d, 3H), 2.25 (s, 3H). HPLC: RT 1.770 min. MS: m/z: 292.1 [M+H]⁺

Example B-6

Synthesis of 2-[4-[[5-chloro-4-(ethylamino)-7H-pyrrolo[2,3-d]pyrimidin-2-yl]amino]-3-methyl-pyrazol-1-yl]-2-methyl-propanenitrile (B-2)

2,5-dichloro-N-ethyl-b 7-(2-trimethylsilylethoxymethyl) pyrrolo[2,3-d]pyrimidin-4-amine To a solution of 2,4,5-trichloro-7-((2-(trimethylsilyl)ethoxy)methyl)-7H-pyrrolo[2,3-d]pyrimidine (400 mg, 1.13 mmol) in ethanol (10 mL) was added ethanamine (61 mg, 1.36 mmol) dropwise at 25° C. The mixture was stirred at 25° C. for 2 h. The mixture was concentrated in vacuo at 35° C. The residue was poured into water (10 mL). The aqueous phase was extracted with EtOAc (3×20 mL). The combined organic phase was washed with brine (2×10 mL), dried with anhydrous Na₂SO₄, filtered and concentrated in vacuo. The residue was purified by prep-TLC (SiO₂, petroleum ether/ethyl acetate=5:1) to afford the desired product as a white solid (250 mg, 61.23%). LC/MS: RT 1.015 min, m/z=361 [M+H]⁺.

2-[4-[[5-chloro-4-(ethylamino)-7H-pyrrolo[2,3-d]pyrimidin-2-yl]amino]-3-methyl-pyrazol-1-yl]-2-methyl-propanenitrile To a mixture of 2,5-dichloro-N-ethyl-7-(2-trimethylsilylethoxymethyl) pyrrolo[2,3-d]pyrimidin-4-amine (240 mg, 664.19 umol) and 2-(4-amino-3-methyl-1H-pyrazol-1-yl)-2-methylpropanenitrile (120 mg, 730.61 umol) in 1,4-dioxane (5 mL) was added Pd₂(dba)₃ (61 mg, 66.42 umol), X-Phos (32 mg, 66.42 umol) and Cs₂CO₃ (650 mg, 1.99 mmol) in one portion at 25° C. under N₂. The mixture was stirred at 90° C. for 12 h. The mixture was cooled to 25° C. and concentrated in vacuo at 35° C. The residue was poured into water (10 mL). The aqueous phase was extracted with ethyl acetate (3×20 mL). The combined organic phase was washed with brine (2×10 mL), dried with anhydrous Na₂SO₄, filtered and concentrated in vacuo. The residue was purified by TLC (petroleum ether/ethyl acetate=3:1) to afford the desired product as a white solid (250 mg, quantitative). LC/MS: RT 0.883 min, m/z=489 [M+H]+.

2-[4-[[5-chloro-4-(ethylamino)-7H-pyrrolo[2,3-d]
pyrimidin-2-yl]amino]-3-methyl-pyrazol-1-yl]-2-
methyl-propanenitrile To a mixture of 2-[4-[[5-chloro-4-(ethylamino)-7H-pyrrolo[2,3-d]pyrimidin-2-yl]amino]-3-methyl-pyrazol-1-yl]-2-methyl-propanenitrile (150 mg, 306.69 μmol) in DCM (10 mL) was added TFA (2 mL) in one portion at 25° C. The mixture was stirred at 25° C. for 3 h. The reaction mixture was concentrated in vacuo to remove DCM. The crude product was dissolved in THF (10 mL) and aq. NaHCO$_3$ (10 mL) was added. The mixture was stirred at 25° C. for 12 h. The mixture was extracted with ethyl acetate (3×50 mL). The combined organic layers were washed with brine, dried over Na$_2$SO$_4$, filtered and concentrated in vacuo to give a residue. The residue was purified by prep-HPLC (neutral condition) to afford the desired product. $^1$H NMR (400 MHz, CDCl3): δ 8.518 (s, 1H), 8.232 (s, 1H), 6.602 (s, 1H), 6.224 (s, 1H) 5.747 (s, 1H) 3.673-3.606 (m, 2H) 2.288 (s, 3H) 1.968 (s, 6H) 1.363-1.327 (t, 3H, J=7.2 Hz). HPLC. RT 2.609 min. MS: [M+H]+ m/z: 359.1

Example B-7

Synthesis of 2-[4-[[5-chloro-4-ethoxy-7H-pyrrolo[2,
3-d]pyrimidin-2-yl]amino]-3-methyl-pyrazol-1-yl]-
2-methyl-propanenitrile (B-3)

2-[(2,5-dichloro-4-ethoxy-pyrrolo[2,3-d]pyrimidin-
7-yl)methoxy]ethyl-trimethyl-silane To a mixture of 2,4,5-trichloro-7-((2-(trimethylsilyl)ethoxy)methyl)-7H-pyrrolo[2,3-d]pyrimidine (500 mg, 1.42 mmol) in ethanol (5 mL) was added freshly prepared NaOEt (193.26 mg, 2.84 mmol) in one portion at 25° C. The mixture was stirred at 25° C. for 3 h. The reaction mixture was quenched by water, extracted with ethyl acetate. The combined organic layers were washed with brine, dried over Na$_2$SO$_4$, filtered and concentrated in vacuo to give a residue. The residue was purified by prep-TLC (SiO$_2$, petroleum ether/ethyl acetate=8:1) to afford the desired product (280 mg, 54.42%). LC/MS: RT 1.016 min, m/z=362 [M+H]+.

2-[4-[[5-chloro-4-ethoxy-7-(2-trimethylsily-
lethoxymethyl)pyrrolo[2,3-d]pyrimidin-2-yl]amino]-
3-methyl-pyrazol-1-yl]-2-methyl-propanenitrile To a mixture of 2-[(2,5-dichloro-4-ethoxy-pyrrolo[2,3-d]pyrimidin-7-yl)methoxy]ethyl-trimethyl-silane (280 mg, 773 umol) and 2-(4-amino-3-methyl-1H-pyrazol-1-yl)-2-methylpropanenitrile (140 mg, 850 umol) in dioxane (5 mL) was added Pd$_2$(dba)$_3$ (71 mg, 77.3 umol), Cs$_2$CO$_3$ (755 mg, 2.32 mmol) and BINAP (48 mg, 77 umol) in one portion at 25° C. under N$_2$. The mixture was heated to 120° C. and stirred for 16 h. The mixture was cooled to 25° C. and concentrated in vacuo at 35° C. The residue was poured into water, extracted with ethyl acetate. The combined organic phase was washed with brine, dried with anhydrous Na$_2$SO$_4$, filtered and concentrated in vacuo. The residue was purified by prep-TLC (SiO$_2$, PE:EtOAc=5:1) to afford the desired product as a white solid (315 mg, 83.18%). LC/MS: RT 0.993 min, m/z=490 [M+H]+.

2-[4-[[5-chloro-4-ethoxy-7H-pyrrolo[2,3-d]pyrimi-
din-2-yl]amino]-3-methyl-pyrazol-1-yl]-2-methyl-
propanenitrile To a mixture of 2-[4-[[5-chloro-4-ethoxy-7-(2-trimethylsilylethoxymethyl)pyrrolo[2,3-d]pyrimidin-2-yl]amino]-3-methyl-pyrazol-1-yl]-2-methyl-propanenitrile (315 mg, 643 mmol) in DCM (10 mL) was added TFA (2 mL) in one portion at 25° C. The mixture was stirred at 25° C. for 3 h. The reaction mixture was concentrated in vacuo to remove DCM. The residue was dissolved in THF (10 mL) and added with aq. NaHCO$_3$ (10 mL). The mixture was stirred at 25° C. for 12 h, and extracted with ethyl acetate. The combined organic layers were washed with brine, dried over Na$_2$SO$_4$, filtered and concentrated in vacuo, purified by prep-HPLC (neutral condition) to afford the desired product. $^1$H NMR (400 MHz, CDCl3): δ 8.720 (s, 1H), 8.222 (s, 1H), 6.703-6.698 (d, 1H, J=2 Hz), 6.327 (s, 1H), 4.608-4.555 (m, 2H), 2.314 (s, 3H), 1.990 (s, 6H), 1.535-1.500 (t, 3H, J=7 Hz). HPLC: RT 2.847 min. MS: m/z: 360.1 [M+H]+

Example B-8

Synthesis of 2-(4-((6-methoxy-9H-purin-2-yl)
amino)-3-methyl-1H-pyrazol-1-yl)-2-methylpropa-
nenitrile (B-7)

2,6-dichloro-9-((2-(trimethylsilyl)ethoxy)methyl)-
9H-purine

To a solution of 2,6-dichloro-9H-purine (3 g, 15.87 mmol) in DMF (10 mL) was added NaH (698 mg, 17.46 mmol) at 0° C. The mixture was stirred at 0° C. for 1 h. Then SEM-Cl (3.18 g, 19.05 mmol) was added to the suspension, the mixture was stirred at 25° C. for 2 h. The reaction mixture was quenched by addition of H$_2$O (10 mL) at 25° C., and extracted with ethyl acetate (3×330 mL). The combined organic layers were washed with brine (20 mL), dried over Na$_2$SO$_4$, filtered and concentrated in vacuo to get a residue. The residue was purified by column chromatography on silica gel (petroleum ether/ethyl acetate=5:1-3:1) to afford the desired product was a white solid (3.8 g, 75%). LC/MS: RT 0.89 min, m/z=319[M+H]+.

2-chloro-6-methoxy-9-((2-(trimethylsilyl)ethoxy)
methyl)-9H-purine

To a solution of 2,6-dichloro-9-((2-(trimethylsilyl)ethoxy)methyl)-9H-purine (1.3 g, 4.07 mmol) in MeOH (20 mL) was added sodium methoxide (330 mg, 6.11 mmol). The mixture was stirred at 25° C. for 10 h. The reaction mixture was concentrated in vacuo to remove MeOH. The residue was diluted with H$_2$O (30 mL) and extracted with DCM (3×30 mL). The combined organic layers were washed with brine (25 mL×2), dried over Na$_2$SO$_4$, filtered and concentrated in vacuo to give a residue. The residue was purified by prep-TLC (SiO$_2$, petroleum ether/ethyl acetate=3:1) to afford die desired compound as a white solid (600 mg, 47%). LC/MS: RT 0.88 min, m/z=315 [M+H]+.

2-(4-((6-methoxy-9-((2-(trimethylsilyl)ethoxy)
methyl)-9H-purin-2-yl)amino)-3-methyl-1H-pyra-
zol-1-yl)-2-methylpropanenitrile To a solution of 2-(4-amino-3-methyl-1H-pyrazol-1-yl)-2-methylpropanenitrile (203 mg, 1.24 mmol), 2-chloro-6-methoxy-9-((2-(trimethylsilyl)ethoxy)methyl)-9H-purine (300 mg, 952.86 umol) in 1,4-dioxane (25 mL) was added Pd$_2$(dba)$_3$ (87 mg, 95.29 umol), Cs$_2$CO$_3$ (621 mg, 1.91 mmol) and X-Phos (91 mg, 190.57 umol) under N$_2$. The mixture was stirred at 110° C. for 10 h. The reaction mixture was concentrated in vacuo to remove 1,4-dioxane. The residue was diluted with H$_2$O (20 mL) and extracted with ethyl acetate (2<25 mL). The combined organic layers were washed with brine (2×15 mL), dried over Na$_2$SO$_4$, filtered and concentrated in vacuo to give a residue. The residue was purified by prep-TLC (SiO$_2$, petroleum ether/ethyl acetate=1:1) to afford the desired product as a white solid (320 mg, 76%). LC/MS: RT 0.82 min, m/z=443 [M+H]$^+$.

2-(4-((6-methoxy-9H-purin-2-yl)amino)-3-methyl-1H-pyrazol-1-yl)-2-methylpropanenitrile To a solution of 2-(4-((6-methoxy-9-((2-(trimethylsilyl)ethoxy)methyl)-9H-purin-2-yl)amino)-3-methyl-1H-pyrazol-1-yl)-2-methylpropanenitrile (162 mg, 366.03 umol) in DCM (10 mL) was added TFA (3.34 g, 29.28 mmol) in one portion at 25° C. The mixture was heated to 40° C. and stirred for 6 h. The reaction mixture was concentrated in vacuo to get a residue. The residue was dissolved in THF (10 mL) and added with aq. NaHCO$_3$ (10 mL). The mixture was stirred at 25° C. for 12 h. The mixture was extracted with ethyl acetate (30 mL). The organic layer was washed with brine (15 mL), dried over Na$_2$SO$_4$, filtered and concentrated in vacuo to get a residue. The residue was purified by prep-TLC (SiO$_2$, DCM:MeOH=10:1) to afford the desired product. $^1$H NMR (400 MHz, DMSO-d6): δ 12.64 (s, 1H), 8.57 (s, 1H), 8.19 (s, 1H), 7.91 (s, 1H), 4.04 (s, 3H), 2.19 (s, 3H), 1.94 (s, 6H). HPLC: RT 1.59 min MS: [M+H]$^+$ m/z: 313.2.

Example B-9

Synthesis of 2-(4-((5-fluoro-4-(methylamino)-7H-pyrrolo[2,3-d]pyrimidin-2-yl)amino)-3-methyl-1H-pyrazol-1-yl)-2-methylpropanenitrile 2,4-dichloro-5-fluoro-7H-pyrrolo[2,3-d]pyrimidine A mixture of 2,4-dichloro-7H-pyrrolo[2,3-d]pyrimidine (7 g, 37.23 mmol) and selectfluor (13.19 g, 37.23 mmol) in CH$_3$CN (360 mL) and AcOH (72 mL) was degassed and then the mixture was stirred at 60° C. for 16 h under N$_2$. The reaction mixture was concentrated under reduced pressure. The residue was diluted with water (200 mL), adjusted to pH=7 with aq. NaHCO$_3$, and extracted with EtOAc (3×300 mL). The combined organic layers were washed with brine (300 mL), dried over Na$_2$SO$_4$, filtered and concentrated under reduced pressure to give a residue, which was purified by silica gel column chromatography (PE:EtOAc=10:1 to 5:1) to give 2,4-dichloro-5-fluoro-7H-pyrrolo[2,3-d]pyrimidine (2.5 g, 22.82%) as a yellow oil. LCMS: RT 0.732 min, m/z=206.0 [M+H]$^+$.

2,4-dichloro-5-fluoro-7-((2-(trimethylsilyl)ethoxy)methyl)-7H-pyrrolo[2,3-d]pyrimidine To a solution of 2,4-dichloro-5-fluoro-7H-pyrrolo[2,3-d]pyrimidine (2.5 g, 12.14 mmol) in DMF (25 mL) was added NaH (582 mg, 14.57 mmol) at 0° C. The mixture was stirred at this temperature for 1 h, and then SEM-Cl (2.43 g, 14.57 mmol) was added dropwise at 0° C. The resulting mixture was stirred at 25° C. for 1 h. The mixture was slowly poured into ice-water, and then extracted with EtOAc (3×80 mL). The combined organic phase was washed with brine (50 mL), dried over anhydrous Na$_2$SO$_4$, filtered and concentrated under reduced pressure to give 2,4-dichloro-5-fluoro-7-((2-(trimethylsilyl)ethoxy)methyl)-7H-pyrrolo[2,3-d]pyrimidine (2.5 g, 61.24%) as a yellow oil. LCMS: RT 0.975 min, m/z=336.1 [M+H]$^+$.

2-chloro-5-fluoro-N-methyl-7-(2-trimethylsilylethoxymethyl)pyrrolo[2,3-d]pyrimidin-4-amine To a mixture of 2,4-dichloro-5-fluoro-7-((2-(trimethylsilyl)ethoxy)methyl)-7H-pyrrolo[2,3-d]pyrimidine (1.1 g, 3.27 mmol) in EtOH (15 mL) was added MeNH$_2$ (522 mg, 5.55 mmol, 33% purity) at 0° C. under N$_2$ and stirred at 25° C. for 8 h. The mixture was concentrated under reduced pressure. The residue was purified by silica gel column chromatography (SiO$_2$, PE:EtOAc=50:1) to give 2-chloro-5-fluoro-N-methyl-7-(2-trimethylsilylethoxymethyl)pyrrolo[2,3-d]pyrimidin-4-amine (645 mg, 59.61%) as a yellow syrup. LCMS: RT 0.912 min. m/z=331.2 [M+H]$^+$. $^1$H NMR (400 MHz, CDCl$_3$): δ 7.29 (s, 1H), 6.75 (d, J=2.51 Hz, 1H), 5.48 (s, 2H), 3.49-3.56 (m, 2H), 3.19 (d, J=5.02 Hz, 2H), 0.90-0.97 (m, 2H).

2-[4-[[5-fluoro-4-(methylamino)-7-(2-trimethylsilylethoxymethyl)pyrrolo[2,3-d]pyrimidin-2-yl]amino]-3-methyl-pyrazol-1-yl]-2-methyl-propanenitrile To a solution of 2-chloro-5-fluoro-N-methyl-7-(2-trimethylsilylethoxymethyl)pyrrolo[2,3-d]pyrimidin-4-amine (350 mg, 1.06 mmol) in 1,4-dioxane (5 mL) was added Pd$_2$(dba)$_3$ (97 mg, 106 umol), Cs$_2$CO$_3$ (1.04 g, 3.18 mmol) and dicyclohexyl-[2-(2,4,6-triisopropylphenyl)phenyl]phosphane (505 mg, 1.06 mmol) under N$_2$. The mixture was stirred at 120° C. for 16 h. The mixture was concentrated under reduced pressure. The residue was purified by prep-TLC (SiO$_2$. PE:EtOAc=2:1), to give 2-[4-[[5-fluoro-4-(methylamino)-7-(2-trimethylsilylethoxymethyl)pyrrolo[2,3-d]pyrimidin-2-yl]amino]-3-methyl-pyrazol-1-yl]-2-methyl-propanenitrile (310 mg, 63.77%) as a brown syrup. LCMS: RT 0.807 min, m/z=459.3 [M+H]$^+$.

2-(4-((5-fluoro-4-(methylamino)-7H-pyrrolo[2,3-d]pyrimidin-2-yl)amino)-3-methyl-1H-pyrazol-1-yl)-2-methylpropanenitrile To a solution of 2-[4-[[5-fluoro-4-(methylamino)-7-(2-trimethylsilylethoxymethyl)pyrrolo[2,3-d]pyrimidin-2-yl]amino]-3-methyl-pyrazol-1-yl]-2-methyl-propanenitrile (120 mg, 261.66 umol) in DCM (5 mL) was added dropwise SnCl$_4$ (886 mg, 3.40 mmol) at 0° C. over 30 min. After addition, the mixture was stirred at this temperature for 30 min. The resulting mixture was stirred at 20° C. for 2 h. The reaction mixture was quenched by addition of H$_2$O (20 mL) at 0° C., and then added with sat. NaHCO$_3$ (20 mL) to pH=8 and extracted with DCM (3×20 mL). The combined organic layers were washed with brine (10 mL), and concentrated under reduced pressure at 20° C. The residue was dissolved with THF/H$_2$O (4/1, 20 mL) and added with excessive K$_2$CO$_3$. The resulting mixture was stirred at 20° C. for 2 h. The reaction mixture was diluted with H$_2$O (40 mL) at 0° C., and extracted with EtOAc (3×20 mL). The combined organic layers were washed with brine (10 mL), dried over Na$_2$SO$_4$, filtered and concentrated under reduced pressure at 20° C. The residue was purified by prep-HPLC (neutral) to give 2-(4-((5-fluoro-4-(methylamino)-7H-pyrrolo[2,3-d]pyrimidin-2-yl)amino)-3-methyl-1H-pyrazol-1-yl)-2-methylpropanenitrile. ¹HNMR: (400 MHz, CDCl3): δ ppm 8.87 (br, 1H), 8.21 (s, 1H), 6.31-6.37 (m, 1H), 6.25-6.30 (m, 1H), 5.13-5.25 (m, 1H), 3.15 (d, J=4.8 Hz, 3H), 2.28 (s, 3H), 1.92 (s, 6H) HPLC: RT 1.992 min. MS: [M+H]$^+$ m/z: 329.2.

Example B-10

Synthesis of 2-[4-[(5-fluoro-4-methoxy-7H-pyrrolo[2,3-d]pyrimidin-2-yl)amino]-3-methyl-pyrazol-1-yl]-2-methyl-propanenitrile (B-11)

2-[(2-chloro-5-fluoro-4-methoxy-pyrrolo[2,3-d]pyrimidin-7-yl)methoxy]ethyl-trimethyl-silane To a mixture of 2-[(2,4-dichloro-5-fluoro-pyrrolo[2,3-d]pyrimidin-7-yl)methoxy]ethyl-trimethyl-silane (1.16 g, 3.45 mmol) in MeOH (13 mL) was added NaOMe (559 mg, 10.35 mmol) at 0° C. under N$_2$ and stirred at 25° C. for 2 h. The mixture was concentrated under reduced pressure and poured into ice water (12 mL). The aqueous phase was extracted with EtOAc (3×4 mL). The combined organic phase was washed with brine (4 mL), dried over anhydrous Na$_2$SO$_4$, filtered and concentrated under reduced pressure. The residue was purified by silica gel column chromatography (PE:EtOAc=50:1) to afford 2-[(2-chloro-5-fluoro-4-methoxy-pyrrolo[2,3-d]pyrimidin-7-yl)methoxy]ethyl-trimethyl-silane (1.08 g, 94.20%) as a yellow solid. ¹H NMR (400 MHz, CDCl$_3$): δ 6.88-6.91 (m, 1H), 5.52 (s, 2H), 4.17 (s, 3H), 3.48-3.54 (m, 2H), 0.89-0.95 (m, 2H).

2-[4-[[5-fluoro-4-methoxy-7-(2-trimethylsilylethoxymethyl)pyrrolo[2,3-d]pyrimidin-2-yl]amino]-3-methyl-pyrazol-1-yl]-2-methyl-propanenitrile To a solution of 2-(4-amino-3-methyl-pyrazol-1-yl)-2-methyl-propanenitrile (327 mg, 1.99 mmol) in 1,4-dioxane (7 mL) was added Pd$_2$(dba)$_3$ (166 mg, 181 umol), Cs$_2$CO$_3$ (1.77 g, 5.43 mmol) and XPhos (86 mg, 181 umol) under N$_2$. The mixture was stirred at 120° C. for 16 h. The mixture was concentrated under reduced pressure. The residue was purified by prep-TLC (SiO$_2$, PE:EtOAc=2:1), to give 2-[4-[[5-fluoro-4-methoxy-7-(2-trimethylsilylethoxymethyl)pyrrolo[2,3-d]pyrimidin-2-yl]amino]-3-methyl-pyrazol-1-yl]-2-methyl-propanenitrile (294 mg, 35.34%) as a yellow solid. LCMS: RT 0.947 min, m/z=460.3 [M+H]$^+$.

2-[4-[(5-fluoro-4-methoxy-7H-pyrrolo[2,3-d]pyrimidin-2-yl)amino]-3-methyl-pyrazol-1-yl]-2-methyl-propanenitrile To a solution of 2-[4-[[5-fluoro-4-methoxy-7-(2-trimethylsilylethoxymethyl)pyrrolo[2,3-d]pyrimidin-2-yl]amino]-3-methyl-pyrazol-1-yl]-2-methyl-propanenitrile (250 mg, 543.96 umol) in DCM (10 mL) was added SnCl$_4$ (1.84 g, 7.07 mmol, 826.13 uL) at 0° C. under N$_2$. The mixture was stirred at 25° C. for 2 h. The mixture was poured into ice-water (10 mL) and adjusted to pH=8 by adding aq. NaHCO$_3$. The reaction mixture was extracted with EtOAc (3×4 mL). The combined organic phase was washed with brine (10 mL), and concentrated under reduced pressure. The residue was dissolved in THF (7.5 mL) and H$_2$O (2.5 mL), then added with K$_2$CO$_3$ (3.38 g, 24.48 mmol). The mixture stirred at 25° C. for 3 h. The reaction mixture was extracted with EtOAc (3×4 mL). The combined organic phase was washed with brine (10 mL), dried over anhydrous Na$_2$SO$_4$, filtered and concentrated under reduced pressure. The residue was purified by prep-HPLC (neutral), to give 2-[4-[(5-fluoro-4-methoxy-7H-pyrrolo[2,3-d]pyrimidin-2-yl)amino]-3-methyl-pyrazol-1-yl]-2-methyl-propanenitrile. ¹H NMR (400 MHz, CDCl$_3$): δ 8.23 (s, 2H), 6.49 (t, J=2.51 Hz, 1H), 6.34 (s, 1H), 4.11 (s, 3H), 2.30 (s, 3H), 1.98 (s, 6H). HPLC: RT: 2.68 min. MS: [M+H]$^+$ m/z=330.2.

Example B-11

Synthesis of 2-[4-[(6-ethoxy-9H-purin-2-yl)amino]-3-methyl-pyrazol-1-yl]-2-methyl-propanenitrile (B-12)

2-[(2-chloro-6-ethoxy-purin-9-yl)methoxy]ethyl-trimethyl-silane

To a mixture of 2-[(2,6-dichloropurin-9-yl)methoxy]ethyl-trimethyl-silane (3.00 g, 9.40 mmol) in EtOH (30 mL) was added fresh EtONa (216 mg, 3.18 mmol, 273 uL) at 25° C. The mixture was stirred at 25° C. for 3 h. The reaction mixture was quenched by adding water (10 mL) at 25° C. and concentrated. Then the mixture was extracted with EtOAc (3×5 mL). The combined organic phase was washed with brine (5 mL), dried over anhydrous Na$_2$SO$_4$, filtered and concentrated under reduced pressure to give 2-[(2-chloro-6-ethoxy-purin-9-yl)methoxy]ethyl-trimethyl-silane (2.82 g, 91.22%) as a white solid. LCMS: RT 0.922 min, m/z=329.2 [M+H]$^+$. ¹H NMR (400 MHz, CDCl$_3$): δ ppm 8.03 (s, 1H), 5.58 (s, 2H), 4.68 (q, J=7.06 Hz, 2H), 3.58-3.64 (m, 2H), 1.52 (t, J=7.06 Hz, 3H), 0.91-0.96 (m, 2H) −0.03 (s, 9H).

2-[4-[[6-ethoxy-9-(2-trimethylsilylethoxymethyl)purin-2-yl]amino]-3-methyl-pyrazol-1-yl]-2-methyl-propanenitrile To a mixture of 2-[(2-chloro-6-ethoxy-purin-9-yl)methoxy]ethyl-trimethyl-silane (200 mg, 608.14 umol) and 2-(4-amino-3-methyl-1H-pyrazol-1-yl)-2-methylpropanenitrile (119.84 mg, 729.77 umol) in 1,4-dioxane (2 mL) was added Cs$_2$CO$_3$ (475 mg, 1.46 mmol), XPhos (57 mg, 121.63 umol) and Pd$_2$(dba)$_3$ (56 mg, 60.81 umol) at 20° C. under N$_2$. The mixture was heated to 110° C. and stirred for 5 h. The mixture was cooled to 20° C. and added with water (10 mL), then extracted with EtOAc (3×5 mL), washed with brine (5 mL), dried over anhydrous Na$_2$SO$_4$, filtered and concentrated under reduced pressure. The residue was purified by prep-TLC (PE:EtOAc=1:1) to give 2-[4-[[6-ethoxy-9-(2-trimethylsilylethoxymethyl)purin-2-yl]amino]-3-methyl-pyrazol-1-yl]-2-methyl-propanenitrile (259 mg, 93.27%) as a yellow oil. LCMS: RT 0.874 min, m/z=457.3 [M+H]+

2-[4-[(6-ethoxy-9H-purin-2-yl)amino]-3-methyl-pyrazol-1-yl]-2-methyl-propanenitrile To a mixture of 2-[4-[[6-ethoxy-9-(2-trimethylsilylethoxymethyl)purin-2-yl]amino]-3-methyl-pyrazol-1-yl]-2-methyl-propanenitrile (256 mg, 560.64 umol) in DCM (20 mL) was added TFA (6.16 g, 54.03 mmol, 4 mL) at 20° C. under N$_2$. The mixture was heated to 40° C. and stirred for 5 h. The mixture was cooled to 20° C. and concentrated. The residue was adjusted pH=7-8 by adding aq.NaHCO$_3$. The mixture was extracted with EtOAc (10 mL×3), washed with brine (10 mL), dried over anhydrous Na$_2$SO$_4$, filtered and concentrated under reduced pressure. The residue was purified by prep-HPLC (neutral) to give 2-[4-[(6-ethoxy-9H-purin-2-yl)amino]-3-methyl-pyrazol-1-yl]-2-methyl-propanenitrile. LCMS: RT 0.629 min, m/z=327.2 [M+H]⁺. ¹H NMR (400 MHz, MeOD): δ ppm 8.25 (s, 1H), 7.90 (s, 1H), 4.59 (q, J=7.06 Hz, 2H), 2.25-2.29 (m, 3H), 1.99 (s, 6H), 1.48 (t, J=7.06 Hz, 3H). HPLC: RT: 1.652 min. MS: [M+H]⁺ m/z: 327.2.

Example B-12

Synthesis of 2-[4-[(5-cyclopropyl-4-methoxy-7H-pyrrolo[2,3-d]pyrimidin-2-yl)amino]-3-methyl-pyrazol-1-yl]-2-methyl-propanenitrile (B-13)

2-[(2,4-dichloro-5-cyclopropyl-pyrrolo[2,3-d]pyrimidin-7-yl)methoxy]ethyl-trimethyl-silane A mixture of 2-[(2,4-dichloro-5-iodo-pyrrolo[2,3-d]pyrimidin-7-yl)methoxy]ethyl-trimethyl-silane (3 g, 6.75 mmol), cyclopropylboronic acid (928 mg, 10.80 mmol), Pd(dppf)Cl₂ (494 mg, 675 umol), Ag₂O (782 mg, 3.38 mmol) and K₃PO₄ (4.3 g, 20.25 mmol) in 1,4-dioxane (30 mL) was degassed and purged with N₂ for 3 times. The mixture was stirred at 90° C. for 16 h under N₂. The mixture was cooled to 20° C. and poured into ice-water (30 mL). The aqueous phase was extracted with EtOAc (3×20 mL). The combined organic phase was washed with brine (3×20 mL), dried over anhydrous Na₂SO₄, filtered and concentrated under reduced pressure. The residue was purified by silica gel column chromatography (PE:EtOAc=5:1), to give 2-[(2,4-dichloro-5-cyclopropyl-pyrrolo[2,3-d]pyrimidin-7-yl)methoxy]ethyl-trimethyl-silane (2 g, 82.69%) as a yellow solid. LCMS: RT 1.069 min, m/z=358.1 [M+H]⁺. ¹H NMR (400 MHz, CDCl₃): δ 6.97 (d, J=1.13 Hz, 1H), 5.51-5.53 (m, 2H), 3.49-3.53 (m, 2H), 2.11-2.20 (m, 1H), 0.96-1.00 (m, 2H), 0.90-0.94 (m, 2H), 0.64 (dd, J=5.21, 1.57 Hz, 2H), −0.04 (s, 9H).

2-[(2-chloro-5-cyclopropyl-4-methoxy-pyrrolo[2,3-d]pyrimidin-7-yl)methoxy]ethyl-trimethyl-silane To a mixture of 2-[(2,4-dichloro-5-cyclopropyl-pyrrolo[2,3-d]pyrimidin-7-yl)methoxy]ethyl-trimethyl-silane (1 g, 2.79 mmol) in MeOH (2 mL) was added CH₃ONa (880 mg, 16.29 mmol) in one portion at 0° C., warmed to 20° C. and stirred for 16 h. The mixture was poured into ice-water (10 mL). The aqueous phase was extracted with EtOAc (3×10 mL). The combined organic phase was washed with brine (10 mL), dried over anhydrous Na₂SO₄, filtered and concentrated under reduced pressure, to give 2-[(2-chloro-5-cyclopropyl-4-methoxy-pyrrolo[2,3-d]pyrimidin-7-yl)methoxy]ethyl-trimethyl-silane (1 g, crude) as a yellow oil. LCMS: RT 1.051 min, m/z=354.2 [M+H]⁺. ¹H NMR (400 MHz, CDCl₃): δ 6.71 (s, 1H), 5.47 (s, 2H), 4.14 (s, 3H), 3.44-3.53 (m, 2H), 2.06-2.15 (m, 1H), 0.89-0.95 (m, 4H), 0.58-0.64 (m, 2H), −0.05 (s, 9H).

2-[4-[[5-cyclopropyl-4-methoxy-7-(2-trimethylsilylethoxymethyl)pyrrolo[2,3-d]pyrimidin-2-yl]amino]-3-methyl-pyrazol-1-yl]-2-methyl-propanenitrile A mixture of 2-[(2-chloro-5-cyclopropyl-4-methoxy-pyrrolo[2,3-d]pyrimidin-7-yl)methoxy]ethyl-trimethyl-silane (300 mg, 847.65 umol), 2-(4-amino-3-methyl-pyrazol-1-yl)-2-methyl-propanenitrile (278 mg, 1.70 mmol), Pd₂(dba)₃ (78 mg, 84.77 umol), XPhos (81 mg, 169.53 umol) and Cs₂CO₃ (690 mg, 2.12 mmol) in 1,4-dioxane (5 mL) was degassed and purged with N₂ for 3 times, and then the mixture was stirred at 110° C. for 16 h under N₂. The mixture was cooled to 20° C. and poured into ice-water (5 mL). The aqueous phase was extracted with EtOAc (3×4 mL). The combined organic phase was washed with brine (4 mL), dried over anhydrous Na₂SO₄, filtered and concentrated under reduced pressure. The residue was purified by prep-TLC (SiO₂, PE:EtOAc=3:1), to give 2-[4-[[5-cyclopropyl-4-methoxy-7-(2-trimethylsilylethoxymethyl)pyrrolo[2,3-d]pyrimidin-2-yl]amino]-3-methyl-pyrazol-1-yl]-2-methyl-propanenitrile (279 mg, 68.34%) as a yellow oil. LCMS: RT 1.021 min, m/z=482.4 [M+H]⁺.

2-[4-[(5-cyclopropyl-4-methoxy-7H-pyrrolo[2,3-d]pyrimidin-2-yl)amino]-3-methyl-pyrazol-1-yl]-2-methyl-propanenitrile To a mixture of 2-[4-[[5-cyclopropyl-4-methoxy-7-(2-trimethylsilylethoxymethyl)pyrrolo[2,3-d]pyrimidin-2-yl]amino]-3-methyl-pyrazol-1-yl]-2-methyl-propanenitrile (279 mg, 579.25 umol) in DCM (20 mL) was added TFA (6.16 g, 54.03 mmol, 4 mL) at 0° C. under N₂. The mixture was stirred at 20° C. for 8 h and concentrated under reduced pressure. The residue in THF (20 mL) and H₂O (5 mL) was added with K₂CO₃ (7 g, 50.65 mmol). The mixture was stirred at 20° C. for 12 h. The mixture was poured into ice-water (10 mL). The aqueous phase was extracted with EtOAc (3×10 mL). The combined organic phase was washed with brine (10 mL), dried over anhydrous Na₂SO₄, filtered and concentrated under reduced pressure. The residue was purified by prep-HPLC (neutral), to give 2-[4-[(5-cyclopropyl-4-methoxy-7H-pyrrolo[2,3-d]pyrimidin-2-yl)amino]-3-methyl-pyrazol-1-yl]-2-methyl-propanenitrile. ¹H NMR (400 MHz, CDCl₃): δ 8.71 (br. s., 1H), 8.24 (s, 1H), 6.33 (s, 2H), 4.10 (s, 3H), 2.29 (s, 3H), 2.03-2.12 (m, 1H), 1.93 (s, 6H), 0.84-0.90 (m, 2H), 0.58 (dd, J=5.21, 1.69 Hz, 2H). HPLC: RT: 2.77 min. MS: [M+H]⁺ m/z=352.2.

Example B-13

Synthesis of 2-(4-((4-methoxy-5-(trifluoromethyl)-7H-pyrrolo[2,3-d]pyrimidin-2-yl)amino)-3-methyl-1H-pyrazol-1-yl)-2-methylpropanenitrile (B-14)

2-chloro-4-methoxy-5-(trifluoromethyl)-7-((2-(trimethylsilyl)ethoxy)methyl)-7H-pyrrolo[2,3-d]pyrimidine To a solution of CuI (146 mg, 0.77 mmol), KF (668 mg, 11.5 mmol) and 1,10-phenanthroline (138 mg, 0.77 mmol) in DMSO (2 mL) was added (MeO)₃B (1.2 g, 11.5 mmol), 2,4-dichloro-5-iodo-7-((2-(trimethylsilyl)ethoxy)methyl)-7H-pyrrolo[2,3-d]pyrimidine (1.7 g, 3.83 mmol) and TMSCF₃ (1.63 g, 11.5 mmol). The reaction mixture was stirred at 60° C. for 12 h under N₂. The mixture was cooled to 20° C. and poured into ice-water (20 mL). The aqueous phase was extracted with EtOAc (2×20 mL). The combined organic phase was washed with brine (20 mL), dried over anhydrous Na₂SO₄, filtered and concentrated under reduced pressure to give a residue, which was purified by silica gel column chromatography (PE:EtOAc=20:1 to 1:1) to give 2-chloro-4-methoxy-5-(trifluoromethyl)-7-((2-(trimethylsilyl)ethoxy)methyl)-7H-pyrrolo[2,3-d]pyrimidine (900 mg, 61.54%) as a yellow solid. LCMS: RT 1.222 min, m/z=382.1 [M+H]⁺.

2-(4-((4-methoxy-5-(trifluoromethyl)-7-((2-(trimethylsilyl)ethoxy)methyl)-7H-pyrrolo[2,3-d]pyrimidin-2-yl)amino)-3-methyl-1H-pyrazol-1-yl)-2-methyl-propanenitrile To a solution of 2-chloro-4-methoxy-5-(trifluoromethyl)-7-((2-(trimethylsilyl)ethoxy)methyl)-7H-pyrrolo[2,3-d]pyrimidine (200 mg, 0.52 mmol) in 1,4-dioxane (5 mL) was added 2-(4-amino-3-methyl-1H-pyrazol-1-yl)-2-methylpropanenitrile (94 mg, 0.57 mmol), XPhos (248 mg, 0.52 umol), $Cs_2CO_3$ (170 mg, 0.52 mmol) and $Pd_2(dba)_3$ (477 mg, 0.52 umol) under $N_2$, then the mixture was stirred at 100° C. for 2 h. The reaction mixture was cooled to ambient temperature and poured into ice-water (5 mL), and extracted with EtOAc (3×5 mL). Combined organic layers were washed with brine (10 mL), dried over $Na_2SO_4$ and concentrated under reduced pressure to give a residue, which was purified by prep-TLC ($SiO_2$, PE:EtOAc=1:1) to give 2-(4-((4-methoxy-5-(trifluoromethyl)-7-((2-(trimethylsilyl)ethoxy)methyl)-7H-pyrrolo[2,3-d]pyrimidin-2-yl)amino)-3-methyl-1H-pyrazol-1-yl)-2-methylpropanenitrile (200 mg, 75.33%) as a yellow solid. LCMS: RT 1.412 min, m/z=510.4 $[M+H]^+$.

2-(4-((4-methoxy-5-(trifluoromethyl)-7H-pyrrolo[2,3-d]pyrimidin-2-yl)amino)-3-methyl-1H-pyrazol-1-yl)-2-methylpropanenitrile To a solution of 2-(4-((4-methoxy-5-(trifluoromethyl)-7-((2-(trimethylsilyl)ethoxy)methyl)-7H-pyrrolo[2,3-d]pyrimidin-2-yl)amino)-3-methyl-1H-pyrazol-1-yl)-2-methylpropanenitrile (150 mg, 0.29 mmol) in DCM (4 mL) was added TFA (671 mg, 0.44 mL, 5.89 mmol) at 0° C., then the mixture was stirred at 40° C. for 24 h. The reaction mixture was concentrated under reduced pressure. The residue in THF (4 mL) and water (4 mL) was added with $K_2CO_3$ (540 mg, 3.91 mmol) at 20° C. Then the mixture was stirred at 50° C. for 4 h. The mixture was concentrated under reduced pressure to give a residue, which was purified by prep-HPLC (FA) to give 2-(4-((4-methoxy-5-(trifluoromethyl)-7H-pyrrolo[2,3-d]pyrimidin-2-yl)amino)-3-methyl-1H-pyrazol-1-yl)-2-methylpropanenitrile. $^1$H NMR (400 MHz, CHLOROFORM-d): δ 8.74 (br. s., 1H), 8.22 (s, 1H), 7.14 (br. s., 1H), 6.37 (s, 1H), 4.10 (s, 3H), 2.30 (s, 3H), 1.98 (s, 6H). HPLC: RT: 2.98 min. MS: $[M+H]^+$ m/z: 380.1.

Other compounds of structure (B-I) were prepared according to the above procedures.

C: Compound Preparation

In the following Examples, all non-aqueous reactions were carried out in oven-dried or flame-dried glassware under nitrogen atmosphere. All chemicals were purchased from commercial vendors and used as is, unless otherwise specified. Reactions were magnetically stirred and monitored by thin layer chromatography (TLC) with 250 μm pre-coated silica gel plates, visualized either with UV, or in an iodine chamber. Flash column chromatography was performed using silica gel (100-200 mesh). Chemical shifts are reported relative to chloroform (δ7.26), methanol (δ3.31), or DMSO (δ2.50) for 1H NMR. HPLC analysis was performed on Shimadzu 20AB HPLC system with a photodiode array detector and Luna-C18(2) 2.0×50 mm, 5 μm column at a flow rate of 1.2 mL/min with a gradient solvent Mobile phase A (MPA, H2O+0.037% (v/v) TFA): Mobile phase B (MPB, ACN+0.018% (v/v) TFA) (0.01 min, 10% MPB; 4 min, 80% MPB; 4.9 min, 80% MPB; 4.92 min, 10% MPB; 5.5 min, 10% MPB). LCMS was detected under 220 and 254 nm or used evaporative light scattering (ELSD) detection as well as positive electrospray ionization (MS). Semi-preparative HPLC was performed by either acidic or neutral condition. Acidic: Luna C18 100×30 mm, 5 μm; MPA: HCl/$H_2O$=0.04%, or formic acid/$H_2O$=0.2% (v/v); MPB: ACN. Neutral. Waters Xbridge 150×25, 5 μm; MPA: 10 mM $NH_4HCO_3$ in $H_2O$; MPB: ACN. Gradient for both conditions: 10% of MPB to 80% of MPB within 12 min at a flow rate of 20 mL/min, then 100% MPB over 2 min, 10% MPB over 2 min, UV detector. Compounds were named by using either ChemBioDraw Ultra 13.0 or Chemaxon.

Example C-1 and C-2

Synthesis of 6-cyclopropyl-N-[1-[2-fluoro-1-(fluoromethyl)ethyl]-3-methyl-pyrazol-4-yl]-9H-purin-2-amine (C-1) and 6-cyclopropyl-N-(1-(1,3-difluoropropan-2-yl)-5-methyl-1H-pyrazol-4-yl)-9H-purin-2-amine (C-2)

2-[(2,6-dichloropurin-9-yl)methoxy]ethyl-trimethyl-silane

To a solution of compound 2,6-dichloro-9H-purine (10.00 g, 52.91 mmol) in DMF (100 mL) was added NaH (2.54 g, 63.49 mmol, 60% purity) at 0° C. over a period of 15 min under $N_2$. The mixture was then warmed up to 20° C. and stirred at 20° C. for 30 min. Then compound SEMCl (11.35 g, 63.49 mmol) was dropwise at 0° C. over a period of 15 min under $N_2$. The mixture was then warmed up to 20° C. and stirred at 20° C. for 3 h. The reaction was quenched by pouring into ice-water (500 mL) and extracted with MTBE (3×200 mL), washed with brine (100 mL), dried over anhydrous $Na_2SO_4$, filtered and concentrated under reduced pressure. The residue was purified by silica gel column chromatography (PE:EtOAc=20:1 to 2:1) to give compound 2-[(2,6-dichloropurin-9-yl)methoxy]ethyl-trimethyl-silane as a light yellow solid.

2-[(2-chloro-6-cyclopropyl-purin-9-yl)methoxy]ethyl-trimethyl-silane

To a mixture of compound 2-[(2,6-dichloropurin-9-yl)methoxy]ethyl-trimethyl-silane (5.00 g, 15.66 mmol) and cyclopropaneboronic acid (4.04 g, 46.98 mmol) in 1,4-dioxane (50 mL) was added $Ag_2O$ (1.81 g, 7.83 mmol), $K_3PO_4$ (9.97 g, 46.98 mmol) and Pd(dppf)Cl2 (1.15 g, 1.57 mmol) in one portion at 20° C. under N2. The mixture was then heated to 90° C. and stirred for 5 h. The mixture was cooled to 20° C. filtered and concentrated under reduced pressure. The residue was purified by silica gel column chromatography (PE:EtOAc=10:1 to 1:1) to give compound 2-[(2-chloro-6-cyclopropyl-purin-9-yl)methoxy]ethyl-trimethyl-si lane as a light yellow solid.

6-cyclopropyl-N-[1-(1,3-difluoropropan-2-yl)-3-methyl-1H-pyrazol-4-yl]-9-{[2-(trimethylsilyl)ethoxy]methyl}-9H-purin-2-amine and 6-cyclopropyl-N-[1-(1,3-difluoropropan-2-yl)-5-methyl-1H-pyrazol-4-yl]-9-{[2-(trimethylsilyl)ethoxy]methyl}-9H-purin-2-amine To a mixture of compound 2-[(2-chloro-6-cyclopropyl-purin-9-yl)methoxy]ethyl-trimethyl-silane (500 mg, 1.54 mmol) and 1-(1,3-difluoropropan-2-yl)-3-methyl-1H-pyrazol-4-amine and 1-(1,3-difluoropropan-2-yl)-5-methyl-1H-pyrazol-4-amine (405 mg, 2.31 mmol, mixture) in 1,4-dioxane (15 mL) was added XPhos (147 mg, 308 umol), Cs2CO3 (1.20 g, 3.70 mmol) and Pd2(dba)3 (141 mg, 154 umol) in one portion at 20° C. under N2. The mixture was then heated to 110° C. and stirred for 16 h. The mixture was cooled to 20° C., added with EtOAc (5 mL), filtered and the filtrate was concentrated under reduced pressure. The residue was purified by prep-TLC (PE:EtOAc=1:1) to give crude product compound 6-cyclopropyl-N-[1-(1,3-difluoropropan-2-yl)-3-methyl-1H-pyrazol-4-yl]-9-{[2-(trimethylsilyl)ethoxy]methyl}-9H-purin-2-amine and 6-cyclopropyl-N-[1-(1,3-difluoropropan-2-yl)-5-methyl-1H-pyrazol-4-yl]-9-{[2-(trimethylsilyl)ethoxy]methyl}-9H-purin-2-amine as a red brown oil which was used into the next step without further purification.

6-cyclopropyl-N-[1-[2-fluoro-1-(fluoromethyl)ethyl]-3-methyl-pyrazol-4-yl]-9H-purin-2-amine and 6-cyclopropyl-N-(1-(1,3-difluoropropan-2-yl)-5-methyl-1H-pyrazol-4-yl)-9H-purin-2-amine To a mixture of compound 6-cyclopropyl-N-[1-(1,3-difluoropropan-2-yl)-3-methyl-1H-pyrazol-4-yl]-9-{[2-(trimethylsilyl)ethoxy]methyl}-9H-purin-2-amine and 6-cyclopropyl-N-[1-(1,3-difluoropropan-2-yl)-5-methyl-1H-pyrazol-4-yl]-9-{[2-(trimethylsilyl)ethoxy]methyl}-9H-purin-2-amine (220 mg, 474 umol) in DCM (20 mL) was added TFA (6.16 g, 54.03 mmol) at 0° C. The mixture was heated to 40° C. and stirred for 3.5 h. The mixture was cooled to 25° C. and adjusted pH to 7 by adding aq. NaHCO3 and stirred for 10 min. The mixture was then extracted with EtOAc (3×5 mL). The combined organic phase was washed with brine (5 mL), dried over anhydrous Na2SO4, filtered and concentrated under reduce pressure. The residue was purified by prep-HPLC (FA condition) to give 6-cyclopropyl-N-[1-[2-fluoro-1-(fluoromethyl)ethyl]-3-methyl-pyrazol-4-yl]-9H-purin-2-amine and 6-cyclopropyl-N-(1-(1,3-difluoropropan-2-yl)-5-methyl-1H-pyrazol-4-yl)-9H-purin-2-amine.

6-cyclopropyl-N-[1-[2-fluoro-1-(fluoromethyl)ethyl]-3-methyl-pyrazol-4-yl]-9H-purin-2-amine $^1$H NMR (400 MHz, CDCl3): δ ppm 7.95 (s, 1H), 7.68 (s, 1H), 6.50 (br. s., 1H), 4.38-5.08 (m, 5H), 2.66 (d, J=4.52 Hz, 1H), 2.26 (s, 3H), 1.33-1.47 (m, 2H), 1.14-1.24 (m, 2H). HPLC: RT 1.574 min. MS: m/z: 334.2 [M+H]+.

6-cyclopropyl-N-(1-(1,3-difluoropropan-2-yl)-5-methyl-1H-pyrazol-4-yl)-9H-purin-2-amine $^1$H NMR (400 MHz, CDCl3): δ ppm 11.66 (br. s., 1H), 7.67 (s, 1H) 7.21 (s, 1H), 6.23 (s, 1H), 4.57-4.83 (m, 5H), 2.59 (br. s., 1H), 2.11-2.24 (m, 3H), 1.29 (br. s., 2H), 1.03-1.14 (m, 2H). HPLC: RT 1.556 min. MS: m/z: 334.2 [M+H]+.

Example C-3

Synthesis of 6-cyclopropyl-N-(1-(difluoromethyl)-3-methyl-1H-pyrazol-4-yl)-9H-purin-2-amine (C-3)

6-cyclopropyl-N-(1-(difluoromethyl)-3-methyl-1H-pyrazol-4-yl)-9-((2-(trimethylsilyl)ethoxy)methyl)-9H-purin-2-amine To a solution of 2-[(2,6-dichloropurin-9-yl)methoxy]ethyl-trimethyl-silane (180 mg, 554.05 nmol) in 1,4-dioxane (10 mL) was added compound 1-(difluoromethyl)-3-methyl-1H-pyrazol-4-amine (98 mg, 664.86 umol), XPhos (53 mg, 110.81 umol), Cs2CO3 (361 mg, 1.11 mmol) and Pd2(dba)3 (51 mg, 55.41 umol). The mixture was stirred at 110° C. for 6 h under N2. The mixture was concentrated under reduced pressure to give a residue, which was purified by prep-TLC (SiO2, PE:EtOAc=1:1) to give compound 6-cyclopropyl-N-(1-(difluoromethyl)-3-methyl-1H-pyrazol-4-yl)-9-((2-(trimethylsilyl)ethoxy)methyl)-9H-purin-2-amine as a yellow solid. LCMS: RT 0.880 min. m/z=436.1 [M+H]+.

6-cyclopropyl-N-(1-(difluoromethyl)-3-methyl-1H-pyrazol-4-yl)-9H-purin-2-amine

To a solution of 6-cyclopropyl-N-(1-(difluoromethyl)-3-methyl-1H-pyrazol-4-yl)-9H-purin-2-amine (205 mg, 476.67 umol) in DCM (20 mL) was added TFA (6.8 g, 59.65 mmol) in one portion at 25° C. The mixture was stirred at 40° C. for 4 h. The reaction mixture was concentrated under reduced pressure to get a residue, which was dissolved in THF (20 mL) and treated with aq. NaHCO3 (20 mL). The mixture was stirred at 25° C. for 12 h. The mixture was extracted with EtOAc (30 mL). The organic layer was separated and washed with brine (15 mL), dried over Na2SO4, filtered and concentrated under reduced pressure to get a residue, which was purified by prep-HPLC (neutral) to get 6-cyclopropyl-N-(1-(difluoromethyl)-3-methyl-1H-pyrazol-4-yl)-9H-purin-2-amine. $^1$H NMR (400 MHz, MeOD): δ 8.40 (s, 1H), 8.07 (s, 1H), 7.12-7.48 (m, 1H), 2.56-2.66 (m, 1H), 2.29 (s, 3H), 1.27-1.35 (m, 2H), 1.12-1.21 (m, 2H). HPLC: RT 1.96 min. MS: m/z: 306.2 [M+H]+.

Example C-4

Synthesis of 6-cyclopropyl-N-(1-(difluoromethyl)-5-methyl-1H-pyrazol-4-yl)-9H-purin-2-amine (C-4)

6-cyclopropyl-N-(1-(difluoromethyl)-5-methyl-1H-pyrazol-4-yl)-9-((2-(trimethylsilyl)ethoxy)methyl)-9H-purin-2-amine To a solution of 2-[(2,6-dichloropurin-9-yl)methoxy]ethyl-trimethyl-silane (180 mg, 554.05 umol) in 1,4-dioxane (10 mL) was added 1-(difluoromethyl)-5-methyl-1H-pyrazol-4-amine (98 mg, 664.86 umol), XPhos (53 mg, 110.81 umol), Cs2CO3 (361 mg, 1.11 mmol) and Pd2(dba)3 (51 mg, 55.41 umol). The mixture was stirred at 110° C. for 6 h under N2. The mixture was concentrated under reduced pressure to give a residue, which was purified by prep-TLC (SiO2, PE:EtOAc=1:1) to give 6-cyclopropyl-N-(1-(difluoromethyl)-5-methyl-1H-pyrazol-4-yl)-9-((2-(trimethylsilyl)ethoxy)methyl)-9H-purin-2-amine as a yellow solid. LCMS: RT 2.831 min, m/z=436.1 [M+H]+.

6-cyclopropyl-N-(1-(difluoromethyl)-5-methyl-1H-pyrazol-4-yl)-9H-purin-2-amine

To a solution of 6-cyclopropyl-N-(1-(difluoromethyl)-5-methyl-1H-pyrazol-4-yl)-9-((2-(trimethylsilyl)ethoxy)methyl)-9H-purin-2-amine (140 mg, 321.43 umol) in DCM (20 mL) was added TFA (6.8 g, 59.65 mmol) in one portion at 25° C. The mixture was heated to 40° C. and stirred for 4 h. The reaction mixture was concentrated under reduced pressure to get a residue, which was dissolved in THF (20 mL) and added with aq.NaHCO3 (20 mL). The mixture was stirred at 25° C. for 12 h. The mixture was extracted with EtOAc (30 mL). The organic layer was separated and washed with brine (15 mL), dried over Na2SO4, filtered and concentrated under reduced pressure to get a residue, which was purified by prep-HPLC (neutral) to get 6-cyclopropyl-N-(1-(difluoromethyl)-5-methyl-1H-pyrazol-4-yl)-9H-purin-2-amine. $^1$H NMR (400 MHz, MeOD): δ 8.02 (br. s., 1H), 7.93 (s, 1H), 7.24-7.57 (m, 1H), 2.59 (br. s., 1H), 2.39

(s, 3H), 1.23-1.32 (m, 2H), 1.08-1.18 (m, 2H). HPLC. RT: 1.87 min. MS: m/z: 306.1 [M+H]$^+$.

Example C-5 and C-6

Synthesis of 6-cyclopropyl-N-(1,5-dimethylpyrazol-4-yl)-9H-purin-2-amine (C-5) and 6-cyclopropyl-N-(1,3-dimethylpyrazol-4-yl)-9H-purin-2-amine (C-6)

6-cyclopropyl-N-(1,5-dimethylpyrazol-4-yl)-9-(2-trimethylsilylethoxymethyl)purin-2-amine 2-[(2,6-dichloropurin-9-yl)methoxy]ethyl-trimethyl-silane (400 mg, 1.23 mmol), 1,3-dimethyl-1H-pyrazol-4-amine and 1,5-dimethyl-1H-pyrazol-4-amine (205 mg, 1.85 mmol, mixture), XPhos (117 mg, 246.24 umol), Cs$_2$CO$_3$ (963 mg, 2.95 mmol) and Pd$_2$(dba)$_3$ (112 mg, 123.12 umol) in 1,4-dioxane (10 mL) were taken up into a microwave tube. The sealed tube was heated at 110° C. for 14 h under microwave irradiation. After cooled to 25° C., EtOAc (10 mL) was added. The mixture was then filtered and concentrated under reduced pressure. The residue was purified by silica gel column chromatography (PE:EtOAc=10:1 to 0:1) to give 6-cyclopropyl-N-(1,3-dimethyl-1H-pyrazol-4-yl)-9-{[2-(trimethylsilyl)ethoxy]methyl}-9H-purin-2-amine and 6-cyclopropyl-N-(1,5-dimethyl-1H-pyrazol-4-yl)-9-{[2-(trimethylsilyl)ethoxy]methyl}-9H-purin-2-amine as a yellow oil.

6-cyclopropyl-N-(1,5-dimethylpyrazol-4-yl)-9H-purin-2-amine and 6-cyclopropyl-N-(1,3-dimethylpyrazol-4-yl)-9H-purin-2-amine To a solution of 6-cyclopropyl-N-(1,3-dimethyl-1H-pyrazol-4-yl)-9-{[2-(trimethylsilyl)ethoxy]methyl}-9H-purin-2-amine and 6-cyclopropyl-N-(1,5-dimethyl-1H-pyrazol-4-yl)-9-{[2-(trimethylsilyl)ethoxy]methyl}-9H-purin-2-amine (200 mg, 500.54 μmol, mixture) in DCM (20 mL) was added TFA (6.16 g, 54.02 mmol) in one portion at 0° C. Then the mixture was heated to 40° C. and stirred for 6 h. The mixture was adjusted pH to 7-8 by adding aq. sat. NaHCO$_3$ and stirred for 10 min. The aqueous phase was extracted with EtOAc (3×5 mL). The combined organic phase was washed with brine (5 mL), dried over anhydrous Na$_2$SO$_4$, filtered and concentrated under reduced pressure. The residue was purified by prep-HPLC (FA condition) and further separated by SFC to give 6-cyclopropyl-N-(1,5-dimethylpyrazol-4-yl)-9H-purin-2-amine and 6-cyclopropyl-N-(1,3-dimethylpyrazol-4-yl)-9H-purin-2-amine. LCMS: RT 0.148 min, m/z=270.2 [M+H]$^+$.

6-cyclopropyl-N-(1,5-dimethylpyrazol-4-yl)-9H-purin-2-amine $^1$H NMR (400 MHz, CDCl$_3$): δ ppm 11.89 (br. s., 1H), 7.58 (s, 1H), 7.17 (s, 1H), 6.32 (br. s., 1H), 3.83 (s, 1H), 3.75 (s, 3H), 2.60-2.70 (m, 1H), 2.23 (s, 1H), 2.17 (s, 3H), 1.37 (br. s., 2H), 1.17 (d, J=4.52 Hz, 2H), 0.08 (s, 1H). HPLC: RT: 1.287 min. MS: m/z: 270.2 [M+H]$^+$.

6-cyclopropyl-N-(1,3-dimethylpyrazol-4-yl)-9H-purin-2-amine $^1$H NMR (400 MHz, CDCl3): δ ppm 10.46 (br. s., 1H), 7.69 (s, 1H), 7.53 (s, 1H), 6.34 (s, 1H), 3.84 (s, 3H), 2.63-2.72 (m, 1H), 2.25 (s, 3H), 1.34-1.41 (m, 2H), 1.18 (dd, J=8.16, 3.31 Hz, 2H). HPLC: RT: 1.262 min. MS: m/z: 270.1 [M+H]$^+$.

Example C-7

Synthesis of 6-cyclopropyl-N-(1-(cyclopropylmethyl)-5-methyl-1H-pyrazol-4-yl)-9H-purin-2-amine (C-7)

6-cyclopropyl-N-(1-(cyclopropylmethyl)-5-methyl-1H-pyrazol-4-yl)-9-((2-(trimethylsilyl)ethoxy)methyl)-9H-purin-2-amine To a solution of 2-[(2,6-dichloropurin-9-yl)methoxy] ethyl-trimethyl-silane (232 mg, 714.14 umol) in 1,4-dioxane (10 mL) was added 1-(cyclopropylmethyl)-5-methyl-1H-pyrazol-4-amine (90 mg, 595.20 umol), XPhos (57 mg, 119.04 umol), Cs$_2$CO$_3$ (388 mg, 1.19 mmol) and Pd$_2$(dba)$_3$ (55 mg, 59.52 umol). The mixture was stirred at 110° C. for 6 h under N$_2$. The mixture was concentrated under reduced pressure to give a residue, which was purified by prep-TLC (SiO$_2$, PE:EtOAc=1:1) to give 6-cyclopropyl-N-(1-(cyclopropylmethyl)-5-methyl-1H-pyrazol-4-yl)-9-((2-(trimethylsilyl)ethoxy)methyl)-9H-purin-2-amine as a yellow solid. LCMS: RT 0.839 min, m/z=440.3 [M+H]$^+$.

6-cyclopropyl-N-(1-(cyclopropylmethyl)-5-methyl-1H-pyrazol-4-yl)-9H-purin-2-amine To a solution of 6-cyclopropyl-N-(1-(cyclopropylmethyl)-5-methyl-1H-pyrazol-4-yl)-9-((2-(trimethylsilyl)ethoxy)methyl)-9H-purin-2-amine (160 mg, 363.94 umol) in DCM (20 mL) was added TFA (7.7 g, 67.53 mmol) in one portion at 25° C. The mixture was heated to 40° C. and stirred for 4 h. The reaction mixture was concentrated under reduced pressure to get a residue, which was dissolved in THF (20 mL) and added with aq. NaHCO$_3$ (20 mL). The mixture was stirred at 25° C. for 12 h. The mixture was extracted with EtOAc (30 mL). The organic layer was separated and washed with brine (15 mL), dried over Na$_2$SO$_4$, filtered and concentrated under reduced pressure to get a residue, which was purified by prep-HPLC (neutral) to get 6-cyclopropyl-N-(1-(cyclopropylmethyl)-5-methyl-1H-pyrazol-4-yl)-9H-purin-2-amine. $^1$H NMR (400 MHz, CDCl$_3$): δ 11.82-12.27 (m, 1H), 7.62 (s, 1H), 7.19 (s, 1H), 6.30 (s, 1H), 3.88 (d, J=6.90 Hz, 2H), 2.63 (d, J=4.14 Hz, 1H), 2.21 (s, 3H), 1.36 (br. s, 2H), 1.15 (dd, J=7.65, 2.89 Hz, 3H), 0.53 (d, J=7.53 Hz, 2H), 0.33 (d, J=5.02 Hz, 2H). HPLC: RT 1.74 min. MS: m/z: 310.2 [M+H]$^+$.

Example C-8

Synthesis of N-(6-cyclopropyl-9H-purin-2-yl)spiro [4,6-dihydropyrrolo[1,2-b]pyrazole-5,1 cyclopropane]-3-amine (C-8)

[1-[(4-nitropyrazol-1-yl)methyl]cyclopropyl]methanol

To a solution of 3-nitropyrazole (16.61 g, 146 mmol), [1-(hydroxymethyl) cyclopropyl]methanol (15 g, 146 mmol) and PPh$_3$ (38.52 g, 146 mmol) in THF (300 mL) was added DIAD (29.7 g, 146 mmol) dropwise at 0° C. over a period of 30 min under N$_2$. The reaction mixture was stirred at 25° C. for another 12 h. The reaction was concentrated under reduced pressure. The residue was purified by silica gel column chromatography (PE:EtOAc=50:1 to 2:1) to give [1-[(4-nitropyrazol-1-yl)methyl]cyclopropyl]methanol as a white solid.

1-[[1-(bromomethyl)cyclopropyl]methyl]-4-nitropyrazole

To a mixture of [1-[(4-nitropyrazol-1-yl)methyl]cyclopropyl]methanol (7 g, 35.5 mmol) in DCM (100 mL) was added PBr$_3$ (19.22 g, 71 mmol) at 0° C. over a period of 15 min. The mixture was stirred at 0° C. for 2 h. The mixture was poured into ice-water (100 mL) and stirred for 5 min. The aqueous phase was extracted with DCM (50 mL×2). The combined organic phase was washed with brine (100 mL), dried over anhydrous Na$_2$SO$_4$, filtered and concentrated under reduced pressure. The residue was purified by silica gel column chromatography (SiO$_2$, PE:EtOAc=100:1 to 10:1) to give 1-[[1-(bromomethyl)cyclopropyl]methyl]-4-nitro-pyrazole as a white solid. $^1$H NMR (400 MHz, CDCl$_3$): δ ppm 8.24 (s, 1H), 8.11 (s, 1H), 4.23, (s, 2H), 3.23, (s, 2H), 1.03-1.08 (m, 2H), 0.82-0.87 (m, 2H).

3-nitrospiro[4,6-dihydropyrrolo[1,2-b]pyrazole-5,1'-cyclopropane]

To a solution of 1-[[1-(bromomethyl)cyclopropyl]methyl]-4-nitro-pyrazole (560 mg, 2.15 mmol) in THF (500 mL) was added a solution of LiHMDS (4.3 mmol, 1 M, 4.3 mL) dropwise at −78° C. under N$_2$. After addition the reaction was allowed to warm to 25° C. over a period of 2 h, and stirred at 60° C. for 4 h. The five parallel reactions were combined to workup. The mixture was quenched by aq. NH$_4$Cl (100 ml) and extracted with MTBE (3×100 mL). The combined organic phase was washed with brine (2×100 mL), dried over anhydrous Na$_2$SO$_4$, filtered and concentrated under reduced pressure. The product was purified by prep-HPLC (TFA) to give 3-nitrospiro[4,6-dihydropyrrolo[1,2-b]pyrazole-5,1'-cyclopropane] as a yellow solid. LCMS: RT 0.986 min, m/z=180 [M+H]$^+$. $^1$H NMR (400 MHz, CDCl$_3$): δ ppm 8.09 (s, 1H), 4.15 (s, 2H), 3.24 (s, 2H), 0.92 (s, 4H).

Spiro [4,6-dihydropyrrolo[1,2-b]pyrazole-5,1'-cyclopropane]-3-amine

To a solution of 3-nitrospiro[4,6-dihydropyrrolo[1,2-b]pyrazole-5,1'-cyclopropane] (90 mg, 502 umol) in MeOH (5 mL) was added Pd/C under N$_2$. The suspension was degassed under vacuum and purged with H$_2$ three times. The mixture was stirred under H$_2$ (20 psi) at 25° C. for 2 h. The reaction mixture was filtered and the filtrate was concentrated under reduced pressure to give spiro [4,6-dihydropyrrolo[1,2-b]pyrazole-5,1'-cyclopropane]-3-amine as a brown solid. LCMS: RT 0.911 min, m/z=150 [M+H]$^+$. $^1$H NMR (400 MHz, CDCl3): δ ppm 7.24 (s, 1H), 4.01 (s, 2H), 2.81 (s, 2H), 2.72 (br. s., 1H), 0.77-0.86 (m, 4H).

N-[6-cyclopropyl-9-(2-trimethylsilylethoxymethyl)purin-2-yl]spiro[4,6-dihydropyrrolo[1,2-b]pyrazole-5,1'-cyclopropane]-3-amine To a mixture of spiro [4,6-dihydropyrrolo[1,2-b]pyrazole-5, V-cyclopropane]-3-amine (80 mg, 536.23 umol) and 2-[(2,6-dichloropurin-9-yl)methoxy]ethyl-trimethyl-silane (261 mg, 804.35 umol) in 1,4-dioxane (1 mL) was added XPhos (51 mg, 107.25 umol), Cs$_2$CO$_3$ (419 mg, 1.29 mmol) and Pd$_2$(dba)$_3$ (49 mg, 53.62 umol) at 20° C. under N$_2$. The mixture was heated to 110° C. and stirred for 5 h. The mixture was cooled to 20° C. then added with water (5 mL). The aqueous phase was extracted with EtOAc (3<3 mL). The combined organic phase was washed with brine (3 mL), dried over anhydrous Na$_2$SO$_4$, filtered and concentrated under reduced pressure. The residue was purified by prep-TLC (PE:EtOAc=1:1) to give N-[6-cyclopropyl-9-(2-trimethylsilylethoxymethyl)purin-2-yl]spiro[4,6-dihydropyrrolo[1,2-b]pyrazole-5,1'-cyclopropane]-3-amine as a yellow oil.

N-(6-cyclopropyl-9H-purin-2-yl)spiro[4,6-dihydropyrrolo[1,2-b]pyrazole-5,1'-cyclopropane]-3-amine To a mixture of N-[6-cyclopropyl-9-(2-trimethylsilylethoxymethyl)purin-2-yl]spiro[4,6-dihydropyrrolo[1,2-b]pyrazole-5,1'-cyclopropane]-3-amine (230 mg, 525.58 umol) in DCM (20 mL) was added TFA (6.16 g, 54.02 mmol) in one portion at 20° C. The mixture was heated to 40° C. and stirred for 5 h. The mixture was then cooled to 20° C. and concentrated under reduced pressure. The residue was added with THF (10 mL) and aq. K$_2$CO$_3$ (10 mL) then stirred for 2 h. The mixture was filtered and the filtrate was concentrated, extracted with EtOAc (3×5 mL). The combined organic phase was washed with brine (5 mL), dried over anhydrous Na$_2$SO$_4$, filtered and concentrated under reduced pressure. The residue was purified by prep-HPLC (neutral condition) to give N-(6-cyclopropyl-9H-purin-2-yl) spiro[4,6-dihydropyrrolo[1,2-b]pyrazole-5,1'-cyclopropane]-3-amine. LCMS: RT 0.212 min, m/z=308.1 [M+H]$^+$. $^1$H NMR (400 MHz, CDCl3): δ ppm 12.53 (br. s., 1H), 7.64 (s, 1H), 7.06 (s, 1H), 6.48 (s, 1H), 3.94 (s, 2H), 2.77 (s, 2H), 2.60-2.69 (m, 1H), 1.36 (br. s., 2H), 1.17 (dd, J=7.53, 3.01 Hz, 2H), 0.39-0.60 (m, 4H). HPLC. RT: 1.658 min. MS: m/z: 308.2 [M+H]$^+$.

Example C-9

Synthesis of 2-(4-((6-cyclopropyl-9H-purin-2-yl)amino)-3-methyl-1H-pyrazol-1-yl)-2-methylpropanenitrile (C-9)

Methyl 2-methyl-2-(3-methyl-4-nitro-pyrazol-1-yl)propanoate

To a solution of 3-methyl-4-nitro-1H-pyrazole (40 g, 314.71 mmol) in DMF (700 mL) was added NaH (18.88 g, 472.06 mmol, 60% purity) at 0° C. over a period of 30 min under N$_2$. The reaction was then stirred at 25° C. for 2 h followed by the addition of methyl 2-bromo-2-methylpropanoate (85.46 g, 472.06 mmol, 61.04 mL) dropwise at 0° C. The reaction mixture was warmed to 25° C. and stirred at 25° C. for another 16 h. TLC (petroleum ether/ethyl acetate=5:1) showed the starting material was consumed completely. The reaction was quenched by ice water slowly and then extracted with EtOAc (3×700 mL). The combined organic phase was washed with brine (3×200 mL), dried over anhydrous Na$_2$SO$_4$, filtered and concentrated in vacuo. The residue was purified by column chromatography on silica gel (petroleum ether/ethyl acetate=30:1-15:1), to yield the desired product as a light yellow solid. $^1$H NMR (400 MHz, CDCl$_3$): δ 8.29 (s, 1H), 3.72 (s, 1H), 2.51 (s, 1H), 1.84 (s, 6H).

2-Methyl-2-(3-methyl-4-nitro-pyrazol-1-yl) propanoic acid

To a mixture of methyl 2-methyl-2-(3-methyl-4-nitro-pyrazol-1-yl)propanoate (69.7 g, 306.75 mmol) in THF (1 L)

and H$_2$O (250 mL) was added LiOH.H$_2$O (15.45 g, 368.10 mmol) at 25° C. under N$_2$. The mixture was then stirred at 25° C. for 16 h. TLC (petroleum ether/ethyl acetate=5:1) showed die reaction was completed. The reaction mixture was concentrated in vacuo. The residual aqueous solution was washed with ethyl acetate (50 mL). The aqueous phase was then cooled to 0° C., adjusted to approximately pH 1-2, and filtered to yield the desired product as a white solid. $^1$H NMR (400 MHz, CDCl$_3$): δ 8.65 (s, 1H), 2.48 (s, 1H), 1.83 (s, 6H).

2-Methyl-2-(3-methyl-4-nitro-pyrazol-1-yl)propanamide

To a solution of 2-methyl-2-(3-methyl-4-nitro-pyrazol-1-yl) propanoic acid (25 g, 117.27 mmol) in DCM (500 mL) was added 8 drops of DMF, followed by oxalyl chloride (29.77 g, 234.54 mmol) at 0° C. under N$_2$. The mixture was then stirred at 25° C. for a further 2 h. TLC (petroleum ether/ethyl acetate=3:1) showed reaction was completed. The reaction solution was concentrated in vacuo. The residue solid was dissolved in THF (300 mL) and added dropwise into a stirred solution of NH$_4$OH (413.61 g, 11.80 mol, 454.52 mL) at 0° C. The reaction was stirred at 25° C. for 1 h. TLC (ethyl acetate) showed reaction was completed. The solution was then concentrated in vacuo and partitioned between EtOAc (100 mL) and water (100 mL), and the aqueous phase was extracted with ethyl acetate (3×80 mL). The combined organic phase was washed with brine (3×40 mL), dried over anhydrous Na$_2$SO$_4$, filtered and concentrated in vacuo, to yield the desired compound as a yellow solid. $^1$H NMR (400 MHz, MeOD): δ 8.81 (s, 1H), 7.16-7.26 (m, 2H), 2.42 (s, 3H), 1.71 (s, 3H).

2-Methyl-2-(3-methyl-4-nitro-1H-pyrazol-1-yl)propanenitrile

A solution of 2-methyl-2-(3-methyl-4-nitro-pyrazol-1-yl)-propanamide (22 g, 103.67 mmol) in POCl$_3$ (132 g, 860.89 mmol, 80 mL) was stirred at 90° C. for 1 h. TLC showed the reaction was completed. The mixture was cooled to 20° C. and concentrated in vacuo at 50° C. The residue was poured into ice-water (w/w=1/1) (200 mL) and stirred for 10 min. The aqueous phase was adjusted to pH=7 with NaHCO$_3$ solution, extracted with ethyl acetate (4×80 mL). The combined organic phase was washed with brine (40 mL), dried with anhydrous Na$_2$SO$_4$, filtered and concentrated in vacuo. The desired product was afforded as a yellow solid.

2-(4-Amino-3-methyl-pyrazol-1-yl)-2-methyl-propanenitrile

To a mixture of 2-methyl-2-(3-methyl-4-nitro-1H-pyrazol-1-yl)propanenitrile (10 g, 51.5 mmol) in EtOH (240 mL) and H$_2$O (60 mL) was added NH$_4$Cl (13.77 g, 257.5 mmol) in one portion at 25° C., followed by Fe (14.38 g, 257.5 mmol). The mixture was heated to 80° C. and stirred for 1 h. TLC showed the reaction was completed. The solution was cooled to 20° C. The mixture was extracted with ethyl acetate (3×100 mL), the combined organic layers were washed with NaHCO$_3$ solution (50 mL) and brine (50 mL). The organic layers were dried over Na$_2$SO$_4$, filtered and concentrated. The desired product was afforded as a dark brown solid. $^1$H NMR (400 MHz, CDCl$_3$): δ 7.17 (s, 1H), 2.18 (s, 3H), 1.91 (s, 6H).

2-(4-((6-cyclopropyl-9-((2-(trimethylsilyl)ethoxy)methyl)-9H-purin-2-yl)amino)-3-methyl-1H-pyrazol-1-yl)-2-methylpropanenitrile To a solution of 2-[(2,6-dichloropurin-9-yl)methoxy]ethyl-trimethyl-silane (450 mg, 1.39 mmol) and 2-(4-Amino-3-methyl-pyrazol-1-yl)-2-methyl-propanenitrile (342 mg, 2.09 mmol) in 1,4-dioxane (20 mL) was added Pd$_2$(dba)$_3$ (127 mg, 139 umol), Cs$_2$CO$_3$ (1.13 g, 3.47 mmol) and X-Phos (132 mg, 278 umol) under N$_2$. The mixture was stirred at 110° C. for 12 h. The reaction mixture was concentrated under reduced pressure to get a residue, which was diluted with H$_2$O (20 mL) and extracted with EtOAc (2<25 mL). The combined organic layers were washed with brine (15 mL), dried over Na$_2$SO$_4$, filtered and concentrated under reduced pressure to give a residue, which was purified by prep-TLC (SiO$_2$, PE:EtOAc=3:1) to give 2-(4-((6-cyclopropyl-9-((2-(trimethylsilyl)ethoxy)methyl)-9H-purin-2-yl)amino)-3-methyl-1H-pyrazol-1-yl)-2-methylpropanenitrile as a white solid. LCMS: RT 0.843 min, m/z=453.2 [M+H]$^+$.

2-(4-((6-cyclopropyl-9H-purin-2-yl)amino)-3-methyl-1H-pyrazol-1-yl)-2-methylpropanenitrile To a solution of 2-(4-((6-cyclopropyl-9-((2-(trimethylsilyl)ethoxy)methyl)-9H-purin-2-yl)amino)-3-methyl-1H-pyrazol-1-yl)-2-methylpropanenitrile (350 mg, 773.26 umol) in DCM (20 mL) was added TFA (7.05 g, 61.86 mmol) in one portion at 25° C. The mixture was heated to 40° C. and stirred for 5 h. The reaction mixture w as concentrated under reduced pressure to get a residue, which was dissolved in THF (20 mL) and added with aq. NaHCO$_3$ (20 mL). The mixture was stirred at 25° C. for 10 h. The mixture was extracted with EtOAc (40 mL). The organic layer was washed with brine (20 mL), dried over Na$_2$SO$_4$, filtered and concentrated under reduced pressure to get a residue, which was purified by prep-HPLC (neutral) to give of 2-(4-((6-cyclopropyl-9H-purin-2-yl)amino)-3-methyl-1H-pyrazol-1-yl)-2-methylpropanenitrile. $^1$H NMR (400 MHz, DMSO-d6):δ12.27 (br. s, 1H), 8.44 (s, 1H), 8.13 (s, 1H), 8.06 (s, 1H), 2.53-2.57 (m, 1H), 2.18 (s, 3H), 1.94 (s, 6H), 1.25 (br. s, 2H), 1.12 (dd, J=7.72, 3.31 Hz, 2H). HPLC: RT: 1.87 min. MS: m/z: 323.2 [M+H]$^+$.

Example C-10

Synthesis of 2-[[1-(1-cyano-1-methyl-ethyl)-3-methyl-pyrazol-4-yl]amino]-4-cyclopropyl-7H-pyrrolo[2,3-d]pyrimidine-5-carbonitrile (C-10)

2,4-dichloro-5-iodo-7H-pyrrolo[2,3-d]pyrimidine

To a mixture of 2,4-dichloro-7H-pyrrolo[2,3-d]pyrimidine (7 g, 37.23 mmol) in DMF (37 mL) was added NIS (8.79 g, 39.09 mmol) in one portion at 0° C. under N$_2$. The mixture was stirred at 25° C. for 1.5 h. The reaction solution was poured into ice-water (100 mL), and die resulting precipitate was isolated by filtration. The filter cake was washed with ice water (2×50 mL) and dried under reduced pressure to give 2,4-dichloro-5-iodo-7H-pyrrolo[2,3-d]pyrimidine as a yellow solid. LCMS: RT 0.771 min, m/z=313.9 [M+H]$^+$. $^1$H NMR (400 MHz, DMSO): δ 13.12 (br. s., 1H), 7.97 (d, J=2.01 Hz, 1H).

2-[(2,4-dichloro-5-iodo-pyrrolo[2,3-d]pyrimidin-7-yl)methoxy]ethyl-trimethyl-silane To a mixture of 2,4-dichloro-5-iodo-7H-pyrrolo[2,3-d]pyrimidine (5 g, 15.93 mmol) in DMF (40 mL) was added NaH (764 mg, 19.11 mmol, 60% purity) in one portion at 0° C. under $N_2$. The mixture was stirred at 25° C. for 30 min, SEMCl (3.19 g, 19.12 mmol, 3.39 mL) was added to the mixture at 0° C. and stirred for 1.5 h at 25° C. The mixture was poured into ice-water (40 mL), extracted with EtOAc (3×30 mL). The combined organic phase was washed with brine (50 mL), dried over anhydrous $Na_2SO_4$, filtered and concentrated under reduced pressure. The residue was purified by silica gel column chromatography (PE:EtOAc=10:1) to afford 2-[(2,4-dichloro-5-iodo-pyrrolo[2,3-d]pyrimidin-7-yl)methoxy]ethyl-trimethyl-silane as a yellow solid. LCMS: RT 0.996 min, m/z=444 [M+H]$^+$. $^1$H NMR (400 MHz, DMSO): δ 8.15 (s, 1H), 5.55 (s, 2H), 3.49-3.56 (m, 2H), 0.81-0.87 (m, 2H), −0.08 (s, 9H).

2,4-dichloro-7-(2-trimethylsilylethoxymethyl)pyrrolo[2,3-d]pyrimidine-5-carbonitrile To a mixture of 2-[(2,4-dichloro-5-iodo-pyrrolo[2,3-d]pyrimidin-7-yl)methoxy]ethyl-trimethyl-silane (2 g, 4.50 mmol) in NMP (32 mL) was added CuCN (806.54 mg, 9.01 mmol, 1.97 mL) in one portion at 25° C. under $N_2$. The mixture was heated to 120° C. and stirred for 4.5 h. The mixture was cooled to 25° C. and poured into ice-water (150 mL). The aqueous phase was extracted with EtOAc (3×60 mL). The combined organic phase was washed with brine (3×60 mL), dried over anhydrous $Na_2SO_4$, filtered and concentrated under reduced pressure. The residue was purified by silica gel column chromatography (PE:EtOAc=15:1) to afford 2,4-dichloro-7-(2-trimethylsilylethoxymethyl)pyrrolo[2,3-d]pyrimidine-5-carbonitrile as a yellow solid. LCMS: RT 0.912 min, m/z=343.1 [M+H]$^+$.

2-chloro-4-cyclopropyl-7-(2-trimethylsilylethoxymethyl)pyrrolo[2,3-d]pyrimidine-5-carbonitrile To a solution of 2,4-dichloro-7-(2-trimethylsilylethoxymethyl)pyrrolo[2,3-d]pyrimidine-5-carbonitrile (1.48 g, 4.31 mmol) and cyclopropylboronic acid (630 mg, 7.33 mmol) in 1,4-dioxane (30 mL) was added $K_3PO_4$ (2.74 g, 12.93 mmol), $Ag_2O$ (499 mg, 2.15 mmol), Pd(dppf)Cl$_2$ (315 mg, 431 umol) under $N_2$. The mixture was stirred at 90° C. for 4.5 h. The mixture was cooled to 25° C. and poured into ice-water (30 mL). The aqueous phase was extracted with EtOAc (3×20 mL). The combined organic phase was washed with brine (20 mL×3), dried over anhydrous $Na_2SO_4$, filtered and concentrated under reduced pressure. The residue was purified by silica gel column chromatography (PE:EtOAc=30:1) to afford 2-chloro-4-cyclopropyl-7-(2-trimethylsilylethoxymethyl)pyrrolo[2,3-d]pyrimidine-5-carbonitrile as a yellow solid. LCMS: RT 1.023 min, m/z=349.2 [M+H]$^+$. $^1$H NMR (400 MHz, CDCl$_3$): δ 7.82-7.83 (m, 1H), 5.60-5.62 (m, 2H), 3.55-3.61 (m, 2H), 2.73-2.81 (m, 1H), 1.45-1.48 (m, 2H), 1.30-1.34 (m, 2H), 0.92-0.97 (m, 2H), −0.01 (s, 9H).

2-[[1-(1-cyano-1-methyl-ethyl)-3-methyl-pyrazol-4-yl]amino]-4-cyclopropyl-7-(2-trimethylsilylethoxymethyl)pyrrolo[2,3-d]pyrimidine-5-carbonitrile To a solution of 2-chloro-4-cyclopropyl-7-(2-trimethylsilylethoxymethyl)pyrrolo[2,3-d]pyrimidine-5-carbonitrile (100 mg, 286.62 umol) and 2-(4-amino-3-methyl-pyrazol-1-yl)-2-methyl-propanenitrile (56 mg, 343.94 umol) in 1,4-dioxane (10 mL) was added Pd$_2$(dba)$_3$ (26 mg, 28.66 umol), Cs$_2$CO$_3$ (233 mg, 716.55 umol) and X-Phos (27 mg, 57.32 umol) under $N_2$. The mixture was stirred at 110° C. for 16 h. The mixture was cooled to 25° C. and poured into ice-water (16 mL). The aqueous phase was extracted with EtOAc (3×8 mL). The combined organic phase was washed with brine (3×8 mL), dried over anhydrous $Na_2SO_4$, filtered and concentrated under reduced pressure. The residue was purified by prep-TLC (SiO$_2$, PE:EtOAc=5:1) to give 2-[[1-(1-cyano-1-methyl-ethyl)-3-methyl-pyrazol-4-yl]amino]-4-cyclopropyl-7-(2-trimethylsilylethoxymethyl)pyrrolo[2,3-d]pyrimidine-5-carbonitrile as a yellow solid. LCMS: RT 1.722 min, m/z=477.3 [M+H]$^+$. $^1$H NMR (400 MHz, CDCl$_3$): δ 8.28-8.32 (m, 1H), 7.57 (s, 1H), 5.52 (s, 2H), 3.80 (s, 1H), 3.54-3.61 (m, 2H), 2.68-2.76 (m, 1H), 2.31 (s, 3H), 2.00 (s, 6H), 1.33-1.37 (m, 2H), 1.21-1.24 (m, 2H), 0.92-0.97 (m, 2H), −0.04 (s, 9H).

2-[[1-(1-cyano-1-methyl-ethyl)-3-methyl-pyrazol-4-yl]amino]-4-cyclopropyl-7H-pyrrolo[2,3-d]pyrimidine-5-carbonitrile To a mixture of 2-[[1-(1-cyano-1-methyl-ethyl)-3-methyl-pyrazol-4-yl]amino]-4-cyclopropyl-7-(2-trimethylsilylethoxymethyl)pyrrolo[2,3-d]pyrimidine-5-carbonitrile (95 mg, 199.31 umol) in DCM (20 mL) was added TFA (6.16 g, 54.02 mmol, 4 mL) in one portion at 0° C. under $N_2$. The mixture was stirred at 20° C. for 8 h. The mixture was concentrated under reduced pressure. The residue in THF (10 mL) was added with NaHCO$_3$ (12.96 g, 154.27 mmol, 6 mL), stirred at 20° C. for 16 h. The mixture was poured into ice-water (10 mL). The aqueous phase was extracted with EtOAc (3×8 mL). The combined organic phase was washed with brine (3×8 mL), dried over anhydrous Na$_2$SO$_4$, filtered and concentrated under reduced pressure. The residue was purified by prep-HPLC (neutral condition) to provide 2-[[1-cyano-1-methyl-ethyl)-3-methyl-pyrazol-4-yl]amino]-4-cyclopropyl-7H-pyrrolo[2,3-d]pyrimidine-5-carbonitrile. $^1$H NMR (400 MHz, DMSO): δ 8.60 (br. s., 1H), 8.10 (d, J=12.80 Hz, 2H), 2.17 (s, 3H), 1.94 (s, 6H), 1.15-1.25 (m, 4H). HPLC: RT: 2.498 min. MS: m/z=347.2 [M+H]$^+$.

Example C-11 and C-12

Synthesis of 4-cyclopropyl-2-[[1-[2-fluoro-1-(fluoromethyl)ethyl]-5-methyl-pyrazol-4-yl]amino]-7H-pyrrolo[2,3-d]pyrimidine-5-carbonitrile (C-11) and 4-cyclopropyl-2-[[1-[2-fluoro-1-(fluoromethyl)ethyl]-3-methyl-pyrazol-4-yl]amino]-7H-pyrrolo[2,3-d]pyrimidine-5-carbonitrile (C-12)

4-cyclopropyl-2-[[1-[2-fluoro-1-(fluoromethyl)ethyl]-5-methyl-pyrazol-4-yl]amino]-7-(2-trimethylsilylethoxymethyl)pyrrolo[2,3-d]pyrimidine-5-carbonitrile and 4-cyclopropyl-2-[[1-[2-fluoro-1-(fluoromethyl)ethyl]-3-methyl-pyrazol-4-yl]amino]-7-(2-trimethylsilylethoxymethyl)pyrrolo[2,3-d]pyrimidine-5-carbonitrile To a solution of 2-chloro-4-cyclopropyl-7-(2-trimethylsilylethoxymethyl)pyrrolo[2,3-d]pyrimidine-5-carbonitrile (300 mg, 859.85 umol), mixture of 1-(1,3-difluoropropan-2-yl)-3-methyl-1H-pyrazol-4-amine and 1-(1,3-difluoropropan-2-yl)-5-methyl-1H-pyrazol-4-amine (196 mg, 1.12 mmol) in 1,4-dioxane (10 mL) was added Pd$_2$(dba)$_3$ (79 mg, 85.99 umol), Cs$_2$CO$_3$ (700 mg, 2.15 mmol) and XPhos (82 mg, 171.97 umol). The mixture was stirred at 110° C. for 16 h. The mixture was cooled to 20° C. and concentrated under reduced pressure. The residue was poured into ice-water (20 mL). The aqueous phase was extracted with EtOAc (3×10 mL). The combined organic phase was washed with brine (3×10 mL), dried over anhydrous $Na_2SO_4$, filtered and concentrated under reduced pressure. The residue was purified by prep-TLC ($SiO_2$, PE:EtOAc=3:1) and two products were separated. 4-cyclopropyl-2-[[1-[2-fluoro-1-(fluoromethyl)ethyl]-5-methyl-pyrazol-4-yl]amino]-7-(2-trimethylsilylethoxymethyl)pyrrolo[2,3-d]pyrimidine-5-carbonitrile was obtained as a yellow oil. 4-cyclopropyl-2-[[1-[2-fluoro-1-(fluoromethyl)ethyl]-3-methyl-pyrazol-4-yl]amino]-7-(2-trimethylsilylethoxymethyl)pyrrolo[2,3-d]pyrimidine-5-carbonitrile was obtained as a yellow oil. LCMS: RT 0.926 min, m/z=488.3 $[M+H]^+$. $^1H$ NMR (400 MHz, $CDCl_3$): δ8.10-8.12 (m, 1H), 7.55 (s, 1H), 6.49 (s, 1H), 5.50 (s, 2H), 4.87-4.93 (m, 2H), 4.77-4.82 (m, 2H), 4.13 (q, J=7.15 Hz, 1H), 3.55 (t, J=8.16 Hz, 2H), 2.65-2.75 (m, 1H), 2.29 (s, 3H), 1.30-1.36 (m, 2H), 1.21 (dd, J=7.53, 3.14 Hz, 2H), 0.88-0.95 (m, 2H), −0.05 (s, 9H)

4-cyclopropyl-2-[[1-[2-fluoro-1-(fluoromethyl)ethyl]-5-methyl-pyrazol-4-yl]amino]-7H-pyrrolo[2,3-d]pyrimidine-5-carbonitrile To a solution of 4-cyclopropyl-2-[[1-[2-fluoro-1-(fluoromethyl)ethyl]-5-methyl-pyrazol-4-yl]amino]-7-(2-trimethylsilylethoxymethyl)pyrrolo[2,3-d]pyrimidine-5-carbonitrile (124 mg, 254.30 umol) in DCM (20 mL) was added TFA (6.16 g, 54.03 mmol, 4 mL) in one portion at 0° C. under $N_2$. The mixture was stirred at 20° C. for 8 h. The mixture was concentrated under reduced pressure. The residue in THF (10 mL) was added with aq. $NaHCO_3$ (12.96 g, 154.27 mmol, 6 mL). The mixture was stirred at 20° C. for 16 h. The mixture was poured into ice-water (10 mL). The aqueous phase was extracted with EtOAc (3×8 mL). The combined organic phase was washed with brine (3×8 mL), dried over anhydrous $Na_2SO_4$, filtered and concentrated under reduced pressure. The residue was purified by prep-HPLC (neutral condition) to give 4-cyclopropyl-2-[[1-[2-fluoro-1-(fluoromethyl)ethyl]-5-methyl-pyrazol-4-yl]amino]-7H-pyrrolo[2,3-d]pyrimidine-5-carbonitrile. $^1H$ NMR (400 MHz, DMSO): δ8.35-8.40 (m, 1H), 8.01-8.04 (m, 1H), 7.63-7.67 (m, 1H), 4.89-5.02 (m, 1H), 4.85 (br. s., 2H), 4.70-4.76 (m, 2H), 2.18 (s, 3H), 1.09-1.21 (m, 4H). HPLC: RT: 2.333 min. MS: m/z=358.2 $[M+H]^+$.

4-cyclopropyl-2-[[1-[2-fluoro-1-(fluoromethyl)ethyl]-3-methyl-pyrazol-4-yl]amino]-7H-pyrrolo[2,3-d]pyrimidine-5-carbonitrile 4-cyclopropyl-2-[[1-[2-fluoro-1-(fluoromethyl)ethyl]-3-methyl-pyrazol-4-yl]amino]-7-(2-trimethylsilylethoxymethyl)pyrrolo[2,3-d]pyrimidine-5-carbonitrile (209 mg, 428.61 µmol) was treated with TFA (48.87 mg, 428.61 umol, 31.73 µL) in one portion at 0° C. under $N_2$. The mixture was stirred at 20° C. for 8 h. The mixture was concentrated under reduced pressure. The residue in THF (10 mL) was added with aq. $NaHCO_3$ (12.96 g, 154.27 mmol). The mixture was stirred at 20° C. for 16 h. The mixture was poured into ice-water (10 mL). The aqueous phase was extracted with EtOAc (3×38 mL). The combined organic phase was washed with brine (3<38 mL), dried with anhydrous $Na_2SO_4$, filtered and concentrated under reduced pressure. The residue was purified by prep-HPLC (neutral condition) to give 4-cyclopropyl-2-[[1-[2-fluoro-1-(fluoromethyl)ethyl]-3-methyl-pyrazol-4-yl]amino]-7H-pyrrolo[2,3-d]pyrimidine-5-carbonitrile. $^1H$ NMR (400 MHz, DMSO): δ8.39 (br. s., 1H), 8.03 (s, 1H), 7.94 (s, 1H), 4.70-4.89 (m, 5H), 2.12 (s, 3H), 1.21 (br. s., 2H), 1.14 (d, J=7.78 Hz, 2H). HPLC: RT: 2.63 min. MS: m/z=358.2 $[M+H]^+$.

Example C-13

Synthesis of 4-cyclopropyl-2-(spiro[4,6-dihydropyrrolo[1,2-b]pyrazole-5,1'-cyclopropane]-3-ylamino)-7H-pyrrolo[2,3-d]pyrimidine-5-carbonitrile (C-13)

4-cyclopropyl-2-(spiro[4,6-dihydropyrrolo[1,2-b]pyrazole-5,1'-cyclopropane]-3-ylamino)-7-(2-trimethylsilylethoxymethyl)pyrrolo[2,3-d]pyrimidine-5-carbonitrile A mixture of spiro [4,6-dihydropyrrolo[1,2-b]pyrazole-5,1'-cyclopropane]-3-amine (135 mg, 904.89 umol), 2-chloro-4-cyclopropyl-7-(2-trimethylsilylethoxymethyl)pyrrolo[2,3-d]pyrimidine-5-carbonitrile (379 mg, 1.09 mmol), $Cs_2CO_3$ (737 mg, 2.26 mmol), $Pd_2(dba)_3$ (83 mg, 90.49 umol) and XPhos (86 mg, 180.98 umol) in 1,4-dioxane (5 mL) was degassed and purged with $N_2$ for 3 times, and then the mixture was stirred at 110° C. for 16 h under $N_2$. The mixture was cooled to 20° C. and concentrated under reduced pressure. The residue was poured into ice-water (5 mL). The aqueous phase was extracted with EtOAc (4 mL×3). The combined organic phase was washed with brine (10 mL), dried over anhydrous $Na_2SO_4$, filtered and concentrated under reduced pressure. The residue was purified by prep-TLC ($SiO_2$, PE:EtOAc=1:1) to give 4-cyclopropyl-2-(spiro[4,6-dihydropyrrolo[1,2-b]pyrazole-5,1'-cyclopropane]-3-ylamino)-7-(2-trimethylsilylethoxymethyl)pyrrolo[2,3-d]pyrimidine-5-carbonitrile as a yellow oil. LCMS: 1.019 min, m/z=462.3 $[M+H]^+$.

4-cyclopropyl-2-(spiro[4,6-dihydropyrrolo[1,2-b]pyrazole-5,1'-cyclopropane]-3-ylamino)-7H-pyrrolo[2,3-d]pyrimidine-5-carbonitrile To a solution of 4-cyclopropyl-2-(spiro[4,6-dihydropyrrolo[1,2-b]pyrazole-5,1'-cyclopropane]-3-ylamino)-7-(2-trimethylsilylethoxymethyl)pyrrolo[2,3-d]pyrimidine-5-carbonitrile (352 mg, 762.50 umol) in DCM (20 mL) was added TFA (6.16 g, 54.02 mmol, 4 mL) in one portion at 0° C. under $N_2$. The mixture was stirred at 20° C. for 8 h. The mixture was concentrated under reduced pressure. The residue in THF (20 mL) and water (4 mL) was added with $K_2CO_3$ (5 g, 36.18 mmol). The mixture was stirred at 20° C. for 16 h. The mixture was poured into ice-water (10 mL) and extracted with EtOAc (3×8 mL). The combined organic phase was washed with brine (3×8 mL), dried over anhydrous $Na_2SO_4$, filtered and concentrated under reduced pressure. The residue was purified by prep-HPLC (neutral condition) to give 4-cyclopropyl-2-(spiro[4,6-dihydropyrrolo[1,2-b]pyrazole-5,1'-cyclopropane]-3-ylamino)-7H-pyrrolo[2,3-d]pyrimidine-5-carbonitrile. $^1H$ NMR (400 MHz, $CDCl_3$): δ 11.68 (br. s., 1H), 7.63 (s, 1H), 6.71 (s, 1H), 6.43 (s, 1H), 3.93 (s, 2H), 2.80 (s, 2H), 2.65-2.73 (m, 1H), 1.30-1.35 (m, 2H), 1.16-1.22 (m, 2H), 0.60-0.65 (m, 2H), 0.48-0.53 (m, 2H). HPLC: RT: 2.402 min. MS: m/z=332.2 $[M+H]^+$.

Example C-14

Synthesis of 2-[4-[(4-cyclopropyl-5-fluoro-7H-pyrrolo[2,3-d]pyrimidin-2-yl)amino]-3-methyl-pyrazol-1-yl]-2-methyl-propanenitrile (C-14)

2,4-dichloro-5-fluoro-7H-pyrrolo[2,3-d]pyrimidine

To a solution of 2,4-dichloro-7H-pyrrolo[2,3-d]pyrimidine (50 g, 0.27 mol) in $CH_3CN$ (1 L) and AcOH (200 mL)

was added selectfluor (131.9 g, 0.37 mol) in one portion. The reaction mixture was stirred at 60° C. for 12 h under Ar. The reaction mixture was poured into cold water (1 L) and crystallized for 30 min, filtrated to give 2,4-dichloro-5-fluoro-7H-pyrrolo[2,3-d]pyrimidine as a brown solid. LCMS: RT 1.268 min, m/z=206.0 [M+H]$^+$.

2,4-dichloro-5-fluoro-7-((2-(trimethylsilyl)ethoxy)methyl)-7H-pyrrolo[2,3-d]pyrimidine To a solution of 2,4-dichloro-5-fluoro-7H-pyrrolo[2,3-d]pyrimidine (2.17 g, 10.53 mmol) in DMF (22 mL) was added NaH (843 mg, 21.06 mmol, 60% purity) at 0° C., then the mixture was warmed to 25° C. and stirred for 30 min. A solution of SEMCl (1.84 g, 11.06 mmol, 1.96 mL) in DMF (10 mL) was added dropwise to the mixture and stirred continuously for 3 h. The reaction mixture was quenched by pouring into ice water (150 mL). The resulting aqueous layer was extracted with EtOAc (3×100 mL). The combined organics were washed with brine (two times) and dried over Na$_2$SO$_4$, concentrated under reduced pressure to give a residue, which was purified with a short silica gel plug eluting with PE:EtOAc=200:1 to 50:1 to give 2,4-dichloro-5-fluoro-7-((2-(trimethylsilyl)ethoxy)methyl)-7H-pyrrolo[2,3-d]pyrimidine as a yellow oil $^1$H NMR (400 MHz, CHLOROFORM-d):δ7.17 (d, J=2.8 Hz, 1H), 5.61 (s, 2H), 3.50-3.63 (m, 2H), 0.94-1.01 (m, 2H), −0.02-0.03 (m, 9H).

2-[(2-chloro-4-cyclopropyl-5-fluoro-pyrrolo[2,3-d]pyrimidin-7-yl)methoxy]ethyl-trimethyl-silane To a mixture of 2,4-dichloro-5-fluoro-7-((2-(trimethylsilyl)ethoxy)methyl)-7H-pyrrolo[2,3-d]pyrimidine (2.9 g, 8.62 mmol) and cyclopropylboronic acid (1.26 g, 14.65 mmol) in 1,4-dioxane (40 mL) was added Ag$_2$O (999 mg, 4.31 mmol), Pd(dppf)Cl$_2$ (631 mg, 862 umol) and K$_3$PO$_4$ (5.49 g, 25.86 mmol) at 20° C. under N$_2$. The mixture was stirred at 90° C. for 4.5 h, then cooled to 20° C. and poured into ice-water (80 mL). The aqueous phase was extracted with EtOAc (40 mL×3). The combined organic phase was washed with brine (40 mL×3), dried over anhydrous Na$_2$SO$_4$, filtered and concentrated under reduced pressure. The residue was purified by silica gel column chromatography (PE:EtOAc=30:1) to give 2-[(2-chloro-4-cyclopropyl-5-fluoro-pyrrolo[2,3-d]pyrimidin-7-yl)methoxy]ethyl-trimethyl-silane as a yellow solid. LCMS: RT 1.006 min, m/z=342.1 [M+H]$^+$ $^1$H NMR (400 MHz, CDCl$_3$): δ 6.99 (d, J=2.51 Hz, 1H), 5.53 (s, 2H), 3.48-3.54 (m, 2H), 2.48-2.56 (m, 1H), 1.40-1.44 (m, 2H), 1.19-1.25 (m, 2H), 0.90-0.94 (m, 2H), −0.03 (s, 9H).

2-[4-[[4-cyclopropyl-5-fluoro-7-(2-trimethylsilylethoxymethyl)pyrrolo[2,3-d]pyrimidin-2-yl]amino]-3-methyl-pyrazol-1-yl]-2-methyl-propanenitrile A mixture of 2-[(2-chloro-4-cyclopropyl-5-fluoro-pyrrolo[2,3-d]pyrimidin-7-yl)methoxy]ethyl-trimethyl-silane (200 mg, 585 umol), 2-(4-Amino-3-methyl-pyrazol-1-yl)-2-methyl-propanenitrile (134 mg, 819.00 μmol), Pd$_2$(dba)$_3$ (54 mg, 58.50 μmol), XPhos (56 mg, 117 μmol) and Cs$_2$CO$_3$ (477 mg, 1.46 mmol) in 1,4-dioxane (15 mL) was degassed and purged with N$_2$ for 3 times, then the mixture was stirred at 110° C. for 16 h under N$_2$. The mixture was cooled to 20° C. and poured into ice-water (30 mL). The aqueous phase was extracted with EtOAc (3×15 mL). The combined organic phase was washed with brine (15 mL×3), dried over anhydrous Na$_2$SO$_4$, filtered and concentrated under reduced pressure. The residue was purified by prep-TLC (SiO$_2$, PE:EtOAc=3:1) to give 2-[4-[[4-cyclopropyl-5-fluoro-7-(2-trimethylsilylethoxymethyl)pyrrolo[2,3-d]pyrimidin-2-yl]amino]-3-methyl-pyrazol-1-yl]-2-methyl-propanenitrile as a yellow oil. LCMS: RT 1.005 min, m/z=470.3 [M+H]$^+$.

2-[4-[(4-cyclopropyl-5-fluoro-7H-pyrrolo[2,3-d]pyrimidin-2-yl)amino]-3-methyl-pyrazol-1-yl]-2-methyl-propanenitrile To a solution of 2-[4-[[4-cyclopropyl-5-fluoro-7-(2-trimethylsilylethoxymethyl)pyrrolo[2,3-d]pyrimidin-2-yl]amino]-3-methyl-pyrazol-1-yl]-2-methyl-propanenitrile (169 mg, 359.86 μmol) in DCM (20 mL) was added SnCl$_4$ (1.22 g, 4.68 mmol, 546.53 uL) at 0° C. under N$_2$. The mixture was stirred at 20° C. for 4 h, poured into ice-water (10 mL). The mixture was neutralized with aq. NaHCO$_3$ (21.6 g, 257.11 mmol, 10 mL) to pH=8. The mixture was extracted with EtOAc (3×10 mL). The combined organic phase was washed with brine (10 mL), dried over anhydrous Na$_2$SO$_4$, filtered and concentrated under reduced pressure. To a solution of the residue in THF (20 mL) and Water (4 mL) was added K$_2$CO$_3$ (3.00 g, 21.71 mmol), and the mixture stirred at 20° C. for 16 h. The reaction mixture was poured into ice-water (10 mL) and extracted with EtOAc (3×10 mL). The combined organic phase was washed with brine (10 mL), dried over anhydrous Na$_2$SO$_4$, filtered and concentrated under reduced pressure. The residue was purified by prep-HPLC (neutral condition) to give 2-[4-[(4-cyclopropyl-5-fluoro-7H-pyrrolo[2,3-d]pyrimidin-2-yl)amino]-3-methyl-pyrazol-1-yl]-2-methyl-propanenitrile. $^1$H NMR (400 MHz, CDCl$_3$): δ 8.26-8.32 (m, 1H), 8.18 (s, 1H), 6.58 (t, J=2.45 Hz, 1H), 6.38 (s, 1H), 2.44-2.53 (m, 1H), 2.29 (s, 3H), 1.97 (s, 6H), 1.31-1.36 (m, 2H), 1.11-1.18 (m, 2H). HPLC: RT: 2.731 min. MS: m/z=340.2 [M+H]$^+$.

Example C-15 and C-16

Synthesis of 4-cyclopropyl-2-((1,5-dimethyl-1H-pyrazol-4-yl)amino)-6-methyl-7H-pyrrolo[2,3-d]pyrimidine-5-carbonitrile (C-15) and 4-cyclopropyl-2-((1,3-dimethyl-1H-pyrazol-4-yl)amino)-6-methyl-7H-pyrrolo[2,3-d]pyrimidine-5-carbonitrile (C-16)

2,4-dichloro-5-iodo-6-methyl-7-((2-(trimethylsilyl)ethoxy)methyl)-7H-pyrrolo[2,3-d]pyrimidine To a solution of 2,4-dichloro-5-iodo-7H-pyrrolo[2,3-d]pyrimidine (10 g, 22.5 mmol) in THF (400 mL) was added LDA (113 mL, 0.23 mol, 2M) at −78° C., the mixture was stirred at −20° C. for 2 h. Then re-cooled to −78° C., to the reaction solution was added CH$_3$I (32 g, 225.1 mmol, 14 mL), then the mixture stirred at −20° C. for 2 h. The reaction mixture was quenched with sat. NH$_4$Cl (300 mL), and extracted with EtOAc (3×300 mL). The combined organic phase was washed with brine (3×200 mL), dried over anhydrous Na$_2$SO$_4$, filtered and concentrated under reduced pressure to give a residue, which was purified by silica gel column chromatography (PE:EtOAc=10:1) to give 2,4-dichloro-5-iodo-6-methyl-7-((2-(trimethylsilylethoxy)methyl)-7H-pyrrolo[2,3-d]pyrimidine as a yellow solid. $^1$H NMR (400 MHz, CHLOROFORM-d): δ 5.59-5.67 (m, 2H), 3.47-3.56 (m, 2H), 2.57 (s, 3H), 0.89-0.96 (m, 2H), −0.03 (s, 9H).

2,4-dichloro-6-methyl-7-((2-(trimethylsilyl)ethoxy)methyl)-7H-pyrrolo[2,3-d]pyrimidine-5-carbonitrile To a solution of 2,4-dichloro-5-iodo-6-methyl-7-((2-(trimethylsilyl)ethoxy)methyl)-7H-pyrrolo[2,3-d]pyrimidine (5 g, 10.9 mmol) in NMP (50 mL) was added CuCN (1.95 g, 21.8 mmol) at 25° C. under $N_2$. The reaction mixture was heated to 120° C. and stirred for 12 h. Then the reaction was poured into ice-water (200 mL), and extracted with EtOAc (3×200 mL). The combined organic phase was washed with brine (200 mL), dried over anhydrous $Na_2SO_4$, filtered and concentrated under reduced pressure. The residue was purified by silica gel column chromatography (PE:EtOAc=10:1) to give 2,4-dichloro-6-methyl-7-((2-(trimethylsilyl)ethoxy)methyl)-7H-pyrrolo[2,3-d]pyrimidine-5-carbonitrile as a yellow oil. LCMS: RT 1.006 min, m/z=357.2 $[M+H]^+$.

2-chloro-4-cyclopropyl-6-methyl-7-((2-(trimethylsilyl)ethoxy)methyl)-7H-pyrrolo[2,3-d]pyrimidine-5-carbonitrile To a solution of 2,4-dichloro-6-methyl-7-((2-(trimethylsilyl)ethoxy)methyl)-7H-pyrrolo[2,3-d]pyrimidine-5-carbonitrile (300 mg, 0.84 mmol) and cyclopropylboronic acid (87 mg, 1.01 mmol) in dioxane (2 mL) was added $K_3PO_4$ (535 mg, 2.52 mmol), $Ag_2O$ (98 mg, 0.42 mmol) and $Pd(dppf)Cl_2$ (61 mg, 84 umol) under $N_2$. The reaction mixture was stirred at 90° C. for 12 h. The mixture was cooled to 20° C. and poured into ice-water (w/w=1/1) (2 mL). The aqueous phase was extracted with EtOAc (3<2 mL). The combined organic phase was washed with brine (2 mL), dried over anhydrous $Na_2SO_4$, filtered and concentrated under reduced pressure to give a residue, which was purified by silica gel column chromatography (PE:EtOAc=1:1) to give 2-chloro-4-cyclopropyl-6-methyl-7-((2-(trimethylsilyl)ethoxy)methyl)-7H-pyrrolo[2,3-d]pyrimidine-5-carbonitrile as a brown oil. LCMS: RT 1.05 min. m/z=363.1 $[M+H]^+$.

4-cyclopropyl-2-((1,3-dimethyl-1H-pyrazol-4-yl)amino)-6-methyl-7-((2-(trimethylsilyl)ethoxy)methyl)-7H-pyrrolo[2,3-d]pyrimidine-5-carbonitrile and 4-cyclopropyl-2-((1,5-dim ethyl-1H-pyrazol-4-yl)amino)-6-methyl-7-((2-(trimethylsilyl)ethoxy)methyl)-7H-pyrrolo[2,3-d]pyrimidine-5-carbonitrile To a solution of 2-chloro-4-cyclopropyl-6-methyl-7-((2-(trimethylsilyl)ethoxy)methyl)-7H-pyrrolo[2,3-d]pyrimidine-5-carbonitrile (200 mg, 0.55 mmol) in 1,4-dioxane (4 mL) was added a mixture of 1,3-dimethyl-1H-pyrazol-4-amine and 1,5-dimethyl-1H-pyrazol-4-amine (49 mg, 0.44 mmol), $Cs_2CO_3$ (450 mg, 1.38 mmol), XPhos (53 mg, 0.11 umol) and $Pd_2(dba)_3$ (51 mg, 55 umol) under $N_2$, then the mixture was stirred at 110° C. for 12 h. The reaction mixture was concentrated under reduced pressure to give residue, which was purified by prep-TLC ($SiO_2$, PE:EtOAc=1:1) to give a mixture of compound 4-cyclopropyl-2-((1,3-dimethyl-1H-pyrazol-4-yl)amino)-6-methyl-7-((2-(trimethylsilyl)ethoxy)methyl)-7H-pyrrolo[2,3-d]pyrimidine-5-carbonitrile and 4-cyclopropyl-2-((1,5-dimethyl-1H-pyrazol-4-yl)amino)-6-methyl-7-((2-(trimethylsilyl)ethoxy)methyl)-7H-pyrrolo[2,3-d]pyrimidine-5-carbonitrile as a yellow oil. MS: m/z=438.2 $[M+H]^+$.

4-cyclopropyl-2-((1,5-dimethyl-1H-pyrazol-4-yl)amino)-6-methyl-7H-pyrrolo[2,3-d]pyrimidine-5-carbonitrile and 4-cyclopropyl-2-((1,3-dimethyl-1H-pyrazol-4-yl)amino)-6-methyl-7H-pyrrolo[2,3-d]pyrimidine-5-carbonitrile To a solution of mixture of 4-cyclopropyl-2-((1,3-dimethyl-1H-pyrazol-4-yl)amino)-6-methyl-7-((2-(trimethylsilyl)ethoxy)methyl)-7H-pyrrolo[2,3-d]pyrimidine-5-carbonitrile and 4-cyclopropyl-2-((1,5-dimethyl-1H-pyrazol-4-yl)amino)-6-methyl-7-((2-(trimethylsilyl)ethoxy)methyl)-7H-pyrrolo[2,3-d]pyrimidine-5-carbonitrile (70 mg, 0.16 mmol) in DCM (4 mL) was added TFA (365 mg, 0.24 mL, 3.2 mmol) at 0° C., then the mixture was stirred at 40° C. for 24 h. The reaction mixture was concentrated under reduced pressure to give a yellow oil. LCMS: RT 1.075 min, m/z=338.2 $[M+H]^+$. To a solution of this crude material in THF (4 mL) and water (4 mL) was added $K_2CO_3$ (225 mg, 1.63 mmol) at 20° C. Then the mixture was stirred at 50° C. for 4 h. The mixture was concentrated under reduced pressure to give a residue, which was purified by prep-HPLC (FA) to give 4-cyclopropyl-2-((1,5-dimethyl-1H-pyrazol-4-yl)amino)-6-methyl-7H-pyrrolo[2,3-d]pyrimidine-5-carbonitrile and 4-cyclopropyl-2-((1,3-dimethyl-1H-pyrazol-4-yl)amino)-6-methyl-7H-pyrrolo[2,3-d]pyrimidine-5-carbonitrile.

4-cyclopropyl-2-((1,5-dimethyl-1H-pyrazol-4-yl)amino)-6-methyl-7H-pyrrolo[2,3-d]pyrimidine-5-carbonitrile $^1$H NMR (400 MHz, DMSO-$d_6$): δ 12.23 (br. s., 1H), 8.25 (s, 1H), 7.69 (s, 1H), 3.68-3.73 (m, 3H), 2.43 (s, 4H), 2.05 (s, 3H), 1.16 (d, J=4.0 Hz, 2H), 1.06-1.12 (m, 2H). HPLC: RT: 2.34 min. MS: m/z: 308.1 $[M+H]^+$.

4-cyclopropyl-2-((1,5-dimethyl-1H-pyrazol-4-yl)amino)-6-methyl-7H-pyrrolo[2,3-d]pyrimidine-5-carbonitrile $^1$H NMR (400 MHz, DMSO-d6): δ 12.19 (br. s., 1H), 8.21 (s, 1H), 7.42 (s, 1H), 3.68 (s, 3H), 2.42 (s, 4H), 2.11 (s, 3H), 1.13 (br. s, 2H), 1.09 (d, J=7.94 Hz, 2H). HPLC: RT: 2.25 min. MS: m/z: 308.2 $[M+H]^+$.

Example C-17

Synthesis of 7-cyclopropyl-N-(1-methyl-1H-pyrazol-3-yl)-3H-imidazo[4,5-b]pyridin-5-amine (C-17)

4-chloropyridine-2,3-diamine

To a solution of 4-chloropyridine-2,3-diamine (6 g, 34.57 mmol) in i-PrOH (60 mL) and $H_2O$ (15 mL) was added Fe (9.65 g, 172.85 mmol) and $NH_4Cl$ (9.25 g, 172.85 mmol). The mixture was stirred at 80° C. for 2 h. The reaction mixture was filtered and to the filtrate was added $H_2O$ (100 mL) at 0° C. Then it was extracted with DCM/i-PrOH (60 mL×4). The combined organic layers were washed with brine (60 mL), dried over $Na_2SO_4$, filtered and concentrated under reduced pressure to give 4-chloropyridine-2,3-diamine as a dark brown solid. LCMS: RT 0.107 min, m/z=144.1 $[M+H]^+$.

7-chloro-3H-imidazo[4,5-b]pyridine

A solution of 4-chloropyridine-2,3-diamine (1 g, 6.97 mmol) in $CH(OEt)_3$ (20 mL) and HCOOH (0.5 mL) was degassed and purged with $N_2$ for 3 times, and then the mixture was stirred at 100° C. for 3 h under $N_2$. The reaction mixture was concentrated under reduced pressure. The residue was diluted with water (20 mL) and extracted with DCM/i-PrOH (20 mL×3). The combined organic layers were washed with brine (20 mL), dried over $Na_2SO_4$, filtered and concentrated under reduced pressure to give 7-chloro-3H-imidazo[4,5-b]pyridine as a dark brown solid. LCMS: RT 0.140 min. m/z=154.1 [M+H]+. 1H NMR (400 MHz, DMSO-d6): δ 13.43 (br. s, 1H), 8.52 (d, J=5.14 Hz, 1H), 8.29 (d, J=5.14 Hz, 1H), 7.39 (d, J=5.15 Hz, 1H).

7-chloro-3-((2-(trimethylsilyl)ethoxy)methyl)-3H-imidazo[4,5-b]pyridine

To a solution of 7-chloro-3H-imidazo[4,5-b]pyridine (1 g, 6.51 mmol) in DMF (10 mL) was added NaH (312 mg, 7.81 mmol, 60% purity) in three portions at 0° C. The mixture was stirred at 20° C. for 1 h. SEM-Cl (1.3 g, 7.81 mmol, 1.39 mL) was added at 0° C. and the mixture was stirred at 20° C. for 1 h. The reaction mixture was quenched by addition of water (60 mL) at 0° C., and then extracted with EtOAc (30 mL×3). The combined organic layers were washed with brine (20 mL×3), dried over $Na_2SO_4$, filtered and concentrated under reduced pressure to give a residue, which was purified by silica gel column chromatography (PE:EtOAc=6:1) to give 7-chloro-3-((2-(trimethylsilyl)ethoxy)methyl)-3H-imidazo[4,5-b]pyridine as a yellow oil. LCMS: RT 0.901 min, m/z=284.1 [M+H]+. 1H NMR (400 MHz, CDCl3): δ 8.32 (d, J=5.27 Hz, 1H), 8.24 (s, 1H), 7.32 (d, J=5.27 Hz, 1H), 5.69 (s, 2H), 3.58-3.66 (m, 2H), 0.91-0.96 (m, 2H), −0.04 (s, 9H).

7-cyclopropyl-3-((2-(trimethylsilyl)ethoxy)methyl)-3H-imidazo[4,5-b]pyridine

A mixture of cyclopropylboronic acid (181 mg, 2.12 mmol), 7-chloro-3-((2-(trimethylsilyl)ethoxy)methyl)-3H-imidazo[4,5-b]pyridine (400 mg, 1.41 mmol), $Cs_2CO_3$ (918 mg, 2.82 mmol), $Pd_2(dba)_3$ (64 mg, 70.5 umol) and DavePhos (55 mg, 141 umol) in toluene (20 mL) was degassed and purged with $N_2$ for 3 times, and then the mixture was stirred at 120° C. for 3 h under $N_2$. The reaction mixture was concentrated under reduced pressure to give a residue, which was purified by silica gel column chromatography (PE:EtOAc=8:1) to give 7-cyclopropyl-3-((2-(trimethylsilylethoxy)methyl)-3H-imidazo[4,5-b]pyridine. LCMS: RT 0.835 min, m/z=290.1 [M+H]+.

7-cyclopropyl-3-((2-(trimethylsilyl)ethoxy)methyl)-3H-imidazo[4,5-b]pyridine 4-oxide To a solution of 7-cyclopropyl-3-((2-(trimethylsilyl)ethoxy)methyl)-3H-imidazo[4,5-b]pyridine (6.7 g, 23.15 mmol) in $CHCl_3$ (70 mL) was added m-CPBA (9.4 g, 46.3 mmol, 85% purity). The mixture was stirred at 75° C. for 16 h. The reaction mixture was quenched by addition of $H_2O$ (120 mL) and $Na_2S_2O_3$ (12 g) at 0° C., and then extracted with DCM (50 mL×3). The combined organic layers were washed with saturated $NaHCO_3$ solution (60 mL) and brine (60 mL), dried over $Na_2SO_4$, filtered and concentrated under reduced pressure to give a residue, which was purified by silica gel column chromatography (DCM:MeOH=10:1) to give 7-cyclopropyl-3-((2-(trimethylsilyl)ethoxy)methyl)-3H-imidazo[4,5-b]pyridine 4-oxide as a dark brown gum. LCMS: RT 0.765 min, m/z=306.2 [M+H]+

5-chloro-7-cyclopropyl-3-((2-(trimethylsilyl)ethoxy)methyl)-3H-imidazo[4,5-b]pyridine (intermediate 15)

To a solution of 7-cyclopropyl-3-((2-(trimethylsilyl)ethoxy)methyl)-3H-imidazo[4,5-b]pyridine 4-oxide (3 g, 9.82 mmol) in DMF (30 mL) was added MsCl (4.50 g, 39.29 mmol, 3.04 mL). The mixture was stirred at 80° C. for 20 min. The reaction mixture was quenched by addition of $H_2O$ (180 mL) at 0° C., alkalified with aq. $NaHCO_3$ to pH=8 and extracted with EtOAc (60 mL×3). The combined organic layers were washed with brine (3×30 mL), dried over $Na_2SO_4$, filtered and concentrated under reduced pressure to give 5-chloro-7-cyclopropyl-3-((2-(trimethylsilyl)ethoxy)methyl)-3H-imidazo[4,5-b]pyridine. LCMS: RT 0.953 min, m/z=324.1 [M+H]+

7-cyclopropyl-N-(1-methyl-1H-pyrazol-3-yl)-3-((2-(trimethylsilyl)ethoxy)methyl)-3H-imidazo[4,5-b]pyridin-5-amine A mixture of 5-chloro-7-cyclopropyl-3-((2-(trimethylsilyl)ethoxy)methyl)-3H-imidazo[4,5-b]pyridine (170 mg, 524.87 umol), 1-methylpyrazol-3-amino (102 mg, 1.05 mmol), $Cs_2CO_3$ (427 mg, 1.31 mmol), $Pd_2(dba)_3$ (48 mg, 52.49 umol) and XPhos (50 mg, 104.97 umol) in 1,4-dioxane (4 mL) was degassed and purged with $N_2$ for 3 times, and then the mixture was stirred at 110° C. for 16 h under $N_2$. The reaction mixture was concentrated under reduced pressure. The residue was diluted with $H_2O$ (20 mL) and extracted with DCM (3×10 mL). The combined organic layers were washed with brine (10 mL), dried over $Na_2SO_4$, filtered and concentrated under reduced pressure to give a residue, which was purified by prep-TLC ($SiO_2$, EtOAc) to give 7-cyclopropyl-N-(1-methyl-1H-pyrazol-3-yl)-3-((2-(trimethylsilyl)ethoxy)methyl)-3H-imidazo[4,5-b]pyridin-5-amine as a yellow gum. LCMS: RT 0.832 min, m/z=385.3 [M+H]+

7-cyclopropyl-N-(1-methyl-1H-pyrazol-3-yl)-3H-imidazo[4,5-b]pyridin-5-amine)

To a solution of 7-cyclopropyl-N-(1-methyl-1H-pyrazol-3-yl)-3-((2-(trimethylsilyl)ethoxy)methyl)-3H-imidazo[4,5-b]pyridin-5-amine (80 mg, 208.04 umol) in DCM (9 mL) was added TFA (4.62 g, 40.52 mmol, 3 mL). The mixture was stirred at 40° C. for 6 h. The reaction mixture was concentrated under reduced pressure to get a residue, which was purified by prep-HPLC (neutral condition) to give 7-cyclopropyl-N-(1-methyl-1H-pyrazol-3-yl)-3H-imidazo[4,5-b]pyridin-5-amine. 1H NMR (400 MHz, CDCl3): δ 7.89 (s, 1H), 7.33 (d, J=2.26 Hz, 1H), 6.62 (s, 1H), 6.27 (d, J=2.26 Hz, 1H), 3.94 (s, 3H), 2.44-2.54 (m, 1H), 1.15-1.20 (m, 4H). HPLC: RT: 2.65 min. MS: m/z: 255.1 [M+H]+.

Example C-18 and C-19

Synthesis of 4-cyclopropyl-2-[(1,5-dimethylpyrazol-4-yl)amino]-7H-pyrrolo[2,3-d]pyrimidine-5-carbonitrile (C-18) and 4-cyclopropyl-2-[(1,3-dimethylpyrazol-4-yl)amino]-7H-pyrrolo[2,3-d]pyrimidine-5-carbonitrile (C-19)

4-cyclopropyl-2-[(1,5-dimethylpyrazol-4-yl)amino]-7-(2-trimethylsilylethoxymethyl)pyrrolo[2,3-d]pyrimidine-5-carbonitrile and 4-cyclopropyl-2-[(1,3-dimethylpyrazol-4-yl)amino]-7-(2-trimethylsilylethoxymethyl)pyrrolo[2,3-d]pyrimidine-5-carbonitrile To a mixture of 2-chloro-4-cyclopropyl-7-(2-trimethylsilylethoxymethyl)pyrrolo[2,3-d]pyrimidine-5-carbonitrile (400 mg, 1.15 mmol) and 1,3-dimethyl-1H-pyrazol-4-amine and 1,5-dimethyl-1H-pyrazol-4-amine (217 mg, 1.95 mmol, mixture) in 1,4-dioxane (15 mL) was added Pd$_2$(dba)$_3$ (105 mg, 115 umol) in one portion at 20° C. under N$_2$. The mixture was heated to 110° C. and stirred for 16 h, cooled to 20° C. and concentrated under reduced pressure. The residue was purified by silica gel column chromatography (PE:EtOAc=1:1) to afford 4-cyclopropyl-2-[(1,5-dimethylpyrazol-4-yl)amino]-7-(2-trimethylsilylethoxymethyl)pyrrolo[2,3-d]pyrimidine-5-carbonitrile and 4-cyclopropyl-2-[(1,3-dimethylpyrazol-4-yl)amino]-7-(2-trimethylsilylethoxymethyl)pyrrolo[2,3-d]pyrimidine-5-carbonitrile as a yellow oil. LCMS: RT 1.589 min, m/z=424.3 [M+H]$^+$. $^1$H NMR (400 MHz, CDCl$_3$): δ 7.81 (s, 1H), 7.73 (s, 1H), 7.54 (s, 1H), 7.52 (s, 1H), 5.46 (s, 2H), 3.86 (s, 2H), 3.79-3.83 (m, 3H), 3.54 (dt, J=12.05, 8.22 Hz, 4H), 2.63-2.74 (m, 2H), 2.27 (s, 2H), 2.22 (s, 3H), 1.13-1.22 (m, 4H), 0.91 (dt, J=11.45, 8.27 Hz, 4H), −0.05 (s, 9H).

4-cyclopropyl-2-[(1,5-dimethylpyrazol-4-yl)amino]-7H-pyrrolo[2,3-d]pyrimidine-5-carbonitrile and 4-cyclopropyl-2-[(1,3-dimethylpyrazol-4-yl)amino]-7H-pyrrolo[2,3-d]pyrimidine-5-carbonitrile To a solution of 4-cyclopropyl-2-[(1,5-dimethylpyrazol-4-yl)amino]-7-(2-trimethylsilylethoxymethyl)pyrrolo[2,3-d]pyrimidine-5-carbonitrile (297 mg, 701.15 umol, mixture) and 4-cyclopropyl-2-[(1,3-dimethylpyrazol-4-yl)amino]-7-(2-trimethylsilylethoxymethyl)pyrrolo[2,3-d]pyrimidine-5-carbonitrile in DCM (20 mL) was added TFA (6.16 g, 54.03 mmol, 4 mL) in one portion at 0° C. under N$_2$. The mixture was stirred at 20° C. for 8 h. The mixture was concentrated under reduced pressure. The residue in THF (10 mL) was added with aq. NaHCO$_3$ (12.96 g, 154.27 mmol, 6 mL). The mixture was stirred at 20° C. for 16 h, and poured into ice-water (10 mL) and extracted with EtOAc (3×8 mL). The combined organic phase was washed with brine (3<8 mL), dried over anhydrous Na$_2$SO$_4$, filtered and concentrated under reduced pressure. The residue was purified by prep-HPLC (FA condition) to provide 4-cyclopropyl-2-[(1,5-dimethylpyrazol-4-yl)amino]-7H-pyrrolo[2,3-d]pyrimidine-5-carbonitrile was as a white solid and 4-cyclopropyl-2-[(1,3-dimethylpyrazol-4-yl)amino]-7H-pyrrolo[2,3-d]pyrimidine-5-carbonitrile.

4-cyclopropyl-2-[(1,5-dimethylpyrazol-4-yl)amino]-7H-pyrrolo[2,3-d]pyrimidine-5-carbonitrile $^1$H NMR (400 MHz, DMSO): δ 12.29 (br. s., 1H), 8.30 (s, 1H), 8.01 (s, 1H), 7.44 (s, 1H), 3.69 (s, 3H), 2.12 (s, 3H), 1.10-1.20 (m, 4H). HPLC: RT: 2.17 min. MS: m/z=294.2 [M+H]$^+$.

4-cyclopropyl-2-[(1,3-dimethylpyrazol-4-yl)amino]-7H-pyrrolo[2,3-d]pyrimidine-5-carbonitrile $^1$H NMR (400 MHz, DMSO): δ 12.31 (br. s., 1H), 8.34 (s, 1H), 8.03 (s, 1H), 7.72 (s, 1H), 3.72 (s, 3H), 2.07 (s, 3H), 1.20 (br. s., 2H), 1.14 (d, J=7.40 Hz, 2H). HPLC: RT: 2.20 min. MS: m/z=294.2 [M+H]$^+$.

Example C-20

Synthesis of 4-cyclopropyl-6-((1,4-dimethyl-1H-pyrazol-3-yl)amino)-1H-pyrrolo[2,3-b]pyridine-3-carbonitrile (C-20)

4-chloro-3-iodo-1H-pyrrolo[2,3-b]pyridine

To a solution of 4-chloro-7-azaindole (20 g, 131.08 mmol) in AcOH (200 mL) was added NIS (30.96 g, 137.63 mmol) in portions at 0° C. under N$_2$. The mixture was stirred at 20° C. for 16 h. The reaction mixture was diluted with water (500 mL) and extracted with DCM (3×400 mL). The combined organic layers were washed with saturated aq. NaHCO$_3$ (300 mL) and brine (400 mL), dried over Na$_2$SO$_4$, filtered and concentrated under reduced pressure to give 4-chloro-3-iodo-1H-pyrrolo[2,3-b]pyridine as a black brown solid crude material. LCMS: RT 0.83 min. m/z=279.0 [M+H]$^+$. $^1$H NMR (400 MHz, DMSO-d6): δ 12.53 (br. s., 1H), 8.18 (d, J=5.14 Hz, 1H), 7.79 (d, J=2.13 Hz, 1H), 7.18 (d, J=5.02 Hz, 1H).

4-chloro-3-iodo-1-((2-(trimethylsilyl)ethoxy)methyl)-1H-pyrrolo[2,3-b]pyridine

To a mixture of 4-chloro-3-iodo-1H-pyrrolo[2,3-b]pyridine (50 g, 179.55 mmol) in DMF (500 mL) was added NaH (8.62 g, 215.46 mmol, 60% purity) in portions at 0° C. under N$_2$. The mixture was stirred at 20° C. for 1 h. Then SEM-Cl (35.92 g, 215.46 mmol) was added to die mixture and stirred at 20° C. for 2 h. The mixture was poured into ice-water (1000 mL) and stirred for 5 min. The aqueous phase was extracted with ethyl acetate (3×500 mL). The combined organic phase was washed with brine (3×500 mL), dried over anhydrous Na$_2$SO$_4$, filtered and concentrated under reduced pressure to give a residue, which was purified by silica gel column chromatography (PE:EtOAc=20:1) to give 4-chloro-3-iodo-1-((2-(trimethylsilyl)ethoxy)methyl)-1H-pyrrolo[2,3-b]pyridine as a black brown solid.

4-chloro-1-((2-(trimethylsilyl)ethoxy)methyl)-1H-pyrrolo[2,3-b]pyridine-3-carbonitrile A mixture of 4-chloro-3-iodo-1-((2-(trimethylsilyl)ethoxy)methyl)-1H-pyrrolo[2,3-b]pyridine (3 g, 7.34 mmol) and CuCN (1.31 g, 14.68 mmol) in NMP (20 mL) was degassed and purged with N$_2$ for 3 times, and then the mixture was stirred at 120° C. for 4.5 h under N$_2$ atmosphere. The mixture was cooled to 20° C. and poured into ice-water (20 mL). The aqueous phase was extracted with ethyl acetate (3×15 mL). The combined organic phase was washed with brine (3×15 mL), dried with anhydrous Na$_2$SO$_4$, filtered and concentrated to give a residue, which was purified by silica gel column chromatography (PE:EtOAc=15:1) to afford 4-chloro-1-((2-(trimethylsilyl)ethoxy)methyl)-1H-pyrrolo[2,3-b]pyridine-3-carbonitrile as a yellow solid. LCMS: RT 0.938 min, m/z=308.1 [M+H]$^+$.

4-cyclopropyl-1-((2-(trimethylsilyl)ethoxy)methyl)-1H-pyrrolo[2,3-b]pyridine-3-carbonitrile A mixture of 4-chloro-1-((2-(trimethylsilyl)ethoxy)methyl)-1H-pyrrolo[2,3-b]pyridine-3-carbonitrile (1.03 g, 3.35 mmol), cyclopropylboronic acid (575 mg, 6.70 mmol). Pd$_2$(dba)$_3$ (460 mg, 502.50 umol), Cs$_2$CO$_3$ (2.18 g, 6.70 mmol) and DavePhos (132 mg, 335 umol) in toluene (15 mL) was degassed and purged with N$_2$ for 3 times, and then the mixture was stirred at 120° C. for 8 h under N$_2$. The mixture was concentrated under reduced pressure to give a residue, which was purified by silica gel column chromatography (PE:EtOAc=30:1) to give 4-cyclopropyl-1-((2-(trimethylsilyl)ethoxy)methyl)-1H-pyrrolo[2,3-b]pyridine-3-carbonitrile as a yellow solid. LCMS: RT 0.937 min, m/z=314.2 [M+H]$^+$.

3-cyano-4-cyclopropyl-1-((2-(trimethylsilyl)ethoxy)methyl)-1H-pyrrolo[2,3-b]pyridine 7-oxide To a solution of 4-cyclopropyl-1-((2-(trimethylsilyl)ethoxy)methyl)-1H-pyrrolo[2,3-b]pyridine-3-carbonitrile (3.3 g, 10.53 mmol) in CHCl$_3$ (40 mL) was added m-CPBA (6.41 g, 31.59 mmol, 85% purity). The mixture was stirred at 75° C. for 16 h. The reaction mixture was quenched by addition of water (150 mL) and Na$_2$S$_2$O$_3$ (8 g) at 0° C., and then extracted with DCM (3×50 mL). The combined organic layers were washed with saturated NaHCO$_3$ solution (50 mL) and brine (50 mL), dried over Na$_2$SO$_4$, filtered and concentrated under reduced pressure to give a residue, which was purified by silica gel column chromatography (DCM: MeOH=10:1) to give 3-cyano-4-cyclopropyl-1-((2-(trimethylsilyl)ethoxy)methyl)-1H-pyrrolo[2,3-b]pyridine 7-oxide as a white solid. LCMS: RT 1.015 min, m/z=330.2 [M+H]$^+$. $^1$H NMR (400 MHz, CDCl$_3$): δ 8.09 (d, J=6.53 Hz, 1H), 7.87 (s, 1H), 6.67 (d, J=6.53 Hz, 1H), 6.35 (s, 2H), 3.65-3.73 (m, 2H), 2.57-2.68 (m, 1H), 1.23-1.28 (m, 2H), 0.93-0.98 (m, 2H), 0.87-0.92 (m, 2H), −0.02 (s, 9H).

6-chloro-4-cyclopropyl-1-((2-(trimethylsilyl)ethoxy)methyl)-1H-pyrrolo[2,3-b]pyridine-3-carbonitrile To a solution of 3-cyano-4-cyclopropyl-1-((2-(trimethylsilyl)ethoxy)methyl)-1H-pyrrolo[2,3-b]pyridine 7-oxide (1.78 g, 5.40 mmol) in DMF (18 mL) was added MsCl (2.47 g, 21.60 mmol) and the mixture was stirred at 80° C. for 20 min. The reaction mixture was quenched by addition H$_2$O (120 mL) at 0° C. and treated with saturated aq. NaHCO$_3$ solution to pH=8 and extracted with EtOAc (3×40 mL). The combined organic layers were washed with brine (3×30 mL), dried over Na$_2$SO$_4$, filtered and concentrated under reduced pressure to give 6-chloro-4-cyclopropyl-1-((2-(trimethylsilyl)ethoxy)methyl)-1H-pyrrolo[2,3-b]pyridine-3-carbonitrile as a black brown gum. LCMS: RT 1.004 min, m/z=348.1 [M+H]$^+$.

3-iodo-1,4-dimethyl-pyrazole

To a solution of 1,4-dimethyl-pyrazole (10 g, 104.03 mmol) in DMF (150 mL) was added NIS (21.06 g, 93.63 mmol) in one portion at 25° C. under N$_2$. The mixture was stirred at 60° C. for 12 h. The mixture was poured into ice-water (300 mL) and stirred for 5 min. The aqueous phase was extracted with MTBE (3×300 mL). The combined organic phase was washed with brine (3×200 mL), dried over anhydrous Na$_2$SO$_4$, filtered and concentrated under reduced pressure. The residue was purified by silica gel column chromatography (PE:EtOAc=10:1-1:1) to give 3-iodo-1,4-dimethyl-pyrazole as a brown solid. $^1$H NMR (400 MHz, CDCl$_3$): δ ppm 7.05 (s, 1H), 3.86 (s, 3H), 1.98 (s, 3H).

Tert-butyl N-(1,4-dimethylpyrazol-3-yl)carbamate

A mixture of 3-iodo-1,4-dimethyl-pyrazole (5 g, 22.52 mmol), tert-butyl carbamate (3.43 g, 29.28 mmol), CuI (2.14 g, 11.26 mmol), K$_2$CO$_3$ (6.22 g, 45.04 mmol) and (1S,2S)—N1,N2-dimethylcyclohexane-1,2-diamine (1.6 g, 11.26 mmol) in 1,4-dioxane (60 mL) was degassed and purged with N$_2$ for 3 times, and then the mixture solution was stirred at 110° C. for 12 h under N$_2$. To the reaction solution was added water (80 mL), extracted with EtOAc (30 mL×3), organic layers were combined, washed with brine (30 mL), dried over Na$_2$SO$_4$, filtered and concentrated under reduced pressure. The residue was purified by silica gel column chromatography (PE:EtOAc=5:1 to 3:1) to give tert-butyl N-(1,4-dimethylpyrazol-3-yl)carbamate as a light brown solid. $^1$H NMR (400 MHz, CDCl$_3$): δ ppm 7.06 (s, 1H), 6.44 (br. s., 1H), 3.71-3.81 (m, 3H), 1.98 (s, 3H), 1.48 (s, 9H).

1,4-dimethylpyrazol-3-amine

To a mixture of tert-butyl N-(1,4-dimethylpyrazol-3-yl)carbamate (700 mg, 3.31 mmol) in 1,4-dioxane (10 mL) was added HCl/dioxane (15 mL) at 20° C. The mixture was stirred at 20° C. for 5 h. The mixture was concentrated under reduced pressure to give 1,4-dimethylpyrazol-3-amine (HCl salt) as a brown oil. $^1$H NMR (400 MHz, DMSO-d$_6$): δ ppm 10.21 (br. s., 2H), 7.58 (s, 1H), 3.74 (s, 3H), 3.39 (s, 1H), 1.98 (s, 3H).

4-cyclopropyl-6-((1,4-dimethyl-1H-pyrazol-3-yl)amino)-1-((2-(trimethylsilyl)ethoxy)methyl)-1H-pyrrolo[2,3-b]pyridine-3-carbonitrile A mixture of 6-chloro-4-cyclopropyl-1-((2-(trimethylsilyl)ethoxy)methyl)-1H-pyrrolo[2,3-b]pyridine-3-carbonitrile (250 mg, 718.56 umol), 1,4-dimethylpyrazol-3-amine (160 mg, 1.44 mmol), Cs$_2$CO$_3$ (1.05 g, 3.23 mmol), Pd$_2$(dba)$_3$ (66 mg, 71.86 umol) and XPhos (68 mg, 143.71 umol) in 1,4-dioxane (6 mL) was degassed and purged with N$_2$ for 3 times, and then the mixture was stirred at 110° C. for 16 h under N$_2$. The reaction mixture was concentrated under reduced pressure. The residue was diluted with H$_2$O (60 mL) and extracted with EtOAc (3×20 mL). The combined organic layers were washed with brine (20 mL), dried over Na$_2$SO$_4$, filtered and concentrated under reduced pressure to give a residue, which was purified by prep-TLC (SiO$_2$, PE:EtOAc=1:1) to give 4-cyclopropyl-6-((1,4-dimethyl-1H-pyrazol-3-yl)amino)-1-((2-(trimethylsilyl)ethoxy)methyl)-1H-pyrrolo[2,3-b]pyridine-3-carbonitrile as a yellow gum. LCMS: RT 0.902 min, m/z=423.3 [M+H]$^+$. $^1$H NMR (400 MHz, CDCl3): δ ppm 7.59 (s, 1H), 7.12 (s, 1H), 6.69 (s, 1H), 6.33 (s, 1H), 5.54 (s, 2H), 3.82 (s, 3H), 3.53-3.58 (m, 2H), 2.52-2.64 (m, 1H), 1.96 (s, 3H), 1.14 (dd, J=8.34, 2.07 Hz, 2H), 0.90-0.95 (m, 2H), 0.86 (dd, J=4.77, 1.63 Hz, 2H), −0.03 (s, 9H).

4-cyclopropyl-6-((1,4-dimethyl-1H-pyrazol-3-yl)amino)-1H-pyrrolo[2,3-b]pyridine-3-carbonitrile To a solution of 4-cyclopropyl-6-((1,4-dimethyl-1H-pyrazol-3-yl)amino)-1-((2-(trimethylsilyl)ethoxy)methyl)-1H-pyrrolo[2,3-b]pyridine-3-carbonitrile (210 mg, 496.92 umol) in DCM (9 mL) was added TFA (4.62 g, 40.52 mmol, 3 mL). The mixture was stirred at 40° C. for 6 h and concentrated under reduced pressure to get a residue. K$_2$CO$_3$ (15 g, 108.53 mmol) was added to the residue in THF (12 mL) and water (12 mL). The mixture was stirred at 40° C. for 16 h. The mixture was poured into ice-water (30 mL) and extracted with EtOAc (10 mL×3). The combined organic phase was washed with brine (10 mL), dried over anhydrous Na$_2$SO$_4$, filtered and concentrated under reduced pressure. The residue was triturated with CH$_3$CN to give 4-cyclopropyl-6-((1,4-dimethyl-1H-pyrazol-3-yl)amino)-1H-pyrrolo[2,3-b]pyridine-3-carbonitrile. $^1$HNMR (400 MHz, MeOD): δ 7.70 (s, 1H), 7.33 (s, 1H), 6.35 (s, 1H) 3.78 (s, 3H), 2.47-2.55 (m, 1H), 1.92 (s, 3H), 1.09-1.15 (m, 2H), 0.79-0.85 (m, 2H). HPLC: RT 2.22 min. MS: m/z: 293.1 [M+H]$^+$.

Example C-21

Synthesis of 4-cyclopropyl-6-((1-methyl-1H-pyrazol-3-yl)amino)-1H-pyrrolo[2,3-b]pyridine-3-carbonitrile (C-21)

4-cyclopropyl-6-((1-methyl-1H-pyrazol-3-yl)amino)-1-((2-(trimethylsilyl)ethoxy)methyl)-1H-pyrrolo[2,3-b]pyridine-3-carbonitrile A mixture of 6-chloro-4-cyclopropyl-1-((2-(trimethylsilyl)ethoxy)methyl)-1H-pyrrolo[2,3-b]pyridine-3-carbonitrile (250 mg, 718.56 umol), 1-methylpyrazol-3-amine (70 mg, 718.56 umol), $Cs_2CO_3$ (585 mg, 1.80 mmol), $Pd_2(dba)_3$ (66 mg, 71.86 umol) and XPhos (68 mg, 143.71 umol) in 1,4-dioxane (4 mL) was degassed and purged with $N_2$ for 3 times, and then the mixture was stirred at 110° C. for 16 h under $N_2$. The reaction mixture was concentrated under reduced pressure. The residue was diluted with $H_2O$ (20 mL) and extracted with DCM (3×10 mL). The combined organic layers were washed with brine (10 mL), dried over $Na_2SO_4$, filtered and concentrated under reduced pressure to give a residue, which was purified by prep-TLC ($SiO_2$, PE:EtOAc=1:1). LCMS: RT 0.974 min, m/z=409.3 [M+H]$^+$. $^1$H NMR (400 MHz, $CDCl_3$): δ 7.60 (s, 1H), 6.92 (s, 1H), 6.51 (d, J=1.76 Hz, 1H), 6.39 (s, 1H), 5.58 (s, 2H), 3.83 (s, 3H), 3.53-3.60 (m, 2H), 2.53-2.61 (m, 1H), 1.17 (dd, J=8.16, 1.98 Hz, 2H), 0.90-0.94 (m, 2H), 0.87 (dd, J=4.85, 1.76 Hz, 2H), −0.06 (s, 9H).

4-cyclopropyl-6-((1-methyl-1H-pyrazol-3-yl)amino)-1H-pyrrolo[2,3-b]pyridine-3-carbonitrile To a solution of 4-cyclopropyl-6-((1-methyl-1H-pyrazol-3-yl)amino)-1-((2-(trimethylsilyl)ethoxy)methyl)-1H-pyrrolo[2,3-b]pyridine-3-carbonitrile (200 mg, 489.51 umol) in DCM (9 mL) was added TFA (4.62 g, 40.52 mmol, 3 mL). The mixture was stirred at 40° C. for 4 h. The mixture was concentrated under reduced pressure to give a residue. $K_2CO_3$ (15 g, 108.53 mmol) was added to the residue in THF (10 mL) and water (10 mL) and stirred at 40° C. for 16 h. The mixture was poured into ice-water (30 mL) and extracted with EtOAc (10 mL×3). The combined organic phase was washed with brine (10 mL), dried over anhydrous $Na_2SO_4$, filtered and concentrated under reduced pressure. The residue was purified by prep-HPLC (neutral condition) to give 4-cyclopropyl-6-((1-methyl-1H-pyrazol-3-yl)amino)-1H-pyrrolo[2,3-b]pyridine-3-carbonitrile. $^1$H NMR (400 MHz, DMSO-d6): δ 9.14 (s, 1H), 7.95 (s, 1H), 7.50 (d, J=2.13 Hz, 1H), 6.56 (d, J=2.13 Hz, 1H), 6.53 (s, 1H), 3.72 (s, 3H), 2.37-2.44 (m, 1H) 1.06-1.14 (m, 2H), 0.77 (dd, J=4.89, 2.01 Hz, 2H). HPLC: RT. 2.12 min. MS: m/z=279.1 [M+H]$^+$.

The following compounds were prepared according to the Examples above and/or general procedures described herein.

| No. | [M + H]$^+$ |
|---|---|
| C-22 | 356.1 |
| C-23 | 322.2 |
| C-24 | 269.1 |
| C-25 | 269.1 |
| C-26 | 403.2 |
| C-27 | 378.2 |
| C-28 | 412.2 |
| C-29 | 396.2 |
| C-30 | 333.2 |
| C-31 | 333.2 |
| C-32 | 367.1 |
| C-33 | 284.1 |
| C-34 | 284.1 |
| C-35 | 269.1 |
| C-36 | 310.2 |
| C-37 | 378.2 |
| C-38 | 330.1 |
| C-39 | 330.1 |
| C-40 | 330.1 |
| C-41 | 362.2 |
| C-42 | 390.1 |
| C-43 | 360.1 |
| C-44 | 360.2 |
| C-45 | 334.1 = [M − H]$^−$ |
| C-46 | 336.2 |
| C-47 | 374.1 |
| C-48 | 350.1 |
| C-49 | 296.1 |
| C-50 | 296.1 |
| C-51 | 310.1 |
| C-52 | 310.1 |
| C-53 | 319.1 |
| C-54 | 319.1 |
| C-55 | 367.1 |

D: Compound Preparation

In die following examples, all non-aqueous reactions were carried out in oven-dried or flame-dried glassware under nitrogen atmosphere. All chemicals were purchased from commercial vendors and used as is, unless otherwise specified. Reactions were magnetically stirred and monitored by thin layer chromatography (TLC) with 250 μm pre-coated silica gel plates, visualized either with UV, or in an iodine chamber. Flash column chromatography was performed using silica gel (100-200 mesh). Chemical shifts are reported relative to chloroform (δ7.26), methanol (δ3.31), or DMSO (δ2.50) for $^1$H NMR. HPLC analysis was performed on Shimadzu 20AB HPLC system with a photodiode array detector and Luna-C18(2) 2.0×50 mm, 5 um column at a flow rate of 1.2 mL/min with a gradient solvent Mobile phase A (MPA, $H_2O$+0.037% (v/v) TFA): Mobile phase B (MPB, ACN+0.018% (v/v) TFA) (0.01 min, 10% MPB; 4 min, 80% MPB; 4.9 min, 80% MPB; 4.92 min, 10% MPB; 5.5 min, 10% MPB). LCMS was detected under 220 and 254 nm or used evaporative light scattering (ELSD) detection as well as positive electrospray ionization (MS). Semi-preparative HPLC was performed by either acidic or neutral condition. Acidic: Luna C18 100×30 mm, 5 μm; MPA: HCl/$H_2O$=0.04%, or formic acid/$H_2O$=0.2% (v/v); MPB: ACN. Neutral: Waters Xbridge 150×25, 5 μm; MPA: 10 mM $NH_4HCO_3$ in $H_2O$; MPB: ACN. Gradient for both conditions: 10% of MPB to 80% of MPB within 12 min at a flow rate of 20 mL/min, then 100% MPB over 2 min, 10% MPB over 2 min, UV detector. SFC analysis was performed on Thar analytical SFC system with a UV/Vis detector and series of chiral columns including AD-3, AS-H, OJ-3, OD-3, AY-3 and IC-3, 4.6×100 mm, 3 um column at a flow rate of 4 mL/min with a gradient solvent Mobile phase A (MPA, $CO_2$): Mobile phase B (MPB, MeOH+0.05% (v/v) IPAm) (0.01 min. 10% MPB; 3 min, 40% MPB; 3.5 min, 40% MPB; 3.56-5 min, 10% MPB). SFC preparative was performed on Thar 80 preparative SFC system with a UV/Vis detector and series of chiral preparative columns including AD-H, AS-H, OJ-H, OD-H, AY-H and IC-H, 30×250 mm, 5 um column at a flow rate of 65 mL/min with a gradient solvent Mobile phase A (MPA, $CO_2$): Mobile phase B (MPB, MeOH+0.1% (v/v) NH₃H₂O) (0.01 min, 10% MPB; 5 min, 40% MPB; 6 min, 40% MPB; 6.1-10 min, 10% MPB).

Compounds were named by using either ChemBioDraw Ultra 13.0 or Chemaxon.

Example D-1

Synthesis of 2-methyl-2-[3-methyl-4-[[4-methylsulfanyl-5-(trifluoromethyl)pyrimidin-2-yl]amino]pyrazol-1-yl]propanenitrile (D-46)

Methyl 2-methyl-2-(3-methyl-4-nitro-pyrazol-1-yl)propanoate

To a solution of 3-methyl-4-nitro-1H-pyrazole (1-1, 40 g, 314.71 mmol) in DMF (700 mL) was added NaH (18.88 g, 472.06 mmol, 60% purity) at 0° C. over a period of 30 min under $N_2$. The reaction was then stirred at 25° C. for 2 h followed by die addition of methyl 2-bromo-2-methylpropanoate (85.46 g, 472.06 mmol, 61.04 mL) dropwise at 0° C. The reaction mixture was warmed to 25° C. and stirred at 25° C. for another 16 h. TLC (petroleum ether/ethyl acetate=5:1) showed the starting material was consumed completely. The reaction was quenched by ice water slowly and then extracted with EtOAc (3×700 mL). The combined organic phase was washed with brine (3×200 mL), dried over anhydrous $Na_2SO_4$, filtered and concentrated in vacuo. The residue was purified by column chromatography on silica gel (petroleum ether/ethyl acetate=30:1-15:1), to yield the desired product as a light yellow solid. $^1$H NMR (400 MHz, CDCl₃): δ 8.29 (s, 1H), 3.72 (s, 1H), 2.51 (s, 1H), 1.84 (s, 6H).

2-Methyl-2-(3-methyl-4-nitro-pyrazol-1-yl) propanoic acid

To a mixture of methyl 2-methyl-2-(3-methyl-4-nitropyrazol-1-yl)propanoic (69.7 g, 306.75 mmol) in THF (1 L) and $H_2O$ (250 mL) was added LiOH.H₂O (15.45 g, 368.10 mmol) at 25° C. under $N_2$. The mixture was then stirred at 25° C. for 16 h. TLC (petroleum ether/ethyl acetate=5:1) showed the reaction was completed. The reaction mixture was concentrated in vacuo. The residual aqueous solution was washed with ethyl acetate (50 mL). The aqueous phase was then cooled to 0° C., adjusted to approximately pH 1-2, and filtered to yield the desired product as a white solid. $^1$H NMR (400 MHz, CDCl₃): δ 8.65 (s, 1H), 2.48 (s, 1H), 1.83 (s, 6H).

2-Methyl-2-(3-methyl-4-nitro-pyrazol-1-yl)propanamide

To a solution of 2-methyl-2-(3-methyl-4-nitro-pyrazol-1-yl) propanoic acid (25 g, 117.27 mmol) in DCM (500 mL) was added 8 drops of DMF, followed by oxalyl chloride (29.77 g, 234.54 mmol) at 0° C. under $N_2$. The mixture was then stirred at 25° C. for a further 2 h. TLC (petroleum ether/ethyl acetate=3:1) showed reaction was completed. The reaction solution was concentrated in vacuo. The residue solid was dissolved in THF (300 mL) and added dropwise into a stirred solution of NH₄OH (413.61 g, 11.80 mol, 454.52 mL) at 0° C. The reaction was stirred at 25° C. for 1 h. TLC (ethyl acetate) showed reaction was completed. The solution was then concentrated in vacuo and partitioned between EtOAc (100 mL) and water (100 mL), and the aqueous phase was extracted with ethyl acetate (3×80 mL). The combined organic phase was washed with brine (3×40 mL), dried over anhydrous $Na_2SO_4$, filtered and concentrated in vacuo, to yield the desired compound as a yellow solid. $^1$H NMR (400 MHz. MeOD): δ 8.81 (s, 1H), 7.16-7.26 (m, 2H), 2.42 (s, 3H), 1.71 (s, 3H).

2-Methyl-2-(3-methyl-4-nitro-1H-pyrazol-1-yl)propanenitrile

A solution of 2-methyl-2-(3-methyl-4-nitro-pyrazol-1-yl)propanamide (22 g, 103.67 mmol) in POCl₃ (132 g, 860.89 mmol, 80 mL) was stirred at 90° C. for 1 h. TLC showed the reaction was completed. The mixture was cooled to 20° C. and concentrated in vacuo at 50° C. The residue was poured into ice water (w/w=1/1) (200 mL) and stirred for 10 min. The aqueous phase was adjusted to pH=7 with NaHCO₃ solution, extracted with ethyl acetate (4×80 mL). The combined organic phase was washed with brine (40 mL), dried with anhydrous $Na_2SO_4$, filtered and concentrated in vacuo. The desired product was afforded as a yellow solid.

2-(4-Amino-3-methyl-pyrazol-1-yl)-2-methyl-propanenitrile

To a mixture of 2-methyl-2-(3-methyl-4-nitro-1H-pyrazol-1-ylpropanenitrile (10 g, 51.5 mmol) in EtOH (240 mL) and $H_2O$ (60 mL) was added NH₄Cl (13.77 g, 257.5 mmol) in one portion at 25° C., followed by Fe (14.38 g, 257.5 mmol). The mixture was heated to 80° C. and stirred for 1 h. TLC showed the reaction was completed. The solution was cooled to 20° C. The mixture was extracted with ethyl acetate (3×100 mL), the combined organic layers were washed with NaHCO₃ solution (50 mL) and brine (50 mL). The organic layers were dried over $Na_2SO_4$, filtered and concentrated. The desired product was afforded as a dark brown solid. $^1$H NMR (400 MHz, CDCl₃): δ 7.17 (s, 1H), 2.18 (s, 3H), 1.91 (s, 6H).

2-chloro-4-methylsulfanyl-5-(trifluoromethyl)pyrimidine and 4-chloro-2-methylsulfanyl-5-(trifluoromethyl)pyrimidine To a solution of 2,4-dichloro-5-(trifluoromethyl)pyrimidine (1-6, 1 g, 4.61 mmol) in THF (10 mL) was added a solution of NaSMe (2.42 g, 6.92 mmol, 2.20 mL) dropwise at −25° C. under $N_2$. The reaction mixture was then stirred at −25° C. for 1 hour followed by stirred at 25° C. for 15 h. The reaction mixture was diluted with $CH_2Cl_2$ (20 mL) and washed with 1 N HCl (3<10 mL). The organic phase was dried over anhydrous $Na_2SO_4$, filtered and concentrated to afford a mixture of 2-chloro-4-methylsulfanyl-5-(trifluoromethyl)pyrimidine and 4-chloro-2-methylsulfanyl-5-(trifluoromethyl)pyrimidine as yellow oil.

2-methyl-2-[3-methyl-4-[[4-methylsulfanyl-5-(trifluoromethyl)pyrimidin-2-yl]amino]pyrazol-1-yl] propanenitrile and 2-methyl-2-[3-methyl-4-[[2-methylsulfanyl-5-(trifluoromethyl)pyrimidin-4-yl]amino]pyrazol-1-yl]propanenitrile To a mixture of 2-chloro-4-methylsulfanyl-5-(trifluoromethyl)pyrimidine and 4-chloro-2-methylsulfanyl-5-(trifluoromethyl)pyrimidine (150 mg, 656.12 μmol) in n-BuOH (3 mL) was added 2-(4-amino-3-methyl-pyrazol-1-yl)-2-methyl-propanenitrile (161 mg, 984.18 μmol) and TEA (99 mg, 984.18 μmol) at 25° C. under $N_2$. The mixture was then heated under microwave at 120° C. and stirred for 1 h. The mixture was cooled to 25° C., poured into water (10 mL) and extracted with ethyl acetate (3×10 mL). The combined organic phase was washed with brine (10 mL), dried over anhydrous $Na_2SO_4$, filtered and concentrated. The residue was purified by prep-HPLC (HCl) to give 2-methyl-2-[3-methyl-4-[[4-methylsulfanyl-5-(trifluoromethyl)pyrimidin-2-yl]amino]pyrazol-1-yl]propanenitrile and 2-methyl-2-[3-methyl-4-[[2-methylsulfanyl-5-(trifluoromethyl)pyrimidin-4-yl]amino]pyrazol-1-yl]propanenitrile.

2-methyl-2-[3-methyl-4-[[4-methylsulfanyl-5-(trifluoromethyl)pyrimidin-2-yl]amino]pyrazol-1-yl]propanenitrile (D-46)

$^1$H NMR (400 MHz, $CDCl_3$): δ 9.45 (br. s., 1H), 8.18 (br. s., 2H), 2.68 (br. s., 3H), 2.35 (br. s., 3H), 1.88-2.02 (m, 6H); HPLC: RT 3.48 min; MS: m/z: 357.1 [M+H]$^+$.

2-methyl-2-[3-methyl-4-[[2-methylsulfanyl-5-(trifluoromethyl)pyrimidin-4-yl]amino]pyrazol-1-yl]propanenitrile $^1$H NMR (400 MHz, DMSO-$d_6$): δ 8.74 (s, 1H), 8.41 (s, 1H), 8.09 (s, 1H), 2.33 (s, 3H), 2.06 (s, 3H), 1.94 (s, 6H); HPLC: RT 3.19 min; MS: m/z: 357.1 [M+H]$^+$.

Example D-2

Synthesis of 2-[[1-(1-cyano-1-methyl-ethyl)-3-methyl-pyrazol-4-yl]amino]-4-ethylsulfanyl-pyrimidine-5-carbonitrile (D-47)

2-chloro-4-ethylsulfanyl-pyrimidine-5-carbonitrile and 4-chloro-2-ethylsulfanyl-pyrimidine-5-carbonitrile NaH (172 mg, 4.31 mmol, 60%) was added to a solution of EtSH (178 mg, 2.87 mmol) in dry THF (5 mL) at 0° C. under $N_2$. The resulting suspension was slowly added to a solution of 2,4-dichloropyrimidine-5-carbonitrile (2-1,500 mg, 2.87 mmol) in dry THF (10 mL). The reaction was stirred at −20° C. for 1 h. The reaction mixture was quenched by addition of aqueous $NH_4Cl$ (20 mL) at 0° C., and then extracted with EtOAc (3×20 mL). The combined organic layers were washed with brine, dried over $Na_2SO_4$, filtered and concentrated under reduced pressure to afford a mixture of 2-chloro-4-ethylsulfanyl-pyrimidine-5-carbonitrile and 4-chloro-2-ethylsulfanyl-pyrimidine-5-carbonitrile as yellow oil. LCMS: RT 0.793 min, m/z=199.9 [M+H]$^+$.

2-[[1-(1-cyano-1-methyl-ethyl)-3-methyl-pyrazol-4-yl]amino]-4-ethylsulfanyl-pyrimidine-5-carbonitrile (47) and 4-[[1-(1-cyano-1-methyl-ethyl)-3-methyl-pyrazol-4-yl]amino]-2-ethylsulfanyl-pyrimidine-5-carbonitrile To a mixture of 2-chloro-4-ethylsulfanyl-pyrimidine-5-carbonitrile and 4-chloro-2-ethylsulfanyl-pyrimidine-5-carbonitrile (200 mg, 1 mmol) in n-BuOH (2 mL) was added 2-(4-amino-3-methyl-pyrazol-1-yl)-2-methyl-propanenitrile (246 mg, 1.5 mmol) and TEA (50 mg, 500.85 μmol) at 25° C. under $N_2$. The mixture was then heated at 120° C. under microwave for 1.5 h. The reaction mixture was concentrated under reduced pressure. The residue was purified by prep-HPLC (neutral) to give 2-[[1-(1-cyano-1-methyl-ethyl)-3-methyl-pyrazol-4-yl]amino]-4-ethylsulfanyl-pyrimidine-5-carbonitrile and 4-[[1-(1-cyano-1-methyl-ethyl)-3-methyl-pyrazol-4-yl]amino]-2-ethylsulfanyl-pyrimidine-5-carbonitrile.

2-[[1-(1-cyano-1-methyl-ethyl)-3-methyl-pyrazol-4-yl]amino]-4-ethylsulfanyl-pyrimidine-5-carbonitrile (D-47)

$^1$H NMR (400 MHz, $CDCl_3$): δ 8.26-8.39 (m, 1H), 8.09-8.18 (m, 1H), 6.75-6.97 (m, 1H), 3.25 (q, J=7.06 Hz, 2H), 2.29 (br. s., 3H), 1.93-2.05 (m, 6H), 1.42 (t, J=7.50 Hz, 3H); HPLC: RT 2.597 min: MS: m/z: 328.2 [M+H]$^+$.

4-[[1-(1-cyano-1-methyl-ethyl)-3-methyl-pyrazol-4-yl]amino]-2-ethylsulfanyl-pyrimidine-5-carbonitrile $^1$H NMR (400 MHz, $CDCl_3$): δ 8.36 (s, 1H), 8.12 (br. s., 1H), 6.70 (br. s., 1H), 3.11 (q, J=7.35 Hz, 2H), 2.28 (s, 3H), 1.97-2.03 (m, 6H), 1.38 (t, J=7.28 Hz, 3H); HPLC: RT 2.382 min; MS: m/z: 328.2 [M+H]$^+$.

Example D-3

Synthesis of 2-[4-[(5-chloro-4-ethylsulfanyl-pyrimidin-2-yl)amino]-3-methyl-pyrazol-1-yl]-2-methyl-propanenitrile (D-44)

2,5-dichloro-4-ethylsulfanyl-pyrimidine

NaH (654 mg, 16.35 mmol, 60%) was added to a solution of ethanethiol (677 mg, 10.90 mmol) in dry THF (10 mL) at 0° C. under $N_2$. The resulting suspension was slowly added to a solution of 2,4,5-trichloropyrimidine (2 g, 10.90 mmol) in dry THF (15 mL) at −20° C. under $N_2$. The reaction was then stirred at −20° C. for 1 h. The mixture was poured into aqueous $NH_4Cl$ (50 mL), extracted with EtOAc (3×20 mL). The combined organic layer was washed with brine, dried over $Na_2SO_4$, concentrated to afford 2,5-dichloro-4-ethylsulfanyl-pyrimidine as yellow solid. LCMS: RT 0.876 min, m/z=209.0 [M+H]$^+$.

2-[4-[(5-chloro-4-ethylsulfanyl-pyrimidin-2-yl)amino]-3-methyl-pyrazol-1-yl]-2-methyl-propanenitrile (D-44)

To a mixture of 2,5-dichloro-4-ethylsulfanyl-pyrimidine (200 mg, 956.48 μmol) and 2-(4-amino-3-methyl-pyrazol-1-yl)-2-methyl-propanenitrile (235 mg, 1.43 mmol) in n-BuOH (3 mL) was added TEA (290 mg, 2.87 mmol) at 25° C. under $N_2$. The mixture was heated under microwave at 120° C. for 1.5 h. The mixture was cooled to 25° C. and concentrated under reduced pressure. The residue was purified by prep-HPLC (neutral) to afford 2-[4-[(5-chloro-4-ethylsulfanyl-pyrimidin-2-yl)amino]-3-methyl-pyrazol-1-yl]-2-methyl-propanenitrile (D-44). $^1$H NMR (400 MHz, $CDCl_3$): δ 8.13 (s, 1H), 8.03 (s, 1H), 6.53 (br. s., 1H), 3.20 (q, J=50 Hz, 2H), 2.28 (s, 3H), 1.99 (s, 6H), 1.41 (t, J=7.28 Hz, 3H); HPLC: RT 3.47 min: MS: m/z: 337.1 [M+H]$^+$.

Example D-4

Synthesis of 2-[4-[[4-ethylsulfanyl-5-(trifluoromethyl)pyrimidin-2-yl]amino]-3-methyl-pyrazol-1-yl]-2-methyl-propanenitrile (D-45)

2-chloro-4-ethylsulfanyl-5-(trifluoromethyl)pyrimidine and 4-chloro-2-ethylsulfanyl-5-(trifluoromethyl)pyrimidine NaH (138 mg, 3.45 mmol, 60%) was added to a solution of ethanethiol (143 mg, 2.30 mmol, 170.12 μL) in dry THF (5 mL) at 0° C. under N₂. The resulting suspension was slowly added to a solution of 2,4-dichloro-5-(trifluoromethyl)pyrimidine (500 mg, 2.30 mmol) in dry THF (10 mL) at −20° C. under N₂. The reaction was then stirred at −20° C. for 1 h. The mixture was poured into aqueous NH₄Cl (50 mL), extracted with EtOAc (3×20 mL). The combined organic layer was washed with brine, dried over Na₂SO₄, concentrated to afford a mixture of 2-chloro-4-ethylsulfanyl-5-(trifluoromethyl)pyrimidine and 4-chloro-2-ethylsulfanyl-5-(trifluoromethyl)pyrimidine as yellow oil.

2-[4-[[4-ethylsulfanyl-5-(trifluoromethyl)pyrimidin-2-yl]amino]-3-methyl-pyrazol-1-yl]-2-methyl-propanenitrile (D-45) and 2-[4-[[2-ethylsulfanyl-5-(trifluoromethyl)pyrimidin-4-yl]amino]-3-methyl-pyrazol-1-yl]-2-methyl-propanenitrile To a mixture of 2-chloro-4-ethylsulfanyl-5-(trifluoromethyl)pyrimidine and 4-chloro-2-ethylsulfanyl-5-(trifluoromethyl)pyrimidine (300 mg, 1.24 mmol) in n-BuOH (3 mL) was added 2-(4-amino-3-methyl-pyrazol-1-yl)-2-methyl-propanenitrile (305 mg, 1.86 mmol) and TEA (375 mg, 3.71 mmol) al 25° C. under N₂. The mixture was heated in microwave at 120° C. for 1.5 h. The reaction mixture was concentrated under reduced pressure to give a residue. The residue was purified by prep-HPLC (neutral) to give 2-[4-[[4-ethylsulfanyl-5-(trifluoromethyl)pyrimidin-2-yl]amino]-3-methyl-pyrazol-1-yl]-2-methyl-propanenitrile (45) and 2-[4-[[2-ethylsulfanyl-5-(trifluoromethyl)pyrimidin-4-yl]amino]-3-methyl-pyrazol-1-yl]-2-methyl-propanenitrile.

2-[4-[[4-ethylsulfanyl-5-(trifluoromethyl)pyrimidin-2-yl]amino]-3-methyl-pyrazol-1-yl]-2-methyl-propanenitrile (D-45)

¹H NMR (400 MHz, CDCl₃): δ 8.31 (br. s., 1H), 8.12 (s, 1H), 6.73 (br. s., 1H), 3.23 (q, J=7.53 Hz, 2H), 2.29 (s, 3H), 1.95-2.06 (m, 6H), 1.40 (t, J=7.28 Hz, 3H); HPLC: RT 3.60 min; MS: m/z: 371.2 [M+H]⁺.

2-[4-[[2-ethylsulfanyl-5-(trifluoromethyl)pyrimidin-4-yl]amino]-3-methyl-pyrazol-1-yl]-2-methyl-propanenitrile ¹H NMR (400 MHz, CDCl₃): δ 8.33 (s, 1H), 8.14 (s, 1H), 6.53 (br. s., 1H), 3.10 (q, J=7.20 Hz, 2H), 2.25 (s, 3H), 2.00 (s, 6H), 1.37 (t, J=7.28 Hz, 3H); HPLC: RT 3.30 min; MS: m/z: 371.2 [M+H]⁺.

Example D-5

Synthesis of 2-(1-((3-methyl-4-((4-(methylamino)-5-(trifluoromethyl)pyrimidin-2-yl)amino)-1H-pyrazol-1-yl)methyl)cyclopropyl)acetonitrile (D-1)

2-(1-((3-methyl-4-nitro-1H-pyrazol-1-yl)methyl)cyclopropyl)acetonitrile

To a mixture of PPh₃ (2.63 g, 10 mmol) in THF (30 mL) was added DIAD (2 mL, 10 mmol), 3-methyl-4-nitro-1H-pyrazole (850 mg, 6.7 mmol) and 2-(1-(hydroxymethyl)cyclopropyl)acetonitrile (982 mg, 8 mmol) at 25° C. The mixture was stirred at 25° C. for 12 h. The reaction mixture was concentrated under reduced pressure. The residue was purified by silica gel column chromatography (PE: EtOAc=50:1 to 5:1) to give 2-(1-((3-methyl-4-nitro-1H-pyrazol-1-yl)methyl)cyclopropyl)acetonitrile.

2-(1-((4-amino-3-methyl-1H-pyrazol-1-yl)methyl)cyclopropyl)acetonitrile

To a mixture of 2-(1-((3-methyl-4-nitro-1H-pyrazol-1-yl)methyl)cyclopropyl)acetonitrile (400 mg, 1.82 mmol) in EtOH (2 mL) was added Fe (507 mg, 9.08 mmol) and NH₄Cl (486 mg, 9.08 mmol) in one portion at 25° C. under N₂. The mixture was heated to 90° C. and stirred for 1 h. The mixture was concentrated under reduced pressure. The residue was purified by prep-TLC (SiO₂, PE:EtOAc=1:1) to give 2-(1-((4-amino-3-methyl-1H-pyrazol-1-yl)methyl)cyclopropyl)acetonitrile as pale yellow oil.

2-(1-((3-methyl-4-((4-(methylamino)-5-(trifluoromethyl)pyrimidin-2-yl)amino)-1H-pyrazol-1-yl)methyl)cyclopropyl)acetonitrile (D-1)

To a mixture of 2-(1-((4-amino-3-methyl-1H-pyrazol-1-yl)methyl)cyclopropyl)acetonitrile (100 mg, 0.53 mmol) and 2-chloro-N-methyl-5-(trifluoromethyl)pyrimidin-4-amine (110 mg, 0.53 mmol) in n-BuOH (2 mL) was added TEA (0.2 mL) in one portion at 25° C. under N₂. The mixture was stirred at 25° C. for 1 h. The reaction mixture was concentrated under reduced pressure to remove n-BuOH. The residue was purified by prep-HPLC (neutral) to give 2-(1-((3-methyl-4-((4-(methylamino)-5-(trifluoromethyl)pyrimidin-2-yl)amino)-1H-pyrazol-1-yl)methyl)cyclopropyl)acetonitrile (D-1). ¹H NMR (400 MHz, CDCl₃): δ 7.98-8.27 (m, 1H), 7.90 (d, J=20 Hz, 1H), 4.11 (s, 2H), 3.09 (d, J=16 Hz, 3H), 2.41-2.61 (m, 2H), 2.10-2.32 (m, 3H), 0.89 (br. s., 2H), 0.73 (br. s., 2H); HPLC: RT 1.63 min; MS: m/z: 366.1 [M+H]⁺.

Example D-6, D-7, and D-8

Synthesis of N2-[1-(6,7-dihydro-5H-pyrrolo[1,2-a]imidazol-7-yl)-5-methyl-pyrazol-4-yl]-N4-methyl-5-(trifluoromethyl)pyrimidine-2,4-diamine (D-2), N2-[1-[6,7-dihydro-5H-pyrrolo[1,2-a]imidazol-7-yl]-3-methyl-1H-pyrazol-4-yl]-N4-methyl-5-(trifluoromethyl)pyrimidine-2,4-diamine (First Eluting Stereoisomer, D-3), and N2-[1-[6,7-dihydro-5H-pyrrolo[1,2-a]imidazol-7-yl]-3-methyl-1H-pyrazol-4-yl]-N4-methyl-5-(trifluoromethyl)pyrimidine-2,4-diamine (Second Eluting Stereoisomer, D-4)

7-(3-methyl-4-nitro-pyrazol-1-yl)-6,7-dihydro-5H-pyrrolo[1,2-a]imidazole and 7-(5-methyl-4-nitro-1H-pyrazol-1-yl)-6,7-dihydro-5H-pyrrolo[1,2-a]imidazole To a mixture of 6,7-dihydro-5H-pyrrolo[1,2-a]imidazol-7-ol (1 g, 8.06 mmol) and 3-methyl-4-nitro-1H-pyrazole (1.13 g, 8.87 mmol) in THF (20 mL) was added PPh₃ (3.17 g, 12.09 mmol) and then DIAB (2.44 g, 12.09 mmol, 2.4 mL) dropwise at 0° C. over a period of 30 min under N₂. The mixture was warmed to 20° C. and stirred for 12 h, then concentrated under reduced pressure. The residue was purified by silica gel column chromatography (gradient PE:EtOAc from 10:1 to 0:1) to give the mixture of 7-(3-methyl-4-nitro-pyrazol-1-yl)-6,7-dihydro-5H-pyrrolo[1,2-a]imidazole and 7-(5-methyl-4-nitro-1H-pyrazol-1-yl)-6,7- dihydro-5H-pyrrolo[1,2-a]imidazole as a white solid. LCMS: RT 0.112 min, m/z=234.1 [M+H]⁺.

1-(6,7-dihydro-5H-pyrrolo[1,2-a]imidazol-7-yl)-3-methyl-pyrazol-4-amine and 1-(6,7-dihydro-5H-pyrrolo[1,2-a]imidazol-7-yl)-5-methyl-1H-pyrazol-4-amine To a solution of 7-(3-methyl-4-nitro-pyrazol-1-yl)-6,7-dihydro-5H-pyrrolo[1,2-a]imidazole and 7-(5-methyl-4-nitro-1H-pyrazol-1-yl)-6,7-dihydro-5H-pyrrolo[1,2-a]imidazole (650 mg, 2.79 mmol) in MeOH (20 mL) was added Pd—C (10%, 0.3 g) under N$_2$. The suspension was degassed under vacuum and purged with H$_2$ several times. The mixture was stirred under H$_2$ (15 psi) at 20° C. for 4 h, then filtered and concentrated under reduced pressure, to give the mixture of 1-(6,7-dihydro-5H-pyrrolo[1,2-a]imidazol-7-yl)-3-methyl-pyrazol-4-amine and 1-(6,7-dihydro-5H-pyrrolo[1,2-a]imidazol-7-yl)-5-methyl-1H-pyrazol-4-amine as a light yellow solid. LCMS: RT 0.62-0.878 min, m/z=204.2 [M+H]⁺.

N2-[1-(6,7-dihydro-5H-pyrrolo[1,2-a]imidazol-7-yl)-5-methyl-pyrazol-4-yl]-N4-methyl-5-(trifluoromethyl)pyrimidin-2,4-diamine (D-2), N2-[1-[6,7-dihydro-5H-pyrrolo[1,2-a]imidazol-7-yl]-3-methyl-pyrazol-4-yl]-N4-methyl-5-(trifluoromethyl)pyrimidine-2,4-diamine (D-3), and N2-[1-[6,7-dihydro-5H-pyrrolo[1,2-a]imidazol-7-yl]-3-methyl-pyrazol-4-yl]-N4-methyl-5-(trifluoromethyl)pyrimidine-2,4-diamine (D-4)

To a solution of the mixture 1-(6,7-dihydro-5H-pyrrolo[1,2-a]imidazol-7-yl)-3-methyl-pyrazol-4-amine and 1-(6,7-dihydro-5H-pyrrolo[1,2-a]imidazol-7-yl)-5-methyl-1H-pyrazol-4-amine (220 mg, 1.08 mol) and 2-chloro-N-methyl-5-(trifluoromethyl)pyrimidin-4-amino (251.35 mg, 1.19 mol, 1.10 eq) in 1,4-dioxane (2 mL) was added TFA (246 mg, 2.16 mol, 0.16 mL) at 20° C. The mixture was heated to 90° C. and stirred for 1 h. The mixture was cooled to 20° C. and concentrated under reduced pressure. To die residue was added aq. sat. NaHCO$_3$, extracted with EtOAc (3×5 mL). The combined organics were washed with brine (5 mL), dried over anhydrous Na$_2$SO$_4$, filtered and concentrated under reduced pressure. The residue was purified by prep-HPLC (neutral) to give N2-[1-(6,7-dihydro-5H-pyrrolo[1,2-a]imidazol-7-yl)-5-methyl-pyrazol-4-yl]-N4-methyl-5-(trifluoromethyl)pyrimidine-2,4-diamine (D-2) and N2-[1-[6,7-dihydro-5H-pyrrolo[1,2-a]imidazol-7-yl]-3-methyl-pyrazol-4-yl]-N4-methyl-5-(trifluoromethyl)pyrimidine-2,4-diamine, which was further purified by chiral SFC to give the corresponding enantiomer N2-[1-[6,7-dihydro-5H-pyrrolo[1,2-a]imidazol-7-yl]-3-methyl-pyrazol-4-yl]-N4-methyl-5-(trifluoromethyl)pyrimidine-2,4-diamine (First eluting stereoisomer, D-3) and N2-[1-[6,7-dihydro-5H-pyrrolo[1,2-a]imidazol-7-yl]-3-methyl-pyrazol-4-yl]-N4-methyl-5-(trifluoromethyl)pyrimidine-2,4-diamine (Second eluting stereoisomer, D-4).

N2-[1-(6,7-dihydro-5H-pyrrolo[1,2-a]imidazol-7-yl)-5-methyl-pyrazol-4-yl]-N4-methyl-5-(trifluoromethyl)pyrimidine-2,4-diamine (D-2)

$^1$H NMR (400 MHz, CDCl$_3$): δ ppm 8.09 (s, 1H), 7.76 (br. s., 1H), 7.12 (s, 1H), 6.96 (s, 1H), 6.44 (br. s., 1H), 5.55-5.66 (m, 1H), 5.13 (br. s., 1H), 4.39-4.51 (m, 1H), 4.10 (t, J=11.04 Hz, 1H), 3.08-3.26 (m, 2H), 3.00 (d, J=4.52 Hz, 3H), 2.40 (s, 3H); HPLC: RT: 1.703 min; MS: m/z: 379.1 [M+H]⁺.

N2-[1-[6,7-dihydro-5H-pyrrolo[1,2-a]imidazol-7-yl]-3-methyl-1H-pyrazol-4-yl]-N4-methyl-5-(trifluoromethyl)pyrimidine-2,4-diamine (First Eluting Stereoisomer, D-3)

$^1$H NMR (400 MHz, CDCl$_3$): δ ppm 8.09 (br. s., 1H), 7.89 (s, 1H), 7.18 (s, 1H), 6.99 (s, 1H), 6.72 (br. s., 1H), 5.57-5.68 (m, 1H), 5.19 (br. s., 1H), 4.22 (br. s., 1H), 3.99-4.12 (m, 1H), 3.02-3.24 (m, 2H), 2.97 (d, J=3.09 Hz, 3H), 2.25 (s, 3H); HPLC: RT 1.769 min; MS: m/z: 379.1 [M+H]⁺; SFC: RT 2.71 min.

N2-[1-[6,7-dihydro-5H-pyrrolo[1,2-a]imidazol-7-yl]-3-methyl-1H-pyrazol-4-yl]-N4-methyl-5-(trifluoromethyl)pyrimidine-2,4-diamine (Second Eluting Stereoisomer, D-4)

$^1$H NMR (400 MHz, CDCl$_3$): δ ppm 8.09 (br. s., 1H), 7.88 (br. s., 1H), 7.18 (s, 1H), 6.99 (s, 1H), 6.66 (br. s., 1H), 5.58-5.67 (m, 1H), 5.18 (br. s., 1H), 4.22 (br. s., 1H), 4.03-4.12 (m, 1H), 3.04-3.24 (m, 2H), 2.97 (br. s., 3H) 2.24 (s, 3H); HPLC. RT 1.768 min; MS: m/z: 379.1 [M+H]⁺; SFC: RT 3.21 min.

Example D-9 and D-10

Synthesis of N2-(1-((1-((1H-1,2,4-triazol-1-yl)methyl)cyclopropyl)methyl)-3-methyl-1H-pyrazol-4-yl)-N4-methyl-5-(trifluoromethyl)pyrimidine-2,4-diamine (D-5) and N2-(1-((1-((1H-1,2,4-triazol-1-yl)methyl)cyclopropyl)methyl)-5-methyl-1H-pyrazol-4-yl)-N4-methyl-5-(trifluoromethyl)pyrimidine-2,4-diamine (D-6)

(1-((3-methyl-4-nitro-1H-pyrazol-1-yl)methyl)cyclopropyl)methanol and (1-((5-methyl-4-nitro-1H-pyrazol-1-yl)methyl)cyclopropyl)methanol To a solution of [1-(hydroxymethyl)cyclopropyl]methanol (9-1, 3 g, 29.37 mmol), 3-methyl-4-nitro-1H-pyrazole (3.39 g, 26.70 mmol) and PPh$_3$ (7 g, 26.70 mmol) in THF (30 mL) was added dropwise DIAB (5.4 g, 26.70 mmol) at 0° C. over 30 min. After addition, the mixture was stirred at this temperature for 30 min. The resulting mixture was stirred at 25° C. for 11 h. The reaction mixture was diluted with H$_2$O (90 mL) and extracted with EtOAc (3×30 mL). The combined organic layers were washed with brine (20 mL), dried over Na$_2$SO$_4$, filtered and concentrated under reduced pressure. The residue was purified by column chromatography (SiO$_2$, PE:EtOAc=10:1 to 0:1) to give a mixture of (1-((3-methyl-4-nitro-1H-pyrazol-1-yl)methyl)cyclopropyl)methanol and (1-((5-methyl-4-nitro-1H-pyrazol-1-yl)methyl)cyclopropyl)methanol as an off-white solid, which was used into the next step without further purification. LCMS: RT 0.568 min, m/z=212.2 [M+H]⁺.

(1-((3-methyl-4-nitro-1H-pyrazol-1-yl)methyl)cyclopropyl)methyl methanesulfonate and (1-((5-methyl-4-nitro-1H-pyrazol-1-yl)methyl)cyclopropyl)methyl methanesulfonate To a solution of (1-((3-methyl-4-nitro-1H-pyrazol-1-yl)methyl)cyclopropyl)methanol and (1-((5-methyl-4-nitro-1H-pyrazol-1-yl)methyl)cyclopropyl)methanol (5.2 g, 24.62 mmol) and Et₃N (7.47 g, 73.86 mmol) in DCM (50 mL) was added dropwise MsCl (3.38 g, 29.54 mmol) at 0° C. for 0.5 h. The mixture was stirred at 0° C. for 0.5 h. The reaction mixture was diluted with H₂O (50 mL) and extracted with DCM (3×10 mL). The combined organic layers were washed with brine (50 mL), dried over Na₂SO₄, filtered and concentrated under reduced pressure to give (1-((3-methyl-4-nitro-1H-pyrazol-1-yl)methyl)cyclopropyl)methyl methanesulfonate and (1-((5-methyl-4-nitro-1H-pyrazol-1-yl)methyl)cyclopropyl)methyl methanesulfonate as a yellow oil. The crude product was used into the next step without further purification. LCMS: RT 1.018 min, m/z=290.0 [M+H]⁺.

1-((1-((3-methyl-4-nitro-1H-pyrazol-1-yl)methyl)cyclopropyl)methyl)-1H-1,2,4-triazole and 1-((1-((5-methyl-4-nitro-1H-pyrazol-1-yl)methyl)cyclopropyl)methyl)-1H-1,2,4-triazole To a solution of 1H-1,2,4-triazole (2.01 g, 29.04 mmol) in DMF (30 mL) was added NaH (1.16 g, 29.04 mmol, 60% purity) at 0° C. After addition, the mixture was stirred at this temperature for 0.5 h, and then (1-((3-methyl-4-nitro-1H-pyrazol-1-yl)methyl)cyclopropyl)methyl methanesulfonate and (1-((5-methyl-4-nitro-1H-pyrazol-1-yl)methyl)cyclopropyl)methyl methanesulfonate (7 g, 24.20 mmol) in DMF (20 mL) was added dropwise at 0° C. The resulting mixture was stirred at 50° C. for 3.5 h. The reaction mixture was quenched by addition H₂O (150 mL) at 0° C., and extracted with EtOAc (3×10 mL). The combined organic layers were washed with brine (50 mL), dried over Na₂SO₄, filtered and concentrated under reduced pressure. The residue was purified by column chromatography (SiO₂, PE:EtOAc=10:1 to 0:1) to give a mixture of 1-((1-((3-methyl-4-nitro-1H-pyrazol-1-ylmethyl)cyclopropyl)methyl)-1H-1,2,4-triazole and 1-((1-((5-methyl-4-nitro-1H-pyrazol-1-yl)methyl)cyclopropyl)methyl)-1H-1,2,4-triazole as a pale-yellow solid, which was used into the next step without further purification. LCMS: RT 0.604 min, m/z=263.2 [M+H]⁺.

1-((1-((1H-1,2,4-triazol-1-yl)methyl)cyclopropyl)methyl)-3-methyl-1H-pyrazol-4-amine and 1-((1-((1H-1,2,4-triazol-1-yl)methyl)cyclopropyl)methyl)-5-methyl-1H-pyrazol-4-amine To a solution of 1-((1-((3-methyl-4-nitro-1H-pyrazol-1-yl)methyl)cyclopropyl)methyl)-1H-1,2,4-triazole and 1-((1-((5-methyl-4-nitro-1H-pyrazol-1-yl)methyl)cyclopropyl)methyl)-1H-1,2,4-triazole (1 g, 3.81 mmol) in MeOH (20 mL) was added Pd—C (10%, 0.32 g) under N₂. The suspension was degassed under vacuum and purged with H₂ several times. The mixture was stirred under H₂ (15 psi) at 25° C. for 2 h. The reaction mixture was filtered and the filtrate was concentrated to give a mixture of 1-((1-((1H-1,2,4-triazol-1-yl)methyl)cyclopropyl)methyl)-3-methyl-1H-pyrazol-4-amine and 1-((1-((1H-1,2,4-triazol-1-yl)methyl)cyclopropyl)methyl)-5-methyl-1H-pyrazol-4-amino as a brown oil, which was used into the next step without further purification.

N2-(1-((1-((1H-1,2,4-triazol-1-yl)methyl)cyclopropyl)methyl)-3-methyl-1H-pyrazol-4-yl)-N4-methyl-5-(trifluoromethyl)pyrimidine-2,4-diamine (D-5) and N2-(1-((1-((1H-1,2,4-triazol-1-yl)methyl)cyclopropyl)methyl)-5-methyl-1H-pyrazol-4-yl)-N4-methyl-5-(trifluoromethyl)pyrimidine-2,4-diamine (D-6)

A mixture of 1-((1-((1H-1,2,4-triazol-1-yl)methyl)cyclopropyl)methyl)-3-methyl-1H-pyrazol-4-amine and 1-((1-((1H-1,2,4-triazol-1-yl)ethylcyclopropyl)methyl)-5-methyl-1H-pyrazol-4-amine (200 mg, 861.03 μmol), 2-chloro-N-methyl-5-(trifluoromethyl)pyrimidin-4-amine (164 mg, 774.93 μmol) and Et₃N (261 mg, 2.58 mmol) were taken up into a microwave tube in w-BuOH (5 mL). The sealed tube was heated at 120° C. for 1.5 h under microwave. The reaction mixture was concentrated under reduced pressure. The residue was purified by prep-HPLC (neutral) to give N2-(1-((1-((1H-1,2,4-triazol-1-yl)methyl)cyclopropyl)methyl)-5-methyl-1H-pyrazol-4-yl)-N4-methyl-5-(trifluoromethyl)pyrimidine-2,4-diamine (D-6) and N2-(1-((1-((1H-1,2,4-triazol-1-yl)methyl)cyclopropyl)methyl)-3-methyl-1H-pyrazol-4-yl)-N4-methyl-5-(trifluoromethyl)pyrimidine-2,4-diamine (D-5).

N2-(1-((1-((1H-1,2,4-triazol-1-yl)methyl)cyclopropyl)methyl)-3-methyl-1H-pyrazol-4-yl)-N4-methyl-5-(trifluoromethyl)pyrimidine-2,4-diamine (D-5)

¹H NMR (400 MHz, CDCl₃): δ ppm 8.25-8.34 (m, 1H), 8.08-8.20 (m, 1H), 7.98-8.04 (m, 1H), 7.96 (m, 1H), 6.49-6.78 (m, 1H), 5.10-5.37 (m, 1H), 3.99-4.06 (m, 2H), 3.82-3.92 (m, 2H), 3.04-3.16 (m, 3H), 2.29 (s, 3H), 0.85-0.89 (m, 2H), 0.81-0.85 (m, 2H); HPLC. RT 1.973 min; MS: m/z: 408.2 [M+H]⁺.

N2-(1-((1-((1H-1,2,4-triazol-1-yl)methyl)cyclopropyl)methyl)-5-methyl-1H-pyrazol-4-yl)-N4-methyl-5-(trifluoromethyl)pyrimidine-2,4-diamine (D-6)

¹H NMR (400 MHz, CDCl₃): δ ppm 8.32 (s, 1H), 8.07-8.14 (m, 1H), 7.97 (s, 1H), 7.69-7.90 (m, 1H), 6.38-6.62 (m, 1H), 5.09-5.24 (m, 1H), 4.12 (s, 2H), 3.90 (s, 2H), 3.02 (d, J=4.52 Hz, 3H), 2.12 (s, 3H), 0.85-0.91 (m, 2H), 0.77-0.83 (m, 2H); HPLC. RT 1.913 min; MS: m/z: 408.2 [M+H]⁺.

Example D-11 and D-12

Synthesis of N4-methyl-N2-[5-methyl-1-(3-methyl-5,6,7,8-tetrahydro-[1,2,4]triazolo[4,3-a]pyridin-6-yl)pyrazol-4-yl]-5-(trifluoromethyl)pyrimidine-2,4-diamine (D-7) and N4-methyl-N2-[3-methyl-1-(3-methyl-5,6,7,8-tetrahydro-[1,2,4]triazolo[4,3-a]pyridin-6-yl)pyrazol-4-yl]-5-(trifluoromethyl)pyrimidine-2,4-diamine (D-8)

5-[tert-butyl(diphenyl)silyl]oxypiperidin-2-one

To a solution of 5-hydroxypiperidin-2-one (4.5 g, 39.09 mmol) in DMF was added imidazole (7.98 g, 117.27 mmol), followed by TBDPSCl (16.11 g, 58.64 mmol) at 0° C. The mixture was stirred at 20° C. for 16 h. The solution was added with water (120 mL), extracted with EtOAc (3×30 mL). The organic layers were combined, washed with brine (3×20 mL), dried over Na₂SO₄, filtered and concentrated under reduced pressure. The residue was purified by silica gel column chromatography (PE:EtOAc=10:1 to 1:1) to give compound 5-[tert-butyl(diphenyl)silyl]oxypiperidin-2-one as an off-white solid. ¹H NMR (400 MHz, CDCl₃): δ 7.62-7.69 (m, 4H), 7.42-7.48 (m, 2H), 7.36-7.42 (m, 4H), 6.19 (br. s., 1H), 4.06-4.12 (m, 1H), 3.15-3.27 (m, 2H), 2.66 (ddd, J=17.42, 9.48, 6.17 Hz, 1H), 2.27 (dt, J=17.86, 5.84 Hz, 1H), 1.74-1.95 (m, 2H), 1.02-1.12 (m, 9H).

5-[tert-butyl(diphenyl)silyl]oxypiperidine-2-thione

To a solution of 5-[tert-butyl(diphenyl)silyl]oxypiperidin-2-one (3 g, 8.49 mmol) in toluene (5 mL) was added lawesson's reagent (1.72 g, 4.25 mmol). The mixture was stirred at 110° C. for 2 h. The reaction solution was concentrated under reduced pressure. The residue was purified by silica gel column chromatography (PE:EtOAc=10:1 to 3:1) to give 5-[tert-butyl(diphenyl)silyl]oxypiperidine-2-thione as a yellow gum. LCMS: RT 0.940 min, m/z=370.2 [M+H]$^+$. $^1$H NMR (400 MHz, CDCl$_3$): δ 7.64 (dd, J=6.46, 5.08 Hz, 4H), 7.44-7.50 (m, 2H), 7.38-7.43 (m, 4H), 4.13 (q, J=6.86 Hz, 2H), 3.11-3.29 (m, 3H), 2.89 (dt, J=18.95, 5.46 Hz, 1H), 1.70-1.90 (m, 2H), 1.07 (s, 9H).

Tert-butyl-[(6-methylsulfanyl-2,3,4,5-tetrahydropyridin-3-yl)oxy]-diphenyl-silane To a solution of 5-[tert-butyl(diphenyl)silyl]oxypiperidine-2-thione (2.2 g, 5.95 mmol) in THF (50 mL) was added K$_2$CO$_3$ (4.11 g, 29.75 mmol) and MeI (4.22 g, 29.75 mmol). The mixture was stirred at 20° C. for 16 h. The reaction mixture was filtered through a pad of celite. The cake was washed with EtOAc (50 mL), and the filtrate was washed with water (20 mL) and brine (20 mL), dried over Na$_2$SO$_4$, filtered and concentrated under reduced pressure to give Tert-butyl-[(6-methylsulfanyl-2,3,4,5-tetrahydropyridin-3-yl)oxy]-diphenyl-silane as yellow gum, which was used in next step without further purification. $^1$H NMR (400 MHz, CDCl$_3$): δ7.66 (m, 4H), 7.33-7.49 (m, 6H), 3.93 (quin, J=5.02 Hz, 1H), 3.54-3.73 (m, 2H), 2.53-2.64 (m, 1H), 2.27 (s, 3H), 2.15-2.24 (m, 1H), 1.74 (q, J=6.40 Hz, 2H), 1.00-1.16 (s, 9H).

Tert-butyl-[(3-methyl-5,6,7,8-tetrahydro-[1,2,4]triazolo[4,3-a]pyridin-6-yl)oxy]-diphenyl-silane To a solution of Tert-butyl-[(6-methylsulfanyl-2,3,4,5-tetrahydropyridin-3-yl)oxy]-diphenyl-silane (1.9 g, 4.95 mmol) in EtOH (20 mL) was added acetohydrazide (477 mg, 6.44 mmol). The mixture was stirred at 80° C. for 16 h. The reaction was concentrated under reduced pressure. The residue was added with water (20 mL), extracted with EtOAc (3×10 mL). The organic layers were combined, washed with brine (10 mL), dried over Na$_2$SO$_4$, filtered and concentrated to give a crude of tert-butyl-[(3-methyl-5,6,7,8-tetrahydro-[1,2,4]triazolo[4,3-a]pyridin-6-yl)oxy]-diphenyl-silane as a colorless gum, which was used in next step without further purification. $^1$H NMR (400 MHz, CDCl$_3$): δ 7.66-7.68 (m, 2H), 7.54-7.56 (m, 2H), 7.36-7.47 (m, 6H), 4.36 (d, J=3.26 Hz, 1H), 3.49-3.65 (m, 2H), 2.91-3.29 (m, 2H), 2.18-2.24 (m, 3H), 1.75-2.15 (m, 2H), 1.03 (s, 9H).

3-methyl-5,6,7,8-tetrahydro-[1,2,4]triazolo[4,3-a]pyridin-6-ol

To a solution of Tert-butyl-[(3-methyl-5,6,7,8-tetrahydro-[1,2,4]triazolo[4,3-a]pyridin-6-yl)oxy]-diphenyl-silane (1.9 g, 4.85 mmol) in MeOH (30 mL) was added KF (4.23 g, 72.75 mmol). The mixture was stirred at 80° C. for 16 h. The reaction mixture was concentrated under reduced pressure. The residue was added with DCM:MeOH (50 mL, ratio=10:1), stirred for 10 min, filtered and the filtrate was concentrated under reduced pressure. The residue was added with MTBE (15 mL), stirred for 10 min, filtered and the solid was dried under reduced pressure to give 3-methyl-5,6,7,8-tetrahydro-[1,2,4]triazolo[4,3-a]pyridin-6-ol as a yellow solid. $^1$H NMR (400 MHz, CDCl$_3$): δ 4.35 (dd, J=6.17, 2.21 Hz, 1H), 3.73-3.96 (m, 2H), 2.78-2.90 (m, 2H), 2.18-2.29 (m, 3H), 1.83-2.07 (m, 2H).

(3-methyl-5,6,7,8-tetrahydro-[1,2,4]triazolo[4,3-a]pyridin-6-yl) methanesulfonate To a solution of 3-methyl-5,6,7,8-tetrahydro-[1,2,4]triazolo[4,3-a]pyridin-6-ol (400 mg, 2.61 mmol) in DCM (50 mL) was added TEA (528 mg, 5.22 mmol) and followed by MsCl (448 mg, 3.92 mmol). The mixture solution was stirred at 0° C. for 2 h. The reaction was added with water (5 mL), extracted with DCM (5×10 mL). The organic layers were combined, dried over Na$_2$SO$_4$, filtered and concentrated under reduced pressure to give a crude (3-methyl-5,6,7,8-tetrahydro-[1,2,4]triazolo[4,3-a]pyridin-6-yl) methanesulfonate as a yellow oil, which was used in next step without further purification. $^1$H NMR (400 MHz, CDCl3): δ 5.36-5.43 (m, 1H), 3.99-4.25 (m, 2H), 3.05-3.18 (m, 5H), 2.36-2.52 (m, 4H), 2.03-2.14 (m, 1H).

3-methyl-6-(3-methyl-4-nitro-pyrazol-1-yl)-5,6,7,8-tetrahydro-[1,2,4]triazolo[4,3-a]pyridine and 3-methyl-6-(5-methyl-4-nitro-pyrazol-1-yl)-5,6,7,8-tetrahydro-[1,2,4]triazolo[4,3-a]pyridine To a solution of 3-methyl-4-nitro-1H-pyrazole (1-1, 398 mg, 3.13 mmol) in DMF (10 mL) was added NaH (125 mg, 3.13 mmol, 60% purity) at 0° C., then the reaction was stirred at 20° C. for 1 h. Then, (3-methyl-5,6,7,8-tetrahydro-[1,2,4]triazolo[4,3-a]pyridin-6-yl) methanesulfonate (604 mg, 2.61 mmol, 70% purity) in DMF (4 mL) was added to the solution at 20° C. Then, the mixture was stirred at 80° C. for 12 h. The reaction solution was added with NH$_4$Cl solution (20 mL), extracted with DCM:MeOH (20 mL×3, ratio=3:1). The organic layers were combined, dried over Na$_2$SO$_4$, filtered and concentrated under reduced pressure. The crude product was purified by prep-TLC (DCM:MeOH=5:1) to give a mixture of 3-methyl-6-(3-methyl-4-nitro-pyrazol-1-yl)-5,6,7,8-tetrahydro-[1,2,4]triazolo[4,3-a]pyridine and 3-methyl-6-(5-methyl-4-nitro-pyrazol-1-yl)-5,6,7,8-tetrahydro-[1,2,4]triazolo[4,3-a]pyridine as a yellow gum. LCMS: RT 0.925 min, m/z=263.1 [M+H]$^+$. $^1$H NMR (400 MHz, CDCl$_3$): δ 8.25 (s, 0.6H), 8.13 (s, 0.3H), 4.68-4.81 (m, 1H), 4.14-4.42 (m, 2H), 3.02-3.31 (m, 2H), 2.77 (s, 1H), 2.55 (s, 2H), 2.44-2.53 (m, 4H), 2.43 (s, 1H).

5-methyl-1-(3-methyl-5,6,7,8-tetrahydro-[1,2,4]triazolo[4,3-a]pyridin-6-yl)pyrazol-4-amine and 3-methyl-1-(3-methyl-5,6,7,8-tetrahydro-[1,2,4]triazolo[4,3-a]pyridin-6-yl)pyrazol-4-amine To a mixture of 3-methyl-6-(3-methyl-4-nitro-pyrazol-1-yl)-5,6,7,8-tetrahydro-[1,2,4]triazolo[4,3-a]pyridine and 3-methyl-6-(5-methyl-4-nitro-pyrazol-1-yl)-5,6,7,8-tetrahydro-[1,2,4]triazolo[4,3-a]pyridine (100 mg, 381.29 μmol) in MeOH (10 mL) was added Pd/C (10%, 50 mg) under N$_2$. The suspension was degassed and purged with H$_2$ for 3 times. The mixture was stirred under H$_2$ (15 psi) at 20° C. for 5 h. The reaction solution was filtered through a pad of celite, the filtrate was concentrated under reduced pressure to give a crude 5-methyl-1-(3-methyl-5,6,7,8-tetrahydro-[1,2,4]triazolo[4,3-a]pyridin-6-yl)pyrazol-4-amine and 3-methyl-1-(3-methyl-5,6,7,8-tetrahydro-[1,2,4]triazolo[4,3-a]pyridin-6-yl)pyrazol-4-amino. LCMS: RT 0.173 min, m/z=233.1 [M+H]$^+$.

N4-methyl-N2-[5-methyl-1-(3-methyl-5,6,7,8-tetrahydro-[1,2,4]triazolo[4,3-a]pyridin-6-yl)pyrazol-4-yl]-5-(trifluoromethyl)pyrimidine-2,4-diamine (D-7) and N4-methyl-N2-[3-methyl-1-(3-methyl-5,6,7,8-tetrahydro-[1,2,4]triazolo[4,3-a]pyridin-6-yl)pyrazol-4-yl]-5-(trifluoromethyl)pyrimidine-2,4-diamine (D-8)

A mixture of 5-methyl-1-(3-methyl-5,6,7,8-tetrahydro-[1,2,4]triazolo[4,3-a]pyridin-6-yl)pyrazol-4-amine and 3-methyl-1-(3-methyl-5,6,7,8-tetrahydro-[1,2,4]triazolo[4,3-a]pyridin-6-yl)pyrazol-4-amine (70 mg, 301.36 µmol), 2-chloro-N-methyl-5-(trifluoromethyl)pyrimidin-4-amine (64 mg, 301.36 µmol) and TEA (91 mg, 904.08 µmol) in 1,4-dioxane (10 mL) was degassed and purged with $N_2$ for 3 times, and then the mixture was stirred at 110° C. for 12 h under $N_2$. The reaction solution was concentrated under reduced pressure. The crude product was purified by prep-HPLC (HCOOH) to give N4-methyl-N2-[5-methyl-1-(3-methyl-5,6,7,8-tetrahydro-[1,2,4]triazolo[4,3-a]pyridin-6-yl)pyrazol-4-yl]-5-(trifluoromethyl)pyrimidine-2,4-diamino (D-7, HCOOH salt) and N4-methyl-N2-[3-methyl-1-(3-methyl-5,6,7,8-tetrahydro-[1,2,4]triazolo[4,3-a]pyridin-6-yl)pyrazol-4-yl]-5-(trifluoromethyl)pyrimidine-2,4-diamine (D-8. HCOOH salt).

N4-methyl-N2-[5-methyl-1-(3-methyl-5,6,7,8-tetrahydro-[1,2,4]triazolo[4,3-a]pyridin-6-yl)pyrazol-4-yl]-5-(trifluoromethyl)pyrimidine-2,4-diamine (D-7)

$^1$H NMR (400 MHz, CDCl$_3$): δ 8.24 (s, 0.39H), 8.07 (s, 1H), 7.90 (s, 1H), 5.50 (br. s., 0.14H), 5.28 (br. s., 0.8H), 4.65 (br. s., 1H), 4.39 (dd, J=12.11, 9.22 Hz, 1H), 4.15 (dd, J=12.36, 5.58 Hz, 1H), 3.20-3.31 (m, 1H), 2.97-3.09 (m, 4H), 2.39-2.45 (m, 4H), 2.33-2.42 (m, 4H); HPLC: RT 2.754 min; MS: m/z: 408.2 [M+H]$^+$.

N4-methyl-N2-[3-methyl-1-(3-methyl-5,6,73-tetrahydro-[1,2,4]triazolo[4,3-a]pyridin-6-yl)pyrazol-4-yl]-5-(trifluoromethyl)pyrimidine-2,4-diamine (D-8)

$^1$H NMR (400 MHz, CDCl$_3$): δ 8.22 (s, 0.52H), 8.09 (s, 1H), 7.96 (s, 1H) 5.34 (br. s., 1H), 4.71 (s, 1H) 4.18-4.35 (m, 2H) 3.22 (d, J=17.07 Hz, 1H), 3.00-3.13 (m, 3H), 2.43 (m, 5H), 2.29 (s, 3H); HPLC: RT 2.847 min; MS: m/z: 408.2 [M+H]$^+$.

Example D-13

Synthesis of N2-[1-[2-(difluoromethoxy)ethyl]-5-methyl-pyrazol-4-yl]-N4-methyl-5-(trifluoromethyl)pyrimidine-2,4-diamine (D-9)

1-[2-(difluoromethoxy)ethyl]-5-methyl-pyrazol-4-amine

To a solution of 1-[2-(difluoromethoxy)ethyl]-5-methyl-4-nitro-pyrazole (13-1, 100 mg, 452.16 µmol) in MeOH (10 mL) was added Pd—C (10%, 50 mg) under $N_2$ at 20° C. The suspension was degassed under vacuum and purged with $H_2$ several times. The mixture was stirred under $H_2$ (15 psi) at 40° C. for 5 h. The reaction mixture was filtered and the filtrate was concentrated, to give 1-[2-(difluoromethoxy)ethyl]-5-methyl-pyrazol-4-amine was obtained as a yellow oil. LCMS: RT 1.037 min. m/z=192.2 [M+H]$^+$.

N2-[1-[2-(difluoromethoxy)ethyl]-5-methyl-pyrazol-4-yl]-N4-methyl-5-(trifluoromethyl)pyrimidine-2,4-diamine (D-9)

2-chloro-N-methyl-5-(trifluoromethyl)pyrimidin-4-amine (5-5, 54 mg, 253.69 µmol), 1-[2-(difluoromethoxy)ethyl]-5-methyl-pyrazol-4-amine (97 mg, 507.38 µmol) and TEA (51 mg, 507.38 µmol, 7 µL) were taken up into a microwave tube in 1,4-dioxane (1.00 mL) at 20° C. The sealed tube was heated at 120° C. for 1.5 h under microwave. The mixture was cooled to 20° C. and concentrated. The residue was purified by prep-HPLC (neutral) to give compound N2-[1-[2-(difluoromethoxy)ethyl]-5-methyl-pyrazol-4-yl]-N4-methyl-5-(trifluoromethyl)pyrimidine-2,4-diamine (D-9). LCMS: RT 0.605 min, m/z=367.2 [M+H]$^+$ $^1$H NMR (400 MHz, MeOD): δ ppm 7.97 (br. s., 1H), 7.62 (br. s., 1H), 6.12-6.52 (m, 1H), 4.31-4.36 (m, 2H), 4.16-4.22 (m, 2H), 2.91 (br. s., 3H), 2.24 (s, 3H); HPLC: RT 2.216 min. MS: m/z: 367.1[M+H]$^+$.

Example D-14

Synthesis of N2-[1-[2-(difluoromethoxy)ethyl]-3-methyl-pyrazol-4-yl]-N4-methyl-5-(trifluoromethyl)pyrimidine-2,4-diamine (D-10)

1-[2-(difluoromethoxy)ethyl]-3-methyl-pyrazol-4-amine

To a solution of 1-[2-(difluoromethoxy)ethyl]-3-methyl-4-nitro-pyrazole (14-1, 100 mg, 452.16 µmol) (100 mg, 452.16 nmol) in MeOH (10 mL) was added Pd—C (10%, 50 mg) under $N_2$. The suspension was degassed under vacuum and purged with $H_2$ several times. The mixture was stirred under $H_2$ (15 psi) at 40° C. for 5 h. The reaction mixture was filtered and the filtrate was concentrated to give compound 1-[2-(difluoromethoxy)ethyl]-3-methyl-pyrazol-4-amine as a black brown oil. LCMS: RT 0.802 min, m/z=192.3 [M+H]$^+$.

N2-[1-[2-(difluoromethoxy)ethyl]-3-methyl-pyrazol-4-yl]-N4-methyl-5-(trifluoromethyl)pyrimidine-2,4-diamine (D-10)

1-[2-(difluoromethoxy)ethyl]-3-methyl-pyrazol-4-amine (73 mg, 381.84 µmol), 2-chloro-N-methyl-5-(trifluoromethyl)pyrimidin-4-amine (40 mg, 190.92 nmol) and TEA (38 mg, 381.84 nmol, 52.93 nL) were taken up into a microwave tube in 1,4-dioxane (1.00 mL) at 20° C. The sealed tube was heated at 120° C. for 1.5 h under microwave. The mixture was cooled to 20° C. and concentrated. The residue was purified by prep-HPLC (neutral) to give compound N2-[1-[2-(difluoromethoxy)ethyl]-3-methyl-pyrazol-4-yl]-N4-methyl-5-(trifluoromethyl)pyrimidine-2,4-diamine (D-10). LCMS: RT 0.671 min, m/z=367.1 [M+H]$^+$; $^1$H NMR (400 MHz, MeOD): δ ppm 8.02 (s, 1H), 7.90 (br. s., 1H), 6.14-6.55 (m, 1H), 4.27-4.34 (m, 2H), 4.15-4.22 (m, 2H), 2.97 (s, 3H), 2.22 (s, 3H); HPLC: RT 2.277 min; MS: m/z: 367.1 [M+H]$^+$.

Example D-15

Synthesis of N2-[5-chloro-1-[2-(difluoromethoxy)ethyl]pyrazol-4-yl]-N4-methyl-5-(trifluoromethyl)pyrimidine-2,4-diamine (D-11)

N2-[5-chloro-1-[2-(difluoromethoxy)ethyl]pyrazol-4-yl]-N4-methyl-5-(trifluoromethyl)pyrimidine-2,4-diamine (D-11)

Compound 5-chloro-1-(2-(difluoromethoxy)ethyl)-1H-pyrazol-4-amine (80 mg, 378.07 nmol), compound 2-chloro- N-methyl-5-(trifluoromethyl)pyrimidin-4-amine (80 mg, 378.07 nmol) and TEA (115 mg, 1.13 mmol, 157 nL) were taken up into a microwave tube in 1,4-dioxane (10 mL). The sealed tube was heated at 120° C. for 90 min under microwave. After cooling to 20° C., the mixture was concentrated under reduced pressure. The residue was purified by prep-HPLC (neutral) to give N2-[5-chloro-1-[2-(difluoromethoxy)ethyl]pyrazol-4-yl]-N4-methyl-5-(trifluoromethyl)pyrimidine-2,4-diamine (D-11). $^1$H NMR (400 MHz, CDCl$_3$): δ 8.14 (br. s., 2H), 6.60-6.79 (m, 1H), 5.99-6.40 (m, 1H), 5.22 (br. s., 1H), 4.36-4.41 (m, 2H), 4.23-4.29 (m, 2H), 3.07 (d, J=4.64 Hz, 3H); HPLC. RT 2.521 min; MS: m/z=387.0 [M+H]$^+$.

Example D-16

Synthesis of N2-[5-chloro-1-[[1-(methoxymethyl)cyclopropyl]methyl]pyrazol-4-yl]-N4-methyl-5-(trifluoromethyl)pyrimidine-2,4-diamine (D-12)

N2-[5-chloro-1-[[1-(methoxymethyl)cyclopropyl]methyl]pyrazol-4-yl]-N4-methyl-5-(trifluoromethyl)pyrimidine-2,4-diamine (D-12)

To a mixture of compound 5-chloro-1-((1-(methoxymethyl)cyclopropyl)methyl)-1H-pyrazol-4-amine (70 mg, 324.55 μmol) and compound 2-chloro-N-methyl-5-(trifluoromethyl)pyrimidin-4-amine (68.67 mg, 324.55 μmol) in 1,4-dioxane (10 mL) was added TFA (74 mg, 649.10 μmol, 48 μL) at 20° C. under N$_2$. The mixture was heated to 90° C. and stirred for 5 h. The mixture was cooled to 20° C. and was adjusted to pH=8 by adding aq. sat. NaHCO$_3$ and extracted with EtOAc (3×8 mL). The combined organic phase was washed with brine (20 mL), dried over anhydrous Na$_2$SO$_4$, filtered and concentrated under reduced pressure. The residue was purified by prep-HPLC (neutral) to give N2-[5-chloro-1-[[1-(methoxymethyl)cyclopropyl]methyl]pyrazol-4-yl]-N4-methyl-5-(trifluoromethyl)pyrimidine-2,4-diamine (D-12). $^1$H NMR (400 MHz, CDCl$_3$): δ 8.13 (s, 2H), 6.79 (br. s., 1H), 5.18-5.26 (m, 1H), 4.16 (s, 2H), 3.34 (s, 3H), 3.16 (s, 2H), 3.07 (d, J=4.64 Hz, 3H), 0.74-0.78 (m, 2H), 0.55-0.60 (m, 2H); HPLC: RT 2.574 min; MS: m/z=391.1 [M+H]$^+$.

Example D-17 and D-18

Synthesis of 2,2-difluoro-2-[3-methyl-4-[[4-(methylamino)-5-(trifluoromethyl)pyrimidin-2-yl]amino]pyrazol-1-yl]acetamide (D-14) and 2,2-difluoro-2-[3-methyl-4-[[4-(methylamino)-5-(trifluoromethyl)pyrimidin-2-yl]amino]pyrazol-1-yl]acetonitrile (D-13)

Ethyl 2,2-difluoro-2-(3-methyl-4-nitro-pyrazol-1-yl)acetate

To a solution of 5-methyl-4-nitro-1H-pyrazole (20 g, 157.36 mmol) in DMF (300 mL) was added NaH (9.44 g, 236.04 mmol, 60% purity) at 0° C. under N$_2$. After addition, the mixture was allowed to 25° C. and stirred for 2 h. 1-bromo-3-ethoxy-1,1-difluoro-propan-2-one (51.22 g, 236.04 mmol) was then added at 0° C. The mixture was stirred at 25° C. for 16 h. The mixture was poured into aqueous NH$_4$Cl (900 mL). The aqueous phase was extracted with MTBE (3×300 mL). The combined organic phase was washed with brine (2×200 mL), dried over anhydrous Na$_2$SO$_4$, filtered and concentrated under reduced pressure. The residue was purified by silica gel column chromatography (PE:EtOAc=20:1) to give ethyl 2,2-difluoro-2-(3-methyl-4-nitro-pyrazol-1-yl)acetate as a light yellow liquid. LCMS: RT 1.190 min, m/z=250.1 [M+H]$^+$.

Ethyl 2-(4-amino-3-methyl-pyrazol-1-yl)-2,2-difluoro-acetate

To a solution of ethyl 2,2-difluoro-2-(3-methyl-4-nitro-pyrazol-1-yl)acetate (10 g, 40.13 mmol) in EtOH (100 mL) was added Pd/C (1 g, 10% purity) under N$_2$. The suspension was degassed under vacuum and purged with H$_2$ for three times. The mixture was stirred under H$_2$ (15 psi) at 15° C. for 3 h. The reaction solution was filtered and the filtrate was concentrated under reduced pressure to give ethyl 2-(4-amino-3-methyl-pyrazol-1-yl)-2,2-di fluoro-acetate as a brown oil. LCMS: RT 0.23 min, m/z=220 [M+H]$^+$ Ethyl 2-[4-[bis(tert-butoxycarbonyl)amino]-3-methyl-pyrazol-1-yl]-2,2-difluoro-acetate A mixture of ethyl 2-(4-amino-3-methyl-pyrazol-1-yl)-2,2-difluoro-acetate (8.3 g, 37.87 mmol), Boc$_2$O (12.4 g, 56.81 mmol, 13.05 mL), TEA (6.9 g, 68.17 mmol, 9.45 mL) and DMAP (4.63 g, 37.87 mmol) in DCM (160 mL) was degassed and purged with N$_2$ for 3 times, and then the mixture was stirred at 25° C. for 12 h under N$_2$. The reaction mixture was concentrated under reduced pressure. The residue was purified by silica gel column chromatography (PE:EtOAc=5/1 to 3:1) to give ethyl 2-[4-[bis(tert-butoxycarbonyl)amino]-3-methyl-pyrazol-1-yl]-2,2-difluoro-acetate as a yellow oil. LCMS: RT 0.23 min, m/z=320 [M+H]$^+$ Tert-butyl N-[1-(2-amino-1,1-difluoro-2-oxo-ethyl)-3-methyl-pyrazol-4-yl]carbamate To a solution of ethyl 2-[4-(tert-butoxycarbonylamino)-3-methyl-pyrazol-1-yl]-2,2-difluoro-acetate (4 g, 12.53 mmol) in MeOH (10 mL) was added a methanolic solution of NH$_3$ (70 mL). The mixture was stirred at 50° C. for 12 h in an autoclave. The reaction solution was concentrated under reduced pressure to give tert-butyl N-[1-(2-amino-1,1-difluoro-2-oxo-ethyl)-3-methyl-pyrazol-4-yl]carbamate as a yellow solid. LCMS: RT 0.705 min, m/z=291.2 [M+H]$^+$. $^1$H NMR (400 MHz, chloroform-d): δ 8.01-8.21 (m, 1H), 6.83 (s, 1H), 6.01-6.31 (br, 2H), 3.49 (s, 1H), 2.23 (s, 3H), 1.50-1.55 (m, 9H).

2,2-difluoro-2-[3-methyl-4-[[4-(methylamino)-5-(trifluoromethyl)pyrimidin-2-yl]amino]pyrazol-1-yl]acetamide (D-14)

To a solution of tert-butyl N-[1-(2-amino-1,1-difluoro-2-oxo-ethyl)-3-methyl-pyrazol-4-yl]carbamate (500 mg, 1.72 mmol) and 2-chloro-N-methyl-5-(trifluoromethyl)pyrimidin-4-amino (400 mg, 1.89 mmol) in 1,4-dioxane (30 mL) was added p-TsOH (296 mg, 1.72 mmol). The mixture was stirred at 100° C. for 10 h. The reaction solution was concentrated under reduced pressure. The residue was adjusted to pH 7 with aq. NaHCO$_3$, extracted with EtOAc (3×10 ml). The organic layers were combined, washed with brine (5 ml), dried over Na$_2$SO$_4$, filtered and concentrated under reduced pressure. The crude product was washed with MeCN (5 mL), the solid was filtered and dried under reduced pressure to give 2,2-difluoro-2-[3-methyl-4-[[4-(methylamino)-5-(trifluoromethyl)pyrimidin-2-yl]amino]pyrazol-1-yl]acetamide (14). Additional crude compound 14 was obtained by concentration of the MeCN mother liquor. $^1$H NMR (400 MHz, chloroform-d): δ 9.33 (br. s., 1H), 8.58 (s, 1H), 8.34 (br. s., 2H), 8.17 (s, 1H), 7.16 (br. s., 1H), 2.90 (d, J=4.27 Hz, 3H), 2.24 (s, 3H); HPLC. RT 2.49 min; MS: m/z: 366.0 [M+H]$^+$.

2,2-difluoro-2-[3-methyl-4-[[4-(methylamino)-5-(trifluoromethyl)pyrimidin-2-yl]amino]pyrazol-1-yl]acetonitrile (D-13)

The solution of 2,2-difluoro-2-[3-methyl-4-[[4-(methylamino)-5-(trifluoromethyl)pyrimidin-2-yl]amino]pyrazol-1-yl]acetamide (100 mg, 273.78 μmol) in POCl$_3$ (3.3 g, 21.52 mmol, 2.00 mL) was heated at 90° C. for 10 h. The reaction solution was concentrated under reduced pressure. The residue was adjusted to pH 7 with aq. NaHCO$_3$, extracted with EtOAc (3×10 mL), organic layers were combined, washed with brine (10 mL), dried over Na$_2$SO$_4$, filtered and concentrated under reduced pressure. The crude product was purified by prep-TLC (PE:EtOAc=1:1) and further purified by prep-HPLC (FA) to give 2,2-difluoro-2-[3-methyl-4-[[4-(methylamino)-5-(trifluoromethyl)pyrimidin-2-yl]amino]pyrazol-1-yl]acetonitrile (D-13). $^1$H NMR (400 MHz, chloroform-d): δ 8.42 (s, 1H), 8.19 (s., 1H), 6.71 (br. s., 1H), 5.30 (br. s., 1H), 3.10 (d, J=4.27 Hz, 3H), 2.37 (s, 3H); HPLC: RT 2.48 min; MS: m/z: 348.2 [M+H]$^+$ Example D-19 and D-20

Synthesis of N2-[1-[2-(difluoromethoxy)ethyl]-5-methyl-pyrazol-4-yl]-N4-ethyl-5-(trifluoromethyl)pyrimidine-2,4-diamine (D-15) and N2-[1-[2-(difluoromethoxy)ethyl]-3-methyl-pyrazol-4-yl]-N4-ethyl-5-(trifluoromethyl)pyrimidine-2,4-diamine (D-16)

2-(5-methyl-4-nitro-pyrazol-1-yl)ethanol and 2-(3-methyl-4-nitro-pyrazol-1-yl)ethanol A mixture of 3-methyl-4-nitro-1H-pyrazole (5 g, 39.34 mmol), 2-bromoethanol (9.83 g, 78.68 mmol, 5.59 mL) and K$_2$CO$_3$ (16.31 g, 118.02 mmol) in CH$_3$CN (50 mL) was degassed and purged with N$_2$ for 3 times, and then the mixture was stirred at 80° C. for 16 h under N$_2$. The mixture was cooled to 20° C. and concentrated under reduced pressure. The residue was poured into ice water (100 mL). The aqueous phase was extracted with EtOAc (3×35 mL). The combined organic phase was washed with brine (35 mL), dried over anhydrous Na$_2$SO$_4$, filtered and concentrated under reduced pressure. The residue was purified by silica gel column chromatography (PE:EtOAc=2:1), to give 2-(5-methyl-4-nitro-pyrazol-1-yl)ethanol and 2-(3-methyl-4-nitro-pyrazol-1-yl)ethanol as a yellow oil. LCMS: RT 0.161 min. m/z=172.2 [M+H]$^+$. $^1$H NMR (400 MHz, CDCl$_3$): δ 8.20 (s, 1H), 8.03 (s, 1H), 4.14-4.22 (m, 4H), 3.94-4.03 (m, 4H), 3.07 (d, J=5.27 Hz, 2H), 2.64 (s, 3H), 2.47 (s, 3H).

1-[2-(difluoromethoxy)ethyl]-5-methyl-4-nitro-pyrazole and 1-[2-(difluoromethoxy)ethyl]-3-methyl-4-nitro-pyrazole To a solution of 2-(5-methyl-4-nitro-pyrazol-1-yl)ethanol (19-2, 4.26 g, 24.89 mmol), 2-(3-methyl-4-nitro-pyrazol-1-yl)ethanol (948 mg, 4.98 mmol) in CH$_3$CN (100 mL) was added a solution of 2,2-difluoro-2-fluorosulfonyl-acetic acid (6.65 g, 37.34 mmol, 3.87 mL) in CH$_3$CN (10 mL) dropwise at 55° C. over a period of 30 min under N$_2$. The reaction mixture was stirred at 55° C. for another 2 h. The mixture was cooled to 20° C. and concentrated under reduced pressure. The residue was purified by silica gel column chromatography (PE:EtOAc=5:1), to give a mixture of 1-[2-(difluoromethoxy)ethyl]-5-methyl-4-nitro-pyrazole and 1-[2-(difluoromethoxy)ethyl]-3-methyl-4-nitro-pyrazole as a yellow oil. LCMS: RT 0.707 min, m/z=222.1 [M+H]$^+$.

1-[2-(difluoromethoxy)ethyl]-5-methyl-pyrazol-4-amine and 1-[2-(difluoromethoxy)ethyl]-3-methyl-pyrazol-4-amine To a mixture of 1-[2-(difluoromethoxy)ethyl]-5-methyl-4-nitro-pyrazole and 1-[2-(difluoromethoxy)ethyl]-3-methyl-4-nitro-pyrazole (800 mg, 1.81 mmol) and NH$_4$Cl (484 mg, 9.05 mmol) in EtOH (20 mL) and H$_2$O (5 mL) was added Fe (505 mg, 9.05 mmol). The mixture was stirred at 80° C. for 2 h. The mixture was cooled to 20° C. and concentrated in reduced pressure. The residue was poured into ice water (10 mL). The aqueous phase was extracted with EtOAc (5×5 mL). The combined organic phase was washed with brine (5 mL), dried over anhydrous Na$_2$SO$_4$, filtered and concentrated under reduced pressure, to give the crude product 1-[2-(difluoromethoxy)ethyl]-5-methyl-pyrazol-4-amine and 1-[2-(difluoromethoxy)ethyl]-3-methyl-pyrazol-4-amine, which was used in the next step without further purification. LCMS: RT 0.095 min, m/z=192.2 [M+H]$^+$.

N2-[1-[2-(difluoromethoxy)ethyl]-5-methyl-pyrazol-4-yl]-N4-ethyl-5-(trifluoromethyl)pyrimidine-2,4-diamine (D-15) and N2-[1-[2-(difluoromethoxy)ethyl]-3-methyl-pyrazol-4-yl]-N4-ethyl-5-(trifluoromethyl)pyrimidine-2,4-diamine (D-16)

To a mixture of 1-[2-(difluoromethoxy)ethyl]-5-methyl-pyrazol-4-amine and 1-[2-(difluoromethoxy)ethyl]-3-methyl-pyrazol-4-amine (100 mg, 523.07 μmol), and 2-chloro-N-ethyl-5-(trifluoromethyl)pyrimidin-4-amine (130 mg, 575.38 μmol) in 1,4-dioxane (5.00 mL) was added TEA (159 mg, 1.57 mmol) under N$_2$. The mixture was stirred at 120° C. for 2 h. The mixture was cooled to 20° C. and concentrated under reduced pressure. The residue was purified by prep-HPLC (FA condition), to give N2-[1-[2-(difluoromethoxy)ethyl]-5-methyl-pyrazol-4-yl]-N4-ethyl-5-(trifluoromethyl)pyrimidine-2,4-diamine (D-15) and N2-[1-[2-(difluoromethoxy)ethyl]-3-methyl-pyrazol-4-yl]-N4-ethyl-5-(trifluoromethyl)pyrimidine-2,4-diamine (D-16, peak 2).

N2-[1-[2-(difluoromethoxy)ethyl]-5-methyl-pyrazol-4-yl]-N4-ethyl-5-(trifluoromethyl)pyrimidine-2,4-diamine (D-15)

$^1$H NMR (400 MHz, CDCl$_3$): δ 8.09 (s, 1H), 7.75 (br. s., 1H), 5.91-6.36 (m, 1H), 5.06 (br. s., 1H), 4.27-4.32 (m, 2H), 4.22-4.27 (m, 2H), 3.44-3.53 (m, 2H), 2.24 (s, 3H), 1.66 (br. s., 1H), 1.20-1.27 (m, 3H); HPLC: RT 1.75 min; MS: m/z=381.1 [M+H]$^+$.

N2-[1-[2-(difluoromethoxy)ethyl]-3-methyl-pyrazol-4-yl]-N4-ethyl-5-(trifluoromethyl)pyrimidine-2,4-diamine (D-16)

$^1$H NMR (400 MHz, CDCl$_3$): δ 8.12 (br. s., 1H), 7.87 (s, 1H), 5.94-6.39 (m, 1H), 5.13 (br. s., 1H), 4.26-4.33 (m, 2H), 4.17-4.24 (m, 2H), 3.48-3.59 (m, 2H), 2.26 (s, 3H), 1.90 (br. s., 1H), 1.28 (t, J=7.28 Hz, 3H); HPLC: RT 2.508 min; MS: m/z=381.1 [M+H]$^+$ Example D-21 and D-22

Synthesis of N2-[1-[(2R)-2-(difluoromethoxy)propyl]-5-methyl-pyrazol-4-yl]-N4-methyl-5-(trifluoromethyl)pyrimidine-2,4-diamine (D-19) and N2-[1-[(2R)-2-(difluoromethoxy)propyl]-3-methyl-pyrazol-4-yl]-N4-methyl-5-(trifluoromethyl)pyrimidine-2,4-diamine (D-20)

(R)-1-(5-methyl-4-nitro-1H-pyrazol-1-yl)propan-2-ol and (R)-1-(3-methyl-4-nitro-1H-pyrazol-1-yl)propan-2-ol To a mixture of 3-methyl-4-nitro-1H-pyrazole (5 g, 39.34 mmol) and (R)-2-methyloxirane (3.43 g, 59.01 mmol, 4.13 mL) in DMF (50 mL) was added Cs$_2$CO$_3$ (19.23 g, 59.01 mmol) at 20° C. The mixture was heated to 80° C. and stirred for 15 h then cooled to 20° C. and concentrated under reduced pressure. The residue was purified by silica gel column chromatography (PE:EtOAc=10:1 to 0:1) to give the mixture of (R)-1-(5-methyl-4-nitro-1H-pyrazol-1-yl)propan-2-ol and (R)-1-(3-methyl-4-nitro-1H-pyrazol-1-yl)propan-2-ol as a yellow liquid. LCMS: RT 0.133 min, m/z=186.1 [M+H]$^+$.

(R)-1-(2-(difluoromethoxy)propyl)-5-methyl-4-nitro-1H-pyrazole and (R)-1-(2-(difluoromethoxy)propyl)-3-methyl-4-nitro-1H-pyrazole To a solution of the mixture (R)-1-(5-methyl-4-nitro-1H-pyrazol-1-yl)propan-2-ol and (R)-1-(3-methyl-4-nitro-1H-pyrazol-1-yl)propan-2-ol (3 g, 16.2 mmol) in CH$_3$CN (150 mL) was added CuI (617 mg, 3.24 mmol), then a solution of 2,2-difluoro-2-fluorosulfonyl-acetic acid (4.33 g, 24.30 mmol, 2.5 mL) in CH3CN (150 mL) dropwise at 20° C. over a period of 30 min under N$_2$. The reaction mixture was warmed to 55° C. and stirred for 2 h then cooled to 20° C. and concentrated under reduced pressure. The residue was purified by silica gel column chromatography (PE:EtOAc=10:1 to 0:1) to give the mixture of (R)-1-(2-(difluoromethoxy)propyl)-5-methyl-4-nitro-1H-pyrazole and (R)-1-(2-(difluoromethoxy)propyl)-3-methyl-4-nitro-1H-pyrazole as a yellow oil. LCMS: RT 0.873 min, m/z=236.1 [M+H]$^+$.

(R)-1-(2-(difluoromethoxy)propyl)-5-methyl-1H-pyrazol-4-amine and (R)-1-(2-(difluoromethoxy)propyl)-3-methyl-1H-pyrazol-4-amine To a solution of the mixture (R)-1-(2-(difluoromethoxy)propyl)-5-methyl-4-nitro-1H-pyrazole and (R)-1-(2-(difluoromethoxy)propyl)-3-methyl-4-nitro-1H-pyrazole (4 g, 17.01 mmol) in EtOH (96 mL) and H$_2$O (24 mL) was added NH$_4$Cl (4.55 g, 85.04 mmol, 2.97 mL) and Fe (4.75 g, 85.04 mmol) at 20° C. The mixture was heated to 80° C. and stirred for 2 h then cooled to 20° C. and concentrated under reduced pressure. The residue was washed with DCM:MeOH=10:1 (3×10 mL) then filtered and the filtrate was concentrated under reduced pressure to give the mixture compound (R)-1-(2-(difluoromethoxy)propyl)-5-methyl-1H-pyrazol-4-amine and (R)-1-(2-(difluoromethoxy)propyl)-3-methyl-1H-pyrazol-4-amine as a light yellow oil. LCMS: RT 1.046 min, m/z=206.2 [M+H]$^+$.

N2-[1-[(2R)-2-(difluoromethoxy)propyl]-5-methyl-pyrazol-4-yl]-N4-methyl-5-(trifluoromethyl)pyrimidine-2,4-diamine (D-19) and N2-[1-[(2R)-2-(difluoromethoxy)propyl]-3-methyl-pyrazol-4-yl]-N4-methyl-5-(trifluoromethyl)pyrimidine-2,4-diamine (D-20)

To a solution of the mixture (R)-1-(2-(difluoromethoxy)propyl)-5-methyl-1H-pyrazol-4-amine and (R)-1-(2-(difluoromethoxy)propyl)-3-methyl-1H-pyrazol-4-amine (300 mg, 1.46 mmol) and 2-chloro-N-methyl-5-(trifluoromethyl)pyrimidin-4-amine (238 mg, 1.12 mmol) in 1,4-dioxane (3 mL) was added p-TsOH (97 mg, 562.30 µmol) at 20° C. The mixture was heated to 90° C. and stirred for 2 h, then cooled to 20° C. and adjusted to pH 7-8 by aq. NaHCO$_3$. The mixture was extracted with EtOAc (3×5 mL), washed with brine (5 mL), dried over anhydrous Na$_2$SO$_4$, filtered and concentrated under reduced pressure. The residue was purified by prep-HPLC (FA) to give compound N2-[1-[(2R)-2-(difluoromethoxy)propyl]-5-methyl-pyrazol-4-yl]-N4-methyl-5-(trifluoromethyl)pyrimidine-2,4-diamine (D-19) and N2-[1-[(2R)-2-(difluoromethoxy)propyl]-3-methyl-pyrazol-4-yl]-N4-methyl-5-(trifluoromethyl)pyrimidine-2,4-diamine (D-20).

N2-[1-[(2R)-2-(difluoromethoxy)propyl]-5-methyl-pyrazol-4-yl]-N4-methyl-5-(trifluoromethyl)pyrimidine-2,4-diamine (D-19)

$^1$H NMR (400 MHz, CDCl$_3$) δ ppm 8.08 (br. s., 1H), 7.76 (br. s., 1H), 6.85 (br. s., 1H), 5.80-6.24 (m, 1H), 5.15 (br. s., 1H), 4.59-4.75 (m, 1H), 4.04-4.24 (m, 2H), 2.99 (d, J=4.02 Hz, 3H), 2.24 (s, 3H), 1.34 (d, J=6.53 Hz, 3H); HPLC: RT 2.406 min; MS: (M+H$^+$) m/z: 381.1; SFC: RT 3.15 min.

N2-[1-[(2R)-2-(difluoromethoxy)propyl]-3-methyl-pyrazol-4-yl]-N4-methyl-5-(trifluoromethyl)pyrimidine-2,4-diamine (D-20)

$^1$H NMR (400 MHz, CDCl$_3$) δ ppm 8.13 (br. s., 1H), 7.89 (br. s., 1H), 6.58 (br. s, 1H), 5.85-6.31 (m, 1H), 5.19 (br. s., 1H), 4.55-4.69 (m, 1H), 4.13 (d, J=5.52 Hz, 2H), 3.06 (d, J=4.52 Hz, 3H), 2.26 (s, 3H), 1.30 (d, J=6.53 Hz, 3H); HPLC: RT: 2.463 min; MS: (M+H$^+$) m/z: 381.1; SFC: RT: 3.44 min.

Example D-23 and D-24

Synthesis of N2-[1-[2-(difluoromethoxy)-1-methyl-ethyl]-5-methyl-pyrazol-4-yl]-5-(difluoromethylfluoranyl)-N4-methyl-pyrimidine-2,4-diamine (D-48) and N2-[1-[2-(difluoromethoxy)-1-methyl-ethyl]-3-methyl-pyrazol-4-yl]-N4-methyl-5-(trifluoromethyl)pyrimidine-2,4-diamine (D-21)

Ethyl 2-(5-methyl-4-nitro-pyrazol-1-yl)propanoate and ethyl 2-(3-methyl-4-nitro-pyrazol-1-yl)propanoate To a solution of 3-methyl-4-nitro-1H-pyrazole (5 g, 39.34 mmol) in DMF (50 mL) was added NaH (1.89 g, 47.21 mmol, 60% purity) at 0° C. under N$_2$. The mixture was stirred at 20° C. for 1 h, then added with ethyl 2-chloropropanoate (10.75 g, 78.68 mmol, 10.05 mL) and stirred for 15 h. The mixture was poured into ice water (250 mL). The aqueous phase was extracted with EtOAc (3×100 mL). The combined organic phase was washed with brine (3<100 mL), dried over anhydrous $Na_2SO_4$, filtered and concentrated under reduced pressure. The residue was purified by silica gel column chromatography (PE:EtOAc=2:1), to give a mixture of ethyl 2-(5-methyl-4-nitro-pyrazol-1-yl)propanoate and ethyl 2-(3-methyl-4-nitro-pyrazol-1-yl)propanoate as a yellow oil. LCMS: RT 0.745 min, m/z=228.2 $[M+H]^+$.

2-(5-methyl-4-nitro-pyrazol-1-yl)propan-1-ol and 2-(3-methyl-4-nitro-pyrazol-1-yl)propan-1-ol To a mixture of ethyl 2-(5-methyl-4-nitro-pyrazol-1-yl-propanoate and ethyl 2-(3-methyl-4-nitro-pyrazol-1-ylpropanoate (9.3 g, 40.93 mmol) in MeOH (90 mL) was added $NaBH_4$ (3.87 g, 102.33 mmol) at 0° C. under $N_2$. The mixture was stirred at 0° C. for 2 h. The mixture was concentrated under reduced pressure and purified by silica gel column chromatography (PE:EtOAc=3:1), to give a mixture of 2-(5-methyl-4-nitro-pyrazol-1-yl)propan-1-ol and 2-(3-methyl-4-nitro-pyrazol-1-yl)propan-1-ol was obtained as a yellow solid. LCMS: RT 0.707 min, m/z=222.1 $[M+H]^+$.

1-[2-(difluoromethoxy)-1-methyl-ethyl]-5-methyl-4-nitro-pyrazole and 1-[2-(difluoromethoxy)-1-methyl-ethyl]-3-methyl-4-nitro-pyrazole To a solution of 2-(5-methyl-4-nitro-pyrazol-1-yl)propan-1-ol, 2-(3-methyl-4-nitro-pyrazol-1-ylpropan-1-ol (2.08 g, 11.23 mmol) and CuI (428 mg, 2.25 mmol) in $CH_3CN$ (20 mL) was added a solution of 2,2-difluoro-2-fluorosulfonyl-acetic acid (3 g, 16.85 mmol, 1.74 mL) in $CH_3CN$ (10 mL) dropwise at 55° C. over a period of 30 min under $N_2$. The reaction mixture was stirred at 55° C. for 2.5 h. The mixture was concentrated under reduced pressure and purified by silica gel column chromatography (PE:EtOAc=6:1), to give a mixture of 1-[2-(difluoromethoxy)-1-methyl-ethyl]-5-methyl-4-nitro-pyrazole and 1-[2-(difluoromethoxy)-1-methyl-ethyl]-3-methyl-4-nitro-pyrazole was obtained as a yellow oil. LCMS: RT 0.758 min, m/z=236.52 $[M+H]^+$.

1-[2-(difluoromethoxy)-1-methyl-ethyl]-5-methyl-pyrazol-4-amine and 1-[2-(difluoromethoxy)-1-methyl-ethyl]-3-methyl-pyrazol-4-amine To a mixture of 1-[2-(difluoromethoxy)-1-methyl-ethyl]-5-methyl-4-nitro-pyrazole and 1-[2-(difluoromethoxy)-1-methyl-ethyl]-3-methyl-4-nitro-pyrazole (760 mg, 3.23 mmol) in EtOH (20 mL) was added Fe (902.38 mg, 16.15 mmol) and $NH_4Cl$ (864 mg, 16.15 mmol, 564.87 µL). The mixture was stirred at 80° C. for 2 h. The mixture was cooled to 20° C. and concentrated under reduced pressure. The residue was poured into ice water (10 mL). The aqueous phase was extracted with EtOAc (3×10 mL). The combined organic phase was washed with brine (10 mL), dried over anhydrous $Na_2SO_4$, filtered and concentrated under reduced pressure, to give a erode 1-[2-(difluoromethoxy)-1-methyl-ethyl]-5-methyl-pyrazol-4-amine and 1-[2-(difluoromethoxy)-1-methyl-ethyl]-3-methyl-pyrazol-4-amine, which was used into the next step without further purification. LCMS: RT 1.026 min, m/z=186.1 $[M+H]^+$ N2-[1-[2-(difluoromethoxy)-1-methyl-ethyl]-5-methyl-pyrazol-4-yl]-5-(difluoromethyl-fluoranyl)-N4-methyl-pyrimidine-2,4-diamine (D-48) and N2-[1-[2-(difluoromethoxy)-1-methyl-ethyl]-3-methyl-pyrazol-4-yl]-N4-methyl-5-(trifluoromethyl) pyrimidine-2,4-diamine (D-21)

To a mixture of 2-chloro-N-methyl-5-(trifluoromethyl) pyrimidin-4-amine (372 mg, 1.75 mmol), 1-[2-(difluoromethoxy)-1-methyl-ethyl]-3-methyl-pyrazol-4-amine and 1-[2-(difluoromethoxy)-1-methyl-ethyl]-5-methyl-pyrazol-4-amino (300 mg, 1.46 mmol) in 1,4-dioxane (10 mL) was added TEA (295 mg, 2.92 mmol, 404.75 µL) in one portion under $N_2$. The mixture was stirred at 120° C. for 2 h. The mixture was concentrated under reduced pressure. The residue was purified by prep-HPLC (FA).

N2-[1-[2-(difluoromethoxy)-1-methyl-ethyl]-5-methyl-pyrazol-4-yl]-5-(difluoromethyl-fluoranyl)-N4-methyl-pyrimidine-2,4-diamine (D-48)

$^1$H NMR (400 MHz, $CDCl_3$): δ 8.10 (s, 1H), 7.85 (br. s., 1H), 6.62 (br. s., 1H), 5.86-6.31 (m, 1H), 5.14 (br. s., 1H), 4.44-4.55 (m, 1H), 4.22 (t, J=9.48 Hz, 1H), 4.08 (dd, J=10.36, 5.07 Hz, 1H), 3.00 (d, J=4.85 Hz, 3H), 2.18-2.30 (m, 3H), 1.53 (d, J=7.06 Hz, 3H); HPLC. RT 1.94 min; MS; m/z=381.1 $[M+H]^+$ N2-[1-[2-(difluoromethoxy)-1-methyl-ethyl]-3-methyl-pyrazol-4-yl]-N4-methyl-5-(trifluoromethyl) pyrimidine-2,4-diamine (D-21)

$^1$H NMR (400 MHz, $CDCl_3$): δ 8.12 (br. s., 1H), 7.92 (br. s., 1H), 6.97 (br. s., 1H), 5.88-6.38 (m, 1H), 5.21 (br. s., 1H), 4.47 (d, J=5.52 Hz, 1H), 3.99-4.20 (m, 2H), 3.06 (d, J=2.89 Hz, 3H), 2.26 (s, 3H), 1.56 (d, 7=6.78 Hz, 3H). HPLC. RT 1.93 min; MS: m/z: 381.1 $[M+H]^+$.

Example D-25, D-26, and D-27

Synthesis of N2-(1-(6,7-dihydro-5H-pyrrolo[1,2-a] imidazol-7-yl)-3-methyl-1H-pyrazol-4-yl)-N4-ethyl-5-(trifluoromethyl)pyrimidine-2,4-diamine (First Eluting Stereoisomer, D-23), N2-(1-(6,7-dihydro-5H-pyrrolo[1,2-a]imidazol-7-yl)-3-methyl-1H-pyrazol-4-yl)-N4-ethyl-5-(trifluoromethyl)pyrimidine-2,4-diamine (Second Eluting Stereoisomer, D-24), and N2-(1-(6,7-dihydro-5H-pyrrolo[1,2-a]imidazol-7-yl)-5-methyl-1H-pyrazol-4-yl)-N4-ethyl-5-(trifluoromethyl)pyrimidine-2,4-diamine (D-22)

N2-(1-(6,7-dihydro-5H-pyrrolo[1,2-a]imidazol-7-yl)-3-methyl-1H-pyrazol-4-yl)-N4-ethyl-5-(trifluoromethyl)pyrimidine-2,4-diamine (First Eluting Stereoisomer, D-23), N2-(1-(6,7-dihydro-5H-pyrrolo[1,2-a]imidazol-7-yl)-3-methyl-1H-pyrazol-4-yl)-N4-ethyl-5-(trifluoromethyl)pyrimidine-2,4-diamine (Second Eluting Stereoisomer, D-24), and N2-(1-(6,7-dihydro-5H-pyrrolo[1,2-a]imidazol-7-yl)-5-methyl-1H-pyrazol-4-yl)-N4-ethyl-5-(trifluoromethyl)pyrimidine-2,4-diamine (D-22)

To a solution of 1-(6,7-dihydro-5H-pyrrolo[1,2-a]imidazol-7-yl)-5-methyl-pyrazol-4-amine (200 mg, 984.06 µmol)

and 1-(6,7-dihydro-5H-pyrrolo[1,2-a]imidazol-7-yl)-3-methyl-pyrazol-4-amine and 2-chloro-N-ethyl-5-(trifluoromethyl)pyrimidin-4-amine (222 mg, 984.06 µmol) in 1,4-dioxane (5 mL) was added TFA (56 mg, 492.03 µmol). The mixture was stirred at 100° C. for 1 h. The reaction mixture was diluted with $H_2O$ (20 mL), and adjusted with aq. $NaHCO_3$ (10 mL) to pH 8 and extracted with EtOAc (3×10 mL). The combined organic layers were washed with brine (5 mL), dried over $Na_2SO_4$, filtered and concentrated under reduced pressure. The residue was purified by prep-HPLC (TFA) to give crude N2-(1-(6,7-dihydro-5H-pyrrolo[1,2-a]imidazol-7-yl)-5-methyl-1H-pyrazol-4-yl)-N4-ethyl-5-(trifluoromethyl)pyrimidine-2,4-diamine (Peak 1 in HPLC) and racemic N2-(1-(6,7-dihydro-5H-pyrrolo[1,2-a]imidazol-7-yl)-3-methyl-1H-pyrazol-4-yl)-N4-ethyl-5-(trifluoromethyl)pyrimidine-2,4-diamine (Peak 2 in HPLC).

Crude N2-(1-(6,7-dihydro-5H-pyrrolo[1,2-a]imidazol-7-yl)-5-methyl-1H-pyrazol-4-yl)-N4-ethyl-5-(trifluoromethyl)pyrimidine-2,4-diamine was further purified by prep-HPLC (FA) to give N2-(1-(6,7-dihydro-5H-pyrrolo[1,2-a]imidazol-7-yl)-5-methyl-1H-pyrazol-4-yl)-N4-ethyl-5-(trifluoromethyl)pyrimidine-2,4-diamine (D-22, FA salt, racemers). Racemic N2-(1-(6,7-dihydro-5H-pyrrolo[1,2-a]imidazol-7-yl)-3-methyl-1H-pyrazol-4-yl)-N4-ethyl-5-(trifluoromethyl)pyrimidine-2,4-diamine was separated by SFC to give N2-(1-(6,7-dihydro-5H-pyrrolo[1,2-a]imidazol-7-yl)-3-methyl-1H-pyrazol-4-yl)-N4-ethyl-5-(trifluoromethyl)pyrimidine-2,4-diamine (D-23, First eluting stereoisomer in SFC), and N2-(1-(6,7-dihydro-5H-pyrrolo[1,2-a]imidazol-7-yl)-3-methyl-1H-pyrazol-4-yl)-N4-ethyl-5-(trifluoromethyl)pyrimidine-2,4-diamine (D-24, Second eluting stereoisomer in SFC).

N2-(1-(6,7-dihydro-5H-pyrrolo[1,2-a]imidazol-7-yl)-3-methyl-1H-pyrazol-4-yl)-N4-ethyl-5-(trifluoromethyl)pyrimidine-2,4-diamine (First Eluting Stereoisomer, D-23)

$^1$H NMR (400 MHz, $CD_3OD$): δ ppm 7.99-8.07 (m, 1H), 7.77-7.87 (m, 1H), 7.20-7.27 (m, 1H), 7.08-7.17 (m, 1H), 5.70-5.79 (m, 1H), 4.26-4.36 (m, 1H), 4.08-4.22 (m, 1H), 3.38-3.52 (m, 2H), 3.18-3.30 (m, 1H), 2.74-2.90 (m, 1H), 2.22 (s, 3H), 1.07-1.24 (m, 3H); HPLC: RT 2.018 min; MS: m/z: 393.2 $[M+H]^+$; SFC: RT 2.47 min.

N2-(1-(6,7-dihydro-5H-pyrrolo[1,2-a]imidazol-7-yl)-3-methyl-1H-pyrazol-4-yl)-N4-ethyl-5-(trifluoromethyl)pyrimidine-2,4-diamine (Second Eluting Stereoisomer, D-24)

$^1$H NMR (400 MHz, $CD_3OD$): δ ppm 7.99-8.08 (m, 1H), 7.77-7.87 (m, 1H), 7.19-7.26 (m, 1H), 7.09-7.16 (m, 1H), 5.70-5.78 (m, 1H), 4.26-4.38 (m, 1H), 4.09-4.20 (m, 1H), 3.38-3.51 (m, 2H), 3.19-3.29 (m, 1H), 2.72-2.88 (m, 1H), 2.22 (s, 3H), 1.05-1.25 (m, 3H); HPLC: RT 2.016 min; MS: m/z: 393.2 $[M+H]^+$; SFC: RT 2.67 min.

N2-(1-(6,7-dihydro-5H-pyrrolo[1,2-a]imidazol-7-yl)-5-methyl-1H-pyrazol-4-yl)-N4-ethyl-5-(trifluoromethyl)pyrimidine-2,4-diamine (D-22)

$^1$H NMR (400 MHz, $CD_3OD$): δ ppm 8.11-8.24 (m, 1H), 7.95-8.07 (m, 1H), 7.49-7.75 (m, 1H), 7.25 (br. s., 1H), 7.09-7.21 (m, 1H), 5.88-6.01 (m, 1H), 4.35-4.51 (m, 1H), 4.12-4.29 (m, 1H), 3.41-3.57 (m, 2H), 3.22-3.31 (m, 1H), 2.84-3.04 (m, 1H), 2.34 (s, 3H), 1.18 (m, 3H); HPLC: RT 1.967 min; MS: m/z: 393.2 $[M+H]^+$.

Example D-28 and D-29

Synthesis of trans-N2-[1-[3-(difluoromethoxy)cyclobutyl]-5-methyl-pyrazol-4-yl]-N4-methyl-5-(trifluoromethyl)pyrimidine-2,4-diamine (D-25) and trans-N2-[1-[3-(difluoromethoxy)cyclobutyl]-3-methyl-pyrazol-4-yl]-N4-methyl-5-(trifluoromethyl)pyrimidine-2,4-diamine (D-26)

cis-3-benzyloxycyclobutanol

To a solution of 3-benzyloxycyclobutanone (28-1, 19.7 g, 111.8 mmol) in MeOH (200 mL) was added $NaBH_4$ (6.77 g, 178.9 mmol) at 0° C., and the mixture was stirred at 15° C. for 2 h. The reaction mixture was poured into water (100 mL) slowly. The methanol was removed under reduced pressure. The residue was extracted with EtOAc (3×50 mL). The organic phase was washed with brine (30 mL), dried over $Na_2SO_4$, filtered and concentrated to give cis-3-benzyloxycyclobutanol as colorless oil. $^1$H NMR (400 MHz, $CDCl_3$): δ ppm 7.29-7.35 (m, 5H), 4.43 (s, 2H), 3.90-3.95 (m, 1H), 3.62-3.66 (m, 1H), 2.71-2.75 (m, 2H), 1.83-1.96 (m, 3H).

trans-1-(3-benzyloxycyclobutyl)-5-methyl-4-nitro-pyrazole and trans-1-(3-benzyloxycyclobutyl)-3-methyl-4-nitro-pyrazole To a solution of cis-3-benzyloxy cyclobutanol (17 g, 95.4 mmol) and 3-methyl-4-nitro-1H-pyrazole (12.1 g, 95.4 mmol) in THF (350 mL) was added $PPh_3$ (37.5 g, 143 mmol). Then, DIAD (28.9 g, 143 mmol) was added slowly at 0° C., and the mixture was stirred at 15° C. for 20 h. The mixture was quenched with $H_2O$ (100 mL), then filtered. The filtrate was then extracted with EtOAc (3×70 mL). The organic phase was washed with brine (30 mL), dried over anhydrous $Na_2SO_4$, filtered and concentrated. The residue was purified by silica gel column chromatography (PE: EtOAc=10:1 to 7:1), to give trans-1-(3-benzyloxycyclobutyl)-5-methyl-4-nitro-pyrazole and trans-1-(3-benzyloxycyclobutyl)-3-methyl-4-nitro-pyrazole.

trans-3-[5-methyl-4-nitro-pyrazol-1-yl]cyclobutanol and trans-3-[3-methyl-4-nitro-pyrazol-1-yl]cyclobutanol To a solution of trans-1-(3-benzyloxycyclobutyl)-5-methyl-4-nitro-pyrazole and trans-1-(3-benzyloxycyclobutyl)-3-methyl-4-nitro-pyrazole (19.5 g, 67.9 mmol) in DCM (200 mL) was added $BCl_3$ (1 M, 26.5 mL) at 0° C., and the mixture was stirred at 0° C. for 2 h. The mixture was poured into water (200 mL) slowly, then extracted with DCM (2×100 mL). The organic phase was washed with aqueous $NaHCO_3$ (50 mL), brine (40 mL), dried over anhydrous $Na_2SO_4$, filtered and concentrated. The residue was purified by silica gel column chromatography (PE/EtOAc=2:1 to 1:1), to give trans-3-[5-methyl-4-nitro-pyrazol-1-yl]cyclobutanol and trans-3-[3-methyl-4-nitro-pyrazol-1-yl]cyclobutanol as a mixture as a white solid.

trans-1-[3-(difluoromethoxy)cyclobutyl]-5-methyl-4-nitro-pyrazole and trans-1-[3-(difluoromethoxy)cyclobutyl]-3-methyl-4-nitro-pyrazole To a mixture of trans-3-[5-methyl-4-nitro-pyrazol-1-yl]cyclobutanol and trans-3-[3-methyl-4-nitro-pyrazol-1-yl]cyclobutanol (1.4 g, 7.1 mmol) in CH₃CN (100 mL) was added CuI (541 mg, 2.84 mmol) and 2,2-difluoro-2-fluorosulfonyl-acetic acid (1.9 g, 10.65 mmol) at 15° C., and the mixture was stirred at 55° C. for 2 h. The mixture was quenched with water (5 mL). The solvent was filtered through celite and the filtrate was concentrated under reduced pressure. The residue was purified by silica gel column chromatography (PE:EtOAc=10:1), to give trans-1-[3-(difluoromethoxy)cyclobutyl]-5-methyl-4-nitro-pyrazole and trans-1-[3-(difluoromethoxy)cyclobutyl]-3-methyl-4-nitro-pyrazole as a yellow solid.

trans-1-[3-(difluoromethoxy)cyclobutyl]-5-methyl-pyrazol-4-amine and trans-1-[3-(difluoromethoxy)cyclobutyl]-3-methyl-pyrazol-4-amine To a mixture of tram-1-[3-(difluoromethoxy)cyclobutyl]-5-methyl-4-nitro-pyrazole and trans-1-[3-(difluoromethoxy Cyclobutyl]-3-methyl-4-nitro-pyrazole (350 mg, 1.42 mmol) and NH₄Cl (379 mg, 7.08 mmol) in EtOH (8.8 mL) and H₂O (2.2 mL) was added powder Fe (395 mg, 7.08 mmol) at 15° C., then the mixture was stirred at 80° C. for 2 h. The mixture was filtered through celite, and the filtrate was concentrated under reduced pressure. The mixture was extracted with EtOAc (2×30 mL). The organic phase was washed with brine (10 mL), dried over anhydrous Na₂SO₄, filtered and concentrated to give trans-1-[3-(difluoromethoxy)cyclobutyl]-5-methyl-pyrazol-4-amine and trans-1-[3-(difluoromethoxy)cyclobutyl]-3-methyl-pyrazol-4-amine as a brown oil. LCMS: RT 2.06 min, m/z=393.1 [M+H]⁺.

trans-N2-[1-[3-(difluoromethoxy)cyclobutyl]-5-methyl-pyrazol-4-yl]-N4-methyl-5-(trifluoromethyl)pyrimidine-2,4-diamine (D-25) and trans-N2-[1-[3-(difluoromethoxy)cyclobutyl]-3-methyl-pyrazol-4-yl]-N4-methyl-5-(trifluoromethyl)pyrimidine-2,4-diamine (D-26)

To a mixture of trans-1-[3-(difluoromethoxy)cyclobutyl]-5-methyl-pyrazol-4-amine and trans-1-[3-(difluoromethoxy)cyclobutyl]-3-methyl-pyrazol-4-amine (270 mg, 1.24 mmol) in 1,4-dioxane (10 mL) was added 2-chloro-N-methyl-5-(trifluoromethyl)pyrimidin-4-amine (262 mg, 1.24 mmol) and TsOH H₂O (236 mg, 1.24 mmol) at 15° C. The mixture was warmed to 90° C. and stirred for 2 h. The reaction was quenched with H₂O (1 mL), then concentrated under reduced pressure. The crude was purified by prep-HPLC (FA) to give trans-N2-[1-[3-(difluoromethoxy)cyclobutyl]-5-methyl-pyrazol-4-yl]-N4-methyl-5-(trifluoromethyl)pyrimidine-2,4-diamine (25) and trans-N2-[1-[3-(difluoromethoxy)cyclobutyl]-3-methyl-pyrazol-4-yl]-N4-methyl-5-(trifluoromethyl)pyrimidine-2,4-diamine (26).

trans-N2-[1-[3-(difluoromethoxy)cyclobutyl]-5-methyl-pyrazol-4-yl]-N4-methyl-5-(trifluoromethyl)pyrimidine-2,4-diamine (D-25)

¹H NMR (400 MHz, CDCl₃): δ ppm 8.08 (s, 1H) 7.71-7.98 (br. s., 1H), 6.23 (t, J=3.2 Hz, 1H), 5.20 (t, J=3.2 Hz, 1H), 4.1 (t, J=3.2 Hz, 1H), 4.75 (br. s., 1H), 3.03 (s, 3H), 2.97-3.03 (m, 2H), 2.68-2.73 (m, 2H), 2.20 (s, 3H); HPLC. RT 2.06 min; MS: m/z: 393.1 [M+H]⁺.

trans-N2-[1-[3-(difluoromethoxy)cyclobutyl]-3-methyl-pyrazol-4-yl]-N4-methyl-5-(trifluoromethyl)pyrimidine-2,4-diamine (D-26)

¹H NMR (400 MHz, CDCl₃): δ ppm 8.21 (s, 1H), 8.07 (br. s., 1H), 7.89 (s, 1H), 6.22 (t, J=3.2 Hz, 1H), 5.34 (br. s., 1H), 4.96-5.02 (m, 1H), 4.81-4.90 (m, 1H) 3.04-3.15 (m, 3H), 2.84-2.96 (m, 2H), 2.65-2.78 (m, 2H), 2.31 (s, 3H); HPLC: RT 2.06 min; MS: m/z: 393.1 [M+H]⁺.

Example D-30 and D-31

Synthesis of m-N4-methyl-N2-[5-methyl-1-(3-pyrazol-1-ylcyclobutyl)pyrazol-4-yl]-5-(trifluoromethyl)pyrimidine-2,4-diamine (D-49) and m-N4-methyl-N2-[3-methyl-1-(3-pyrazol-1-ylcyclo butyl)pyrazol-4-yl]-5-(trifluoromethyl)pyrimidine-2,4-diamine (D-27)

cis-[3-[(1R)-5-methyl-4-nitro-pyrazol-1-yl]cyclobutyl]methanesulfonate and cis-[3-[(1S)-3-methyl-4-nitro-pyrazol-1-yl]cyclobutyl]methanesulfonate To a mixture of 3-[(1R)-5-methyl-4-nitro-pyrazol-1-yl]cyclobutanol and 3-[(1R)-3-methyl-4-nitro-pyrazol-1-yl]cyclobutanol (2 g, 10.14 mmol) in DCM (20 mL) was added TEA (2.05 g, 20.29 mmol) and MsCl (1.74 g, 15.21 mmol) at 0° C., then stirred at 20° C. for 30 min. The reaction mixture was quenched by water (100 mL) at 0° C., and extracted with DCM (2×50 mL). The combined organic layers were washed with brine (50 mL), dried over Na₂SO₄, filtered and concentrated under reduced pressure to give the crude product, which was used to the next step directly without purification. The mixture of [3-[(1R)-5-methyl-4-nitro-pyrazol-1-yl]cyclobutyl]methanesulfonate and [3-[(1S)-3-methyl-4-nitro-pyrazol-1-yl]cyclobutyl]methanesulfonate was obtained as a yellow solid. LCMS: RT 0.715 min, m/z=2762 [M+H]⁺.

cis-5-methyl-4-nitro-1-(3-pyrazol-1-ylcyclobutyl)pyrazole and cis-3-methyl-4-nitro-1-(3-pyrazol-1-ylcyclobutyl)pyrazole To a mixture of 1H-pyrazole (30-3, 297 mg, 4.36 mmol) in DMF (10 mL) was added NaH (174 mg, 4.36 mmol, 60% purity) at 0° C. and stirred for 30 min, then added the mixture of [3-[(1R)-5-methyl-4-nitro-pyrazol-1-yl]cyclobutyl]methanesulfonate and [3-[(1S)-3-methyl-4-nitro-pyrazol-1-yl]cyclobutyl]methanesulfonate (1 g, 3.63 mmol) in DMF (1 mL), then heated to 60° C. and stirred for 16 h. Then, a mixture of 1H-pyrazole (297 mg, 4.36 mmol) and NaH (174 mg, 4.36 mmol) in DMF (3 mL) was added into the reaction at 0° C., then heated to 60° C. and stirred for 16 h. The reaction mixture was quenched by aq. sat. NH₄Cl (100 mL) at 0° C., and extracted with EtOAc (3×50 mL). The combined organic layers were washed with brine (50 mL), dried over Na₂SO₄, filtered and concentrated under reduced pressure to give a residue, which was purified by silica gel column chromatography (EtOAc/PE=0~50%). The mixture of m-5-methyl-4-nitro-1-(3-pyrazol-1-ylcyclobutyl)pyrazole and m-3-methyl-4-nitro-1-(3-pyrazol-1-ylcyclobutyl)pyrazole was obtained as a yellow solid. LCMS: RT 0.730 min, m/z=248.2 [M+H]⁺.

cis-5-methyl-1-(3-pyrazol-1-ylcyclobutyl)pyrazol-4-amine and cis-3-methyl-1-(3-pyrazol-1-ylcyclobutyl)pyrazol-4-amine To a mixture of 5-methyl-4-nitro-1-(3-pyrazol-1-ylcyclobutyl)pyrazole and (1S)-3-methyl-4-nitro-1-(3-pyrazol-1-ylcyclobutyl)pyrazole (400 mg, 1.62 mmol) in EtOH (8 mL) and H₂O (2 mL) was added Fe (271 mg, 4.86 mmol)

and NH$_4$Cl (260 mg, 4.86 mmol) at 0° C. The mixture was heated to 90° C. for 1 h. The mixture was filtered and the filtrate was concentrated under reduced pressure to give a residue. The residue was dissolved in acetonitrile (10 mL), and then filtered. The filtrate was concentrated under reduced pressure to give crude mixture of m-5-methyl-1-(3-pyrazol-1-ylcyclobutyl)pyrazol-4-amine and m-3-methyl-1-(3-pyrazol-1-ylcyclobutyl)pyrazol-4-amine as a brown oil, which was used to the next step without purification. LCMS: RT 1.126 min, m/z=218.2 [M+H]$^+$.

cis-N4-methyl-N2-[5-methyl-1-(3-pyrazol-1-ylcyclobutyl)pyrazol-4-yl]-5-(trifluoromethyl)pyrimidine-2,4-diamine (D-49) and cis-N4-methyl-N2-[3-methyl-1-(3-pyrazol-1-ylcyclo butyl)pyrazol-4-yl]-5-(trifluoromethyl)pyrimidine-2,4-diamine (D-27)

To a mixture of cis-5-methyl-1-(3-pyrazol-1-ylcyclobutyl)pyrazol-4-amine and m-3-methyl-1-(3-pyrazol-1-ylcyclobutyl)pyrazol-4-amine (180 mg, 828 µmol) in 1,4-dioxane (5 mL) was added TsOH H$_2$O (48 mg, 249 µmol) and 2-chloro-N-methyl-5-(trifluoromethyl)pyrimidin-4-amino (175 mg, 828 µmol) at 20° C. The mixture was heated to 80° C. and stirred for 2 h. The mixture was added with water (1 mL) and stirred for 2 min, then concentrated under reduced pressure to give a residue, which was purified by prep-HPLC (FA condition) to give m-N4-methyl-N2-[5-methyl-1-(3-pyrazol-1-ylcyclobutyl)pyrazol-4-yl]-5-(trifluoromethyl)pyrimidine-2,4-diamine (D-49) and m-N4-methyl-N2-[3-methyl-1-(3-pyrazol-1-ylcyclo butyl)pyrazol-4-yl]-5-(trifluoromethyl)pyrimidine-2,4-diamino (D-27).

cis-N4-methyl-N2-[5-methyl-1-(3-pyrazol-1-ylcyclobutyl)pyrazol-4-yl]-5-(trifluoromethyl)pyrimidine-2,4-diamine (D-49)

$^1$H NMR (400 MHz, chloroform-d) δ ppm 2.24 (s, 3H) 2.96-3.18 (m, 5H) 3.22-3.36 (m, 2H) 4.50-4.61 (m, 1H) 4.68-4.80 (m, 1H) 5.18 (br. s., 1H) 6.31 (d, J=2.20 Hz, 1H) 6.84 (br. s., 1H) 7.54 (s, 1H) 7.67 (br. s., 1H) 7.90 (br. s., 1H) 8.09 (br. s., 1H); HPLC: RT 1.72 min; MS: m/z: 393.1 [M+H]$^+$.

cis-N4-methyl-N2-[3-methyl-1-(3-pyrazol-1-ylcyclo butyl)pyrazol-4-yl]-5-(trifluoromethyl)pyrimidine-2,4-diamine (D-27)

$^1$H NMR (400 MHz, chloroform-d) δ ppm 2.28 (s, 3H) 3.13 (t, J=8.16 Hz, 7H) 4.53-4.75 (m, 2H) 5.25 (br. s., 1H) 6.29 (s, 1H) 6.99 (d, J=13.23 Hz, 1H) 7.55 (br. s., 2H) 8.13 (br. s., 1H) 8.21 (br. s., 1H); HPLC: RT 1.91 min; MS: m/z: 393.1 [M+H]$^+$.

Example D-32 and D-33

Synthesis of cis-N4-methyl-N2-[5-methyl-1-(3-methylsulfonylcyclobutyl)pyrazol-4-yl]-5-(trifluoromethyl)pyrimidine-2,4-diamine (D-50) and cis-N4-methyl-N2-[3-methyl-1-(3-methylsulfonyl cyclobutyl)pyrazol-4-yl]-5-(trifluoromethyl)pyrimidine-2,4-diamine (D-28)

cis-5-methyl-1-(3-methylsulfanylcyclobutyl)-4-nitro-pyrazole and cis-3-methyl-1-(3-methylsulfanylcyclobutyl)-4-nitro-pyrazole To a mixture of cis-[3-[5-methyl-4-nitro-pyrazol-1-yl]cyclobutyl]methanesulfonate and cis-[3-[-3-methyl-4-nitro-pyrazol-1-yl]cyclobutyl]methanesulfonate (1 g, 3.63 mmol) in NMP (10 mL) was added NaSMe (1.02 g, 14.52 mmol) at 20° C. The mixture was heated to 100° C. and stirred for 16 h. The reaction mixture was quenched by aq. sat. NH$_4$Cl (100 mL) at 0° C., and extracted with EtOAc (3×50 mL). The combined organic phases were washed with brine (50 mL), dried over Na$_2$SO$_4$, filtered and concentrated under reduced pressure to give a residue. The residue was purified by silica gel column chromatography (PE:EtOAc=30:1 to 10:1), to give a mixture of m-5-methyl-1-(3-methylsulfanylcyclobutyl)-4-nitro-pyrazole and cis-3-methyl-1-(3-methylsulfanylcyclobutyl)-4-nitro-pyrazole as a yellow oil. LCMS: RT 0.798 min, m/z=228.2 [M+H]$^+$.

cis-5-methyl-1-(3-methylsulfanylcyclobutyl)pyrazol-4-amine and cis-3-methyl-1-(3-methylsulfanylcyclobutyl)pyrazol-4-amine To a mixture of cis-5-methyl-1-(3-methylsulfanylcyclobutyl)-4-nitro-pyrazole and m-3-methyl-1-(3-methylsulfanylcyclobutyl)-4-nitro-pyrazole (200 mg, 879.97 µmol) in EtOH (4 mL) and H$_2$O (1 mL) was added Fe (148 mg, 2.64 mmol) and NH$_4$Cl (141 mg, 2.64 mmol) at 0° C. The mixture was heated to 90° C. for 1 h. The mixture was filtered and the filtrate was concentrated under reduced pressure to give a residue. Then, the residue was dissolved by MeCN (5 mL) and filtered. The filtrate was concentrated under reduce pressure to give crude cis-5-methyl-1-(3-methylsulfanylcyclobutyl)pyrazol-4-amine and cis-3-methyl-1-(3-methylsulfonylcyclobutyl)pyrazol-4-amine as brown oil, which was used in the next step without purification. LCMS: RT 1.113 min, m/z=198.1 [M+H]$^+$.

cis-N4-methyl-N2-[(5-methyl-1-(3-methylsulfanyl-cyclobutyl)pyrazol-4-yl]-5-(trifluoromethyl)pyrimidine-2,4-diamine and cis-N4-methyl-N2-[3-methyl-1-(3-methylsulfanylcyclobutyl)pyrazol-4-yl]-5-(trifluoromethyl)pyrimidine-2,4-diamine To a mixture of cis-5-methyl-1-(3-methylsulfanylcyclobutyl)pyrazol-4-amine and cis-3-methyl-1-(3-methylsulfanylcyclobutyl)pyrazol-4-amino (190 mg, 963 µmol) in 1,4-dioxane (4 mL) was added 2-chloro-N-methyl-5-(trifluoromethyl)pyrimidin-4-amine (204 mg, 963 µmol) and TsOH.H$_2$O (55 mg, 289 µmol) at 20° C. The mixture was heated to 80° C. and stirred for 2 h. The mixture was added with water (1 mL) and stirred for 3 min, then concentrated under reduced pressure to give a residue, which was purified by silica gel column chromatography (DCM:MeOH=20:1 to 5:1), to give a mixture of cis-N4-methyl-N2-[-5-methyl-1-(3-methylsulfanylcyclobutyl) pyrazol-4-yl]-5-(trifluoromethyl)pyrimidine-2,4-diamine and m-N4-methyl-N2-[3-methyl-1-(3-methylsulfanylcyclobutyl)pyrazol-4-yl]-5-(trifluoromethyl)pyrimidine-2,4-diamine as a yellow oil. LCMS: RT 2.747 min, m/z=373.1 [M+H]$^+$.

cis-N4-methyl-N2-[5-methyl-1-(3-methylsulfonylcyclobutyl)pyrazol-4-yl]-5-(trifluoromethyl)pyrimidine-2,4-diamine (D-50) and cis-N4-methyl-N2-[3-methyl-1-(3-methylsulfonyl cyclobutyl)pyrazol-4-yl]-5-(trifluoromethyl)pyrimidine-2,4-diamine (D-28)

To a mixture of N4-methyl-N2-[(1R)-5-methyl-1-(3-methylsulfanyl cyclobutyl)pyrazol-4-yl]-5-(trifluoromethyl)pyrimidine-2,4-diamine and N4-methyl-N2-[(1S)-3-methyl-1-(3-methylsulfanylcyclobutyl)pyrazol-4-yl]-5-(trifluororomethyl)pyrimidine-2,4-diamine (280 mg, 752 µmol) in THF (5 mL) and H$_2$O (1 mL) was added oxone (229 mg, 1.5 mmol) at 0° C. The mixture was stirred at 20° C. for 2 h. The mixture was quenched by aq. Na$_2$S$_2$O$_3$ (60 mL) and extracted with EtOAc (3×20 mL). The organic phase was washed by brine (20 mL), dried over Na$_2$SO$_4$, and concentrated under reduced pressure to give a residue, which was purified by prep-HPLC (FA condition) to give m-N4-methyl-N2-[5-methyl-1-(3-methylsulfonylcyclobutyl)pyrazol-4-yl]-5-(trifluoromethyl)pyrimidine-2,4-diamine (D-50) and cis-N4-methyl-N2-[3-methyl-1-(3-methylsulfonyl cyclobutyl)pyrazol-4-yl]-5-(trifluoromethyl)pyrimidine-2,4-diamine (D-28).

cis-N4-methyl-N2-[5-methyl-1-(3-methylsulfonylcyclobutyl)pyrazol-4-yl]-5-(trifluoromethyl)pyrimidine-2,4-diamine (D-50)

$^1$H NMR (400 MHz, chloroform-d) δ ppm 2.23 (br. s., 3H) 2.79-2.86 (m, 2H) 2.94 (s, 3H) 3.04 (d, J=4.85 Hz, 3H) 3.27 (q, J=9.70 Hz, 2H) 3.57-3.67 (m, 1H) 4.69 (quint., J=8.05 Hz, 1H) 5.20 (br. s., 1H) 6.27 (br. s., 1H) 7.94 (br. s., 1H) 8.07 (br. s., 1H); HPLC: RT 1.24 min: MS: m/z: 405.1 [M+H]$^+$.

cis-N4-methyl-N2-[3-methyl-1-(3-methylsulfonyl cyclobutyl)pyrazol-4-yl]-5-(trifluoromethyl)pyrimidine-2,4-diamine (D-28)

$^1$H NMR (400 MHz, chloroform-d) δ ppm 2.27 (s, 3H) 2.88 (s, 3H) 2.90-3.04 (m, 4H) 3.14 (br. s., 3H) 3.61 (quint, J=8.60 Hz, 1H) 4.80 (br. s., 1H) 5.32 (br. s., 1H) 7.46 (br. s, 1H) 8.10 (br. s., 1H) 8.23 (s, 1H): HPLC: RT 2.58 min; MS: m/z: 405.1 [M+H]$^+$.

Example D-34 and D-35

Synthesis of trans-2-[3-[4-[[5-(difluoromethyl-fluoranyl)-4-(methylamino)pyrimidin-2-yl]amino]-5-methyl-pyrazol-1-yl]cyclobutyl]acetonitrile (D-29) and traits-2-[3-[4-[[5-(difluoromethyl-fluoranyl)-4-(methylamino)pyrimidin-2-yl]amino]-3-methyl-pyrazol-1-yl]cyclobutyl]acetonitrile (D-30)

trans-methyl 3-(5-methyl-4-nitro-pyrazol-1-yl)cyclobutanecarboxylate and trans-methyl 3-(3-methyl-4-nitro-pyrazol-1-yl)cyclobutanecarboxylate To a solution of methyl 3-hydroxycyclobutanecarboxylate (2 g, 15.37 mmol), 5-methyl-4-nitro-1H-pyrazole (1.95 g, 15.37 mmol) and PPh$_3$ (6.05 g, 23.06 mmol) in THF (30 mL) was added dropwise DIAB (4.66 g, 23.06 mmol, 4.48 mL) at 0° C. and degassed and purged with N$_2$ for 3 times, and then the mixture was stirred at 25° C. for 16 h under N$_2$. The reaction mixture was concentrated under reduced pressure to remove THF. The residue was washed with PE:EtOAc (1:1, 30 mL), filtered and concentrated under reduced pressure to give a residue. The residue was purified by column chromatography (SiO$_2$, PE:EtOAc=10:1 to 5:1) to give the mixture of trans-methyl 3-(5-methyl-4-nitro-pyrazol-1-yl) cyclobutanecarboxylate and trans-methyl 3-(3-methyl-4-nitro-pyrazol-1-yl)cyclobutanecarboxylate as a white solid. LCMS: RT 0.729 min, m/z=240.2 [M+H]$^+$.

trans-[3-(5-methyl-4-nitro-pyrazol-1-yl)cyclobutyl] methanol and trans-[3-(3-methyl-4-nitro-pyrazol-1-yl)cyclobutyl]methanol To a solution of methyl 3-(5-methyl-4-nitro-pyrazol-1-yl) cyclobutanecarboxylate and methyl 3-(3-methyl-4-nitro-pyrazol-1-yl)cyclobutanecarboxylate (1.7 g, 7.11 mmol, mixture) in MeOH (20 mL) was added NaBH$_4$ (672 mg, 17.77 mmol) at 0° C. The mixture was stirred at 25° C. for 2 h. The reaction mixture was quenched by addition of aq. NH$_4$Cl (20 mL) at 0° C., and extracted with EtOAc (3×10 mL), washed with brine (5 mL), dried over Na$_2$SO$_4$, filtered and concentrated under reduced pressure. The residue was purified by column chromatography (SiO$_2$, PE:EtOAc=5:1 to 1:1) to give the mixture of trans-[3-(5-methyl-4-nitro-pyrazol-1-yl)cyclobutyl]methanol and trans-[3-(3-methyl-4-nitro-pyrazol-1-yl)cyclobutyl]methanol as a yellow solid. LCMS: RT 0.645 min, m/z=212.2 [M+H]$^+$.

trans-[3-(5-methyl-4-nitro-pyrazol-1-yl)cyclobutyl] methyl methanesulfonate and trans-[3-(3-methyl-4-nitro-pyrazol-1-yl)cyclobutyl]methyl methanesulfonate To a solution of [3-(5-methyl-4-nitro-pyrazol-1-yl)cyclobutyl]methanol and [3-(3-methyl-4-nitro-pyrazol-1-yl) cyclobutyl]methanol (300 mg, 1.42 mmol, mixture) in DCM (10 mL) was added MsCl (243 mg, 2.13 mmol, 164.86 µL) and TEA (287 mg, 2.84 mmol) at 0° C. Then the mixture was stirred at 25° C. for 20 min. The reaction mixture was concentrated under reduced pressure to remove CH$_3$CN (10 mL). The reaction mixture was quenched by addition water (20 mL) at 0° C., and then extracted with DCM (3×10 mL). The combined organic layers were washed with brine 10 mL, dried over Na$_2$SO$_4$, filtered and concentrated under reduced pressure to give the mixture of trans-[3-(5-methyl-4-nitro-pyrazol-1-yl)cyclobutyl]methyl methanesulfonate and trans-[3-(3-methyl-4-nitro-pyrazol-1-yl)cyclobutyl] methyl methanesulfonate as a yellow oil. LCMS: RT 0.746 min, m/z=290 [M+H]$^+$.

trans-2-[3-(3-methyl-4-nitro-pyrazol-1-yl)cyclobutyl]acetonitrile and trans-1-[3-(5-methyl-4-nitro-pyrazol-1-yl)cyclobutyl]acetonitrile A mixture of trans-[3-(5-methyl-4-nitro-pyrazol-1-yl)cyclobutyl]methyl methanesulfonate and trans-[3-(3-methyl-4-nitro-pyrazol-1-yl)cyclobutyl]methyl methanesulfonate (500 mg, 1.73 mmol), KCN (563 mg, 8.65 mmol) in DMF (10 mL) was degassed and purged with N$_2$ for 3 times, and then the mixture was stirred at 65° C. for 12 h under N$_2$. The reaction mixture was quenched by addition H$_2$O 50 mL at 0° C., and then extracted with EtOAc (3×10 mL). The combined organic layers were washed with brine 10 mL, dried over Na$_2$SO$_4$, filtered and concentrated under reduced pressure to give the mixture compound trans-2-[3-(3-methyl-4-nitro-pyrazol-1-yl)cyclobutyl]acetonitrile and trans-2-[3-(5-methyl-4-nitro-pyrazol-1-yl)cyclobutyl]acetonitrile as a red oil. LCMS: RT 0.792 min, m/z=221 [M+H]$^+$.

trans-2-[3-(4-amino-5-methyl-pyrazol-1-yl)cyclobutyl]acetonitrile and trans-2-[3-(4-amino-3-methyl-pyrazol-1-yl)cyclobutyl]acetonitrile A mixture of 2-[3-(5-methyl-4-nitro-pyrazol-1-yl)cyclobutyl]acetonitrile, and 2-[3-(3-methyl-4-nitro-pyrazol-1-yl)cyclobutyl]acetonitrile (300 mg, 1.36 mmol), Fe (379 mg, 6.80 mmol), NH$_4$Cl (363 mg, 6.80 mmol) in EtOH (4 mL) and H$_2$O (1 mL) was degassed and purged with N$_2$ for 3 times, and then the mixture was stirred at 80° C. for 2 h under N$_2$ atmosphere. The reaction mixture was concentrated under reduced pressure to remove EtOH. The residue was diluted with H$_2$O (20 mL) and extracted with EtOAc (3×10 mL). The combined organic layers were washed with aqueous brine 10 mL, dried over Na$_2$SO$_4$, filtered and concentrated under reduced pressure to give the mixture compound trans-2-[3-(4-amino-5-methyl-pyrazol-1-yl)cyclobutyl]acetonitrile and trans-2-[3-(4-amino-3-methyl-pyrazol-1-yl)cyclobutyl]acetonitrile as a red oil. LCMS: RT 0.099 min, m/z=191 [M+H]$^+$.

trans-2-[3-[4-[[5-(difluoromethyl-fluoranyl)-4-(methylamino)pyrimidin-2-yl]amino]-5-methyl-pyrazol-1-yl]cyclobutyl]acetonitrile (D-29) and trans-2-[3-[4-[[5-(difluoromethyl-fluoranyl)-4-(methylamino)pyrimidin-2-yl]amino]-3-methyl-pyrazol-1-yl]cyclobutyl]acetonitrile (D-30)

To a solution of 2-[3-(4-amino-5-methyl-pyrazol-1-yl)cyclobutyl]acetonitrile, and 2-[3-(4-amino-3-methyl-pyrazol-1-yl)cyclobutyl]acetonitrile (100 mg, 525.62 µmol) in 1,4-dioxane (3 mL) was added TsOH (45 mg, 262.81 µmol) and 2-chloro-N-methyl-5-(trifluoromethyl)pyrimidin-4-amine (89 mg, 420.50 µmol). The mixture was stirred at 80° C. for 2 h. The reaction mixture was concentrated under reduced pressure, and then purified by twice of prep-HPLC (FA condition, followed by neutral condition), to give desired compound trans-2-[3-[4-[[5-(difluoromethyl-fluoranyl)-4-(methylamino)pyrimidin-2-yl]amino]-5-methyl-pyrazol-1-yl]cyclobutyl]acetonitrile (D-29) and compound trans-2-[3-[4-[[5-(difluoromethyl-fluoranyl)-4-(methylamino)pyrimidin-2-yl]amino]-3-methyl-pyrazol-1-yl]cyclobutyl]acetonitrile (D-30). LCMS: RT 0.765 min, m/z=366.1 [M+H]$^+$.

trans-2-[3-[4-[[5-(difluoromethyl-fluoranyl)-4-(methylamino)pyrimidin-2-yl]amino]-5-methyl-pyrazol-1-yl]cyclobutyl]acetonitrile (D-29)

$^1$HNMR (400 MHz, CDCl$_3$) δ ppm 2.18 (s, 3H) 2.42 (ddd, J=12.57, 8.38, 3.75 Hz, 2H) 2.62 (d, J=6.62 Hz, 2H) 2.89-3.01 (m, 3H) 3.03 (d, J=4.85 Hz, 3H) 4.82-4.94 (m, 1H) 5.15 (br. s., 1H) 8.10 (s, 1H): HPLC. RT 2.71 min; MS: m/z: 366.1 [M+H]$^+$.

trans-2-[3-[4-[[5-(difluoromethyl-fluoranyl)-4-(methylamino)pyrimidin-2-yl]amino]-3-methyl-pyrazol-1-yl]cyclobutyl]acetonitrile (D-30)

$^1$H NMR (400 MHz, CDCl$_3$) δ ppm 2.28 (s, 3H) 2.42 (t, J=8.38 Hz, 2H) 2.60 (d, J=5.73 Hz, 2H) 2.79-2.93 (m, 3H) 2.99-3.14 (m, 3H) 4.77-4.90 (m, 1H) 5.18 (br. s., 1H) 6.54 (br. s., 1H) 7.88 (br. s, 1H) 8.14 (br. s., 1H); HPLC: RT 1.55 min; MS: m/z: 366.1 [M+H]$^+$.

Example D-36 and D-37

Synthesis of trans-N2-[1-[3-(difluoromethoxymethyl)cyclobutyl]-5-methyl-pyrazol-4-yl]-5-(difluoromethyl-fluoranyl)-N4-methyl-pyrimidine-2,4-diamine (D-31) and trans-N2-[1-[3-(difluoromethoxymethyl)cyclobutyl]-3-methyl-pyrazol-4-yl]-5-(difluoromethyl-fluoranyl)-N4-methyl-pyrimidine-2,4-diamine (D-32)

trans-methyl 3-(5-methyl-4-nitro-pyrazol-1-yl)cyclobutanecarboxylate and trans-methyl 3-(3-methyl-4-nitro-pyrazol-1-yl)cyclobutanecarboxylate To a solution of methyl 3-hydroxycyclobutanecarboxylate (2 g, 15.37 mmol), 5-methyl-4-nitro-1H-pyrazole (1.95 g, 15.37 mmol) and PPh$_3$ (6.05 g, 23.06 mmol) in THF (30 mL) was added dropwise DIAB (4.66 g, 23.06 mmol, 4.48 mL) at 0° C. and degassed and purged with N$_2$ for 3 times, and then the mixture was stirred at 25° C. for 16 h under N$_2$. The reaction mixture was concentrated under reduced pressure to remove THF. The residue was washed with PE:EtOAc (1:1.30 mL), filtered and concentrated under reduced pressure. The residue was purified by column chromatography (SiO$_2$, PE:EtOAc=10:1 to 5:1) to give the mixture of trans-methyl 3-(5-methyl-4-nitro-pyrazol-1-yl)cyclobutanecarboxylate and trans-methyl 3-(3-methyl-4-nitro-pyrazol-1-yl)cyclobutanecarboxylate as a white solid. LCMS: RT 0.729 min, m/z=240.2 [M+H]$^+$.

trans-[3-(5-methyl-4-nitro-pyrazol-1-yl)cyclobutyl]methanol and trans-[3-(3-methyl-4-nitro-pyrazol-1-yl)cyclobutyl]methanol To a solution of trans-methyl 3-(5-methyl-4-nitro-pyrazol-1-yl)cyclobutanecarboxylate, and trans-methyl 3-(3-methyl-4-nitro-pyrazol-1-yl)cyclobutanecarboxylate (1.7 g, 7.11 mmol, mixture) in MeOH (20 mL) was added NaBH$_4$ (672 mg, 17.77 mmol) at 0° C. The mixture was stirred at 25° C. for 2 h. The reaction mixture was quenched by addition of aq. NH$_4$Cl (20 mL) at 0° C., and extracted with EtOAc (3×10 mL), washed with brine (5 mL), dried over Na$_2$SO$_4$, filtered and concentrated under reduced pressure. The residue was purified by column chromatography (SiO$_2$, PE:EtOAc=5:1 to 1:1) to give the mixture of trans-[3-(5-methyl-4-nitro-pyrazol-1-yl)cyclobutyl]methanol and trans-[3-(3-methyl-4-nitro-pyrazol-1-yl)cyclobutyl]methanol as a yellow solid. LCMS: RT 0.645 min. m/z=212.2 [M+H]$^+$.

trans-1-[3-(difluoromethoxymethyl)cyclobutyl]-3-methyl-4-nitro-pyrazole and trans-1-[3-(difluoromethoxymethyl)cyclobutyl]-5-methyl-4-nitro-pyrazole A mixture of trans-[3-(5-methyl-4-nitro-pyrazol-1-yl)cyclobutyl]methanol, and trans-[3-(5-methyl-4-nitro-pyrazol-1-yl)cyclobutyl]methanol (500 mg, 2.37 mmol, mixture), CuI (90 mg, 474.00 µmol), 2,2-difluoro-2-(fluorosulfonyl)acetic acid (633 mg, 3.56 mmol, 368 µL) in CH$_3$CN (10 mL) was degassed and purged with N$_2$ for 3 times, and then the mixture was stirred at 55° C. for 2 h under N$_2$. The reaction mixture was concentrated under reduced pressure to remove CH$_3$CN (10 mL). The residue was purified by prep-TLC (SiO$_2$, PE:EtOAc=3:1) to give the mixture of trans-1-[3-(difluoromethoxymethyl)cyclobutyl]-3-methyl-4-nitro-pyrazole and trans-1-[3-(difluoromethoxymethyl)cyclobutyl]-5-methyl-4-nitro-pyrazole as a colorless oil. LCMS: RT 0.834 min, m/z=262 [M+H]$^+$.

trans-1-[3-(difluoromethoxymethyl)cyclobutyl]-5-methyl-pyrazol-4-amine and trans-1-[3-(difluoromethoxymethyl)cyclobutyl]-3-methyl-pyrazol-4-amine To a solution of 1-[3-(difluoromethoxymethyl)cyclobutyl]-3-methyl-4-nitro-pyrazole, and 1-[3-(difluoromethoxymethyl)cyclobutyl]-5-methyl-4-nitro-pyrazole (300 mg, 1.15 mmol, mixture) in EtOH (4 mL) and H$_2$O (1 mL) was added Fe (321 mg, 5.75 mmol) and NH$_4$Cl (307 mg, 5.75 mmol). The mixture was stirred at 80° C. for 2 h. The reaction mixture was concentrated under reduced pressure to remove EtOH. The residue was diluted with H$_2$O (10 mL) and extracted with EtOAc (3×10 mL). The combined organic layers were washed with brine (10 mL), dried over Na₂SO₄, filtered and concentrated under reduced pressure to give the mixture compound trans-1-[3-(difluoromethoxymethyl)cyclobutyl]-5-methyl-pyrazol-4-amine and trans-1-[3-(difluoromethoxymethyl)cyclobutyl]-3-methyl-pyrazol-4-amine as a red oil. LCMS: RT 0.266 min, m/z=232 [M+H]⁺.

trans-N2-[1-[3-(difluoromethoxymethyl)cyclobutyl]-5-methyl-pyrazol-4-yl]-5-(difluoromethyl-fluoranyl)-N4-methyl-pyrimidine-2,4-diamine (D-31) and trans-N2-[1-[3-(difluoromethoxymethyl)cyclobutyl]-3-methyl-pyrazol-4-yl]-5-(difluoromethyl-fluoranyl)-N4-methyl-pyrimidine-2,4-diamine (D-32)

A mixture of 2-chloro-N-methyl-5-(trifluoromethyl)pyrimidin-4-amino (123 mg, 583.81 µmol), trans-1-[3-(difluoromethoxy methyl)cyclobutyl]-5-methyl-pyrazol-4-amine, and trans-1-[3-(difluoromethoxymethyl)cyclobutyl]-3-methyl-pyrazol-4-amine (150 mg, 648.68 µmol, mixture), TsOH (111 mg, 648.68 µmol) in 1,4-dioxane (2 mL) was degassed and purged with N₂ for 3 times, and then the mixture was stirred at 80° C. for 2 h under N₂. The reaction mixture was concentrated under reduced pressure. The residue was purified by prep-HPLC (FA condition), to give desired compound trans-N2-[1-[3-(difluoromethoxymethyl)cyclobutyl]-5-methyl-pyrazol-4-yl]-5-(difluoromethyl-fluoranyl)-N4-methyl-pyrimidine-2,4-diamine (D-31) and compound trans-N2-[1-[3-(difluoromethoxymethyl)cyclobutyl]-3-methyl-pyrazol-4-yl]-5-(difluoromethyl-fluoranyl)-N4-methyl-pyrimidine-2,4-diamine (D-32). LCMS: RT 0.720 min, m/z=407.3 [M+H]⁺.

trans-N2-[1-[3-(difluoromethoxymethyl)cyclobutyl]-5-methyl-pyrazol-4-yl]-5-(difluoromethyl-fluoranyl)-N4-methyl-pyrimidine-2,4-diamine (D-31)

¹H NMR (400 MHz, CDCl₃) δ ppm 2.19 (s, 3H) 2.32-2.41 (m, 2H) 2.69-2.81 (m, 1H) 2.84-2.96 (m, 2H) 3.03 (d, J=4.85 Hz, 3H) 3.95-4.04 (m, 2H) 4.78 (quin, J=7.94 Hz, 1H) 5.18 (br. s., 1H) 6.08-6.51 (m, 2H) 8.08 (s, 1H); HPLC: RT 2.07 min; MS: m/z: 407.1 [M+H]⁺.

trans-N2-[1-[3-(difluoromethoxymethyl)cyclobutyl]-3-methyl-pyrazol-4-yl]-5-(difluoromethyl-fluoranyl)-N4-methyl-pyrimidine-2,4-diamine (D-32)

¹H NMR (400 MHz, CDCl₃) δ ppm 2.29 (s, 3H) 2.40 (t, J=8.82 Hz, 2H) 2.62-2.80 (m, 3H) 3.08 (br. s., 3H) 3.97 (d, J=5.73 Hz, 2H) 4.67-4.84 (m, 1H) 5.30 (br. s., 1H) 6.06-6.49 (m, 2H) 7.89 (br. s., 1H) 8.09 (br. s., 1H); HPLC: RT 2.06 min; MS: m/z: 407.3.

Example D-38

Synthesis of 2-(1-((5-chloro-4-((4-(methylamino)-5-(trifluoromethyl)pyrimidin-2-yl)amino)-1H-pyrazol-1-yl)methyl)cyclopropyl)acetonitrile (D-33)

A mixture of 2-[1-[(4-amino-5-chloro-pyrazol-1-yl)methyl]cyclopropyl]acetonitrile (70 mg, 332.29 µmol), 2-chloro-N-methyl-5-(trifluoromethyl)pyrimidin-4-amine (70 mg, 332.29 µmol) and TFA (76 mg, 664.58 µmol) in dioxane (3 mL) was degassed and purged with N₂ for 3 times, and then the mixture was stirred at 100° C. for 2 h under N₂. The reaction mixture was concentrated under reduced pressure. The residue was diluted with H₂O (20 mL), adjusted pH to 8 by adding aq. NaHCO₃ and then extracted with EtOAc (3×10 mL). The combined organic layers were washed with brine (10 mL), dried over Na₂SO₄, filtered and concentrated under reduced pressure. The residue was purified by prep-HPLC (neutral condition) to give 2-(1-((5-chloro-4-((4-(methylamino)-5-(trifluoromethyl)pyrimidin-2-yl)amino)-1H-pyrazol-1-yl)methyl)cyclopropyl) acetonitrile (D-33). ¹H NMR (400 MHz, CDCl₃): δ ppm 8.26 (s, 1H), 8.20 (s, 1H), 7.16 (br. s., 1H), 5.30 (br. s., 1H), 4.32 (s, 2H), 3.43 (s, 2H), 3.11 (d, J=4.77 Hz, 3H), 0.97-1.02 (m, 2H), 0.78-0.82 (m, 2H); HPLC: RT 2.50 min; MS: m/z: 386.0 [M+H]⁺.

Example D-39

Synthesis of N⁴-methyl-N²-(3-methyl-1-(5,6,7,8-tetrahydroimidazo[1,2-a]pyridin-8-yl)-1H-pyrazol-4-yl)-5-(trifluoromethyl)pyrimidine-2,4-diamine (D-34)

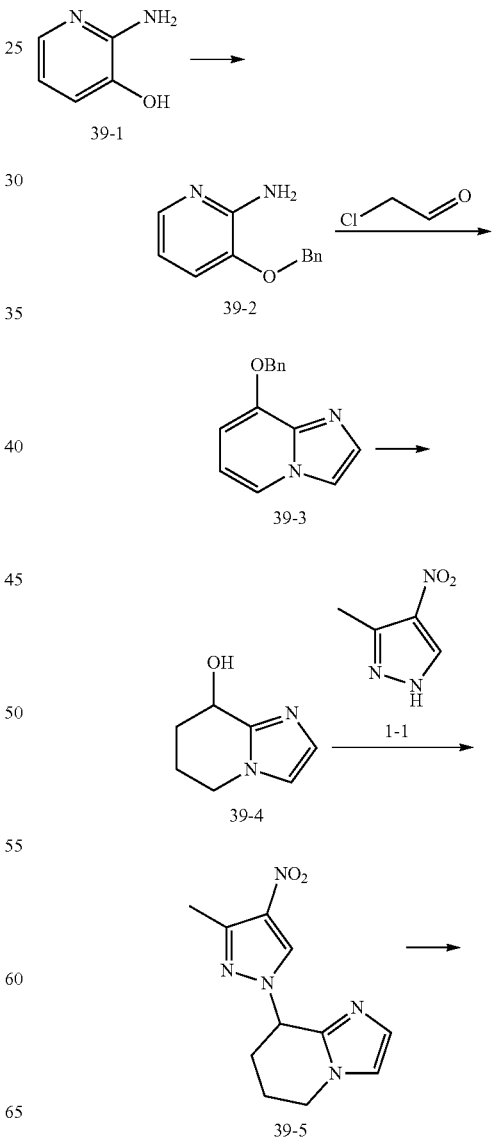

-continued

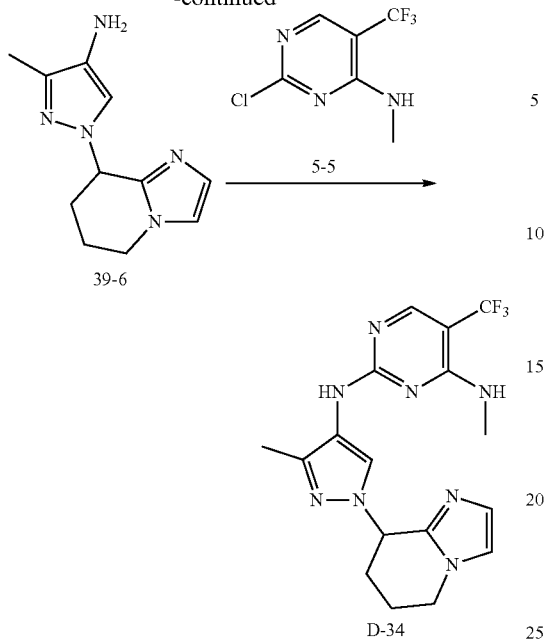

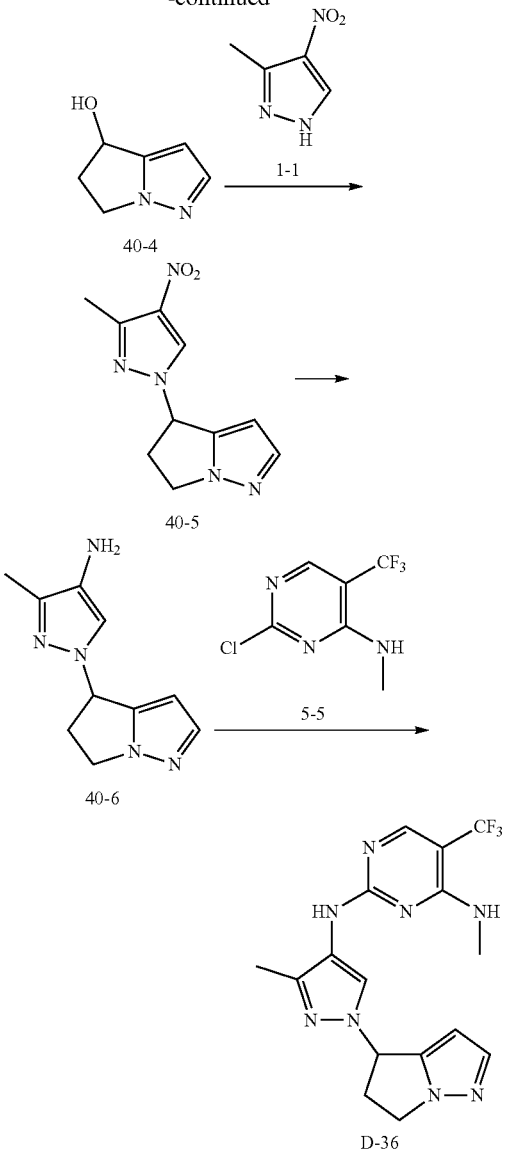

Compound 39-1 was combined with BnBr and CsCO₃ in DMF to give compound 39-2. Compound 39-2 was combined with 2-chloroacetaldehyde and K₂CO₃ in DMF to give compound 39-3. To compound 39-3 in MeOH was added Pd/C, and the mixture was stirred under H₂ to produce compound 39-4. Compound 39-4 was combined with compound 1-1, PPh₃, and DIAD in THF to give compound 39-5. To compound 39-5 in MeOH was added Pd/C, and the mixture was stirred under H₂ to produce compound 39-6. Compound 39-6, compound 5-5, and TsOH were combined in 1,4-dioxane to give compound D-34. MS m/z=393.1 [M+H]⁺.

Example D-40

Synthesis of N²-(1-(5,6-dihydro-4H-pyrrolo[1,2-b]pyrazol-4-yl)-3-methyl-1H-pyrazol-4-yl)-N⁴-methyl-5-(trifluoromethyl)pyrimidine-2,4-diamine (D-36)

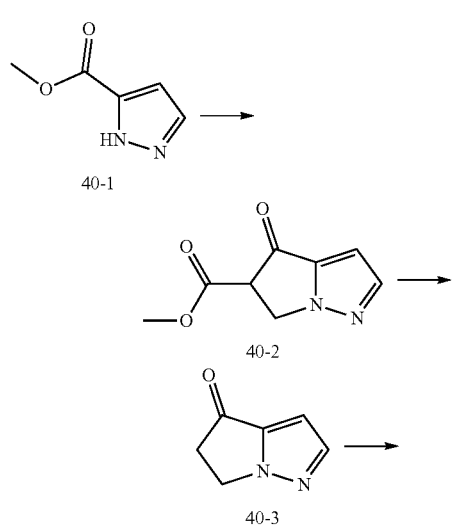

Compound 40-1 is first combined with methyl acrylate, and the subsequent product is then combined with potassium t-butoxide to give compound 40-2. To Compound 40-2 is added HCl to give compound 40-3. Compound 40-3 is combined with NaBH₄ in MeOH to produce compound 40-4. Compound 40-4 is combined with compound 1-1, PPh₃, and DIAD in THF to give compound 40-5. To compound 40-5 in MeOH is added Pd/C, and the mixture is stirred under H₂ to produce compound 40-6. Compound 40-6, compound 5-5, and TsOH are combined in 1,4-dioxane to give compound D-36.

Compound D-36 can also be synthesized according to the scheme below.

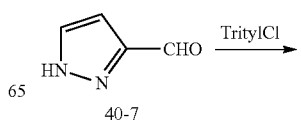

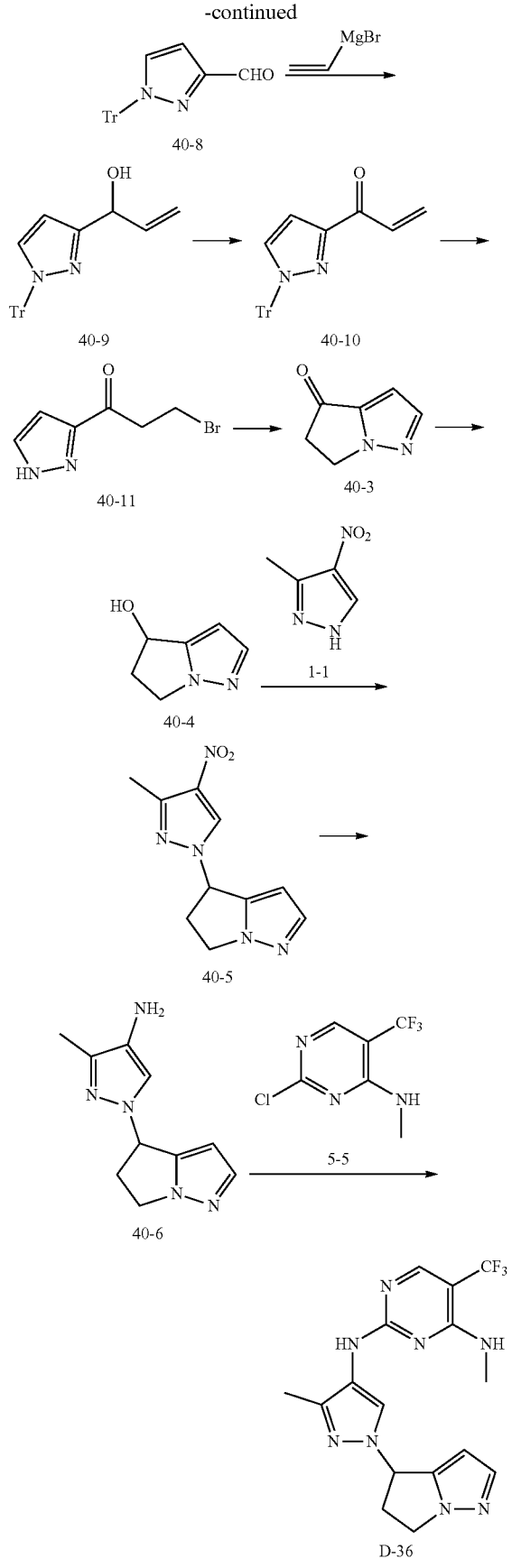

Compound 40-7 was combined with trityl chloride and TEA in DMF to give compound 40-8. Compound 40-8 was combined with vinylmagnesium bromide in THF to give compound 40-9. Compound 40-9 was combined with $MnO_2$ in dioxane to give compound 40-10. Compound 40-10 was combined with HBr and acetic acid to give Compound 40-11. Compound 40-11 was combined with $Cs_2CO_3$ in acetonitrile to give compound 40-3. Compound 40-3 was combined with $NaBH_4$ in MeOH to produce compound 40-4. Compound 40-4 was combined with compound 1-1, $PPh_3$, and DIAD in THF to give compound 40-5. To compound 40-5 in MeOH was added Pd/C, and the mixture is stirred under $H_2$ to produce compound 40-6. Compound 40-6, compound 5-5, and TsOH were combined in 1,4-dioxane to give compound D-36. MS m/z=379.2 $[M+H]^+$.

Example D-41

Synthesis of $N^2$-(1-(6,7-dihydro-5H-pyrrolo[1,2-c]imidazol-7-yl)-3-methyl-1H-pyrazol-4-yl)-$N^4$-methyl-5-(trifluoromethyl)pyrimidine-2,4-diamine (D-38)

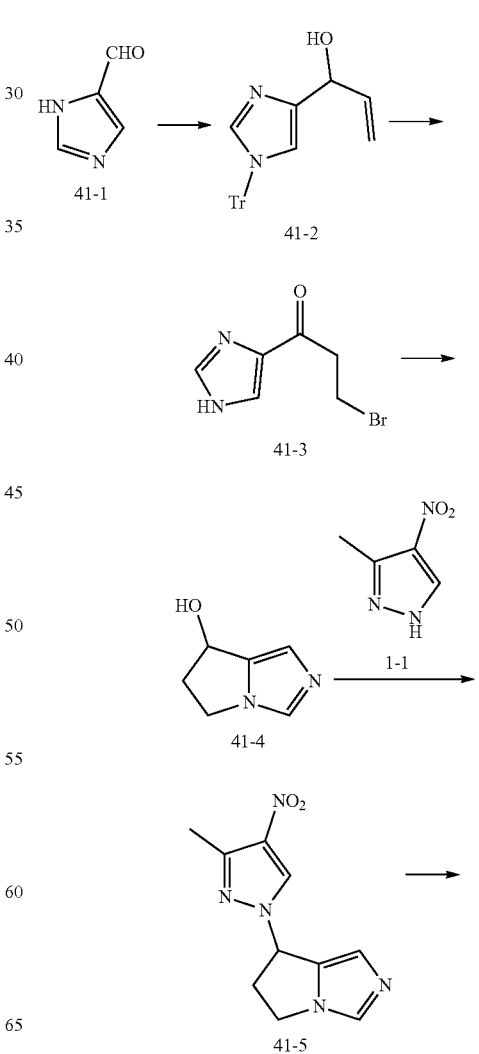

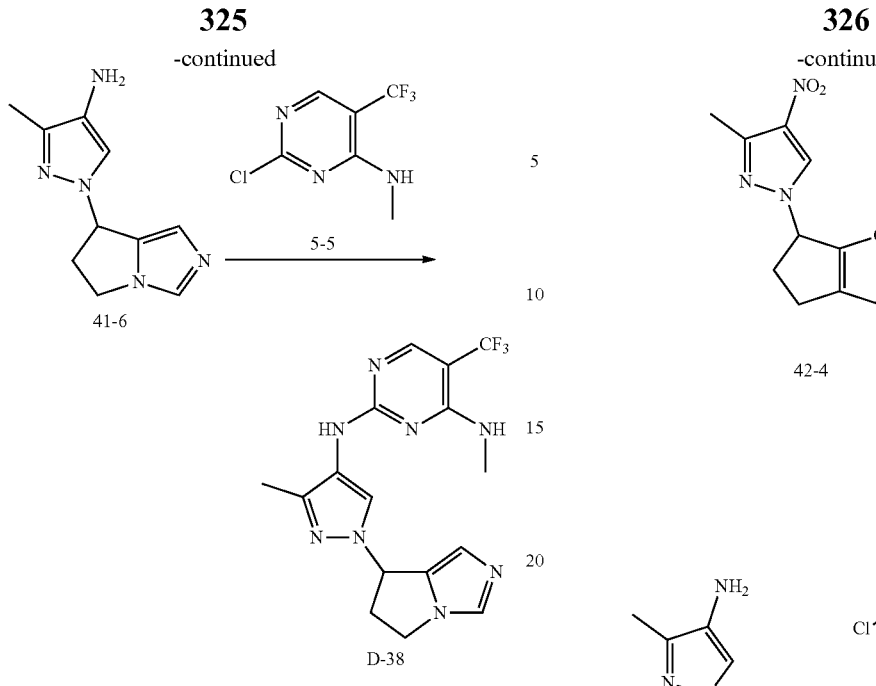

Compound 41-1 was combined with trityl chloride and TEA in DMF, and vinylmagnesium bromide was subsequently added to give compound 41-2. Compound 41-2 was combined with MnO$_2$, and HBr was subsequently added to give compound 41-3. Compound 41-3 was combined with TEA in MeCN, and NaBH) was subsequently added to give compound 41-4. Compound 41-4 was combined with compound 1-1, PPh$_3$, and DIAB in THF to give compound 41-5. To compound 41-5 in MeOH was added Pd/C, and the mixture was stirred under H$_2$ to produce compound 41-6. Compound 41-6, compound 5-5, and TsOH were combined in 1,4-dioxane to give compound D-38.

Example D-42

Synthesis of N$^4$-methyl-N$^2$-(3-methyl-1-(3-methyl-5,6-dihydro-4H-cyclopenta[d]isoxazol-6-yl)-1H-pyrazol-4-yl)-5-(trifluoromethyl)pyrimidine-2,4-diamine (D-35)

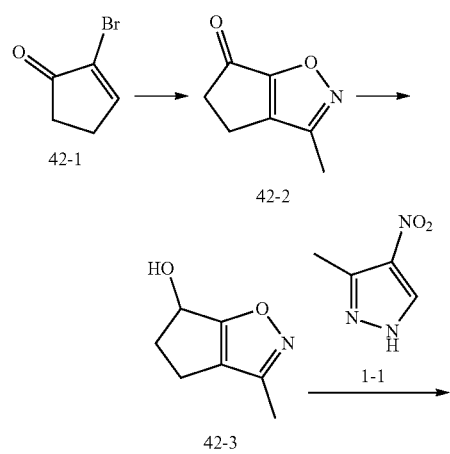

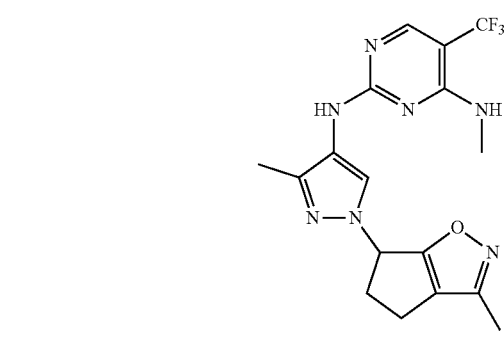

Compound 42-1 was combined with acetaldehyde oxime. N-chlorosuccinimide, and NaHCO$_3$ to give compound 42-2. Compound 42-2 was combined with NaBH$_4$ in MeOH to provide compound 42-3. Compound 42-3 was combined with compound 1-1, PPh$_3$, and DIAB in THF to give compound 42-4. To compound 42-4 in MeOH was added Pd/C, and the mixture was stirred under H$_2$ to produce compound 42-5. Compound 42-5, compound 5-5, and TsOH were combined in 1,4-dioxane to give compound B-35. MS m/z=394.1 [M+H]$^+$.

Example D-43

Synthesis of N⁴-methyl-N²-(3-methyl-1-(1-methyl-1,4,5,6-tetrahydrocyclopenta[c]pyrazol-4-yl)-1H-pyrazol-4-yl)-5-(trifluoromethyl)pyrimidine-2,4-diamine (D-37)

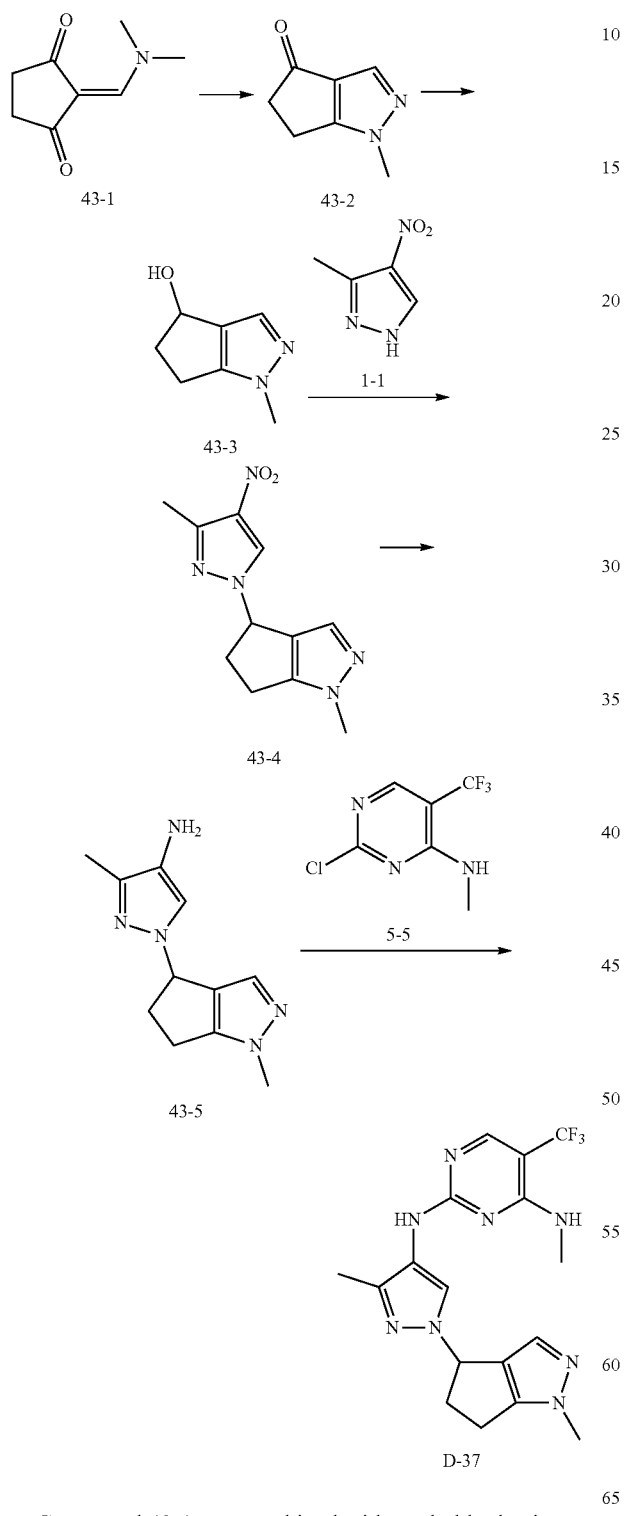

Compound 43-1 was combined with methyl hydrazine to give compound 43-2. Compound 43-2 was combined with NaBH₄ in MeOH to give compound 43-3. Compound 43-3 was combined with compound 1-1, PPh₃, and DIAB in THF to give compound 43-4. To compound 43-4 in MeOH was added Pd/C, and the mixture was stirred under H₂ to produce compound 43-5. Compound 43-5, compound 5-5, and TsOH were combined in 1,4-dioxane to give compound D-37. MS m/z=393.1 [M+H]⁺.

Example D-44

Synthesis of N2-(1-(5,6-dihydro-4H-cyclopenta[d]thiazol-6-yl)-3-methyl-1H-pyrazol-4-yl)-N4-methyl-5-(trifluoromethyl)pyrimidine-2,4-diamine (D-53), N2-(1-(5,6-dihydro-4H-cyclopenta[d]oxazol-6-yl)-3-methyl-1H-pyrazol-4-yl)-N4-methyl-5-(trifluoromethyl)pyrimidine-2,4-diamine (D-54), N2-(1-(5,6-dihydro-4H-cyclopenta[d]oxazol-4-yl)-3-methyl-1H-pyrazol-4-yl)-N4-methyl-5-(trifluoromethyl)pyrimidine-2,4-diamine (D-51), and N⁴-methyl-N²-(3-methyl-1-(1,4,5,6-tetrahydrocyclopenta[c]pyrazol-6-yl)-1H-pyrazol-4-yl)-5-(trifluoromethyl)pyrimidine-2,4-diamine (D-39)

Compounds D-53, D-43, D-51, and D-39 can be prepared according to the following general scheme, wherein: X is S, Y is CH, and Z is N for compound D-53; X is O, Y is CH, and Z is N for compound D-54; X is N, Y is CH, Z is O for compound D-51; and X is NH, Y is N, and Z is CH for compound D-39.

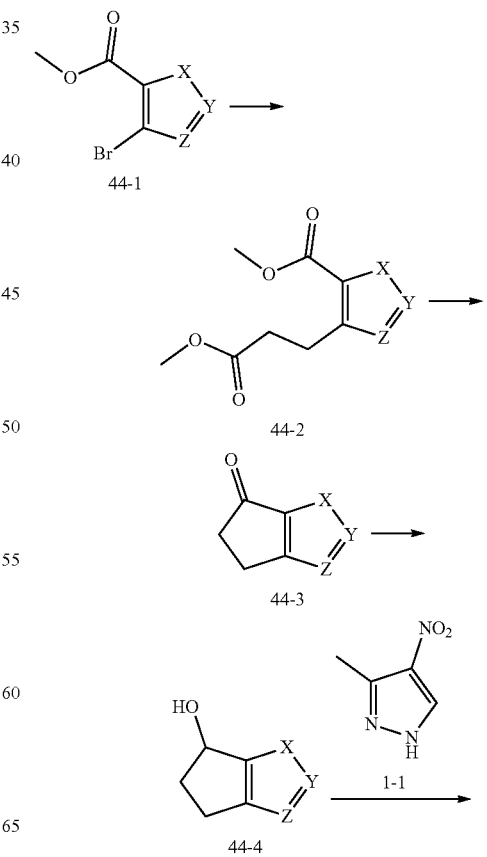

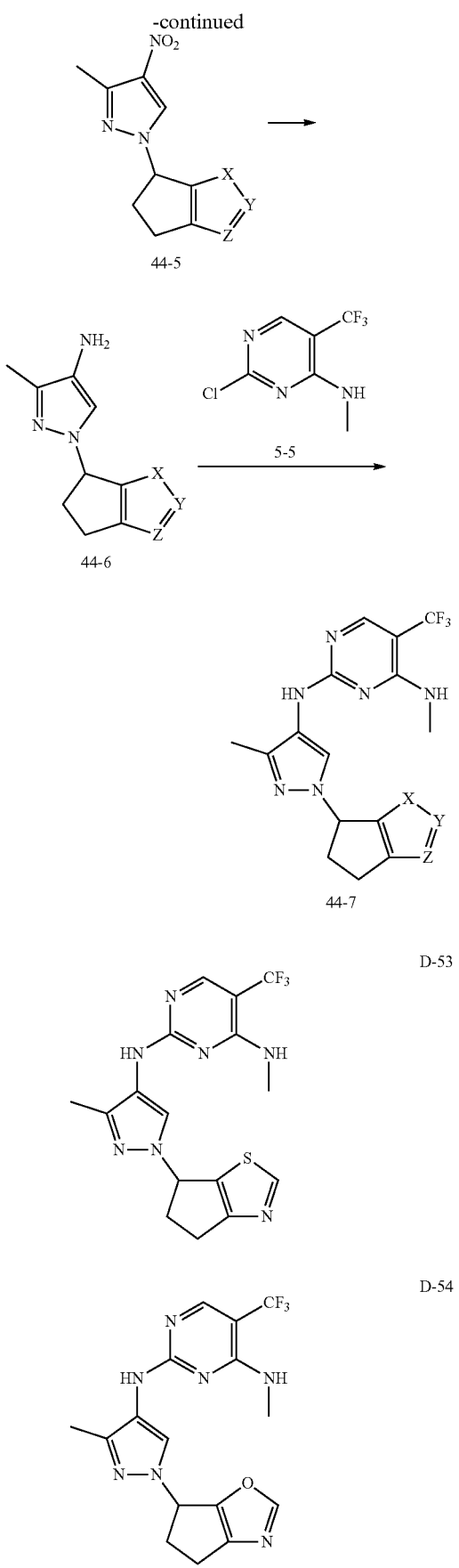
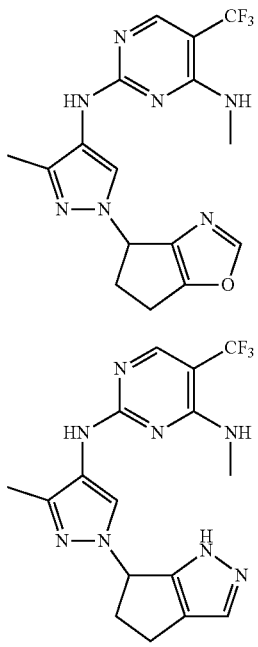

Compound 44-1 is combined with methyl acylate, Pd(PPh$_3$)$_4$, and TEA. Then, to the subsequent product is added Pd/C, and the mixture is stirred under H$_2$ to produce compound 44-2. Compound 44-2 is combined with potassium t-butoxide, followed by HCl, to give compound 44-3. Compound 44-3 is combined with NaBH$_4$ in MeOH to give compound 44-4. Compound 44-4 is combined with compound 1-1, PPh$_3$, and DIAD in THF to give compound 44-5. To compound 44-5 in MeOH is added Pd/C, and the mixture is stirred under H$_2$ to produce compound 44-6. Compound 44-6, compound 5-5, and TsOH are combined in 1,4-dioxane to give compound 44-7.

Example D-45

Synthesis of N$^2$-(1-(2-chloro-6,7-dihydro-5H-pyrrolo[1,2-a]imidazol-7-yl)-3-methyl-1H-pyrazol-4-yl)-N$^4$-methyl-5-(trifluoromethyl)pyrimidine-2,4-diamine (D-41)

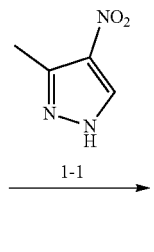

331
-continued

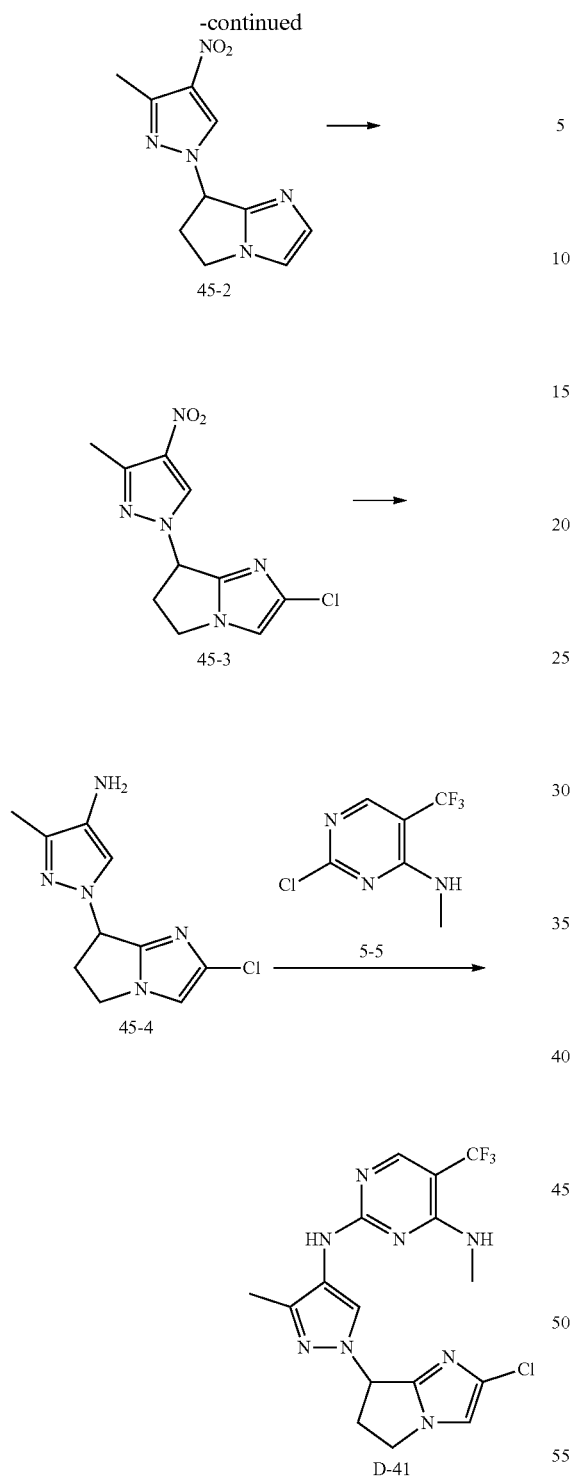

Compound 45-1 is combined with compound 1-1. PPh₃, and DIAB in THF to give compound 45-2. Compound 45-2 is combined with N-chlorosuccinimide to give compound 45-3. To compound 45-3 in MeOH is added Pd/C, and the mixture is stirred under H₂ to produce compound 45-4. Compound 45-4, compound 5-5, and TsOH are combined in 1,4-dioxane to give compound D-41.

332

Example D-46

Synthesis of N2-(1-(6,7-dihydro-5H-pyrrolo[1,2-a]imidazol-6-yl)-5-methyl-1H-pyrazol-4-yl)-N4-methyl-5-(trifluoromethyl)pyrimidine-2,4-diamine (D-55)

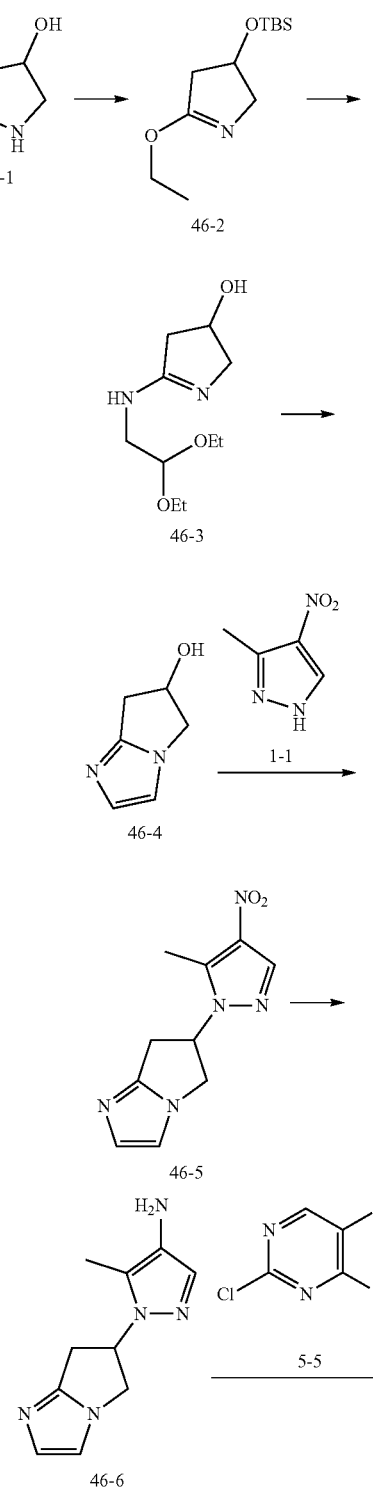

333
-continued

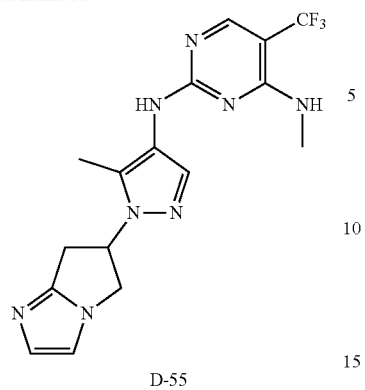

D-55

Compound 46-1 is combined with TBSCl and imidazole in DMF, and then $Et_3OBF_4$ is subsequently added to give compound 46-2. Compound 46-2 is combined with 2,2-diethoxyethan-1-amine and HCl in EtOH to give compound 46-3. Compound 46-3 is combined with HCl in 1,4-dioxane to give compound 46-4. Compound 46-4 is combined with compound 1-1, $PPh_3$, and DIAB in THF to give compound 46-5. To compound 46-5 in MeOH is added Pd/C, and the mixture is stirred under $H_2$ to produce compound 46-6. Compound 46-6, compound 5-5, and TsOH are combined in 1,4-dioxane to give compound D-55.

Example D-47

Synthesis of N2-(1-(5,6-dihydro-4H-pyrrolo[1,2-b]pyrazol-5-yl)-5-methyl-1H-pyrazol-4-yl)-N4-methyl-5-(trifluoromethyl)pyrimidine-2,4-diamine (D-52)

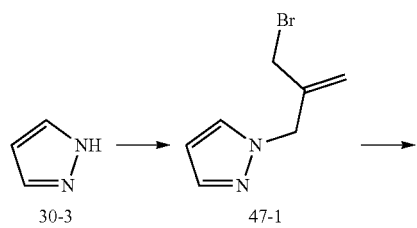

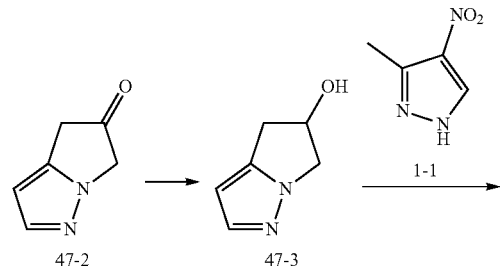

334
-continued

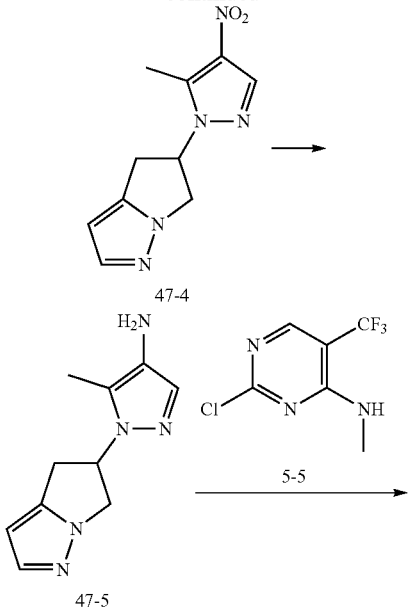

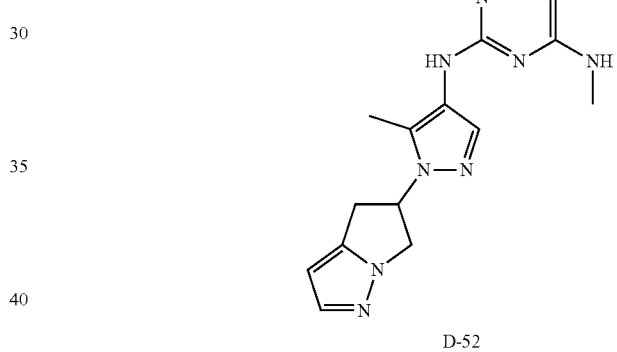

D-52

Compound 30-3 and 3-bromo-2-(bromomethyl)prop-1-ene are combined with $K_2CO_3$ in DMF to give compound 47-1. Compound 47-1 is combined with lithium bis(trimethylsilyl)amide to give compound 47-2. Compound 47-2 is combined with $NaBH_4$ in MeOH to give compound 47-3. Compound 47-3 is combined with compound 1-1, $PPh_3$, and DIAB in THF to give compound 47-4. To compound 47-4 in MeOH is added Pd/C, and the mixture is stirred under $H_2$ to produce compound 47-5. Compound 47-5, compound 5-5, and TsOH are combined in 1,4-dioxane to give compound D-52.

Compounds D-17 (MS: (M+H$^+$) m/z: 381.1) and D-18 (MS: (M+H$^+$) m/z: 381.1) were prepared according to Example D-21 and D-22. Compounds D-40, D-42, and D-43, are prepared according to the Examples above and/or general procedures described herein. Compounds D-176 to D-187 are also prepared according to the Examples above and/or general procedures described herein.

Compounds listed in Table D-3 were prepared according to the Examples above and/or general procedures described herein. Further, compound numbers of Table D-3 correspond to die compound numbers of Table D-1.

TABLE D-3

| No. | MS [M + H]+ |
|---|---|
| D-56 | 393.1 |
| D-57 | 410.1 |
| D-58 | 408.2 |
| D-59 | 408.1 |
| D-60 | 393.1 |
| D-61 | 476.2 |
| D-62 | 413.1 |
| D-63 | 443.2 |
| D-64 | 411.2 |
| D-65 | 393.7 |
| D-66 | 408.1 |
| D-67 | 379.1 |
| D-68 | 394.1 |
| D-69 | 408.2 |
| D-70 | 381.2 |
| D-71 | 393.1 |
| D-72 | 408.2 |
| D-73 | 408.1 |
| D-74 | 393.1 |
| D-75 | 444.1 |
| D-76 | 408.2 |
| D-77 | 394.2 |
| D-78 | 407.2 |
| D-79 | 408.1 |
| D-80 | 395.1 |
| D-81 | 426.2 |
| D-82 | 395.1 |
| D-83 | 411.1 |
| D-84 | 408.2 |
| D-85 | 420.1 |
| D-86 | 410.1 |
| D-87 | 443.2 |
| D-88 | 425.2 |
| D-89 | 425.2 |
| D-90 | 408.2 |
| D-91 | 408.1 |
| D-92 | 407.2 |
| D-93 | 407.2 |
| D-94 | 393.1 |
| D-95 | 407.2 |
| D-96 | 381.2 |
| D-97 | 410.1 |
| D-98 | 407.1 |
| D-99 | 413.1 |
| D-100 | 394.1 |
| D-101 | 380 |
| D-102 | 393.1 |
| D-103 | 424.2 |
| D-104 | 413.1 |
| D-105 | 413.1 |
| D-106 | 419.2 |
| D-107 | 408.2 |
| D-108 | 408.2 |
| D-109 | 408.1 |
| D-110 | 393.1 |
| D-111 | 403.1 |
| D-112 | 408.1 |
| D-113 | 408.2 |
| D-114 | 408.2 |
| D-115 | 394.2 |
| D-116 | 407.1 |
| D-117 | 408.2 |
| D-118 | 476.2 |
| D-119 | 420.1 |
| D-120 | 381.1 |
| D-121 | 379.1 |
| D-122 | 393.1 |
| D-123 | 408.1 |
| D-124 | 408.2 |
| D-125 | 408.2 |
| D-126 | 393.2 |
| D-127 | 380.1 |
| D-128 | 404.1 |
| D-129 | 407.1 |
| D-130 | 379.1 |
| D-131 | 393.1 |
| D-132 | 394.2 |

TABLE D-3-continued

| No. | MS [M + H]+ |
|---|---|
| D-133 | 408.2 |
| D-134 | 408.2 |
| D-135 | 476.2 |
| D-136 | 408.2 |
| D-137 | 379.1 |
| D-138 | 407.1 |
| D-139 | 424.2 |
| D-140 | 420.1 |
| D-141 | 408.1 |
| D-142 | 380.1 |
| D-143 | 408.2 |
| D-144 | 352.2 |
| D-145 | 393.1 |
| D-146 | 393.1 |
| D-147 | 419.2 |
| D-148 | 408.1 |
| D-149 | 408.2 |
| D-150 | 379.1 |
| D-151 | 407.2 |
| D-152 | 393.2 |
| D-153 | 426.2 |
| D-154 | 374.2 |
| D-155 | 366.1 |
| D-156 | 408.2 |
| D-157 | 393.1 |
| D-157a | 366.1 |
| D-158 | 380.2 |
| D-159 | 380.1 |
| D-160 | 394.1 |
| D-161 | 381 |
| D-162 | 394.2 |
| D-163 | 393.1 |
| D-164 | 400 |
| D-165 | 411.2 |
| D-166 | 379.1 |
| D-167 | 411.1 |
| D-168 | 411.1 |
| D-169 | 393.1 |
| D-170 | 407.2 |
| D-171 | 408.2 |
| D-172 | 393.1 |
| D-173 | 394.1 |
| D-174 | 395.1 |
| D-175 | 408.2 |
| D-178 | 406.1 |
| D-183 | 377.1 |
| D-184 | 405.0 |
| D-185 | 404.1 |
| D-186 | 361.1 |
| D-187 | 439.3 |
| D-188 | 393.1 |
| D-189 | 393.1 |
| D-190 | 358.1 |
| D-191 | 358.1 |
| D-192 | 421.1 |
| D-193 | 421.2 |
| D-194 | 439.3 |
| D-195 | 428.3 |
| D-196 | 428.3 |
| D-197 | 428.3 |
| D-198 | 428.3 |
| D-199 | 376.2 |
| D-200 | 376.1 |
| D-201 | 384.2 |
| D-202 | 384.2 |
| D-203 | 372.2 |
| D-204 | 390.3 |
| D-205 | 407.2 |
| D-206 | 407.2 |

Biological Example

Biochemical Assay of the Compounds

Materials.

LRRK2 G2019S enzyme, Substrate (LRRKtide), ATP, TR-FRET dilution buffer, pLRRKtide antibody, 384-well assay plate, and DMSO.

Enzyme Reaction Conditions:

50 mM Tris pH 7.5, 10 mM $MgCl_2$, 1 mM EGTA, 0.01% Brij-35, 2 mM DTT, 5 nM LRRK2, 134 μM ATP, 60 minute reaction time, 23° C. reaction temperature, and 10 μL total reaction volume.

Detection Reaction Conditions:

1×TR-FRET dilution buffer, 10 mM EDTA, 2 nM antibody, 23° C. reaction temperature, and 10 μL total reaction volume.

Compound solutions were prepared by initially diluting to 1 mM with DMSO. 35 μL of reference compound solution, 35 μL of test compound solution, and 35 μL HPE were successively added to the source plate (384-well assay plate, Labcyte). The plates were centrifuged at 2500 rpm for 1 minute and sealed in foil. POD was used to perform a 3.162 fold serial dilution and 100 nL of reference compound solution, test compound solution, HPE and ZPE were transferred to assay plates. The assay plate was centrifuged at 2500 rpm for 1 minute, and sealed with foil.

To perform the enzyme reaction, 5 μL of LRRKtide substrate and kinase mixture in assay buffer was added to all wells of the assay plate. The plate was centrifuged to concentrate the mixture at the bottom of the wells. The assay plate was incubated at 23° C. for 20 minutes. Following incubation, 5 μL of 2×ATP in assay buffer was added to each well, and plates were centrifuged to concentrate the mixture at the bottom of the wells. The plate was incubated at 23° C. for 60 minutes.

To perform the detection of the reaction, EDTA completely mixed in TR-FRET dilution buffer was added to antibody reagent. 10 μL of detection reagent was added to all wells of each well of the assay-plate and the plate was centrifuged to concentrate the mixture at the bottom of the wells. The plate was then incubated at 23° C. for 60 minutes. Plates were read on Perkin Elmer Envision 2104 instrument in TR-FRET mode using a 340 nm excitation filter, 520 nm fluorescence emission filter, and 490 or 495 nm terbium emission filter.

Representative compounds found in Table A-1, B-1, C-1, and D-1 were tested according to the above methods and found to exhibit an LRRK2 G2019S $IC_{50}$ as indicated in Table A-2. B-2, C2, and D-4 respectively.

TABLE A-2

Activity of Representative Compounds

| No. | $IC_{50}$ |
|---|---|
| A-1 | +++ |
| A-2 | +++ |
| A-3 | + |
| A-4 | ++ |
| A-5 | ++ |
| A-7 | +++ |
| A-8 | +++ |
| A-9 | ++ |
| A-10 | + |
| A-11 | ++ |

TABLE A-2-continued

Activity of Representative Compounds

| No. | $IC_{50}$ |
|---|---|
| A-12 | + |
| A-13 | + |
| A-14 | +++ |
| A-15 | +++ |
| A-16 | +++ |
| A-17 | ++ |
| A-18 | ++ |
| A-19 | ++ |
| A-20 | +++ |
| A-21 | ++ |
| A-22 | + |
| A-23 | +++ |
| A-24 | +++ |
| A-25 | ++ |
| A-26 | +++ |
| A-27 | + |
| A-28 | +++ |
| A-29 | +++ |
| A-30 | +++ |
| A-31 | +++ |
| A-32 | + |
| A-33 | + |
| A-34 | +++ |
| A-35 | +++ |
| A-36 | +++ |
| A-37 | + |
| A-38 | + |
| A-39 | +++ |
| A-40 | +++ |
| A-41 | +++ |
| A-42 | + |
| A-43 | +++ |
| A-44 | +++ |
| A-45 | +++ |
| A-46 | +++ |
| A-47 | +++ |
| A-48 | +++ |
| A-49 | + |
| A-50 | +++ |
| A-51 | +++ |
| A-52 | + |
| A-53 | +++ |
| A-54 | +++ |
| A-55 | +++ |
| A-56 | +++ |
| A-57 | + |
| A-58 | +++ |
| A-59 | +++ |
| A-60 | +++ |
| A-61 | ++ |
| A-62 | + |
| A-63 | ++ |
| A-64 | ++ |
| A-65 | +++ |
| A-66 | + |
| A-67 | +++ |
| A-68 | +++ |
| A-69 | +++ |
| A-70 | +++ |
| A-71 | +++ |
| A-72 | + |
| A-73 | +++ |
| A-74 | ++ |
| A-75 | +++ |
| A-76 | + |
| A-77 | +++ |
| A-78 | + |
| A-79 | +++ |
| A-80 | +++ |
| A-81 | +++ |
| A-82 | +++ |
| A-83 | +++ |
| A-84 | +++ |
| A-85 | +++ |

TABLE A-2-continued

Activity of Representative Compounds

| No. | IC$_{50}$ |
|---|---|
| A-86 | +++ |
| A-87 | +++ |
| A-88 | + |
| A-89 | +++ |
| A-90 | +++ |
| A-91 | ++ |
| A-92 | +++ |
| A-93 | +++ |
| A-94 | +++ |
| A-95 | +++ |
| A-96 | +++ |
| A-97 | ++ |

+++ = IC$_{50}$ less than 30 nM;
++ = IC$_{50}$ between 30 nM and 60 nM;
+ = IC$_{50}$ greater than 60 nM

TABLE B-2

Activity of Representative Compounds

| No. | IC$_{50}$ |
|---|---|
| B-1 | ++ |
| B-2 | +++ |
| B-3 | +++ |
| B-4 | + |
| B-5 | ++ |
| B-6 | +++ |
| B-7 | + |
| B-8 | ++ |
| B-9 | + |
| B-10 | ++ |
| B-11 | ++ |
| B-12 | + |
| B-13 | + |
| B-14 | + |

+ = IC$_{50}$ greater than 2 nm to 20 nM;
++ = IC$_{50}$ greater than 1 nm to 2 nM;
+++ = IC$_{50}$ 1 nM or less

TABLE C-2

Activity and MS data of Representative Compounds

| No. | IC$_{50}$ | [M + H]$^+$ |
|---|---|---|
| C-1 | +++ | 334.2 |
| C-2 | +++ | 334.2 |
| C-3 | ++ | 306.2 |
| C-4 | +++ | 306.1 |
| C-5 | +++ | 270.2 |
| C-6 | +++ | 270.1 |
| C-7 | +++ | 310.2 |
| C-8 | +++ | 308.2 |
| C-9 | +++ | 323.2 |
| C-10 | +++ | 347.2 |
| C-11 | +++ | 358.2 |
| C-12 | +++ | 358.2 |
| C-13 | +++ | 332.2 |
| C-14 | +++ | 340.2 |
| C-15 | + | 308.1 |
| C-16 | + | 308.2 |
| C-17 | + | 255.1 |
| C-18 | +++ | 294.2 |

TABLE C-2-continued

Activity and MS data of Representative Compounds

| No. | IC$_{50}$ | [M + H]$^+$ |
|---|---|---|
| C-19 | +++ | 294.2 |
| C-20 | +++ | 293.1 |
| C-21 | +++ | 279.1 |
| C-22 | +++ | 356.1 |
| C-23 | +++ | 322.2 |
| C-24 | +++ | 269.1 |
| C-25 | +++ | 269.1 |
| C-26 | +++ | 403.2 |
| C-27 | +++ | 378.2 |
| C-28 | +++ | 412.2 |
| C-29 | +++ | 396.2 |
| C-30 | +++ | 333.2 |
| C-31 | +++ | 333.2 |
| C-32 | +++ | 367.1 |
| C-33 | + | 284.1 |
| C-34 | + | 284.1 |
| C-35 | + | 269.1 |
| C-36 | +++ | 310.2 |
| C-37 | +++ | 378.2 |
| C-38 | +++ | 330.1 |
| C-39 | +++ | 330.1 |
| C-40 | +++ | 330.1 |
| C-41 | +++ | 362.2 |
| C-42 | +++ | 390.1 |
| C-43 | +++ | 360.1 |
| C-44 | +++ | 360.2 |
| C-45 | +++ | 334.1 = [M − H]$^-$ |
| C-46 | +++ | 336.2 |
| C-47 | +++ | 374.1 |
| C-48 | +++ | 350.1 |
| C-49 | +++ | 296.1 |
| C-50 | +++ | 296.1 |
| C-51 | +++ | 310.1 |
| C-52 | +++ | 310.1 |
| C-53 | +++ | 319.1 |
| C-54 | +++ | 319.1 |
| C-55 | +++ | 367.1 |

+++ = IC$_{50}$ less than 50 nM;
++ = IC$_{50}$ between 50 nM and 100 nM;
+ = IC$_{50}$ greater than 100 nM

TABLE D-4

Activity of Representative Compounds

| No. | IC$_{50}$ |
|---|---|
| D-1 | + |
| D-2 | +++ |
| D-3 | + |
| D-4 | +++ |
| D-5 | + |
| D-6 | +++ |
| D-7 | +++ |
| D-8 | + |
| D-9 | +++ |
| D-10 | ++ |
| D-11 | +++ |
| D-12 | +++ |
| D-13 | +++ |
| D-14 | +++ |
| D-15 | +++ |
| D-16 | +++ |
| D-17 | +++ |
| D-18 | + |
| D-19 | +++ |
| D-20 | + |

TABLE D-4-continued

Activity of Representative Compounds

| No. | IC$_{50}$ |
|---|---|
| D-21 | ++ |
| D-22 | +++ |
| D-23 | + |
| D-24 | +++ |
| D-25 | +++ |
| D-26 | +++ |
| D-27 | +++ |
| D-28 | +++ |
| D-29 | +++ |
| D-30 | +++ |
| D-31 | +++ |
| D-32 | +++ |
| D-33 | +++ |
| D-34 | +++ |
| D-35 | +++ |
| D-36 | + |
| D-37 | ++ |
| D-44 | +++ |
| D-45 | +++ |
| D-46 | ++ |
| D-47 | + |
| D-48 | +++ |
| D-49 | +++ |
| D-50 | +++ |
| D-56 | +++ |
| D-57 | +++ |
| D-58 | +++ |
| D-59 | +++ |
| D-60 | +++ |
| D-61 | +++ |
| D-62 | + |
| D-63 | +++ |
| D-64 | +++ |
| D-65 | +++ |
| D-66 | +++ |
| D-67 | + |
| D-68 | + |
| D-69 | +++ |
| D-70 | +++ |
| D-71 | +++ |
| D-72 | + |
| D-73 | +++ |
| D-74 | +++ |
| D-75 | +++ |
| D-76 | +++ |
| D-77 | +++ |
| D-78 | + |
| D-79 | +++ |
| D-80 | +++ |
| D-81 | +++ |
| D-82 | +++ |
| D-83 | +++ |
| D-84 | +++ |
| D-85 | +++ |
| D-86 | +++ |
| D-87 | +++ |
| D-88 | +++ |
| D-89 | +++ |
| D-90 | +++ |
| D-91 | +++ |
| D-92 | ++ |
| D-93 | +++ |
| D-94 | +++ |
| D-95 | + |
| D-96 | +++ |
| D-97 | +++ |
| D-98 | +++ |
| D-99* | +++ |
| D-100 | +++ |
| D-101 | +++ |
| D-102 | +++ |
| D-103 | +++ |
| D-104 | +++ |
| D-105 | +++ |
| D-106 | +++ |
| D-107 | +++ |
| D-108 | +++ |
| D-109 | +++ |
| D-110 | +++ |
| D-111 | +++ |
| D-112 | +++ |
| D-113 | +++ |
| D-114 | +++ |
| D-115 | + |
| D-116 | +++ |
| D-117 | +++ |
| D-118 | +++ |
| D-119 | +++ |
| D-120 | +++ |
| D-121 | +++ |
| D-122 | +++ |
| D-123 | +++ |
| D-124 | +++ |
| D-125 | ++ |
| D-126 | + |
| D-127 | +++ |
| D-128 | +++ |
| D-129 | +++ |
| D-130 | ++ |
| D-131 | +++ |
| D-132 | +++ |
| D-133 | +++ |
| D-134 | +++ |
| D-135 | +++ |
| D-136 | +++ |
| D-137 | +++ |
| D-138 | +++ |
| D-139 | +++ |
| D-140 | +++ |
| D-141 | +++ |
| D-142 | + |
| D-143 | ++ |
| D-144 | +++ |
| D-145 | +++ |
| D-146 | +++ |
| D-147 | +++ |
| D-148 | +++ |
| D-149 | ++ |
| D-150 | +++ |
| D-151 | +++ |
| D-152 | +++ |
| D-153 | +++ |
| D-154 | +++ |
| D-155 | +++ |
| D-156 | +++ |
| D-157 | +++ |
| D-157a | +++ |
| D-158 | +++ |
| D-159 | +++ |
| D-160 | +++ |
| D-161 | +++ |
| D-162 | +++ |
| D-163 | +++ |
| D-164 | +++ |
| D-165 | +++ |
| D-166 | +++ |
| D-167 | +++ |
| D-168 | +++ |
| D-169 | + |
| D-170 | +++ |
| D-171 | +++ |
| D-172 | +++ |
| D-173 | + |
| D-174 | +++ |
| D-175 | +++ |
| D-178 | +++ |
| D-183 | +++ |
| D-184 | +++ |

TABLE D-4-continued

Activity of Representative Compounds

| No. | IC$_{50}$ |
|---|---|
| D-185 | +++ |
| D-186 | +++ |
| D-187 | +++ |
| D-188 | + |
| D-189 | +++ |
| D-190 | +++ |
| D-191 | +++ |
| D-192 | +++ |
| D-193 | +++ |
| D-194 | +++ |
| D-195 | +++ |
| D-196 | +++ |
| D-197 | +++ |
| D-198 | +++ |
| D-199 | +++ |
| D-200 | +++ |
| D-201 | +++ |
| D-202 | +++ |
| D-203 | +++ |
| D-204 | +++ |
| D-205 | + |
| D-206 | +++ |

+++ = IC$_{50}$ less than 30 nM;
++ = IC$_{50}$ between 30 nM and 60 nM;
+ = IC$_{50}$ greater than 60 nM
*Data for D-99 either refers to D-99, D-41, or a mixture of D-41 and D-99.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of die invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within die generic disclosure also form part of the invention. This includes the generic description of the invention with a proviso or negative limitation removing any subject matter from die genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to diose skilled in the art to which the disclosure pertains.

What is claimed is:
1. A compound of formula (D-I):

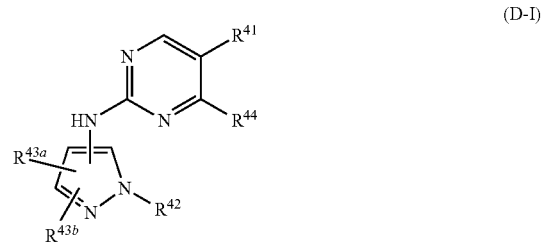

(D-I)

or a pharmaceutically acceptable salt, stereoisomer, or a mixture of stereoisomers thereof, wherein:

$R^{41}$ is halo, cyano, $C_{1-6}$ alkyl, $C_{1-6}$ haloalkyl, $C_{1-6}$ alkoxy, $C_{1-6}$ haloalkoxy, cycloalkyl, cycloalkoxy, cycloalkylalkyl, cycloalkylalkoxy, or —C(O)R$^{45}$;

$R^{42}$ is:

a fused bicyclic ring system having a heterocyclyl or cycloalkyl fused to a heteroaryl, wherein the ring system is attached to the remainder of the molecule via the heterocyclyl or cycloalkyl and the ring system is independently optionally substituted with one or more halo, cyano, $C_{1-6}$ alkyl, $C_{1-6}$ haloalkyl, $C_{1-6}$ alkoxy, amino, $C_{1-6}$ hydroxyalkyl, $C_{1-6}$ alkoxyalkyl, $C_{1-6}$ cyanoalkyl, $C_{1-6}$ aminoalkyl, —S(O)$_2$(C$_{1-6}$ alkyl), —C$_{1-6}$ alkylene-S(O)$_2$(C$_{1-6}$ alkyl), —C(O)NR$^{46}$R$^{47}$, —NR$^{46}$C(O)R$^{47}$, —C$_{1-6}$ alkylene-C(O)NR$^{46}$R$^{47}$, —C$_{1-6}$ alkylene-NR$^{46}$C(O)R$^{47}$, —SO$_2$NR$^{46}$R$^{47}$, —NR$^{46}$SO$_2$R$^{47}$, —C$_{1-6}$ alkylene-SO$_2$NR$^{46}$R$^{47}$, —C$_{1-6}$ alkylene-NR$^{46}$SO$_2$R$^{47}$, —C(O)R$^{46}$, —OC(O)R$^{46}$, —C(O)$_2$R$^{46}$, —C$_{1-6}$ alkylene-C(O)R$^{46}$, —C$_{1-6}$ alkylene-OC(O)R$^{46}$, —C$_{1-6}$ alkylene-C(O)$_2$R$^{46}$, —O—C(O)NR$^{46}$R$^{47}$, —NR$^{46}$C(O)OR$^{47}$, —C$_{1-6}$ alkylene-O—C(O)NR$^{46}$R$^{47}$, —C$_{1-6}$ alkylene-NR$^{46}$C(O)OR$^{47}$, cycloalkyl, cycloalkylalkyl, heterocyclyl, heterocyclylalkyl, aryl, arylalkyl, heteroaryl, or heteroarylalkyl;

$C_{1-6}$ alkoxyalkyl substituted with one or more substituents independently selected from halo, amino, cyano, hydroxy, $C_{1-6}$ haloalkoxy, $C_{2-6}$ alkenyl, $C_{2-6}$ alkynyl, cyanoalkyl, —S(O)$_2$(C$_{1-6}$ alkyl), —C(O)NR$^{46}$R$^{47}$, —NR$^{46}$C(O)R$^{47}$, —SO$_2$NR$^{46}$R$^{47}$, —NR$^{46}$SO$_2$R$^{47}$, —C(O)R$^{46}$, —OC(O)R$^{46}$, —C(O)$_2$R$^{46}$, —O—C(O) NR$^{46}$R$^{47}$, —NR$^{46}$C(O)OR$^{47}$, cycloalkyl, cycloalkylalkyl, heterocyclyl, heterocyclylalkyl, aryl, arylalkyl, heteroaryl, or heteroarylalkyl;

$C_{1-6}$ haloalkyl substituted with one or more substituents independently selected from amino, cyano, hydroxy, $C_{1-6}$ alkoxy, $C_{1-6}$ haloalkoxy, $C_{2-6}$ alkenyl, $C_{2-6}$ alkynyl, cyanoalkyl, —S(O)$_2$(C$_{1-6}$ alkyl), —C(O)NR$^{46}$R$^{47}$, —NR$^{46}$C(O)R$^{47}$, —SO$_2$NR$^{46}$R$^{47}$, —NR$^{46}$SO$_2$R$^{47}$, —C(O)R$^{46}$, —OC(O)R$^{46}$, —C(O)$_2$R$^{46}$, —O—C(O)NR$^{46}$R$^{47}$, —NR$^{46}$C(O)OR$^{47}$, cycloalkyl, cycloalkylalkyl, heterocyclyl, heterocyclylalkyl, aryl, arylalkyl, heteroaryl, or heteroarylalkyl;

C$_{1-6}$ cyanoalkyl optionally substituted with one or more substituents independently selected from halo, amino, hydroxy, C$_{1-6}$ haloalkoxy, C$_{2-6}$ alkenyl, C$_{2-6}$ alkynyl, —S(O)$_2$(C$_{1-6}$ alkyl), —C(O)NR$^{46}$R$^{47}$, —NR$^{46}$C(O)R$^{47}$, —SO$_2$NR$^{46}$R$^{47}$, —NR$^{46}$SO$_2$R$^{47}$, —C(O)R$^{46}$, —OC(O)R$^{46}$, —C(O)$_2$R$^{46}$, —O—C(O)NR$^{46}$R$^7$, —NR$^{46}$C(O)OR$^{47}$, cycloalkyl, cycloalkylalkyl, heterocyclyl, heterocyclylalkyl, aryl, arylalkyl, heteroaryl, or heteroarylalkyl;

C$_{3-10}$ cycloalkyl substituted with one or more substituents independently selected from amino, C$_{2-6}$ alkenyl, C$_{2-6}$ alkynyl, cyanoalkyl, —S(C$_{1-6}$ alkyl), —S(O)(C$_{1-6}$ alkyl), —S(O)$_2$(C$_{1-6}$ alkyl), —C$_{1-6}$ alkylene-S(O)$_2$(C$_{1-6}$ alkyl), C$_{1-6}$ haloalkoxy, C$_{1-6}$ hydroxyalkyl, C$_{1-6}$ alkoxyalkyl substituted with one or more halo, cycloalkyl, cycloalkylalkyl, heterocyclyl, aryl, arylalkyl, heteroaryl, or heteroarylalkyl, wherein the heterocyclyl, heteroaryl or heteroarylalkyl are optionally substituted with one or more substituents independently selected from C$_{1-6}$ alkyl, C$_{1-6}$ haloalkyl, or halo; or X—C(R$^{48}$)(R$^{49}$)(R$^{50}$), wherein:
X is C$_{1-6}$ alkylene optionally substituted with one or more halo;
R$^{48}$ and R$^{49}$, together with the carbon atom to which they are attached, form an optionally substituted C$_{3-10}$ cycloalkyl; and
R$^{50}$ is cyanoalkyl, C$_{1-6}$ alkoxyalkyl, C$_{2-6}$ alkenyl, C$_{2-6}$alkynyl, —S(O)$_2$(C$_{1-6}$ alkyl), C$_{1-6}$ haloalkoxy, C$_{1-6}$ hydroxyalkyl, C$_{1-6}$ alkoxyalkyl, cycloalkyl, cycloalkylalkyl, heterocyclyl, heterocyclylalkyl, aryl, arylalkyl, heteroaryl, or heteroarylalkyl;

R$^{43a}$ and R$^{43b}$ are each independently H, halo, cyano, C$_{1-6}$ alkyl, C$_{1-6}$ haloalkyl, C$_{1-6}$ hydroxyalkyl, C$_{1-6}$ alkoxyalkyl, C$_{1-6}$ cyanoalkyl, C$_{1-6}$ aminoalkyl, —S(O)$_2$(C$_{1-6}$ alkyl), —C$_{1-6}$ alkylene-S(O)$_2$(C$_{1-6}$ alkyl), cycloalkyl, cycloalkylalkyl, heterocyclyl, heterocyclylalkyl, aryl, arylalkyl, heteroaryl, heteroarylalkyl, amido, or —C(O)R$^{45}$;

R$^{44}$ is —N(R$^{51}$)$_2$, —OR$^{51}$, or —SR$^{51}$;

each R$^{45}$ is independently C$_{1-6}$ alkyl, C$_{1-6}$ alkoxy, —N(R$^{52}$)$_2$, or heterocyclyl, wherein each C$_{1-6}$ alkyl, C$_{1-6}$ alkoxy, or heterocyclyl is optionally substituted;

each R$^{56}$ and R$^{57}$ is independently H, C$_{1-6}$ alkyl, C$_{2-6}$ alkenyl, C$_{2-6}$ alkynyl, cycloalkyl, heterocyclyl, aryl, heteroalkyl, or heteroaryl, wherein each C$_{1-6}$ alkyl, C$_{2-6}$ alkenyl, C$_{2-6}$ alkynyl, cycloalkyl, heterocyclyl, aryl, heteroalkyl, or heteroaryl is optionally substituted;

each R$^{51}$ is independently H, unsubstituted C$_{1-6}$ alkyl, C$_{2-6}$ alkenyl, C$_{2-6}$ alkynyl, C$_{1-6}$ haloalkyl, C$_{1-6}$ alkoxyalkyl, C$_{1-6}$ hydroxyalkyl, C$_{1-6}$ aminoalkyl, —C$_{1-6}$ alkylene-S(O)$_2$(C$_{1-6}$ alkyl), C$_{3-6}$ cycloalkyl optionally substituted with one or more C$_{1-6}$ alkyl, C$_{3-6}$ cycloalkylalkyl optionally substituted with one or more C$_{1-6}$ alkyl, heterocyclyl optionally substituted with one or more R$^{53}$, or heterocyclylalkyl optionally substituted with one or more R$^{53}$; or two R$^{51}$, together with the nitrogen to which they are attached, form a three- to six-membered heterocyclyl optionally substituted with one or more R$^{53}$;

each R$^{52}$ is independently H or optionally substituted C$_{1-6}$ alkyl;

each R$^{53}$ is independently C$_{1-6}$ alkyl, C$_{1-6}$ haloalkyl, halo, oxo, C$_{1-6}$ alkoxy, amino, —S(O)$_2$(C$_{1-6}$ alkyl), C$_{1-6}$ alkoxyalkyl, cyano, heterocyclyl, heterocyclylalkyl, C$_{3-6}$ cycloalkyl, C$_{3-6}$ cycloalkylalkyl, C$_{3-6}$ cycloalkylsulfonyl, —C(O)R$^{54}$, or —C$_{1-6}$alkylene-C(O)R$^{54}$;

each R$^{54}$ is independently C$_{1-6}$ alkyl, C$_{1-6}$ alkoxy, amino optionally substituted with halo, C$_{1-6}$ haloalkyl, C$_{1-6}$ hydroxyalkyl, hydroxy, C$_{1-6}$ alkoxyalkyl, C$_{1-6}$ cyanoalkyl, —C$_{1-6}$ alkylene-S(O)$_2$(C$_{1-6}$ alkyl), C$_{1-6}$ aminoalkyl, C$_{3-6}$ cycloalkyl, C$_{3-6}$ cycloalkylalkyl, heterocyclyl, or heterocyclylalkyl;

wherein each heterocyclyl is independently a 3- to 18-membered non-aromatic heterocyclyl comprising two to twelve carbon atoms and one to six heteroatoms selected from the group consisting of nitrogen, oxygen and sulfur; and each heteroaryl is independently a 5- to 14-membered heteroaryl comprising one to thirteen carbon atoms and one to six heteroatoms selected from the group consisting of nitrogen, oxygen and sulfur; and provided that when R$^{44}$ is —N(R$^{51}$)$_2$ or —OR$^{51}$, R$^{42}$ is not an unsubstituted C$_{1-6}$ cyanoalkyl.

2. The compound of claim 1, wherein R$^{41}$ is halo, cyano, C$_{1-6}$ alkyl, or C$_{1-6}$ haloalkyl.

3. The compound of claim 1, wherein one of R$^{43a}$ or R$^{43b}$ is H, and the other of R$^{43a}$ or R$^{43b}$ is halo, cyano, C$_{1-6}$ alkyl, C$_{1-6}$ haloalkyl, C$_{1-6}$ hydroxyalkyl, C$_{1-6}$ alkoxyalkyl, C$_{1-6}$ cyanoalkyl, C$_{1-6}$ aminoalkyl, —S(O)$_2$(C$_{1-6}$ alkyl), —C$_{1-6}$ alkylene-S(O)$_2$(C$_{1-6}$ alkyl), cycloalkyl, cycloalkylalkyl, heterocyclyl, heterocyclylalkyl, aryl, arylalkyl, heteroaryl, heteroarylalkyl, amido, or —C(O)R$^{45}$.

4. The compound of claim 1, wherein R$^{42}$ is C$_{1-6}$ alkoxyalkyl substituted with one or more halo.

5. The compound of claim 1, wherein R$^{42}$ is C$_{1-6}$ haloalkyl substituted with —C(O)NR$^{46}$R$^{47}$ or cyano.

6. The compound of claim 1, wherein R$^{42}$ is C$_{3-6}$ cycloalkyl substituted with one or more substituents independently selected from cyanoalkyl, —S(C$_{1-6}$ alkyl), —S(O)(C$_{1-6}$ alkyl), —S(O)$_2$(C$_{1-6}$ alkyl), C$_{1-6}$ haloalkoxy, C$_{1-3}$ alkoxyalkyl substituted with one or more halo, heterocyclyl, or heteroaryl, wherein the heterocyclyl or heteroaryl is optionally substituted with one or more substituents independently selected from C$_{1-6}$ alkyl, C$_{1-6}$ haloalkyl, or halo.

7. The compound of claim 3, wherein R$^{43b}$ is hydrogen.

8. The compound of claim 1, having the formula (D-II):

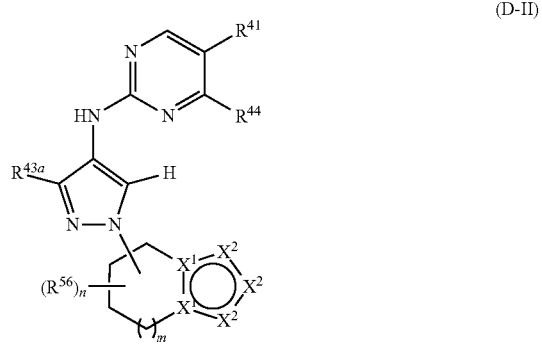

(D-II)

or a pharmaceutically acceptable salt, stereoisomer, or a mixture of stereoisomers thereof, wherein each $X^1$ is independently C or N;

each $X^2$ is independently $CR^{55}$, N, $NR^{55}$, O, or S;

each $R^{55}$ and $R^{56}$ is independently H, halo, cyano, $C_{1-6}$ alkyl, $C_{1-6}$ haloalkyl, $C_{1-6}$ alkoxy, amino, $C_{1-6}$ hydroxyalkyl, $C_{1-6}$ alkoxyalkyl, $C_{1-6}$ cyanoalkyl, $C_{1-6}$ aminoalkyl, $-S(O)_2(C_{1-6}$ alkyl$)$, $-C_{1-6}$ alkylene-$S(O)_2(C_{1-6}$ alkyl$)$, $-C(O)NR^{46}R^{47}$, $-NR^{46}C(O)R^{47}$, $-C_{1-6}$ alkylene-$C(O)NR^{46}R^{47}$, $-C_{1-6}$ alkylene-$NR^{46}C(O)R^{47}$, $-SO_2NR^{46}R^{47}$, $-NR^{46}SO_2R^{47}$, $-C_{1-6}$ alkylene-$SO_2NR^{46}R^{47}$, $-C_{1-6}$ alkylene-$NR^{46}SO_2R^{47}$, $-C(O)R^{46}$, $-OC(O)R^{46}$, $-C(O)_2R^{46}$, $-C_{1-6}$ alkylene-$C(O)R^{46}$, $-C_{1-6}$ alkylene-$OC(O)R^{46}$, $-C_{1-6}$ alkylene-$C(O)_2 R^{46}$, $-O-C(O)NR^{46}R^{47}$, $-NR^6C(O)OR^{47}$, $-C_{1-6}$ alkylene-$O-C(O)NR^{46}R^{47}$, $-C_{1-6}$ alkylene-$NR^{46}C(O)OR^{47}$, cycloalkyl, cycloalkylalkyl, heterocyclyl, heterocyclylalkyl, aryl, arylalkyl, heteroaryl, or heteroarylalkyl;

wherein each heterocyclyl is independently a 3- to 18-membered non-aromatic heterocyclyl comprising two to twelve carbon atoms and one to six heteroatoms selected from the group consisting of nitrogen, oxygen and sulfur; and each heteroaryl is independently a 5- to 14-membered heteroaryl comprising one to thirteen carbon atoms and one to six heteroatoms selected from the group consisting of nitrogen, oxygen and sulfur;

m is 0 or 1; and n is 0, 1, 2 or 3.

9. The compound of claim 1, having the formula (D-III):

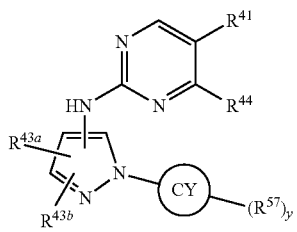

(D-III)

or a pharmaceutically acceptable salt, stereoisomer, or a mixture of stereoisomers thereof, wherein:

Cy is $C_{3-10}$ cycloalkyl;

y is 1, 2, or 3;

each $R^{57}$ is independently selected from amino, $C_{2-6}$ alkenyl, $C_{2-6}$ alkynyl, cyanoalkyl, $-S(C_{1-6}$ alkyl$)$, $-S(O)(C_{1-6}$ alkyl$)$, $-S(O)_2(C_{1-6}$ alkyl$)$, $-C_{1-6}$ alkylene-$S(O)_2(C_{1-6}$ alkyl$)$, $C_{1-6}$ haloalkoxy, $C_{1-6}$ hydroxyalkyl, $C_{1-6}$ alkoxyalkyl substituted with one or more halo, cycloalkyl, cycloalkylalkyl, heterocyclyl, aryl, arylalkyl, heteroaryl, or heteroarylalkyl, wherein the heterocyclyl, heteroaryl or heteroarylalkyl are optionally substituted with one or more substituents independently selected from $C_{1-6}$ alkyl, $C_{1-6}$ haloalkyl, or halo.

10. The compound of claim 8, wherein Cy is $C_{3-6}$ cycloalkyl.

11. The compound of claim 1 selected from:

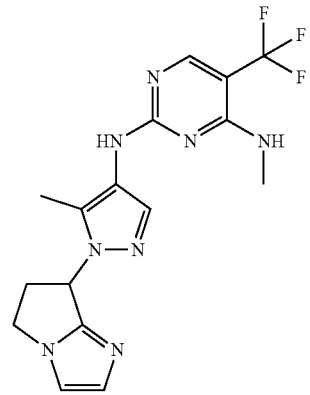

D-2

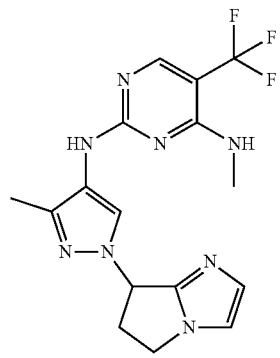

D-3: First eluting stereoisomer
D-4: Second eluting stereoisomer

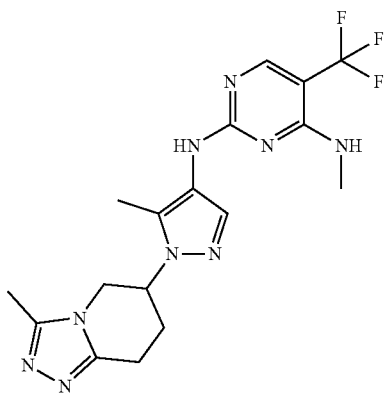

D-7

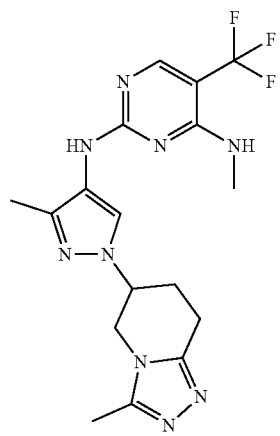

D-8

| 349 | 350 |
|---|---|
| -continued | -continued |
D22
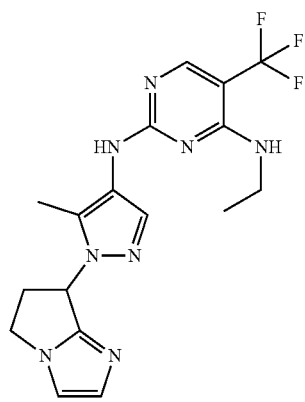
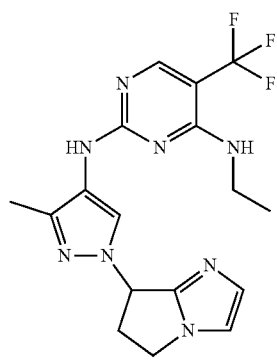
D-23: First eluting stereoisomer
D-24: Second eluting stereoisomer
D-25
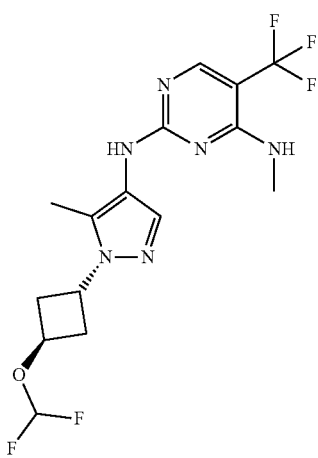
D-26
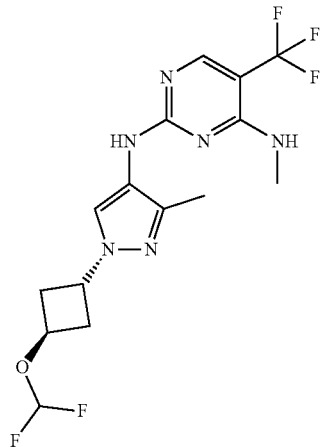
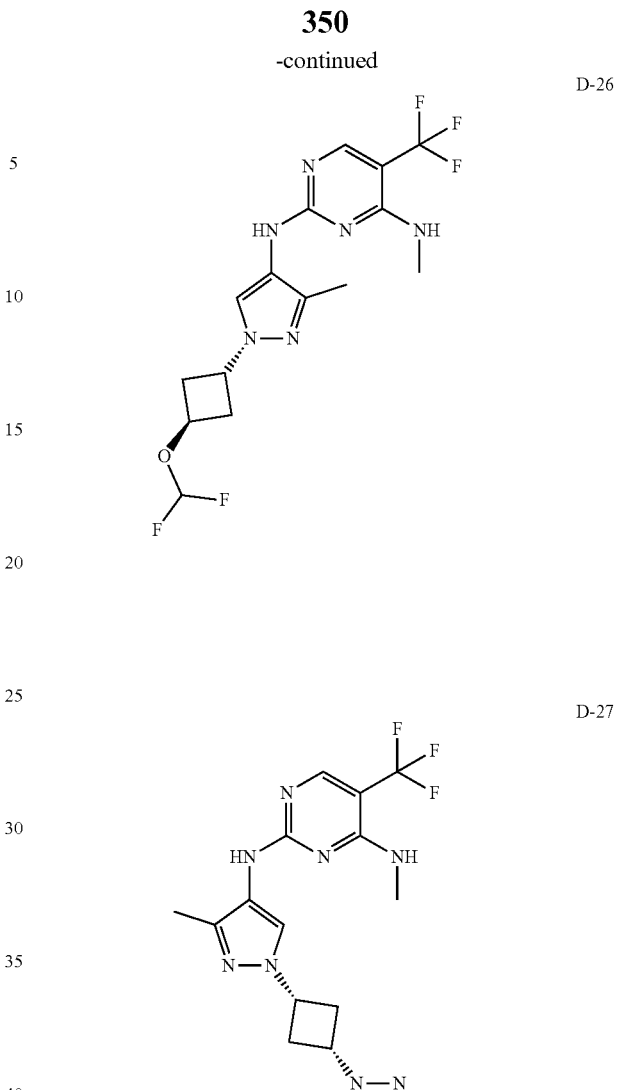
D-28
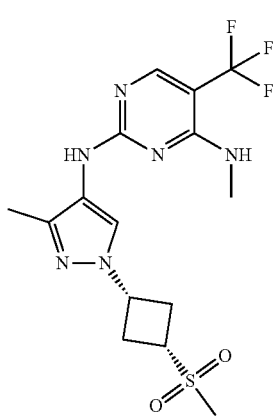

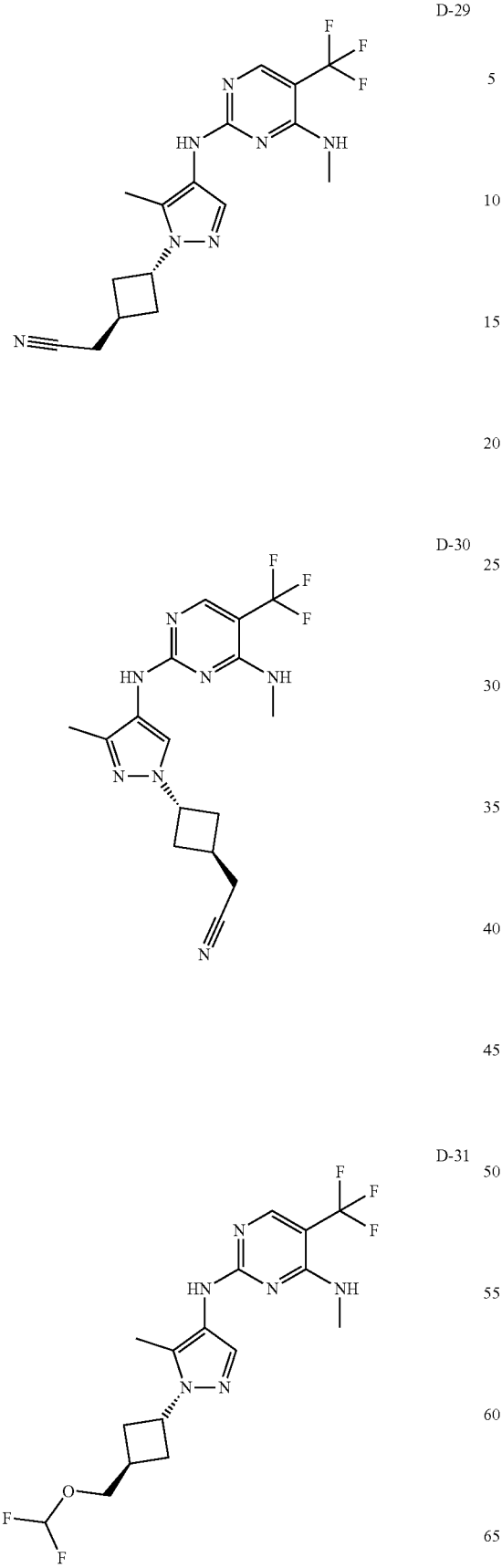
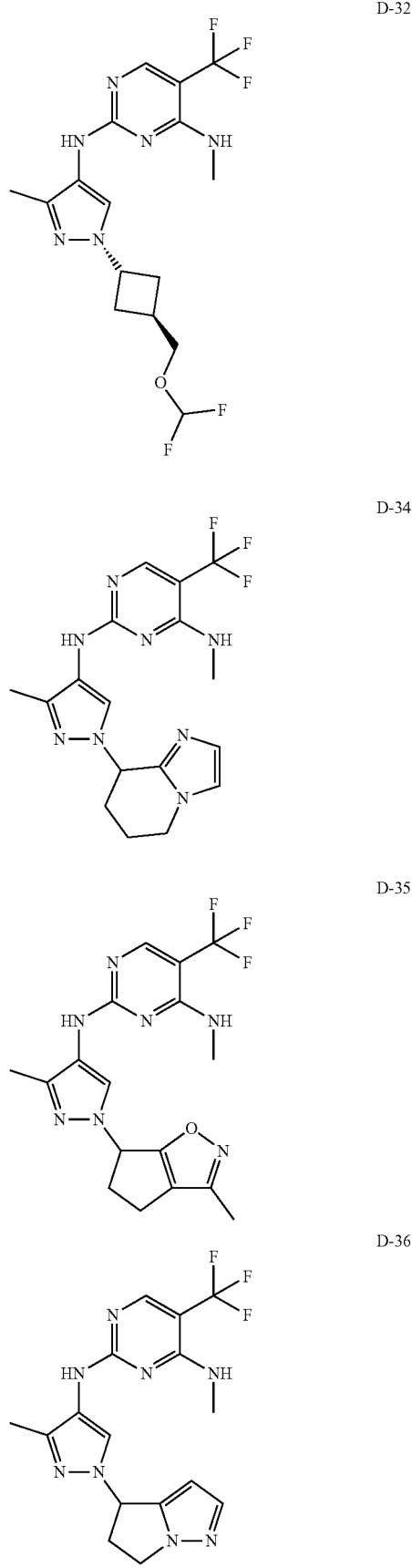

D-37 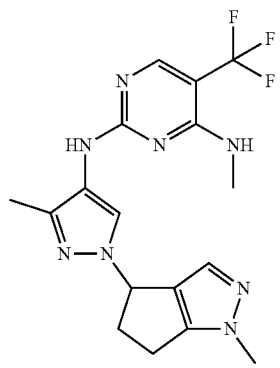
D-38 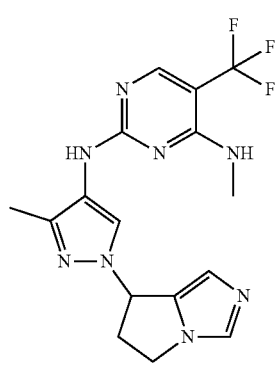
D-39 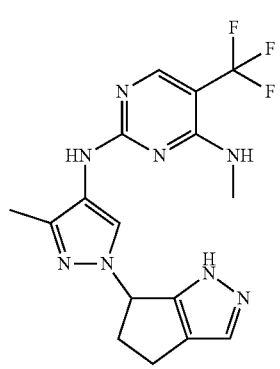
D-40 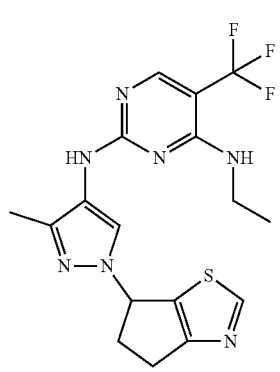
D-41 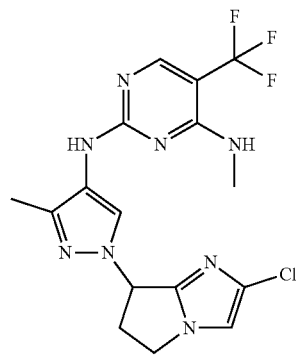
D-42 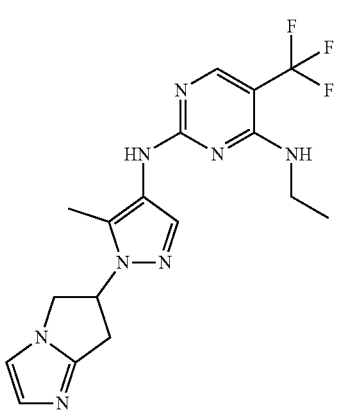
D-43 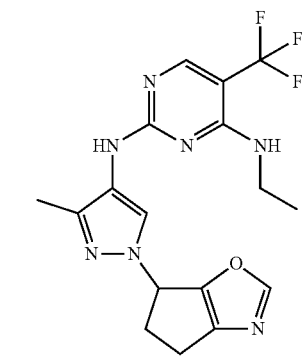
D-49 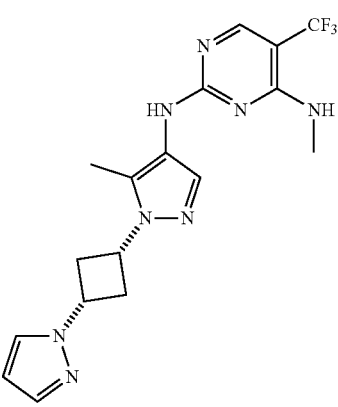

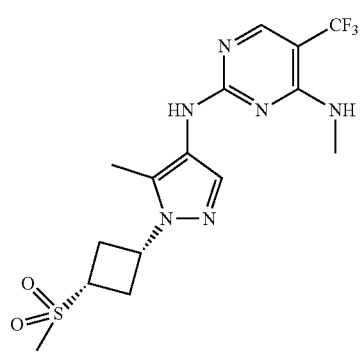 D-50
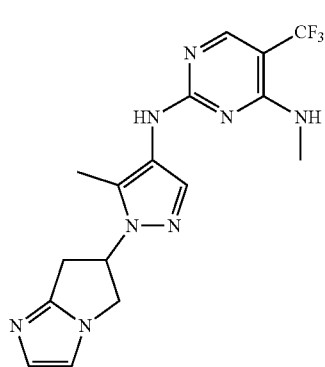 D-55
D-51
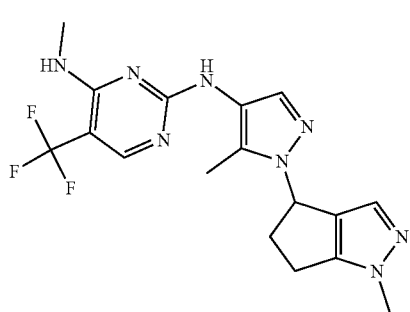 D-56
D-52
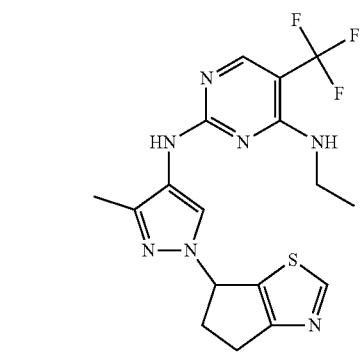
D-57 First eluting stereoisomer
D-86: Second eluting stereoisomer
D-53
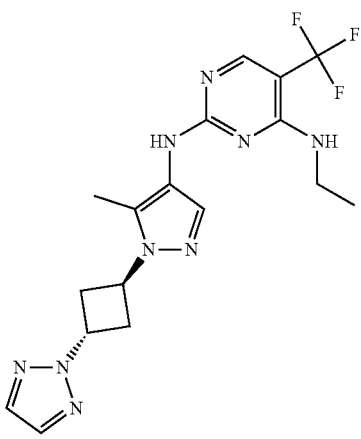 D-58
D-54

D-59
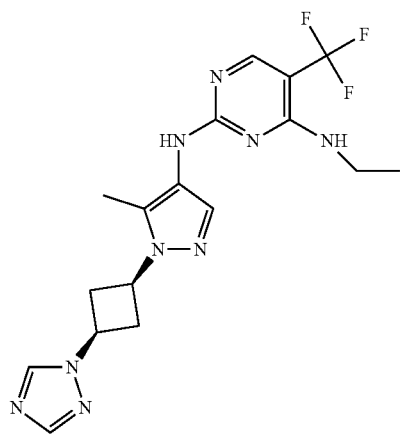
D-60: First eluting stereoisomer
D-163: Second eluting stereoisomer
D-61
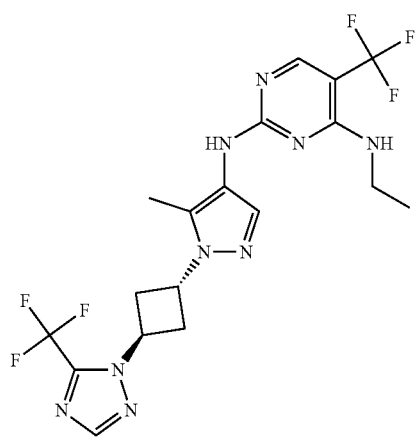
D-62: First eluting stereoisomer
D-105: Second eluting stereoisomer
D-63
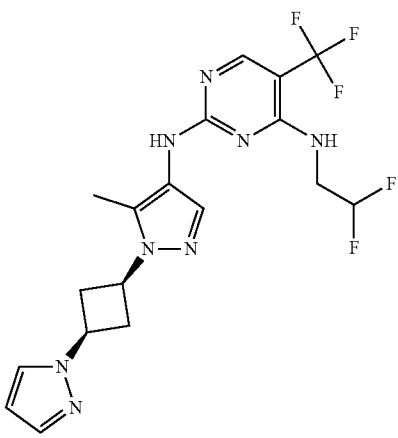
D-64
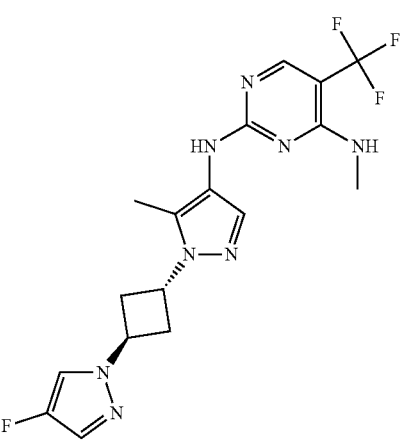
D-65: Second eluting stereoisomer
D-122: First eluting stereoisomer D-66
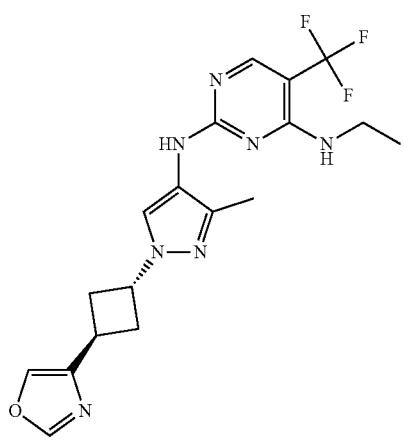
D-67: First eluting stereoisomer
D-130: Second eluting stereoisomer
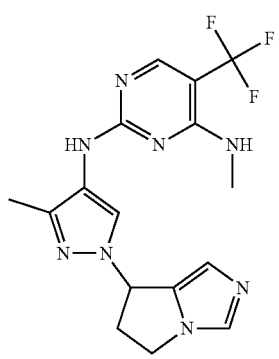
D-68: Second eluting stereoisomer
D-132: First eluting stereoisomer
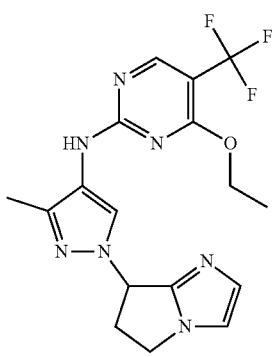
D-69: Third eluting stereoisomer
D-143: Fourth eluting stereoisomer
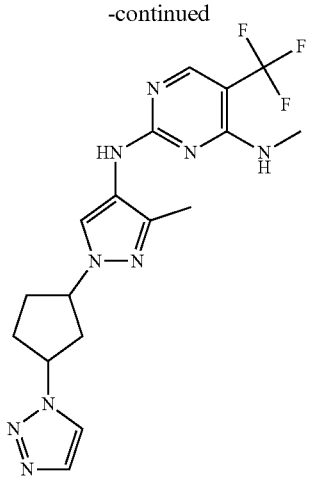
D-71
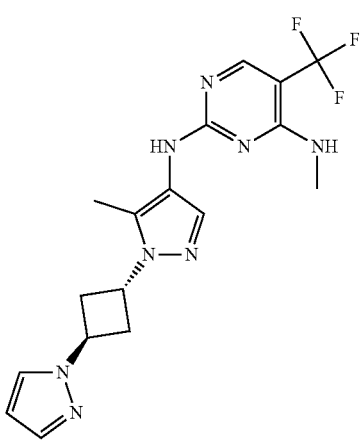
D-72
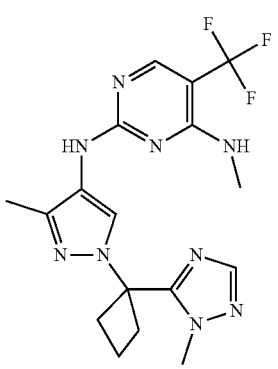

-continued
D-73
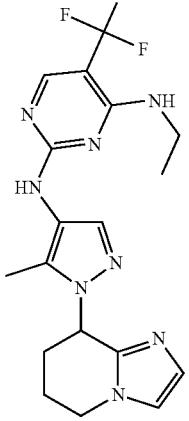
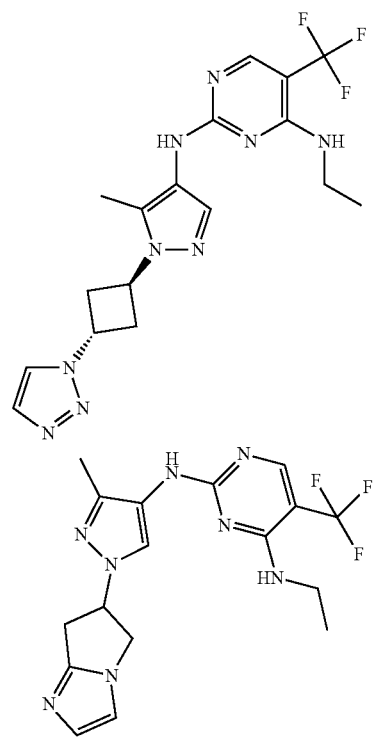
D-74: Second eluting stereoisomer
D-102: First eluting stereoisomer
D-75
-continued
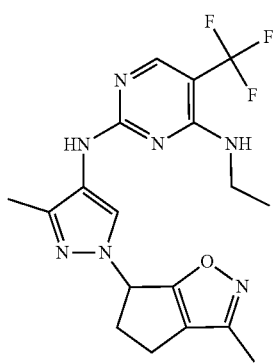
D-78: First eluting stereoisomer
D-151: Second eluting stereoisomer
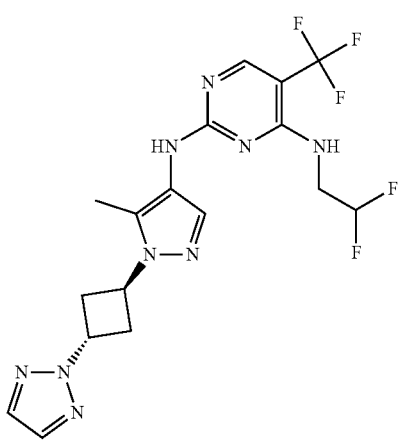
D-79: Second eluting stereoisomer
D-171: First eluting stereoisomer
D-77
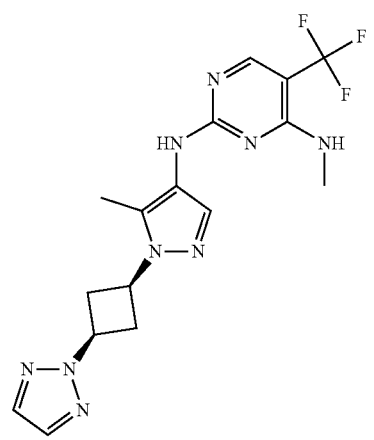
D-81
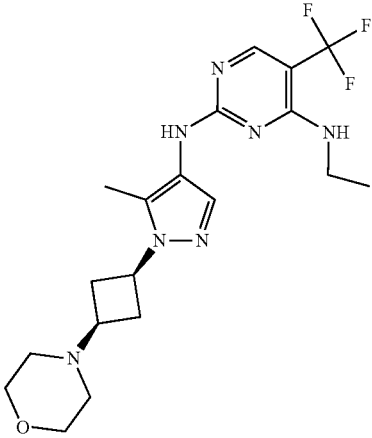

363
-continued
D-83
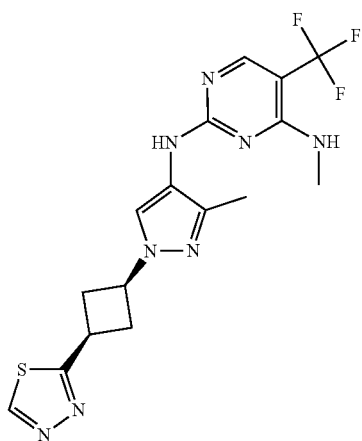
D-84
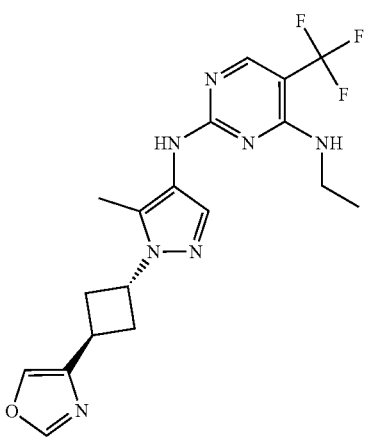
D-85
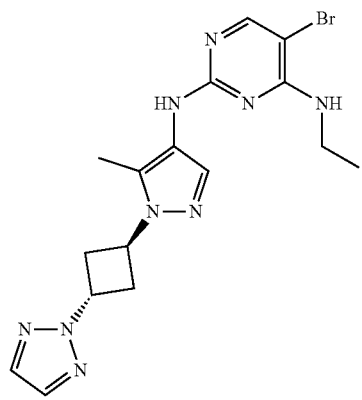
364
-continued
D-87
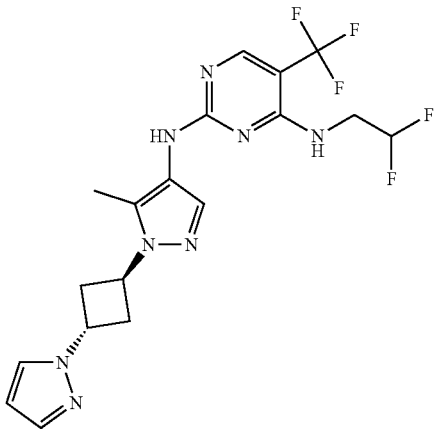
D-88
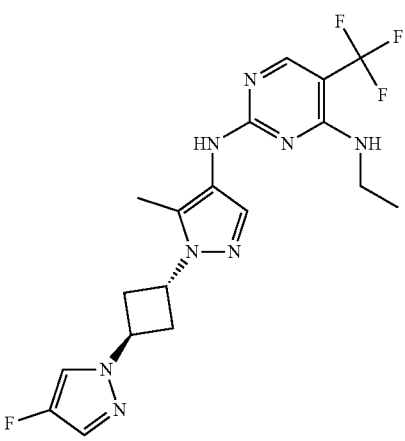
D-89
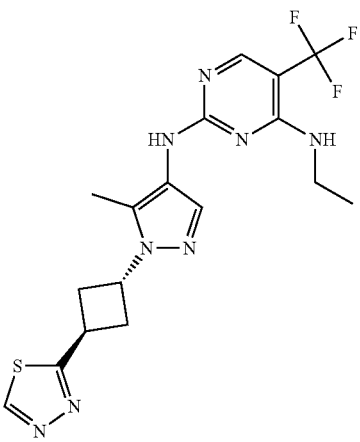

-continued
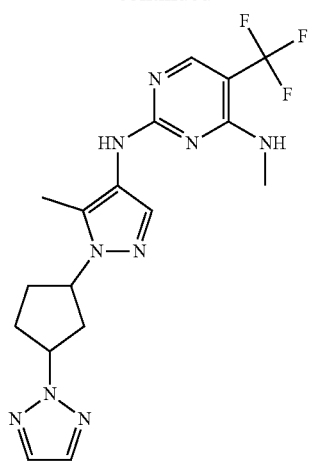
D-90: First eluting stereoisomer
D-107: Second eluting stereoisomer
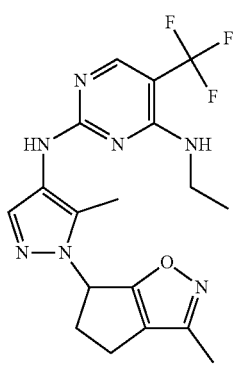
D-91
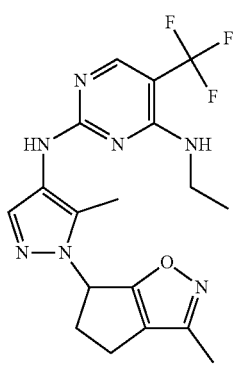
D-92: First eluting stereoisomer
D-170: Second eluting stereoisomer
-continued
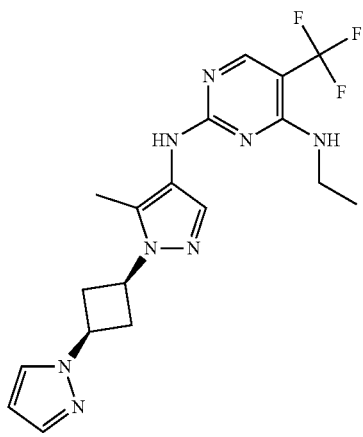
D-93
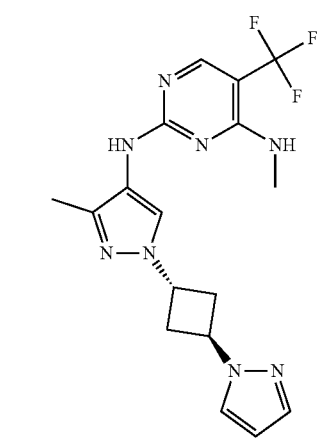
D-94
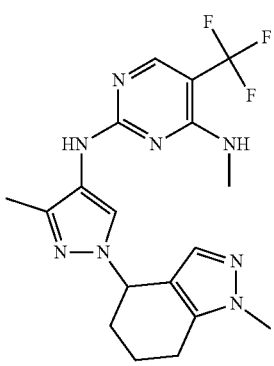
D-95
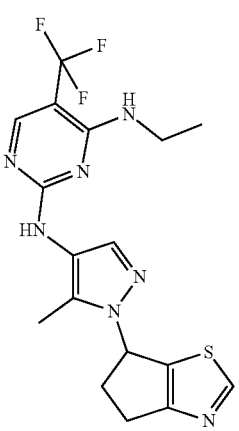
D-97

-continued
D-98
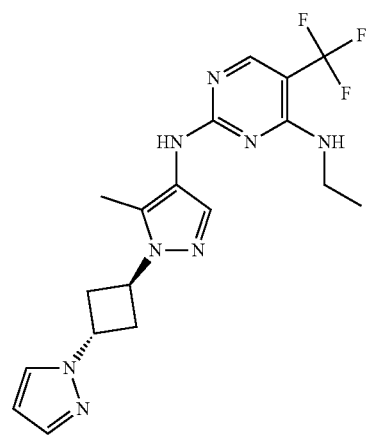
D-99
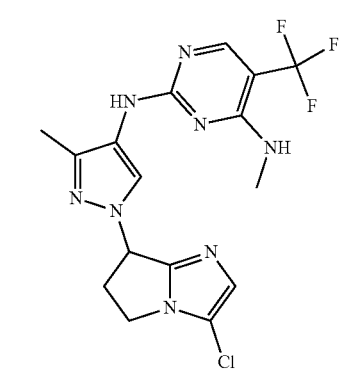
D-103
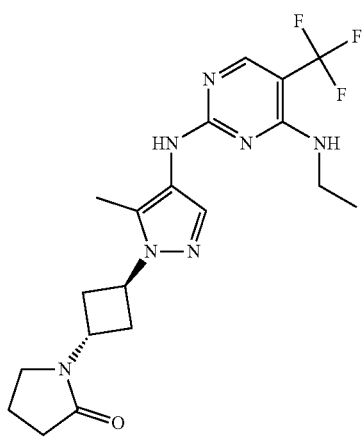
D-104
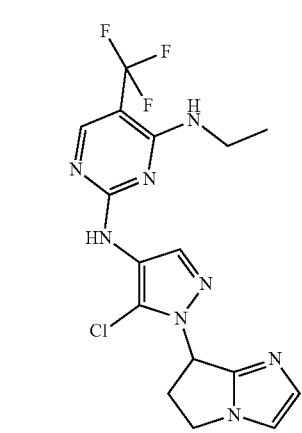
-continued
D-106
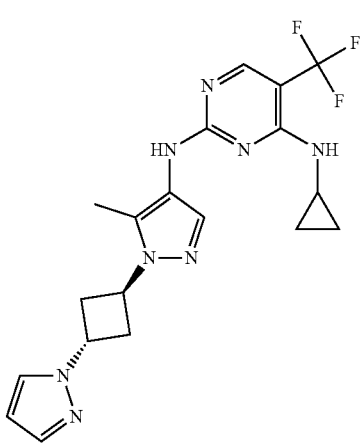
D-108
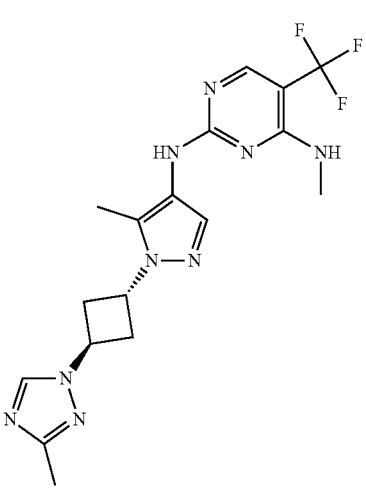
D-109
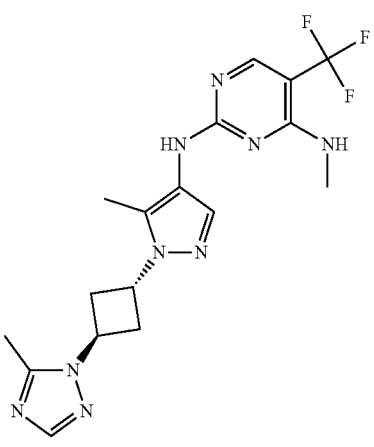

-continued
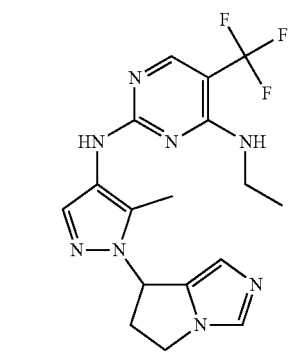
D-110
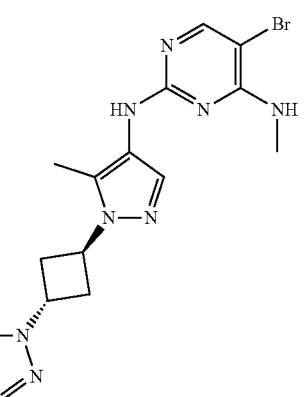
D-112: First eluting stereoisomer
D-175: Second eluting stereoisomer
-continued
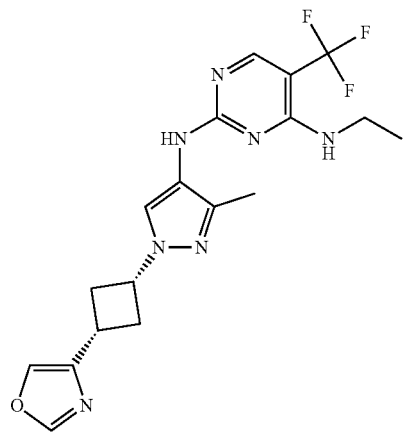
D-113
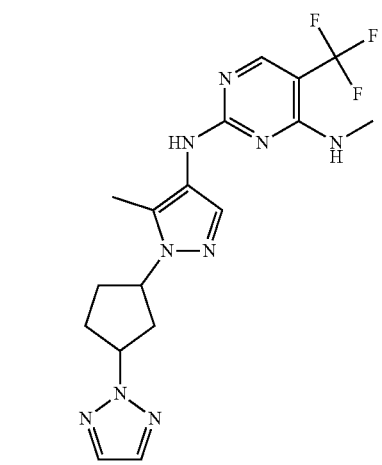
D-114: Third eluting stereoisomer
D-156: Fourth eluting stereoisomer
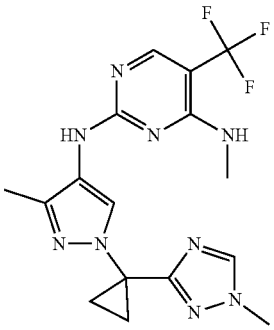
D-115
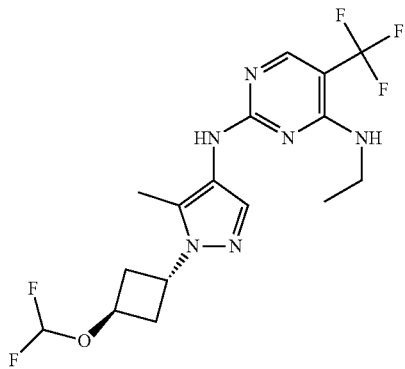
D-116

D-117
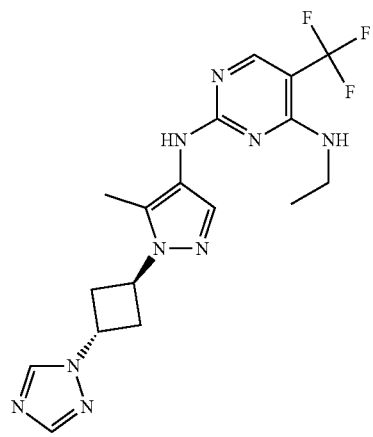
D-118
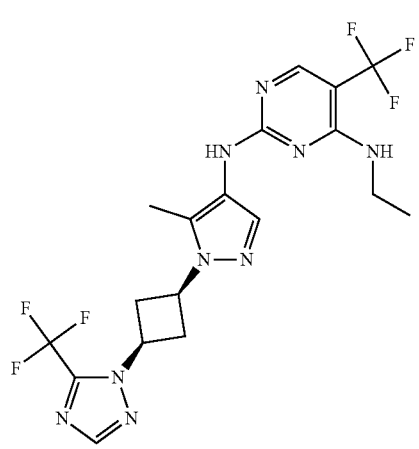
D-119
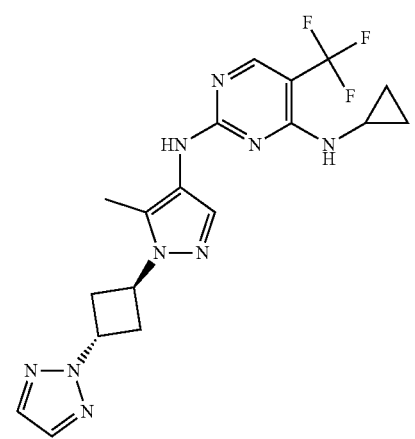
D-121: Second eluting stereoisomer
D-166: First eluting stereoisomer
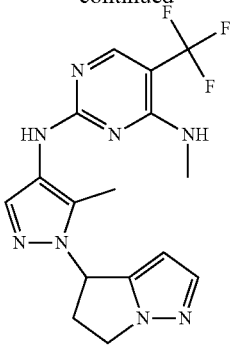
D-123
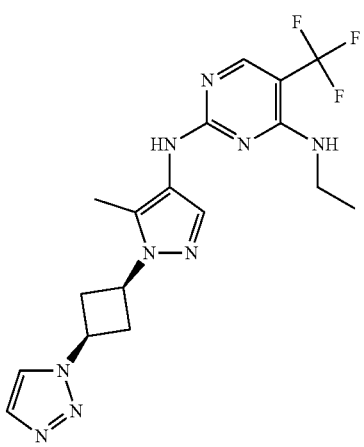
D-124
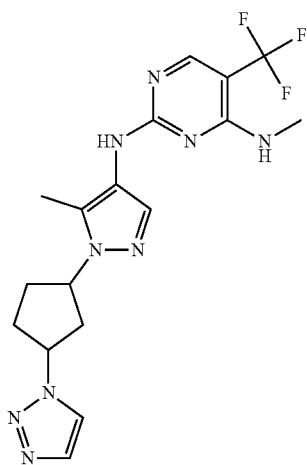

D-125
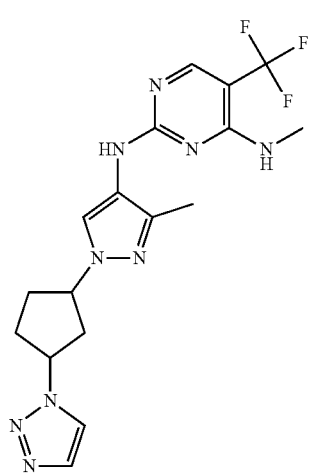
D-126
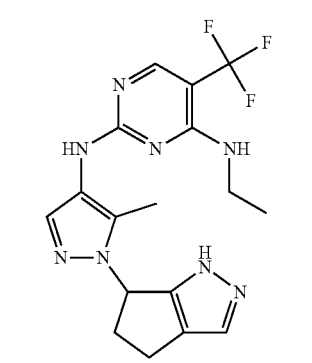
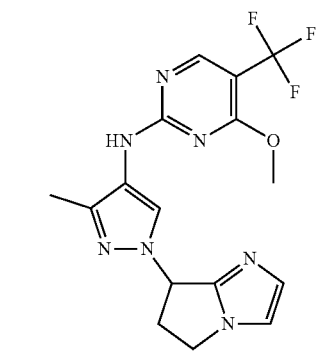
D-127: First eluting stereoisomer
D-142: Second eluting stereoisomer
D-128
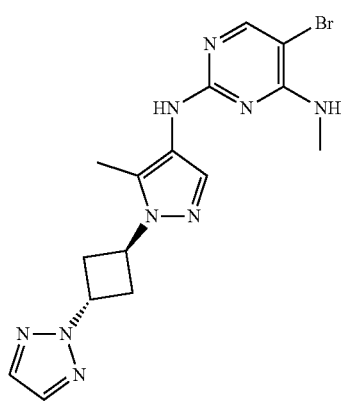
D-129
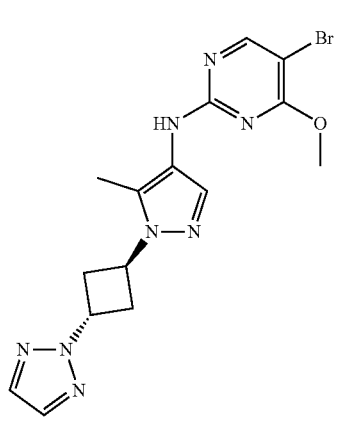
D-131
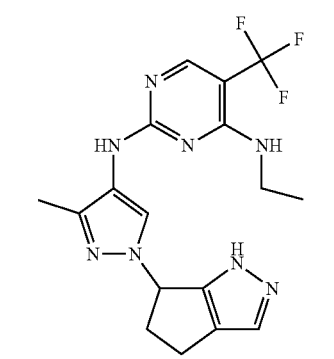
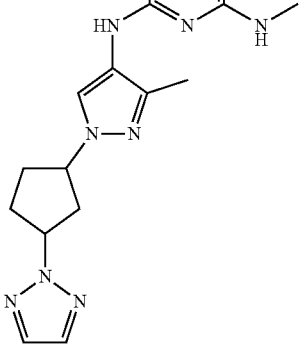
D-133: First eluting stereoisomer
D-134: Second eluting stereoisomer -continued
D-135
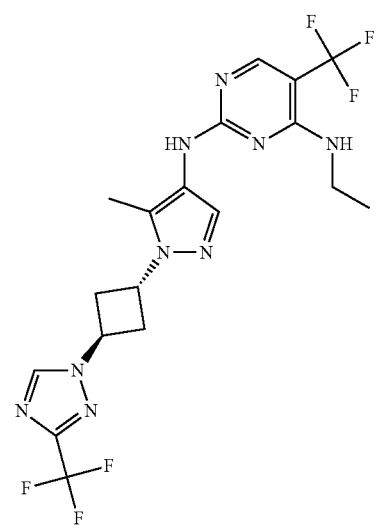
D-136
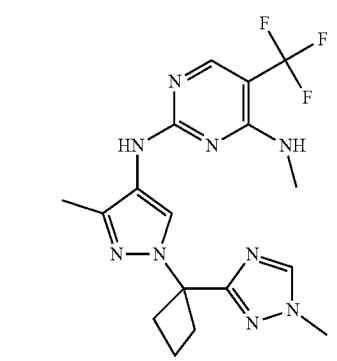
D-137
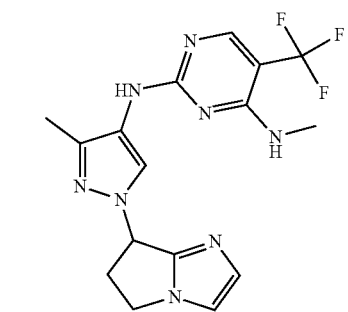
D-138
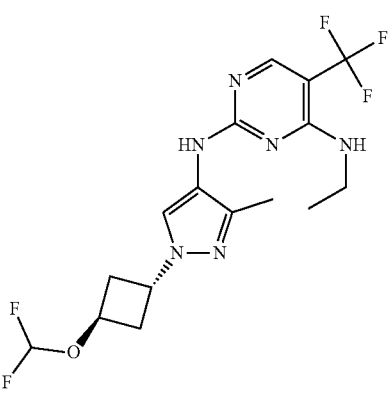
-continued
D-139
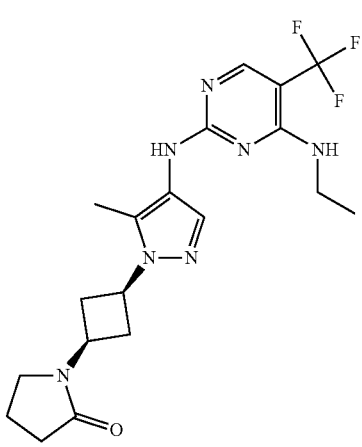
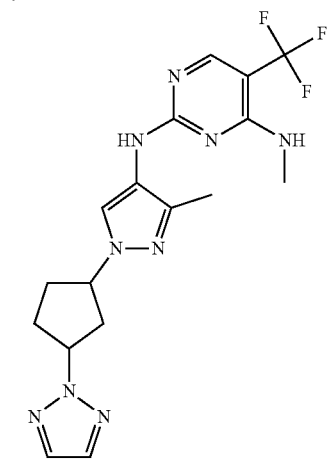
D-141: First eluting stereoisomer
D-149: Second eluting stereoisomer
D-144
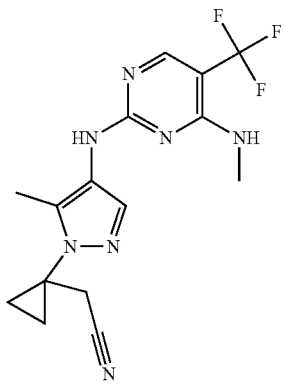
D-145
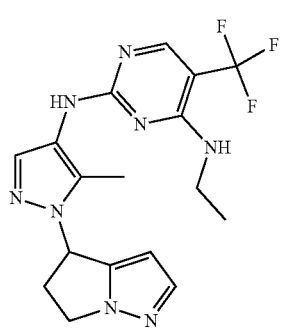

D-146
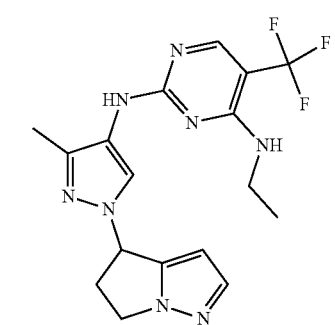
D-147
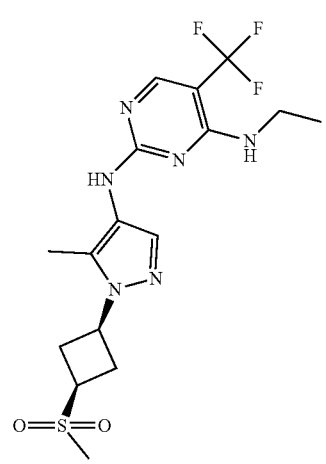
D-148
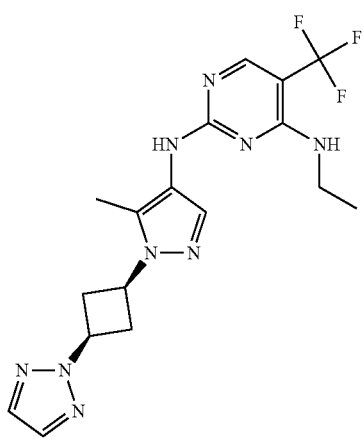
D-150
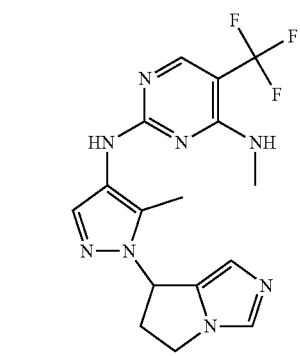
D-
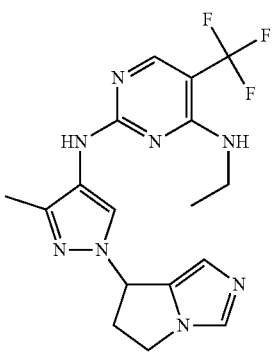
D-152: Second eluting stereoisomer
D-172: First eluting stereoisomer
D-153
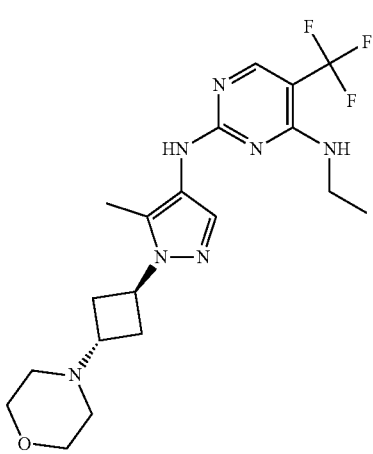
D-154
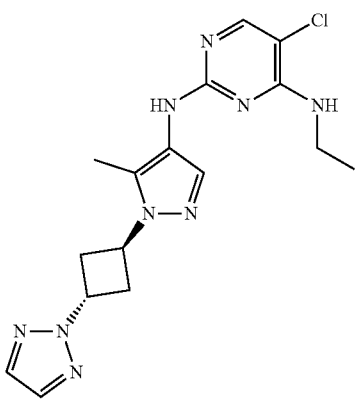
D-155
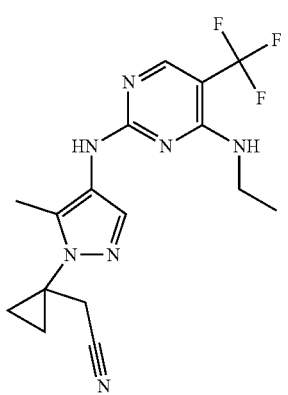

D-157 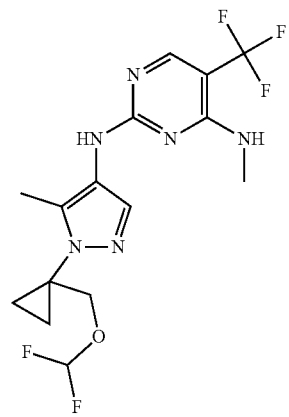
D-162 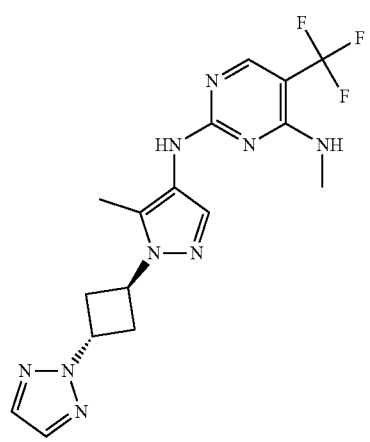
D-165 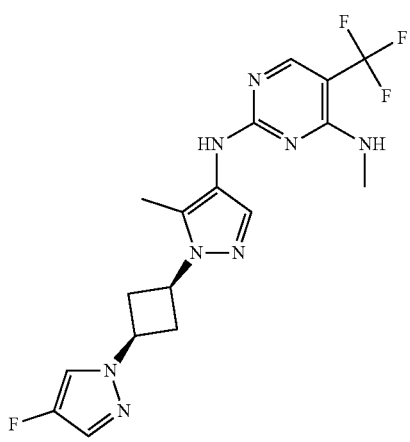
D-167 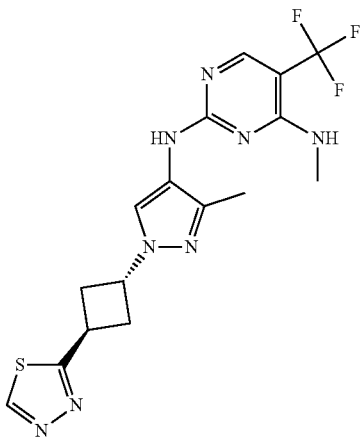
D-168 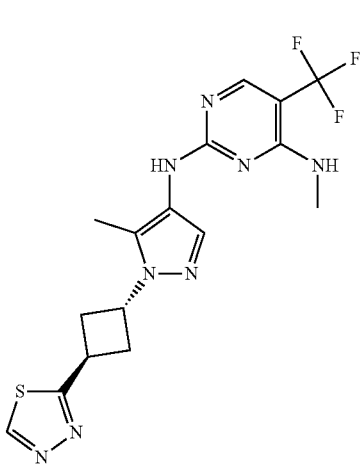
D-169 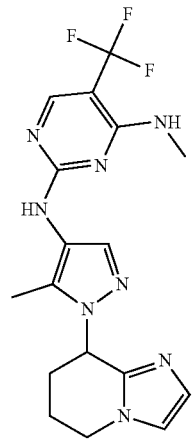

D-173
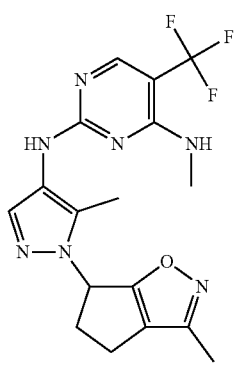
Second eluting stereoisomer
D-176
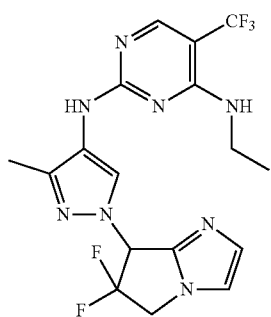
D-177
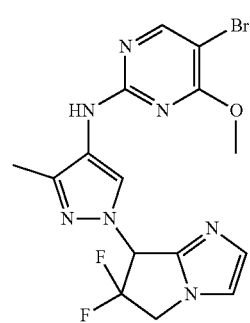
D-178
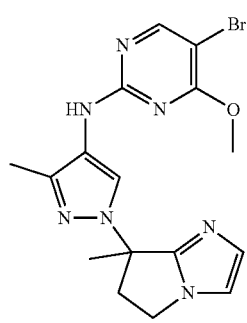
D-179
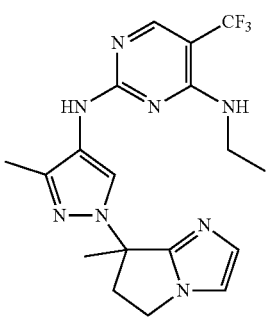
D-180
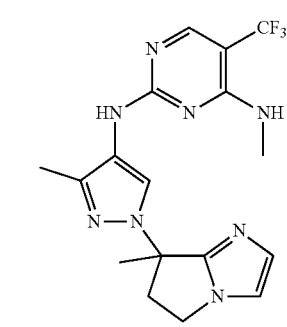
D-184
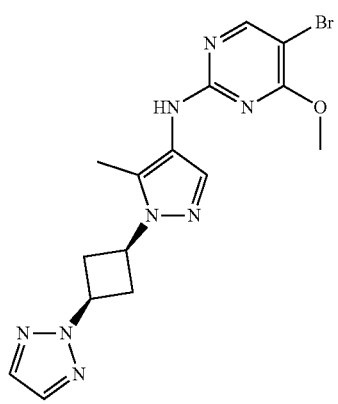
D-185
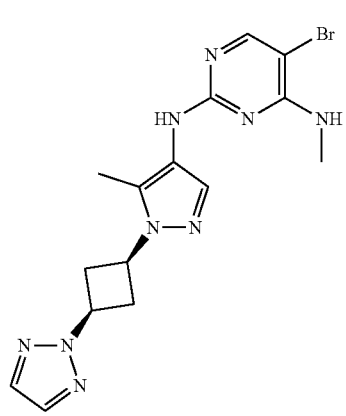

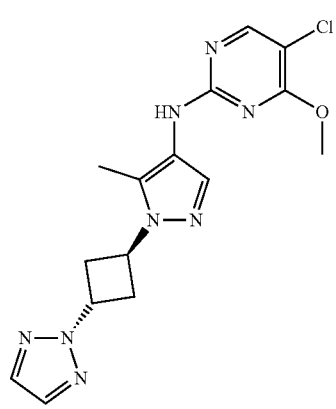
D-186
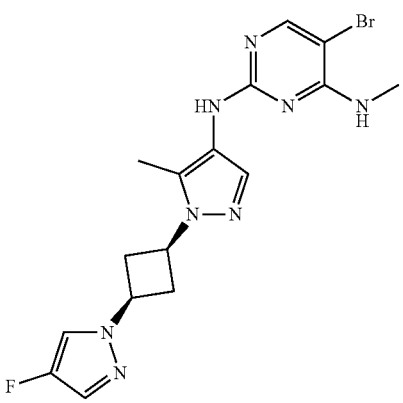
D-192
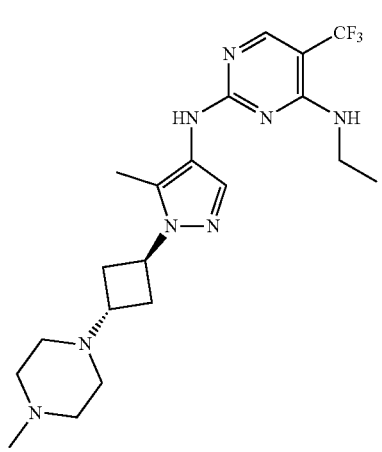
D-187
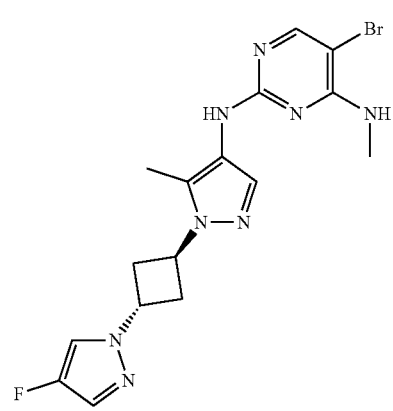
D-193
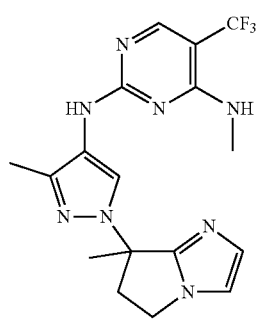
D-188
First eluting stereoisomer
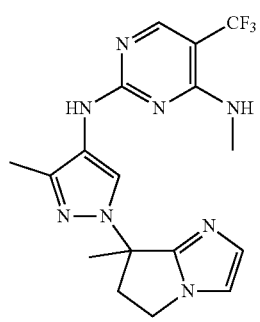
D-189
Second eluting stereoisomer
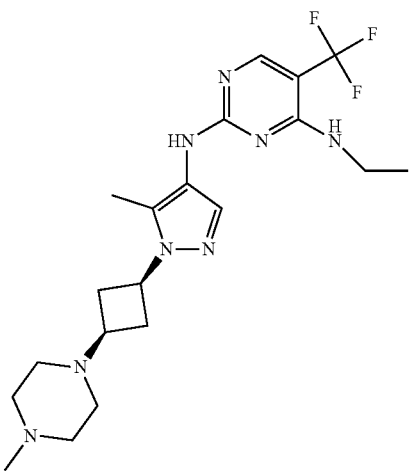
D-194

-continued

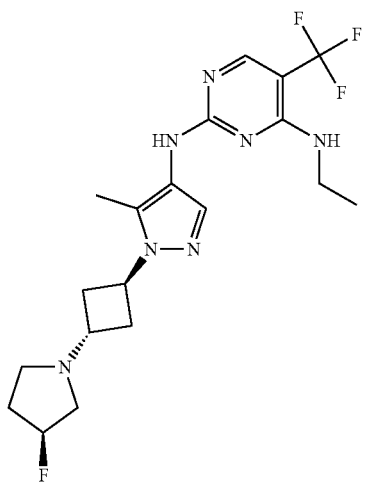
D-195

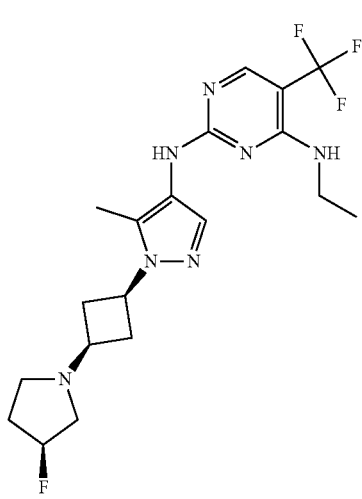
D-196

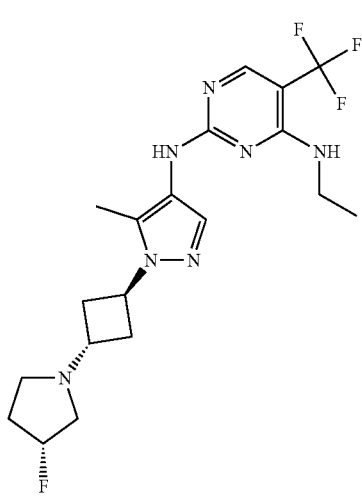
D-197

-continued

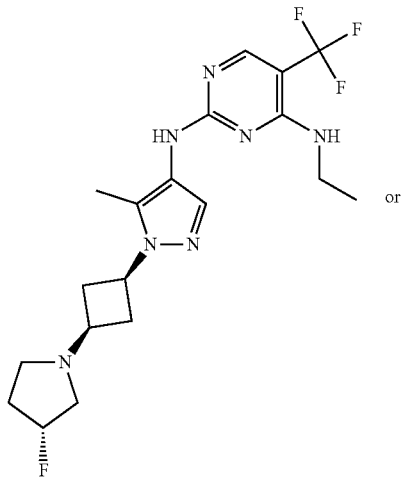
D-198 or

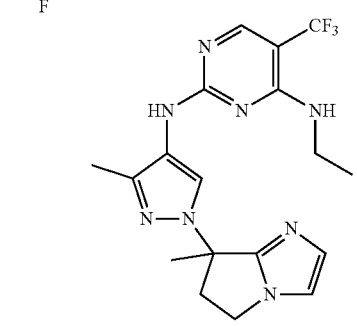

D-205: First eluting stereoisomer
D-206: Second eluting stereoisomer or a pharmaceutically acceptable salt, stereoisomer, mixture of stereoisomers, or tautomer thereof.

12. A pharmaceutical composition comprising the compound of claim 1, or a pharmaceutically acceptable salt, stereoisomer, mixture of stereoisomers, or tautomer thereof, and a pharmaceutically acceptable carrier, diluent or excipient.

13. A pharmaceutical composition comprising a compound of claim 11, a pharmaceutically acceptable salt, stereoisomer, mixture of stereoisomers, or tautomer thereof, and a pharmaceutically acceptable carrier, diluent or excipient.

14. The compound of claim 1 selected from:

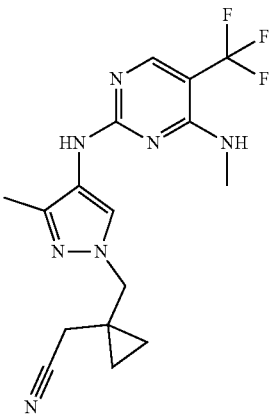
D-1

-continued
D-5
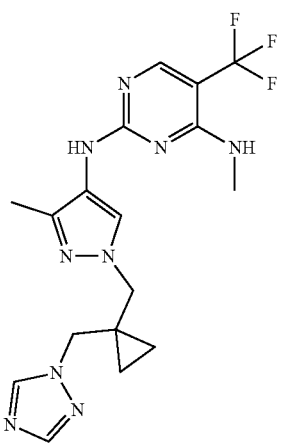
D-6
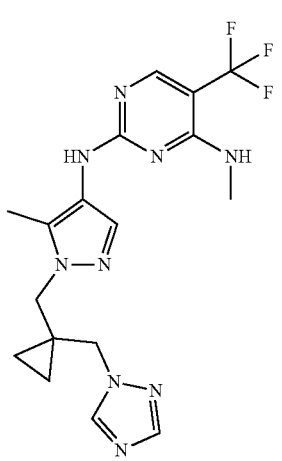
D-9
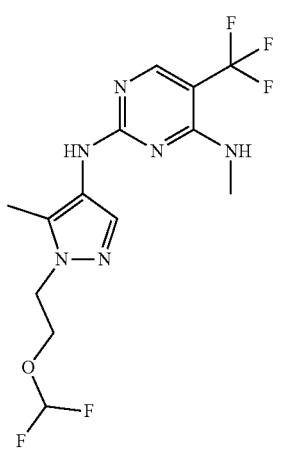
-continued
D-10
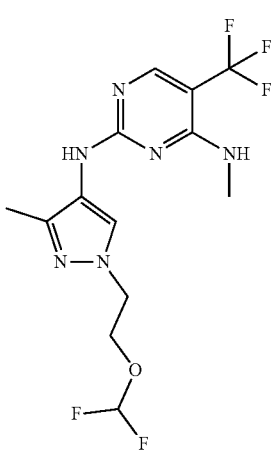
D-11
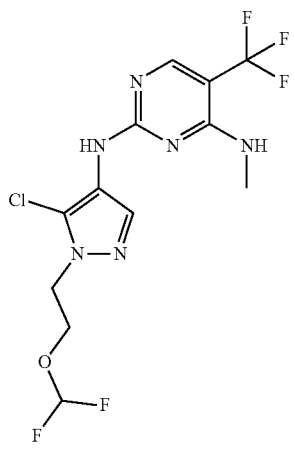
D-12
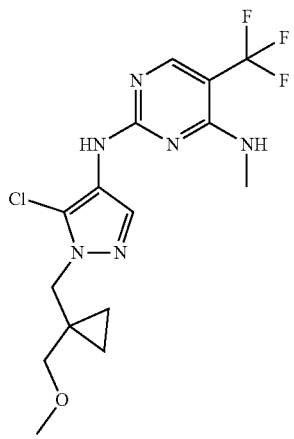
D-13
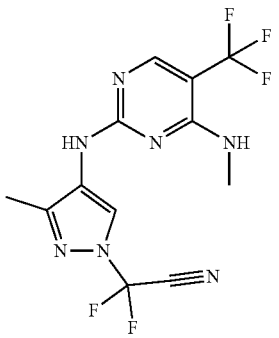

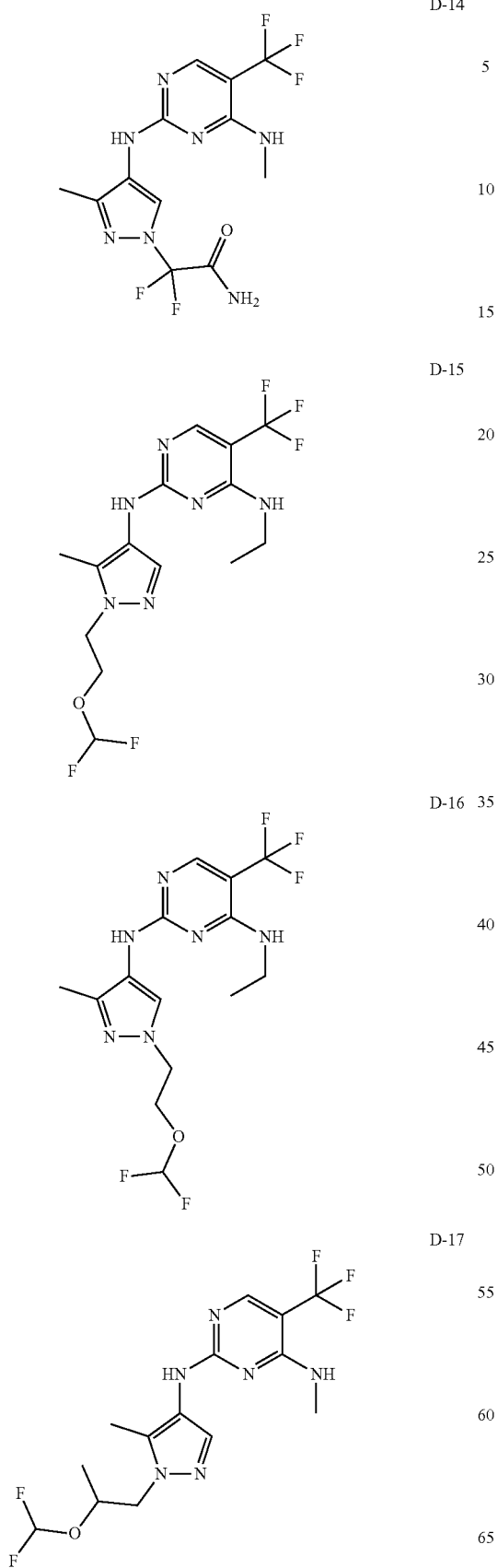
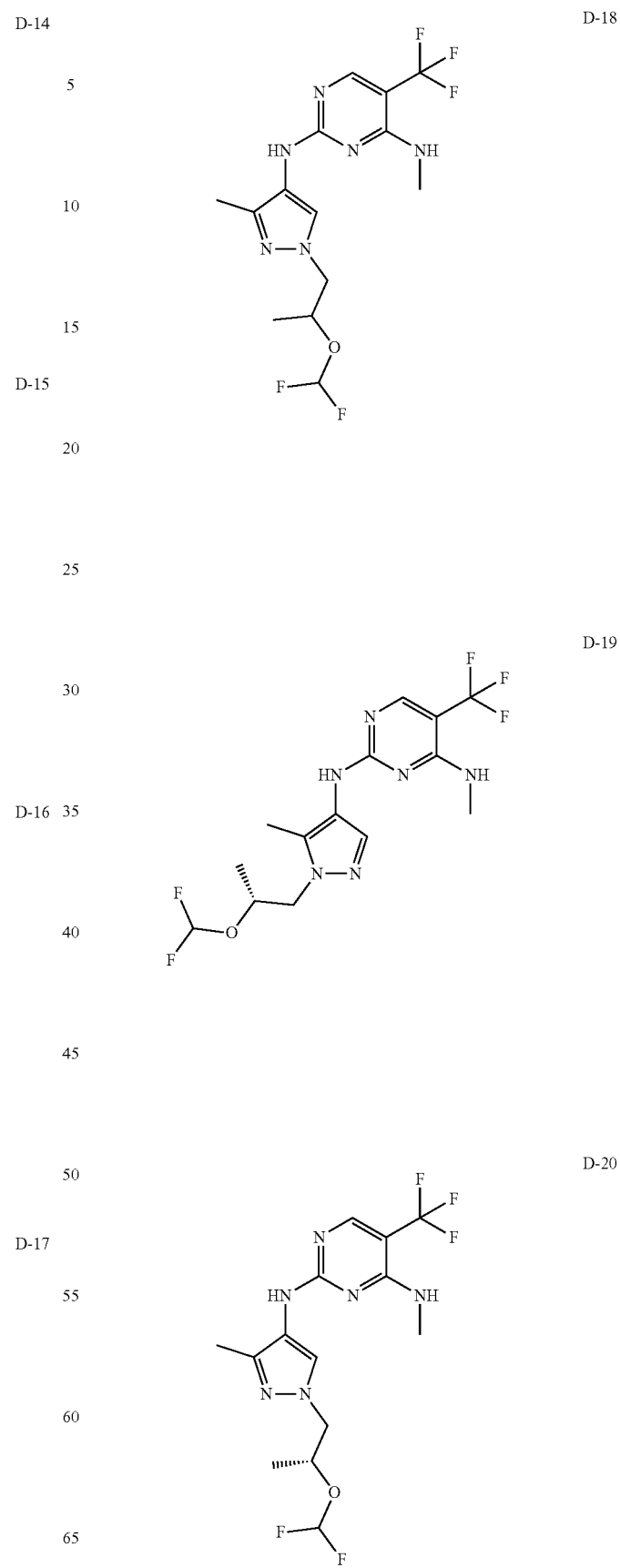

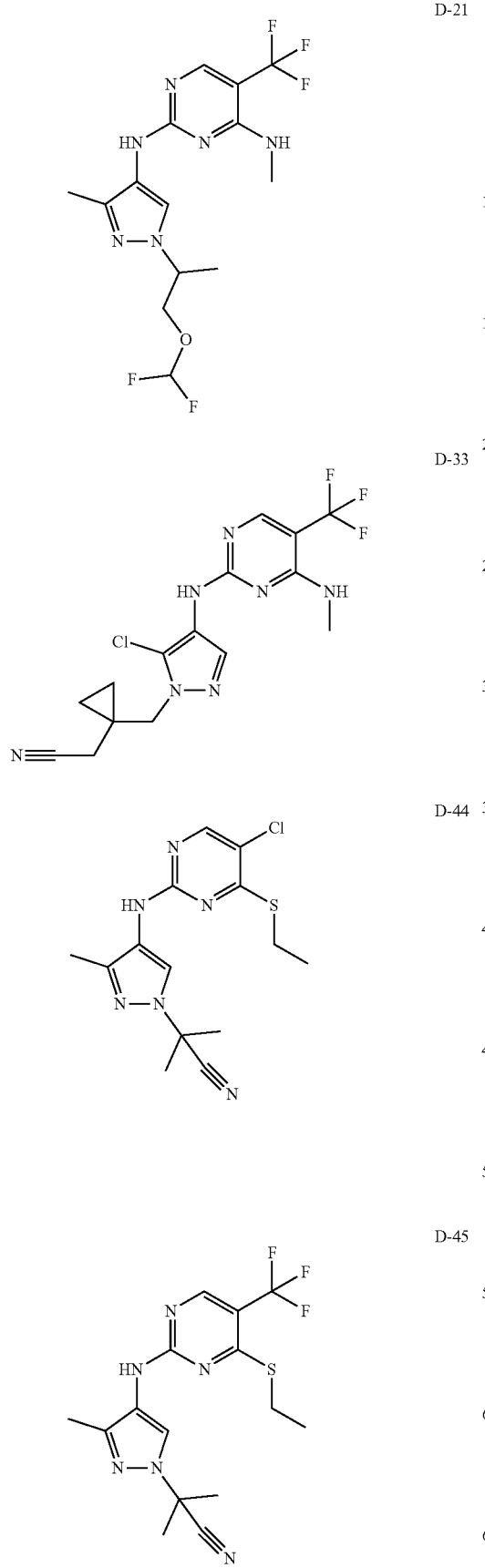
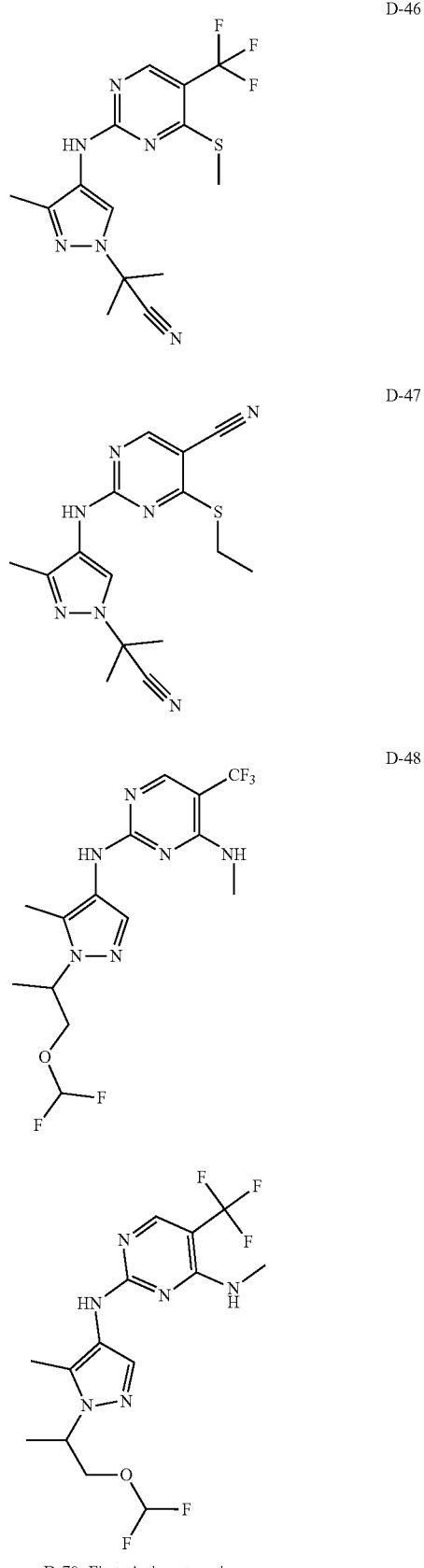
D-70: First eluting stereoisomer
D-96: Second eluting stereoisomer -continued
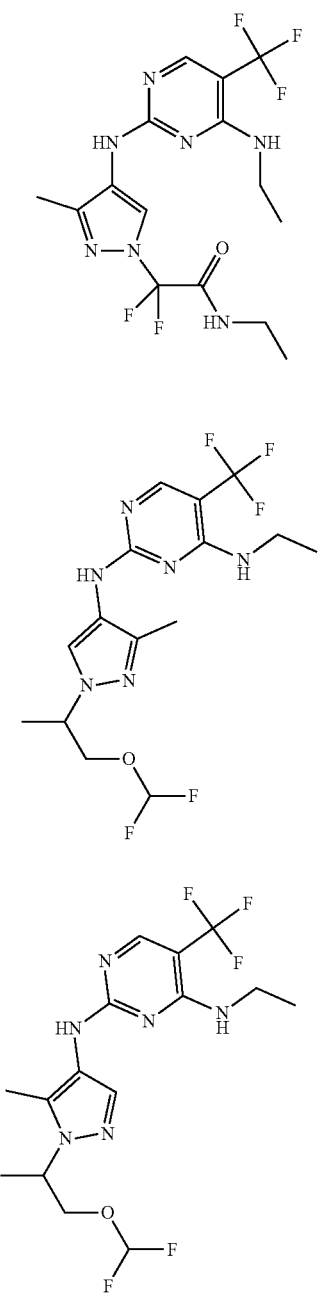
D-82: Secomd eluting stereoisomer
D-174: First eluting stereoisomer
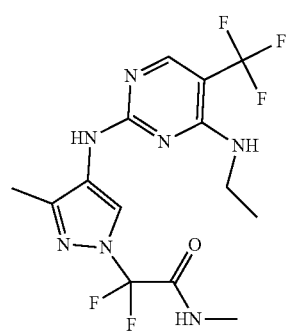
-continued
D-76
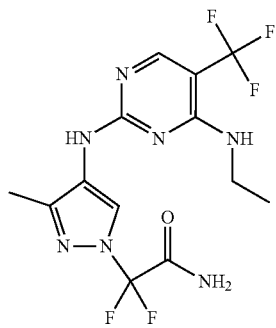
D-80
D-101
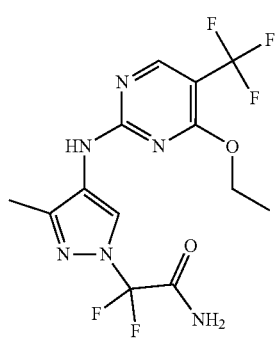
D-120
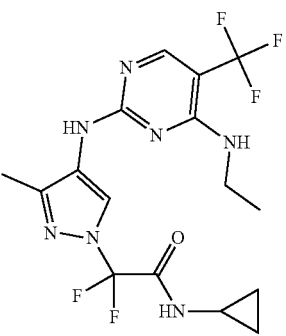
D-140
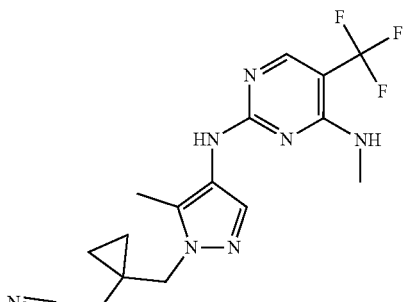
D-157a
D-100
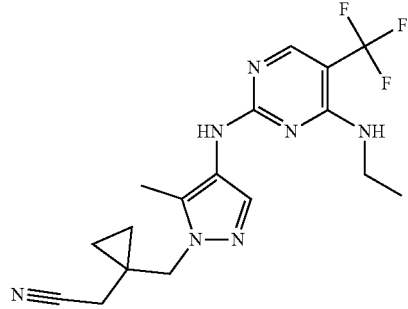
D-158

-continued
D-159
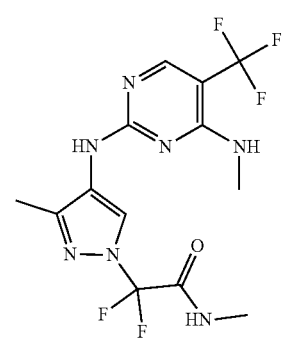
D-160
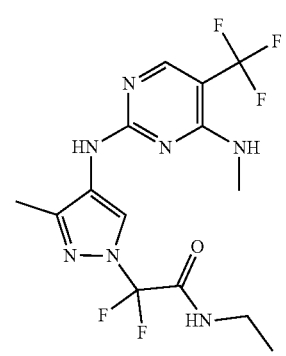
D-161
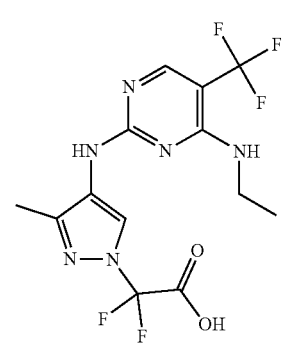
D-164
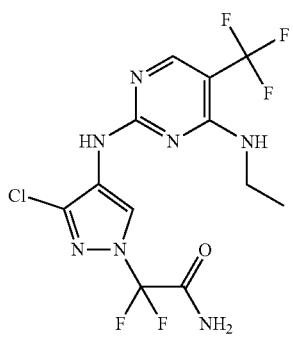
D-181
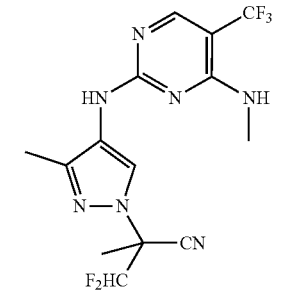
-continued
D-182
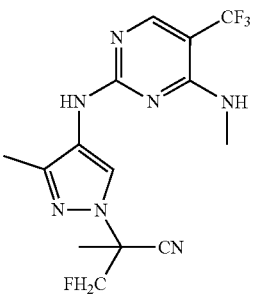
D-183
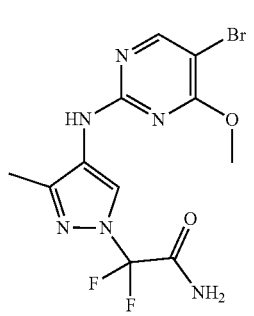
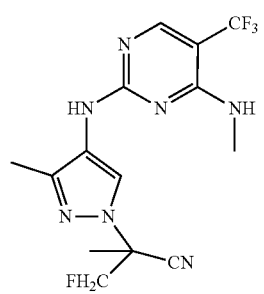
D-190: First eluting stereoisomer
D-191: Second eluting stereoisomer
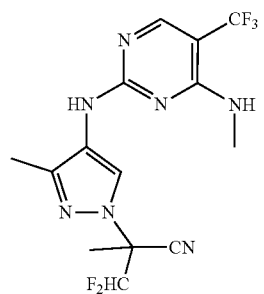
D-199: First eluting stereoisomer
D-200: Second eluting stereoisomer -continued

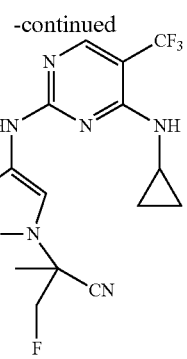

D-201: First eluting stereoisomer
D-202: Second eluting stereisomer

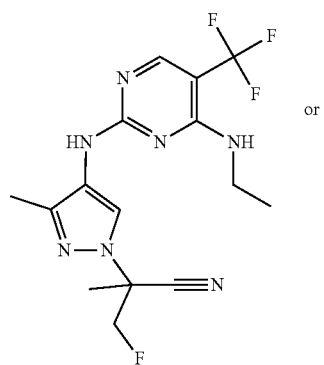

D-203 or

-continued

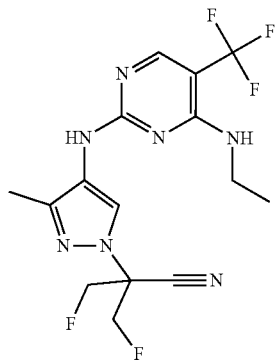

D-204 or a pharmaceutically acceptable salt, stereoisomer, mixture of stereoisomers, or tautomer thereof.

15. A pharmaceutical composition comprising a compound of claim 14, or a pharmaceutic ally acceptable salt, stereoisomer, mixture of stereoisomers, or tautomer thereof, and a pharmaceutically acceptable carrier, diluent or excipient.

* * * * *